US011291721B2

(12) United States Patent
Loew et al.

(10) Patent No.: US 11,291,721 B2
(45) Date of Patent: Apr. 5, 2022

(54) MULTISPECIFIC AND MULTIFUNCTIONAL MOLECULES AND USES THEREOF

(71) Applicant: MARENGO THERAPEUTICS, INC., Cambridge, MA (US)

(72) Inventors: Andreas Loew, Somerville, MA (US); Brian Edward Vash, Cambridge, MA (US)

(73) Assignee: Marengo Therapeutics, Inc., Cambridge, MA (US)

( * ) Notice: Subject to any disclaimer, the term of this patent is extended or adjusted under 35 U.S.C. 154(b) by 539 days.

(21) Appl. No.: 15/465,564

(22) Filed: Mar. 21, 2017

(65) Prior Publication Data

US 2017/0368169 A1    Dec. 28, 2017

Related U.S. Application Data

(60) Provisional application No. 62/310,899, filed on Mar. 21, 2016, provisional application No. 62/310,929, filed on Mar. 21, 2016.

(51) Int. Cl.

| | | |
|---|---|---|
| *A61K 39/395* | (2006.01) |
| *C07K 16/30* | (2006.01) |
| *C07K 16/28* | (2006.01) |
| *C07K 16/40* | (2006.01) |
| *C07K 16/32* | (2006.01) |
| *C07K 14/55* | (2006.01) |
| *C07K 14/71* | (2006.01) |
| *C07K 14/705* | (2006.01) |
| *C07K 14/47* | (2006.01) |
| *A61K 39/00* | (2006.01) |
| *A61K 38/17* | (2006.01) |

(52) U.S. Cl.
CPC ........ *A61K 39/3955* (2013.01); *A61K 38/177* (2013.01); *A61K 39/0011* (2013.01); *A61K 39/39558* (2013.01); *C07K 14/4748* (2013.01); *C07K 14/55* (2013.01); *C07K 14/70596* (2013.01); *C07K 14/71* (2013.01); *C07K 16/2803* (2013.01); *C07K 16/2809* (2013.01); *C07K 16/2827* (2013.01); *C07K 16/2863* (2013.01); *C07K 16/30* (2013.01); *C07K 16/32* (2013.01); *C07K 16/40* (2013.01); *A61K 2039/507* (2013.01); *A61K 2039/515* (2013.01); *C07K 2317/31* (2013.01); *C07K 2317/55* (2013.01); *C07K 2317/73* (2013.01); *C07K 2317/76* (2013.01); *C07K 2317/92* (2013.01); *C07K 2317/94* (2013.01); *C07K 2319/00* (2013.01); *C07K 2319/75* (2013.01)

(58) Field of Classification Search
CPC ........... C07K 2319/00; C07K 2317/31; C07K 2319/75; C07K 14/52; C07K 14/55; C07K 14/57; C07K 14/5418; C07K 14/5434; C07K 14/5443; C07K 14/54; A61K 39/39558; A61K 39/0011; A61K 39/3955; A61K 39/001102; A61K 39/00114; A61K 39/001141

See application file for complete search history.

(56) References Cited

U.S. PATENT DOCUMENTS

| | | | |
|---|---|---|---|
| 5,116,615 A * | 5/1992 | Gokcen ................. A61K 38/47 424/94.2 |
| 7,361,360 B2 * | 4/2008 | Kitabwalla ............. A61P 37/00 424/277.1 |
| 7,501,121 B2 | 3/2009 | Tchistiakova et al. |
| 7,741,446 B2 | 6/2010 | Pardridge et al. |
| 7,906,118 B2 * | 3/2011 | Chang ................. C07K 16/283 424/134.1 |
| 7,919,257 B2 | 4/2011 | Hoogenboom et al. |
| 8,034,326 B2 * | 10/2011 | Hjorth ..................... A61P 31/12 424/85.2 |
| 8,227,577 B2 | 7/2012 | Klein et al. |
| 8,703,132 B2 | 4/2014 | Imhof-Jung et al. |
| 9,145,588 B2 | 9/2015 | Throsby et al. |
| 9,359,437 B2 | 6/2016 | Davis et al. |
| 9,382,323 B2 | 7/2016 | Brinkmann et al. |
| 2004/0009530 A1 | 1/2004 | Wilson et al. |
| 2006/0141581 A1 * | 6/2006 | Gillies ............... C07K 14/5418 435/69.52 |
| 2008/0069820 A1 | 3/2008 | Fuh et al. |

(Continued)

FOREIGN PATENT DOCUMENTS

| | | |
|---|---|---|
| WO | 9509917 A1 | 4/1995 |
| WO | 9856915 A2 | 12/1998 |

(Continued)

OTHER PUBLICATIONS

Vallera et al (Cancer Biotherapy and Radiopharmaceuticals, 2013, vol. 28, pp. 274-282) (Year: 2013).*
Chaudry et al (British Journal of Cancer, 2007, vol. 96, pp. 1013-1019) (Year: 2007).*
Provenzano et al (Cancer Cell, 2012, vol. 21, pp. 418-429) (Year: 2012).*
Kirkin et al, APMIS, 1998, vol. 106, pp. 665-679 (Year: 1998).*
Hirai et al, Genes to Cells, 2013, vol. 18, pp. 780-797 (Year: 2013).*
Kushner et al, J Oral Pathol Med, 1999, vol. 28, pp. 77-81 (Year: 1999).*

(Continued)

*Primary Examiner* — Karen A. Canella
(74) *Attorney, Agent, or Firm* — Wilson Sonsini Goodrich & Rosati

(57) ABSTRACT

Multispecific molecules that include i) a tumor-targeting moiety; and one, two or all of: (ii) an immune cell engager (e.g., chosen from an NK cell engager, a T cell engager, a B cell engager, a dendritic cell engager, or a macrophage cell engager); (iii) a cytokine molecule; and/or (iv) a stromal modifying moiety are disclosed. Additionally disclosed are nucleic acids encoding the same, methods of producing the aforesaid molecules, and methods of treating a cancer using the aforesaid molecules.

22 Claims, 110 Drawing Sheets

Specification includes a Sequence Listing.

(56) References Cited

U.S. PATENT DOCUMENTS

| | | | |
|---|---|---|---|
| 2009/0324538 A1* | 12/2009 | Wong | A61K 38/2086 |
| | | | 424/85.2 |
| 2010/0260704 A1* | 10/2010 | Berenguer | A61P 13/12 |
| | | | 424/85.2 |
| 2010/0316645 A1 | 12/2010 | Imhof-Jung et al. | |
| 2011/0293613 A1 | 12/2011 | Brinkmann et al. | |
| 2012/0201746 A1 | 8/2012 | Liu et al. | |
| 2013/0017200 A1 | 1/2013 | Scheer et al. | |
| 2013/0022601 A1 | 1/2013 | Brinkmann et al. | |
| 2013/0078249 A1 | 3/2013 | Ast et al. | |
| 2013/0165638 A1 | 6/2013 | Hsu et al. | |
| 2013/0243775 A1 | 9/2013 | Papadopoulos et al. | |
| 2013/0266568 A1 | 10/2013 | Brinkmann et al. | |
| 2013/0267686 A1 | 10/2013 | Brinkmann et al. | |
| 2013/0303396 A1 | 11/2013 | Igawa et al. | |
| 2014/0051833 A1 | 2/2014 | Fischer et al. | |
| 2014/0072581 A1 | 3/2014 | Dixit et al. | |
| 2014/0099254 A1* | 4/2014 | Chang | C07K 16/30 |
| | | | 424/1.11 |
| 2014/0308285 A1 | 10/2014 | Yan et al. | |
| 2014/0322221 A1 | 10/2014 | Miller et al. | |
| 2014/0377269 A1 | 12/2014 | Mabry et al. | |
| 2015/0017187 A1 | 1/2015 | Thanos et al. | |
| 2015/0018529 A1 | 1/2015 | Humphreys et al. | |
| 2015/0133638 A1 | 5/2015 | Wranik et al. | |
| 2015/0166670 A1 | 6/2015 | Castoldi et al. | |
| 2015/0203591 A1 | 7/2015 | Yancopoulos et al. | |
| 2015/0232560 A1 | 8/2015 | Heindl et al. | |
| 2015/0315296 A1 | 11/2015 | Schaefer et al. | |
| 2016/0075785 A1 | 3/2016 | Ast et al. | |
| 2016/0102135 A1 | 4/2016 | Escobar-Cabrera | |
| 2016/0114057 A1 | 4/2016 | Dixit et al. | |
| 2016/0130347 A1 | 5/2016 | Bruenker et al. | |
| 2016/0145340 A1 | 5/2016 | Borges et al. | |

FOREIGN PATENT DOCUMENTS

| | | | | |
|---|---|---|---|---|
| WO | 9945110 A1 | 9/1999 | | |
| WO | 2000/34784 A1 | 6/2000 | | |
| WO | 0060070 A1 | 10/2000 | | |
| WO | 2001/64942 A1 | 9/2001 | | |
| WO | WO-02070647 A2 * | 9/2002 | | C07K 14/415 |
| WO | 2004056392 A1 | 7/2004 | | |
| WO | 2015127158 A1 | 8/2015 | | |
| WO | WO-2015164815 A1 * | 10/2015 | | A61P 17/06 |
| WO | 2015/197582 A1 | 12/2015 | | |
| WO | 2015/197593 A1 | 12/2015 | | |
| WO | 2015197598 A2 | 12/2015 | | |
| WO | 2016016299 A1 | 2/2016 | | |
| WO | 2016087416 A1 | 6/2016 | | |
| WO | 2016087650 A1 | 6/2016 | | |
| WO | 2016115274 A1 | 7/2016 | | |
| WO | WO-2017062604 A1 * | 4/2017 | | C07K 16/1045 |
| WO | 2017165464 A1 | 9/2017 | | |

OTHER PUBLICATIONS

Akiyama et al, BBRC, 2004, vol. 316, pp. 528-532 (Year: 2004).*
Stauber et al, Cancer Research, 2007, vol. 67, pp. 5999-6002 (Year: 2007).*
Chang et al, Journal of Clinical Investigation, 2017, vol. 127, pp. 2705-2718 (Year: 2017).*
Leutkens et al, CII, 2014, vol. 63, pp. 1151-1162 (Year: 2014).*
Funayama et al, Journal of Cell Biology, 1995, vol. 128, pp. 959-968 (Year: 1995).*
Chen et al, Journal of Biological Chemistry, 1996, vol. 271, pp. 32863-32868) (Year: 1996).*
Jiang et al, Histopathology, ePub Dec. 31, 2013, 9 pages (Year: 2013).*
Wang et al, Cancer Letters, 2008, vol. 269, pp. 127-138 (Year: 2008).*
Lain et al, Experimental Cell Research, 1999, vol. 253, pp. 315-324 (Year: 1999).*
Wurzer et al, J of Cellular Biochemistry, 2001, vol. 36, supplement, pp. 1-11 (Year: 2001).*
Gjerstorff et al, PLOS one, 2012, vol. 7, p. e45819 (Year: 2012).*
Wang et al, Science, 1999, vol. 284, pp. 1351-1354 (Year: 1999).*
Falini et al, NEJM, 2005, vol. 352, pp. 254-266 (Year: 2005).*
Gao et al, JBC, 2005, vol. 280, pp. 36254-36262 (Year: 2005).*
Abstract of Gokden et al, Appl Immunohistochem Mol Morphol, 2003, vol. 11, pp. 116-119) (Year: 2003).*
Morel et al, Immunology, 2000, vol. 12, pp. 107-117 (Year: 2000).*
Chen et al, Human Reproduction, 2011, vol. 26, pp. 3232-3243 (Year: 2011).*
Novellino et al, CII, 2005, vol. 54, pp. 187-207 (Year: 2005).*
Trenevska et al, Frontiers in Immunology, 2017, vol. 8, 12 pgs (Year: 2017).*
Liddy et al (Nature Medicine, 2012, vol. 18, pp. 980-987) (Year: 2012).*
Koch et al (Trends in Immunology, 2013, vol. 34, pp. 182-191) (Year: 2013).*
Swencki-Underwood (Cytokine, 2006, vol. 34, pp. 114-124) (Year: 2006).*
International Search Report and Written Opinion issued in PCT/US2017/023483, dated Aug. 29, 2017.
Miller, Jeffrey S., et al. "Trispecific Killer Engagers (TriKEs) that contain IL-15 to make NK cells antigen specific and to sustain their persistence and expansion." (2015): 232-232.
Aigner, Maximilian, et al. "An effective tumor vaccine optimized for costimulation via bispecific and trispecific fusion proteins." International journal of oncology 32.4 (2008): 777-789.
Nandi, Dipankar, Jane A. Gross, and James P. Allison. "CD28-mediated costimulation is necessary for optimal proliferation of murine NK cells." The Journal of Immunology 152.7 (1994): 3361-3369.
Cruz, Jay Soriano Dela, et al. "Anti-HER2/neu IgG3-(IL-2) and anti-HER2/neu IgG3-(GM-CSF) promote HER2/neu processing and presentation by dendritic cells: Implications in immunotherapy and vaccination strategies." Molecular immunology 43.6 (2006): 667-676.
Nagarajan, Shanmugam, et al. "Ligand binding and phagocytosis by CD16 (FC ? receptor III) isoforms phagocytic signaling by associated ? and ? subunits in Chinese hamster ovary cells." Journal of Biological Chemistry 270.43 (1995): 25762-25770.
Ortiz-Sánchez, Elizabeth, et al. "Antibody-cytokine fusion proteins: applications in cancer therapy." Expert opinion on biological therapy 8.5 (2008): 609-632.
Modak, Shakeel, William Gerald, and Nai-Kong V. Cheung. "Disialoganglioside GD2 and a novel tumor antigen: potential targets for immunotherapy of desmoplastic small round cell tumor." Pediatric Blood & Cancer 39.6 (2002): 547-551.
Newman, Robert G., Eckhard R. Podack, and Robert B. Levy. "Combining Early Heat Shock Protein Vaccination with Directed IL-2 Leads to Effective Anti-Tumor Immunity in Autologous Hematopoietic Cell Transplantation Recipients." (2011): 998-998.
Rohena-Rivera, Krizia, et al. "IL-15 regulates migration, invasion, angiogenesis and genes associated with lipid metabolism and inflammation in prostate cancer." PloS one 12.4 (2017): e0172786.
Schliemann, Christoph, et al. "Targeting interleukin-2 to the bone marrow stroma for therapy of acute myeloid leukemia relapsing after allogeneic hematopoietic stem cell transplantation." Cancer immunology research 3.5 (2015): 547-556.
Mao, Huawei, et al. "Inhibition of human natural killer cell activity by influenza virions and hemagglutinin." Journal of virology 84.9 (2010): 4148-4157.
Ali, S. A., R. C. Rees, and J. Oxford. "Modulation of human natural killer cytotoxicity by influenza virus and its subunit protein." Immunology 52.4 (1984): 687.
Kellner, Christian, et al. "Enhancing natural killer cell-mediated lysis of lymphoma cells by combining therapeutic antibodies with CD20-specific immunoligands engaging NKG2D or NKp30." Oncoimmunology 5.1 (2016): e1058459.
Arenas-Ramirez et al., "Interleukin-2: Biology, Design and Application," Trends in Immunology (2015) vol. 36, No. 12, pp. 763-777.
Arnon et al., "Recognition of viral hemagglutinins by NKp44 but not by NKp30," Eur J Immunol (2001) vol. 31, pp. 2680-2689.

(56) References Cited

OTHER PUBLICATIONS

Coloma et al., "Design and production of novel tetravalent bispecific antibodies," Nat Biotechnol (1997) vol. 15, No. 2, pp. 159-163.
Farrar et al., "The Molecular Cell Biology of Interferon-gamma and Its Receptor," Annu Rev Immunol (1993) vol. 11, pp. 571-611.
Garrity et al., "The activating NKG2D receptor assembles in the membrane with two signaling dimers into a hexameric structure," PNAS (2005) vol. 102, No. 21, pp. 7641-7646.
Hamming et al., "Crystal Structure of Interleukin-21 Receptor (IL-21R) Bound to IL-21 Reveals That Sugar Chain Interacting with WSXWS Motif Is Integral Part of IL-21R," The Journal of Biological Chemistry (2012) vol. 287, No. 12, pp. 9454-9460.
Hudspeth et al., "Natural cytotoxicity receptors: broader expression patterns and functions in innate and adaptive immune cells," Frontiers in Immunology (2013) vol. 4, Article 69, 15 pages.
Ju et al., "Structure-Function Amalysis of Human Interleukin-2," The Journal of Biological Chemistry (1987) vol. 262, No. 12, pp. 5723-5731.
Kato et al., "The structure and binding mode of interleukin-18," Nature Structural Biology (2003) vol. 10, No. 11, pp. 966-971.
Leong et al., "Optimized expression and specific activity of IL-12 by directed molecular evolution," PNAS (2003) vol. 100, No. 3, pp. 1163-1168.
Mandelboim et al., "Recognition of haemagglutinins on virus-infected cells by NKp46 activates lysis by human NK cells," Nature (2001) vol. 409, No. 6823, pp. 1055-1060.
Martin et al., "The affinity-selection of a minibody polypeptide inhibitor of human interleukin-6," The EMBO Journal (1994) vol. 13, No. 22, pp. 5303-5309.
McConnell et al., "Tendamistat as a Scaffold for Conformationally Constrained Phage Peptide Libraries," J Mol Biol (1995) vol. 250, No. 4, pp. 460-470.
McElroy et al., "Structural and Biophysical Studies of the Human IL-7/IL-7R alpha Complex," Structure (2009) vol. 17, pp. 54-65.
Park et al., "Complex regulation of human NKG2D-DAP10 cll surface expression: opposing roles of the gamma-c cytokines and TGF-Beta1," Blood (2011) vol. 118, No. 11, pp. 3019-3027.
Pettit et al., "Structure-Function Studies of Interleukin 15 using Site-specific Mutagenesis, Polyethylene Glycol Conjugation, and Homology Modeling," Journal of Biological Chemistry (1997) vol. 272, No. 4, pp. 2312-2318.
Seidel et al., "Natural Killer cell mediated antibody-dependent cellular cytotoxicity in tumor immunotherapy with therapeutic antibodies," Frontiers in Immunology (2013) vol. 4, Article 76, 8 pages.
Spiess et al., "Alternative molecular formats and therapeutic applications for bispecific antibodies," Molecular Immunology (2015) vol. 67, pp. 95-106.
Tramontano et al., "The Making of the Minibody: an Engineered Beta-Protein for the Dsplay of Conformationaly Constrained Peptides," J Mol Recognit (1994) vol. 7, No. 1, pp. 9-24.
Weidle et al., "The Intriguing Options of Multispecific Antibody Formats for Treatment of Cancer," Cancer Genomics & Proteomics (2013) vol. 10, pp. 1-18.
Yoon et al., "Charged residues dominate a unique interlocking topography in the heterodimeric cytokine interleukin-12," The EMBO Journal (2000) vol. 19, No. 14, pp. 3530-3541.
Ring et al., "Mechanistic and structural insight into the functional dichotomy between interleukin-2 and interleukin-15," Nat Immunol (2012) vol. 13, No. 12, pp. 1187-1195.

\* cited by examiner

A  Trispecific Fab based construct

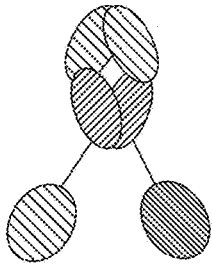

B  >human-Fab heavy chain_mesoSS1_IL15
*MEFGLSWVFLVALFRGVQC*QVQLQQSGRELEKPGASVKISCKASGYSFTGYTMNWVKQSHGKSLEWIGLIT
PYNGASSYNQKFRGKATLTVDKSSSTAYMDLLSLTSEDSAVYFCARGGYDGRGFDYWGQGTTVTVSS**ASTK
GPSVFPLAPSSKSTSGGTAALGCLVKDYFPEPVTVSWNSGALTSGVHTFPAVLQSSGLYSLSSVVTVPSSSL
GTQTYICNVNHKPSNTKVDKRVEPKSCDKTHT**<u>GGGGSGGGGSGGGGS</u>NWVNVISDLKKIEDLIQSMHIDA
TLYTESDVHPSCKVTAMKCALLELQVISLESGDASIHDTVENLIILANNSLSSNGNVTESGCKECEELEEKNIKEF
LQSFVHIVQMFINTS**

C  >human kappa light mesoSS1xCD40L
*MKYLLPTAAAGLLLLAAQPAMA*
<u>DIELTQSPAIMSASPGEKVTMTCSASSSVSYMHWYQQKSGTSPKRWIYDTSKLASGVPGRFSGSGSGNSYSL
TISSVEAEDDATYYCQQWSGYPLTFGAGTKLEIK</u>
**RTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC**
DVPSGPGGGGSGGGGSMQKGDQNPQIAAHVISEASSKTTSVLQWAEKGYYTMSNNLVTLENGKQLTVK
RQGLYYIYAQVTFCSNREASSQAPFIASLCLKSPGRFERILLRAANTHSSAKPCGQQSIHLGGVFELQPGASVFV
NVTDPSQVSHGTGFTSFGLLKL**

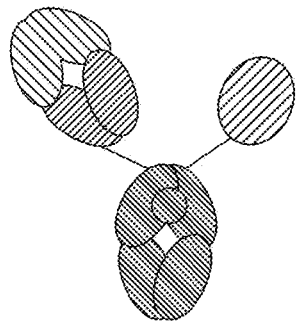

Bi-specific knob-in-hole construct example

B >il15-knob-cyc-hFc
*MEFGLSWVFLVALFRGVQC*NWVNVISDLKKIEDLIQSMHIDATLYTESDVHPSCKVTAMKCFLLELQVISLES
GDASIHDTVENLIILANNSLSSNGNVTESGCKECEELEEKNIKEFLQSFVHIVQMFINTSGGGGSDKTHTCPPC
PAPELLGGPSVFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPCREEMTKNQVSLWCLVKGFY
PSDIAVEWESNGQPENNYKTTPPVLDSDGSFFLYSKLTVDKSRWQQGNVFSCSVMHEALHNHYTQKSLSLS
PGK**

C >KiH-CHIg-hole-cys_FAP (Sibrotuzumab)
*MEFGLSWVFLVALFRGVQCEV* QVQLVQSGAEVKKPGASVKVSCKTSRYTFTEYTIHWVRQAPGQRLEWIG
GINPNNGIPNYNQKFKGRVTITVDTSASTAYMELSSLRSEDTAVYYCARRRIAYGYDEGHAMDYWGQGTLV
TVSS
**ASTKGPSVFPLAPSSKSTSGGTAALGCLVKDYFPEPVTVSWNSGALTSGVHTFPAVLQSSGLYSLSSVVTVP
SSSLGTQTYICNVNHKPSNTKVDKRVEPKSC**DKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKALPAPIE
KTISKAKGQPREPQVCTLPPSREEMTKNQVSLSCAVKGFYPSDIAVEWESNGQPENNYKTTPPVLDSDGSFFL
VSKLTVDKSRWQQGNVFSCSVMHEALHNHYTQKSLSLSPGK*

D >human kappa light FAP (Sibrotuzumab)
*MKYLLPTAAAGLLLLAAQPAMA*
DIVMTQSPDSLAVSLGERATINCKSSQSLLYSRNQKNYLAWYQQKPGQPPKLLIFWASTRESGVPDRFSGSG
FGTSFTLTISSLQAEDVAVYYCQQYFSYPLTFGQGTKVEIK
**RTVAAPSVFIFPPSDEQLKSGTASVVCLLNNFYPREAKVQWKVDNALQSGNSQESVTEQDSKDSTYSLSST
LTLSKADYEKHKVYACEVTHQGLSSPVTKSFNRGEC***

FIG. 12A-12D

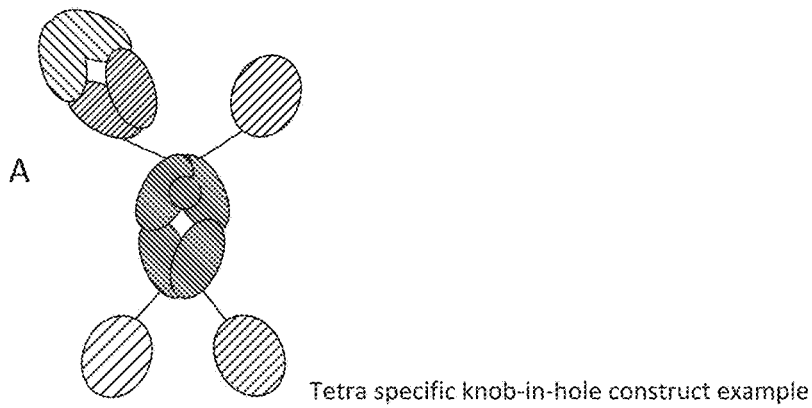

Tetra specific knob-in-hole construct example

B >il15-knob-cys-hFc-CD40L
*MEFGLSWVFLVALFRGVQC*<u>NWVNVISDLKKIEDLIQSMHIDATLYTESDVHPSCKVTAMKCFLLELQVISLESGDASIHD
TVENLIILANNSLSSNGNVTESGCKECEELEEKNIKEFLQSFVHIVQMFINTS</u>
<u>GGGGS</u>
**DKTHTCPPCPAPELLGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPCREEMTKNQVSLWCLVKGFY
PSDIAVEWESNGQPENNYKTTPPVLDSDGSFFLYSKLTVDKSRWQQGNVFSCSVMHEALHNHYTQKSLSLSPGK**
<u>GGGGS</u>
<u>MQKGDQNPQIAAHVISEASSKTTSVLQWAEKGYYTMSNNLVTLENGKQLTVKRQGLYYIYAQVTFCSNREASSQAPFI
ASLCLKSPGRFERILLRAANTHSSAKPCGQQSIHLGGVFELQPGASVFVNVTDPSQVSHGTGFTSFGLLKL**</u>

C >KiH-CHIg-hole-cys_FAP (Sibrotuzumab)
*MEFGLSWVFLVALFRGVQCEV*<u>QVQLVQSGAEVKKPGASVKVSCKTSRYTFTEYTIHWVRQAPGQRLEWIGGINPNNG
IPNYNQKFKGRVTITVDTSASTAYMELSSLRSEDTAVYYCARRRIAYGYDEGHAMDYWGQGTLVTVSS</u>
**ASTKGPSVFPLAPSSKSTSGGTAALGCLVKDYFPEPVTVSWNSGALTSGVHTFPAVLQSSGLYSLSSVVTVPSSSLGTQ
TYICNVNHKPSNTKVDKRVEPKSC**DKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPREPQVCTLPP
SREEMTKNQVSLSCAVKGFYPSDIAVEWESNGQPENNYKTTPPVLDSDGSFFLVSKLTVDKSRWQQGNVFSCSVMHE
ALHNHYTQKSLSLSPGK<u>GGGGS</u>
<u>DLKVEMMAGGTQITPLNDNVTIFCNIFYSQPLNITSMGITWFWKSLTFDKEVKVFEFFGD
HQEAFRPGAIVSPWRLKSGDASLRLPGIQLEEAGEYRCEVVVTPLKAQGTVQLEVVASPA
SRLLLDQVGMKENEDKYMCESSGFYPEAINITWEKQTQKFPHPIEISEDVITGPTIKNMD
GTFNVTSCLKLNSSQEDPGTVYQCVVRHASLHTPLRSNFTLTAARHSLSETEKTDNFS</u>

D >human kappa light FAP (Sibrotuzumab)
*MKYLLPTAAAGLLLLAAQPAMA*
<u>DIVMTQSPDSLAVSLGERATINCKSSQSLLYSRNQKNYLAWYQQKPGQPPKLLIFWASTRESGVPDRFSGSGFGTDFTL
TISSLQAEDVAVYYCQQYFSYPLTFGQGTKVEIK</u>
RTVAAPSVFIFPPSDEQLKSGTASVVCLLNNFYPREAKVQWKVDNALQSGNSQESVTEQDSKDSTYSLSSTLTLSKADYE
KHKVYACEVTHQGLSSPVTKSFNRGEC*

FIG. 13A-13D

Protein Name: a_hMeso_SS1_Fab-hIL21hKiH_Fc_Cys-h41BBL-hCD40L

Molecule Details

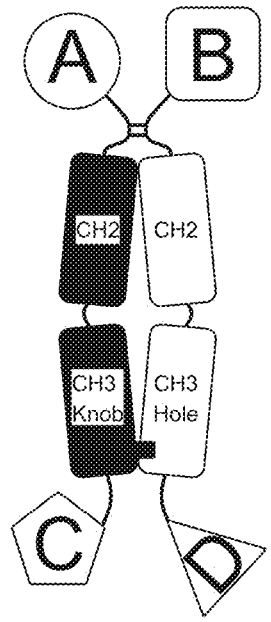

Molecule A: a_hMeso_SS1_Fab
QVQLQQSGPELEKPGASVKISCKASGYSFTGYTMNWVKQSHGKSLEWIGL
ITPYNGASSYNQKFRGKATLTVDKSSSTAYMDLLSLTSEDSAVYFCARGG
YDGRGFDYWGQGTTVTVSS DIELTQSPAIMSASPGEKVTMTCSASSSVSYMHWYQQKSGTSPKRWIYDT
SKLASGVPGRFSGSGSGNSYSLTISSVEAEDDATYYCQQWSGYPLTFGAG
TKLEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC

Molecule B: hIL21
QGQDRHMIRMRQLIDIVDQLKNYVNDLVPEFLPAPEDVETNCEWSAFSCF
QKAQLKSANTGNNERIINVSIKKLKRKPPSTNAGRRQKHRLTCPSCDSYE
KKPPKEFLERFKSLLQKMIHQHLSSRTHGSEDS

Molecule B to KiH_Fc linker: GGGGSGGGGS

KiH_Fc to Molecule C linker: GGGSGGGGSGGGGS

FIG. 14A

Molecule C: h41BBL
ACPWAVSGARASPGSAASPRLREGPELSPDDPAGLLDLRQGMFAQLVAQN
VLLIDGPLSWYSDPGLAGVSLTGGLSYKEDTKELVVAKAGVYYVFFQLEL
RRVVAGEGSGSVSLALHLQPLRSAAGAAALALTVDLPPASSEARNSAFGF
QGRLLHLSAGQRLGVHLHTEARARHAWQLTQGATVLGLFRVTPEIPAGLP
SPRSE

KiH Fc to Molecule D linker: GGGGSGGGGSGGGGS

Molecule D: hCD40L
HRRLDKIEDERNLHEDFVFMKTIQRCNTGERSLSLLNCEEIKSQFEGFVK
DIMLNKEETKKENSFEMQKGDQNPQIAAHVISEASSKTTSVLQWAEKGYY
TMSNNLVTLENGKQLTVKRQGLYYIYAQVTFCSNREASSQAPFIASLCLK
SPGRFERILLRAANTHSSAKPCGQQSIHLGGVFELQPGASVFVNVTDPSQ
VSHGTGFTSFGLLKL

KiH Knob

KiH Hole

FIG. 14B

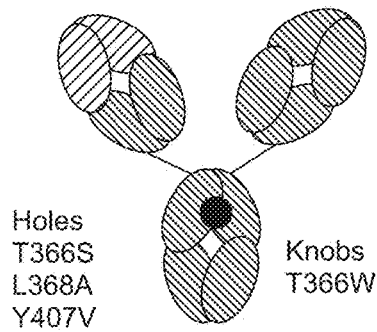
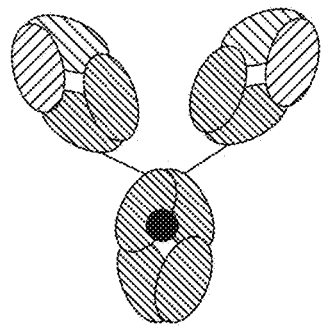
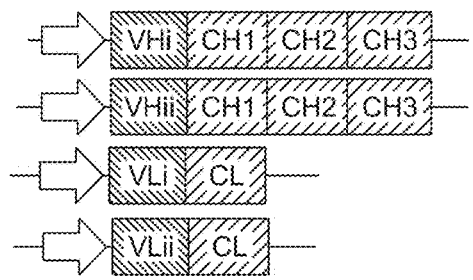
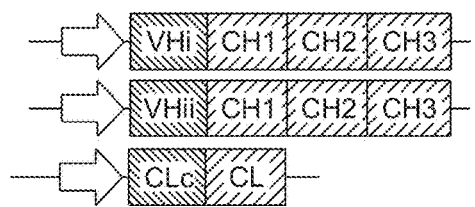
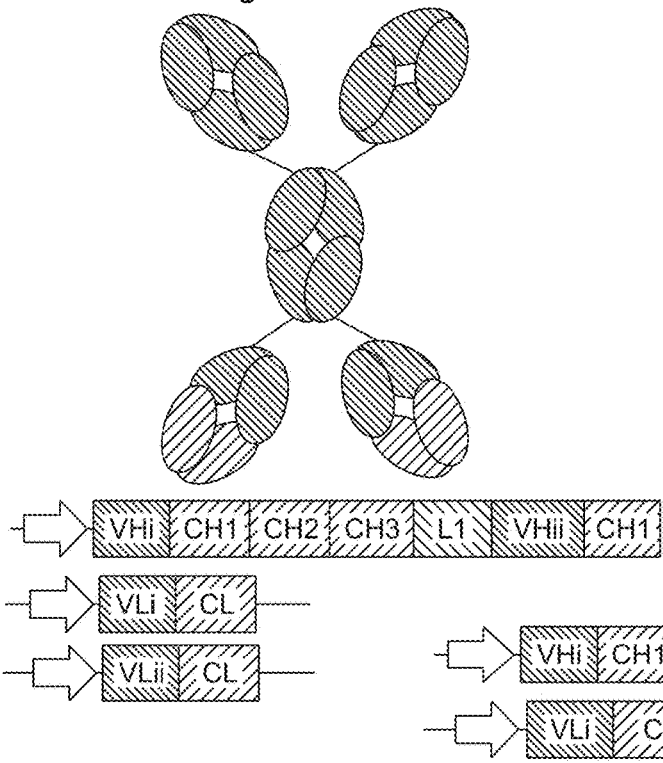
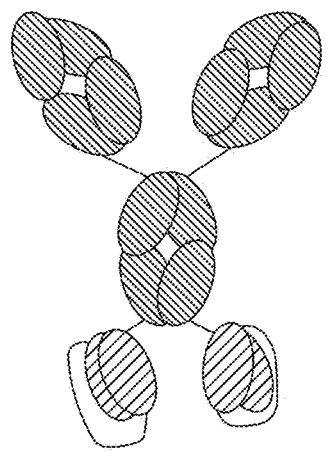
FIG. 15A-15D

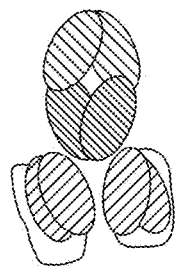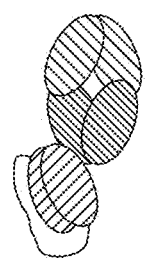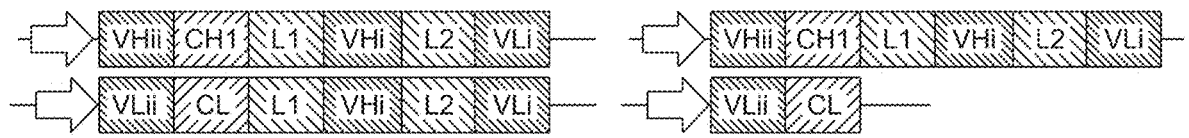
FIG. 15I-15J

SEQUENCE LISTING

```
<160> NUMBER OF SEQ ID NOS: 242

<210> SEQ ID NO 1
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Gln Gly
            100                 105                 110

Thr Thr Val Thr Val Ser Ser
```

```
                115

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Ser Phe Thr Gly Tyr Thr Met Asn
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Ile Thr Pro Tyr Asn Gly Ala Ser Ser Tyr Asn Gln Lys Phe Arg
1               5                   10                  15

Gly

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Tyr Asp Gly Arg Gly Phe Asp Tyr
1               5                   10

<210> SEQ ID NO 5
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr
            100                 105
```

```
<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Met Glu Phe Gly Leu Ser Trp Val Phe Leu Val Ala Leu Phe Arg Gly
1               5                   10                  15

Val Gln Cys

<210> SEQ ID NO 7
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Gly Arg Phe Ser Gly Ser
        50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Gly Tyr Pro Leu Thr
                85                  90                  95

Phe Gly Ala Gly Thr Lys Leu Glu Ile Lys
            100                 105

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Ala Ser Ser Ser Val Ser Tyr Met His
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Thr Ser Lys Leu Ala Ser
1               5

<210> SEQ ID NO 10
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 10

Gln Gln Trp Ser Gly Tyr Pro Leu Thr
1               5

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 13
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Thr Ser Arg Tyr Thr Phe Thr Glu Tyr
            20                  25                  30

Thr Ile His Trp Val Arg Gln Ala Pro Gly Gln Arg Leu Glu Trp Ile
        35                  40                  45
```

Gly Gly Ile Asn Pro Asn Asn Gly Ile Pro Asn Tyr Asn Gln Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ile Ala Tyr Gly Tyr Asp Glu Gly His Ala Met Asp
            100                 105                 110

Tyr Trp Gly Gln Gly Thr Leu Val Thr Val Ser Ser
            115                 120

<210> SEQ ID NO 14
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys
            100

<210> SEQ ID NO 15
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Met Glu Phe Gly Leu Ser Trp Val Phe Leu Val Ala Leu Phe Arg Gly
1               5                   10                  15

Val Gln Cys Glu Val
            20

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Glu Thr Asp Thr Leu Leu Leu Trp Val Leu Leu Leu Trp Val Pro
1               5                   10                  15

Gly Ser Thr Gly

<210> SEQ ID NO 17
<211> LENGTH: 114
<212> TYPE: PRT
<213> ORGANISM: Homo sapiens

<400> SEQUENCE: 17

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 18
<211> LENGTH: 77
<212> TYPE: PRT
<213> ORGANISM: Homo sapiens

<400> SEQUENCE: 18

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
50                  55                  60

Arg Lys Ala Gly Thr Ser Ser Leu Thr Glu Cys Val Leu
65                  70                  75
```

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Ser Gly Gly Ser Gly Gly Gly Gly Ser Gly Gly Ser Gly Gly Gly Gly
1               5                   10                  15

Gly Ser Leu Gln
            20
```

<210> SEQ ID NO 20
<211> LENGTH: 133
<212> TYPE: PRT
<213> ORGANISM: Homo sapiens

```
<400> SEQUENCE: 20

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 21
<211> LENGTH: 157
<212> TYPE: PRT
<213> ORGANISM: Homo sapiens

<400> SEQUENCE: 21

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 22
<211> LENGTH: 133
<212> TYPE: PRT
<213> ORGANISM: Homo sapiens

<400> SEQUENCE: 22

Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
```

```
                20                  25                  30
Pro Ala Pro Glu Asp Val Glu Thr Asn Cys Glu Trp Ser Ala Phe Ser
            35                  40                  45

Cys Phe Gln Lys Ala Gln Leu Lys Ser Ala Asn Thr Gly Asn Asn Glu
        50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
        130

<210> SEQ ID NO 23
<211> LENGTH: 138
<212> TYPE: PRT
<213> ORGANISM: Homo sapiens

<400> SEQUENCE: 23

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
                20                  25                  30

Leu Lys Asn Trp Lys Glu Glu Ser Asp Arg Lys Ile Met Gln Ser Gln
            35                  40                  45

Ile Val Ser Phe Tyr Phe Lys Leu Phe Lys Asn Phe Lys Asp Asp Gln
        50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly
        130                 135

<210> SEQ ID NO 24
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Leu Lys Val Glu Met Met Ala Gly Gly Thr Gln Ile Thr Pro Leu
1               5                   10                  15

Asn Asp Asn Val Thr Ile Phe Cys Asn Ile Phe Tyr Ser Gln Pro Leu
                20                  25                  30

Asn Ile Thr Ser Met Gly Ile Thr Trp Phe Trp Lys Ser Leu Thr Phe
            35                  40                  45

Asp Lys Glu Val Lys Val Phe Glu Phe Phe Gly Asp His Gln Glu Ala
```

```
                    50                  55                  60
Phe Arg Pro Gly Ala Ile Val Ser Pro Trp Arg Leu Lys Ser Gly Asp
 65                  70                  75                  80

Ala Ser Leu Arg Leu Pro Gly Ile Gln Leu Glu Ala Gly Glu Tyr
                 85                  90                  95

Arg Cys Glu Val Val Thr Pro Leu Lys Ala Gln Gly Thr Val Gln
                100                 105                 110

Leu Glu Val Val Ala Ser Pro Ala Ser Arg Leu Leu Asp Gln Val
                115                 120                 125

Gly Met Lys Glu Asn Glu Asp Lys Tyr Met Cys Glu Ser Ser Gly Phe
    130                 135                 140

Tyr Pro Glu Ala Ile Asn Ile Thr Trp Glu Lys Gln Thr Gln Lys Phe
145                 150                 155                 160

Pro His Pro Ile Glu Ile Ser Glu Asp Val Ile Thr Gly Pro Thr Ile
                165                 170                 175

Lys Asn Met Asp Gly Thr Phe Asn Val Thr Ser Cys Leu Lys Leu Asn
                180                 185                 190

Ser Ser Gln Glu Asp Pro Gly Thr Val Tyr Gln Cys Val Val Arg His
                195                 200                 205

Ala Ser Leu His Thr Pro Leu Arg Ser Asn Phe Thr Leu Thr Ala Ala
    210                 215                 220

Arg His Ser Leu Ser Glu Thr Glu Lys Thr Asp Asn Phe Ser
225                 230                 235

<210> SEQ ID NO 25
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Pro His Ser Leu Arg Tyr Asn Leu Thr Val Leu Ser Trp Asp Gly
  1               5                  10                  15

Ser Val Gln Ser Gly Phe Leu Thr Glu Val His Leu Asp Gly Gln Pro
                 20                  25                  30

Phe Leu Arg Cys Asp Arg Gln Lys Cys Arg Ala Lys Pro Gln Gly Gln
             35                  40                  45

Trp Ala Glu Asp Val Leu Gly Asn Lys Thr Trp Asp Arg Glu Thr Arg
 50                  55                  60

Asp Leu Thr Gly Asn Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                 85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Lys Glu Trp Thr
            115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175
```

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
        210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
                260                 265                 270

Pro Ser Gly Lys Val Leu Val Leu Gln Ser His Trp
        275                 280

<210> SEQ ID NO 26
<211> LENGTH: 287
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Glu Pro His Ser Leu Arg Tyr Asn Leu Met Val Leu Ser Gln Asp
1               5                   10                  15

Glu Ser Val Gln Ser Gly Phe Leu Ala Glu Gly His Leu Asp Gly Gln
            20                  25                  30

Pro Phe Leu Arg Tyr Asp Arg Gln Lys Arg Arg Ala Lys Pro Gln Gly
        35                  40                  45

Gln Trp Ala Glu Asp Val Leu Gly Ala Lys Thr Trp Asp Thr Glu Thr
    50                  55                  60

Glu Asp Leu Thr Glu Asn Gly Gln Asp Leu Arg Arg Thr Leu Thr His
65                  70                  75                  80

Ile Lys Asp Gln Lys Gly Gly Leu His Ser Leu Gln Glu Ile Arg Val
                85                  90                  95

Cys Glu Ile His Glu Asp Ser Ser Thr Arg Gly Ser Arg His Phe Tyr
            100                 105                 110

Tyr Asp Gly Glu Leu Phe Leu Ser Gln Asn Leu Glu Thr Gln Glu Ser
        115                 120                 125

Thr Val Pro Gln Ser Ser Arg Ala Gln Thr Leu Ala Met Asn Val Thr
    130                 135                 140

Asn Phe Trp Lys Glu Asp Ala Met Lys Thr Lys Thr His Tyr Arg Ala
145                 150                 155                 160

Met Gln Ala Asp Cys Leu Gln Lys Leu Gln Arg Tyr Leu Lys Ser Gly
                165                 170                 175

Val Ala Ile Arg Arg Thr Val Pro Pro Met Val Asn Val Thr Cys Ser
            180                 185                 190

Glu Val Ser Glu Gly Asn Ile Thr Val Thr Cys Arg Ala Ser Ser Phe
        195                 200                 205

Tyr Pro Arg Asn Ile Thr Leu Thr Trp Arg Gln Asp Gly Val Ser Leu
        210                 215                 220

Ser His Asn Thr Gln Gln Trp Gly Asp Val Leu Pro Asp Gly Asn Gly
225                 230                 235                 240

Thr Tyr Gln Thr Trp Val Ala Thr Arg Ile Arg Gln Gly Glu Glu Gln
                245                 250                 255

```
Arg Phe Thr Cys Tyr Met Glu His Ser Gly Asn His Gly Thr His Pro
                260                 265                 270

Val Pro Ser Gly Lys Val Leu Val Leu Gln Ser Gln Arg Thr Asp
            275                 280                 285

<210> SEQ ID NO 27
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Trp Val Asp Thr His Cys Leu Cys Tyr Asp Phe Ile Ile Thr Pro
1               5                   10                  15

Lys Ser Arg Pro Glu Pro Gln Trp Cys Glu Val Gln Gly Leu Val Asp
            20                  25                  30

Glu Arg Pro Phe Leu His Tyr Asp Cys Val Asn His Lys Ala Lys Ala
        35                  40                  45

Phe Ala Ser Leu Gly Lys Lys Val Asn Val Thr Lys Thr Trp Glu Glu
    50                  55                  60

Gln Thr Glu Thr Leu Arg Asp Val Val Asp Phe Leu Lys Gly Gln Leu
65                  70                  75                  80

Leu Asp Ile Gln Val Glu Asn Leu Ile Pro Ile Glu Pro Leu Thr Leu
                85                  90                  95

Gln Ala Arg Met Ser Cys Glu His Glu Ala His Gly His Gly Arg Gly
            100                 105                 110

Ser Trp Gln Phe Leu Phe Asn Gly Gln Lys Phe Leu Leu Phe Asp Ser
        115                 120                 125

Asn Asn Arg Lys Trp Thr Ala Leu His Pro Gly Ala Lys Lys Met Thr
130                 135                 140

Glu Lys Trp Glu Lys Asn Arg Asp Val Thr Met Phe Phe Gln Lys Ile
145                 150                 155                 160

Ser Leu Gly Asp Cys Lys Met Trp Leu Glu Glu Phe Leu Met Tyr Trp
                165                 170                 175

Glu Gln Met Leu Asp Pro Thr Lys Pro Pro Ser Leu Ala Pro Gly
            180                 185                 190

<210> SEQ ID NO 28
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Asp Val Arg Val Gln Val Leu Pro Glu Val Arg Gly Gln Leu Gly
1               5                   10                  15

Gly Thr Val Glu Leu Pro Cys His Leu Leu Pro Pro Val Pro Gly Leu
            20                  25                  30

Tyr Ile Ser Leu Val Thr Trp Gln Arg Pro Asp Ala Pro Ala Asn His
        35                  40                  45

Gln Asn Val Ala Ala Phe His Pro Lys Met Gly Pro Ser Phe Pro Ser
    50                  55                  60

Pro Lys Pro Gly Ser Glu Arg Leu Ser Phe Val Ser Ala Lys Gln Ser
65                  70                  75                  80
```

Thr Gly Gln Asp Thr Glu Ala Glu Leu Gln Asp Ala Thr Leu Ala Leu
                85                  90                  95

His Gly Leu Thr Val Glu Asp Glu Gly Asn Tyr Thr Cys Glu Phe Ala
            100                 105                 110

Thr Phe Pro Lys Gly Ser Val Arg Gly Met Thr Trp Leu Arg Val Ile
        115                 120                 125

Ala Lys Pro Lys Asn Gln Ala Glu Ala Gln Lys Val Thr Phe Ser Gln
    130                 135                 140

Asp Pro Thr Thr Val Ala Leu Cys Ile Ser Lys Glu Gly Arg Pro Pro
145                 150                 155                 160

Ala Arg Ile Ser Trp Leu Ser Ser Leu Asp Trp Glu Ala Lys Glu Thr
                165                 170                 175

Gln Val Ser Gly Thr Leu Ala Gly Thr Val Thr Val Thr Ser Arg Phe
            180                 185                 190

Thr Leu Val Pro Ser Gly Arg Ala Asp Gly Val Thr Val Thr Cys Lys
        195                 200                 205

Val Glu His Glu Ser Phe Glu Glu Pro Ala Leu Ile Pro Val Thr Leu
    210                 215                 220

Ser Val Arg Tyr Pro Pro Glu Val Ser Ile Ser Gly Tyr Asp Asp Asn
225                 230                 235                 240

Trp Tyr Leu Gly Arg Thr Asp Ala Thr Leu Ser Cys Asp Val Arg Ser
                245                 250                 255

Asn Pro Glu Pro Thr Gly Tyr Asp Trp Ser Thr Thr Ser Gly Thr Phe
            260                 265                 270

Pro Thr Ser Ala Val Ala Gln Gly Ser Gln Leu Val Ile His Ala Val
        275                 280                 285

Asp Ser Leu Phe Asn Thr Thr Phe Val Cys Thr Val Thr Asn Ala Val
    290                 295                 300

Gly Met Gly Arg Ala Glu Gln Val Ile Phe Val Arg Glu Thr Pro Asn
305                 310                 315                 320

Thr Ala Gly Ala Gly Ala Thr Gly Gly
                325

<210> SEQ ID NO 29
<211> LENGTH: 323
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Trp Pro Pro Pro Gly Thr Gly Asp Val Val Gln Ala Pro Thr Gln
1               5                   10                  15

Val Pro Gly Phe Leu Gly Asp Ser Val Thr Leu Pro Cys Tyr Leu Gln
            20                  25                  30

Val Pro Asn Met Glu Val Thr His Val Ser Gln Leu Thr Trp Ala Arg
        35                  40                  45

His Gly Glu Ser Gly Ser Met Ala Val Phe His Gln Thr Gln Gly Pro
    50                  55                  60

Ser Tyr Ser Glu Ser Lys Arg Leu Glu Phe Val Ala Ala Arg Leu Gly
65                  70                  75                  80

Ala Glu Leu Arg Asn Ala Ser Leu Arg Met Phe Gly Leu Arg Val Glu
                85                  90                  95

Asp Glu Gly Asn Tyr Thr Cys Leu Phe Val Thr Phe Pro Gln Gly Ser 100                 105                 110
Arg Ser Val Asp Ile Trp Leu Arg Val Leu Ala Lys Pro Gln Asn Thr
                115                 120                 125

Ala Glu Val Gln Lys Val Gln Leu Thr Gly Glu Pro Val Pro Met Ala
            130                 135                 140

Arg Cys Val Ser Thr Gly Gly Arg Pro Pro Ala Gln Ile Thr Trp His
145                 150                 155                 160

Ser Asp Leu Gly Gly Met Pro Asn Thr Ser Gln Val Pro Gly Phe Leu
                165                 170                 175

Ser Gly Thr Val Thr Val Thr Ser Leu Trp Ile Leu Val Pro Ser Ser
            180                 185                 190

Gln Val Asp Gly Lys Asn Val Thr Cys Lys Val Glu His Glu Ser Phe
        195                 200                 205

Glu Lys Pro Gln Leu Leu Thr Val Asn Leu Thr Val Tyr Tyr Pro Pro
    210                 215                 220

Glu Val Ser Ile Ser Gly Tyr Asp Asn Asn Trp Tyr Leu Gly Gln Asn
225                 230                 235                 240

Glu Ala Thr Leu Thr Cys Asp Ala Arg Ser Asn Pro Glu Pro Thr Gly
                245                 250                 255

Tyr Asn Trp Ser Thr Thr Met Gly Pro Leu Pro Pro Phe Ala Val Ala
            260                 265                 270

Gln Gly Ala Gln Leu Leu Ile Arg Pro Val Asp Lys Pro Ile Asn Thr
        275                 280                 285

Thr Leu Ile Cys Asn Val Thr Asn Ala Leu Gly Ala Arg Gln Ala Glu
    290                 295                 300

Leu Thr Val Gln Val Lys Glu Gly Pro Pro Ser Glu His Ser Gly Ile
305                 310                 315                 320

Ser Arg Asn

<210> SEQ ID NO 30
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Asn Leu Phe Thr Lys Asp Val Thr Val Ile Glu Gly Glu Val Ala
1               5                   10                  15

Thr Ile Ser Cys Gln Val Asn Lys Ser Asp Asp Ser Val Ile Gln Leu
            20                  25                  30

Leu Asn Pro Asn Arg Gln Thr Ile Tyr Phe Arg Asp Phe Arg Pro Leu
        35                  40                  45

Lys Asp Ser Arg Phe Gln Leu Leu Asn Phe Ser Ser Ser Glu Leu Lys
    50                  55                  60

Val Ser Leu Thr Asn Val Ser Ile Ser Asp Glu Gly Arg Tyr Phe Cys
65                  70                  75                  80

Gln Leu Tyr Thr Asp Pro Pro Gln Glu Ser Tyr Thr Thr Ile Thr Val
                85                  90                  95

Leu Val Pro Pro Arg Asn Leu Met Ile Asp Ile Gln Lys Asp Thr Ala
            100                 105                 110

Val Glu Gly Glu Glu Ile Glu Val Asn Cys Thr Ala Met Ala Ser Lys
        115                 120                 125

Pro Ala Thr Thr Ile Arg Trp Phe Lys Gly Asn Thr Glu Leu Lys Gly

```
            130                 135                 140
Lys Ser Glu Val Glu Trp Ser Asp Met Tyr Thr Val Thr Ser Gln
145                 150                 155                 160

Leu Met Leu Lys Val His Lys Glu Asp Gly Val Pro Val Ile Cys
                165                 170                 175

Gln Val Glu His Pro Ala Val Thr Gly Asn Leu Gln Thr Gln Arg Tyr
            180                 185                 190

Leu Glu Val Gln Tyr Lys Pro Gln Val His Ile Gln Met Thr Tyr Pro
        195                 200                 205

Leu Gln Gly Leu Thr Arg Glu Gly Asp Ala Leu Glu Leu Thr Cys Glu
        210                 215                 220

Ala Ile Gly Lys Pro Gln Pro Val Met Val Thr Trp Val Arg Val Asp
225                 230                 235                 240

Asp Glu Met Pro Gln His Ala Val Leu Ser Gly Pro Asn Leu Phe Ile
                245                 250                 255

Asn Asn Leu Asn Lys Thr Asp Asn Gly Thr Tyr Arg Cys Glu Ala Ser
                260                 265                 270

Asn Ile Val Gly Lys Ala His Ser Asp Tyr Met Leu Tyr Val Tyr Asp
            275                 280                 285

Pro Pro Thr Thr Ile Pro Pro Pro Thr Thr Thr Thr Thr Thr Thr Thr
        290                 295                 300

Thr Thr Thr Thr Thr Ile Leu Thr Ile Ile Thr Asp Ser Arg Ala Gly
305                 310                 315                 320

Glu Glu Gly Ser Ile Arg Ala Val Asp His
                325                 330

<210> SEQ ID NO 31
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Arg Phe Ala Gln Ala Gln Gln Leu Pro Leu Glu Ser Leu Gly
1               5                   10                  15

Trp Asp Val Ala Glu Leu Gln Leu Asn His Thr Gly Pro Gln Gln Asp
                20                  25                  30

Pro Arg Leu Tyr Trp Gln Gly Gly Pro Ala Leu Gly Arg Ser Phe Leu
            35                  40                  45

His Gly Pro Glu Leu Asp Lys Gly Gln Leu Arg Ile His Arg Asp Gly
        50                  55                  60

Ile Tyr Met Val His Ile Gln Val Thr Leu Ala Ile Cys Ser Ser Thr
65                  70                  75                  80

Thr Ala Ser Arg His His Pro Thr Thr Leu Ala Val Gly Ile Cys Ser
                85                  90                  95

Pro Ala Ser Arg Ser Ile Ser Leu Leu Arg Leu Ser Phe His Gln Gly
            100                 105                 110

Cys Thr Ile Ala Ser Gln Arg Leu Thr Pro Leu Ala Arg Gly Asp Thr
        115                 120                 125

Leu Cys Thr Asn Leu Thr Gly Thr Leu Leu Pro Ser Arg Asn Thr Asp
    130                 135                 140

Glu Thr Phe Phe Gly Val Gln Trp Val Arg Pro
145                 150                 155
```

```
<210> SEQ ID NO 32
<211> LENGTH: 294
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Trp Thr Tyr His Tyr Ser Glu Lys Pro Met Asn Trp Gln Arg Ala Arg
1               5                  10                  15

Arg Phe Cys Arg Asp Asn Tyr Thr Asp Leu Val Ala Ile Gln Asn Lys
                20                  25                  30

Ala Glu Ile Glu Tyr Leu Glu Lys Thr Leu Pro Phe Ser Arg Ser Tyr
            35                  40                  45

Tyr Trp Ile Gly Ile Arg Lys Ile Gly Gly Ile Trp Thr Trp Val Gly
    50                  55                  60

Thr Asn Lys Ser Leu Thr Glu Glu Ala Glu Asn Trp Gly Asp Gly Glu
65                  70                  75                  80

Pro Asn Asn Lys Lys Asn Lys Glu Asp Cys Val Glu Ile Tyr Ile Lys
                85                  90                  95

Arg Asn Lys Asp Ala Gly Lys Trp Asn Asp Asp Ala Cys His Lys Leu
                100                 105                 110

Lys Ala Ala Leu Cys Tyr Thr Ala Ser Cys Gln Pro Trp Ser Cys Ser
            115                 120                 125

Gly His Gly Glu Cys Val Glu Ile Ile Asn Asn Tyr Thr Cys Asn Cys
    130                 135                 140

Asp Val Gly Tyr Tyr Gly Pro Gln Cys Gln Phe Val Ile Gln Cys Glu
145                 150                 155                 160

Pro Leu Glu Ala Pro Glu Leu Gly Thr Met Asp Cys Thr His Pro Leu
                165                 170                 175

Gly Asn Phe Ser Phe Ser Ser Gln Cys Ala Phe Ser Cys Ser Glu Gly
                180                 185                 190

Thr Asn Leu Thr Gly Ile Glu Glu Thr Thr Cys Gly Pro Phe Gly Asn
            195                 200                 205

Trp Ser Ser Pro Glu Pro Thr Cys Gln Val Ile Gln Cys Glu Pro Leu
    210                 215                 220

Ser Ala Pro Asp Leu Gly Ile Met Asn Cys Ser His Pro Leu Ala Ser
225                 230                 235                 240

Phe Ser Phe Thr Ser Ala Cys Thr Phe Ile Cys Ser Glu Gly Thr Glu
                245                 250                 255

Leu Ile Gly Lys Lys Lys Thr Ile Cys Glu Ser Ser Gly Ile Trp Ser
                260                 265                 270

Asn Pro Ser Pro Ile Cys Gln Lys Leu Asp Lys Ser Phe Ser Met Ile
            275                 280                 285

Lys Glu Gly Asp Tyr Asn
    290

<210> SEQ ID NO 33
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33
```

```
Arg Tyr Leu Gln Val Ser Gln Gln Leu Gln Thr Asn Arg Val Leu
1               5                   10                  15

Glu Val Thr Asn Ser Ser Leu Arg Gln Gln Leu Arg Leu Lys Ile Thr
            20                  25                  30

Gln Leu Gly Gln Ser Ala Glu Asp Leu Gln Gly Ser Arg Arg Glu Leu
            35                  40                  45

Ala Gln Ser Gln Glu Ala Leu Gln Val Glu Gln Arg Ala His Gln Ala
50                  55                  60

Ala Glu Gly Gln Leu Gln Ala Cys Gln Ala Asp Arg Gln Lys Thr Lys
65                  70                  75                  80

Glu Thr Leu Gln Ser Glu Gln Gln Arg Arg Ala Leu Glu Gln Lys
                85                  90                  95

Leu Ser Asn Met Glu Asn Arg Leu Lys Pro Phe Phe Thr Cys Gly Ser
                100                 105                 110

Ala Asp Thr Cys Cys Pro Ser Gly Trp Ile Met His Gln Lys Ser Cys
                115                 120                 125

Phe Tyr Ile Ser Leu Thr Ser Lys Asn Trp Gln Glu Ser Gln Lys Gln
        130                 135                 140

Cys Glu Thr Leu Ser Ser Lys Leu Ala Thr Phe Ser Glu Ile Tyr Pro
145                 150                 155                 160

Gln Ser His Ser Tyr Tyr Phe Leu Asn Ser Leu Leu Pro Asn Gly Gly
                165                 170                 175

Ser Gly Asn Ser Tyr Trp Thr Gly Leu Ser Ser Asn Lys Asp Trp Lys
            180                 185                 190

Leu Thr Asp Asp Thr Gln Arg Thr Arg Thr Tyr Ala Gln Ser Ser Lys
                195                 200                 205

Cys Asn Lys Val His Lys Thr Trp Ser Trp Trp Thr Leu Glu Ser Glu
210                 215                 220

Ser Cys Arg Ser Ser Leu Pro Tyr Ile Cys Glu Met Thr Ala Phe Arg
225                 230                 235                 240

Phe Pro Asp

<210> SEQ ID NO 34
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Lys Leu Thr Arg Asp Ser Gln Ser Leu Cys Pro Tyr Asp Trp Ile Gly
1               5                   10                  15

Phe Gln Asn Lys Cys Tyr Tyr Phe Ser Lys Glu Glu Gly Asp Trp Asn
            20                  25                  30

Ser Ser Lys Tyr Asn Cys Ser Thr Gln His Ala Asp Leu Thr Ile Ile
            35                  40                  45

Asp Asn Ile Glu Glu Met Asn Phe Leu Arg Arg Tyr Lys Cys Ser Ser
        50                  55                  60

Asp His Trp Ile Gly Leu Lys Met Ala Lys Asn Arg Thr Gly Gln Trp
65                  70                  75                  80

Val Asp Gly Ala Thr Phe Thr Lys Ser Phe Gly Met Arg Gly Ser Glu
                85                  90                  95

Gly Cys Ala Tyr Leu Ser Asp Asp Gly Ala Ala Thr Ala Arg Cys Tyr
                100                 105                 110
```

Thr Glu Arg Lys Trp Ile Cys Arg Lys Arg Ile His
            115                 120

<210> SEQ ID NO 35
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Gly His Leu Val His Met Thr Val Val Ser Gly Ser Asn Val Thr
1               5                   10                  15

Leu Asn Ile Ser Glu Ser Leu Pro Glu Asn Tyr Lys Gln Leu Thr Trp
            20                  25                  30

Phe Tyr Thr Phe Asp Gln Lys Ile Val Glu Trp Asp Ser Arg Lys Ser
        35                  40                  45

Lys Tyr Phe Glu Ser Lys Phe Lys Gly Arg Val Arg Leu Asp Pro Gln
    50                  55                  60

Ser Gly Ala Leu Tyr Ile Ser Lys Val Gln Lys Glu Asp Asn Ser Thr
65                  70                  75                  80

Tyr Ile Met Arg Val Leu Lys Lys Thr Gly Asn Glu Gln Glu Trp Lys
                85                  90                  95

Ile Lys Leu Gln Val Leu Asp Pro Val Pro Lys Pro Val Ile Lys Ile
            100                 105                 110

Glu Lys Ile Glu Asp Met Asp Asp Asn Cys Tyr Leu Lys Leu Ser Cys
        115                 120                 125

Val Ile Pro Gly Glu Ser Val Asn Tyr Thr Trp Tyr Gly Asp Lys Arg
    130                 135                 140

Pro Phe Pro Lys Glu Leu Gln Asn Ser Val Leu Glu Thr Thr Leu Met
145                 150                 155                 160

Pro His Asn Tyr Ser Arg Cys Tyr Thr Cys Gln Val Ser Asn Ser Val
                165                 170                 175

Ser Ser Lys Asn Gly Thr Val Cys Leu Ser Pro Pro Cys Thr Leu Ala
            180                 185                 190

Arg Ser

<210> SEQ ID NO 36
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys

```
                    85                  90                  95
Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130

<210> SEQ ID NO 37
<211> LENGTH: 149
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
            20                  25                  30

Tyr Tyr Thr Met Ser Asn Asn Leu Val Thr Leu Glu Asn Gly Lys Gln
        35                  40                  45

Leu Thr Val Lys Arg Gln Gly Leu Tyr Tyr Ile Tyr Ala Gln Val Thr
50                  55                  60

Phe Cys Ser Asn Arg Glu Ala Ser Ser Gln Ala Pro Phe Ile Ala Ser
65                  70                  75                  80

Leu Cys Leu Lys Ser Pro Gly Arg Phe Glu Arg Ile Leu Leu Arg Ala
                85                  90                  95

Ala Asn Thr His Ser Ser Ala Lys Pro Cys Gly Gln Gln Ser Ile His
            100                 105                 110

Leu Gly Gly Val Phe Glu Leu Gln Pro Gly Ala Ser Val Phe Val Asn
        115                 120                 125

Val Thr Asp Pro Ser Gln Val Ser His Gly Thr Gly Phe Thr Ser Phe
130                 135                 140

Gly Leu Leu Lys Leu
145

<210> SEQ ID NO 38
<211> LENGTH: 205
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30

Ala Gly Leu Leu Asp Leu Arg Gln Gly Met Phe Ala Gln Leu Val Ala
        35                  40                  45

Gln Asn Val Leu Leu Ile Asp Gly Pro Leu Ser Trp Tyr Ser Asp Pro
50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
```

```
                85                  90                  95
Gln Leu Glu Leu Arg Arg Val Ala Gly Glu Gly Ser Gly Ser Val
            100                 105                 110

Ser Leu Ala Leu His Leu Gln Pro Leu Arg Ser Ala Ala Gly Ala Ala
            115                 120                 125

Ala Leu Ala Leu Thr Val Asp Leu Pro Pro Ala Ser Ser Glu Ala Arg
        130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
            180                 185                 190

Pro Glu Ile Pro Ala Gly Leu Pro Ser Pro Arg Ser Glu
        195                 200                 205

<210> SEQ ID NO 39
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240
```

```
Leu Tyr Val Arg Asn Arg Val Arg Glu Ala Ile Arg Val Ser Lys Ile
            245                 250                 255

Pro Asp Ala Lys Ser Pro Leu Pro Val Phe Ala Tyr Thr Arg Ile Val
        260                 265                 270

Phe Thr Asp Gln Val Leu Lys Phe Leu Ser Gln Asp Glu Leu Val Tyr
    275                 280                 285

Thr Phe Gly Glu Thr Val Ala Leu Gly Ala Ser Gly Ile Val Ile Trp
290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455

<210> SEQ ID NO 40
<211> LENGTH: 77
<212> TYPE: PRT
<213> ORGANISM: Homo sapiens

<400> SEQUENCE: 40

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu
65                  70                  75

<210> SEQ ID NO 41
<211> LENGTH: 157
<212> TYPE: PRT
<213> ORGANISM: Homo sapiens

<400> SEQUENCE: 41

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30
```

```
Met Thr Asp Ser Asp Cys Arg Asp Asn Ala Pro Arg Thr Ile Phe Ile
         35                  40                  45

Ile Ser Met Tyr Lys Asp Ser Gln Pro Arg Gly Met Ala Val Thr Ile
 50                  55                  60

Ser Val Lys Cys Glu Lys Ile Ser Thr Leu Ser Cys Glu Asn Lys Ile
 65                  70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
            115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155
```

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Gly Gly Gly Gly Ser
1               5
```

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Gly Gly Gly Gly Ser Gly Gly Gly Gly Ser
1               5                   10
```

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Gly Gly Gly Gly Ser Gly Gly Gly Ser Gly Gly Gly Gly Ser
1               5                   10                  15
```

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Asp Val Pro Ser Gly Pro Gly Gly Gly Gly Ser Gly Gly Gly Gly
1               5                   10                  15
```

Ser

<210> SEQ ID NO 46
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Gly Gly Gly Gly Ser Gly Gly Gly Gly Ser Gly Gly Gly
225                 230                 235                 240

Gly Ser Asn Trp Val Asn Val Ile Ser Asp Leu Lys Lys Ile Glu Asp
                245                 250                 255

Leu Ile Gln Ser Met His Ile Asp Ala Thr Leu Tyr Thr Glu Ser Asp
            260                 265                 270

Val His Pro Ser Cys Lys Val Thr Ala Met Lys Cys Phe Leu Leu Glu
        275                 280                 285

Leu Gln Val Ile Ser Leu Glu Ser Gly Asp Ala Ser Ile His Asp Thr
    290                 295                 300

Val Glu Asn Leu Ile Ile Leu Ala Asn Asn Ser Leu Ser Ser Asn Gly
305                 310                 315                 320

Asn Val Thr Glu Ser Gly Cys Lys Glu Cys Glu Glu Leu Glu Glu Lys
                325                 330                 335

Asn Ile Lys Glu Phe Leu Gln Ser Phe Val His Ile Val Gln Met Phe
            340                 345                 350
```

Ile Asn Thr Ser
        355

<210> SEQ ID NO 47
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Gly Tyr Pro Leu Thr
                85                  90                  95

Phe Gly Ala Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Asp Val Pro Ser Gly Pro Gly Gly Gly Gly
    210                 215                 220

Ser Gly Gly Gly Gly Ser Met Gln Lys Gly Asp Gln Asn Pro Gln Ile
225                 230                 235                 240

Ala Ala His Val Ile Ser Glu Ala Ser Ser Lys Thr Thr Ser Val Leu
                245                 250                 255

Gln Trp Ala Glu Lys Gly Tyr Tyr Thr Met Ser Asn Asn Leu Val Thr
            260                 265                 270

Leu Glu Asn Gly Lys Gln Leu Thr Val Lys Arg Gln Gly Leu Tyr Tyr
        275                 280                 285

Ile Tyr Ala Gln Val Thr Phe Cys Ser Asn Arg Glu Ala Ser Ser Gln
    290                 295                 300

Ala Pro Phe Ile Ala Ser Leu Cys Leu Lys Ser Pro Gly Arg Phe Glu
305                 310                 315                 320

Arg Ile Leu Leu Arg Ala Ala Asn Thr His Ser Ser Ala Lys Pro Cys
                325                 330                 335

Gly Gln Gln Ser Ile His Leu Gly Gly Val Phe Glu Leu Gln Pro Gly

-continued

```
                    340                 345                 350
Ala Ser Val Phe Val Asn Val Thr Asp Pro Ser Gln Val Ser His Gly
                355                 360                 365

Thr Gly Phe Thr Ser Phe Gly Leu Leu Lys Leu
        370                 375

<210> SEQ ID NO 48
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Thr Ser Arg Tyr Thr Phe Thr Glu Tyr
            20                  25                  30

Thr Ile His Trp Val Arg Gln Ala Pro Gly Gln Arg Leu Glu Trp Ile
        35                  40                  45

Gly Gly Ile Asn Pro Asn Asn Gly Ile Pro Asn Tyr Asn Gln Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ile Ala Tyr Gly Tyr Asp Glu Gly His Ala Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320
```

```
Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Cys Thr Leu Pro Pro Ser Arg Glu Glu Met Thr Lys Asn
        355                 360                 365

Gln Val Ser Leu Ser Cys Ala Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 49
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Arg Asn Gln Lys Asn Tyr Leu Ala Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Phe Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Tyr Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 50
<211> LENGTH: 346
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Ser Asp Lys Thr His Thr Cys Pro Pro Cys
        115                 120                 125

Pro Ala Pro Glu Leu Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Cys Arg Glu Glu
                245                 250                 255

Met Thr Lys Asn Gln Val Ser Leu Trp Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345
```

```
<210> SEQ ID NO 51
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Gly Gly Gly Ser Asp Lys Thr His Thr Cys Pro Pro Cys
        115                 120                 125

Pro Ala Pro Glu Leu Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
            180                 185                 190

Glu Gln Tyr Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Cys Arg Glu Glu
                245                 250                 255

Met Thr Lys Asn Gln Val Ser Leu Trp Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
    290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys Gly Gly Gly Gly Ser Met
            340                 345                 350

Gln Lys Gly Asp Gln Asn Pro Gln Ile Ala Ala His Val Ile Ser Glu
        355                 360                 365
```

```
Ala Ser Ser Lys Thr Thr Ser Val Leu Gln Trp Ala Glu Lys Gly Tyr
    370                 375                 380

Tyr Thr Met Ser Asn Asn Leu Val Thr Leu Glu Asn Gly Lys Gln Leu
385                 390                 395                 400

Thr Val Lys Arg Gln Gly Leu Tyr Tyr Ile Tyr Ala Gln Val Thr Phe
                405                 410                 415

Cys Ser Asn Arg Glu Ala Ser Ser Gln Ala Pro Phe Ile Ala Ser Leu
                420                 425                 430

Cys Leu Lys Ser Pro Gly Arg Phe Glu Arg Ile Leu Leu Arg Ala Ala
            435                 440                 445

Asn Thr His Ser Ala Lys Pro Cys Gly Gln Gln Ser Ile His Leu
450                 455                 460

Gly Gly Val Phe Glu Leu Gln Pro Gly Ala Ser Val Phe Val Asn Val
465                 470                 475                 480

Thr Asp Pro Ser Gln Val Ser His Gly Thr Gly Phe Thr Ser Phe Gly
                485                 490                 495

Leu Leu Lys Leu
            500

<210> SEQ ID NO 52
<211> LENGTH: 697
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Thr Ser Arg Tyr Thr Phe Thr Glu Tyr
                20                  25                  30

Thr Ile His Trp Val Arg Gln Ala Pro Gly Gln Arg Leu Glu Trp Ile
            35                  40                  45

Gly Gly Ile Asn Pro Asn Asn Gly Ile Pro Asn Tyr Asn Gln Lys Phe
        50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ile Ala Tyr Gly Tyr Asp Glu Gly His Ala Met Asp
                100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
210                 215                 220
```

```
Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
        340                 345                 350

Pro Gln Val Cys Thr Leu Pro Pro Ser Arg Glu Glu Met Thr Lys Asn
    355                 360                 365

Gln Val Ser Leu Ser Cys Ala Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
            405                 410                 415

Leu Thr Val Asp Lys Ser Arg Trp Gln Gln Gly Asn Val Phe Ser Cys
        420                 425                 430

Ser Val Met His Glu Ala Leu His Asn His Tyr Thr Gln Lys Ser Leu
    435                 440                 445

Ser Leu Ser Pro Gly Lys Gly Gly Gly Ser Asp Leu Lys Val Glu
450                 455                 460

Met Met Ala Gly Gly Thr Gln Ile Thr Pro Leu Asn Asp Asn Val Thr
465                 470                 475                 480

Ile Phe Cys Asn Ile Phe Tyr Ser Gln Pro Leu Asn Ile Thr Ser Met
            485                 490                 495

Gly Ile Thr Trp Phe Trp Lys Ser Leu Thr Phe Asp Lys Glu Val Lys
        500                 505                 510

Val Phe Glu Phe Phe Gly Asp His Gln Glu Ala Phe Arg Pro Gly Ala
    515                 520                 525

Ile Val Ser Pro Trp Arg Leu Lys Ser Gly Asp Ala Ser Leu Arg Leu
530                 535                 540

Pro Gly Ile Gln Leu Glu Glu Ala Gly Glu Tyr Arg Cys Glu Val Val
545                 550                 555                 560

Val Thr Pro Leu Lys Ala Gln Gly Thr Val Gln Leu Glu Val Val Ala
            565                 570                 575

Ser Pro Ala Ser Arg Leu Leu Leu Asp Gln Val Gly Met Lys Glu Asn
        580                 585                 590

Glu Asp Lys Tyr Met Cys Glu Ser Ser Gly Phe Tyr Pro Glu Ala Ile
    595                 600                 605

Asn Ile Thr Trp Glu Lys Gln Thr Gln Lys Phe Pro His Pro Ile Glu
610                 615                 620

Ile Ser Glu Asp Val Ile Thr Gly Pro Thr Ile Lys Asn Met Asp Gly
625                 630                 635                 640
```

Thr Phe Asn Val Thr Ser Cys Leu Lys Leu Asn Ser Ser Gln Glu Asp
            645                 650                 655

Pro Gly Thr Val Tyr Gln Cys Val Val Arg His Ala Ser Leu His Thr
        660                 665                 670

Pro Leu Arg Ser Asn Phe Thr Leu Thr Ala Ala Arg His Ser Leu Ser
    675                 680                 685

Glu Thr Glu Lys Thr Asp Asn Phe Ser
690                 695

<210> SEQ ID NO 53
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Thr Ser Arg Tyr Thr Phe Thr Glu Tyr
            20                  25                  30

Thr Ile His Trp Val Arg Gln Ala Pro Gly Gln Arg Leu Glu Trp Ile
        35                  40                  45

Gly Gly Ile Asn Pro Asn Asn Gly Ile Pro Asn Tyr Asn Gln Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ile Ala Tyr Gly Tyr Asp Glu Gly His Ala Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

```
Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Cys Thr Leu Pro Pro Ser Arg Glu Glu Met Thr Lys Asn
            355                 360                 365

Gln Val Ser Leu Ser Cys Ala Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys Gly Gly Gly Ser
    450                 455

<210> SEQ ID NO 54
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Arg Asn Gln Lys Asn Tyr Leu Ala Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Phe Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Tyr Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
```

```
                195                 200                 205
Ser Pro Val Thr Lys Ser Phe Asn Arg Gly Glu Cys
    210                 215                 220

<210> SEQ ID NO 55
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Glu Phe Gly Leu Ser Trp Val Phe Leu Val Ala Leu Phe Arg Gly
1               5                   10                  15

Val Gln Cys Glu Val Gln Val Gln Leu Val Gln Ser Gly Ala Glu Val
            20                  25                  30

Lys Lys Pro Gly Ala Ser Val Lys Val Ser Cys Lys Thr Ser Arg Tyr
        35                  40                  45

Thr Phe Thr Glu Tyr Thr Ile His Trp Val Arg Gln Ala Pro Gly Gln
    50                  55                  60

Arg Leu Glu Trp Ile Gly Gly Ile Asn Pro Asn Asn Gly Ile Pro Asn
65                  70                  75                  80

Tyr Asn Gln Lys Phe Lys Gly Arg Val Thr Ile Thr Val Asp Thr Ser
                85                  90                  95

Ala Ser Thr Ala Tyr Met Glu Leu Ser Ser Leu Arg Ser Glu Asp Thr
            100                 105                 110

Ala Val Tyr Tyr Cys Ala Arg Arg Ile Ala Tyr Gly Tyr Asp Glu
        115                 120                 125

Gly His Ala Met Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335
```

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Cys Thr Leu Pro Pro Ser Arg Glu
        370                 375                 380

Glu Met Thr Lys Asn Gln Val Ser Leu Ser Cys Ala Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Val Ser Lys Leu Thr Val Asp Lys Ser Arg Trp Gln Gln Gly
            435                 440                 445

Asn Val Phe Ser Cys Ser Val Met His Glu Ala Leu His Asn His Tyr
        450                 455                 460

Thr Gln Lys Ser Leu Ser Leu Ser Pro Gly Lys
465                 470                 475

<210> SEQ ID NO 56
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Gly Tyr Pro Leu Thr
                85                  90                  95

Phe Gly Ala Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Asp Val Pro Ser Gly Pro Gly Gly Gly Gly Gly
    210                 215                 220

-continued

```
Ser Gly Gly Gly Gly Ser Met Gln Lys Gly Asp Gln Asn Pro Gln Ile
225                 230                 235                 240

Ala Ala His Val Ile Ser Glu Ala Ser Ser Lys Thr Thr Ser Val Leu
            245                 250                 255

Gln Trp Ala Glu Lys Gly Tyr Tyr Thr Met Ser Asn Asn Leu Val Thr
        260                 265                 270

Leu Glu Asn Gly Lys Gln Leu Thr Val Lys Arg Gln Gly Leu Tyr Tyr
    275                 280                 285

Ile Tyr Ala Gln Val Thr Phe Cys Ser Asn Arg Glu Ala Ser Ser Gln
290                 295                 300

Ala Pro Phe Ile Ala Ser Leu Cys Leu Lys Ser Pro Gly Arg Phe Glu
305                 310                 315                 320

Arg Ile Leu Leu Arg Ala Ala Asn Thr His Ser Ser Ala Lys Pro Cys
            325                 330                 335

Gly Gln Gln Ser Ile His Leu Gly Gly Val Phe Glu Leu Gln Pro Gly
        340                 345                 350

Ala Ser Val Phe Val Asn Val Thr Asp Pro Ser Gln Val Ser His Gly
    355                 360                 365

Thr Gly Phe Thr Ser Phe Gly Leu Leu Lys Leu
    370                 375
```

<210> SEQ ID NO 57
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Arg Asn Gln Lys Asn Tyr Leu Ala Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Phe Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Tyr Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
```

195                 200                 205

Ser Pro Val Thr Lys Ser Phe Asn Arg Gly Glu Cys
    210                 215                 220

<210> SEQ ID NO 58
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Glu Phe Gly Leu Ser Trp Val Phe Leu Val Ala Leu Phe Arg Gly
1               5                   10                  15

Val Gln Cys Asn Trp Val Asn Val Ile Ser Asp Leu Lys Lys Ile Glu
            20                  25                  30

Asp Leu Ile Gln Ser Met His Ile Asp Ala Thr Leu Tyr Thr Glu Ser
        35                  40                  45

Asp Val His Pro Ser Cys Lys Val Thr Ala Met Lys Cys Phe Leu Leu
    50                  55                  60

Glu Leu Gln Val Ile Ser Leu Glu Ser Gly Asp Ala Ser Ile His Asp
65                  70                  75                  80

Thr Val Glu Asn Leu Ile Ile Leu Ala Asn Asn Ser Leu Ser Ser Asn
                85                  90                  95

Gly Asn Val Thr Glu Ser Gly Cys Lys Glu Cys Glu Glu Leu Glu Glu
            100                 105                 110

Lys Asn Ile Lys Glu Phe Leu Gln Ser Phe Val His Ile Val Gln Met
        115                 120                 125

Phe Ile Asn Thr Ser Gly Gly Gly Gly Ser Asp Lys Thr His Thr Cys
    130                 135                 140

Pro Pro Cys Pro Ala Pro Glu Leu Leu Gly Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190

Phe Asn Trp Tyr Val Asp Gly Val Glu Val His Asn Ala Lys Thr Lys
        195                 200                 205

Pro Arg Glu Glu Gln Tyr Asn Ser Thr Tyr Arg Val Val Ser Val Leu
    210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255

Ala Lys Gly Gln Pro Arg Glu Pro Gln Val Tyr Thr Leu Pro Pro Cys
            260                 265                 270

Arg Glu Glu Met Thr Lys Asn Gln Val Ser Leu Trp Cys Leu Val Lys
        275                 280                 285

Gly Phe Tyr Pro Ser Asp Ile Ala Val Glu Trp Glu Ser Asn Gly Gln
    290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

```
Gln Gly Asn Val Phe Ser Cys Ser Val Met His Glu Ala Leu His Asn
            340                 345                 350

His Tyr Thr Gln Lys Ser Leu Ser Leu Ser Pro Gly Lys Gly Gly Gly
        355                 360                 365

Gly Ser Met Gln Lys Gly Asp Gln Asn Pro Gln Ile Ala Ala His Val
    370                 375                 380

Ile Ser Glu Ala Ser Ser Lys Thr Thr Ser Val Leu Gln Trp Ala Glu
385                 390                 395                 400

Lys Gly Tyr Tyr Thr Met Ser Asn Asn Leu Val Thr Leu Glu Asn Gly
            405                 410                 415

Lys Gln Leu Thr Val Lys Arg Gln Gly Leu Tyr Tyr Ile Tyr Ala Gln
        420                 425                 430

Val Thr Phe Cys Ser Asn Arg Glu Ala Ser Ser Gln Ala Pro Phe Ile
    435                 440                 445

Ala Ser Leu Cys Leu Lys Ser Pro Gly Arg Phe Glu Arg Ile Leu Leu
450                 455                 460

Arg Ala Ala Asn Thr His Ser Ser Ala Lys Pro Cys Gly Gln Gln Ser
465                 470                 475                 480

Ile His Leu Gly Gly Val Phe Glu Leu Gln Pro Gly Ala Ser Val Phe
            485                 490                 495

Val Asn Val Thr Asp Pro Ser Gln Val Ser His Gly Thr Gly Phe Thr
        500                 505                 510

Ser Phe Gly Leu Leu Lys Leu
        515

<210> SEQ ID NO 59
<211> LENGTH: 718
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Glu Phe Gly Leu Ser Trp Val Phe Leu Val Ala Leu Phe Arg Gly
1               5                   10                  15

Val Gln Cys Glu Val Gln Val Gln Leu Val Gln Ser Gly Ala Glu Val
            20                  25                  30

Lys Lys Pro Gly Ala Ser Val Lys Val Ser Cys Lys Thr Ser Arg Tyr
        35                  40                  45

Thr Phe Thr Glu Tyr Thr Ile His Trp Val Arg Gln Ala Pro Gly Gln
    50                  55                  60

Arg Leu Glu Trp Ile Gly Gly Ile Asn Pro Asn Asn Gly Ile Pro Asn
65                  70                  75                  80

Tyr Asn Gln Lys Phe Lys Gly Arg Val Thr Ile Thr Val Asp Thr Ser
            85                  90                  95

Ala Ser Thr Ala Tyr Met Glu Leu Ser Ser Leu Arg Ser Glu Asp Thr
        100                 105                 110

Ala Val Tyr Tyr Cys Ala Arg Arg Ile Ala Tyr Gly Tyr Asp Glu
    115                 120                 125

Gly His Ala Met Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
            165                 170                 175
```

```
Tyr Phe Pro Glu Pro Val Thr Val Ser Trp Asn Ser Gly Ala Leu Thr
                180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
        210                 215                 220

Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
        290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Cys Thr Leu Pro Pro Ser Arg Glu
        370                 375                 380

Glu Met Thr Lys Asn Gln Val Ser Leu Ser Cys Ala Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Val Ser Lys Leu Thr Val Asp Lys Ser Arg Trp Gln Gln Gly
        435                 440                 445

Asn Val Phe Ser Cys Ser Val Met His Glu Ala Leu His Asn His Tyr
        450                 455                 460

Thr Gln Lys Ser Leu Ser Leu Ser Pro Gly Lys Gly Gly Gly Gly Ser
465                 470                 475                 480

Asp Leu Lys Val Glu Met Met Ala Gly Gly Thr Gln Ile Thr Pro Leu
                485                 490                 495

Asn Asp Asn Val Thr Ile Phe Cys Asn Ile Phe Tyr Ser Gln Pro Leu
            500                 505                 510

Asn Ile Thr Ser Met Gly Ile Thr Trp Phe Trp Lys Ser Leu Thr Phe
        515                 520                 525

Asp Lys Glu Val Lys Val Phe Glu Phe Phe Gly Asp His Gln Glu Ala
        530                 535                 540

Phe Arg Pro Gly Ala Ile Val Ser Pro Trp Arg Leu Lys Ser Gly Asp
545                 550                 555                 560

Ala Ser Leu Arg Leu Pro Gly Ile Gln Leu Glu Glu Ala Gly Glu Tyr
                565                 570                 575

Arg Cys Glu Val Val Val Thr Pro Leu Lys Ala Gln Gly Thr Val Gln
            580                 585                 590
```

```
Leu Glu Val Ala Ser Pro Ala Ser Arg Leu Leu Leu Asp Gln Val
            595                 600                 605

Gly Met Lys Glu Asn Glu Asp Lys Tyr Met Cys Glu Ser Ser Gly Phe
610                 615                 620

Tyr Pro Glu Ala Ile Asn Ile Thr Trp Glu Lys Gln Thr Gln Lys Phe
625                 630                 635                 640

Pro His Pro Ile Glu Ile Ser Glu Asp Val Ile Thr Gly Pro Thr Ile
                645                 650                 655

Lys Asn Met Asp Gly Thr Phe Asn Val Thr Ser Cys Leu Lys Leu Asn
            660                 665                 670

Ser Ser Gln Glu Asp Pro Gly Thr Val Tyr Gln Cys Val Val Arg His
        675                 680                 685

Ala Ser Leu His Thr Pro Leu Arg Ser Asn Phe Thr Leu Thr Ala Ala
    690                 695                 700

Arg His Ser Leu Ser Glu Thr Glu Lys Thr Asp Asn Phe Ser
705                 710                 715
```

<210> SEQ ID NO 60
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Met Lys Tyr Leu Leu Pro Thr Ala Ala Ala Gly Leu Leu Leu Leu Ala
1               5                   10                  15

Ala Gln Pro Ala Met Ala Asp Ile Val Met Thr Gln Ser Pro Asp Ser
            20                  25                  30

Leu Ala Val Ser Leu Gly Glu Arg Ala Thr Ile Asn Cys Lys Ser Ser
        35                  40                  45

Gln Ser Leu Leu Tyr Ser Arg Asn Gln Lys Asn Tyr Leu Ala Trp Tyr
    50                  55                  60

Gln Gln Lys Pro Gly Gln Pro Pro Lys Leu Leu Ile Phe Trp Ala Ser
65                  70                  75                  80

Thr Arg Glu Ser Gly Val Pro Asp Arg Phe Ser Gly Ser Gly Phe Gly
                85                  90                  95

Thr Asp Phe Thr Leu Thr Ile Ser Ser Leu Gln Ala Glu Asp Val Ala
            100                 105                 110

Val Tyr Tyr Cys Gln Gln Tyr Phe Ser Tyr Pro Leu Thr Phe Gly Gln
        115                 120                 125

Gly Thr Lys Val Glu Ile Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240
```

Glu Cys

```
<210> SEQ ID NO 61
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 61

| | | | | | | | | | | | | | | |
|---|---|---|---|---|---|---|---|---|---|---|---|---|---|---|
| Leu | Asn | Phe | Arg | Ala | Pro | Pro | Val | Ile | Pro | Asn | Val | Pro | Phe | Leu | Trp |
| 1 | | | | 5 | | | | | 10 | | | | | 15 | |
| Ala | Trp | Asn | Ala | Pro | Ser | Glu | Phe | Cys | Leu | Gly | Lys | Phe | Asp | Glu | Pro |
| | | | 20 | | | | | 25 | | | | | 30 | | |
| Leu | Asp | Met | Ser | Leu | Phe | Ser | Phe | Ile | Gly | Ser | Pro | Arg | Ile | Asn | Ala |
| | | | 35 | | | | | 40 | | | | | 45 | | |
| Thr | Gly | Gln | Gly | Val | Thr | Ile | Phe | Tyr | Val | Asp | Arg | Leu | Gly | Tyr | Tyr |
| | 50 | | | | | 55 | | | | | 60 | | | | |
| Pro | Tyr | Ile | Asp | Ser | Ile | Thr | Gly | Val | Thr | Val | Asn | Gly | Gly | Ile | Pro |
| 65 | | | | | 70 | | | | | 75 | | | | | 80 |
| Gln | Lys | Ile | Ser | Leu | Gln | Asp | His | Leu | Asp | Lys | Ala | Lys | Lys | Asp | Ile |
| | | | | 85 | | | | | 90 | | | | | 95 | |
| Thr | Phe | Tyr | Met | Pro | Val | Asp | Asn | Leu | Gly | Met | Ala | Val | Ile | Asp | Trp |
| | | | 100 | | | | | 105 | | | | | 110 | | |
| Glu | Glu | Trp | Arg | Pro | Thr | Trp | Ala | Arg | Asn | Trp | Lys | Pro | Lys | Asp | Val |
| | | | | 115 | | | | | 120 | | | | | 125 | |
| Tyr | Lys | Asn | Arg | Ser | Ile | Glu | Leu | Val | Gln | Gln | Asn | Val | Gln | Leu |
| | 130 | | | | | 135 | | | | | 140 | | | | |
| Ser | Leu | Thr | Glu | Ala | Thr | Glu | Lys | Ala | Lys | Gln | Glu | Phe | Glu | Lys | Ala |
| 145 | | | | | 150 | | | | | 155 | | | | | 160 |
| Gly | Lys | Asp | Phe | Leu | Val | Glu | Thr | Ile | Lys | Leu | Gly | Lys | Leu | Leu | Arg |
| | | | | 165 | | | | | 170 | | | | | 175 | |
| Pro | Asn | His | Leu | Trp | Gly | Tyr | Tyr | Leu | Phe | Pro | Asp | Cys | Tyr | Asn | His |
| | | | 180 | | | | | 185 | | | | | 190 | | |
| His | Tyr | Lys | Lys | Pro | Gly | Tyr | Asn | Gly | Ser | Cys | Phe | Asn | Val | Glu | Ile |
| | | | | 195 | | | | | 200 | | | | | 205 | |
| Lys | Arg | Asn | Asp | Asp | Leu | Ser | Trp | Leu | Trp | Asn | Glu | Ser | Thr | Ala | Leu |
| | 210 | | | | | 215 | | | | | 220 | | | | |
| Tyr | Pro | Ser | Ile | Tyr | Leu | Asn | Thr | Gln | Gln | Ser | Pro | Val | Ala | Ala | Thr |
| 225 | | | | | 230 | | | | | 235 | | | | | 240 |
| Leu | Tyr | Val | Arg | Asn | Arg | Val | Arg | Glu | Ala | Ile | Arg | Val | Ser | Lys | Ile |
| | | | | 245 | | | | | 250 | | | | | 255 | |
| Pro | Asp | Ala | Lys | Ser | Pro | Leu | Pro | Val | Phe | Ala | Tyr | Thr | Arg | Ile | Val |
| | | | 260 | | | | | 265 | | | | | 270 | | |
| Phe | Thr | Asp | Gln | Val | Leu | Lys | Phe | Leu | Ser | Gln | Asp | Glu | Leu | Val | Tyr |
| | | | | 275 | | | | | 280 | | | | | 285 | |
| Thr | Phe | Gly | Glu | Thr | Val | Ala | Leu | Gly | Ala | Ser | Gly | Ile | Val | Ile | Trp |
| | | | 290 | | | | | 295 | | | | | 300 | | |
| Gly | Thr | Leu | Ser | Ile | Met | Arg | Ser | Met | Lys | Ser | Cys | Leu | Leu | Leu | Asp |
| 305 | | | | | 310 | | | | | 315 | | | | | 320 |
| Asn | Tyr | Met | Glu | Thr | Ile | Leu | Asn | Pro | Tyr | Ile | Ile | Asn | Val | Thr | Leu |
| | | | | 325 | | | | | 330 | | | | | 335 | |
| Ala | Ala | Lys | Met | Cys | Ser | Gln | Val | Leu | Cys | Gln | Glu | Gln | Gly | Val | Cys |
| | | | 340 | | | | | 345 | | | | | 350 | | |

```
Ile Arg Lys Asn Trp Asn Ser Ser Asp Tyr Leu His Leu Asn Pro Asp
            355                 360                 365

Asn Phe Ala Ile Gln Leu Glu Lys Gly Gly Lys Phe Thr Val Arg Gly
        370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Pro Gln Ile Phe Tyr Asn
        435                 440                 445

Ala Ser Pro Ser Thr Leu Ser
        450                 455

<210> SEQ ID NO 62
<211> LENGTH: 413
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Phe Arg Gly Pro Leu Pro Asn Arg Pro Phe Thr Thr Val Trp Asn
1               5                   10                  15

Ala Asn Thr Gln Trp Cys Leu Glu Arg His Gly Val Asp Val Asp Val
            20                  25                  30

Ser Val Phe Asp Val Val Ala Asn Pro Gly Gln Thr Phe Arg Gly Pro
        35                  40                  45

Asp Met Thr Ile Phe Tyr Ser Ser Gln Gly Thr Tyr Pro Tyr Tyr Thr
    50                  55                  60

Pro Thr Gly Glu Pro Val Phe Gly Gly Leu Pro Gln Asn Ala Ser Leu
65                  70                  75                  80

Ile Ala His Leu Ala Arg Thr Phe Gln Asp Ile Leu Ala Ala Ile Pro
                85                  90                  95

Ala Pro Asp Phe Ser Gly Leu Ala Val Ile Asp Trp Glu Ala Trp Arg
            100                 105                 110

Pro Arg Trp Ala Phe Asn Trp Asp Thr Lys Asp Ile Tyr Arg Gln Arg
        115                 120                 125

Ser Arg Ala Leu Val Gln Ala Gln His Pro Asp Trp Pro Ala Pro Gln
    130                 135                 140

Val Glu Ala Val Ala Gln Asp Gln Phe Gln Gly Ala Ala Arg Ala Trp
145                 150                 155                 160

Met Ala Gly Thr Leu Gln Leu Gly Arg Ala Leu Arg Pro Arg Gly Leu
                165                 170                 175

Trp Gly Phe Tyr Gly Phe Pro Asp Cys Tyr Asn Tyr Asp Phe Leu Ser
            180                 185                 190

Pro Asn Tyr Thr Gly Gln Cys Pro Ser Gly Ile Arg Ala Gln Asn Asp
        195                 200                 205

Gln Leu Gly Trp Leu Trp Gly Gln Ser Arg Ala Leu Tyr Pro Ser Ile
    210                 215                 220

Tyr Met Pro Ala Val Leu Glu Gly Thr Gly Lys Ser Gln Met Tyr Val
225                 230                 235                 240

Gln His Arg Val Ala Glu Ala Phe Arg Val Ala Val Ala Ala Gly Asp
```

```
            245                 250                 255
Pro Asn Leu Pro Val Leu Pro Tyr Val Gln Ile Phe Tyr Asp Thr Thr
            260                 265                 270

Asn His Phe Leu Pro Leu Asp Glu Leu Glu His Ser Leu Gly Glu Ser
            275                 280             285

Ala Ala Gln Gly Ala Ala Gly Val Val Leu Trp Val Ser Trp Glu Asn
    290                 295                 300

Thr Arg Thr Lys Glu Ser Cys Gln Ala Ile Lys Glu Tyr Met Asp Thr
305                 310                 315                 320

Thr Leu Gly Pro Phe Ile Leu Asn Val Thr Ser Gly Ala Leu Leu Cys
                325                 330                 335

Ser Gln Ala Leu Cys Ser Gly His Gly Arg Cys Val Arg Arg Thr Ser
            340                 345                 350

His Pro Lys Ala Leu Leu Leu Asn Pro Ala Ser Phe Ser Ile Gln
            355                 360                 365

Leu Thr Pro Gly Gly Pro Leu Ser Leu Arg Gly Ala Leu Ser Leu
    370                 375                 380

Glu Asp Gln Ala Gln Met Ala Val Glu Phe Lys Cys Arg Cys Tyr Pro
385                 390                 395                 400

Gly Trp Gln Ala Pro Trp Cys Glu Arg Lys Ser Met Trp
                405                 410

<210> SEQ ID NO 63
<211> LENGTH: 551
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Tyr Asn Phe Phe Pro Arg Lys Pro Lys Trp Asp Lys Asn Gln Ile Thr
1               5                   10                  15

Tyr Arg Ile Ile Gly Tyr Thr Pro Asp Leu Asp Pro Glu Thr Val Asp
            20                  25                  30

Asp Ala Phe Ala Arg Ala Phe Gln Val Trp Ser Asp Val Thr Pro Leu
        35                  40                  45

Arg Phe Ser Arg Ile His Asp Gly Glu Ala Asp Ile Met Ile Asn Phe
    50                  55                  60

Gly Arg Trp Glu His Gly Asp Gly Tyr Pro Phe Asp Gly Lys Asp Gly
65                  70                  75                  80

Leu Leu Ala His Ala Phe Ala Pro Gly Thr Gly Val Gly Gly Asp Ser
                85                  90                  95

His Phe Asp Asp Asp Glu Leu Trp Thr Leu Gly Glu Gly Gln Val Val
            100                 105                 110

Arg Val Lys Tyr Gly Asn Ala Asp Gly Glu Tyr Cys Lys Phe Pro Phe
        115                 120                 125

Leu Phe Asn Gly Lys Glu Tyr Asn Ser Cys Thr Asp Thr Gly Arg Ser
    130                 135                 140

Asp Gly Phe Leu Trp Cys Ser Thr Thr Tyr Asn Phe Glu Lys Asp Gly
145                 150                 155                 160

Lys Tyr Gly Phe Cys Pro His Glu Ala Leu Phe Thr Met Gly Gly Asn
                165                 170                 175

Ala Glu Gly Gln Pro Cys Lys Phe Pro Phe Arg Phe Gln Gly Thr Ser
            180                 185                 190
```

Tyr Asp Ser Cys Thr Thr Glu Gly Arg Thr Asp Gly Tyr Arg Trp Cys
                195                 200                 205

Gly Thr Thr Glu Asp Tyr Asp Arg Asp Lys Lys Tyr Gly Phe Cys Pro
    210                 215                 220

Glu Thr Ala Met Ser Thr Val Gly Gly Asn Ser Glu Gly Ala Pro Cys
225                 230                 235                 240

Val Phe Pro Phe Thr Phe Leu Gly Asn Lys Tyr Glu Ser Cys Thr Ser
                245                 250                 255

Ala Gly Arg Ser Asp Gly Lys Met Trp Cys Ala Thr Thr Ala Asn Tyr
            260                 265                 270

Asp Asp Asp Arg Lys Trp Gly Phe Cys Pro Asp Gln Gly Tyr Ser Leu
        275                 280                 285

Phe Leu Val Ala Ala His Glu Phe Gly His Ala Met Gly Leu Glu His
    290                 295                 300

Ser Gln Asp Pro Gly Ala Leu Met Ala Pro Ile Tyr Thr Tyr Thr Lys
305                 310                 315                 320

Asn Phe Arg Leu Ser Gln Asp Asp Ile Lys Gly Ile Gln Glu Leu Tyr
                325                 330                 335

Gly Ala Ser Pro Asp Ile Asp Leu Gly Thr Gly Pro Thr Pro Thr Leu
            340                 345                 350

Gly Pro Val Thr Pro Glu Ile Cys Lys Gln Asp Ile Val Phe Asp Gly
        355                 360                 365

Ile Ala Gln Ile Arg Gly Glu Ile Phe Phe Lys Asp Arg Phe Ile
    370                 375                 380

Trp Arg Thr Val Thr Pro Arg Asp Lys Pro Met Gly Pro Leu Leu Val
385                 390                 395                 400

Ala Thr Phe Trp Pro Glu Leu Pro Glu Lys Ile Asp Ala Val Tyr Glu
                405                 410                 415

Ala Pro Gln Glu Glu Lys Ala Val Phe Phe Ala Gly Asn Glu Tyr Trp
            420                 425                 430

Ile Tyr Ser Ala Ser Thr Leu Glu Arg Gly Tyr Pro Lys Pro Leu Thr
        435                 440                 445

Ser Leu Gly Leu Pro Pro Asp Val Gln Arg Val Asp Ala Ala Phe Asn
450                 455                 460

Trp Ser Lys Asn Lys Lys Thr Tyr Ile Phe Ala Gly Asp Lys Phe Trp
465                 470                 475                 480

Arg Tyr Asn Glu Val Lys Lys Met Asp Pro Gly Phe Pro Lys Leu
                485                 490                 495

Ile Ala Asp Ala Trp Asn Ala Ile Pro Asp Asn Leu Asp Ala Val Val
            500                 505                 510

Asp Leu Gln Gly Gly Gly His Ser Tyr Phe Phe Lys Gly Ala Tyr Tyr
        515                 520                 525

Leu Lys Leu Glu Asn Gln Ser Leu Lys Ser Val Lys Phe Gly Ser Ile
    530                 535                 540

Lys Ser Asp Trp Leu Gly Cys
545                 550

<210> SEQ ID NO 64
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Met Glu Thr Asp Thr Leu Leu Leu Trp Val Leu Leu Leu Trp Val Pro
1               5                   10                  15

Gly Ser Thr Gly
            20

<210> SEQ ID NO 65
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Thr Ser Arg Tyr Thr Phe Thr Glu Tyr
                20                  25                  30

Thr Ile His Trp Val Arg Gln Ala Pro Gly Gln Arg Leu Glu Trp Ile
            35                  40                  45

Gly Gly Ile Asn Pro Asn Asn Gly Ile Pro Asn Tyr Asn Gln Lys Phe
        50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Ile Ala Tyr Gly Tyr Asp Glu Gly His Ala Met Asp
            100                 105                 110

Tyr Trp Gly Gln Gly Thr Leu Val Thr Val Ser Ser
        115                 120

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Arg Tyr Thr Phe Thr Glu Tyr Thr Ile His
1               5                   10

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ile Asn Pro Asn Asn Gly Ile Pro Asn Tyr Asn Gln Lys Phe Lys
1               5                   10                  15

Gly

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 68

Arg Arg Ile Ala Tyr Gly Tyr Asp Glu Gly His Ala Met Asp Tyr
1               5                   10                  15

<210> SEQ ID NO 69
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Arg Asn Gln Lys Asn Tyr Leu Ala Trp Tyr Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Phe Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Tyr Pro Leu Thr Phe Gly Gln Gly Thr Lys Val Glu Ile
            100                 105                 110

Lys

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Ser Ser Gln Ser Leu Leu Tyr Ser Arg Asn Gln Lys Asn Tyr Leu
1               5                   10                  15

Ala

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Trp Ala Ser Thr Arg Glu Ser
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Gln Tyr Phe Ser Tyr Pro Leu Thr
1               5

<210> SEQ ID NO 73
<211> LENGTH: 77
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu
65                  70                  75

<210> SEQ ID NO 74
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
            20                  25                  30

Met Thr Asp Ser Asp Cys Arg Asp Asn Ala Pro Arg Thr Ile Phe Ile
        35                  40                  45

Ile Ser Met Tyr Lys Asp Ser Gln Pro Arg Gly Met Ala Val Thr Ile
    50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
    130                 135                 140

Gly Asp Arg Ser Ile Met Phe Thr Val Gln Asn Glu Asp
145                 150                 155

<210> SEQ ID NO 75
<211> LENGTH: 14
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 75

Ala Glu Ala Ala Ala Lys Glu Ala Ala Ala Lys Ala Ala Ala
1               5                   10

<210> SEQ ID NO 76
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Glu Ala Ala Ala Lys Glu Ala Ala Ala Lys Glu Ala Ala Ala Lys
1               5                   10                  15

Ala Ala Ala

<210> SEQ ID NO 77
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Glu Ala Ala Ala Lys Glu Ala Ala Ala Lys Glu Ala Ala Ala Lys
1               5                   10                  15

Glu Ala Ala Ala Lys Ala Ala Ala
                20

<210> SEQ ID NO 78
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala Ala Ala
                20                  25

<210> SEQ ID NO 79
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
                20                  25                  30

Thr Met Asn Trp Val Lys Gln Ser His Gly Lys Ser Leu Glu Trp Ile
            35                  40                  45

Gly Leu Ile Thr Pro Tyr Asn Gly Ala Ser Ser Tyr Asn Gln Lys Phe

```
            50                  55                  60
Arg Gly Lys Ala Thr Leu Thr Val Asp Lys Ser Ser Thr Ala Tyr
 65                  70                  75                  80

Met Asp Leu Leu Ser Leu Thr Ser Glu Asp Ser Ala Val Tyr Phe Cys
                 85                  90                  95

Ala Arg Gly Gly Tyr Asp Gly Arg Gly Phe Asp Tyr Trp Gly Gln Gly
                100                 105                 110

Thr Thr Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
        210                 215                 220

Thr His Thr
225

<210> SEQ ID NO 80
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Ile Glu Leu Thr Gln Ser Pro Ala Ile Met Ser Ala Ser Pro Gly
 1               5                  10                  15

Glu Lys Val Thr Met Thr Cys Ser Ala Ser Ser Val Ser Tyr Met
                 20                  25                  30

His Trp Tyr Gln Gln Lys Ser Gly Thr Ser Pro Lys Arg Trp Ile Tyr
             35                  40                  45

Asp Thr Ser Lys Leu Ala Ser Gly Val Pro Gly Arg Phe Ser Gly Ser
         50                  55                  60

Gly Ser Gly Asn Ser Tyr Ser Leu Thr Ile Ser Ser Val Glu Ala Glu
 65                  70                  75                  80

Asp Asp Ala Thr Tyr Tyr Cys Gln Gln Trp Ser Gly Tyr Pro Leu Thr
                 85                  90                  95

Phe Gly Ala Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175
```

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 81
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Thr Ser Arg Tyr Thr Phe Thr Glu Tyr
            20                  25                  30

Thr Ile His Trp Val Arg Gln Ala Pro Gly Gln Arg Leu Glu Trp Ile
        35                  40                  45

Gly Gly Ile Asn Pro Asn Asn Gly Ile Pro Asn Tyr Asn Gln Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Ile Ala Tyr Gly Tyr Asp Glu Gly His Ala Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys
225

<210> SEQ ID NO 82
<211> LENGTH: 227
<212> TYPE: PRT
<213> ORGANISM: Homo sapiens

<400> SEQUENCE: 82

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

```
Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                      55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Cys Thr Leu Pro Pro Ser Arg Glu Glu Met Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 83
<211> LENGTH: 227
<212> TYPE: PRT
<213> ORGANISM: Homo sapiens

<400> SEQUENCE: 83

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                      55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Glu Glu Met Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 84
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
atggaaaccg acacactgct gctgtgggtg ctgctcttgt gggtgccagg atctacagga      60

<210> SEQ ID NO 85
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
caggtccagc tgcaggaaag cggccctgga ctggtcaagc ctagccagac cctgagcctg      60
acctgtaccg tgtccggcgg cagcatcaac aacaacaatt actactggac atggatccgg     120
cagcaccccg gcaagggcct ggaatggatc ggctacatct actacagcgg ctccaccttc     180
tacaacccca gcctgaagtc cagagtgacc atcagcgtgg acaccagcaa gacccagttc     240
tccctgaagc tgagcagcgt gacagccgcc gacacagccg tgtactactg cgccagagaa     300
gataccatga ccggcctgga tgtgtggggc cagggcacca cagtgacagt gtctagc       357

<210> SEQ ID NO 86
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
gatatccaga tgacacagag ccctagcagc ctgagcgcca gcgtgggcga tagagtgacc      60
atcacctgtc gggccagcca gagcatcaac aactacctga actggtatca gcagaagccc     120
ggcaaggccc ctaccctgct gatctatgcc gcttctagcc tgcagagcgg cgtgcccagc     180 agatttctg gcagcagatc cggcaccgac ttcaccctga caatcagcag cctgcagccc     240
gaggacttcg ccgcctactt ctgccagcag acctacagca tcccaccttt cggccagggc     300
accaaggtgg aagtgaag                                                  318

<210> SEQ ID NO 87
<211> LENGTH: 399
<212> TYPE: DNA
<213> ORGANISM: Homo sapiens

<400> SEQUENCE: 87

```
gcccctacca gcagcagcac caagaaaacc cagctccagc tcgagcacct cctgctggac      60
ctgcagatga tcctgaacgg catcaacaac tacaagaacc ccaagctgac ccggatgctg     120
accttcaagt tctacatgcc caagaaggcc accgagctga agcacctcca gtgcctggaa     180
gaggaactga agcccctgga agaagtgctg aacctggccc agagcaagaa cttccacctg     240
aggcccaggg acctgatcag caacatcaac gtgatcgtgc tggaactgaa aggcagcgag     300
acaaccttca tgtgcgagta cgccgacgag acagccacca tcgtggaatt tctgaaccgg     360
tggatcacct tctgccagag catcatcagc accctgaca                            399
```

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88

```
ggcggcggag gatctggcgg aggcggcagc                                       30
```

<210> SEQ ID NO 89
<211> LENGTH: 687
<212> TYPE: DNA
<213> ORGANISM: Homo sapiens

<400> SEQUENCE: 89

```
gataagaccc acacctgtcc tccatgtcct gcccctgagc tgctgggcgg acctagcgtg      60
ttcctgttcc ctccaaagcc caaggacacc ctgatgatca gccggacccc tgaagtgacc     120
tgcgtggtgg tggatgtgtc ccacgaggat cccgaagtga agttcaattg gtacgtggac     180
ggcgtggaag tgcacaacgc caagaccaag cccagagagg aacagtacaa cagcacctac     240
cgggtggtgt ccgtgctgac cgtgctgcac caggactggc tgaacggcaa agagtacaag     300
tgcaaggtgt ccaacaaggc cctgcctgcc cctatcgaga aaaccatcag caaggccaag     360
ggccagcccc gcgaacctca ggtgtacaca ctgcctccct gcgggaaga gatgaccaag      420 aaccaggtgt ccctgtggtg cctggtcaag ggcttctacc cctccgatat cgccgtggaa     480
tgggagagca acggccagcc cgagaacaac tacaagacca cccctcccgt gctggacagc     540
gacggcagct tcttcctgta ctccaaactg accgtggaca agagccggtg gcagcagggc     600
aatgtgttca gctgtagcgt gatgcacgag gccctgcaca accactacac ccagaagtct     660
ctgagcctga gccccggcaa gtaatga                                         687
```

<210> SEQ ID NO 90
<211> LENGTH: 687
<212> TYPE: DNA
<213> ORGANISM: Homo sapiens

<400> SEQUENCE: 90

```
gataagaccc acacctgtcc tccatgtcct gcccctgagc tgctgggcgg acctagcgtg      60
ttcctgttcc ctccaaagcc caaggacacc ctgatgatca gccggacccc tgaagtgacc     120
tgcgtggtgg tggatgtgtc ccacgaggat cccgaagtga agttcaattg gtacgtggac     180
ggcgtggaag tgcacaacgc caagaccaag cccagagagg aacagtacaa cagcacctac     240
cgggtggtgt ccgtgctgac cgtgctgcac caggactggc tgaacggcaa agagtacaag     300
tgcaaggtgt ccaacaaggc cctgcctgcc cctatcgaga aaaccatcag caaggccaag     360
```

```
ggccagccta gagagcctca ggtctgcacc ctgcctccca gccgggaaga gatgaccaag    420
aaccaggtgt ccctgtcctg cgccgtgaag ggcttctacc cctccgatat cgccgtggaa    480
tgggagagca acggccagcc cgagaacaac tacaagacca cccctcccgt gctggacagc    540
gacggcagct tcttcctggt gtccaaactg accgtggaca gagccggtg gcagcagggc     600 aatgtgttca gctgtagcgt gatgcacgag gccctgcaca accactacac ccagaagtct    660
ctgagcctga gccccggcaa gtaatga                                         687
```

```
<210> SEQ ID NO 91
<211> LENGTH: 309
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
gccagcacca agggccctag cgtgttccct ctggccccta gctctaagag cacatctggc    60
ggaacagccg ccctgggctg cctggtcaag gattactttc ctgagcccgt gaccgtgtcc   120
tggaactctg gtgctctgac cagcggcgtg cacacctttc cagctgtgct gcagagcagc   180
ggcctgtaca gcctgtctag cgtggtcaca gtgcctagca gcagcctggg cacacagacc   240
tacatctgca acgtgaacca caagcccagc aacaccaagg tggacaagcg ggtggaaccc   300
aagagctgc                                                            309
```

```
<210> SEQ ID NO 92
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
agaacagtgg ccgctcccag cgtgttcatc ttcccaccca gcgacgagca gctgaagtct    60
ggcacagcca gcgtcgtgtg cctgctgaac aacttctacc ccagagaagc caaggtgcag   120
tggaaggtgg acaacgccct gcagtccggc aacagccagg aaagcgtcac cgagcaggac   180
agcaaggact ccacctacag cctgtccagc accctgaccc tgagcaaggc cgactacgag   240
aagcacaaag tgtacgcctg cgaagtgacc caccagggcc tgagcagccc cgtgaccaag   300
agcttcaata gaggcgagtg ctaatga                                         327
```

```
<210> SEQ ID NO 93
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
ggccagccca aggccaaccc caccgtgacc ctgttccctc catcctccga ggaactgcag    60
gctaacaagg ccaccctcgt gtgcctgatc tccgacttct accctggcgc cgtgaccgtg   120
gcttggaagg ctgatggctc tcctgtgaag gccggcgtgg aaaccaccaa gccctccaag   180
cagtccaaca caaatacgc cgcctccagc tacctgtccc tgacccctga gcagtggaag    240
tcccaccggt cctacagctg ccaggtcaca catgagggct ccaccgtgga aaagaccgtg   300
```
gcccctaccg agtgctccta atga                                          324

<210> SEQ ID NO 94
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
gaggtgcagc tgctggaatc tggcggagga ctggtgcagc ctggcggctc tctgagactg    60
tcttgtgccg cctccggctt caccttctcc agctatatca tgatgtgggt ccgacaggcc   120
cctggcaagg gcctggaatg ggtgtcctct atctacccct ccggcggcat cacctttac    180 gccgacaccg tgaagggccg gttcaccatc tcccgggaca actccaagaa caccctgtac   240
ctgcagatga actccctgcg ggccgaggac accgccgtgt actactgcgc tagaatcaag   300
ctgggcaccg tgaccaccgt ggactattgg ggccagggca ccctggtcac cgtgtcctct   360

<210> SEQ ID NO 95
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
cagtctgctc tgacccagcc tgcctctgtg tctggctccc ctggccagtc catcaccatc    60
agctgtaccg gcacctcctc cgacgtgggc ggctacaact acgtgtcctg gtatcagcag   120
catcccggca aggcccctaa gctgatgatc tacgacgtgt ccaaccggcc ctccggcgtg   180
tccaatcggt tctctggctc caagtccggc aacaccgcct ccctgacaat cagcggactg   240
caggccgagg acgaggccga ctactactgc tcctcctaca cctccagctc tacccgggtg   300
ttcggcaccg gcaccaaagt gacagtgctg                                    330

<210> SEQ ID NO 96
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ggcggcggag gatctggcgg aggtggaagc ggaggcggtg gatct                    45

<210> SEQ ID NO 97
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
caggttcagt tgcagcagtc cggacctgag ctggttaagc ctggcgcttc cgtgaagatg    60
tcctgcaagg cttccggcta caccttcacc gactacgtga tcaactgggg caagcagaga   120
tctggccagg gactcgagtg gatcggcgag atctatcctg gctccggcac caattactac   180

```
aacgagaagt tcaaggctaa ggctaccctg accgccgaca agtcctccaa tatcgcctac    240
atgcagctgt ccagcctgac ctctgaggac tccgctgtgt acttctgcgc tcggagaggc    300
agatacggcc tgtatgccat ggattactgg ggacagggaa ccagtgtgac agtgtcaagt    360
```

<210> SEQ ID NO 98
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98

```
gatattcaga tgacccagac cacctccagc ctgtccgctt ctctgggcga cagagtgaca     60
atcagctgca gagccagcca ggacatcagc aactacctga actggtatca acagaaaccc    120
gacggcaccg tgaagctgct gatctactac acctctcggc tgcactctgg cgtgccctct    180
agattttctg gcagcggaag cggcaccgac tattccctga ccatcaacaa cctggaacaa    240
gaggatatcg ctacctactt ctgccagcaa ggcaacaccc ggccttggac atttggcggc    300
ggaacaaagc tggaaatcaa gtgatga                                        327
```

<210> SEQ ID NO 99
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99

```
ggtggcggag gaagcggcgg aggcggctct ggtggtggtg gttctggtgg cggtggctcc     60
```

<210> SEQ ID NO 100
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
caggtccagc tgcaggaatc tggccctggc ctggtcaagc cctccgagac actgtctctg     60
acctgcaccg tgtccggcgg ctctgtgtcc tccggctcct actactggtc ctggatccgg    120
cagcctccag gcaagggact ggaatggatc ggctacatct actactccgg cagcaccaac    180
tacaacccca gcctgaagtc cagagtgacc atctccgtgg acacctccaa gaaccagttc    240
tccctgaagc tgtcctccgt gaccgccgct gacaccgccg tgtactactg tgccagagag    300
ggcaagaacg gcgccttcga tatctgggc cagggcacca tggtcaccgt gtctagc       357
```

<210> SEQ ID NO 101
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
gacatccaga tgacccagag ccccttccagc ctgtccgcct ctgtgggcga cagagtgacc    60
atcacctgtc gggcctccca gtccatctcc tcctacctga actggtatca gcagaagccc   120
```

```
ggcaaggccc ctaagctgct gatctacgcc gcctccagtc tgcagtctgg cgtgccatct    180
ggcttctccg gctctggctc tggcaccgac ttcaccctga ccatctccag cctgcagccc    240
gaggacttcg ccacctacta ctgccagcag tcctactcca ccctctgac cttcggcgga    300 ggcaccaagg tggaaatcaa g                                               321
```

<210> SEQ ID NO 102
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102

```
ggcggcggag gctcc                                                      15
```

<210> SEQ ID NO 103

<400> SEQUENCE: 103

000

<210> SEQ ID NO 104
<211> LENGTH: 456
<212> TYPE: DNA
<213> ORGANISM: Homo sapiens

<400> SEQUENCE: 104

```
gactgtgaca tcgaaggcaa ggacggcaag cagtacgaga gcgtgctgat ggtgtccatc    60
gaccagctgc tggacagcat gaaggaaatc ggctccaact gcctgaacaa cgagttcaac   120
ttcttcaagc ggcacatctg cgacgccaac aaagaaggca tgttcctgtt cagagccgcc   180
agaaagctgc ggcagttcct gaagatgaac tccaccggcg acttcgacct gcatctgctg   240
aaagtgtctg agggcaccac catcctgctg aactgtaccg ccaagtgaa gggcagaaag   300 cctgctgctc tgggcgaagc ccagcctacc aagtctctgg aagagaacaa gagcctgaaa   360
gagcagaaga agctgaacga cctctgcttc ctgaagcggc tgctgcaaga gatcaagacc   420
tgctggaaca agattctgat ggggaccaaa gagcac                              456
```

<210> SEQ ID NO 105
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105

```
gaagtgcagc tgttgcagtc tggcggagga ttggttcagc ctggcggatc cctgagactg    60
tcttgtgccg cctctggctt catgttcagc agatacccca tgcactgggt ccgacaggcc   120
cctggaaaag gactggaatg ggtcggatcc atctccggaa gtggcggcgc tacccttac   180 gccgattctg tgaagggcag attcaccatc agccggaca actccaagaa cacccttgtac   240 ctgcagatga actccctgag agccgaggac accgccgtgt actactgcgc caaggacttc   300
taccagatcc tgaccggcaa cgccttcgac tattggggcc agggcacaac cgtgaccgtg   360
tcctct                                                                366
```

<210> SEQ ID NO 106
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
gacatccaga tgacccagtc tccatcctct ctgtctgcca gcctgggcga cagagtgacc    60
atcacctgta gagcctctca gggcatctcc tcctacctgg cctggtatca gcagaagcct   120
ggcaaggctc ccaagctgct gatctacgcc aagagcacac tgcagtctgg cgtgccctct   180
agattctccg gctctggctc tggcaccgac tttaccctga caatctccag cctgcagcct   240
gaggactccg ccacctacta ctgtcagcag tactggacct ttccactgac cttcggcgga   300
ggcaccaagg tggaaatcaa g                                              321

<210> SEQ ID NO 107
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
caggtgcagc tggttcagtc tggcggagga ttggttcagc caggcggatc cctgagactg    60
tcttgtgccg cttctggctt caccttcgac gactacgcta tgcactgggt ccgacaggcc   120
cctggcaaag gattggaatg ggtggccggc atctcttggg actctggctc taccggctac   180
gccgactctg tgaagggcag attcaccatc tctcgggaca cgccaagaa ctccctgtac   240 ctgcagatga acagcctgag agccgaggac accgctctgt actactgcgc tagagatctg   300
ggcgcctacc agtgggtgga aggctttgat tattggggcc agggcaccct ggtcaccgtg   360
tctagt                                                               366

<210> SEQ ID NO 108
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
tcttacgagc tgacccagga tccagccgtg tctgttgctc tgggccagac agtgcggatt    60
acctgccagg gcgactccct gagatcctac tacgcctcct ggtatcagca gaagccaggc   120
caggctcctg tgctggtcat ctacggcaag aacaaccggc ctagcggcat ccctgacaga   180
ttctccggct ctacctccgg caactctgcc agcctgacaa ttactggcgc ccaggctgag   240
gacgaggccg actactactg caactccaga gacagccctg gcaatcagtg ggttttcggc   300
ggaggcacca agtgacagt tcttggt                                         327

<210> SEQ ID NO 109
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 109

| | | |
|---|---|---|
| caagttcagt tggttcaaag cggtggcggc gtggtgcagc ctggaagatc tctcagactg | 60 |
| tcctgcaagg cctccggcta caccttcacc agatacacca tgcattgggt tcgacaagca | 120 |
| ccaggcaagg gcctcgagtg gatcggctac atcaacccct tccagaggct caccaactac | 180 |
| aaccagaaag tgaaggaccg gttcaccatc agcagagaca acagcaagaa taccgccttt | 240 |
| ctgcagatgg actccctgcg gcctgaagat accggcgtgt acttttgcgc ccggtactac | 300 |
| gacgaccact actccctgga ttactgggga cagggaacac ccgtgacagt gtctagc | 357 |

<210> SEQ ID NO 110
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 110

| | | |
|---|---|---|
| gatattcaga tgacccagtc tccttccagc ctgtccgctt ctgtgggcga cagagtgact | 60 |
| attacctgct ccgcctcttc ctccgtgtcc tacatgaact ggtatcaaca aacacccggc | 120 |
| aaggccccta agagatggat ctacgacacc agcaagctgg cctctggcgt gccctctaga | 180 |
| tttttctggct ctggctccgg caccgactat acctttacaa tctccagcct gcagcctgag | 240 |
| gatatcgcca cctactactg tcagcagtgg tctagcaacc cttcacctt tggacagggc | 300 |
| accaagctgc agatcacctg atga | 324 |

<210> SEQ ID NO 111
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111

| | | |
|---|---|---|
| gctcctacct cctccagcac caagaaaacc cagctgcagt ggagcatct gctgctggac | 60 |
| ctccagatga tcctgaatgg catcaacaat acaagaacc ccaagctcac ccggatgctg | 120 |
| accgccaagt tgccatgcc taagaaggcc accgagctga acatctgca gtgcctggaa | 180 |
| gaggaactga agcccctgga agaagtgctg aatctggccc agtccaagaa cttccacctg | 240 |
| aggcctcggg acctgatctc caacatcaac gtgatcgtgc tcgagctgaa gggctccgag | 300 |
| acaaccttca tgtgcgagta cgccgacgag acagctacca tcgtggaatt tctgaaccgg | 360 |
| tggatcacct tctgtcagtc catcatcagc accctgacc | 399 |

<210> SEQ ID NO 112
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112

| | | |
|---|---|---|
| gaagtgcagc tccaagaatc tggacccggg ctcgtgaagc ccagccagtc tctgagtctg | 60 |
| acctgtacag tgaccggcta ctccatcacc tccgactacg cttggaactg gatccggcag | 120 |
| ttccccggca acaagttgga gtggatgggc tatatcaccct acagcggcag cacctcttac | 180 |

```
aacccttctc tggaatcccg atcagcatc accccgggaca cctctaccaa tcagttcttt      240
ctgcagctga acagcgtgac caccgaggac accgccacct actattgtgc tagaggcggc      300
tactacggct cctcctgggg agtgtttgct tactgggac agggaaccct cgtgactgtt       360
tctgct                                                                 366
```

<210> SEQ ID NO 113
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

```
gacatccaga tgacccagtc tccagccagc ctgtctgctt ctgtgggcga cacagtgacc      60
attacctgcc gggtgtccga gaacatctac tcctacctgg cctggtatca acagaaacag     120
ggcaagtccc ctcagctgct ggtgtacaat gctaagaccc tggctgaggg cgtgccctct     180 agatttctg gctctggcag cggcacccag tttagcctga agatcaactc cctgcagcct     240
gaggacttcg gcagctacta ctgccagcac cactatggca cccccttggac atttggcgga   300 ggcaccaagc tggaaatcaa g                                               321
```

<210> SEQ ID NO 114
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114

```
caggttcagt tgcagcagtc tgccgtggaa ctggctagac ctggcgcttc cgtgaagatg      60
tcctgcaagg cctccggcta caccttcacc agcttcacca tgcactgggt caagcagagg     120
cctggacaag gcttggagtg gattggatat atcaaccctca gctctggcta caccgagtac     180
aaccagaagt tcaaggacaa gaccactctg accgccgaca gtcctccag caccgcttac      240 atgcagctcg actccctgac ctctgacgac tctgctgtgt actattgcgt gcggggctcc    300
tccagaggct tcgattattg gggacaaggc acactcgtga cagtgtcagc t              351
```

<210> SEQ ID NO 115
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
gatatccaga tgatccagtc tcctgccagc ctgtccgtgt ctgtgggaga gactgtgacc      60
atcacctgtc gggcctccga gaacatctac tccaacctgg cctggttcca gcagaagcag     120
ggaaagtctc ctcagctgct ggtgtacgcc gccaccaatt tggctgatgg cgtgccctct     180
cggttctccg gatctggatc tggcacacag tattccctga gatcaactc cctgcagtcc     240 gaggacttcg gcatctacta ttgccagcac ttctggggca cccctagaac ctttggcggc    300
ggaacaaagc tggaaatcaa g                                               321
```

<210> SEQ ID NO 116

<211> LENGTH: 1176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116

| | | | | | |
|---|---|---|---|---|---|
| atggaaaccg | atacactgct | gctgtgggtg | ctgctcctct | gggtgccagg | atctacaggc | 60 |
| gccctacca | gcagcagcac | caagaaaacc | cagctccagc | tcgagcacct | cctgctggac | 120 |
| ctgcagatga | tcctgaacgg | catcaacaac | tacaagaacc | ccaagctgac | ccggatgctg | 180 |
| accttcaagt | tctacatgcc | caagaaggcc | accgagctga | agcacctcca | gtgcctggaa | 240 |
| gaggaactga | agcccctgga | agaagtgctg | aacctggccc | agagcaagaa | cttccacctg | 300 |
| aggcccaggg | acctgatcag | caacatcaac | gtgatcgtgc | tggaactgaa | aggcagcgag | 360 |
| acaaccttca | tgtgcgagta | cgccgacgag | acagccacca | tcgtggaatt | tctgaaccgg | 420 |
| tggatcacct | tctgccagag | catcatcagc | accctgacag | gcggcggagg | atctggcgga | 480 |
| ggcggcagcg | ataagaccca | cacctgtcct | ccatgtcccg | ccctgaact | gctgggcgga | 540 |
| cctagcgtgt | tcctgttccc | tccaaagccc | aaggacaccc | tgatgatcag | ccggacccct | 600 |
| gaagtgacct | gcgtggtggt | ggatgtgtcc | cacgaggatc | ccgaagtgaa | gttcaattgg | 660 |
| tacgtggacg | gcgtggaagt | gcacaacgcc | aagaccaagc | cagagagga | acagtacaac | 720 |
| agcacctacc | gggtggtgtc | cgtgctgacc | gtgctgcacc | aggactggct | gaatggcaaa | 780 |
| gagtacaagt | gcaaggtgtc | caacaaggcc | ctgcctgccc | ctatcgagaa | aaccatcagc | 840 |
| aaggccaagg | gccagcctag | agagcctcag | gtctgcaccc | tgcctcccag | ccgggaagag | 900 |
| atgaccaaga | accaggtgtc | cctgagctgc | gccgtgaagg | gcttctaccc | ctccgatatc | 960 |
| gccgtggaat | gggagagcaa | cggccagccc | gagaacaatt | acaagaccac | ccctcccgtg | 1020 |
| ctggacagcg | acggcagctt | cttcctggtg | tccaaactga | ccgtggacaa | gagccggtgg | 1080 |
| cagcagggca | atgtgttcag | ctgtagcgtg | atgcacgagg | ccctgcacaa | ccactacacc | 1140 |
| cagaagtctc | tgagcctgag | ccccggcaag | taatga | | | 1176 |

<210> SEQ ID NO 117
<211> LENGTH: 1452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117

| | | | | | |
|---|---|---|---|---|---|
| atggaaaccg | atacactgct | gctgtgggtg | ctgctcctct | gggtgccagg | atctacaggc | 60 |
| caggtccagc | tgcaggaaag | cggccctgga | ctggtcaagc | ctagccagac | cctgagcctg | 120 |
| acctgtaccg | tgtccggcgg | cagcatcaac | aacaacaatt | actactggac | atggatccgg | 180 |
| cagcaccccg | gcaagggcct | ggaatggatc | ggctacatct | actacagcgg | ctccaccttc | 240 |
| tacaacccca | gcctgaagtc | cagagtgacc | atcagcgtgg | acaccagcaa | gacccagttc | 300 |
| tccctgaagc | tgagcagcgt | gacagccgcc | gacacagccg | tgtactactg | cgccagagaa | 360 |
| gataccatga | ccggcctgga | tgtgtgggc | cagggcacca | cagtgacagt | gtctagcgcc | 420 |
| agcaccaagg | gccctagcgt | gttccctctg | gcccctagct | ctaagagcac | atctggcgga | 480 |
| acagccgccc | tgggctgcct | ggtcaaggat | tactttcctg | agcccgtgac | cgtgtcctgg | 540 |
| aactctggtg | ctctgaccag | cggcgtgcac | acctttccag | ctgtgctgca | gagcagcggc | 600 |

```
ctgtacagcc tgtctagcgt ggtcacagtg cctagcagca gcctgggcac acagacctac      660
atctgcaacg tgaaccacaa gcccagcaac accaaggtgg acaagcgggt ggaacccaag      720
agctgcgaca agaccacaca ctgtcctccc tgtcctgccc ctgaactgct gggcggacct      780
tccgtgttcc tgttccctcc aaagcccaag gacacccctg atcagccg acccctgaa         840 gtgacctgcg tggtggtgga tgtgtcccac gaggatcccg aagtgaagtt caattggtac      900
gtggacggcg tggaagtgca caacgccaag accaagccca gagaggaaca gtacaacagc      960
acctaccggg tggtgtccgt gctgaccgtg ctgcaccagg actggctgaa cggcaaagag     1020
tacaagtgca aggtgtccaa caaggccctg ccagccccta tcgagaaaac catcagcaag     1080
gccaagggcc agccccgcga acctcaggtg tacacactgc ctccctgccg gaagagatg      1140 accaagaacc aggtgtccct gtggtgtctc gtgaagggct tctaccctc cgatatcgcc      1200 gtggaatggg agagcaacgg ccagcccgag aacaactaca agaccacccc tcccgtgctg     1260
gacagcgacg gcagcttctt cctgtactcc aaactgaccg tggacaagag ccggtggcag     1320
cagggcaatg tgttcagctg tagcgtgatg cacgaggccc tgcacaacca ctacacccag     1380
aagtccctgt ccctgagccc tggaaaaggt ggcggaggaa gcggaggcgg aggttctggc     1440
ggcggaggat ct                                                         1452
```

<210> SEQ ID NO 118
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118

```
atggaaaccg atacactgct gctgtgggtg ctgctcctct gggtgccagg cagcaccggc       60
gatatccaga tgacacagag ccctagcagc ctgagcgcca gcgtgggcga tagagtgacc      120
atcacctgtc gggccagcca gagcatcaac aactacctga actggtatca gcagaagccc      180
ggcaaggccc ctaccctgct gatctatgcc gcttctagcc tgcagagcgg cgtgcccagc      240
agattttctg gcagcagatc cggcaccgac ttcaccctga caatcagcag cctgcagccc      300
gaggacttcg ccgcctactt ctgccagcag acctacagca tcccacctt cggccagggc      360 accaaggtgg aagtgaagag aacagtggcc gctcccagcg tgttcatctt cccacccagc     420
gacgagcagc tgaagtctgg cacagccagc gtcgtgtgcc tgctgaacaa cttctacccc     480
agagaagcca aggtgcagtg gaaggtggac aacgccctgc agtccggcaa cagccaggaa     540
agcgtcaccg agcaggacag caaggactcc acctacagcc tgtccagcac cctgaccctg     600
agcaaggccg actacgagaa gcacaaagtg tacgcctgcg aagtgaccca ccagggcctg     660
agcagccccg tgaccaagag cttcaataga ggcgagtgct aatga                     705
```

<210> SEQ ID NO 119
<211> LENGTH: 1176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119

```
atggaaaccg atacactgct gctgtgggtg ctgctcctct gggtgccagg atctacaggc       60
```

```
gcccctacca gcagcagcac caagaaaacc cagctccagc tcgagcacct cctgctggac      120
ctgcagatga tcctgaacgg catcaacaac tacaagaacc ccaagctgac ccggatgctg      180
accttcaagt tctacatgcc caagaaggcc accgagctga agcacctcca gtgcctggaa      240
gaggaactga agcccctgga agaagtgctg aacctggccc agagcaagaa cttccacctg      300
aggcccaggg acctgatcag caacatcaac gtgatcgtgc tggaactgaa aggcagcgag      360
acaaccttca tgtgcgagta cgccgacgag acagccacca tcgtggaatt tctgaaccgg      420
tggatcacct tctgccagag catcatcagc accctgacag gcggcggagg atctggcgga      480
ggcggcagcg ataagaccca cacctgtcct ccatgtcccg cccctgaact gctgggcgga      540
cctagcgtgt tcctgttccc tccaaagccc aaggacaccc tgatgatcag ccggacccct      600
gaagtgacct gcgtggtggt ggatgtgtcc cacgaggatc ccgaagtgaa gttcaattgg      660
tacgtggacg gcgtggaagt gcacaacgcc aagaccaagc ccagagagga acagtacaac      720
agcacctacc gggtggtgtc cgtgctgacc gtgctgcacc aggactggct gaatggcaaa      780
gagtacaagt gcaaggtgtc caacaaggcc ctgcctgccc ctatcgagaa aaccatcagc      840
aaggccaagg gccagcctag agagcctcag gtctgcaccc tgcctcccag ccgggaagag      900
atgaccaaga accaggtgtc cctgagctgc gccgtgaagg gcttctaccc ctccgatatc      960
gccgtggaat gggagagcaa cggccagccc gagaacaatt acaagaccac ccctcccgtg     1020
ctggacagcg acggcagctt cttcctggtg tccaaactga ccgtggacaa gagccggtgg     1080
cagcagggca atgtgttcag ctgtagcgtg atgcacgagg ccctgcacaa ccactacacc     1140
cagaagtctc tgagcctgag ccccggcaag taatga                               1176

<210> SEQ ID NO 120

<400> SEQUENCE: 120

000

<210> SEQ ID NO 121
<211> LENGTH: 714
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
atggaaaccg ataccctgct gctgtgggtg ctgctcctct gggtgccagg ctctaccggc       60
cagtctgctc tgacccagcc tgcctctgtg tctggctccc ctggccagtc catcaccatc      120
agctgtaccg gcacctcctc cgacgtgggc ggctacaact acgtgtcctg gtatcagcag      180
catcccggca aggcccctaa gctgatgatc tacgacgtgt ccaaccggcc ctccggcgtg      240
tccaatcggt tctctggctc caagtccggc aacaccgcct ccctgacaat cagcggactg      300
caggccgagg acgaggccga ctactactgc tcctcctaca cctccagctc tacccgggtg      360
ttcggcaccg gcaccaaagt gacagtgctg ggccagccca ggccaacccc accgtgacc      420 ctgttccctc catcctccga ggaactgcag gctaacaagg ccaccctcgt gtgcctgatc      480
tccgacttct accctggcgc cgtgaccgtg gcttggaagg ctgatggctc tcctgtgaag      540
gccggcgtgg aaaccaccaa gccctccaag cagtccaaca acaaatacgc cgcctccagc      600
tacctgtccc tgacccctga gcagtggaag tccaccggt cctacagctg ccaggtcaca      660
catgagggct ccaccgtgga aaagaccgtg gcccctaccg agtgctccta atga            714
```

```
<210> SEQ ID NO 122
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
atggaaaccg ataccctgct gctgtgggtg ctgctcctct gggtgccagg ctctacagga      60
caggtccagc tgcaggaatc tggccctggc ctggtcaagc cctccgagac actgtctctg     120
acctgcaccg tgtccggcgg ctctgtgtcc tccggctcct actactggtc ctggatccgg     180
cagcctccag gcaagggact ggaatggatc ggctacatct actactccgg cagcaccaac     240
tacaacccca gcctgaagtc cagagtgacc atctccgtgg acacctccaa gaaccagttc     300
tccctgaagc tgtcctccgt gaccgccgct gacaccgccg tgtactactg tgccagagag     360
ggcaagaacg gcgccttcga tatctggggc cagggcacca tggtcaccgt gtctagcgct     420
tccaccaagg gccctccgt gttccctctg gccccttcca gcaagtccac ctctggcgga     480
accgctgctc tgggctgcct cgtgaaggac tacttccccg agcctgtgac cgtgtcctgg     540
aactctggcg ccctgacatc cggcgtgcac acctttccag ccgtgctgca gtccagcggc     600
ctgtactctc tgtccagcgt cgtgaccgtg ccttccagct ctctgggcac acagacctac     660
atctgcaacg tgaaccacaa gccttccaac accaaggtgg acaagcgggt ggaacccaag     720
tcctgcgaca gacccacac ctgtcctccc tgtcctgccc ctgaactgct gggcggaccc     780
agcgtgttcc tgttccctcc aaagcccaag gacaccctga tgatctcccg gacccctgaa     840
gtgacctgcg tggtggtgga cgtgtcccac gaggatcccg aagtgaagtt caattggtac     900
gtggacggcg tggaagtgca caacgccaag accaagccta gagaggaaca gtacaactcc     960
acctaccggg tggtgtccgt gctgacagtg ctgcaccagg actggctgaa cggcaaagag    1020
tacaagtgca aggtgtccaa caaggccctg ccagcccta tcgaaaagac catcagcaag    1080
gctaagggcc agccccgcga gccccaggtt tacacactgc ctccctgccg gaagagatg    1140 accaagaatc aggtgtccct gtggtgtctg gtcaagggct ctaccccctc cgatatcgcc    1200
gtggaatggg agtccaacgg ccagcccgag aacaactaca agaccacccc tcccgtgctg    1260
gactccgacg gctcattctt cctgtactcc aagctgaccg tggacaagtc ccggtggcag    1320
cagggcaacg tgttcctg ctctgtgatg cacgaggccc tgcacaacca ctacacccag    1380
aagtccctgt ccctgagccc cggcaagtaa tga                                 1413

<210> SEQ ID NO 123
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
atggaaaccg ataccctgct gctgtgggtg ctgctcctct gggtgccagg ctctaccggc      60
gacatccaga tgacccagag ccccttccag ctgtccgcct ctgtgggcga cagagtgacc     120
atcacctgtc gggcctccca gtccatctcc tcctacctga actggtatca gcagaagccc     180
ggcaaggccc ctaagctgct gatctacgcc gcctccagtc tgcagtctgg cgtgccatct     240
```

```
ggcttctccg gctctggctc tggcaccgac ttcaccctga ccatctccag cctgcagccc    300
gaggacttcg ccacctacta ctgccagcag tcctactcca cccctctgac cttcggcgga    360
ggcaccaagg tggaaatcaa gcggaccgtg gccgctccct ccgtgttcat cttcccacct    420
tccgacgagc agctgaagtc cggcaccgct tctgtcgtgt gcctgctgaa caacttctac    480
cctcgggaag ccaaggtgca gtggaaggtg gacaatgccc tgcagtccgg caactcccag    540
gaatccgtca ccgagcagga ctccaaggac agcaccctac ccctgtcctc taccctgacc    600
ctgtccaagg ccgactacga aagcacaagg tgtacgcct gcgaagtgac ccaccagggc    660
ctgagcagcc ccgtgaccaa gtccttcaac agaggcgagt gctaatga               708
```

<210> SEQ ID NO 124
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124

```
atggaaaccg atacactgct gctgtgggtg ctgctcctct gggtgccagg cagcaccggc    60
gataagaccc acacctgtcc tccatgtcct gcccctgagc tgctgggcgg acctagcgtg    120
ttcctgttcc ctccaaagcc caaggacacc ctgatgatca gccggacccc tgaagtgacc    180
tgcgtggtgg tggatgtgtc ccacgaggat cccgaagtga agttcaattg gtacgtggac    240
ggcgtggaag tgcacaacgc caagaccaag cccagagagg aacagtacaa cagcacctac    300
cgggtggtgt ccgtgctgac cgtgctgcac caggactggc tgaacggcaa agagtacaag    360
tgcaaggtgt ccaacaaggc cctgcctgcc ctatcgaga aaaccatcag caaggccaag    420
ggccagcccc gcgaacctca ggtgtacaca ctgcctccct gcgggaaga gatgaccaag    480 aaccaggtgt ccctgtggtg cctggtcaag ggcttctacc cctccgatat cgccgtggaa    540
tgggagagca acggccagcc cgagaacaac tacaagacca cccctcccgt gctggacagc    600
gacggcagct tcttcctgta ctccaaactg accgtggaca gagccggtg gcagcagggc    660 aatgtgttca gctgtagcgt gatgcacgag gccctgcaca accactacac ccagaagtct    720
ctgagcctga gccccggcaa gtaatga                                        747
```

<210> SEQ ID NO 125
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125

```
atggaaaccg atacactgct gctgtgggtg ctgctcctct gggtgccagg cagcaccggc    60
gataagaccc acacctgtcc tccatgtcct gcccctgagc tgctgggcgg acctagcgtg    120
ttcctgttcc ctccaaagcc caaggacacc ctgatgatca gccggacccc tgaagtgacc    180
tgcgtggtgg tggatgtgtc ccacgaggat cccgaagtga agttcaattg gtacgtggac    240
ggcgtggaag tgcacaacgc caagaccaag cccagagagg aacagtacaa cagcacctac    300
cgggtggtgt ccgtgctgac cgtgctgcac caggactggc tgaacggcaa agagtacaag    360
tgcaaggtgt ccaacaaggc cctgcctgcc ctatcgaga aaaccatcag caaggccaag    420
ggccagccta gagagcctca ggtctgcacc ctgcctccca gcgggaaga gatgaccaag    480
```

```
aaccaggtgt ccctgtcctg cgccgtgaag ggcttctacc cctccgatat cgccgtggaa    540
tgggagagca acggccagcc cgagaacaac tacaagacca cccctcccgt gctggacagc    600
gacggcagct tcttcctggt gtccaaactg accgtggaca agagccggtg gcagcagggc    660
aatgtgttca gctgtagcgt gatgcacgag gccctgcaca accactacac ccagaagtct    720
ctgagcctga gccccggcaa gtaatga                                        747
```

<210> SEQ ID NO 126
<211> LENGTH: 1422
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126

```
atggaaaccg acacactgct gctgtgggtg ctgctcttgt gggtgccagg atctacaggc     60
gaagtgcagc tgttgcagtc tggcggagga ttggttcagc ctggcggatc cctgagactg    120
tcttgtgccg cctctggctt catgttcagc agataccccca tgcactgggt ccgacaggcc    180
cctggaaaag actggaatgg gtcggatcc atctccggaa gtggcggcgc tacccccttac   240 gccgattctg tgaagggcag attcaccatc agccgggaca actccaagaa caccctgtac   300
ctgcagatga actccctgag agccgaggac accgccgtgt actactgcgc caaggacttc   360
taccagatcc tgaccggcaa cgccttcgac tattggggcc agggcacaac cgtgaccgtg   420
tcctctgctt ctaccaaggg acccagcgtg ttccctctgg ctccttccag caagtctacc   480
tctggcggaa cagctgctct gggctgcctg gtcaaggact actttcctga gcctgtgaca   540
gtgtcctgga actctggcgc tctgacatcc ggcgtgcaca ccttccaagc tgtgctgcaa   600
tccagcggcc tgtactctct gtcctccgtc gtgacagtgc cttccagctc tctgggaacc   660
cagacctaca tctgcaatgt gaaccacaag ccttccaaca ccaaggtgga caagagagtg   720
gaacccaagt cctgcgacaa gacccacacc tgtcctccat gtcctgctcc agaactgctc   780
ggcggaccct tccgtgttcct gtttcctcca agcctaagg acaccctgat gatctctcgg   840
acccctgaag tgacctgcgt ggtggtggat gtgtctcacg aggatcccga agtgaagttc   900
aattggtacg tggacggcgt ggaagtgcac aacgccaaga ccaagcctag agaggaacag   960
tacaactcca cctacagagt ggtgtccgtg ctgaccgtgc tgcaccagga ttggctgaac  1020
ggcaaagagt acaagtgcaa ggtgtccaac aaggccctgc ctgctcctat cgaaaagacc  1080
atctccaagg ccaagggcca gcctcgggaa cctcaagtct gtaccctgcc tcctagccgg  1140
gaagagatga ccaagaacca ggtgtccctg tcctgtgccg tgaagggctt ctacccttcc  1200
gatatcgccg tggaatggga gagcaatggc cagcctgaga caactacaa gacaaccccct  1260 cctgtgctgg actccgacgg ctcattcttc ctggtgtcca gctgacagt ggacaagtcc   1320 agatggcagc agggcaacgt gttctcctgc tccgtgatgc acgaggccct gcacaatcac  1380
tacacccaga gtccctgtc tctgagcccc ggcaagtgat ga                      1422
```

<210> SEQ ID NO 127
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127

```
atggaaaccg acacactgct gctgtgggtg ctgctcttgt gggtgccagg atctaccggc      60
gacatccaga tgacccagtc tccatcctct ctgtctgcca gcctgggcga cagagtgacc     120
atcacctgta gagcctctca gggcatctcc tcctacctgg cctggtatca gcagaagcct     180
ggcaaggctc ccaagctgct gatctacgcc aagagcacac tgcagtctgg cgtgccctct     240
agattctccg gctctggctc tggcaccgac tttaccctga caatctccag cctgcagcct     300
gaggactccg ccacctacta ctgtcagcag tactggacct ttccactgac cttcggcgga     360
ggcaccaagg tggaaatcaa gagaaccgtg gccgctcctt ccgtgttcat cttcccacct     420
tccgacgagc agctgaagtc cggcacagct tctgtcgtgt gcctgctgaa caacttctac     480
cctcgggaag ccaaagtgca gtggaaggtg gacaacgctc tgcagtccgg caactcccaa     540
gagtctgtga ccgagcagga ctccaaggac agcacctaca gcctgtcctc cacactgacc     600
ctgtccaagg ccgactacga aagcacaag gtgtacgcct gcgaagtgac ccatcagggc     660
ctgtctagcc ctgtgaccaa gtctttcaac cggggcgagt gctgatga                  708
```

<210> SEQ ID NO 128
<211> LENGTH: 1866
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 128

```
atggaaaccg acacactgct gctgtgggtg ctgctcttgt gggtgccagg atctacaggc      60
gaagtgcagc tgttgcagtc tggcggagga ttggttcagc ctggcggatc cctgagactg     120
tcttgtgccg cctctggctt catgttcagc agataccca tgcactgggt ccgacaggcc     180
cctggaaaag gactgaatg gtcggatcc atctccggaa gtggcggcgc taccccttac     240
gccgattctg tgaagggcag attcaccatc agccgggaca actccaagaa caccctgtac     300
ctgcagatga ctccctgag agccgaggac accgccgtgt actactgcgc caaggacttc     360
taccagatcc tgaccggcaa cgccttcgac tattggggcc agggcacaac cgtgaccgtg     420
tcctctgctt ctaccaaggg acccagcgtg ttccctctgg ctccttccag caagtctacc     480
tctggcggaa cagctgctct gggctgcctg gtcaaggact actttcctga gcctgtgaca     540
gtgtcctgga actctggcgc tctgacatcc ggcgtgcaca ccttccagc tgtgctgcaa     600
tccagcggcc tgtactctct gtcctccgtc gtgacagtgc cttccagctc tctgggaacc     660
cagacctaca tctgcaatgt gaaccacaag ccttccaaca ccaaggtgga caagagagtg     720
gaacccaagt cctgcgacaa gacccacacc tgtcctccat gcctgctcc agaactgctc     780
ggcggaccct tccgtgttcct gtttcctcca agcctaagg acaccctgat gatctctcgg     840
acccctgaag tgacctgcgt ggtggtggat gtgtctcacg aggatcccga agtgaagttc     900
aattggtacg tggacggcgt ggaagtgcac aacgccaaga ccaagcctag agaggaacag     960
tacaactcca cctacagagt ggtgtccgtg ctgaccgtgc tgcaccagga ttggctgaac    1020
ggcaaagagt acaagtgcaa ggtgtccaac aaggccctgc ctgctcctat cgaaaagacc    1080
atctccaagg ccaagggcca gcctcgggaa cctcaagtct gtaccctgcc tcctagccgg    1140
gaagagatga ccaagaacca ggtgtccctg tcctgtgccg tgaagggctt ctacccttcc    1200
gatatcgccg tggaatggga gagcaatggc cagcctgaga caactacaa gacaacccct    1260
```

```
cctgtgctgg actccgacgg ctcattcttc ctggtgtcca agctgacagt ggacaagtcc    1320
agatggcagc agggcaacgt gttctcctgc tccgtgatgc acgaggccct gcacaatcac    1380
tacacccaga agtccctgtc tctgagccct ggcaaaggcg gaggcggatc tggtggtggc    1440
ggttctggcg gcggtggatc tgctcctaca tcctccagca ccaagaaaac ccagctgcag    1500
ttggagcatc tgctgctgga cctccagatg atcctgaatg gcatcaacaa ttacaagaac    1560
cccaagctca cccggatgct gaccttcaag ttctacatgc caagaaggc caccgagctg    1620 aaacatctgc agtgcctgga agaggaactg aagcctctgg aagaagtgct gaatctggcc    1680
cagtccaaga acttccacct gagggcctcgg gacctgatct ccaacatcaa cgtgatcgtg    1740
ctcgagctga agggctccga gactaccttc atgtgcgagt acgccgacga gacagctacc    1800
atcgtggaat ttctgaaccg gtggatcacc ttctgccagt ccatcatcag caccctgacc    1860
tgatga                                                               1866
```

<210> SEQ ID NO 129
<211> LENGTH: 1923
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129

```
atggaaaccg acacactgct gctgtgggtg ctgctcttgt gggtgccagg atctacaggc     60
gaagtgcagc tgttgcagtc tggcggagga ttggttcagc ctggcggatc cctgagactg    120
tcttgtgccg cctctggctt catgttcagc agatacccca tgcactgggt ccgacaggcc    180
cctggaaaag gactgaatg ggtcggatcc atctccggaa gtggcggcgc taccccttac    240
gccgattctg tgaagggcag attcaccatc agccgggaca actccaagaa caccctgtac    300
ctgcagatga actccctgag agccgaggac accgccgtgt actactgcgc caaggacttc    360
taccagatcc tgaccggcaa cgccttcgac tattggggcc agggcacaac cgtgaccgtg    420
tcctctgctt ctaccaaggg acccagcgtg ttccctctgg ctccttccag caagtctacc    480
tctggcggaa cagctgctct gggctgcctg gtcaaggact actttcctga gcctgtgaca    540
gtgtcctgga actctggcgc tctgacatcc ggcgtgcaca cctttccagc tgtgctgcaa    600
tccagcggcc tgtactctct gtcctccgtc gtgacagtgc cttccagctc tctgggaacc    660
cagacctaca tctgcaatgt gaaccacaag ccttccaaca ccaaggtgga caagagagtg    720
gaacccaagt cctgcgacaa gacccacacc tgtcctccat gcctgctcc agaactgctc    780 ggcggacctt ccgtgttcct gtttcctcca aagcctaagg acaccctgat gatctctcgg    840 accccttgaag tgacctgcgt ggtggtggat gtgtctcacg aggatcccga agtgaagttc    900
aattggtacg tggacggcgt ggaagtgcac aacgccaaga ccaagcctag agaggaacag    960
tacaactcca cctacagagt ggtgtccgtg ctgaccgtgc tgcaccagga ttggctgaac    1020
ggcaaagagt acaagtgcaa ggtgtccaac aaggccctgc ctgctcctat cgaaaagacc    1080
atctccaagg ccaagggcca gcctcgggaa cctcaagtct gtaccctgcc tcctagccgg    1140
gaagagatga ccaagaacca ggtgtccctg tcctgtgccg tgaagggctt ctaccctccc    1200
gatatcgccg tggaatggga gagcaatggc cagcctgaga caactacaa gacaaccct    1260 cctgtgctgg actccgacgg ctcattcttc ctggtgtcca agctgacagt ggacaagtcc    1320
agatggcagc agggcaacgt gttctcctgc tccgtgatgc acgaggccct gcacaatcac    1380
```

```
tacacccaga agtccctgtc tctgagccct ggcaaaggcg gaggcggatc tggtggtggc    1440
ggttctggcg gcggtggatc tgactgtgat atcgaaggca aggacggcaa gcagtacgag    1500
tccgtcctga tggtgtccat cgaccagctg ctggacagca tgaaggaaat cggctccaac    1560
tgcctgaaca acgagttcaa cttcttcaag cggcacatct gcgacgccaa caaagaaggc    1620
atgtttctgt tccgggctgc cagaaagctg cggcagttcc tgaagatgaa cagcaccggc    1680
gacttcgacc tgcacctgtt gaaagtgtct gagggcacca ccatcctgct gaactgtacc    1740
ggccaagtga agggaagaaa gcctgccgct ctgggcgaag cccagcctac aaagtctctg    1800
gaagagaaca gtccctgaa agagcagaag aagctgaacg acctctgttt cctgaagcgg    1860
ctgctgcaag agatcaagac ctgctggaac aagatcctga tgggcaccaa agagcactga    1920
tag                                                                  1923

<210> SEQ ID NO 130
<211> LENGTH: 1539
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
atggaaaccg acacactgct gctgtgggtg ctgctcttgt gggtgccagg atctacagga      60
caggtgcagc tggttcagtc tggcggagga ttggttcagc caggcggatc cctgagactg     120
tcttgtgccg cttctggctt caccttcgac gactacgcta tgcactgggt ccgacaggcc     180
cctggcaaag gattggaatg ggtggccggc atctcttggg actctggctc taccggctac     240
gccgactctg tgaagggcag attcaccatc tctcgggaca acgccaagaa ctccctgtac     300
ctgcagatga acagcctgag agccgaggac accgctctgt actactgcgc tagagatctg     360
ggcgcctacc agtgggtgga aggctttgat tattggggcc agggcaccct ggtcaccgtg     420
tctagtgctt ctactggtgg tggcggatct ggcggcggag gaagcggagg cggaggtagt     480
ggtggcggtg gatcttctta cgagctgacc caggatccag ccgtgtctgt tgctctgggc     540
cagacagtgc ggattacctg ccagggcgac tccctgagat cctactacgc ctcctggtat     600
cagcagaagc caggccaggc tcctgtgctg gtcatctacg gcaagaacaa ccggccagc     660 ggcatccctg acagattctc cggctctacc tccggcaact ctgccagcct gacaattact     720
ggcgcccagg ctgaggacga ggccgactac tactgcaact ccagagacag ccctggcaat     780
cagtgggttt tcggcggagg caccaaagtg acagttcttg gtggcggagg tggaagtggc     840
ggaggcggtt ctgataagac ccacacctgt ccaccttgtc ctgctccaga actgctcggc     900
ggaccttccg tgttcctgtt tcctccaaag cctaaggaca ccctgatgat ctctcggacc     960
cctgaagtga cctgcgtggt ggtggatgtg tctcacgagg atcccgaagt gaagttcaat    1020
tggtacgtgg acggcgtgga agtgcacaat gccaagacca gcctagaga ggaacagtac    1080 aactccacct atagagtggt gtccgtgctg accgtgctgc accaggattg gctgaacggc    1140
aaagagtaca agtgcaaggt gtccaacaag gccctgcctg ctcctatcga aaagaccatc    1200
tccaaggcca gggccagcc tagggaaccc caggtttaca cctgcctcc atgccgggaa    1260 gagatgacca gaaccaggt gtccctgtgg tgcctggtca agggcttcta cccttccgat    1320
atcgccgtgg aatgggagag caatggccag ccagagaaca actacaagac cacacctcca    1380
gtgctggact ccgacggctc attcttcctg tactccaagc tgacagtgga caagtccaga    1440
```

| | |
|---|---:|
| tggcagcagg gcaacgtgtt ctcctgctcc gtgatgcacg aggccctgca caatcactac | 1500 |
| acccagaagt ccctgtctct gagccccggc aagtgatga | 1539 |

<210> SEQ ID NO 131
<211> LENGTH: 2325
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 131

| | |
|---|---:|
| atggaaaccg acacactgct gctgtgggtg ctgctcttgt gggtgccagg atctacagga | 60 |
| caggtgcagc tggttcagtc tggcggagga ttggttcagc caggcggatc cctgagactg | 120 |
| tcttgtgccg cttctggctt caccttcgac gactacgcta tgcactgggt ccgacaggcc | 180 |
| cctggcaaag gattggaatg ggtggccggc atctcttggg actctggctc taccggctac | 240 |
| gccgactctg tgaagggcag attcaccatc tctcgggaca cgccaagaa ctccctgtac | 300 |
| ctgcagatga acagcctgag agccgaggac accgctctgt actactgcgc tagagatctg | 360 |
| ggcgcctacc agtgggtgga aggctttgat tattggggcc agggcacccct ggtcaccgtg | 420 |
| tctagtgctt ctactggtgg tggcggatct ggcggcggag aagcggagg cggaggtagt | 480 |
| ggtggcggtg gatcttctta cgagctgacc caggatccag ccgtgtctgt tgctctgggc | 540 |
| cagacagtgc ggattacctg ccagggcgac tccctgagat cctactacgc ctcctggtat | 600 |
| cagcagaagc caggccaggc tcctgtgctg gtcatctacg gcaagaacaa ccggcctagc | 660 |
| ggcatccctg acagattctc cggctctacc tccggcaact ctgccagcct gacaattact | 720 |
| ggcgcccagg ctgaggacga ggccgactac tactgcaact ccagagacag ccctggcaat | 780 |
| cagtgggttt cggcggagg caccaaagtg acagttcttg gtggcggagg tggaagtggc | 840 |
| ggaggcggtt ctgataagac ccacacctgt ccaccttgtc ctgctccaga actgctcggc | 900 |
| ggaccttccg tgttcctgtt tcctccaaag cctaaggaca cctgatgat ctctcggacc | 960 |
| cctgaagtga cctgcgtggt ggtggatgtg tctcacgagg acccgaagt gaagttcaat | 1020 |
| tggtacgtgg acggcgtgga agtgcacaat gccaagacca gcctagaga ggaacagtac | 1080 |
| aactccacct atagagtggt gtccgtgctg accgtgctgc accaggattg gctgaacggc | 1140 |
| aaagagtaca agtgcaaggt gtccaacaag gccctgcctg ctcctatcga aaagaccatc | 1200 |
| tccaaggcca agggccagcc tagggaaccc caggtttaca ccctgcctcc atgccgggaa | 1260 |
| gagatgacca agaaccaggt gtccctgtgg tgcctggtca agggcttcta cccttccgat | 1320 |
| atcgccgtgg aatgggagag caatggccag ccagagaaca actacaagac cacacctcca | 1380 |
| gtgctggact ccgacggctc attcttcctg tactccaagc tgacagtgga caagtccaga | 1440 |
| tggcagcagg gcaacgtgtt ctcctgctcc gtgatgcacg aggccctgca caatcactac | 1500 |
| acccagaagt ccctgtctct gtctcccgga aaaggcggtg gtggatcagg tggcggaggc | 1560 |
| tcaggcggag gcggatctca agttcagttg cagcagagcg acccgagct ggtcaaacct | 1620 |
| ggcgcttccg tgaagatgtc ctgcaaggcc tccggctaca ccttcaccga ttacgtgatc | 1680 |
| aactggggca gcagcgctc tggccaaggc ctggaatgga tcggcgagat ctatcctggc | 1740 |
| tccggcacca actactacaa cgagaagttc aaggctaagg ctaccctgac cgccgacaag | 1800 |
| tcctccaata tcgcctacat gcagctgtct agcctgacct ccgaggactc tgccgtgtac | 1860 |
| ttctgcgcca agagaggcag atacggcctg tacgccatgg actactgggg acagggaacc | 1920 |

| | |
|---|---|
| tccgtgacag ttagtagcgg tggcggcggt agcggcggtg gtggttctgg cggtggtggt | 1980 |
| agtggcggcg gaggatctga tatccagatg acccagacca ccagcagcct gtctgcttcc | 2040 |
| ctgggcgata gagtgaccat ctcttgcaga gccagccagg acatcagcaa ctacctgaac | 2100 |
| tggtatcaac aaaaacccga cggcaccgtg aagctgctga tctactacac ctctcggctg | 2160 |
| cactctggcg tgccctctag attttctggc agcggctctg gaaccgacta ctccctgacc | 2220 |
| atcaacaacc tggaacaaga ggatatcgct acctacttct gccagcaagg caacacccgg | 2280 |
| ccttggacat ttggaggcgg caccaagctg gaaatcaagt gatga | 2325 |

<210> SEQ ID NO 132
<211> LENGTH: 2319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132

| | |
|---|---|
| atggaaaccg acacactgct gctgtgggtg ctgctcttgt gggtgccagg atctacagga | 60 |
| caggtgcagc tggttcagtc tggcggagga ttggttcagc caggcggatc cctgagactg | 120 |
| tcttgtgccg cttctggctt caccttcgac gactacgcta tgcactgggt ccgacaggcc | 180 |
| cctggcaaag gattggaatg ggtggccggc atctcttggg actctggctc taccggctac | 240 |
| gccgactctg tgaagggcag attcaccatc tctcgggaca cgccaagaa ctccctgtac | 300 |
| ctgcagatga acagcctgag agccgaggac accgctctgt actactgcgc tagagatctg | 360 |
| ggcgcctacc agtgggtgga aggctttgat tattggggcc agggcaccct ggtcaccgtg | 420 |
| tctagtgctt ctactggtgg tggcggatct ggcggcggag aagcggagg cggaggtagt | 480 |
| ggtggcggtg gatcttctta cgagctgacc caggatccag ccgtgtctgt tgctctgggc | 540 |
| cagacagtgc ggattacctg ccagggcgac tccctgagat cctactacgc ctcctggtat | 600 |
| cagcagaagc caggccaggc tcctgtgctg gtcatctacg gcaagaacaa ccggcctagc | 660 |
| ggcatccctg acagattctc cggctctacc tccggcaact ctgccagcct gacaattact | 720 |
| ggcgcccagg ctgaggacga ggccgactac tactgcaact ccagagacag ccctggcaat | 780 |
| cagtgggttt tcggcggagg caccaaagtg acagttcttg gtggcggagg tggaagtggc | 840 |
| ggaggcggtt ctgataagac ccacacctgt ccaccttgtc ctgctccaga actgctcggc | 900 |
| ggaccttccg tgttcctgtt tcctccaaag cctaaggaca ccctgatgat ctctcggacc | 960 |
| cctgaagtga cctgcgtggt ggtggatgtg tctcacgagg atcccgaagt gaagttcaat | 1020 |
| tggtacgtgg acggcgtgga agtgcacaat gccaagacca gcctagaga ggaacagtac | 1080 |
| aactccacct atagagtggt gtccgtgctg accgtgctgc accaggattg gctgaacggc | 1140 |
| aaagagtaca agtgcaaggt gtccaacaag gccctgcctg ctcctatcga aaagaccatc | 1200 |
| tccaaggcca agggccagcc tagggaaccc caggtttaca ccctgcctcc atgccgggaa | 1260 |
| gagatgacca agaaccaggt gtccctgtgg tgcctggtca agggcttcta cccttccgat | 1320 |
| atcgccgtgg aatgggagag caatggccag ccagagaaca actacaagac cacacctcca | 1380 |
| gtgctggact ccgacggctc attcttcctg tactccaagc tgacagtgga caagtccaga | 1440 |
| tggcagcagg gcaacgtgtt ctcctgctcc gtgatgcacg aggccctgca caatcactac | 1500 |
| acccagaagt ccctgtctct gtctcccgga aaaggcggtg gtggatcagg tggcggaggc | 1560 |
| tcaggcggag gcggatctca agttcagttg gttcaaagcg gtggcggcgt ggtgcagcct | 1620 |

|                                                         |      |
| ------------------------------------------------------- | ---- |
| ggaagatctc tcagactgtc ctgcaaggcc tccggctaca ccttcaccag atacaccatg | 1680 |
| cattgggttc gacaagcacc aggcaagggc ctcgagtgga tcggctacat caacccttcc | 1740 |
| agaggctaca ccaactacaa ccagaaagtg aaggaccggt tcaccatcag cagagacaac | 1800 |
| agcaagaata ccgcctttct gcagatggac tccctgcggc ctgaagatac cggcgtgtac | 1860 |
| ttttgcgccc ggtactacga cgaccactac tccctggatt actggggaca gggaacaccc | 1920 |
| gtgacagtgt ctagcggtgg cggtggttca ggcggcggtg gtagtggcgg cggaggtagc | 1980 |
| ggcggtggcg gatctgatat tcagatgacc cagtctcctt ccagcctgtc cgcttctgtg | 2040 |
| ggcgacagag tgactattac ctgctccgcc tcttcctccg tgtcctacat gaactggtat | 2100 |
| caacaaacac ccggcaaggc ccctaagaga tggatctacg acaccagcaa gctggcctct | 2160 |
| ggcgtgccct ctagattttc tggctctggc tccggcaccg actatacctt tacaatctcc | 2220 |
| agcctgcagc ctgaggatat cgccacctac tactgtcagc agtggtctag caacccttc | 2280 |
| accttttggac agggcaccaa gctgcagatc acctgatga | 2319 |

<210> SEQ ID NO 133
<211> LENGTH: 2199
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133

|                                                         |      |
| ------------------------------------------------------- | ---- |
| atggaaaccg acacactgct gctgtgggtg ctgctcttgt gggtgccagg atctacagga | 60   |
| caggtccagc tgcaagagtc tggccctgga ctggtcaagc cctctcagac cctgtctctg | 120  |
| acctgtaccg tgtccggcgg ctccatcaac aacaacaatt actactggac ctggatccgg | 180  |
| cagcaccctg gcaaaggact ggaatggatc ggctacatct actactccgg ctccaccttc | 240  |
| tacaacccca gcctgaagtc cagagtgacc atctccgtgg acaccagcaa gacccagttc | 300  |
| tccctgaagc tgtcctctgt gaccgccgct gataccgccg tgtactactg cgccagagaa | 360  |
| gataccatga ccggcctgga tgtgtggggc cagggaacaa cagtgaccgt gtcctccgct | 420  |
| tccaccaagg gaccttccgt gtttcctctg gctccctcca gcaagtctac ctctggtgga | 480  |
| acagctgccc tgggctgcct ggtcaaggat tactttcctg agcctgtgac agtgtcctgg | 540  |
| aactctggcg ctctgacatc cggcgtgcac acctttccag ctgtgctgca atcctccggc | 600  |
| ctgtactctc tgtcctccgt cgtgaccgtg ccttctagct ctctgggcac ccagacctac | 660  |
| atctgcaatg tgaaccacaa gccttccaac accaaggtgg acaagagagt ggaacccaag | 720  |
| tcctgcgaca gacccacac ctgtcctcca tgtcctgctc cagaactgct cggcggaccc | 780  |
| tctgtgttcc tgtttccacc taagcctaag gacaccctga tgatctctcg gaccctgaa | 840  |
| gtgacctgcg tggtggtgga tgtgtctcac gaggatcccg aagtgaagtt caattggtac | 900  |
| gtggacggcg tggaagtgca caacgccaag accaagccta gagaggaaca gtacaactcc | 960  |
| acctacagag tggtgtccgt gctgaccgtg ctgcaccagg attggctgaa cggcaaagag | 1020 |
| tacaagtgca aggtgtccaa caaggccctg cctgctccta tcgaaaagac catcagcaag | 1080 |
| gccaagggcc agcctaggga accccaggtt tacaccctgc ctccatgccg ggaagagatg | 1140 |
| accaagaacc aggtgtccct gtggtgcctc gtgaagggct tctaccctc cgatatcgcc | 1200 |
| gtggaatggg agagcaatgg ccagcctgag aacaactaca agacaacccc tcctgtgctg | 1260 |
| gactccgacg gctcattctt cctgtactcc aagctgacag tggacaagtc cagatggcag | 1320 |

```
cagggcaacg tgttctcctg ctccgtgatg cacgaggccc tgcacaatca ctacacccag     1380
aagagtctgt ctctgtctcc cggcaaaggc ggcggaggat ctggcggagg cggtagcggt     1440
ggtggcggat ctcaggttca gttgcagcag tccggacctg agctggttaa gcctggcgcc     1500
tccgtgaaga tgtcctgcaa ggcttctggc tacaccttca ccgactacgt gatcaactgg     1560
ggcaagcaga gatctggcca gggactcgag tggatcggag agatctatcc tggctccggc     1620
accaactact acaatgagaa gttcaaggct aaggctaccc tgaccgccga caagtcctcc     1680
aatatcgcct acatgcagct gtccagcctg acctctgagg actccgctgt gtacttctgt     1740
gctcggagag gcagatacgg cctgtatgcc atggattact ggggacaggg cacctccgtg     1800
actgtctcta gcggtggcgg aggtagcgga ggcggtggtt caggcggagg cggctctggt     1860
ggcggtggat ctgatattca gatgacccag accacctcca gcctgtccgc ttctctgggc     1920
gacagagtga caatcagctg cagagccagc caggacatca gcaactacct gaactggtat     1980
cagcagaaac ccgacggcac cgtgaagctg ctgatctact acacctctcg gctgcactct     2040
ggcgtgccct ctagatttc tggcagcgga agcggcaccg attactccct gacaatcaac     2100
aacctcgagc aagaggatat cgctacctac ttctgccagc aaggcaacac ccggccttgg     2160
acatttggcg gcggaacaaa gctggaaatc aagtgatga                           2199

<210> SEQ ID NO 134
<211> LENGTH: 1158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
atggaaaccg acacactgct gctgtggctg ctgctcttgt gggtgccagg atctaccgga      60
cagtctgctc tgacccagcc tgcttctgtg tctggctctc ccggccagtc catcaccatc     120
tcttgtaccg gcacctcctc tgacgtcggc ggctacaact acgtgtcctg gtatcagcag     180
catcccggca aggcccctaa gctgatgatc tacgacgtgt ccaaccggcc ttccggcgtg     240
tccaatagat tctctggctc caagtccggc aacaccgctt tctgacaat cagcggactg     300 caggccgagg acgaggccga ctactactgt tcctcctaca cctcctccag caccagagtg     360
tttggcaccg gcaccaaagt gaccgtgctg ggacagccta aggccaatcc taccgtgaca     420
ctgttccctc catcctccga ggaactgcag gctaacaagg ctaccctcgt gtgcctgatc     480
tccgactttt accctggcgc tgtgaccgtg gcctggaagg ctgatggatc tcctgtgaag     540
gctggcgtgg aaaccaccaa gccttccaag cagtccaaca caaatacgc cgcctcctcc     600 tacctgtctc tgacccctga acagtggaag tccaccggt cctacagctg ccaagtgacc     660
catgagggct ccaccgtgga aaagaccgtg gctcctactg agtgttctgg cggcggagga     720
tctggcggag gtggaagcgg aggcggtgga tctgctccta cctccagctc caccaagaaa     780
acccagctgc agttggagca tctgctgctg gacctgcaga tgatcctgaa cggcatcaac     840
aactacaaga cccccaagct gacccggatg ctgaccgcca gtttgccat gcctaagaag     900 gccaccgagc tgaaacatct gcagtgcctg gaagaggaac tgaagcccct ggaagaagtg     960
ctgaatctgg cccagtccaa gaacttccac ctgaggcctc gggacctgat cagcaacatc     1020
aacgtgatcg tgctcgagct gaagggctcc gagacaacct tcatgtgcga gtacgccgac     1080
gagacagcta ccatcgtgga atttctgaac cggtggatca ccttctgcca gagcatcatc     1140
```

```
agcaccctga cctgatga                                             1158
```

<210> SEQ ID NO 135
<211> LENGTH: 1416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135

```
atggaaaccg ataccctgct gctgtgggtg ctgctcctct gggtgccagg atctacaggc    60
gaggtgcagc tgctggaatc tggcggagga ctggtgcagc ctggcggctc tctgagactg   120
tcttgtgccg cctccggctt caccttctcc agctatatca tgatgtgggt ccgacaggcc   180
cctggcaagg gcctggaatg ggtgtcctct atctacccct ccggcggcat cacctttac    240
gccgacaccg tgaagggccg gttcaccatc tcccgggaca actccaagaa caccctgtac   300
ctgcagatga actccctgcg ggccgaggac accgccgtgt actactgcgc tagaatcaag   360
ctgggcaccg tgaccaccgt ggactattgg ggccagggca cctggtcac cgtgtcctct   420
gcttctacca agggccctc cgtgttccct ctggcccctt ccagcaagtc cacctctggc   480
ggaaccgctg ctctgggctg cctggtcaag gactacttcc ccgagcccgt gaccgtgtct   540
tggaactctg gcgccctgac cagcggcgtg cacacatttc cagccgtgct gcagtccagc   600
ggcctgtact ctctgtcctc cgtcgtgaca gtgccctcca gctctctggg cacacagacc   660
tacatctgca acgtgaacca caagccctcc aacaccaagg tggacaagcg ggtggaaccc   720
aagtcctgcg acaagaccca cacctgtcct ccctgtcctg cccctgaact gctgggcgga   780
cccagcgtgt tcctgttccc tccaaagcct aaggacaccc tgatgatctc ccggaccccct   840
gaagtgacct gcgtggtggt ggacgtgtcc cacgaggatc ccgaagtgaa gttcaattgg   900
tacgtggacg gcgtggaagt gcacaacgcc aagaccaagc ctagagagga acagtacaac   960
tccacctacc gggtggtgtc cgtgctgaca gtgctgcatc aggactggct gaacggcaaa  1020
gagtacaagt gcaaggtgtc caacaaggcc ctgccagccc tatcgaaaa gaccatctcc   1080
aaggccaagg gccagccaag agagcctcaa gtctgcacac tgcctcccag ccgggaagag  1140
atgaccaaga accaggtgtc cctgagctgc gctgtgaagg gcttctaccc ttccgatatc  1200
gccgtggaat gggagagcaa cggccagccc gagaacaatt acaagccac ccctcccgtg    1260
ctggactccg acggctcatt cttcctggtg tccaagctga ccgtggacaa gtcccggtgg  1320
cagcagggca acgtgttctc ctgctctgtg atgcacgagg ccctgcacaa ccactacacc  1380
cagaagtccc tgtccctgtc tcccggcaag taatga                           1416
```

<210> SEQ ID NO 136

<400> SEQUENCE: 136

000

<210> SEQ ID NO 137
<211> LENGTH: 2205
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137

```
atggaaaccg acacactgct gctgtgggtg ctgctcttgt gggtgccagg atctacagga    60
caggtccagc tgcaagagtc tggccctgga ctggtcaagc cttccgagac actgtctctg   120
acctgcaccg tgtctggcgg ctctgtgtcc tctggctcct actactggtc ctggatcaga   180
cagcctcctg gcaaaggcct ggaatggatc ggctacatct actactccgg ctccaccaac   240
tacaacccca gcctgaagtc cagagtgacc atctccgtgg acacctccaa gaaccagttc   300
tccctgaagc tgtcctccgt gaccgctgct gataccgccg tgtactactg tgccagagag   360
ggcaagaacg gcgccttcga tatttgggcc cagggcacca tggtcaccgt gtccagtgct   420
tctaccaagg gcccagcgt gttcccactg gctcccagct ctaagtctac ctctggcgga   480
acagctgccc tgggctgtct ggtcaaggat tacttccctg agcctgtgac cgtgtcctgg   540
aattctggcg ctctgacatc cggcgtgcac acctttccag ctgtgctgca atcctccggc   600
ctgtactctc tgtccagcgt cgtgaccgtg ccttctagcc tctgggcac ccagacctac   660
atctgcaatg tgaaccacaa gcctagcaac accaaggtgg acaagagagt ggaacccaag   720
tcctgcgaca gacccacac ctgtcctcca tgtcctgctc agaactgct cggcggacct   780
tccgtgttcc tgtttcctcc aaagcctaag gacaccctga tgatctctcg gacccctgaa   840
gtgacctgcg tggtggtgga tgtgtctcac gaggatcccg aagtgaagtt caattggtac   900
gtggacggcg tggaagtgca caacgccaag accaagccta gaggaaca gtacaactcc   960
acctacagag tggtgtccgt gctgaccgtg ctgcaccagg attggctgaa cggcaaagag  1020
tacaagtgca aggtgtccaa caaggccctg cctgctccta tcgaaaagac catcagcaag  1080
gccaaggcc agcctaggga accccaggtt tacaccctgc ctccatgccg ggaagagatg  1140
accaagaatc aggtgtccct gtggtgcctc gtgaagggct tctaccctc cgatatcgcc  1200
gtggaatggg agagcaatgg ccagcctgag aacaactaca agacaacccc tcctgtgctg  1260
gactccgacg gctcattctt cctgtactcc aagctgacag tggacaagtc cagatggcag  1320
cagggcaacg tgttctcctg ctccgtgatg cacgaggccc tgcacaatca ctacacccag  1380
aagtccctgt ctctgtcccc tggaaaaggc ggcggaggat ctggcggagg tggaagcgga  1440
ggcggtggat ctgaagtgca gctccaagaa tctggaccg ggctcgtgaa gcccagccag  1500
tctctgagtc tgacctgtac agtgaccggc tactccatca cctccgacta cgcttggaac  1560
tggatccggc agttccccgg caacaagttg agtggatgg gctatatcac ctacagcggc  1620
agcacctctt acaacccttc tctggaatcc cggatcagca tcacccggga cacctctacc  1680
aatcagttct ttctgcagct gaacagcgtg accaccgagg acaccgccac ctactattgt  1740
gctagaggcg gctactacgg ctcctcctgg ggagtgtttg cttactgggg acagggaacc  1800
ctcgtgactg tttctgctgg tggcggagga agcggcggag cggctctgg tggtggtggt  1860
tctggtggcg gcggatctga catccagatg acccagtctc cagccagcct gtctgcttct  1920
gtgggcgaga cagtgaccat tacctgccgg gtgtccgaga acatctactc ctacctggcc  1980
tggtatcaac agaaacaggg caagtcccct cagctgctgg tgtacaatgc taagaccctg  2040
gctgagggcg tgccctctag attttctggc tctggcagcg gcacccagtt tagcctgaag  2100
atcaactccc tgcagcctga ggacttcggc agctactact gccagcacca ctatggcacc  2160
ccttggacat ttggcggagg caccaagctg gaaatcaagt gatga              2205
```

<210> SEQ ID NO 138
<211> LENGTH: 2190
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 138

| | | | | | |
|---|---|---|---|---|---|
| atggaaaccg | acacactgct | gctgtgggtg | ctgctcttgt | gggtgccagg | atctacagga | 60 |
| caggtccagc | tgcaagagtc | tggccctgga | ctggtcaagc | cttccgagac | actgtctctg | 120 |
| acctgcaccg | tgtctggcgg | ctctgtgtcc | tctggctcct | actactggtc | ctggatcaga | 180 |
| cagcctcctg | gcaaaggcct | ggaatggatc | ggctacatct | actactccgg | ctccaccaac | 240 |
| tacaacccca | gcctgaagtc | cagagtgacc | atctccgtgg | acacctccaa | gaaccagttc | 300 |
| tccctgaagc | tgtcctccgt | gaccgctgct | gataccgccg | tgtactactg | tgccagagag | 360 |
| ggcaagaacg | gcgccttcga | tatttggggc | cagggcacca | tggtcaccgt | gtccagtgct | 420 |
| tctaccaagg | gacccagcgt | gttcccactg | gctcccagct | ctaagtctac | ctctggcgga | 480 |
| acagctgccc | tgggctgtct | ggtcaaggat | tacttccctg | agcctgtgac | cgtgtcctgg | 540 |
| aattctggcg | ctctgacatc | cggcgtgcac | acctttccag | ctgtgctgca | atcctccggc | 600 |
| ctgtactctc | tgtccagcgt | cgtgaccgtg | ccttctagct | ctctgggcac | ccagacctac | 660 |
| atctgcaatg | tgaaccacaa | gcctagcaac | accaaggtgg | acaagagagt | ggaacccaag | 720 |
| tcctgcgaca | agacccacac | ctgtcctcca | tgtcctgctc | cagaactgct | cggcggacct | 780 |
| tccgtgttcc | tgtttcctcc | aaagcctaag | gacaccctga | tgatctctcg | gacccctgaa | 840 |
| gtgacctgcg | tggtggtgga | tgtgtctcac | gaggatcccg | aagtgaagtt | caattggtac | 900 |
| gtggacggcg | tggaagtgca | caacgccaag | accaagccta | gagaggaaca | gtacaactcc | 960 |
| acctacagag | tggtgtccgt | gctgaccgtg | ctgcaccagg | attggctgaa | cggcaaagag | 1020 |
| tacaagtgca | aggtgtccaa | caaggccctg | cctgctccta | tcgaaaagac | catcagcaag | 1080 |
| gccaagggcc | agcctaggga | accccaggtt | tacaccctgc | ctccatgccg | ggaagagatg | 1140 |
| accaagaatc | aggtgtccct | gtggtgcctc | gtgaagggct | tctacccttc | cgatatcgcc | 1200 |
| gtggaatggg | agagcaatgg | ccagcctgag | aacaactaca | agacaacccc | tcctgtgctg | 1260 |
| gactccgacg | gctcattctt | cctgtactcc | aagctgacag | tggacaagtc | cagatggcag | 1320 |
| cagggcaacg | tgttctcctg | ctccgtgatg | cacgaggccc | tgcacaatca | ctacacccag | 1380 |
| aagtccctgt | ctctgtcccc | tggaaaaggc | ggcggaggat | ctggcggagg | tggaagcgga | 1440 |
| ggcggtggat | ctcaggttca | gttgcagcag | tctgccgtgg | aactggctag | acctggcgct | 1500 |
| tccgtgaaga | tgtcctgcaa | ggcctccggc | tacaccttca | ccagcttcac | catgcactgg | 1560 |
| gtcaagcaga | ggcctggaca | aggcttggag | tggattggat | atatcaaccc | tagctctggc | 1620 |
| tacaccgagt | acaaccagaa | gttcaaggac | aagaccactc | tgaccgccga | caagtcctcc | 1680 |
| agcaccgctt | acatgcagct | cgactccctg | acctctgacg | actctgctgt | gtactattgc | 1740 |
| gtgcggggct | cctccagagg | cttcgattat | tggggacaag | gcacactcgt | gacagtgtca | 1800 |
| gctggtggtg | gcggtagtgg | cggtggcggt | tcaggtggcg | gaggaagcgg | cggaggcgga | 1860 |
| tctgatatcc | agatgatcca | gtctcctgcc | agcctgtccg | tgtctgtggg | agagactgtg | 1920 |
| accatcacct | gtcgggcctc | cgagaacatc | tactccaacc | tggcctggtt | ccagcagaag | 1980 |
| cagggaaagt | ctcctcagct | gctggtgtac | gccgccacca | atttggctga | tggcgtgccc | 2040 |
| tctcggttct | ccggatctgg | atctggcaca | cagtattccc | tgaagatcaa | ctccctgcag | 2100 |
| tccgaggact | tcggcatcta | ctattgccag | cacttctggg | gcacccctag | aacctttggc | 2160 |
| ggcggaacaa | agctggaaat | caagtgatga | | | | 2190 |

<210> SEQ ID NO 139
<211> LENGTH: 675
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139

```
atggaaaccg acacactgct gctgtgggtg ctgctcttgt gggtgccagg atctacaggc      60
gagctgtgcg acgatgaccc tcctgagatc cctcacgcca ccttcaaggc catggcttac    120
aaagagggca ccatgctgaa ctgcgagtgc aagcggggct tcagacggat caagtccggc    180
agcctgtaca tgctgtgcac cggcaactcc tctcactcct cctgggacaa ccagtgccag    240
tgcacctcct ctgccaccag aaacaccacc aagcaagtga cccctcagcc tgaggaacag    300
aaagagcgca agaccaccga gatgcagagc cccatgcagc ctgtggatca ggcttctctg    360
cctggccact gtagagagcc tccaccttgg agaatgagg ccaccgagcg atctaccac    420 tttgtcgtgg ccagatggt gtactaccag tgcgtgcagg atacagagc cctgcataga    480 ggccctgctg agtccgtgtg caagatgacc catggcaaga ccagatggac ccagcctcag    540
ctgatctgta caggcggagg cggaggatct ggtggtggtg gatctggcct gaacgacatc    600
ttcgaggccc agaaaatcga gtggcacgaa ggcggtggcg gctcccacca tcatcatcac    660
caccatcact gatga                                                     675
```

<210> SEQ ID NO 140
<211> LENGTH: 1734
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140

```
atggaaaccg acaccctgct gctgtgggtg ctgctgctct gggtcccagg ctccaccggc      60
ggactgaacg acatcttcga ggcccagaaa atcgagtggc acgagggcgg aggcggctcc    120
gagcctagaa ccgacaccga cacctgtccc aaccccccg accctgccc tacctgtcct    180 accctgatc tgctgggcgg accctccgtg ttcatcttcc cacccaagcc taaggacgtg    240
ctgatgatct ccctgacccc caagatcacc tgtgtggtgg tggacgtgtc cgaagaggaa    300
cccgacgtgc agttcaattg gtacgtgaac aacgtggaag ataagaccgc ccagaccgag    360
acacggcagc ggcagtacaa ctccaccctac cgggtggtgt ccgtgctgcc catcaagcac    420
caggactgga tgtccggcaa ggtgttcaag tgcaaagtga acaacaacgc cctgcccagc    480
cccatcgaaa agaccatctc caagcctcgg ggccaagtcc agtgccccca gatctacacc    540
ttcccacccc ctatcgagca gaccgtgaag aaagacgtgt ccgtgacctg cctcgtgacc    600
ggattcctgc acaagacat ccacgtggaa tgggagtcca acggccagcc ccagcccgag    660
cagaactaca gaacacccca gcccgtgctg gactccgacg gctcctactt cctgtactcc    720
aagctgaacg tgcccaagtc cagatgggac cagggcgact ccttcacctg ttccgtgatc    780
cacgaggccc tgcacaacca ccacatgacc aagaccatca gccggtccct gggcaatggc    840
ggcggaggct ccgaggtgga aaagaccgcc tgccctctccg gcaagaaggc cagagagatc    900
gacgagtccc tgatcttcta caagaagtgg gagctggaag cctgcgtgga cgccgccctg    960
```

```
ctggccaccc agatggacag agtgaacgcc atcccctca cctacgagca gctggatgtg    1020
ctgaagcaca agctggacga gctgtacccc cagggctacc ccgagagcgt gatccagcac    1080
ctgggctacc tgtttctgaa gatgtccccc gaggacatcc ggaagtggaa cgtgacctcc    1140
ctggaaaccc tgaaggccct gctggaagtg aacaagggcc acgagatgag cccccaggcc    1200
cccagacgac ctctgcctca ggtggcaacc ctgatcgata gattcgtgaa gggcagaggc    1260
cagctggaca aggacaccct ggacacactg accgccttct accccggcta cctgtgctcc    1320
ctgtcccctg aggaactgtc ctccgtgccc ccctcctcta tctgggccgt gcggcctcag    1380
gatctggaca cctgtgaccc tcggcagctg atgtcctgt atcccaaggc ccggctggcc    1440
ttccagaaca tgaacggctc cgagtacttc gtgaagatcc agtccttcct gggcggagcc    1500
cccaccgagg acctgaaggc tctgtcccag cagaacgtgt ccatggacct ggccaccttc    1560
atgaagctgc ggaccgacgc cgtgctgcct ctgaccgtgg ctgaggtgca aagctgctg    1620 ggccccacg tggaaggcct gaaggccgag aacggcaca gacccgtgcg ggactggatc    1680
ctgcggcaga gacaggacga cctggatacc ctgggcctgg gcctgcagta atga          1734
```

<210> SEQ ID NO 141
<211> LENGTH: 822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 141

```
atgagaatct tcgccgtgtt catcttcatg acctactggc atctgctgaa cgccttcacc      60
gtgaccgtgc ccaaggacct gtacgtggtg gaatacggct ccaacatgac catcgagtgc    120
aagttccccg tggaaaagca gctggacctg ccgccctga tcgtgtactg ggagatggaa    180
gataagaaca tcatccagtt cgtgcacggg aagaggacc tgaaggtgca gcactcctcc    240
taccggcaga gagccagact gctgaaggac cagctgtccc tgggcaatgc cgccctgcag    300
atcaccgacg tgaagctgca ggatgccggc gtgtaccggt gcatgatctc ttacggcgga    360
gccgactaca agcggatcac cgtgaaagtg aacgccccct acaacaagat caaccagcgg    420
atcctggtgg tggacccgt gacctctgag cacgagctga cctgtcaggc cgagggctac    480
cctaaggccg aagtgatctg gacctcctcc gaccaccagg tgctgtccgg caagaccacc    540
accacaaact ccaagcggga agagaagctg ttcaacgtga cctccaccct gcggatcaac    600
acaaccacca cgagatcttt ctactgtacc ttccggcggc tggaccccga ggaaaatcac    660
accgctgagc tcgtgatccc cgagctgcct ctggcccacc ctcctaatga gagaacaggc    720
ggcggaggct ccggcctgaa cgacatcttt gaggcccaga aaatcgagtg cacgagggc    780 ggaggcggct cccaccatca tcaccaccac catcactgat ga                       822
```

<210> SEQ ID NO 142
<211> LENGTH: 1182
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 142

```
atggcttgga tgctgctgct gatcctgatc atggtgcacc ccggctcttg cgccctgtgg     60
gtgtcccagc ctcctgagat cagaaccctg gaaggctcct ccgccttcct gccctgctcc    120
```

| | |
|---|---|
| ttcaatgcct ctcagggcag actggccatc ggctccgtga cctggttcag ggatgaggtg | 180 |
| gtgcccggca aagaagtgcg gaacggcaca cctgagttca gaggcagact cgcccctctg | 240 |
| gcctcctcta gattcctgca cgatcaccag gccgagctgc acatcagaga tgtgcggggc | 300 |
| cacgacgcct ccatctacgt gtgcagagtg aagtgctggg cctgggcgt gggcaccggc | 360 |
| aatggaacac ggctggtggt ggaaaaagag ggcggaggcg gatctggcgg cggaggctct | 420 |
| gataagaccc acacctgtcc tccctgtcct gcccctgaac tgctgggcgg accttccgtg | 480 |
| ttcctgttcc ctccaaagcc caaggacacc ctgatgatct cccggacccc tgaagtgacc | 540 |
| tgcgtggtgg tggacgtgtc ccacgaggat cccgaagtga agttcaattg gtacgtggac | 600 |
| ggcgtggaag tgcacaacgc caagaccaag cccagagagg aacagtacaa ctccacctac | 660 |
| cgggtggtgt ccgtgctgac cgtgctgcac caggactggc tgaacggcaa agagtacaag | 720 |
| tgcaaggtgt ccaacaaggc cctgccagcc ccaatcgaaa agaccatctc caaggccaag | 780 |
| ggccagcccc gcgagcctca ggtgtacaca ctgcctccca gccgggaaga gatgaccaag | 840 |
| aaccaggtgt ccctgacctg tctggtcaag ggcttctacc cctccgatat cgccgtggaa | 900 |
| tgggagtcca acggccagcc cgagaacaac tacaagacca cccctcccgt gctggactcc | 960 |
| gacggctcat tcttcctgta ctccaagctg accgtggaca gtcccggtg gcagcagggc | 1020 |
| aacgtgttct cctgctctgt gatgcacgag gccctgcaca accactacac ccagaagtcc | 1080 |
| ctgtccctga gccctggcaa aggtggtggt ggtagcggtg gcggaggcag cggcctgaac | 1140 |
| gatatcttcg aggcccagaa aatcgagtgg cacgagtaat ga | 1182 |

<210> SEQ ID NO 143
<211> LENGTH: 1587
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 143

| | |
|---|---|
| atggaaaccg acacactgct gctgtgggtg ctgctcttgt gggtgccagg atctaccggc | 60 |
| cagcagcaga cactgcccaa gcctttatc tgggccgagc ctcacttcat ggtgcccaaa | 120 |
| gaaaagcaag tgaccatctg ctgccagggc aactacggcg ctgtggaata ccagctgcac | 180 |
| ttcgagggct ccctgttcgc cgtggataga cctaagcctc ctgagcggat caacaaagtg | 240 |
| aagttctaca cccccgacat gaactcccgg atggctggcc agtactcctg catctataga | 300 |
| gtgggcgagc tttggagcga gccctccaat ctgctggatc tggtggtcac cgagatgtac | 360 |
| gacaccccta cactgagcgt gcaccccgga cctgaagtga tctctggcga gaaagtgacc | 420 |
| ttctactgca gactggatac cgccacctcc atgtttctgc tgctcaaaga gggcagatcc | 480 |
| tctcacgtgc agcgcggcta tgaaaaggtg caggctgagt tcctctgggg ccctgtgacc | 540 |
| accgctcaca gaggcaccta cagatgcttc ggctcctaca caaccacgc ctggtctttc | 600 |
| ccatccgagc ctgtgaagct gctggtcacc ggcgacatcg agaacacatc tctggcccct | 660 |
| gaggacccca cctttcctga tacctgggc acctatctgc tgaccaccga gacaggcctg | 720 |
| cagaaagatc acgccctgtg ggatcacacc gctcagaatg tggcggagg atctggcgga | 780 |
| ggcggatctg aacctagaac cgacaccgac acctgtccta atcctccaga tcctgtcct | 840 |
| acctgtccaa cacctgacct gctcggcgga ccttccgtgt tcatcttccc acctaagcca | 900 |
| aaggacgtgc tgatgatctc tctgacccct aagatcacct gtgtggtggt ggacgtgtcc | 960 |

```
gaagaggaac ccgacgtgca gttcaattgg tacgtgaaca acgtcgagga caagacagcc    1020
cagaccgaga cacggcagcg gcagtacaac tctacctaca gagtggtgtc cgtgctgccc    1080
atcaagcacc aggattggat gtccggcaag gtgttcaagt gcaaagtgaa caacaacgcc    1140
ctgccttctc caatcgaaaa gaccatctcc aagcctcggg gccaagtgcg agtgccccag    1200
atctatacct ttccacctcc tatcgagcag accgtgaaga agatgtgtc cgtgacctgc     1260 ctcgtgaccg gcttcctgcc tcaagacatc catgtggaat gggagtccaa cggccagcct    1320
cagcctgagc agaactacaa gaacacccag cctgtgctgg actccgacgg cagctacttc    1380
ctgtactcca gctgaacgt gcccaagtcc agatgggacc agggcgactc cttcacctgt     1440
tccgtgatcc acgaggccct gcacaaccac acatgaccca agaccatcag cagatccctc    1500
ggcaatggcg gtggtggttc tggcggcgga ggttccggac tgaacgatat cttcgaggcc    1560
cagaaaatcg agtggcacga gtgatga                                       1587
```

<210> SEQ ID NO 144
<211> LENGTH: 1041
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144

```
atggaaactg acaccctcct cctttgggtg ctgctgcttt gggtgcctgg atcgaccggg    60
atgaaggaca ataccgtgcc tctgaagctc attgccctgc tggccaacgg agaattccat    120
tccggcgaac agctgggga gactctcggg atgtcccggg ccgccatcaa caagcacatc    180
cagactttgc gcgactgggg agtcgacgtg ttcacggtgc cggggaaggg ctactcgctc    240
ccggaaccga tccagctgct gaacgccaag cagattctgg acagctggga tggcggaagc    300
gtggcagtgc tgcccgtgat cgactcaacc aaccagtatc tgctggatag aatcggtgaa    360
ctgaaatccg gcgacgcttg cattgccgag taccaacagg ccggaagggg acggcgcggc    420
aggaagtggt tctctccatt cggcgcgaac ctctacctga gcatgttctg gagattggag    480
cagggtcccg ccgcggccat cggcctctcc ctggtcatcg gcattgtgat ggctgaagtg    540
ctgaggaagt tgggtgccga caaggtccgc gtgaagtggc cgaacgacct gtacctccaa    600
gaccggaaat tggcggggat tctcgtcgag cttaccggaa agactggcga tgccgcacaa    660
attgtgatcg gggcgggaat caacatggcg atgcgacggg tggaagagag cgtcgtgaac    720
cagggatgga tcaccctgca agaggccgga atcaacctgg atcgcaacac cctggctgcc    780
atgctcattc gcgaactgag agccgcactg gagctgtttg agcaggaggg tctggccccc    840
tacctgtcac gctgggaaaa gcttgataac ttcatcaatc ggcctgtgaa gctgatcatc    900
ggagacaagg agattttcgg catctcgaga ggcatcgaca acaaggagc cctcctgctg    960 gaacaggacg gaatcattaa gccctggatg ggtggagaga tctccctgcg gtccgccgaa    1020
aagtccggga aggatgaact c                                              1041
```

<210> SEQ ID NO 145
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
            20                  25                  30

Asn Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Phe Tyr Asn Pro Ser
    50                  55                  60

Leu Lys Ser Arg Val Thr Ile Ser Val Asp Thr Ser Lys Thr Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Thr Met Thr Gly Leu Asp Val Trp Gly Gln Gly
            100                 105                 110

Thr Thr Val Thr Val Ser Ser
            115

<210> SEQ ID NO 146
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Asn Trp Tyr Gln Gln Lys Pro Gly Lys Ala Pro Thr Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Ala Tyr Phe Cys Gln Gln Thr Tyr Ser Asn Pro Thr
                85                  90                  95

Phe Gly Gln Gly Thr Lys Val Glu Val Lys
            100                 105

<210> SEQ ID NO 147
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn

```
                    50                  55                  60
Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                     85                  90                  95

Glu Lys Thr Val Ala Pro Thr Glu Cys Ser
                100                 105
```

<210> SEQ ID NO 148
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
                20                  25                  30

Ile Met Met Trp Val Arg Gln Ala Pro Gly Lys Gly Leu Glu Trp Val
            35                  40                  45

Ser Ser Ile Tyr Pro Ser Gly Gly Ile Thr Phe Tyr Ala Asp Thr Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ile Lys Leu Gly Thr Val Thr Val Asp Tyr Trp Gly Gln
                100                 105                 110

Gly Thr Leu Val Thr Val Ser Ser
            115                 120
```

<210> SEQ ID NO 149
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Gln Ser Ala Leu Thr Gln Pro Ala Ser Val Ser Gly Ser Pro Gly Gln
 1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr Arg Val Phe Gly Thr Gly Thr Lys Val Thr Val Leu
                100                 105                 110
```

```
<210> SEQ ID NO 150
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Val Ile Asn Trp Gly Lys Gln Arg Ser Gly Gln Gly Leu Glu Trp Ile
            35                  40                  45

Gly Glu Ile Tyr Pro Gly Ser Gly Thr Asn Tyr Tyr Asn Glu Lys Phe
        50                  55                  60

Lys Ala Lys Ala Thr Leu Thr Ala Asp Lys Ser Ser Asn Ile Ala Tyr
65                  70                  75                  80

Met Gln Leu Ser Ser Leu Thr Ser Glu Asp Ser Ala Val Tyr Phe Cys
                85                  90                  95

Ala Arg Arg Gly Arg Tyr Gly Leu Tyr Ala Met Asp Tyr Trp Gly Gln
                100                 105                 110

Gly Thr Ser Val Thr Val Ser Ser
            115                 120

<210> SEQ ID NO 151
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Asn Asn Leu Glu Gln
65                  70                  75                  80

Glu Asp Ile Ala Thr Tyr Phe Cys Gln Gln Gly Asn Thr Arg Pro Trp
                85                  90                  95

Thr Phe Gly Gly Gly Thr Lys Leu Glu Ile Lys
                100                 105

<210> SEQ ID NO 152
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Gly Gly Gly Ser Gly Gly Gly Gly Ser Gly Gly Gly Gly Ser Gly
1               5                   10                  15
```

Gly Gly Gly Ser
            20

<210> SEQ ID NO 153
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Lys Asn Gly Ala Phe Asp Ile Trp Gly Gln Gly
            100                 105                 110

Thr Met Val Thr Val Ser Ser
        115

<210> SEQ ID NO 154
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 155

<400> SEQUENCE: 155

000

```
<210> SEQ ID NO 156
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150

<210> SEQ ID NO 157
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Glu Val Gln Leu Leu Gln Ser Gly Gly Gly Leu Val Gln Pro Gly Gly
1               5                   10                  15

Ser Leu Arg Leu Ser Cys Ala Ala Ser Gly Phe Met Phe Ser Arg Tyr
            20                  25                  30

Pro Met His Trp Val Arg Gln Ala Pro Gly Lys Gly Leu Glu Trp Val
        35                  40                  45

Gly Ser Ile Ser Gly Ser Gly Gly Ala Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Tyr Gln Ile Leu Thr Gly Asn Ala Phe Asp Tyr Trp
            100                 105                 110

Gly Gln Gly Thr Thr Val Thr Val Ser Ser
        115                 120

<210> SEQ ID NO 158
<211> LENGTH: 107
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 158

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Lys Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Tyr Trp Thr Phe Pro Leu
                85                  90                  95

Thr Phe Gly Gly Gly Thr Lys Val Glu Ile Lys
            100                 105

<210> SEQ ID NO 159
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Gly Ile Ser Trp Asp Ser Gly Ser Thr Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Leu Gly Ala Tyr Gln Trp Val Glu Gly Phe Asp Tyr Trp
            100                 105                 110

Gly Gln Gly Thr Leu Val Thr Val Ser Ser
        115                 120

<210> SEQ ID NO 160
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Ser Tyr Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

```
Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Thr Ser Gly Asn Ser Ala Ser Leu Thr Ile Thr Gly Ala Gln Ala Glu
65                  70                  75                  80

Asp Glu Ala Asp Tyr Tyr Cys Asn Ser Arg Asp Ser Pro Gly Asn Gln
                85                  90                  95

Trp Val Phe Gly Gly Gly Thr Lys Val Thr Val Leu Gly
                100                 105

<210> SEQ ID NO 161
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
                100                 105                 110

Thr Pro Val Thr Val Ser Ser
        115

<210> SEQ ID NO 162
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95
```

```
Phe Gly Gln Gly Thr Lys Leu Gln Ile Thr
            100                 105

<210> SEQ ID NO 163
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Ala Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 164
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Gln Leu Gln Glu Ser Gly Pro Gly Leu Val Lys Pro Ser Gln Ser Leu
1               5                   10                  15

Ser Leu Thr Cys Thr Val Thr Gly Tyr Ser Ile Thr Ser Asp Tyr Ala
            20                  25                  30

Trp Asn Trp Ile Arg Gln Phe Pro Gly Asn Lys Leu Glu Trp Met Gly
        35                  40                  45

Tyr Ile Thr Tyr Ser Gly Ser Thr Ser Tyr Asn Pro Ser Leu Glu Ser
    50                  55                  60

Arg Ile Ser Ile Thr Arg Asp Thr Ser Thr Asn Gln Phe Phe Leu Gln
65                  70                  75                  80

Leu Asn Ser Val Thr Thr Glu Asp Thr Ala Thr Tyr Tyr Cys Ala Arg
                85                  90                  95

Gly Gly Tyr Tyr Gly Ser Ser Trp Gly Val Phe Ala Tyr Trp Gly Gln
            100                 105                 110

Gly Thr Leu Val Thr Val Ser Ala Gly Gly Gly Ser Gly Gly Gly
        115                 120                 125

Gly Ser Gly Gly Gly Gly Ser Gly Gly Gly Gly Ser
    130                 135                 140
```

<210> SEQ ID NO 165
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Asp Ile Gln Met Thr Gln Ser Pro Ala Ser Leu Ser Ala Ser Val Gly
1               5                   10                  15

Glu Thr Val Thr Ile Thr Cys Arg Val Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Trp
                85                  90                  95

Thr Phe Gly Gly Gly Thr Lys Leu Glu Ile Lys
            100                 105

<210> SEQ ID NO 166
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Gln Val Gln Leu Gln Gln Ser Ala Val Glu Leu Ala Arg Pro Gly Ala
1               5                   10                  15

Ser Val Lys Met Ser Cys Lys Ala Ser Gly Tyr Thr Phe Thr Ser Phe
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Glu Tyr Asn Gln Lys Phe
    50                  55                  60

Lys Asp Lys Thr Thr Leu Thr Ala Asp Lys Ser Ser Ser Thr Ala Tyr
65                  70                  75                  80

Met Gln Leu Asp Ser Leu Thr Ser Asp Ser Ala Val Tyr Tyr Cys
                85                  90                  95

Val Arg Gly Ser Ser Arg Gly Phe Asp Tyr Trp Gly Gln Gly Thr Leu
            100                 105                 110

Val Thr Val Ser Ala
        115

<210> SEQ ID NO 167
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

```
Asp Ile Gln Met Ile Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Phe Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ile Tyr Tyr Cys Gln His Phe Trp Gly Thr Pro Arg
                85                  90                  95

Thr Phe Gly Gly Gly Thr Lys Leu Glu Ile Lys
            100                 105

<210> SEQ ID NO 168
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
            20                  25                  30

Asn Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Phe Tyr Asn Pro Ser
    50                  55                  60

Leu Lys Ser Arg Val Thr Ile Ser Val Asp Thr Ser Lys Thr Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Thr Met Thr Gly Leu Asp Val Trp Gly Gln Gly
            100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 169
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Asn Trp Tyr Gln Gln Lys Pro Gly Lys Ala Pro Thr Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Ala Tyr Phe Cys Gln Gln Thr Tyr Ser Asn Pro Thr
                85                  90                  95

Phe Gly Gln Gly Thr Lys Val Glu Val Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

```
Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 170
<211> LENGTH: 370
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr Gly Gly Gly Gly Ser Gly Gly Gly Gly Ser Asp
    130                 135                 140

Lys Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Lys Phe Asn Trp Tyr Val Asp Gly Val Glu Val His
        195                 200                 205

Asn Ala Lys Thr Lys Pro Arg Glu Glu Gln Tyr Asn Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Cys
            260                 265                 270

Thr Leu Pro Pro Ser Arg Glu Glu Met Thr Lys Asn Gln Val Ser Leu
        275                 280                 285

Ser Cys Ala Val Lys Gly Phe Tyr Pro Ser Asp Ile Ala Val Glu Trp
```

```
                    290                 295                 300

Glu Ser Asn Gly Gln Pro Glu Asn Asn Tyr Lys Thr Thr Pro Val
305                 310                 315                 320

Leu Asp Ser Asp Gly Ser Phe Phe Leu Val Ser Lys Leu Thr Val Asp
                325                 330                 335

Lys Ser Arg Trp Gln Gln Gly Asn Val Phe Ser Cys Ser Val Met His
                340                 345                 350

Glu Ala Leu His Asn His Tyr Thr Gln Lys Ser Leu Ser Leu Ser Pro
                355                 360                 365

Gly Lys
    370

<210> SEQ ID NO 171
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
                100                 105                 110

Pro Lys Ala Asn Pro Thr Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 172
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 172

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Lys Asn Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 173
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Gly Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 174
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
            20                  25                  30
```

-continued

```
Asn Tyr Tyr Trp Thr Trp Ile Arg Gln His Pro Gly Lys Gly Leu Glu
             35                  40                  45
Trp Ile Gly Tyr Ile Tyr Ser Gly Ser Thr Phe Tyr Asn Pro Ser
 50                  55                  60
Leu Lys Ser Arg Val Thr Ile Ser Val Asp Thr Ser Lys Thr Gln Phe
 65                  70                  75                  80
Ser Leu Lys Leu Ser Ser Val Thr Ala Ala Asp Thr Ala Val Tyr Tyr
                 85                  90                  95
Cys Ala Arg Glu Asp Thr Met Thr Gly Leu Asp Val Trp Gly Gln Gly
            100                 105                 110
Thr Thr Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
            195                 200                 205
Ser Asn Thr Lys Val Asp Lys Arg Val Glu Pro Lys Ser Cys Asp Lys
            210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Cys Arg Glu Glu Met Thr Lys Asn Gln Val Ser Leu Trp
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys Gly Gly Gly Gly Ser Gly Gly Gly Gly Ser Gly Gly Gly Gly Ser
```

<210> SEQ ID NO 175

<400> SEQUENCE: 175

000

<210> SEQ ID NO 176
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser
        115                 120
```

<210> SEQ ID NO 177
<211> LENGTH: 598
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Glu Glu Met Thr Lys Asn Gln Val Ser Leu
        355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Gly Gly Gly Ser Gly Gly Gly Gly Ser Gly Gly Gly Gly
450                 455                 460

Ser Ala Pro Thr Ser Ser Ser Thr Lys Lys Thr Gln Leu Gln Leu Glu
465                 470                 475                 480

His Leu Leu Leu Asp Leu Gln Met Ile Leu Asn Gly Ile Asn Asn Tyr
                485                 490                 495

Lys Asn Pro Lys Leu Thr Arg Met Leu Thr Phe Lys Phe Tyr Met Pro
            500                 505                 510

Lys Lys Ala Thr Glu Leu Lys His Leu Gln Cys Leu Glu Glu Glu Leu
        515                 520                 525

Lys Pro Leu Glu Glu Val Leu Asn Leu Ala Gln Ser Lys Asn Phe His
530                 535                 540

Leu Arg Pro Arg Asp Leu Ile Ser Asn Ile Asn Val Ile Val Leu Glu
```

```
545                 550                 555                 560
Leu Lys Gly Ser Glu Thr Thr Phe Met Cys Glu Tyr Ala Asp Glu Thr
                565                 570                 575

Ala Thr Ile Val Glu Phe Leu Asn Arg Trp Ile Thr Phe Cys Gln Ser
                580                 585                 590

Ile Ile Ser Thr Leu Thr
            595

<210> SEQ ID NO 178
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Phe Thr Val Thr Val Pro Lys Asp Leu Tyr Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Thr Gly Gly Gly
    210                 215                 220

Gly Ser Gly Leu Asn Asp Ile Phe Glu Ala Gln Lys Ile Glu Trp His
225                 230                 235                 240

Glu Gly Gly Gly Gly Ser His His His His His His
                245                 250

<210> SEQ ID NO 179
<211> LENGTH: 411
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 179

```
Thr Glu Met Tyr Asp Thr Pro Thr Leu Ser Val His Pro Gly Pro Glu
1               5                   10                  15

Val Ile Ser Gly Glu Lys Val Thr Phe Tyr Cys Arg Leu Asp Thr Ala
            20                  25                  30

Thr Ser Met Phe Leu Leu Lys Glu Gly Arg Ser Ser His Val Gln
        35                  40                  45

Arg Gly Tyr Gly Lys Val Gln Ala Glu Phe Pro Leu Gly Pro Val Thr
    50                  55                  60

Thr Ala His Arg Gly Thr Tyr Arg Cys Phe Gly Ser Tyr Asn Asn His
65                  70                  75                  80

Ala Trp Ser Phe Pro Ser Glu Pro Val Lys Leu Leu Val Thr Gly Asp
                85                  90                  95

Ile Glu Asn Thr Ser Leu Ala Pro Glu Asp Pro Thr Phe Pro Asp Thr
            100                 105                 110

Trp Gly Thr Tyr Leu Leu Thr Thr Glu Thr Gly Leu Gln Lys Asp His
        115                 120                 125

Ala Leu Trp Asp His Thr Ala Gln Asn Gly Gly Gly Ser Gly Gly
    130                 135                 140

Gly Gly Ser Glu Pro Arg Thr Asp Thr Asp Thr Cys Pro Asn Pro Pro
145                 150                 155                 160

Asp Pro Cys Pro Thr Cys Pro Thr Pro Asp Leu Leu Gly Gly Pro Ser
                165                 170                 175

Val Phe Ile Phe Pro Pro Lys Pro Lys Asp Val Leu Met Ile Ser Leu
            180                 185                 190

Thr Pro Lys Ile Thr Cys Val Val Asp Val Ser Glu Glu Glu Pro
        195                 200                 205

Asp Val Gln Phe Asn Trp Tyr Val Asn Asn Val Glu Asp Lys Thr Ala
    210                 215                 220

Gln Thr Glu Thr Arg Gln Arg Gln Tyr Asn Ser Thr Tyr Arg Val Val
225                 230                 235                 240

Ser Val Leu Pro Ile Lys His Gln Asp Trp Met Ser Gly Lys Val Phe
                245                 250                 255

Lys Cys Lys Val Asn Asn Asn Ala Leu Pro Ser Pro Ile Glu Lys Thr
            260                 265                 270

Ile Ser Lys Pro Arg Gly Gln Val Arg Val Pro Gln Ile Tyr Thr Phe
        275                 280                 285

Pro Pro Pro Ile Glu Gln Thr Val Lys Asp Val Ser Val Thr Cys
    290                 295                 300

Leu Val Thr Gly Phe Leu Pro Gln Asp Ile His Val Glu Trp Glu Ser
305                 310                 315                 320

Asn Gly Gln Pro Gln Pro Glu Gln Asn Tyr Lys Asn Thr Gln Pro Val
                325                 330                 335

Leu Asp Ser Asp Gly Ser Tyr Phe Leu Tyr Ser Lys Leu Asn Val Pro
            340                 345                 350

Lys Ser Arg Trp Asp Gln Gly Asp Ser Phe Thr Cys Ser Val Ile His
        355                 360                 365

Glu Ala Leu His Asn His Met Thr Lys Thr Ile Ser Arg Ser Leu
    370                 375                 380

Gly Asn Gly Gly Gly Gly Ser Gly Gly Gly Gly Ser Gly Leu Asn Asp
385                 390                 395                 400

Ile Phe Glu Ala Gln Lys Ile Glu Trp His Glu
                405                 410
```

<210> SEQ ID NO 180
<211> LENGTH: 374
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 180

```
Leu Trp Val Ser Gln Pro Pro Glu Ile Arg Thr Leu Glu Gly Ser Ser
1               5                   10                  15

Ala Phe Leu Pro Cys Ser Phe Asn Ala Ser Gln Gly Arg Leu Ala Ile
            20                  25                  30

Gly Ser Val Thr Trp Phe Arg Asp Glu Val Val Pro Gly Lys Glu Val
        35                  40                  45

Arg Asn Gly Thr Pro Glu Phe Arg Gly Arg Leu Ala Pro Leu Ala Ser
    50                  55                  60

Ser Arg Phe Leu His Asp His Gln Ala Glu Leu His Ile Arg Asp Val
65                  70                  75                  80

Arg Gly His Asp Ala Ser Ile Tyr Val Cys Arg Val Glu Val Leu Gly
                85                  90                  95

Leu Gly Val Gly Thr Gly Asn Gly Thr Arg Leu Val Val Glu Lys Glu
            100                 105                 110

Gly Gly Gly Gly Ser Gly Gly Gly Ser Asp Lys Thr His Thr Cys
        115                 120                 125

Pro Pro Cys Pro Ala Pro Glu Leu Leu Gly Gly Pro Ser Val Phe Leu
130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys Gly Gly Gly
            340                 345                 350

Gly Ser Gly Gly Gly Gly Ser Gly Leu Asn Asp Ile Phe Glu Ala Gln
```

Lys Ile Glu Trp His Glu
        370

<210> SEQ ID NO 181
<211> LENGTH: 556
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gly Leu Asn Asp Ile Phe Glu Ala Gln Lys Ile Glu Trp His Glu Gly
1               5                   10                  15

Gly Gly Gly Ser Glu Pro Arg Thr Asp Thr Asp Thr Cys Pro Asn Pro
            20                  25                  30

Pro Asp Pro Cys Pro Thr Cys Pro Thr Pro Asp Leu Leu Gly Gly Pro
        35                  40                  45

Ser Val Phe Ile Phe Pro Pro Lys Pro Lys Asp Val Leu Met Ile Ser
    50                  55                  60

Leu Thr Pro Lys Ile Thr Cys Val Val Asp Val Ser Glu Glu
65                  70                  75                  80

Pro Asp Val Gln Phe Asn Trp Tyr Val Asn Asn Val Glu Asp Lys Thr
                85                  90                  95

Ala Gln Thr Glu Thr Arg Gln Arg Gln Tyr Asn Ser Thr Tyr Arg Val
            100                 105                 110

Val Ser Val Leu Pro Ile Lys His Gln Asp Trp Met Ser Gly Lys Val
        115                 120                 125

Phe Lys Cys Lys Val Asn Asn Asn Ala Leu Pro Ser Pro Ile Glu Lys
130                 135                 140

Thr Ile Ser Lys Pro Arg Gly Gln Val Arg Val Pro Gln Ile Tyr Thr
145                 150                 155                 160

Phe Pro Pro Pro Ile Glu Gln Thr Val Lys Lys Asp Val Ser Val Thr
                165                 170                 175

Cys Leu Val Thr Gly Phe Leu Pro Gln Asp Ile His Val Glu Trp Glu
            180                 185                 190

Ser Asn Gly Gln Pro Gln Pro Glu Gln Asn Tyr Lys Asn Thr Gln Pro
        195                 200                 205

Val Leu Asp Ser Asp Gly Ser Tyr Phe Leu Tyr Ser Lys Leu Asn Val
    210                 215                 220

Pro Lys Ser Arg Trp Asp Gln Gly Asp Ser Phe Thr Cys Ser Val Ile
225                 230                 235                 240

His Glu Ala Leu His Asn His His Met Thr Lys Thr Ile Ser Arg Ser
                245                 250                 255

Leu Gly Asn Gly Gly Gly Gly Ser Glu Val Glu Lys Thr Ala Cys Pro
            260                 265                 270

Ser Gly Lys Lys Ala Arg Glu Ile Asp Glu Ser Leu Ile Phe Tyr Lys
        275                 280                 285

Lys Trp Glu Leu Glu Ala Cys Val Asp Ala Ala Leu Leu Ala Thr Gln
    290                 295                 300

Met Asp Arg Val Asn Ala Ile Pro Phe Thr Tyr Glu Gln Leu Asp Val
305                 310                 315                 320

Leu Lys His Lys Leu Asp Glu Leu Tyr Pro Gln Gly Tyr Pro Glu Ser
                325                 330                 335

```
Val Ile Gln His Leu Gly Tyr Leu Phe Leu Lys Met Ser Pro Glu Asp
                340                 345                 350

Ile Arg Lys Trp Asn Val Thr Ser Leu Glu Thr Leu Lys Ala Leu Leu
            355                 360                 365

Glu Val Asn Lys Gly His Glu Met Ser Pro Gln Ala Pro Arg Arg Pro
        370                 375                 380

Leu Pro Gln Val Ala Thr Leu Ile Asp Arg Phe Val Lys Gly Arg Gly
385                 390                 395                 400

Gln Leu Asp Lys Asp Thr Leu Asp Thr Leu Thr Ala Phe Tyr Pro Gly
                405                 410                 415

Tyr Leu Cys Ser Leu Ser Pro Glu Glu Leu Ser Ser Val Pro Pro Ser
            420                 425                 430

Ser Ile Trp Ala Val Arg Pro Gln Asp Leu Asp Thr Cys Asp Pro Arg
        435                 440                 445

Gln Leu Asp Val Leu Tyr Pro Lys Ala Arg Leu Ala Phe Gln Asn Met
    450                 455                 460

Asn Gly Ser Glu Tyr Phe Val Lys Ile Gln Ser Phe Leu Gly Gly Ala
465                 470                 475                 480

Pro Thr Glu Asp Leu Lys Ala Leu Ser Gln Gln Asn Val Ser Met Asp
                485                 490                 495

Leu Ala Thr Phe Met Lys Leu Arg Thr Asp Ala Val Leu Pro Leu Thr
            500                 505                 510

Val Ala Glu Val Gln Lys Leu Leu Gly Pro His Val Glu Gly Leu Lys
        515                 520                 525

Ala Glu Glu Arg His Arg Pro Val Arg Asp Trp Ile Leu Arg Gln Arg
    530                 535                 540

Gln Asp Asp Leu Asp Thr Leu Gly Leu Gly Leu Gln
545                 550                 555

<210> SEQ ID NO 182
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140
```

```
Ser Val Cys Lys Met Thr His Gly Lys Thr Arg Trp Thr Gln Pro Gln
145                 150                 155                 160

Leu Ile Cys Thr Gly Gly Gly Gly Ser Gly Gly Gly Gly Ser Gly
            165                 170                 175

Leu Asn Asp Ile Phe Glu Ala Gln Lys Ile Glu Trp His Glu Gly Gly
            180                 185                 190

Gly Gly Ser His His His His His His His
        195                 200
```

<210> SEQ ID NO 183
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

```
Glu Val Gln Leu Leu Gln Ser Gly Gly Gly Leu Val Gln Pro Gly Gly
1               5                   10                  15

Ser Leu Arg Leu Ser Cys Ala Ala Ser Gly Phe Met Phe Ser Arg Tyr
            20                  25                  30

Pro Met His Trp Val Arg Gln Ala Pro Gly Lys Gly Leu Glu Trp Val
            35                  40                  45

Gly Ser Ile Ser Gly Ser Gly Gly Ala Thr Pro Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Tyr Gln Ile Leu Thr Gly Asn Ala Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
```

```
                  290                 295                 300
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Cys Thr Leu Pro Pro Ser Arg Glu Glu Met Thr Lys Asn Gln Val
                355                 360                 365

Ser Leu Ser Cys Ala Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
    450
```

<210> SEQ ID NO 184
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 184

```
Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Lys Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Tyr Trp Thr Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
    210

<210> SEQ ID NO 185
<211> LENGTH: 600
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Glu Val Gln Leu Leu Gln Ser Gly Gly Gly Leu Val Gln Pro Gly Gly
1               5                   10                  15

Ser Leu Arg Leu Ser Cys Ala Ala Ser Gly Phe Met Phe Ser Arg Tyr
            20                  25                  30

Pro Met His Trp Val Arg Gln Ala Pro Gly Lys Gly Leu Glu Trp Val
        35                  40                  45

Gly Ser Ile Ser Gly Ser Gly Gly Ala Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Tyr Gln Ile Leu Thr Gly Asn Ala Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

```
Ile Glu Lys Thr Ile Ser Lys Ala Lys Gly Gln Pro Arg Glu Pro Gln
            340                 345                 350

Val Cys Thr Leu Pro Pro Ser Arg Glu Glu Met Thr Lys Asn Gln Val
        355                 360                 365

Ser Leu Ser Cys Ala Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys Gly Gly Gly Ser Gly Gly Gly Ser Gly Gly
    450                 455                 460

Gly Gly Ser Ala Pro Thr Ser Ser Ser Thr Lys Lys Thr Gln Leu Gln
465                 470                 475                 480

Leu Glu His Leu Leu Leu Asp Leu Gln Met Ile Leu Asn Gly Ile Asn
                485                 490                 495

Asn Tyr Lys Asn Pro Lys Leu Thr Arg Met Leu Thr Phe Lys Phe Tyr
            500                 505                 510

Met Pro Lys Lys Ala Thr Glu Leu Lys His Leu Gln Cys Leu Glu Glu
        515                 520                 525

Glu Leu Lys Pro Leu Glu Glu Val Leu Asn Leu Ala Gln Ser Lys Asn
    530                 535                 540

Phe His Leu Arg Pro Arg Asp Leu Ile Ser Asn Ile Asn Val Ile Val
545                 550                 555                 560

Leu Glu Leu Lys Gly Ser Glu Thr Thr Phe Met Cys Glu Tyr Ala Asp
                565                 570                 575

Glu Thr Ala Thr Ile Val Glu Phe Leu Asn Arg Trp Ile Thr Phe Cys
            580                 585                 590

Gln Ser Ile Ile Ser Thr Leu Thr
            595                 600

<210> SEQ ID NO 186
<211> LENGTH: 619
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Glu Val Gln Leu Leu Gln Ser Gly Gly Gly Leu Val Gln Pro Gly Gly
1               5                   10                  15

Ser Leu Arg Leu Ser Cys Ala Ala Ser Gly Phe Met Phe Ser Arg Tyr
            20                  25                  30

Pro Met His Trp Val Arg Gln Ala Pro Gly Lys Gly Leu Glu Trp Val
        35                  40                  45

Gly Ser Ile Ser Gly Ser Gly Gly Ala Thr Pro Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued

```
                85                  90                  95
Ala Lys Asp Phe Tyr Gln Ile Leu Thr Gly Asn Ala Phe Asp Tyr Trp
                100                 105                 110
Gly Gln Gly Thr Thr Val Thr Val Ser Ser Ala Ser Thr Lys Gly Pro
                115                 120                 125
Ser Val Phe Pro Leu Ala Pro Ser Ser Lys Ser Thr Ser Gly Gly Thr
                130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Gln Thr Tyr Ile Cys Asn Val Asn
                195                 200                 205
His Lys Pro Ser Asn Thr Lys Val Asp Lys Arg Val Glu Pro Lys Ser
                210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
                260                 265                 270
His Glu Asp Pro Glu Val Lys Phe Asn Trp Tyr Val Asp Gly Val Glu
                275                 280                 285
Val His Asn Ala Lys Thr Lys Pro Arg Glu Glu Gln Tyr Asn Ser Thr
                290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
                340                 345                 350
Val Cys Thr Leu Pro Pro Ser Arg Glu Glu Met Thr Lys Asn Gln Val
                355                 360                 365
Ser Leu Ser Cys Ala Val Lys Gly Phe Tyr Pro Ser Asp Ile Ala Val
                370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Val Ser Lys Leu Thr
                405                 410                 415
Val Asp Lys Ser Arg Trp Gln Gln Gly Asn Val Phe Ser Cys Ser Val
                420                 425                 430
Met His Glu Ala Leu His Asn His Tyr Thr Gln Lys Ser Leu Ser Leu
                435                 440                 445
Ser Pro Gly Lys Gly Gly Gly Ser Gly Gly Gly Ser Gly Gly
                450                 455                 460
Gly Gly Ser Asp Cys Asp Ile Glu Gly Lys Asp Gly Lys Gln Tyr Glu
465                 470                 475                 480
Ser Val Leu Met Val Ser Ile Asp Gln Leu Leu Asp Ser Met Lys Glu
                485                 490                 495
Ile Gly Ser Asn Cys Leu Asn Asn Glu Phe Asn Phe Lys Arg His
                500                 505                 510
```

```
Ile Cys Asp Ala Asn Lys Glu Gly Met Phe Leu Phe Arg Ala Ala Arg
            515                 520                 525

Lys Leu Arg Gln Phe Leu Lys Met Asn Ser Thr Gly Asp Phe Asp Leu
        530                 535                 540

His Leu Leu Lys Val Ser Glu Gly Thr Thr Ile Leu Leu Asn Cys Thr
545                 550                 555                 560

Gly Gln Val Lys Gly Arg Lys Pro Ala Ala Leu Gly Glu Ala Gln Pro
                565                 570                 575

Thr Lys Ser Leu Glu Glu Asn Lys Ser Leu Lys Glu Gln Lys Lys Leu
            580                 585                 590

Asn Asp Leu Cys Phe Leu Lys Arg Leu Leu Gln Glu Ile Lys Thr Cys
                595                 600                 605

Trp Asn Lys Ile Leu Met Gly Thr Lys Glu His
            610                 615
```

<210> SEQ ID NO 187
<211> LENGTH: 491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

```
Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ala Gly Ile Ser Trp Asp Ser Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Leu Gly Ala Tyr Gln Trp Val Glu Gly Phe Asp Tyr Trp
            100                 105                 110

Gly Gln Gly Thr Leu Val Thr Val Ser Ser Ala Ser Thr Gly Gly Gly
        115                 120                 125

Gly Ser Gly Gly Gly Gly Ser Gly Gly Gly Gly Ser Gly Gly Gly Gly
    130                 135                 140

Ser Ser Tyr Glu Leu Thr Gln Asp Pro Ala Val Ser Val Ala Leu Gly
145                 150                 155                 160

Gln Thr Val Arg Ile Thr Cys Gln Gly Asp Ser Leu Arg Ser Tyr Tyr
                165                 170                 175

Ala Ser Trp Tyr Gln Gln Lys Pro Gly Gln Ala Pro Val Leu Val Ile
            180                 185                 190

Tyr Gly Lys Asn Asn Arg Pro Ser Gly Ile Pro Asp Arg Phe Ser Gly
        195                 200                 205

Ser Thr Ser Gly Asn Ser Ala Ser Leu Thr Ile Thr Gly Ala Gln Ala
    210                 215                 220

Glu Asp Glu Ala Asp Tyr Tyr Cys Asn Ser Arg Asp Ser Pro Gly Asn
225                 230                 235                 240

Gln Trp Val Phe Gly Gly Gly Thr Lys Val Thr Val Leu Gly Gly Gly
```

```
                    245                 250                 255
Gly Gly Ser Gly Gly Gly Ser Asp Lys Thr His Thr Cys Pro Pro
            260                 265                 270
Cys Pro Ala Pro Glu Leu Leu Gly Gly Pro Ser Val Phe Leu Phe Pro
            275                 280                 285
Pro Lys Pro Lys Asp Thr Leu Met Ile Ser Arg Thr Pro Glu Val Thr
290                 295                 300
Cys Val Val Val Asp Val Ser His Glu Asp Pro Glu Val Lys Phe Asn
305                 310                 315                 320
Trp Tyr Val Asp Gly Val Glu Val His Asn Ala Lys Thr Lys Pro Arg
                325                 330                 335
Glu Glu Gln Tyr Asn Ser Thr Tyr Arg Val Val Ser Val Leu Thr Val
            340                 345                 350
Leu His Gln Asp Trp Leu Asn Gly Lys Glu Tyr Lys Cys Lys Val Ser
            355                 360                 365
Asn Lys Ala Leu Pro Ala Pro Ile Glu Lys Thr Ile Ser Lys Ala Lys
370                 375                 380
Gly Gln Pro Arg Glu Pro Gln Val Tyr Thr Leu Pro Pro Cys Arg Glu
385                 390                 395                 400
Glu Met Thr Lys Asn Gln Val Ser Leu Trp Cys Leu Val Lys Gly Phe
                405                 410                 415
Tyr Pro Ser Asp Ile Ala Val Glu Trp Glu Ser Asn Gly Gln Pro Glu
            420                 425                 430
Asn Asn Tyr Lys Thr Thr Pro Pro Val Leu Asp Ser Asp Gly Ser Phe
            435                 440                 445
Phe Leu Tyr Ser Lys Leu Thr Val Asp Lys Ser Arg Trp Gln Gln Gly
450                 455                 460
Asn Val Phe Ser Cys Ser Val Met His Glu Ala Leu His Asn His Tyr
465                 470                 475                 480
Thr Gln Lys Ser Leu Ser Leu Ser Pro Gly Lys
                485                 490

<210> SEQ ID NO 188
<211> LENGTH: 753
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Gln Val Gln Leu Val Gln Ser Gly Gly Gly Leu Val Gln Pro Gly Gly
1               5                   10                  15
Ser Leu Arg Leu Ser Cys Ala Ala Ser Gly Phe Thr Phe Asp Asp Tyr
            20                  25                  30
Ala Met His Trp Val Arg Gln Ala Pro Gly Lys Gly Leu Glu Trp Val
        35                  40                  45
Ala Gly Ile Ser Trp Asp Ser Gly Ser Thr Gly Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Leu Tyr Tyr Cys
                85                  90                  95
Ala Arg Asp Leu Gly Ala Tyr Gln Trp Val Glu Gly Phe Asp Tyr Trp
            100                 105                 110
```

```
Gly Gln Gly Thr Leu Val Thr Val Ser Ser Ala Ser Thr Gly Gly
            115                 120                 125
Gly Ser Gly Gly Gly Ser Gly Gly Gly Ser Gly Gly Gly Gly
130                 135                 140
Ser Ser Tyr Glu Leu Thr Gln Asp Pro Ala Val Ser Val Ala Leu Gly
145                 150                 155                 160
Gln Thr Val Arg Ile Thr Cys Gln Gly Asp Ser Leu Arg Ser Tyr Tyr
                165                 170                 175
Ala Ser Trp Tyr Gln Gln Lys Pro Gly Gln Ala Pro Val Leu Val Ile
            180                 185                 190
Tyr Gly Lys Asn Asn Arg Pro Ser Gly Ile Pro Asp Arg Phe Ser Gly
        195                 200                 205
Ser Thr Ser Gly Asn Ser Ala Ser Leu Thr Ile Thr Gly Ala Gln Ala
    210                 215                 220
Glu Asp Glu Ala Asp Tyr Tyr Cys Asn Ser Arg Asp Ser Pro Gly Asn
225                 230                 235                 240
Gln Trp Val Phe Gly Gly Gly Thr Lys Val Thr Val Leu Gly Gly Gly
                245                 250                 255
Gly Gly Ser Gly Gly Gly Gly Ser Asp Lys Thr His Thr Cys Pro Pro
            260                 265                 270
Cys Pro Ala Pro Glu Leu Leu Gly Gly Pro Ser Val Phe Leu Phe Pro
        275                 280                 285
Pro Lys Pro Lys Asp Thr Leu Met Ile Ser Arg Thr Pro Glu Val Thr
    290                 295                 300
Cys Val Val Val Asp Val Ser His Glu Asp Pro Glu Val Lys Phe Asn
305                 310                 315                 320
Trp Tyr Val Asp Gly Val Glu Val His Asn Ala Lys Thr Lys Pro Arg
                325                 330                 335
Glu Glu Gln Tyr Asn Ser Thr Tyr Arg Val Val Ser Val Leu Thr Val
            340                 345                 350
Leu His Gln Asp Trp Leu Asn Gly Lys Glu Tyr Lys Cys Lys Val Ser
        355                 360                 365
Asn Lys Ala Leu Pro Ala Pro Ile Glu Lys Thr Ile Ser Lys Ala Lys
    370                 375                 380
Gly Gln Pro Arg Glu Pro Gln Val Tyr Thr Leu Pro Pro Cys Arg Glu
385                 390                 395                 400
Glu Met Thr Lys Asn Gln Val Ser Leu Trp Cys Leu Val Lys Gly Phe
                405                 410                 415
Tyr Pro Ser Asp Ile Ala Val Glu Trp Glu Ser Asn Gly Gln Pro Glu
            420                 425                 430
Asn Asn Tyr Lys Thr Thr Pro Pro Val Leu Asp Ser Asp Gly Ser Phe
        435                 440                 445
Phe Leu Tyr Ser Lys Leu Thr Val Asp Lys Ser Arg Trp Gln Gln Gly
    450                 455                 460
Asn Val Phe Ser Cys Ser Val Met His Glu Ala Leu His Asn His Tyr
465                 470                 475                 480
Thr Gln Lys Ser Leu Ser Leu Ser Pro Gly Lys Gly Gly Gly Gly Ser
                485                 490                 495
Gly Gly Gly Gly Ser Gly Gly Gly Ser Gln Val Gln Leu Gln Gln
            500                 505                 510
Ser Gly Pro Glu Leu Val Lys Pro Gly Ala Ser Val Lys Met Ser Cys
        515                 520                 525
Lys Ala Ser Gly Tyr Thr Phe Thr Asp Tyr Val Ile Asn Trp Gly Lys
```

```
                530                 535                 540
Gln Arg Ser Gly Gln Gly Leu Glu Trp Ile Gly Glu Ile Tyr Pro Gly
545                 550                 555                 560

Ser Gly Thr Asn Tyr Tyr Asn Glu Lys Phe Lys Ala Lys Ala Thr Leu
                565                 570                 575

Thr Ala Asp Lys Ser Ser Asn Ile Ala Tyr Met Gln Leu Ser Ser Leu
                580                 585                 590

Thr Ser Glu Asp Ser Ala Val Tyr Phe Cys Ala Arg Arg Gly Arg Tyr
                595                 600                 605

Gly Leu Tyr Ala Met Asp Tyr Trp Gly Gln Gly Thr Ser Val Thr Val
                610                 615                 620

Ser Ser Gly Gly Gly Ser Gly Gly Gly Ser Gly Gly Gly
625                 630                 635                 640

Ser Gly Gly Gly Ser Asp Ile Gln Met Thr Gln Thr Thr Ser Ser
                645                 650                 655

Leu Ser Ala Ser Leu Gly Asp Arg Val Thr Ile Ser Cys Arg Ala Ser
                660                 665                 670

Gln Asp Ile Ser Asn Tyr Leu Asn Trp Tyr Gln Gln Lys Pro Asp Gly
                675                 680                 685

Thr Val Lys Leu Leu Ile Tyr Tyr Thr Ser Arg Leu His Ser Gly Val
                690                 695                 700

Pro Ser Arg Phe Ser Gly Ser Gly Ser Gly Thr Asp Tyr Ser Leu Thr
705                 710                 715                 720

Ile Asn Asn Leu Glu Gln Glu Asp Ile Ala Thr Tyr Phe Cys Gln Gln
                725                 730                 735

Gly Asn Thr Arg Pro Trp Thr Phe Gly Gly Thr Lys Leu Glu Ile
                740                 745                 750

Lys

<210> SEQ ID NO 189
<211> LENGTH: 751
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ala Gly Ile Ser Trp Asp Ser Gly Ser Thr Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Asp Leu Gly Ala Tyr Gln Trp Val Glu Gly Phe Asp Tyr Trp
                100                 105                 110

Gly Gln Gly Thr Leu Val Thr Val Ser Ser Ala Ser Thr Gly Gly Gly
            115                 120                 125

Gly Ser Gly Gly Gly Gly Ser Gly Gly Gly Gly Ser Gly Gly Gly Gly
```

```
                130             135             140
Ser Ser Tyr Glu Leu Thr Gln Asp Pro Ala Val Ser Val Ala Leu Gly
145             150             155             160
Gln Thr Val Arg Ile Thr Cys Gln Gly Asp Ser Leu Arg Ser Tyr Tyr
                165             170             175
Ala Ser Trp Tyr Gln Gln Lys Pro Gly Gln Ala Pro Val Leu Val Ile
            180             185             190
Tyr Gly Lys Asn Asn Arg Pro Ser Gly Ile Pro Asp Arg Phe Ser Gly
            195             200             205
Ser Thr Ser Gly Asn Ser Ala Ser Leu Thr Ile Thr Gly Ala Gln Ala
            210             215             220
Glu Asp Glu Ala Asp Tyr Tyr Cys Asn Ser Arg Asp Ser Pro Gly Asn
225             230             235             240
Gln Trp Val Phe Gly Gly Gly Thr Lys Val Thr Val Leu Gly Gly Gly
                245             250             255
Gly Ser Gly Gly Gly Gly Ser Asp Lys Thr His Thr Cys Pro Pro
            260             265             270
Cys Pro Ala Pro Glu Leu Leu Gly Gly Pro Ser Val Phe Leu Phe Pro
            275             280             285
Pro Lys Pro Lys Asp Thr Leu Met Ile Ser Arg Thr Pro Glu Val Thr
            290             295             300
Cys Val Val Val Asp Val Ser His Glu Asp Pro Glu Val Lys Phe Asn
305             310             315             320
Trp Tyr Val Asp Gly Val Glu Val His Asn Ala Lys Thr Lys Pro Arg
                325             330             335
Glu Glu Gln Tyr Asn Ser Thr Tyr Arg Val Val Ser Val Leu Thr Val
            340             345             350
Leu His Gln Asp Trp Leu Asn Gly Lys Glu Tyr Lys Cys Lys Val Ser
            355             360             365
Asn Lys Ala Leu Pro Ala Pro Ile Glu Lys Thr Ile Ser Lys Ala Lys
            370             375             380
Gly Gln Pro Arg Glu Pro Gln Val Tyr Thr Leu Pro Pro Cys Arg Glu
385             390             395             400
Glu Met Thr Lys Asn Gln Val Ser Leu Trp Cys Leu Val Lys Gly Phe
                405             410             415
Tyr Pro Ser Asp Ile Ala Val Glu Trp Glu Ser Asn Gly Gln Pro Glu
            420             425             430
Asn Asn Tyr Lys Thr Thr Pro Pro Val Leu Asp Ser Asp Gly Ser Phe
            435             440             445
Phe Leu Tyr Ser Lys Leu Thr Val Asp Lys Ser Arg Trp Gln Gln Gly
            450             455             460
Asn Val Phe Ser Cys Ser Val Met His Glu Ala Leu His Asn His Tyr
465             470             475             480
Thr Gln Lys Ser Leu Ser Leu Ser Pro Gly Lys Gly Gly Gly Gly Ser
                485             490             495
Gly Gly Gly Gly Ser Gly Gly Gly Ser Gln Val Gln Leu Val Gln
            500             505             510
Ser Gly Gly Gly Val Val Gln Pro Gly Arg Ser Leu Arg Leu Ser Cys
            515             520             525
Lys Ala Ser Gly Tyr Thr Phe Thr Arg Tyr Thr Met His Trp Val Arg
            530             535             540
Gln Ala Pro Gly Lys Gly Leu Glu Trp Ile Gly Tyr Ile Asn Pro Ser
545             550             555             560
```

```
Arg Gly Tyr Thr Asn Tyr Asn Gln Lys Val Lys Asp Arg Phe Thr Ile
                565                 570                 575

Ser Arg Asp Asn Ser Lys Asn Thr Ala Phe Leu Gln Met Asp Ser Leu
            580                 585                 590

Arg Pro Glu Asp Thr Gly Val Tyr Phe Cys Ala Arg Tyr Tyr Asp Asp
        595                 600                 605

His Tyr Ser Leu Asp Tyr Trp Gly Gln Gly Thr Pro Val Thr Val Ser
    610                 615                 620

Ser Gly Gly Gly Gly Ser Gly Gly Gly Ser Gly Gly Gly Gly Ser
625                 630                 635                 640

Gly Gly Gly Gly Ser Asp Ile Gln Met Thr Gln Ser Pro Ser Ser Leu
                645                 650                 655

Ser Ala Ser Val Gly Asp Arg Val Thr Ile Thr Cys Ser Ala Ser Ser
            660                 665                 670

Ser Val Ser Tyr Met Asn Trp Tyr Gln Gln Thr Pro Gly Lys Ala Pro
        675                 680                 685

Lys Arg Trp Ile Tyr Asp Thr Ser Lys Leu Ala Ser Gly Val Pro Ser
    690                 695                 700

Arg Phe Ser Gly Ser Gly Ser Gly Thr Asp Tyr Thr Phe Thr Ile Ser
705                 710                 715                 720

Ser Leu Gln Pro Glu Asp Ile Ala Thr Tyr Tyr Cys Gln Gln Trp Ser
                725                 730                 735

Ser Asn Pro Phe Thr Phe Gly Gln Gly Thr Lys Leu Gln Ile Thr
            740                 745                 750

<210> SEQ ID NO 190
<211> LENGTH: 711
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
            20                  25                  30

Asn Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Phe Tyr Asn Pro Ser
    50                  55                  60

Leu Lys Ser Arg Val Thr Ile Ser Val Asp Thr Ser Lys Thr Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Thr Met Thr Gly Leu Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
```

```
                165                 170                 175
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Trp
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Gly Gly Ser Gly Gly Gly Ser Gly Gly Gly Gly Ser
            450                 455                 460

Gln Val Gln Leu Gln Gln Ser Gly Pro Glu Leu Val Lys Pro Gly Ala
465                 470                 475                 480

Ser Val Lys Met Ser Cys Lys Ala Ser Gly Tyr Thr Phe Thr Asp Tyr
            485                 490                 495

Val Ile Asn Trp Gly Lys Gln Arg Ser Gly Gln Gly Leu Glu Trp Ile
            500                 505                 510

Gly Glu Ile Tyr Pro Gly Ser Gly Thr Asn Tyr Tyr Asn Glu Lys Phe
            515                 520                 525

Lys Ala Lys Ala Thr Leu Thr Ala Asp Lys Ser Ser Asn Ile Ala Tyr
            530                 535                 540

Met Gln Leu Ser Ser Leu Thr Ser Glu Asp Ser Ala Val Tyr Phe Cys
545                 550                 555                 560

Ala Arg Arg Gly Arg Tyr Gly Leu Tyr Ala Met Asp Tyr Trp Gly Gln
            565                 570                 575

Gly Thr Ser Val Thr Val Ser Ser Gly Gly Gly Ser Gly Gly Gly
            580                 585                 590
```

```
Gly Ser Gly Gly Gly Ser Gly Gly Gly Ser Asp Ile Gln Met
         595                 600                 605

Thr Gln Thr Thr Ser Ser Leu Ser Ala Ser Leu Gly Asp Arg Val Thr
610                 615                 620

Ile Ser Cys Arg Ala Ser Gln Asp Ile Ser Asn Tyr Leu Asn Trp Tyr
625                 630                 635                 640

Gln Gln Lys Pro Asp Gly Thr Val Lys Leu Leu Ile Tyr Tyr Thr Ser
            645                 650                 655

Arg Leu His Ser Gly Val Pro Ser Arg Phe Ser Gly Ser Gly Ser Gly
            660                 665                 670

Thr Asp Tyr Ser Leu Thr Ile Asn Asn Leu Glu Gln Glu Asp Ile Ala
            675                 680                 685

Thr Tyr Phe Cys Gln Gln Gly Asn Thr Arg Pro Trp Thr Phe Gly Gly
            690                 695                 700

Gly Thr Lys Leu Glu Ile Lys
705                 710

<210> SEQ ID NO 191
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu Gly Gln
            100                 105                 110

Pro Lys Ala Asn Pro Thr Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Gly Ser Pro Val Lys
145                 150                 155                 160

Ala Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser Gly Gly Gly Ser Gly Gly Gly
    210                 215                 220

Gly Ser Gly Gly Gly Gly Ser Ala Pro Thr Ser Ser Ser Thr Lys Lys
```

```
225                 230                 235                 240
Thr Gln Leu Gln Leu Glu His Leu Leu Leu Asp Leu Gln Met Ile Leu
                245                 250                 255
Asn Gly Ile Asn Asn Tyr Lys Asn Pro Lys Leu Thr Arg Met Leu Thr
                260                 265                 270
Ala Lys Phe Ala Met Pro Lys Lys Ala Thr Glu Leu Lys His Leu Gln
                275                 280                 285
Cys Leu Glu Glu Glu Leu Lys Pro Leu Glu Glu Val Leu Asn Leu Ala
                290                 295                 300
Gln Ser Lys Asn Phe His Leu Arg Pro Arg Asp Leu Ile Ser Asn Ile
305                 310                 315                 320
Asn Val Ile Val Leu Glu Leu Lys Gly Ser Glu Thr Thr Phe Met Cys
                325                 330                 335
Glu Tyr Ala Asp Glu Thr Ala Thr Ile Val Glu Phe Leu Asn Arg Trp
                340                 345                 350
Ile Thr Phe Cys Gln Ser Ile Ile Ser Thr Leu Thr
                355                 360

<210> SEQ ID NO 192
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
                20                  25                  30
Ile Met Met Trp Val Arg Gln Ala Pro Gly Lys Gly Leu Glu Trp Val
                35                  40                  45
Ser Ser Ile Tyr Pro Ser Gly Gly Ile Thr Phe Tyr Ala Asp Thr Val
                50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ile Lys Leu Gly Thr Val Thr Thr Val Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Arg Val Glu Pro Lys Ser Cys Asp
                210                 215                 220
```

```
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Glu Glu Met Thr Lys Asn Gln Val Ser Leu
        355                 360                 365

Ser Cys Ala Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 193
<211> LENGTH: 711
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Lys Asn Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125
```

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Trp
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Ser Gly Gly Gly Gly Ser
    450                 455                 460

Gln Val Gln Leu Gln Gln Ser Gly Pro Glu Leu Val Lys Pro Gly Ala
465                 470                 475                 480

Ser Val Lys Met Ser Cys Lys Ala Ser Gly Tyr Thr Phe Thr Asp Tyr
                485                 490                 495

Val Ile Asn Trp Gly Lys Gln Arg Ser Gly Gln Gly Leu Glu Trp Ile
            500                 505                 510

Gly Glu Ile Tyr Pro Gly Ser Gly Thr Asn Tyr Tyr Asn Glu Lys Phe
        515                 520                 525

Lys Ala Lys Ala Thr Leu Thr Ala Asp Lys Ser Ser Asn Ile Ala Tyr
    530                 535                 540
```

```
Met Gln Leu Ser Ser Leu Thr Ser Glu Asp Ser Ala Val Tyr Phe Cys
545                 550                 555                 560

Ala Arg Arg Gly Arg Tyr Gly Leu Tyr Ala Met Asp Tyr Trp Gly Gln
            565                 570                 575

Gly Thr Ser Val Thr Val Ser Ser Gly Gly Gly Gly Ser Gly Gly Gly
            580                 585                 590

Gly Ser Gly Gly Gly Ser Gly Gly Gly Ser Asp Ile Gln Met
        595                 600                 605

Thr Gln Thr Thr Ser Ser Leu Ser Ala Ser Leu Gly Asp Arg Val Thr
        610                 615                 620

Ile Ser Cys Arg Ala Ser Gln Asp Ile Ser Asn Tyr Leu Asn Trp Tyr
625                 630                 635                 640

Gln Gln Lys Pro Asp Gly Thr Val Lys Leu Leu Ile Tyr Tyr Thr Ser
            645                 650                 655

Arg Leu His Ser Gly Val Pro Ser Arg Phe Ser Gly Ser Gly Ser Gly
            660                 665                 670

Thr Asp Tyr Ser Leu Thr Ile Asn Asn Leu Glu Gln Glu Asp Ile Ala
            675                 680                 685

Thr Tyr Phe Cys Gln Gln Gly Asn Thr Arg Pro Trp Thr Phe Gly Gly
            690                 695                 700

Gly Thr Lys Leu Glu Ile Lys
705                 710

<210> SEQ ID NO 194
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Glu Gly Lys Asn Gly Ala Phe Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190
```

-continued

```
Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Trp
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Gly Gly Ser Gly Gly Gly Gly Ser Gly Gly Gly Gly Ser
    450                 455                 460

Glu Val Gln Leu Gln Glu Ser Gly Pro Gly Leu Val Lys Pro Ser Gln
465                 470                 475                 480

Ser Leu Ser Leu Thr Cys Thr Val Thr Gly Tyr Ser Ile Thr Ser Asp
                485                 490                 495

Tyr Ala Trp Asn Trp Ile Arg Gln Phe Pro Gly Asn Lys Leu Glu Trp
            500                 505                 510

Met Gly Tyr Ile Thr Tyr Ser Gly Ser Thr Ser Tyr Asn Pro Ser Leu
            515                 520                 525

Glu Ser Arg Ile Ser Ile Thr Arg Asp Thr Ser Thr Asn Gln Phe Phe
530                 535                 540

Leu Gln Leu Asn Ser Val Thr Thr Glu Asp Thr Ala Thr Tyr Tyr Cys
545                 550                 555                 560

Ala Arg Gly Gly Tyr Tyr Gly Ser Ser Trp Gly Val Phe Ala Tyr Trp
                565                 570                 575

Gly Gln Gly Thr Leu Val Thr Val Ser Ala Gly Gly Gly Gly Ser Gly
            580                 585                 590

Gly Gly Gly Ser Gly Gly Gly Gly Ser Gly Gly Gly Gly Ser Asp Ile
                595                 600                 605
```

Gln Met Thr Gln Ser Pro Ala Ser Leu Ser Ala Ser Val Gly Glu Thr
610                 615                 620

Val Thr Ile Thr Cys Arg Val Ser Glu Asn Ile Tyr Ser Tyr Leu Ala
625                 630                 635                 640

Trp Tyr Gln Gln Lys Gln Gly Lys Ser Pro Gln Leu Leu Val Tyr Asn
                645                 650                 655

Ala Lys Thr Leu Ala Glu Gly Val Pro Ser Arg Phe Ser Gly Ser Gly
            660                 665                 670

Ser Gly Thr Gln Phe Ser Leu Lys Ile Asn Ser Leu Gln Pro Glu Asp
        675                 680                 685

Phe Gly Ser Tyr Tyr Cys Gln His His Tyr Gly Thr Pro Trp Thr Phe
690                 695                 700

Gly Gly Gly Thr Lys Leu Glu Ile Lys
705                 710

<210> SEQ ID NO 195
<211> LENGTH: 708
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Lys Asn Gly Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

```
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Cys Arg Glu Glu Met Thr Lys Asn Gln Val Ser Leu Trp
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Gly Gly Ser Gly Gly Gly Ser Gly Gly Gly Gly Ser
        450                 455                 460

Gln Val Gln Leu Gln Gln Ser Ala Val Glu Leu Ala Arg Pro Gly Ala
465                 470                 475                 480

Ser Val Lys Met Ser Cys Lys Ala Ser Gly Tyr Thr Phe Thr Ser Phe
                485                 490                 495

Thr Met His Trp Val Lys Gln Arg Pro Gly Gln Gly Leu Glu Trp Ile
            500                 505                 510

Gly Tyr Ile Asn Pro Ser Ser Gly Tyr Thr Glu Tyr Asn Gln Lys Phe
            515                 520                 525

Lys Asp Lys Thr Thr Leu Thr Ala Asp Lys Ser Ser Ser Thr Ala Tyr
        530                 535                 540

Met Gln Leu Asp Ser Leu Thr Ser Asp Asp Ser Ala Val Tyr Tyr Cys
545                 550                 555                 560

Val Arg Gly Ser Ser Arg Gly Phe Asp Tyr Trp Gly Gln Gly Thr Leu
                565                 570                 575

Val Thr Val Ser Ala Gly Gly Gly Gly Ser Gly Gly Gly Gly Ser Gly
            580                 585                 590

Gly Gly Ser Gly Gly Gly Gly Ser Asp Ile Gln Met Ile Gln Ser
        595                 600                 605

Pro Ala Ser Leu Ser Val Ser Val Gly Glu Thr Val Thr Ile Thr Cys
            610                 615                 620

Arg Ala Ser Glu Asn Ile Tyr Ser Asn Leu Ala Trp Phe Gln Gln Lys
625                 630                 635                 640

Gln Gly Lys Ser Pro Gln Leu Leu Val Tyr Ala Ala Thr Asn Leu Ala
                645                 650                 655

Asp Gly Val Pro Ser Arg Phe Ser Gly Ser Gly Ser Gly Thr Gln Tyr
            660                 665                 670
```

```
Ser Leu Lys Ile Asn Ser Leu Gln Ser Glu Asp Phe Gly Ile Tyr Tyr
            675                 680                 685

Cys Gln His Phe Trp Gly Thr Pro Arg Thr Phe Gly Gly Gly Thr Lys
        690                 695                 700

Leu Glu Ile Lys
705

<210> SEQ ID NO 196

<400> SEQUENCE: 196

000

<210> SEQ ID NO 197
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 198
<211> LENGTH: 1653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198
tacaacttct tcccacggaa acccaagtgg gacaagaacc agatcaccta ccggatcatc    60
ggctacaccc ctgacctgga tcctgagaca gtggacgatg ccttcgccag agccttccaa   120
gtttggagcg acgtgacccc tctgcggttc tccagaatcc atgatggcga ggccgacatc   180
atgatcaact cggcagatg ggagcacggc acggctacc cttttgatgg caaggatggc    240
ctgctggccc acgcttttgc ccctggaaca ggtgttggcg cgactctca cttcgacgac   300 gatgagttgt ggaccctcgg cgaaggacag gtcgtcagag tgaagtacgg caacgccgat   360
ggcgagtact gcaagttccc cttcctgttc aacggcaaag agtacaactc ctgcaccgac   420
accggcagat ctgacggctt cctgtggtgc tccaccacct acaactttga aggacggc    480 aaatacggct ctgccctca cgaggccctg tttaccatgg gcggaaatgc tgagggccag   540
ccatgcaagt ttccattccg gttccaaggg acctcctacg acagctgtac caccgaggga   600
```

```
agaaccgatg gctatcgttg gtgcggcacc acagaggact acgacagaga caagaagtat    660
ggcttctgtc ccgagacagc catgtctacc gtcggcggca attctgaagg cgcccttgt    720 gtgttccctt tcaccttcct gggcaacaaa tacgagtcct gcacctccgc tggccgctct    780
gatggaaaaa tgtggtgcgc taccaccgcc aactacgacg acgacagaaa gtgggctttt    840
tgtcctgacc agggctactc cctgtttctg gtggccgctc acgagtttgg ccatgctatg    900
ggcctcgagc actctcaaga tcccggtgca ctgatggccc ctatctacac ctacaccaag    960
aacttccggc tgtcccagga cgacatcaag ggcatccaag agctgtacgg cgcctctcct   1020
gatatcgatc tcggcaccgg acctactcct cactgggac ctgtgacacc cgagatctgc    1080
aagcaggaca tcgtgttcga cggaatcgcc cagatccggg gcgagatctt cttttttaag   1140
gaccggttca tctggcggac agtgacccct agagacaagc ctatgggacc tctgctggtg   1200
gctaccttct ggcctgagct gcctgagaag atcgacgccg tgtacgaggc ccctcaagag   1260
gaaaaggccg tcttttttcgc cggcaacgag tactggatct actccgcttc taccctggaa   1320
cggggctacc ccaagcctct gacatctctg ggactgcctc cagacgtgca gagagtggac   1380
gccgccttca actggtccaa gaacaagaaa acctacatct cgccggggga caagttctgg   1440
cggtacaacg aagtgaagaa aaagatggac cctggcttcc ccaagctgat cgccgatgcc   1500
tggaacgcta tccccgataa cctggacgct gtggtggatc tccaaggcgg cggacactcc   1560 tacttttttca agggcgccta ctacctgaag ctggaaaaacc agagcctgaa gtccgtgaag   1620
ttcggctcca tcaagtccga ctggctcgga tgt                                 1653
```

<210> SEQ ID NO 199
<211> LENGTH: 1242
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 199

```
ttcagaggcc ctctgctgcc caacagaccc ttcaccaccg tgtggaacgc caacacccag     60
tggtgcctgg aaagacacgg cgtggacgtg gacgtgtccg tgttcgatgt ggtggccaac    120
cccggccaga ccttcagggg ccctgacatg accatcttct actccagcca gctgggcacc    180 taccccctact acaccccctac aggcgagcct gtgtttggcg gcctgcctca gaacgcctct    240
ctgatcgctc acctggcccg gaccttccag gacatcctgg ctgctatccc tgcccccgac    300
ttttctggcc tggccgtgat cgattgggag gcctggcgac ctagatgggc cttcaactgg    360
gacaccaagg acatctaccg gcagcggtcc agagccctgg tgcaggctca gcatcctgat    420
tggcctgccc ctcaggtgga agccgtggcc caggatcagt tcagggcgc tgccagagct    480 tggatggctg gcacactgca gctgggaagg gccctgaggc ctagaggact gtgggcttc    540 tacggcttcc ccgactgcta caactacgac ttcctgtccc ccaactacac cggccagtgc    600
ccctctggaa tccgggccca gaatgatcag ctgggctggc tgtggggcca gtctagagcc    660 ctgtaccccct ccatctacat gcccgccgtg ctggaaggca ccggcaagtc ccagatgtac    720
gtgcagcaca gagtggccga ggccttcagg gtggcagtgg ctgctggcga tcctaacctg    780
cccgtgctgc cctacgtgca gatcttctac gataccacca ccactttct gcccctggac    840 gagctggaac actccctggg agagtctgct gctcagggtg ctgcaggcgt ggtgctgtgg    900
gtgtcctggg agaacacccg gaccaaagag tcctgccagg ccatcaaaga gtacatggac    960
```

```
accaccctgg gccccttcat cctgaacgtg acctctggcg ccctgctgtg tagccaggct   1020
ctgtgttctg gccacggcag atgcgtgcgg agaacctctc accctaaggc tctgctgctg   1080 ctgaacccg cctccttcag catccagctg acacctggcg gcggacccct gtctctgaga    1140
ggtgctctgt ccctggaaga tcaggcccag atggccgtgg aattcaagtg ccggtgctac   1200
cctggctggc aggccccttg gtgcgagcgg aaatctatgt gg                      1242
```

<210> SEQ ID NO 200
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200

```
caggtgcagc tggttcagtc tggcgccgaa gtgaagaaac ctggcgcctc tgtgaaggtg    60
tcctgcaaga cctctcggta cacctttacc gagtacacca tccactgggt ccgacaggct   120
ccaggccaga gactggaatg gatcggcggc atcaacccca caacggcat ccccaactac    180 aaccagaaat tcaagggccg cgtgaccatc accgtggaca cctctgcttc taccgcctac   240
atggaactgt ccagcctgag atctgaggac accgccgtgt actactgcgc cagaagaaga   300
atcgcctacg gctacgatga gggccacgcc atggattatt ggggccaggg aacactggtc   360
accgtgtcct ct                                                       372
```

<210> SEQ ID NO 201
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201

```
gacatcgtga tgacccagtc tccagactct ctggccgtgt ctctgggcga gagagccacc    60
atcaactgca gtcctctca gtccctgctg tactcccgga accagaagaa ctacctggcc    120
tggtatcagc agaagcccgg ccagcctcct aagctgctga tcttctgggc ctccaccaga   180
gaatctggcg tgcccgatag attctccggc tctggctttg gcaccgactt taccctgacc   240
atcagctccc tgcaggccga ggatgtggcc gtgtactact gccagcagta cttcagctac   300
cctctgacct ttggccaggg caccaaggtg gaaatcaag                          339
```

<210> SEQ ID NO 202
<211> LENGTH: 1428
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202

```
atggaaaccg acacactgct gctgtgggtg ctgctcttgt gggtgccagg atctacagga    60
caggtgcagc tggttcagtc tggcgccgaa gtgaagaaac ctggcgcctc tgtgaaggtg   120
tcctgcaaga cctctcggta cacctttacc gagtacacca tccactgggt ccgacaggct   180
ccaggccaga gactggaatg gatcggcggc atcaacccca caacggcat ccccaactac    240 aaccagaaat tcaagggccg cgtgaccatc accgtggaca cctctgcttc taccgcctac   300
```

```
atggaactgt ccagcctgag atctgaggac accgccgtgt actactgcgc cagaagaaga    360
atcgcctacg gctacgatga gggccacgcc atggattatt ggggccaggg aacactggtc    420
accgtgtcct ctgcctctac aaagggcccc tctgtgttcc ctctggctcc ttccagcaag    480
tctacctctg gcggaacagc tgctctgggc tgcctggtca aggactactt tcctgagcct    540
gtgaccgtgt cttggaactc tggcgctctg acatccggcg tgcacacctt ccagctgtg    600 ctgcaatctt ccggcctgta ctccctgtcc tccgtcgtga cagtgccttc tagctctctg    660
ggcacccaga cctacatctg caatgtgaac cacaagcctt ccaacaccaa ggtggacaag    720
agagtggaac ccaagtcctg cgacaagacc cacacctgtc caccatgtcc tgctccagaa    780
ctgctcggcg gaccttccgt gttcctgttt cctccaaagc taaggacac cctgatgatc    840 tctcggaccc ctgaagtgac ctgcgtggtg gtggatgtgt ctcacgagga cccagaagtg    900
aagttcaatt ggtacgtgga cggcgtggaa gtgcacaacg ccaagaccaa gcctagagag    960
gaacagtaca actccaccta cagagtggtg tccgtgctga ccgtgctgca ccaggattgg   1020
ctgaacggca aagagtacaa gtgcaaggtg tccaacaagg ccctgcctgc tcctatcgaa   1080
aagaccatct ccaaggccaa gggccagcct agggaacccc aggtttacac cctgcctcca   1140
tgccgggaag atgaccaa gaaccaggtg tccctgtggt gcctcgtgaa gggcttctac   1200
ccttccgata tcgccgtgga atgggagagc aatggccagc cagagaacaa ctacaagaca   1260 accccctcctg tgctggactc cgacggctca ttcttcctgt acagcaagct gacagtggac   1320
aagtccagat ggcagcaggg caacgtgttc tcctgctccg tgatgcacga ggccctgcac   1380
aatcactaca cacagaagtc cctgtctctg tcccctggca agtgatga             1428
```

<210> SEQ ID NO 203
<211> LENGTH: 726
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 203

```
atggaaaccg acacactgct gctgtgggtg ctgctcttgt gggtgccagg atctaccggc     60
gacatcgtga tgacccagtc tccagactct ctggccgtgt ctctgggcga gagagccacc    120
atcaactgca gtcctctca gtccctgctg tactcccgga accagaagaa ctacctggcc    180
tggtatcagc agaagcccgg ccagcctcct aagctgctga tcttctgggc ctccaccaga    240
gaatctggcg tgcccgatag attctccggc tctggctttg caccgacttt accctgacc    300 atcagctccc tgcaggccga ggatgtggcc gtgtactact gccagcagta cttcagctac    360
cctctgacct ttggccaggg caccaaggtg gaaatcaagc ggacagtggc cgctccttcc    420
gtgttcatct cccaccttc cgacgagcag ctgaagtctg gcacagcctc tgtcgtgtgc    480
ctgctgaaca acttctaccc tcgggaagcc aaggtgcagt ggaaggtgga caatgccctg    540
cagtccggca actcccaaga gtctgtgacc gagcaggact ccaaggacag cacctacagc    600
ctgtcctcca cactgaccct gtccaaggcc gactacgaga agcacaaggt gtacgcctgc    660
gaagtgaccc atcagggcct gtctagccct gtgaccaagt cttttcaaccg gggcgagtgc    720 tgatga                                                              726
```

<210> SEQ ID NO 204
<211> LENGTH: 3126
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 204

```
atggaaaccg acacactgct gctgtgggtg ctgctcttgt gggtgccagg atctacagga    60
caggtgcagc tggttcagtc tggcgccgaa gtgaagaaac tggcgcctc tgtgaaggtg    120
tcctgcaaga cctctcggta caccttacc gagtacacca tccactgggt ccgacaggct    180
ccaggccaga gactggaatg gatcggcggc atcaaccca caacggcat ccccaactac    240
aaccagaaat tcaagggccg cgtgaccatc accgtgaca cctctgcttc taccgcctac    300
atggaactgt ccagcctgag atctgaggac accgccgtgt actactgcgc cagaagaaga    360
atcgcctacg gctacgatga gggccacgcc atggattatt ggggccaggg aacactggtc    420
accgtgtcct ctgcctctac aaagggcccc tctgtgttcc ctctggctcc ttccagcaag    480
tctacctctg gcggaacagc tgctctgggc tgcctggtca aggactactt tcctgagcct    540
gtgaccgtgt cttggaactc tggcgctctg acatccggcg tgcacacctt ccagctgtg    600
ctgcaatctt ccggcctgta ctccctgtcc tccgtcgtga cagtgccttc tagctctctg    660
ggcacccaga cctacatctg caatgtgaac cacaagcctt ccaacaccaa ggtggacaag    720
agagtggaac ccaagtcctg cgacaagacc cacacctgtc caccatgtcc tgctccagaa    780
ctgctcggcg gaccttccgt gttcctgttt cctccaaagc ctaaggacac cctgatgatc    840
tctcggaccc ctgaagtgac ctgcgtggtg gtggatgtgt ctcacgagga cccagaagtg    900
aagttcaatt ggtacgtgga cggcgtggaa gtgcacaacg ccaagaccaa gcctagagag    960
gaacagtaca actccaccta cagagtggtg tccgtgctga ccgtgctgca ccaggattgg    1020
ctgaacggca agagtacaa gtgcaaggtg tccaacaagg ccctgcctgc tcctatcgaa    1080
aagaccatct ccaaggccaa gggccagcct cgggaacctc aagtctgtac cctgcctcct    1140
agccgggaag agatgaccaa gaaccaggtg tccctgagct gcgccgtgaa gggcttctac    1200
ccttctgata tcgccgtgga atgggagagc aacggccagc cagagaacaa ctacaagaca    1260
accccctcctg tgctggactc cgacggctca ttcttcctgg tgtccaagct gacagtggac    1320
aagtccagat ggcagcaggg caacgtgttc tcctgctccg tgatgcacga ggccctgcac    1380
aatcactaca cacagaagtc cctgtctctg tcccctggca aggtggcgg aggatctggc    1440
ggaggtggaa gcggcggagg cggctcttac aacttcttcc cacggaaacc caagtgggat    1500
aagaaccaga tcacctaccg gatcatcggc tacaccctg acctggatcc tgagactgtg    1560
gacgatgcct cgccagggc cttccaagtt tggagcgacg tgaccctct gcggttctcc    1620
agaatccatg atggcgaggc cgacatcatg atcaacttcg gcagatggga gcacggcgac    1680
ggctaccctt ttgatggcaa ggatggcctg ctggcccacg cttttgcccc tggaacaggt    1740
gttggcggcg actctcactt cgacgacgat gagttgtgga ccctcggcga aggacaggtc    1800
gtcagagtga agtacggcaa cgccgatggc gagtactgca agttccccct cctgttcaat    1860
gggaaagagt ataactcctg caccgacacc ggcagatctg acggcttcct gtggtgctcc    1920
accacctaca acttcgagaa ggacggcaaa tacggcttct gccctcacga ggctctgttc    1980
accatgggcg gaaatgctga gggacagccc tgcaagtttc cattcagatt ccaagggacc    2040
tcctacgact cttgcaccac cgagggaaga accgatggct atcgttggtg cggcaccaca    2100
gaggactacg accgggacaa gaagtatggc ttctgtcccg acagagccat gtctaccgtc    2160
```

```
ggcggcaatt ctgagggtgc cccttgcgtg ttcccttttca ccttcctggg caacaaatac      2220
gagtcctgca cctccgctgg cagatccgat ggaaagatgt ggtgcgctac caccgccaac      2280
tacgacgacg acagaaagtg gggctttttgt cctgaccagg gctacagcct gtttctggtg     2340
gccgctcacg agttcggcca tgctatggga ctcgagcact ctcaagatcc cggcgcactg      2400 atggcccta tctacaccta caccaagaac ttccggctgt cccaggacga catcaagggc       2460
atccaagagc tgtacggcgc ctctcctgat atcgatctcg gcaccggacc tactcctaca      2520
ctgggacctg tgacacccga gatctgcaag caggatatcg tgttcgacgg aatcgcccag      2580
atccggggcg agatcttctt ttttaaggac cgcttcattt ggcggaccgt gactcctcgg      2640
gacaagccta tgggacctct gctggtggct accttctggc ctgaactgcc cgagaagatc      2700
gatgccgtgt acgaggcccc tcaagaggaa aaggccgtct ttttcgccgg caacgagtac      2760
tggatctact ccgctagcac cctggaacgg ggctacccta gcctctgac ttctctggga      2820 ctgccacctg acgtgcagcg agtggatgcc gccttcaact ggtccaagaa caagaaaacc      2880
tatatcttcg ccggggacaa gttctggcgg tacaacgaag tcaagaaaaa gatggaccct      2940
ggcttcccca gctgatcgc cgatgcctgg aacgctatcc ccgataacct ggacgctgtg       3000
gtggacttgc aaggcggcgg acactcctac tttttcaagg cgcctacta cctgaagctg       3060 gaaaaccaga gcctgaagtc cgtgaagttc ggctccatca gtccgactg gctgggctgc       3120 tgatga                                                                 3126

<210> SEQ ID NO 205
<211> LENGTH: 2445
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 205
atggaaaccg acacactgct gctgtgggtg ctgctcttgt gggtgccagg ctctaccggc         60
tacaacttct cccacggaa acccaagtgg gacaagaacc agatcaccta ccggatcatc        120
ggctacaccc ctgacctgga tcctgagaca gtggacgatg ccttcgccag agccttccaa       180
gtttggagcg acgtgacccc tctgcggttc tccagaatcc atgatggcga ggccgacatc       240
atgatcaact tcggcagatg ggagcacggc gacggctacc ttttgatgg caaggatggc        300 ctgctggccc acgcttttgc ccctggaaca ggtgttggcg gcgactctca cttcgacgac       360
gatgagttgt ggaccctcgg cgaaggacag gtcgtcagag tgaagtacgg caacgccgat       420
ggcgagtact gcaagttccc cttcctgttc aacggcaaag agtacaactc ctgcaccgac      480
accggcagat ctgacggctt cctgtggtgc tccaccacct acaactttga aggacggc        540 aaatacggct tctgccctca cgaggccctg tttaccatgg gcggaaatgc tgagggccag      600
ccatgcaagt ttccattccg gttccaaggg acctcctacg acagctgtac caccgaggga     660
agaaccgatg gctatcgttg gtgcggcacc acagaggact acgacagaga caagaagtat      720
ggcttctgtc ccgagacagc catgtctacc gtcggcggca attctgaagg cgcccccttgt     780 gtgttccctt tcaccttcct gggcaacaaa tacgagtcct gcacctccgc tggccgctct      840
gatggaaaaa tgtggtgcgc taccaccgcc aactacgacg acgacagaaa gtgggcttt      900 tgtcctgacc agggctactc cctgtttctg gtggccgctc acgagtttgg ccatgctatg      960
ggcctcgagc actctcaaga tcccggtgca ctgatggccc ctatctacac ctacaccaag     1020
```

| | |
|---|---|
| aacttccggc tgtcccagga cgacatcaag ggcatccaag agctgtacgg cgcctctcct | 1080 |
| gatatcgatc tcggcaccgg acctactcct acactgggac ctgtgacacc cgagatctgc | 1140 |
| aagcaggaca tcgtgttcga cggaatcgcc cagatccggg gcgagatctt cttttttaag | 1200 |
| gaccggttca tctggcggac agtgacccct agagacaagc ctatgggacc tctgctggtg | 1260 |
| gctaccttct ggcctgagct gcctgagaag atcgacgccg tgtacgaggc ccctcaagag | 1320 |
| gaaaaggccg tcttttttcgc cggcaacgag tactggatct actccgcttc taccctggaa | 1380 |
| cggggctacc ccaagcctct gacatctctg ggactgcctc cagacgtgca gagagtggac | 1440 |
| gccgccttca actggtccaa gaacaagaaa acctacatct cgccggggga caagttctgg | 1500 |
| cggtacaacg aagtgaagaa aaagatggac cctggcttcc ccaagctgat cgccgatgcc | 1560 |
| tggaacgcta tccccgataa cctggacgct gtggtggatc tccaaggcgg cggacactcc | 1620 |
| tacttttca agggcgccta ctacctgaag ctggaaaacc agagcctgaa gtccgtgaag | 1680 |
| ttcggctcca tcaagtccga ctggctcgga tgtggtggcg gaggaagcgg aggcggagga | 1740 |
| tctggcggtg gcggatctga taagacccac acctgtccac cttgtcctgc tccagaactg | 1800 |
| ctcggcggac cttccgtgtt cctgtttcct ccaaagccta aggacaccct gatgatctct | 1860 |
| cggaccctg aagtgacctg cgtggtggtg gatgtgtccc acgaggaccc agaagtgaag | 1920 |
| ttcaattggt acgtggacgg cgtggaagtg cacaacgcca agaccaagcc tagagaggaa | 1980 |
| cagtacaaca gcacctacag agtggtgtcc gtgctgaccg tgctgcacca ggattggctg | 2040 |
| aatgggaaag agtataagtg caaggtgtcc aacaaggccc tgcctgctcc tatcgaaaag | 2100 |
| accatcagca aggccaaggg acagccccgg gaacctcaag tctgtaccct gcctcctagc | 2160 |
| cgggaagaga tgaccaagaa tcaggtgtcc ctgtcttgcg ccgtgaaggg cttttacccc | 2220 |
| tccgatatcg ccgtggaatg ggagtctaat ggccagcctg agaacaacta caagaccaca | 2280 |
| cctcctgtgc tggactccga cggctcattc ttcctggtgt ccaagctgac tgtggacaag | 2340 |
| tccagatggc agcagggcaa cgtgttctcc tgctccgtga tgcacgaggc tctgcacaac | 2400 |
| cactacacac agaagtctct gagcctgtct cctggcaagt gatga | 2445 |

<210> SEQ ID NO 206
<211> LENGTH: 1872
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 206

| | |
|---|---|
| atggaaaccg acacactgct gctgtgggtg ctgctcttgt gggtgccagg atctacagga | 60 |
| caggtgcagc tggttcagtc tggcgccgaa gtgaagaaac tggcgcctc tgtgaaggtg | 120 |
| tcctgcaaga cctctcggta caccttacc gagtacacca tccactgggt ccgacaggct | 180 |
| ccaggccaga gactgaatg gatcggcgg atcaaccca caacggcat ccccaactac | 240 |
| aaccagaaat tcaagggccg cgtgaccatc accgtggaca cctctgcttc taccgcctac | 300 |
| atggaactgt ccagcctgag atctgaggac accgccgtgt actactgcgc cagaagaaga | 360 |
| atcgcctacg gctacgatga gggccacgcc atggattatt ggggccaggg aacactggtc | 420 |
| accgtgtcct ctgcctctac aaagggcccc tctgtgttcc ctctggctcc ttccagcaag | 480 |
| tctacctctg gcggaacagc tgctctgggc tgcctggtca aggactactt cctgagcct | 540 |
| gtgaccgtgt cttggaactc tggcgctctg acatccggcg tgcacacctt ccagctgtgt | 600 |

```
ctgcaatctt ccggcctgta ctccctgtcc tccgtcgtga cagtgccttc tagctctctg    660
ggcacccaga cctacatctg caatgtgaac cacaagcctt ccaacaccaa ggtggacaag    720
agagtggaac ccaagtcctg cgacaagacc cacacctgtc caccatgtcc tgctccagaa    780
ctgctcggcg accttccgt gttcctgttt cctccaaagc ctaaggacac cctgatgatc    840
tctcggaccc ctgaagtgac ctgcgtggtg gtggatgtgt ctcacgagga cccagaagtg    900
aagttcaatt ggtacgtgga cggcgtggaa gtgcacaacg ccaagaccaa gcctagagag    960
gaacagtaca actccaccta cagagtggtg tccgtgctga ccgtgctgca ccaggattgg   1020
ctgaacggca agagtacaa gtgcaaggtg tccaacaagg ccctgcctgc tcctatcgaa   1080
aagaccatct ccaaggccaa gggccagcct agggaacccc aggtttacac cctgcctcca   1140
tgccgggaag agatgaccaa gaaccaggtg tccctgtggt gcctcgtgaa gggcttctac   1200
ccttccgata tcgccgtgga atgggagagc aatggccagc cagagaacaa ctacaagaca   1260
acccctcctg tgctggactc cgacggctca ttcttcctgt acagcaagct gacagtggac   1320
aagtccagat ggcagcaggg caacgtgttc tcctgctccg tgatgcacga ggccctgcac   1380
aatcactaca cacagaagtc cctgtctctg tcccctggca aggtggcgg aggatctggc   1440 ggaggtggaa gcggcggagg cggatctgct cctacatcct ccagcaccaa gaaaacccag   1500
ctgcagttgg agcatctgct gctggacctg cagatgatcc tgaatggcat caacaattac   1560
aagaacccca gctgacccg gatgctgacc gccaagtttg ccatgcctaa gaaggccacc   1620
gagctgaaac atctgcagtg cctggaagag gaactgaagc ccctggaaga agtgctgaat   1680
ctggcccagt ccaagaactt ccacctgagg cctcgggacc tgatctccaa catcaacgtg   1740
atcgtgctcg agctgaaggg ctccgagaca accttcatgt gcgagtacgc cgacgagaca   1800
gctaccatcg tggaatttct gaaccggtgg atcaccttct gccagtccat catcagcacc   1860
ctgacctgat ga                                                        1872

<210> SEQ ID NO 207
<211> LENGTH: 2715
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 207
atggaaaccg acacactgct gctgtgggtg ctgctcttgt gggtgccagg atctacagga     60
caggtgcagc tggttcagtc tggcgccgaa gtgaagaaac ctggcgcctc tgtgaaggtg    120
tcctgcaaga cctctcggta cacctttacc gagtacacca tccactgggt ccgacaggct    180
ccaggccaga gactggaatg gatcggcggc atcaaccca caacggcat ccccaactac    240 aaccagaaat tcaagggccg cgtgaccatc accgtggaca cctctgcttc taccgcctac    300
atggaactgt ccagcctgag atctgaggac accgccgtgt actactgcgc cagaagaaga    360
atcgcctacg gctacgatga gggccacgcc atggattatt ggggccaggg aacactggtc    420
accgtgtcct ctgcctctac aaagggcccc tctgtgttcc ctctggctcc ttccagcaag    480
tctacctctg gcggaacagc tgctctgggc tgcctggtca aggactactt tcctgagcct    540
gtgaccgtgt cttggaactc tggcgctctg acatccggcg tgcacacctt ccagctgtg    600 ctgcaatctt ccggcctgta ctccctgtcc tccgtcgtga cagtgccttc tagctctctg    660
ggcacccaga cctacatctg caatgtgaac cacaagcctt ccaacaccaa ggtggacaag    720
```

-continued

```
agagtggaac ccaagtcctg cgacaagacc cacacctgtc caccatgtcc tgctccagaa    780
ctgctcggcg gaccttccgt gttcctgttt cctccaaagc ctaaggacac cctgatgatc    840
tctcggaccc ctgaagtgac ctgcgtggtg gtggatgtgt ctcacgagga cccagaagtg    900
aagttcaatt ggtacgtgga cggcgtggaa gtgcacaacg ccaagaccaa gcctagagag    960
gaacagtaca actccaccta cagagtggtg tccgtgctga ccgtgctgca ccaggattgg    1020
ctgaacggca agagtacaa gtgcaaggtg tccaacaagg ccctgcctgc tcctatcgaa    1080
aagaccatct ccaaggccaa gggccagcct cgggaacctc aagtctgtac cctgcctcct    1140
agccgggaag agatgaccaa gaaccaggtg tccctgagct cgccgtgaa gggcttctac    1200 ccttctgata tcgccgtgga atgggagagc aacggccagc cagagaacaa ctacaagaca    1260 accctcctg tgctggactc cgacggctca ttcttcctgg tgtccaagct gacagtggac    1320
aagtccagat ggcagcaggg caacgtgttc tcctgctccg tgatgcacga ggccctgcac    1380
aatcactaca cacagaagtc cctgtctctg tccctggca aaggtggcgg aggatctggc    1440
ggaggtggaa gcggcggagg cggatctttt agaggacctc tgctgcccaa ccggcctttc    1500
accacagtgt ggaacgctaa cacccagtgt gcctggaaa gacacggcgt tgacgtggac    1560
gtgtccgtgt cgatgtggt ggctaatccc ggccagacct tcagaggccc tgacatgacc    1620
atcttctact ccagccagct gggcacctat ccttactaca cccctacagg cgagcccgtg    1680
tttggaggct tgcctcagaa tgccagcctg atcgctcacc tggccagaac ctttcaggac    1740
atcctggctg ctatccccgc tcctgacttt tccggactgg ccgtgatcga ttgggaagcc    1800
tggcgaccta gatgggcctt caactgggac accaaggaca tctaccggca gcggtctaga    1860
gcactggtgc aggctcaaca tcctgactgg cctgctccac aggttgaggc tgttgcccag    1920
gatcagtttc agggcgctgc cagagcttgg atggctggaa cattgcagct ggggagagcc    1980
ctgaggccta gaggactgtg gggcttttac ggcttccccg actgctacaa ctacgacttc    2040
ctgtctccta actacaccgg ccagtgtcct tccggcatca gagcccagaa tgatcagctc    2100
ggatggctct ggggacagtc cagggctctg taccctcca tctacatgcc tgctgtcctg    2160
gaaggcaccg gcaagtccca gatgtacgtg cagcatagag tggccgaggc cttcagagtg    2220
gctgttgctg ctggcgatcc taacctgcct gtgctgcctt acgtgcagat cttctacgat    2280
accaccaacc actttctgcc cctggacgag ctggaacact ccctgggaga atctgctgct    2340
caaggtgctg caggcgtggt gttgtgggtg tcctgggaaa acacccggac caaagagtcc    2400
tgccaggcca tcaaagagta tatggacacc acactgggcc ccttcatcct gaacgtgaca    2460
tctggcgcac tgctgtgcag ccaggcactg tgttctggac acggaagatg cgtgcggaga    2520
acctctcatc ccaaggctct gctgctgctg aaccctgcca gcttctccat ccagttgaca    2580
ccaggcggag ccctctgtc tttgagaggt gcactgtccc tggaagatca ggcccagatg    2640
gctgtggaat tcaagtgcag atgctacccc ggctggcaag ctccttggtg cgagagaaag    2700
tccatgtggt agtga                                                     2715
```

<210> SEQ ID NO 208
<211> LENGTH: 1416
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 208

| | |
|---|---:|
| atggaaaccg acacactgct gctgtgggtg ctgctcttgt gggtgccagg atctacaggc | 60 |
| gaggtgcagc tgttggaatc tggcggagga ttggttcagc ctggcggctc tctgagactg | 120 |
| tcttgtgccg cttccggctt caccttctcc agctatatca tgatgtgggt ccgacaggcc | 180 |
| cctggcaaag gactggaatg ggtgtcctct atctacccct ctggcggcat cacctttac | 240 |
| gccgacaccg tgaagggcag attcaccatc tctcgggaca actccaagaa caccctgtac | 300 |
| ctgcagatga actccctgag agccgaggac accgccgtgt actactgcgc cagaatcaag | 360 |
| ctgggcaccg tgaccaccgt ggattattgg ggacagggca ccctggtcac cgtgtcctct | 420 |
| gcttctacca agggacccag cgtgttccct ctggctcctt ccagcaagtc tacctccggt | 480 |
| ggaacagctg ctctgggctg cctggtcaag gactactttc ctgagcctgt gaccgtgtct | 540 |
| tggaactccg gcgctctgac atctggcgtg cacacatttc cagccgtgct gcagtcctcc | 600 |
| ggcctgtact ctctcagctc tgtcgtgacc gtgccttcca gctctctggg aacccagacc | 660 |
| tacatctgca atgtgaacca caagccttcc aacaccaagg tggacaagag agtggaaccc | 720 |
| aagtcctgcg acaagaccca cacctgtcct ccatgtcctg ctccagaact gctcggcgga | 780 |
| ccttccgtgt tcctgtttcc tccaaagcct aaggacaccc tgatgatctc tcggacccct | 840 |
| gaagtgacct gcgtggtggt ggatgtgtct cacgaggatc ccgaagtgaa gttcaattgg | 900 |
| tacgtggacg gcgtggaagt gcacaacgcc aagaccaagc ctagagagga acagtacaac | 960 |
| tccacctaca gagtggtgtc cgtgctgaca gtgctgcacc aggattggct gaacggcaaa | 1020 |
| gagtacaagt gcaaggtgtc caacaaggcc ctgcctgctc ctatcgaaaa gaccatctcc | 1080 |
| aaggccaagg gccagcctag ggaacccag gtttacaccc tgcctccatg ccgggaagag | 1140 |
| atgaccaaga accaggtgtc cctgtggtgc ctggttaagg gcttctaccc ttccgatatc | 1200 |
| gccgtggaat gggagagcaa tggccagcct gagaacaact acaagacaac ccctcctgtg | 1260 |
| ctggactccg acggctcatt cttcctgtac tccaagctga ccgtggacaa gtccagatgg | 1320 |
| cagcagggca acgtgttctc ctgctccgtg atgcacgagg ccctgcacaa tcactacacc | 1380 |
| cagaagtccc tgtctctgag ccccggcaag tgatga | 1416 |

<210> SEQ ID NO 209
<211> LENGTH: 1860
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 209

| | |
|---|---:|
| atggaaaccg acacactgct gctgtgggtg ctgctcttgt gggtgccagg atctacaggc | 60 |
| gaggtgcagc tgttggaatc tggcggagga ttggttcagc ctggcggctc tctgagactg | 120 |
| tcttgtgccg cttccggctt caccttctcc agctatatca tgatgtgggt ccgacaggcc | 180 |
| cctggcaaag gactggaatg ggtgtcctct atctacccct ctggcggcat cacctttac | 240 |
| gccgacaccg tgaagggcag attcaccatc tctcgggaca actccaagaa caccctgtac | 300 |
| ctgcagatga actccctgag agccgaggac accgccgtgt actactgcgc cagaatcaag | 360 |
| ctgggcaccg tgaccaccgt ggattattgg ggacagggca ccctggtcac cgtgtcctct | 420 |
| gcttctacca agggacccag cgtgttccct ctggctcctt ccagcaagtc tacctccggt | 480 |
| ggaacagctg ctctgggctg cctggtcaag gactactttc ctgagcctgt gaccgtgtct | 540 |
| tggaactccg gcgctctgac atctggcgtg cacacatttc cagccgtgct gcagtcctcc | 600 |

```
ggcctgtact ctctcagctc tgtcgtgacc gtgccttcca gctctctggg aacccagacc    660
tacatctgca atgtgaacca caagccttcc aacaccaagg tggacaagag agtggaaccc    720
aagtcctgcg acaagaccca cacctgtcct ccatgtcctg ctccagaact gctcggcgga    780
ccttccgtgt tcctgtttcc tccaaagcct aaggacaccc tgatgatctc tcggacccct    840
gaagtgacct gcgtggtggt ggatgtgtct cacgaggatc ccgaagtgaa gttcaattgg    900
tacgtggacg gcgtggaagt gcacaacgcc aagaccaagc ctagagagga acagtacaac    960
tccacctaca gagtggtgtc cgtgctgaca gtgctgcacc aggattggct gaacggcaaa   1020
gagtacaagt gcaaggtgtc caacaaggcc ctgcctgctc ctatcgaaaa gaccatctcc   1080
aaggccaagg gccagcctag ggaaccccag gtttacaccc tgcctccatg ccgggaagag   1140
atgaccaaga accaggtgtc cctgtggtgc ctggttaagg gcttctaccc ttccgatatc   1200
gccgtggaat gggagagcaa tggccagcct gagaacaact acaagacaac ccctcctgtg   1260
ctggactccg acggctcatt cttcctgtac tccaagctga ccgtggacaa gtccagatgg   1320
cagcagggca acgtgttctc ctgctccgtg atgcacgagg ccctgcacaa tcactacacc   1380
cagaagtccc tgtctctgtc tcccggaaaa ggcggaggtg aagcggcgg aggcggatct   1440 ggtggcggtg gatctgctcc tacctcctcc agcaccaaga aacccagct gcagttggag   1500 catctgctgc tggacctcca gatgatcctg aatggcatca acaattacaa gaaccccaag   1560
ctcacccgga tgctgaccgc caagtttgcc atgcctaaga aggccaccga gctgaaacat   1620
ctgcagtgcc tggaagagga actgaagccc ctggaagaag tgctgaatct ggcccagtcc   1680
aagaacttcc acctgaggcc tcgggacctg atctccaaca tcaacgtgat cgtgctcgag   1740
ctgaagggct ccgagacaac cttcatgtgc gagtacgccg acgagacagc taccatcgtg   1800
gaatttctga accggtggat caccttctgt cagtccatca tcagcaccct gacctgatga   1860
```

<210> SEQ ID NO 210
<211> LENGTH: 2703
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210

```
atggaaaccg acacactgct gctgtgggtg ctgctcttgt gggtgccagg atctacagga     60
caggtccagc tgcagcagtc tggccctgaa cttgtgaagc ctggcgcctc cgtgaagatg    120
tcctgcaagg cttctggcta caccttcacc gactacgtga tcaactgggg caagcagaga    180
tctggccagg gcctcgagtg gatcggcgag atctatcctg ctccggcac caactactac    240 aacgagaagt tcaaggccaa ggctaccctg accgccgaca gtcctccaa tatcgcctac    300 atgcagctgt ccagcctgac ctctgaggac tccgccgtgt acttctgcgc cagaagaggc    360
agatacggcc tgtacgccat ggactattgg ggccagggca cctctgtgac cgtgtcctct    420
gcttctacca agggacccag cgtgttccct ctggctcctt ccagcaagtc tacctctggc    480
ggaacagctg ctctgggctg cctggtcaag gactactttc ctgagcctgt gacagtgtct    540
tggaactctg gcgccctgac atccggcgtg cacacatttc cagctgtgct gcagtcctct    600
ggcctgtact ctctgtcctc cgtcgtgacc gtgccttcta gctctctggg cacccagacc    660
tacatctgca atgtgaacca caagccttcc aacaccaagg tggacaagag agtggaaccc    720
aagtcctgcg acaagaccca cacctgtcct ccatgtcctg ctccagaact gctcggcgga    780
```

| | |
|---|---|
| ccttccgtgt tcctgtttcc tccaaagcct aaggacaccc tgatgatctc tcggacccct | 840 |
| gaagtgacct gcgtggtggt ggatgtgtct cacgaggatc ccgaagtgaa gttcaattgg | 900 |
| tacgtggacg gcgtggaagt gcacaacgcc aagaccaagc ctagagagga acagtacaac | 960 |
| tccacctaca gagtggtgtc cgtgctgacc gtgctgcacc aggattggct gaacggcaaa | 1020 |
| gagtacaagt gcaaggtgtc caacaaggcc ctgcctgctc tatcgaaaa gaccatctcc | 1080 |
| aaggctaagg gccagcctcg cgaacccaa gtctgtacac tgcctcctag ccggaagag | 1140 |
| atgaccaaga accaggtgtc cctgtcctgc gccgtgaagg gcttctaccc ttctgatatc | 1200 |
| gccgtggaat gggagtccaa cggccagcct gagaacaact acaagacaac ccctcctgtg | 1260 |
| ctggactccg acggctcatt cttcctggtg tccaagctga cagtggacaa gtcccgatgg | 1320 |
| cagcagggca acgtgttctc ctgctctgtg atgcacgagg ctctgcacaa ccactacacc | 1380 |
| cagaagtccc tgtctctgtc ccctggaaaa ggcggcggag gatctggcgg aggtggaagc | 1440 |
| ggaggcggtg gatcttttag aggacctctg ctgcccaacc ggccttcac cacagtgtgg | 1500 |
| aacgctaaca cccagtggtg cctggaaaga catggcgtcg acgtggacgt gtccgtgttc | 1560 |
| gatgtggtgg ctaatcccgg ccagaccttc agaggccccg acatgaccat cttctactcc | 1620 |
| agccagctgg gcacctatcc ttactacacc cctacaggcg agcccgtgtt tggtggcttg | 1680 |
| cctcagaatg cctctctgat cgcccacctg gctagaacct tccaggatat tctggctgct | 1740 |
| atccccgctc ctgactttc tggcctggcc gtgatcgatt gggaagcttg gaggcctaga | 1800 |
| tgggccttca actgggacac caaggacatc taccggcagc ggtctagagc actggtgcag | 1860 |
| gctcaacatc ctgactggcc tgctccacag gttgaggctg ttgcccagga tcagtttcag | 1920 |
| ggcgctgcca gagcttggat ggctggaaca ttgcagctgg ggagagccct gaggccaaga | 1980 |
| ggattgtggg gcttttacgg cttccccgac tgctacaact acgacttcct gtctcctaac | 2040 |
| tacaccggcc agtgtccttc cggcatcaga gcccagaatg atcagctcgg atggctctgg | 2100 |
| ggacagtcca gggctctgta cccctccatc tacatgcctg ctgtgctcga aggcaccggc | 2160 |
| aagtcccaga tgtacgtgca gcatagagtg gccgaggcct tcagagtggc tgttgctgct | 2220 |
| ggcgatccta acctgcctgt gctgccttac gtgcagatct ctacgatac caccaaccac | 2280 |
| tttctgcccc tggacgagct ggaacactcc ctgggagaat ctgctgctca aggtgctgca | 2340 |
| ggcgtggtgt tgtgggtgtc ctgggaaaac acccggacca agagtcctg ccaggccatc | 2400 |
| aaagagtata tggacaccac actgggcccc ttcatcctga cgtgacatc tggcgctctg | 2460 |
| ctgtgcagcc aggctctgtg ttctggccat ggtagatgcg tgcggagaac ctctcatccc | 2520 |
| aaggctctgc tgctgctgaa ccctgccagc ttctccatcc agttgacacc aggcggaggc | 2580 |
| cctctgtctt tgagaggtgc actgtccctg gaagatcagg cccagatggc tgtggaattc | 2640 |
| aagtgcagat gctaccccgg ctgcaagct ccttggtgcg agagaaagtc catgtggtag | 2700 |
| tga | 2703 |

<210> SEQ ID NO 211
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 211

| | |
|---|---|
| atggaaaccg acacactgct gctgtgggtg ctgctcttgt gggtgccagg atctaccggc | 60 |

```
gacatccaga tgacccagac cacctctagc ctgtctgcct ctctgggcga cagagtgacc    120
atctcctgta gagccagcca ggacatctcc aactacctga actggtatca gcagaaaccc    180
gacggcaccg tgaagctgct gatctactac acctctcggc tgcactctgg cgtgccctct    240
agattttctg gctccggctc tggcaccgac tactccctga ccatcaacaa cctggaacaa    300
gaggatatcg ctacctactt ctgccagcaa ggcaacaccc ggccttggac atttggcggc    360
ggaacaaagc tggaaatcaa gcggacagtg gccgctcctt ccgtgttcat cttcccacct    420
tccgacgagc agctgaagtc cggcacagct tctgtcgtgt gcctgctgaa caacttctac    480
cctcgggaag ccaaggtgca gtggaaggtg acaatgccc tgcagtccgg caactcccaa    540
gagtctgtga ccgagcagga ctccaaggac agcacctaca gcctgtcctc cacactgacc    600
ctgagcaagg ccgactacga aagcacaag gtgtacgcct gcgaagtgac ccatcagggc    660
ctgtctagcc ctgtgaccaa gtctttcaac cggggcgagt gctgatga                 708

<210> SEQ ID NO 212
<211> LENGTH: 2037
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 212
atggctgctc atctgctgcc tatctgcgcc ctgttcctga ccctgctgga tatggcccag    60
ggcttcagag ccctctgct gcccaacaga cccttcacca ccgtgtggaa cgccaacacc    120
cagtggtgcc tggaaagaca cggcgtggac gtggacgtgt ccgtgttcga tgtggtggcc    180
aaccccggcc agaccttcag ggccctgac atgaccatct ctactccag ccagctgggc    240 acctacccct actacacccc tacaggcgag cctgtgtttg cggcctgcc tcagaacgcc    300 tctctgatcg ctcacctggc ccggaccttc aggacatcc tggctgctat ccctgccccc    360
gacttttctg gcctggccgt gatcgattgg gaggcctggc gacctagatg ggccttcaac    420
tgggacacca aggacatcta ccggcagcgg tccagagccc tggtgcaggc tcagcatcct    480
gattggcctg cccctcaggt ggaagccgtg gcccaggatc agtttcaggg cgctgccaga    540
gcttggatgg ctggcacact gcagctggga agggccctga ggcctagagg actgtggggc    600
ttctacggct ccccgactg ctacaactac gacttcctgt ccccaacta caccggccag    660 tgcccctctg gaatccgggc ccagaatgat cagctgggct ggctgtgggg ccagtctaga    720
gccctgtacc cctccatcta catgcccgcc gtgctggaag gcaccggcaa gtcccagatg    780
tacgtgcagc acagagtggc cgaggccttc aggtggcag tggctgctgg cgatcctaac    840
ctgcccgtgc tgccctacgt gcagatcttc tacgatacca ccaaccactt ctgcccctg    900 gacgagctgg aacactcct gggagagtct gctgctcagg gtgctgcagg cgtggtgctg    960
tgggtgtcct gggagaacac ccggaccaaa gagtcctgcc aggccatcaa agagtacatg    1020
gacaccaccc tgggccccctt catcctgaac gtgacctctg cgccctgct gtgtagccag    1080 gctctgtgtt ctggccacgg cagatgcgtg cggagaacct ctcaccctaa ggctctgctg    1140
ctgctgaacc ccgcctcctt cagcatccag ctgcacctg cggcggacc cctgtctctg    1200 agaggtgctc tgtccctgga agatcaggcc cagatggccg tggaattcaa gtgccggtgc    1260
tacccctggc tgcaggcccc cttggtgcga gcggaaatcta tgtggggcgg aggcggatca    1320
ggcggcggag gatctggggg tggtggctct gataagaccc acacctgtcc tcctgccct    1380
```

-continued

| | |
|---|---|
| gcccctgaac tgctgggagg cccttccgtg ttcctgttcc ccccaaagcc caaggacacc | 1440 |
| ctgatgatct cccggacccc cgaagtgacc tgcgtggtgg tggatgtgtc ccacgaggac | 1500 |
| cctgaagtga agttcaattg gtacgtggac ggggtggaag tgcacaacgc caagaccaag | 1560 |
| cccagagagg aacagtacaa ctccacctac agagtggtgt ccgtgctgac cgtgctgcat | 1620 |
| caggactggc tgaacggcaa agagtataag tgcaaggtgt ccaacaaggc cctgcccgct | 1680 |
| cccatcgaaa agaccatctc caaggccaag ggccagcccc gggaacctca agtgtgcacc | 1740 |
| ctgcctccat cccgggaaga gatgaccaag aaccaggtgt ccctgtcctg cgccgtgaag | 1800 |
| ggcttttacc cctccgatat cgctgtgaa tgggagtcca acggccagcc tgagaacaac | 1860 |
| tacaagacca ccccccctgt gctggactcc gacggctcat tcttcctggt gtccaagctg | 1920 |
| acagtggaca gtcccggtg gcagcagggc aacgtgttct cctgctccgt gatgcacgag | 1980 |
| gccctgcaca accactacac ccagaagtcc ctgagcctgt cccctggcaa gtgatga | 2037 |

<210> SEQ ID NO 213
<211> LENGTH: 2385
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 213

| | |
|---|---|
| atgaagacct gggtcaagat cgtgtttggc gtggccacct ctgctgtgct ggctctgctg | 60 |
| gtcatgtgca tcgtgctgcg gccttccaga gtgcacaact ccgaagagaa caccatgcgg | 120 |
| gctctgaccc tgaaggacat cctgaacggc accttcagct acaagacctt ctttcccaac | 180 |
| tggatctccg gccaagagta cctgcaccag tccgccgaca caatatcgt gctgtacaac | 240 |
| atcgagacag gccagtccta caccatcctg tccaaccgga ccatgaagtc cgtgaacgcc | 300 |
| tccaactacg gactgtctcc tgaccggcag ttcgtgtacc tggaatccga ctactccaag | 360 |
| ctgtggcggt actcctacac cgccacctac tacatctacg acctgagcaa cggcgagttc | 420 |
| gtgcggggaa atgagctgcc cagacctatc cagtacctgt gctggtcccc tgtgggctct | 480 |
| aagctggctt acgtgtacca gaacaacatc tacctgaagc agcggcctgg cgaccctcca | 540 |
| ttccagatca ccttcaacgg cagagagaac aagatcttta cggcatccc cgactgggtg | 600 |
| tacgaggaag agatgctgcc cactaagtac gccctctggt ggtcccctaa cggcaagttt | 660 |
| ctggcctacg ccgagttcaa cgacaaggat atccccgtga tcgcctactc ctactacggc | 720 |
| gacgagcagt accctcggac catcaacatc ccttatccta aggctggcgc caagaatccc | 780 |
| gtcgtgcgga tcttcatcat cgacaccacc tatcctgcct acgtgggccc tcaagaggtg | 840 |
| ccagtgcctg ctatgatcgc ctccagcgac tactacttct cctggctgac atgggtcacc | 900 |
| gacgagcgag tttgtctgca gtggctgaag cgggtgcaga acgtgtccgt gctgtccatc | 960 |
| tgcgacttca gagaggactg gcagacctgg gactgcccca gacacaaga gcacatcgag | 1020 |
| gaatctcgga ccggatgggc tggcggcttc ttcgtgtcta gacccgtgtt ctcctacgac | 1080 |
| gccatcagct actataagat cttctccgac aaggacggct acaagcacat ccactacatc | 1140 |
| aaggacaccg tcgagaacgc catccagatt acctccggca gtgggaagc catcaatatc | 1200 |
| ttcagagtga cccaggactc cctgttctac tcctccaacg agttcgagga ataccccggc | 1260 |
| agacggaaca tctacagaat ctccatcggc agctaccctc catccaagaa atgcgtgacc | 1320 |
| tgccaccctga gaaaagagcg gtgccagtac tataccgcca gcttctctga ctacgccaag | 1380 |

```
tactacgccc tcgtgtgtta cggccctggc atccctatct ctaccctgca cgatggcaga   1440
accgaccaag agatcaagat cctggaagaa acaaagagc tggaaaacgc cctgaagaac     1500
attcagctgc ccaaagagga atcaagaag ctggaagtcg acgagatcac cctgtggtac     1560
aagatgatcc tgcctcctca gttcgaccgg tccaagaagt accctctgct gatccaggtg   1620
tacggcggac cttgctctca gtccgtcaga tctgtgttcg ccgtgaattg gatctcctac   1680
ctggcctcca agaaggcat ggttatcgcc ctggtggacg gcagaggcac agcttttcaa    1740
ggcgacaagc tgctgtacgc cgtgtacaga aagctgggcg tgtacgaagt ggaagatcag   1800
atcaccgccg tgcggaagtt catcgagatg ggcttcatcg acgagaagcg gatcgctatc   1860
tggggctggt cttacggcgg ctacgtttcc tctctggccc tggcttctgg caccggcctg   1920
ttcaagtgtg gaatcgctgt tgcccctgtg tcctcctggg agtactatgc ctctgtgtac   1980
accgagcggt tcatgggcct gcctaccaag gacgacaacc tggaacacta caagaacagc   2040
accgtgatgg ccagagccga gtacttccgg aacgtggact acctgctgat tcacggcacc   2100
gccgacgaca acgtgcactt ccaaaacagc gcccagatcg ccaaggctct ggtcaatgcc   2160
caggtggact ttcaggccat gtggtactcc gaccagaacc acggcctgtc tggcctgagc   2220
accaatcacc tgtacaccca catgacccac tttctgaagc agtgcttctc cctgtctgat   2280
ggcggcggag ctctggact gaacgatatc ttcgaggccc agaaaatcga gtggcacgaa   2340
ggcggaggcg gctcccacca tcatcatcac caccatcact gatga                  2385
```

<210> SEQ ID NO 214
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Gln Val Gln Leu Val Gln Ser Gly Ala Glu Val Lys Lys Pro Gly Ala
1               5                   10                  15

Ser Val Lys Val Ser Cys Lys Thr Ser Arg Tyr Thr Phe Thr Glu Tyr
            20                  25                  30

Thr Ile His Trp Val Arg Gln Ala Pro Gly Gln Arg Leu Glu Trp Ile
        35                  40                  45

Gly Gly Ile Asn Pro Asn Asn Gly Ile Pro Asn Tyr Asn Gln Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Ile Ala Tyr Gly Tyr Asp Glu Gly His Ala Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val

```
                180                 185                 190
Val Thr Val Pro Ser Ser Leu Gly Thr Gln Thr Tyr Ile Cys Asn
            195                 200                 205
Val Asn His Lys Pro Ser Asn Thr Lys Val Asp Lys Arg Val Glu Pro
        210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser His Glu Asp Pro Glu Val Lys Phe Asn Trp Tyr Val Asp Gly
        275                 280                 285
Val Glu Val His Asn Ala Lys Thr Lys Pro Arg Glu Glu Gln Tyr Asn
    290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
            340                 345                 350
Pro Gln Val Tyr Thr Leu Pro Pro Cys Arg Glu Glu Met Thr Lys Asn
        355                 360                 365
Gln Val Ser Leu Trp Cys Leu Val Lys Gly Phe Tyr Pro Ser Asp Ile
    370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
            420                 425                 430
Ser Val Met His Glu Ala Leu His Asn His Tyr Thr Gln Lys Ser Leu
        435                 440                 445
Ser Leu Ser Pro Gly Lys
    450

<210> SEQ ID NO 215
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Leu Tyr Ser
            20                  25                  30
Arg Asn Gln Lys Asn Tyr Leu Ala Trp Tyr Gln Gln Lys Pro Gly Gln
        35                  40                  45
Pro Pro Lys Leu Leu Ile Phe Trp Ala Ser Thr Arg Glu Ser Gly Val
    50                  55                  60
Pro Asp Arg Phe Ser Gly Ser Gly Phe Gly Thr Asp Phe Thr Leu Thr
65                  70                  75                  80
```

Ile Ser Ser Leu Gln Ala Glu Asp Val Ala Val Tyr Tyr Cys Gln Gln
            85                  90                  95

Tyr Phe Ser Tyr Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 216
<211> LENGTH: 1020
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Gln Val Gln Leu Val Gln Ser Gly Ala Glu Val Lys Lys Pro Gly Ala
1               5                   10                  15

Ser Val Lys Val Ser Cys Lys Thr Ser Arg Tyr Thr Phe Thr Glu Tyr
            20                  25                  30

Thr Ile His Trp Val Arg Gln Ala Pro Gly Gln Arg Leu Glu Trp Ile
        35                  40                  45

Gly Gly Ile Asn Pro Asn Asn Gly Ile Pro Asn Tyr Asn Gln Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Arg Ile Ala Tyr Gly Tyr Asp Glu Gly His Ala Met Asp
            100                 105                 110

Tyr Trp Gly Gln Gly Thr Leu Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
        210                 215                 220

-continued

```
Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Cys Thr Leu Pro Pro Ser Arg Glu Glu Met Thr Lys Asn
        355                 360                 365

Gln Val Ser Leu Ser Cys Ala Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Gly Ser Gly Gly Gly Gly Ser
450                 455                 460

Gly Gly Gly Gly Ser Tyr Asn Phe Phe Pro Arg Lys Pro Lys Trp Asp
465                 470                 475                 480

Lys Asn Gln Ile Thr Tyr Arg Ile Ile Gly Tyr Thr Pro Asp Leu Asp
            485                 490                 495

Pro Glu Thr Val Asp Asp Ala Phe Ala Arg Ala Phe Gln Val Trp Ser
        500                 505                 510

Asp Val Thr Pro Leu Arg Phe Ser Arg Ile His Asp Gly Glu Ala Asp
    515                 520                 525

Ile Met Ile Asn Phe Gly Arg Trp Glu His Gly Asp Gly Tyr Pro Phe
530                 535                 540

Asp Gly Lys Asp Gly Leu Leu Ala His Ala Phe Ala Pro Gly Thr Gly
545                 550                 555                 560

Val Gly Gly Asp Ser His Phe Asp Asp Glu Leu Trp Thr Leu Gly
            565                 570                 575

Glu Gly Gln Val Val Arg Val Lys Tyr Gly Asn Ala Asp Gly Glu Tyr
        580                 585                 590

Cys Lys Phe Pro Phe Leu Phe Asn Gly Lys Glu Tyr Asn Ser Cys Thr
    595                 600                 605

Asp Thr Gly Arg Ser Asp Gly Phe Leu Trp Cys Ser Thr Thr Tyr Asn
610                 615                 620

Phe Glu Lys Asp Gly Lys Tyr Gly Phe Cys Pro His Glu Ala Leu Phe
625                 630                 635                 640
```

Thr Met Gly Gly Asn Ala Glu Gly Gln Pro Cys Lys Phe Pro Phe Arg
            645                 650                 655

Phe Gln Gly Thr Ser Tyr Asp Ser Cys Thr Thr Glu Gly Arg Thr Asp
        660                 665                 670

Gly Tyr Arg Trp Cys Gly Thr Thr Glu Asp Tyr Asp Arg Asp Lys Lys
    675                 680                 685

Tyr Gly Phe Cys Pro Glu Thr Ala Met Ser Thr Val Gly Gly Asn Ser
690                 695                 700

Glu Gly Ala Pro Cys Val Phe Pro Phe Thr Phe Leu Gly Asn Lys Tyr
705                 710                 715                 720

Glu Ser Cys Thr Ser Ala Gly Arg Ser Asp Gly Lys Met Trp Cys Ala
            725                 730                 735

Thr Thr Ala Asn Tyr Asp Asp Asp Arg Lys Trp Gly Phe Cys Pro Asp
        740                 745                 750

Gln Gly Tyr Ser Leu Phe Leu Val Ala Ala His Glu Phe Gly His Ala
    755                 760                 765

Met Gly Leu Glu His Ser Gln Asp Pro Gly Ala Leu Met Ala Pro Ile
770                 775                 780

Tyr Thr Tyr Thr Lys Asn Phe Arg Leu Ser Gln Asp Asp Ile Lys Gly
785                 790                 795                 800

Ile Gln Glu Leu Tyr Gly Ala Ser Pro Asp Ile Asp Leu Gly Thr Gly
            805                 810                 815

Pro Thr Pro Thr Leu Gly Pro Val Thr Pro Glu Ile Cys Lys Gln Asp
        820                 825                 830

Ile Val Phe Asp Gly Ile Ala Gln Ile Arg Gly Glu Ile Phe Phe Phe
    835                 840                 845

Lys Asp Arg Phe Ile Trp Arg Thr Val Thr Pro Arg Asp Lys Pro Met
850                 855                 860

Gly Pro Leu Leu Val Ala Thr Phe Trp Pro Glu Leu Pro Glu Lys Ile
865                 870                 875                 880

Asp Ala Val Tyr Glu Ala Pro Gln Glu Glu Lys Ala Val Phe Phe Ala
            885                 890                 895

Gly Asn Glu Tyr Trp Ile Tyr Ser Ala Ser Thr Leu Glu Arg Gly Tyr
        900                 905                 910

Pro Lys Pro Leu Thr Ser Leu Gly Leu Pro Pro Asp Val Gln Arg Val
    915                 920                 925

Asp Ala Ala Phe Asn Trp Ser Lys Asn Lys Lys Thr Tyr Ile Phe Ala
930                 935                 940

Gly Asp Lys Phe Trp Arg Tyr Asn Glu Val Lys Lys Lys Met Asp Pro
945                 950                 955                 960

Gly Phe Pro Lys Leu Ile Ala Asp Ala Trp Asn Ala Ile Pro Asp Asn
            965                 970                 975

Leu Asp Ala Val Val Asp Leu Gln Gly Gly Gly His Ser Tyr Phe Phe
        980                 985                 990

Lys Gly Ala Tyr Tyr Leu Lys Leu Glu Asn Gln Ser Leu Lys Ser Val
    995                 1000                1005

Lys Phe Gly Ser Ile Lys Ser Asp Trp Leu Gly Cys
    1010                1015                1020

<210> SEQ ID NO 217
<211> LENGTH: 793
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 217

```
Tyr Asn Phe Phe Pro Arg Lys Pro Lys Trp Asp Lys Asn Gln Ile Thr
1               5                   10                  15
Tyr Arg Ile Ile Gly Tyr Thr Pro Asp Leu Asp Pro Glu Thr Val Asp
            20                  25                  30
Asp Ala Phe Ala Arg Ala Phe Gln Val Trp Ser Asp Val Thr Pro Leu
        35                  40                  45
Arg Phe Ser Arg Ile His Asp Gly Glu Ala Asp Ile Met Ile Asn Phe
    50                  55                  60
Gly Arg Trp Glu His Gly Asp Gly Tyr Pro Phe Asp Gly Lys Asp Gly
65                  70                  75                  80
Leu Leu Ala His Ala Phe Ala Pro Gly Thr Gly Val Gly Gly Asp Ser
                85                  90                  95
His Phe Asp Asp Asp Glu Leu Trp Thr Leu Gly Glu Gly Gln Val Val
            100                 105                 110
Arg Val Lys Tyr Gly Asn Ala Asp Gly Glu Tyr Cys Lys Phe Pro Phe
        115                 120                 125
Leu Phe Asn Gly Lys Glu Tyr Asn Ser Cys Thr Asp Thr Gly Arg Ser
    130                 135                 140
Asp Gly Phe Leu Trp Cys Ser Thr Thr Tyr Asn Phe Glu Lys Asp Gly
145                 150                 155                 160
Lys Tyr Gly Phe Cys Pro His Glu Ala Leu Phe Thr Met Gly Gly Asn
                165                 170                 175
Ala Glu Gly Gln Pro Cys Lys Phe Pro Phe Arg Phe Gln Gly Thr Ser
            180                 185                 190
Tyr Asp Ser Cys Thr Thr Glu Gly Arg Thr Asp Gly Tyr Arg Trp Cys
        195                 200                 205
Gly Thr Thr Glu Asp Tyr Asp Arg Asp Lys Lys Tyr Gly Phe Cys Pro
    210                 215                 220
Glu Thr Ala Met Ser Thr Val Gly Gly Asn Ser Glu Gly Ala Pro Cys
225                 230                 235                 240
Val Phe Pro Phe Thr Phe Leu Gly Asn Lys Tyr Glu Ser Cys Thr Ser
                245                 250                 255
Ala Gly Arg Ser Asp Gly Lys Met Trp Cys Ala Thr Thr Ala Asn Tyr
            260                 265                 270
Asp Asp Asp Arg Lys Trp Gly Phe Cys Pro Asp Gln Gly Tyr Ser Leu
        275                 280                 285
Phe Leu Val Ala Ala His Glu Phe Gly His Ala Met Gly Leu Glu His
    290                 295                 300
Ser Gln Asp Pro Gly Ala Leu Met Ala Pro Ile Tyr Thr Tyr Thr Lys
305                 310                 315                 320
Asn Phe Arg Leu Ser Gln Asp Asp Ile Lys Gly Ile Gln Glu Leu Tyr
                325                 330                 335
Gly Ala Ser Pro Asp Ile Asp Leu Gly Thr Gly Pro Thr Pro Thr Leu
            340                 345                 350
Gly Pro Val Thr Pro Glu Ile Cys Lys Gln Asp Ile Val Phe Asp Gly
        355                 360                 365
Ile Ala Gln Ile Arg Gly Glu Ile Phe Phe Phe Lys Asp Arg Phe Ile
    370                 375                 380
Trp Arg Thr Val Thr Pro Arg Asp Lys Pro Met Gly Pro Leu Leu Val
385                 390                 395                 400
```

Ala Thr Phe Trp Pro Glu Leu Pro Glu Lys Ile Asp Ala Val Tyr Glu
                405                 410                 415

Ala Pro Gln Glu Glu Lys Ala Val Phe Phe Ala Gly Asn Glu Tyr Trp
            420                 425                 430

Ile Tyr Ser Ala Ser Thr Leu Glu Arg Gly Tyr Pro Lys Pro Leu Thr
        435                 440                 445

Ser Leu Gly Leu Pro Pro Asp Val Gln Arg Val Asp Ala Ala Phe Asn
    450                 455                 460

Trp Ser Lys Asn Lys Lys Thr Tyr Ile Phe Ala Gly Asp Lys Phe Trp
465                 470                 475                 480

Arg Tyr Asn Glu Val Lys Lys Met Asp Pro Gly Phe Pro Lys Leu
                485                 490                 495

Ile Ala Asp Ala Trp Asn Ala Ile Pro Asp Asn Leu Asp Ala Val Val
                500                 505                 510

Asp Leu Gln Gly Gly His Ser Tyr Phe Phe Lys Gly Ala Tyr Tyr
                515                 520                 525

Leu Lys Leu Glu Asn Gln Ser Leu Lys Ser Val Lys Phe Gly Ser Ile
                530                 535                 540

Lys Ser Asp Trp Leu Gly Cys Gly Gly Gly Ser Gly Gly Gly Gly
545                 550                 555                 560

Ser Gly Gly Gly Gly Ser Asp Lys Thr His Thr Cys Pro Pro Cys Pro
                565                 570                 575

Ala Pro Glu Leu Leu Gly Gly Pro Ser Val Phe Leu Phe Pro Pro Lys
                580                 585                 590

Pro Lys Asp Thr Leu Met Ile Ser Arg Thr Pro Glu Val Thr Cys Val
                595                 600                 605

Val Val Asp Val Ser His Glu Asp Pro Glu Val Lys Phe Asn Trp Tyr
610                 615                 620

Val Asp Gly Val Glu Val His Asn Ala Lys Thr Lys Pro Arg Glu Glu
625                 630                 635                 640

Gln Tyr Asn Ser Thr Tyr Arg Val Val Ser Val Leu Thr Val Leu His
                645                 650                 655

Gln Asp Trp Leu Asn Gly Lys Glu Tyr Lys Cys Lys Val Ser Asn Lys
                660                 665                 670

Ala Leu Pro Ala Pro Ile Glu Lys Thr Ile Ser Lys Ala Lys Gly Gln
                675                 680                 685

Pro Arg Glu Pro Gln Val Cys Thr Leu Pro Pro Ser Arg Glu Glu Met
                690                 695                 700

Thr Lys Asn Gln Val Ser Leu Ser Cys Ala Val Lys Gly Phe Tyr Pro
705                 710                 715                 720

Ser Asp Ile Ala Val Glu Trp Glu Ser Asn Gly Gln Pro Glu Asn Asn
                725                 730                 735

Tyr Lys Thr Thr Pro Pro Val Leu Asp Ser Asp Gly Ser Phe Phe Leu
                740                 745                 750

Val Ser Lys Leu Thr Val Asp Lys Ser Arg Trp Gln Gln Gly Asn Val
                755                 760                 765

Phe Ser Cys Ser Val Met His Glu Ala Leu His Asn His Tyr Thr Gln
                770                 775                 780

Lys Ser Leu Ser Leu Ser Pro Gly Lys
785                 790

<210> SEQ ID NO 218
<211> LENGTH: 602
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 218

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Thr | Ser | Arg | Tyr | Thr | Phe | Thr | Glu | Tyr |
| | | | 20 | | | | | 25 | | | | | 30 | | |
| Thr | Ile | His | Trp | Val | Arg | Gln | Ala | Pro | Gly | Gln | Arg | Leu | Glu | Trp | Ile |
| | | 35 | | | | | 40 | | | | | 45 | | | |
| Gly | Gly | Ile | Asn | Pro | Asn | Asn | Gly | Ile | Pro | Asn | Tyr | Asn | Gln | Lys | Phe |
| | 50 | | | | | 55 | | | | | 60 | | | | |
| Lys | Gly | Arg | Val | Thr | Ile | Thr | Val | Asp | Thr | Ser | Ala | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Arg | Ile | Ala | Tyr | Gly | Tyr | Asp | Glu | Gly | His | Ala | Met | Asp |
| | | | 100 | | | | | 105 | | | | | 110 | | |
| Tyr | Trp | Gly | Gln | Gly | Thr | Leu | Val | Thr | Val | Ser | Ser | Ala | Ser | Thr | Lys |
| | | | 115 | | | | | 120 | | | | | 125 | | |
| Gly | Pro | Ser | Val | Phe | Pro | Leu | Ala | Pro | Ser | Ser | Lys | Ser | Thr | Ser | Gly |
| | 130 | | | | | 135 | | | | | 140 | | | | |
| Gly | Thr | Ala | Ala | Leu | Gly | Cys | Leu | Val | Lys | Asp | Tyr | Phe | Pro | Glu | Pro |
| 145 | | | | | 150 | | | | | 155 | | | | | 160 |
| Val | Thr | Val | Ser | Trp | Asn | Ser | Gly | Ala | Leu | Thr | Ser | Gly | Val | His | Thr |
| | | | | 165 | | | | | 170 | | | | | 175 | |
| Phe | Pro | Ala | Val | Leu | Gln | Ser | Ser | Gly | Leu | Tyr | Ser | Leu | Ser | Ser | Val |
| | | | 180 | | | | | 185 | | | | | 190 | | |
| Val | Thr | Val | Pro | Ser | Ser | Ser | Leu | Gly | Thr | Gln | Thr | Tyr | Ile | Cys | Asn |
| | | 195 | | | | | 200 | | | | | 205 | | | |
| Val | Asn | His | Lys | Pro | Ser | Asn | Thr | Lys | Val | Asp | Lys | Arg | Val | Glu | Pro |
| | 210 | | | | | 215 | | | | | 220 | | | | |
| Lys | Ser | Cys | Asp | Lys | Thr | His | Thr | Cys | Pro | Pro | Cys | Pro | Ala | Pro | Glu |
| 225 | | | | | 230 | | | | | 235 | | | | | 240 |
| Leu | Leu | Gly | Gly | Pro | Ser | Val | Phe | Leu | Phe | Pro | Pro | Lys | Pro | Lys | Asp |
| | | | | 245 | | | | | 250 | | | | | 255 | |
| Thr | Leu | Met | Ile | Ser | Arg | Thr | Pro | Glu | Val | Thr | Cys | Val | Val | Val | Asp |
| | | | 260 | | | | | 265 | | | | | 270 | | |
| Val | Ser | His | Glu | Asp | Pro | Glu | Val | Lys | Phe | Asn | Trp | Tyr | Val | Asp | Gly |
| | | 275 | | | | | 280 | | | | | 285 | | | |
| Val | Glu | Val | His | Asn | Ala | Lys | Thr | Lys | Pro | Arg | Glu | Glu | Gln | Tyr | Asn |
| | 290 | | | | | 295 | | | | | 300 | | | | |
| Ser | Thr | Tyr | Arg | Val | Val | Ser | Val | Leu | Thr | Val | Leu | His | Gln | Asp | Trp |
| 305 | | | | | 310 | | | | | 315 | | | | | 320 |
| Leu | Asn | Gly | Lys | Glu | Tyr | Lys | Cys | Lys | Val | Ser | Asn | Lys | Ala | Leu | Pro |
| | | | | 325 | | | | | 330 | | | | | 335 | |
| Ala | Pro | Ile | Glu | Lys | Thr | Ile | Ser | Lys | Ala | Lys | Gly | Gln | Pro | Arg | Glu |
| | | | 340 | | | | | 345 | | | | | 350 | | |
| Pro | Gln | Val | Tyr | Thr | Leu | Pro | Pro | Cys | Arg | Glu | Glu | Met | Thr | Lys | Asn |
| | | 355 | | | | | 360 | | | | | 365 | | | |
| Gln | Val | Ser | Leu | Trp | Cys | Leu | Val | Lys | Gly | Phe | Tyr | Pro | Ser | Asp | Ile |
| | 370 | | | | | 375 | | | | | 380 | | | | |

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys Gly Gly Gly Ser Gly Gly Gly Gly Ser
        450                 455                 460

Gly Gly Gly Gly Ser Ala Pro Thr Ser Ser Thr Lys Lys Thr Gln
465                 470                 475                 480

Leu Gln Leu Glu His Leu Leu Leu Asp Leu Gln Met Ile Leu Asn Gly
                485                 490                 495

Ile Asn Asn Tyr Lys Asn Pro Lys Leu Thr Arg Met Leu Thr Ala Lys
                500                 505                 510

Phe Ala Met Pro Lys Lys Ala Thr Glu Leu Lys His Leu Gln Cys Leu
            515                 520                 525

Glu Glu Glu Leu Lys Pro Leu Glu Val Leu Asn Leu Ala Gln Ser
530                 535                 540

Lys Asn Phe His Leu Arg Pro Arg Asp Leu Ile Ser Asn Ile Asn Val
545                 550                 555                 560

Ile Val Leu Glu Leu Lys Gly Ser Glu Thr Thr Phe Met Cys Glu Tyr
                565                 570                 575

Ala Asp Glu Thr Ala Thr Ile Val Glu Phe Leu Asn Arg Trp Ile Thr
            580                 585                 590

Phe Cys Gln Ser Ile Ile Ser Thr Leu Thr
            595                 600

<210> SEQ ID NO 219
<211> LENGTH: 883
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Gln Val Gln Leu Val Gln Ser Gly Ala Glu Val Lys Lys Pro Gly Ala
1               5                   10                  15

Ser Val Lys Val Ser Cys Lys Thr Ser Arg Tyr Thr Phe Thr Glu Tyr
            20                  25                  30

Thr Ile His Trp Val Arg Gln Ala Pro Gly Gln Arg Leu Glu Trp Ile
        35                  40                  45

Gly Gly Ile Asn Pro Asn Asn Gly Ile Pro Asn Tyr Asn Gln Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Ile Ala Tyr Gly Tyr Asp Glu Gly His Ala Met Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
        180                 185                 190

Val Thr Val Pro Ser Ser Ser Leu Gly Thr Gln Thr Tyr Ile Cys Asn
    195                 200                 205

Val Asn His Lys Pro Ser Asn Thr Lys Val Asp Lys Arg Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Cys Thr Leu Pro Pro Ser Arg Glu Glu Met Thr Lys Asn
        355                 360                 365

Gln Val Ser Leu Ser Cys Ala Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Val Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys Gly Gly Gly Ser Gly Gly Gly Ser
    450                 455                 460

Gly Gly Gly Gly Ser Phe Arg Gly Pro Leu Leu Pro Asn Arg Pro Phe
465                 470                 475                 480

Thr Thr Val Trp Asn Ala Asn Thr Gln Trp Cys Leu Glu Arg His Gly
                485                 490                 495

Val Asp Val Asp Val Ser Val Phe Asp Val Val Ala Asn Pro Gly Gln
            500                 505                 510

Thr Phe Arg Gly Pro Asp Met Thr Ile Phe Tyr Ser Ser Gln Leu Gly
        515                 520                 525

Thr Tyr Pro Tyr Tyr Thr Pro Thr Gly Glu Pro Val Phe Gly Gly Leu
    530                 535                 540

Pro Gln Asn Ala Ser Leu Ile Ala His Leu Ala Arg Thr Phe Gln Asp
545                 550                 555                 560

```
Ile Leu Ala Ala Ile Pro Ala Pro Asp Phe Ser Gly Leu Ala Val Ile
                565                 570                 575

Asp Trp Glu Ala Trp Arg Pro Arg Trp Ala Phe Asn Trp Asp Thr Lys
            580                 585                 590

Asp Ile Tyr Arg Gln Arg Ser Arg Ala Leu Val Gln Ala Gln His Pro
        595                 600                 605

Asp Trp Pro Ala Pro Gln Val Glu Ala Val Ala Gln Asp Gln Phe Gln
    610                 615                 620

Gly Ala Ala Arg Ala Trp Met Ala Gly Thr Leu Gln Leu Gly Arg Ala
625                 630                 635                 640

Leu Arg Pro Arg Gly Leu Trp Gly Phe Tyr Gly Phe Pro Asp Cys Tyr
                645                 650                 655

Asn Tyr Asp Phe Leu Ser Pro Asn Tyr Thr Gly Gln Cys Pro Ser Gly
                660                 665                 670

Ile Arg Ala Gln Asn Asp Gln Leu Gly Trp Leu Trp Gly Gln Ser Arg
            675                 680                 685

Ala Leu Tyr Pro Ser Ile Tyr Met Pro Ala Val Leu Glu Gly Thr Gly
        690                 695                 700

Lys Ser Gln Met Tyr Val Gln His Arg Val Ala Glu Ala Phe Arg Val
705                 710                 715                 720

Ala Val Ala Ala Gly Asp Pro Asn Leu Pro Val Leu Pro Tyr Val Gln
                725                 730                 735

Ile Phe Tyr Asp Thr Thr Asn His Phe Leu Pro Leu Asp Glu Leu Glu
                740                 745                 750

His Ser Leu Gly Glu Ser Ala Ala Gln Gly Ala Ala Gly Val Val Leu
            755                 760                 765

Trp Val Ser Trp Glu Asn Thr Arg Thr Lys Glu Ser Cys Gln Ala Ile
770                 775                 780

Lys Glu Tyr Met Asp Thr Thr Leu Gly Pro Phe Ile Leu Asn Val Thr
785                 790                 795                 800

Ser Gly Ala Leu Leu Cys Ser Gln Ala Leu Cys Ser Gly His Gly Arg
                805                 810                 815

Cys Val Arg Arg Thr Ser His Pro Lys Ala Leu Leu Leu Leu Asn Pro
            820                 825                 830

Ala Ser Phe Ser Ile Gln Leu Thr Pro Gly Gly Pro Leu Ser Leu
        835                 840                 845

Arg Gly Ala Leu Ser Leu Glu Asp Gln Ala Gln Met Ala Val Glu Phe
    850                 855                 860

Lys Cys Arg Cys Tyr Pro Gly Trp Gln Ala Pro Trp Cys Glu Arg Lys
865                 870                 875                 880

Ser Met Trp

<210> SEQ ID NO 220
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ile Met Met Trp Val Arg Gln Ala Pro Gly Lys Gly Leu Glu Trp Val
         35                  40                  45
Ser Ser Ile Tyr Pro Ser Gly Gly Ile Thr Phe Tyr Ala Asp Thr Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Ile Lys Leu Gly Thr Val Thr Val Asp Tyr Trp Gly Gln
                100                 105                 110
Gly Thr Leu Val Thr Val Ser Ser Ala Ser Thr Lys Gly Pro Ser Val
             115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Arg Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Cys Arg Glu Glu Met Thr Lys Asn Gln Val Ser Leu
        355                 360                 365
Trp Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
```

<210> SEQ ID NO 221
<211> LENGTH: 598
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 221

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Cys Arg Glu Glu Met Thr Lys Asn Gln Val Ser Leu
            355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Gly Gly Gly Gly Ser Gly Gly Gly Gly Ser Gly Gly Gly Gly
    450                 455                 460

Ser Ala Pro Thr Ser Ser Ser Thr Lys Lys Thr Gln Leu Gln Leu Glu
465                 470                 475                 480

His Leu Leu Leu Asp Leu Gln Met Ile Leu Asn Gly Ile Asn Asn Tyr
                485                 490                 495

Lys Asn Pro Lys Leu Thr Arg Met Leu Thr Ala Lys Phe Ala Met Pro
            500                 505                 510

Lys Lys Ala Thr Glu Leu Lys His Leu Gln Cys Leu Glu Glu Glu Leu
            515                 520                 525

Lys Pro Leu Glu Glu Val Leu Asn Leu Ala Gln Ser Lys Asn Phe His
            530                 535                 540

Leu Arg Pro Arg Asp Leu Ile Ser Asn Ile Asn Val Ile Val Leu Glu
545                 550                 555                 560

Leu Lys Gly Ser Glu Thr Thr Phe Met Cys Glu Tyr Ala Asp Glu Thr
                565                 570                 575

Ala Thr Ile Val Glu Phe Leu Asn Arg Trp Ile Thr Phe Cys Gln Ser
            580                 585                 590

Ile Ile Ser Thr Leu Thr
            595

<210> SEQ ID NO 222
<211> LENGTH: 879
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Asn Trp Gly Lys Gln Arg Ser Gly Gln Gly Leu Glu Trp Ile
            35                  40                  45

Gly Glu Ile Tyr Pro Gly Ser Gly Thr Asn Tyr Tyr Asn Glu Lys Phe
    50                  55                  60

Lys Ala Lys Ala Thr Leu Thr Ala Asp Lys Ser Ser Asn Ile Ala Tyr
65                  70                  75                  80

Met Gln Leu Ser Ser Leu Thr Ser Glu Asp Ser Ala Val Tyr Phe Cys
                85                  90                  95

Ala Arg Arg Gly Arg Tyr Gly Leu Tyr Ala Met Asp Tyr Trp Gly Gln
            100                 105                 110
```

Gly Thr Ser Val Thr Val Ser Ala Ser Thr Lys Gly Pro Ser Val
                115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Glu Glu Met Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Gly Gly Gly Ser Gly Gly Gly Ser Gly Gly Gly Gly
    450                 455                 460

Ser Phe Arg Gly Pro Leu Leu Pro Asn Arg Pro Phe Thr Thr Val Trp
465                 470                 475                 480

Asn Ala Asn Thr Gln Trp Cys Leu Glu Arg His Gly Val Asp Val Asp
                485                 490                 495

Val Ser Val Phe Asp Val Val Ala Asn Pro Gly Gln Thr Phe Arg Gly
            500                 505                 510

Pro Asp Met Thr Ile Phe Tyr Ser Ser Gln Leu Gly Thr Tyr Pro Tyr
        515                 520                 525

Tyr Thr Pro Thr Gly Glu Pro Val Phe Gly Gly Leu Pro Gln Asn Ala
          530                 535                 540

Ser Leu Ile Ala His Leu Ala Arg Thr Phe Gln Asp Ile Leu Ala Ala
545                 550                 555                 560

Ile Pro Ala Pro Asp Phe Ser Gly Leu Ala Val Ile Asp Trp Glu Ala
                565                 570                 575

Trp Arg Pro Arg Trp Ala Phe Asn Trp Asp Thr Lys Asp Ile Tyr Arg
            580                 585                 590

Gln Arg Ser Arg Ala Leu Val Gln Ala Gln His Pro Asp Trp Pro Ala
        595                 600                 605

Pro Gln Val Glu Ala Val Ala Gln Asp Gln Phe Gln Gly Ala Ala Arg
    610                 615                 620

Ala Trp Met Ala Gly Thr Leu Gln Leu Gly Arg Ala Leu Arg Pro Arg
625                 630                 635                 640

Gly Leu Trp Gly Phe Gly Phe Pro Asp Cys Tyr Asn Tyr Asp Phe
                645                 650                 655

Leu Ser Pro Asn Tyr Thr Gly Gln Cys Pro Ser Gly Ile Arg Ala Gln
                660                 665                 670

Asn Asp Gln Leu Gly Trp Leu Trp Gly Gln Ser Arg Ala Leu Tyr Pro
            675                 680                 685

Ser Ile Tyr Met Pro Ala Val Leu Glu Gly Thr Gly Lys Ser Gln Met
        690                 695                 700

Tyr Val Gln His Arg Val Ala Glu Ala Phe Arg Val Ala Val Ala Ala
705                 710                 715                 720

Gly Asp Pro Asn Leu Pro Val Leu Pro Tyr Val Gln Ile Phe Tyr Asp
                725                 730                 735

Thr Thr Asn His Phe Leu Pro Leu Asp Glu Leu Glu His Ser Leu Gly
            740                 745                 750

Glu Ser Ala Ala Gln Gly Ala Ala Gly Val Val Leu Trp Val Ser Trp
        755                 760                 765

Glu Asn Thr Arg Thr Lys Glu Ser Cys Gln Ala Ile Lys Glu Tyr Met
    770                 775                 780

Asp Thr Thr Leu Gly Pro Phe Ile Leu Asn Val Thr Ser Gly Ala Leu
785                 790                 795                 800

Leu Cys Ser Gln Ala Leu Cys Ser Gly His Gly Arg Cys Val Arg Arg
                805                 810                 815

Thr Ser His Pro Lys Ala Leu Leu Leu Asn Pro Ala Ser Phe Ser
            820                 825                 830

Ile Gln Leu Thr Pro Gly Gly Pro Leu Ser Leu Arg Gly Ala Leu
        835                 840                 845

Ser Leu Glu Asp Gln Ala Gln Met Ala Val Glu Phe Lys Cys Arg Cys
850                 855                 860

Tyr Pro Gly Trp Gln Ala Pro Trp Cys Glu Arg Lys Ser Met Trp
865                 870                 875

<210> SEQ ID NO 223
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Asp Ile Gln Met Thr Gln Thr Thr Ser Ser Leu Ser Ala Ser Leu Gly
1               5                   10                  15

```
Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Asn Asn Leu Glu Gln
65                  70                  75                  80

Glu Asp Ile Ala Thr Tyr Phe Cys Gln Gln Gly Asn Thr Arg Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 224
<211> LENGTH: 656
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Phe Arg Gly Pro Leu Leu Pro Asn Arg Pro Phe Thr Thr Val Trp Asn
1               5                   10                  15

Ala Asn Thr Gln Trp Cys Leu Glu Arg His Gly Val Asp Val Asp Val
            20                  25                  30

Ser Val Phe Asp Val Val Ala Asn Pro Gly Gln Thr Phe Arg Gly Pro
        35                  40                  45

Asp Met Thr Ile Phe Tyr Ser Ser Gln Leu Gly Thr Tyr Pro Tyr Tyr
50                  55                  60

Thr Pro Thr Gly Glu Pro Val Phe Gly Leu Pro Gln Asn Ala Ser
65                  70                  75                  80

Leu Ile Ala His Leu Ala Arg Thr Phe Gln Asp Ile Leu Ala Ala Ile
                85                  90                  95

Pro Ala Pro Asp Phe Ser Gly Leu Ala Val Ile Asp Trp Glu Ala Trp
            100                 105                 110

Arg Pro Arg Trp Ala Phe Asn Trp Asp Thr Lys Asp Ile Tyr Arg Gln
        115                 120                 125

Arg Ser Arg Ala Leu Val Gln Ala Gln His Pro Asp Trp Pro Ala Pro
130                 135                 140

Gln Val Glu Ala Val Ala Gln Asp Gln Phe Gln Gly Ala Ala Arg Ala
```

```
                145                 150                 155                 160
Trp Met Ala Gly Thr Leu Gln Leu Gly Arg Ala Leu Arg Pro Arg Gly
                    165                 170                 175
Leu Trp Gly Phe Tyr Gly Phe Pro Asp Cys Tyr Asn Tyr Asp Phe Leu
                    180                 185                 190
Ser Pro Asn Tyr Thr Gly Gln Cys Pro Ser Gly Ile Arg Ala Gln Asn
                    195                 200                 205
Asp Gln Leu Gly Trp Leu Trp Gly Gln Ser Arg Ala Leu Tyr Pro Ser
                210                 215                 220
Ile Tyr Met Pro Ala Val Leu Glu Gly Thr Gly Lys Ser Gln Met Tyr
225                 230                 235                 240
Val Gln His Arg Val Ala Glu Ala Phe Arg Val Ala Val Ala Ala Gly
                    245                 250                 255
Asp Pro Asn Leu Pro Val Leu Pro Tyr Val Gln Ile Phe Tyr Asp Thr
                    260                 265                 270
Thr Asn His Phe Leu Pro Leu Asp Glu Leu Glu His Ser Leu Gly Glu
                    275                 280                 285
Ser Ala Ala Gln Gly Ala Ala Gly Val Val Leu Trp Val Ser Trp Glu
                290                 295                 300
Asn Thr Arg Thr Lys Glu Ser Cys Gln Ala Ile Lys Glu Tyr Met Asp
305                 310                 315                 320
Thr Thr Leu Gly Pro Phe Ile Leu Asn Val Thr Ser Gly Ala Leu Leu
                    325                 330                 335
Cys Ser Gln Ala Leu Cys Ser Gly His Gly Arg Cys Val Arg Arg Thr
                    340                 345                 350
Ser His Pro Lys Ala Leu Leu Leu Asn Pro Ala Ser Phe Ser Ile
                    355                 360                 365
Gln Leu Thr Pro Gly Gly Pro Leu Ser Leu Arg Gly Ala Leu Ser
                370                 375                 380
Leu Glu Asp Gln Ala Gln Met Ala Val Glu Phe Lys Cys Arg Cys Tyr
385                 390                 395                 400
Pro Gly Trp Gln Ala Pro Trp Cys Glu Arg Lys Ser Met Trp Gly Gly
                    405                 410                 415
Gly Gly Ser Gly Gly Gly Gly Ser Gly Gly Gly Ser Asp Lys Thr
                    420                 425                 430
His Thr Cys Pro Pro Cys Pro Ala Pro Glu Leu Leu Gly Gly Pro Ser
                    435                 440                 445
Val Phe Leu Phe Pro Pro Lys Pro Lys Asp Thr Leu Met Ile Ser Arg
                450                 455                 460
Thr Pro Glu Val Thr Cys Val Val Val Asp Val Ser His Glu Asp Pro
465                 470                 475                 480
Glu Val Lys Phe Asn Trp Tyr Val Asp Gly Val Glu Val His Asn Ala
                    485                 490                 495
Lys Thr Lys Pro Arg Glu Glu Gln Tyr Asn Ser Thr Tyr Arg Val Val
                    500                 505                 510
Ser Val Leu Thr Val Leu His Gln Asp Trp Leu Asn Gly Lys Glu Tyr
                515                 520                 525
Lys Cys Lys Val Ser Asn Lys Ala Leu Pro Ala Pro Ile Glu Lys Thr
                530                 535                 540
Ile Ser Lys Ala Lys Gly Gln Pro Arg Glu Pro Gln Val Cys Thr Leu
545                 550                 555                 560
Pro Pro Ser Arg Glu Glu Met Thr Lys Asn Gln Val Ser Leu Ser Cys
                    565                 570                 575
```

```
Ala Val Lys Gly Phe Tyr Pro Ser Asp Ile Ala Val Glu Trp Glu Ser
            580                 585                 590

Asn Gly Gln Pro Glu Asn Asn Tyr Lys Thr Thr Pro Val Leu Asp
            595                 600                 605

Ser Asp Gly Ser Phe Phe Leu Val Ser Lys Leu Thr Val Asp Lys Ser
610                 615                 620

Arg Trp Gln Gln Gly Asn Val Phe Ser Cys Ser Val Met His Glu Ala
625                 630                 635                 640

Leu His Asn His Tyr Thr Gln Lys Ser Leu Ser Leu Ser Pro Gly Lys
                645                 650                 655

<210> SEQ ID NO 225
<211> LENGTH: 775
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Leu Leu Val Met Cys Ile Val Leu Arg Pro Ser Arg Val His Asn Ser
1               5                   10                  15

Glu Glu Asn Thr Met Arg Ala Leu Thr Leu Lys Asp Ile Leu Asn Gly
            20                  25                  30

Thr Phe Ser Tyr Lys Thr Phe Phe Pro Asn Trp Ile Ser Gly Gln Glu
        35                  40                  45

Tyr Leu His Gln Ser Ala Asp Asn Asn Ile Val Leu Tyr Asn Ile Glu
    50                  55                  60

Thr Gly Gln Ser Tyr Thr Ile Leu Ser Asn Arg Thr Met Lys Ser Val
65                  70                  75                  80

Asn Ala Ser Asn Tyr Gly Leu Ser Pro Asp Arg Gln Phe Val Tyr Leu
                85                  90                  95

Glu Ser Asp Tyr Ser Lys Leu Trp Arg Tyr Ser Tyr Thr Ala Thr Tyr
            100                 105                 110

Tyr Ile Tyr Asp Leu Ser Asn Gly Glu Phe Val Arg Gly Asn Glu Leu
        115                 120                 125

Pro Arg Pro Ile Gln Tyr Leu Cys Trp Ser Pro Val Gly Ser Lys Leu
    130                 135                 140

Ala Tyr Val Tyr Gln Asn Asn Ile Tyr Leu Lys Gln Arg Pro Gly Asp
145                 150                 155                 160

Pro Pro Phe Gln Ile Thr Phe Asn Gly Arg Glu Asn Lys Ile Phe Asn
                165                 170                 175

Gly Ile Pro Asp Trp Val Tyr Glu Glu Glu Met Leu Pro Thr Lys Tyr
            180                 185                 190

Ala Leu Trp Trp Ser Pro Asn Gly Lys Phe Leu Ala Tyr Ala Glu Phe
        195                 200                 205

Asn Asp Lys Asp Ile Pro Val Ile Ala Tyr Ser Tyr Tyr Gly Asp Glu
    210                 215                 220

Gln Tyr Pro Arg Thr Ile Asn Ile Pro Tyr Pro Lys Ala Gly Ala Lys
225                 230                 235                 240

Asn Pro Val Val Arg Ile Phe Ile Ile Asp Thr Thr Tyr Pro Ala Tyr
                245                 250                 255

Val Gly Pro Gln Glu Val Pro Val Pro Ala Met Ile Ala Ser Ser Asp
            260                 265                 270

Tyr Tyr Phe Ser Trp Leu Thr Trp Val Thr Asp Glu Arg Val Cys Leu
```

```
            275                 280                 285
Gln Trp Leu Lys Arg Val Gln Asn Val Ser Val Leu Ser Ile Cys Asp
290                 295                 300

Phe Arg Glu Asp Trp Gln Thr Trp Asp Cys Pro Lys Thr Gln Glu His
305                 310                 315                 320

Ile Glu Glu Ser Arg Thr Gly Trp Ala Gly Gly Phe Phe Val Ser Arg
                325                 330                 335

Pro Val Phe Ser Tyr Asp Ala Ile Ser Tyr Tyr Lys Ile Phe Ser Asp
                340                 345                 350

Lys Asp Gly Tyr Lys His Ile His Tyr Ile Lys Asp Thr Val Glu Asn
                355                 360                 365

Ala Ile Gln Ile Thr Ser Gly Lys Trp Glu Ala Ile Asn Ile Phe Arg
370                 375                 380

Val Thr Gln Asp Ser Leu Phe Tyr Ser Ser Asn Glu Phe Glu Glu Tyr
385                 390                 395                 400

Pro Gly Arg Arg Asn Ile Tyr Arg Ile Ser Ile Gly Ser Tyr Pro Pro
                405                 410                 415

Ser Lys Lys Cys Val Thr Cys His Leu Arg Lys Glu Arg Cys Gln Tyr
                420                 425                 430

Tyr Thr Ala Ser Phe Ser Asp Tyr Ala Lys Tyr Tyr Ala Leu Val Cys
                435                 440                 445

Tyr Gly Pro Gly Ile Pro Ile Ser Thr Leu His Asp Gly Arg Thr Asp
450                 455                 460

Gln Glu Ile Lys Ile Leu Glu Glu Asn Lys Glu Leu Glu Asn Ala Leu
465                 470                 475                 480

Lys Asn Ile Gln Leu Pro Lys Glu Glu Ile Lys Lys Leu Glu Val Asp
                485                 490                 495

Glu Ile Thr Leu Trp Tyr Lys Met Ile Leu Pro Pro Gln Phe Asp Arg
                500                 505                 510

Ser Lys Lys Tyr Pro Leu Leu Ile Gln Val Tyr Gly Gly Pro Cys Ser
                515                 520                 525

Gln Ser Val Arg Ser Val Phe Ala Val Asn Trp Ile Ser Tyr Leu Ala
530                 535                 540

Ser Lys Glu Gly Met Val Ile Ala Leu Val Asp Gly Arg Gly Thr Ala
545                 550                 555                 560

Phe Gln Gly Asp Lys Leu Leu Tyr Ala Val Tyr Arg Lys Leu Gly Val
                565                 570                 575

Tyr Glu Val Glu Asp Gln Ile Thr Ala Val Arg Lys Phe Ile Glu Met
                580                 585                 590

Gly Phe Ile Asp Glu Lys Arg Ile Ala Ile Trp Gly Trp Ser Tyr Gly
                595                 600                 605

Gly Tyr Val Ser Ser Leu Ala Leu Ala Ser Gly Thr Gly Leu Phe Lys
                610                 615                 620

Cys Gly Ile Ala Val Ala Pro Val Ser Ser Trp Glu Tyr Tyr Ala Ser
625                 630                 635                 640

Val Tyr Thr Glu Arg Phe Met Gly Leu Pro Thr Lys Asp Asp Asn Leu
                645                 650                 655

Glu His Tyr Lys Asn Ser Thr Val Met Ala Arg Ala Glu Tyr Phe Arg
                660                 665                 670

Asn Val Asp Tyr Leu Leu Ile His Gly Thr Ala Asp Asp Asn Val His
                675                 680                 685

Phe Gln Asn Ser Ala Gln Ile Ala Lys Ala Leu Val Asn Ala Gln Val
690                 695                 700
```

```
Asp Phe Gln Ala Met Trp Tyr Ser Asp Gln Asn His Gly Leu Ser Gly
705                 710                 715                 720

Leu Ser Thr Asn His Leu Tyr Thr His Met Thr His Phe Leu Lys Gln
                725                 730                 735

Cys Phe Ser Leu Ser Asp Gly Gly Gly Ser Gly Leu Asn Asp Ile
            740                 745                 750

Phe Glu Ala Gln Lys Ile Glu Trp His Glu Gly Gly Gly Ser His
            755                 760                 765

His His His His His His
        770             775

<210> SEQ ID NO 226
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
                20                  25                  30

Arg Ala Ala Ile Asn Lys His Ile Gln Thr Leu Arg Asp Trp Gly Val
            35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
```

```
                275                 280                 285
Ser Arg Gly Ile Asp Lys Gln Gly Ala Leu Leu Glu Gln Asp Gly
            290                 295                 300

Ile Ile Lys Pro Trp Met Gly Gly Glu Ile Ser Leu Arg Ser Ala Glu
305                 310                 315                 320

Lys Ser Gly Lys Asp Glu Leu
            325

<210> SEQ ID NO 227
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
            130

<210> SEQ ID NO 228
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Ala Pro Ala Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Ala Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
```

```
              100                 105                 110
Thr Ile Val Glu Phe Leu Asn Arg Trp Ile Thr Phe Ala Gln Ser Ile
         115                 120                 125

Ile Ser Thr Leu Thr
     130

<210> SEQ ID NO 229
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Ile Trp Glu Leu Lys Lys Asp Val Tyr Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Ser Gly Gly Gly Ser Gly Gly Gly Gly
305                 310                 315                 320
```

```
Ser Arg Asn Leu Pro Val Ala Thr Pro Asp Pro Gly Met Phe Pro Cys
            325                 330                 335

Leu His His Ser Gln Asn Leu Leu Arg Ala Val Ser Asn Met Leu Gln
        340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
        370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
                420                 425                 430

Tyr Gln Val Glu Phe Lys Thr Met Asn Ala Lys Leu Leu Met Asp Pro
            435                 440                 445

Lys Arg Gln Ile Phe Leu Asp Gln Asn Met Leu Ala Val Ile Asp Glu
        450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
                500                 505                 510

Ser Tyr Leu Asn Ala Ser
            515

<210> SEQ ID NO 230
<211> LENGTH: 340
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160
```

```
Gly Gly Gly Gly Ser Gly Gly Gly Ser Gly Gly Gly Ser Gly
                165                 170                 175

Gly Gly Gly Ser Ser Pro Gly Gln Gly Thr Gln Ser Glu Asn Ser Cys
            180                 185                 190

Thr His Phe Pro Gly Asn Leu Pro Asn Met Leu Arg Asp Leu Arg Asp
            195                 200                 205

Ala Phe Ser Arg Val Lys Thr Phe Phe Gln Met Lys Asp Gln Leu Asp
210                 215                 220

Asn Leu Leu Leu Lys Glu Ser Leu Leu Glu Asp Phe Lys Gly Tyr Leu
225                 230                 235                 240

Gly Cys Gln Ala Leu Ser Glu Met Ile Gln Phe Tyr Leu Glu Glu Val
                245                 250                 255

Met Pro Gln Ala Glu Asn Gln Asp Pro Asp Ile Lys Ala His Val Asn
            260                 265                 270

Ser Leu Gly Glu Asn Leu Lys Thr Leu Arg Leu Arg Leu Arg Arg Cys
            275                 280                 285

His Arg Phe Leu Pro Cys Glu Asn Lys Ser Lys Ala Val Glu Gln Val
            290                 295                 300

Lys Asn Ala Phe Asn Lys Leu Gln Glu Lys Gly Ile Tyr Lys Ala Met
305                 310                 315                 320

Ser Glu Phe Asp Ile Phe Ile Asn Tyr Ile Glu Ala Tyr Met Thr Met
                325                 330                 335

Lys Ile Arg Asn
            340

<210> SEQ ID NO 231
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Gly Gly Gly Ser Gly Gly Lys Ser Lys Ala Val Glu
        115                 120                 125

Gln Val Lys Asn Ala Phe Asn Lys Leu Gln Glu Lys Gly Ile Tyr Lys
    130                 135                 140

Ala Met Ser Glu Phe Asp Ile Phe Ile Asn Tyr Ile Glu Ala Tyr Met
145                 150                 155                 160

Thr Met Lys Ile Arg Asn
```

<210> SEQ ID NO 232
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

```
Asn Trp Val Asn Val Ile Ser Asp Leu Lys Lys Ile Glu Asp Leu Ile
1               5                   10                  15
Gln Ser Met His Ile Asp Ala Thr Leu Tyr Thr Glu Ser Asp Val His
            20                  25                  30
Pro Ser Cys Lys Val Thr Ala Met Lys Cys Phe Leu Leu Glu Leu Gln
        35                  40                  45
Val Ile Ser Leu Ala Ser Gly Asp Ala Ser Ile His Asp Thr Val Glu
    50                  55                  60
Asn Leu Ile Ile Leu Ala Asn Asn Ser Leu Ser Ser Asn Gly Ala Val
65                  70                  75                  80
Thr Glu Ser Gly Cys Lys Glu Cys Glu Glu Leu Glu Glu Lys Asn Ile
                85                  90                  95
Lys Glu Phe Leu Gln Ser Phe Val His Ile Val Gln Met Phe Ile Asn
            100                 105                 110
Thr Ser
```

<210> SEQ ID NO 233
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

```
Met Glu Phe Gly Leu Ser Trp Val Phe Leu Val Ala Leu Phe Arg Gly
1               5                   10                  15
Val Gln Cys Asn Trp Val Asn Val Ile Ser Asp Leu Lys Lys Ile Glu
            20                  25                  30
Asp Leu Ile Gln Ser Met His Ile Asp Ala Thr Leu Tyr Thr Glu Ser
        35                  40                  45
Asp Val His Pro Ser Cys Lys Val Thr Ala Met Lys Cys Phe Leu Leu
    50                  55                  60
Glu Leu Gln Val Ile Ser Leu Glu Ser Gly Asp Ala Ser Ile His Asp
65                  70                  75                  80
Thr Val Glu Asn Leu Ile Ile Leu Ala Asn Asn Ser Leu Ser Ser Asn
                85                  90                  95
Gly Asn Val Thr Glu Ser Gly Cys Lys Glu Cys Glu Glu Leu Glu Glu
            100                 105                 110
Lys Asn Ile Lys Glu Phe Leu Gln Ser Phe Val His Ile Val Gln Met
        115                 120                 125
Phe Ile Asn Thr Ser Gly Gly Gly Ser Asp Lys Thr His Thr Cys
    130                 135                 140
Pro Pro Cys Pro Ala Pro Glu Leu Leu Gly Gly Pro Ser Val Phe Leu
145                 150                 155                 160
Phe Pro Pro Lys Pro Lys Asp Thr Leu Met Ile Ser Arg Thr Pro Glu
                165                 170                 175
```

```
Val Thr Cys Val Val Asp Val Ser His Glu Asp Pro Glu Val Lys
            180                 185                 190

Phe Asn Trp Tyr Val Asp Gly Val Glu Val His Asn Ala Lys Thr Lys
        195                 200                 205

Pro Arg Glu Glu Gln Tyr Asn Ser Thr Tyr Arg Val Val Ser Val Leu
    210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255

Ala Lys Gly Gln Pro Arg Glu Pro Gln Val Tyr Thr Leu Pro Pro Cys
            260                 265                 270

Arg Glu Glu Met Thr Lys Asn Gln Val Ser Leu Trp Cys Leu Val Lys
        275                 280                 285

Gly Phe Tyr Pro Ser Asp Ile Ala Val Glu Trp Glu Ser Asn Gly Gln
    290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly Lys
        355                 360                 365

<210> SEQ ID NO 234
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Met Glu Phe Gly Leu Ser Trp Val Phe Leu Val Ala Leu Phe Arg Gly
1               5                   10                  15

Val Gln Cys Gln Val Gln Leu Gln Gln Ser Gly Pro Glu Leu Glu Lys
            20                  25                  30

Pro Gly Ala Ser Val Lys Ile Ser Cys Lys Ala Ser Gly Tyr Ser Phe
        35                  40                  45

Thr Gly Tyr Thr Met Asn Trp Val Lys Gln Ser His Gly Lys Ser Leu
    50                  55                  60

Glu Trp Ile Gly Leu Ile Thr Pro Tyr Asn Gly Ala Ser Ser Tyr Asn
65                  70                  75                  80

Gln Lys Phe Arg Gly Lys Ala Thr Leu Thr Val Asp Lys Ser Ser Ser
                85                  90                  95

Thr Ala Tyr Met Asp Leu Leu Ser Leu Thr Ser Glu Asp Ser Ala Val
            100                 105                 110

Tyr Phe Cys Ala Arg Gly Gly Tyr Asp Gly Arg Gly Phe Asp Tyr Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
```

```
                165                 170                 175
Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Ser Leu Gly Thr Gln Thr Tyr Ile Cys Asn Val Asn
                210                 215                 220

His Lys Pro Ser Asn Thr Lys Val Asp Lys Arg Val Glu Pro Lys Ser
225                 230                 235                 240

Cys Asp Lys Thr His Thr Gly Gly Gly Ser Gly Gly Gly Gly Gly Ser
                245                 250                 255

Gly Gly Gly Gly Ser Asn Trp Val Asn Val Ile Ser Asp Leu Lys Lys
                260                 265                 270

Ile Glu Asp Leu Ile Gln Ser Met His Ile Asp Ala Thr Leu Tyr Thr
                275                 280                 285

Glu Ser Asp Val His Pro Ser Cys Lys Val Thr Ala Met Lys Cys Phe
                290                 295                 300

Leu Leu Glu Leu Gln Val Ile Ser Leu Glu Ser Gly Asp Ala Ser Ile
305                 310                 315                 320

His Asp Thr Val Glu Asn Leu Ile Ile Leu Ala Asn Asn Ser Leu Ser
                325                 330                 335

Ser Asn Gly Asn Val Thr Glu Ser Gly Cys Lys Glu Cys Glu Glu Leu
                340                 345                 350

Glu Glu Lys Asn Ile Lys Glu Phe Leu Gln Ser Phe Val His Ile Val
                355                 360                 365

Gln Met Phe Ile Asn Thr Ser
                370                 375

<210> SEQ ID NO 235
<211> LENGTH: 401
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Met Lys Tyr Leu Leu Pro Thr Ala Ala Ala Gly Leu Leu Leu Leu Ala
1               5                   10                  15

Ala Gln Pro Ala Met Ala Asp Ile Glu Leu Thr Gln Ser Pro Ala Ile
                20                  25                  30

Met Ser Ala Ser Pro Gly Glu Lys Val Thr Met Thr Cys Ser Ala Ser
                35                  40                  45

Ser Ser Val Ser Tyr Met His Trp Tyr Gln Gln Lys Ser Gly Thr Ser
                50                  55                  60

Pro Lys Arg Trp Ile Tyr Asp Thr Ser Lys Leu Ala Ser Gly Val Pro
65              70                  75                  80

Gly Arg Phe Ser Gly Ser Gly Ser Gly Asn Ser Tyr Ser Leu Thr Ile
                85                  90                  95

Ser Ser Val Glu Ala Glu Asp Ala Thr Tyr Tyr Cys Gln Gln Trp
                100                 105                 110

Ser Gly Tyr Pro Leu Thr Phe Gly Ala Gly Thr Lys Leu Glu Ile Lys
                115                 120                 125

Arg Thr Val Ala Ala Pro Ser Val Phe Ile Phe Pro Pro Ser Asp Glu
                130                 135                 140
```

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys Asp Val Pro Ser Gly
225                 230                 235                 240

Pro Gly Gly Gly Gly Ser Gly Gly Gly Ser Met Gln Lys Gly
                245                 250                 255

Asp Gln Asn Pro Gln Ile Ala Ala His Val Ile Ser Glu Ala Ser Ser
            260                 265                 270

Lys Thr Thr Ser Val Leu Gln Trp Ala Glu Lys Gly Tyr Tyr Thr Met
    275                 280                 285

Ser Asn Asn Leu Val Thr Leu Glu Asn Gly Lys Gln Leu Thr Val Lys
290                 295                 300

Arg Gln Gly Leu Tyr Tyr Ile Tyr Ala Gln Val Thr Phe Cys Ser Asn
305                 310                 315                 320

Arg Glu Ala Ser Ser Gln Ala Pro Phe Ile Ala Ser Leu Cys Leu Lys
                325                 330                 335

Ser Pro Gly Arg Phe Glu Arg Ile Leu Leu Arg Ala Ala Asn Thr His
            340                 345                 350

Ser Ser Ala Lys Pro Cys Gly Gln Gln Ser Ile His Leu Gly Gly Val
        355                 360                 365

Phe Glu Leu Gln Pro Gly Ala Ser Val Phe Val Asn Val Thr Asp Pro
370                 375                 380

Ser Gln Val Ser His Gly Thr Gly Phe Thr Ser Phe Gly Leu Leu Lys
385                 390                 395                 400

Leu

<210> SEQ ID NO 236
<211> LENGTH: 414
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Phe Arg Gly Pro Leu Leu Pro Asn Arg Pro Phe Thr Thr Val Trp Asn
1               5                   10                  15

Ala Asn Thr Gln Trp Cys Leu Glu Arg His Gly Val Asp Val Asp Val
                20                  25                  30

Ser Val Phe Asp Val Val Ala Asn Pro Gly Gln Thr Phe Arg Gly Pro
            35                  40                  45

Asp Met Thr Ile Phe Tyr Ser Ser Gln Leu Gly Thr Tyr Pro Tyr Tyr
        50                  55                  60

Thr Pro Thr Gly Glu Pro Val Phe Gly Gly Leu Pro Gln Asn Ala Ser
65                  70                  75                  80

Leu Ile Ala His Leu Ala Arg Thr Phe Gln Asp Ile Leu Ala Ala Ile
                85                  90                  95

-continued

Pro Ala Pro Asp Phe Ser Gly Leu Ala Val Ile Asp Trp Glu Ala Trp
                100                 105                 110

Arg Pro Arg Trp Ala Phe Asn Trp Asp Thr Lys Asp Ile Tyr Arg Gln
            115                 120                 125

Arg Ser Arg Ala Leu Val Gln Ala Gln His Pro Asp Trp Pro Ala Pro
        130                 135                 140

Gln Val Glu Ala Val Ala Gln Asp Gln Phe Gln Gly Ala Ala Arg Ala
145                 150                 155                 160

Trp Met Ala Gly Thr Leu Gln Leu Gly Arg Ala Leu Arg Pro Arg Gly
                165                 170                 175

Leu Trp Gly Phe Tyr Gly Phe Pro Asp Cys Tyr Asn Tyr Asp Phe Leu
            180                 185                 190

Ser Pro Asn Tyr Thr Gly Gln Cys Pro Ser Gly Ile Arg Ala Gln Asn
        195                 200                 205

Asp Gln Leu Gly Trp Leu Trp Gly Gln Ser Arg Ala Leu Tyr Pro Ser
    210                 215                 220

Ile Tyr Met Pro Ala Val Leu Glu Gly Thr Gly Lys Ser Gln Met Tyr
225                 230                 235                 240

Val Gln His Arg Val Ala Glu Ala Phe Arg Val Ala Val Ala Ala Gly
                245                 250                 255

Asp Pro Asn Leu Pro Val Leu Pro Tyr Val Gln Ile Phe Tyr Asp Thr
            260                 265                 270

Thr Asn His Phe Leu Pro Leu Asp Glu Leu Glu His Ser Leu Gly Glu
        275                 280                 285

Ser Ala Ala Gln Gly Ala Ala Gly Val Val Leu Trp Val Ser Trp Glu
    290                 295                 300

Asn Thr Arg Thr Lys Glu Ser Cys Gln Ala Ile Lys Glu Tyr Met Asp
305                 310                 315                 320

Thr Thr Leu Gly Pro Phe Ile Leu Asn Val Thr Ser Gly Ala Leu Leu
                325                 330                 335

Cys Ser Gln Ala Leu Cys Ser Gly His Gly Arg Cys Val Arg Arg Thr
            340                 345                 350

Ser His Pro Lys Ala Leu Leu Leu Leu Asn Pro Ala Ser Phe Ser Ile
        355                 360                 365

Gln Leu Thr Pro Gly Gly Gly Pro Leu Ser Leu Arg Gly Ala Leu Ser
    370                 375                 380

Leu Glu Asp Gln Ala Gln Met Ala Val Glu Phe Lys Cys Arg Cys Tyr
385                 390                 395                 400

Pro Gly Trp Gln Ala Pro Trp Cys Glu Arg Lys Ser Met Trp
                405                 410

<210> SEQ ID NO 237
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Gln Gln Gln Thr Leu Pro Lys Pro Phe Ile Trp Ala Glu Pro His Phe
1               5                   10                  15

Met Val Pro Lys Glu Lys Gln Val Thr Ile Cys Cys Gln Gly Asn Tyr
                20                  25                  30

Gly Ala Val Glu Tyr Gln Leu His Phe Glu Gly Ser Leu Phe Ala Val
            35                  40                  45

-continued

Asp Arg Pro Lys Pro Glu Arg Ile Asn Lys Val Lys Phe Tyr Ile
 50                  55                  60

Pro Asp Met Asn Ser Arg Met Ala Gly Gln Tyr Ser Cys Ile Tyr Arg
 65                  70                  75                  80

Val Gly Glu Leu Trp Ser Glu Pro Ser Asn Leu Leu Asp Leu Val Val
                 85                  90                  95

Thr Glu Met Tyr Asp Thr Pro Thr Leu Ser Val His Pro Gly Pro Glu
             100                 105                 110

Val Ile Ser Gly Glu Lys Val Thr Phe Tyr Cys Arg Leu Asp Thr Ala
             115                 120                 125

Thr Ser Met Phe Leu Leu Lys Glu Gly Arg Ser Ser His Val Gln
 130                 135                 140

Arg Gly Tyr Gly Lys Val Gln Ala Glu Phe Pro Leu Gly Pro Val Thr
145                 150                 155                 160

Thr Ala His Arg Gly Thr Tyr Arg Cys Phe Gly Ser Tyr Asn Asn His
                 165                 170                 175

Ala Trp Ser Phe Pro Ser Glu Pro Val Lys Leu Leu Val Thr Gly Asp
                 180                 185                 190

Ile Glu Asn Thr Ser Leu Ala Pro Glu Asp Pro Thr Phe Pro Asp Thr
             195                 200                 205

Trp Gly Thr Tyr Leu Leu Thr Thr Glu Thr Gly Leu Gln Lys Asp His
210                 215                 220

Ala Leu Trp Asp His Thr Ala Gln Asn Gly Gly Gly Ser Gly Gly
225                 230                 235                 240

Gly Gly Ser Glu Pro Arg Thr Asp Thr Asp Thr Cys Pro Asn Pro Pro
                 245                 250                 255

Asp Pro Cys Pro Thr Cys Pro Thr Pro Asp Leu Leu Gly Gly Pro Ser
                 260                 265                 270

Val Phe Ile Phe Pro Pro Lys Pro Lys Asp Val Leu Met Ile Ser Leu
             275                 280                 285

Thr Pro Lys Ile Thr Cys Val Val Asp Val Ser Glu Glu Pro
 290                 295                 300

Asp Val Gln Phe Asn Trp Tyr Val Asn Asn Val Glu Asp Lys Thr Ala
305                 310                 315                 320

Gln Thr Glu Thr Arg Gln Arg Gln Tyr Asn Ser Thr Tyr Arg Val Val
                 325                 330                 335

Ser Val Leu Pro Ile Lys His Gln Asp Trp Met Ser Gly Lys Val Phe
                 340                 345                 350

Lys Cys Lys Val Asn Asn Asn Ala Leu Pro Ser Pro Ile Glu Lys Thr
             355                 360                 365

Ile Ser Lys Pro Arg Gly Gln Val Arg Val Pro Gln Ile Tyr Thr Phe
             370                 375                 380

Pro Pro Pro Ile Glu Gln Thr Val Lys Lys Asp Val Ser Val Thr Cys
385                 390                 395                 400

Leu Val Thr Gly Phe Leu Pro Gln Asp Ile His Val Glu Trp Glu Ser
                 405                 410                 415

Asn Gly Gln Pro Gln Pro Glu Gln Asn Tyr Lys Asn Thr Gln Pro Val
                 420                 425                 430

Leu Asp Ser Asp Gly Ser Tyr Phe Leu Tyr Ser Lys Leu Asn Val Pro
             435                 440                 445

Lys Ser Arg Trp Asp Gln Gly Asp Ser Phe Thr Cys Ser Val Ile His
 450                 455                 460

```
Glu Ala Leu His Asn His His Met Thr Lys Thr Ile Ser Arg Ser Leu
465                 470                 475                 480

Gly Asn Gly Gly Gly Gly Ser Gly Gly Gly Ser Gly Leu Asn Asp
            485                 490                 495

Ile Phe Glu Ala Gln Lys Ile Glu Trp His Glu
            500                 505

<210> SEQ ID NO 238
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Met Glu Phe Gly Leu Ser Trp Val Phe Leu Val Ala Leu Phe Arg Gly
1               5                   10                  15

Val Gln Cys Gln Val Gln Leu Gln Gln Ser Gly Arg Glu Leu Glu Lys
            20                  25                  30

Pro Gly Ala Ser Val Lys Ile Ser Cys Lys Ala Ser Gly Tyr Ser Phe
        35                  40                  45

Thr Gly Tyr Thr Met Asn Trp Val Lys Gln Ser His Gly Lys Ser Leu
    50                  55                  60

Glu Trp Ile Gly Leu Ile Thr Pro Tyr Asn Gly Ala Ser Ser Tyr Asn
65                  70                  75                  80

Gln Lys Phe Arg Gly Lys Ala Thr Leu Thr Val Asp Lys Ser Ser Ser
                85                  90                  95

Thr Ala Tyr Met Asp Leu Leu Ser Leu Thr Ser Glu Asp Ser Ala Val
            100                 105                 110

Tyr Phe Cys Ala Arg Gly Gly Tyr Asp Gly Arg Gly Phe Asp Tyr Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Gly Gly Gly Ser Gly Gly Gly Gly Ser
                245                 250                 255

Gly Gly Gly Gly Ser Asn Trp Val Asn Val Ile Ser Asp Leu Lys Lys
            260                 265                 270

Ile Glu Asp Leu Ile Gln Ser Met His Ile Asp Ala Thr Leu Tyr Thr
        275                 280                 285

Glu Ser Asp Val His Pro Ser Cys Lys Val Thr Ala Met Lys Cys Ala
    290                 295                 300

Leu Leu Glu Leu Gln Val Ile Ser Leu Glu Ser Gly Asp Ala Ser Ile
305                 310                 315                 320
```

```
His Asp Thr Val Glu Asn Leu Ile Ile Leu Ala Asn Asn Ser Leu Ser
                325                 330                 335

Ser Asn Gly Asn Val Thr Glu Ser Gly Cys Lys Glu Cys Glu Leu
            340                 345                 350

Glu Glu Lys Asn Ile Lys Glu Phe Leu Gln Ser Phe Val His Ile Val
            355                 360                 365

Gln Met Phe Ile Asn Thr Ser
        370                 375

<210> SEQ ID NO 239
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Met Lys Tyr Leu Leu Pro Thr Ala Ala Ala Gly Leu Leu Leu Leu Ala
1               5                   10                  15

Ala Gln Pro Ala Met Ala Asp Ile Val Met Thr Gln Ser Pro Asp Ser
            20                  25                  30

Leu Ala Val Ser Leu Gly Glu Arg Ala Thr Ile Asn Cys Lys Ser Ser
        35                  40                  45

Gln Ser Leu Leu Tyr Ser Arg Asn Gln Lys Asn Tyr Leu Ala Trp Tyr
    50                  55                  60

Gln Gln Lys Pro Gly Gln Pro Pro Lys Leu Leu Ile Phe Trp Ala Ser
65                  70                  75                  80

Thr Arg Glu Ser Gly Val Pro Asp Arg Phe Ser Gly Ser Gly Phe Gly
                85                  90                  95

Thr Ser Phe Thr Leu Thr Ile Ser Ser Leu Gln Ala Glu Asp Val Ala
            100                 105                 110

Val Tyr Tyr Cys Gln Gln Tyr Phe Ser Tyr Pro Leu Thr Phe Gly Gln
        115                 120                 125

Gly Thr Lys Val Glu Ile Lys Arg Thr Val Ala Ala Pro Ser Val Phe
    130                 135                 140

Ile Phe Pro Pro Ser Asp Glu Gln Leu Lys Ser Gly Thr Ala Ser Val
145                 150                 155                 160

Val Cys Leu Leu Asn Asn Phe Tyr Pro Arg Glu Ala Lys Val Gln Trp
                165                 170                 175

Lys Val Asp Asn Ala Leu Gln Ser Gly Asn Ser Gln Glu Ser Val Thr
            180                 185                 190

Glu Gln Asp Ser Lys Asp Ser Thr Tyr Ser Leu Ser Ser Thr Leu Thr
        195                 200                 205

Leu Ser Lys Ala Asp Tyr Glu Lys His Lys Val Tyr Ala Cys Glu Val
    210                 215                 220

Thr His Gln Gly Leu Ser Ser Pro Val Thr Lys Ser Phe Asn Arg Gly
225                 230                 235                 240

Glu Cys

<210> SEQ ID NO 240
<211> LENGTH: 716
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 240

Met Glu Phe Gly Leu Ser Trp Val Phe Leu Val Ala Leu Phe Arg Gly
1               5                   10                  15

Val Gln Cys Glu Val Gln Val Gln Leu Val Gln Ser Gly Ala Glu Val
            20                  25                  30

Lys Lys Pro Gly Ala Ser Val Lys Val Ser Cys Lys Thr Ser Arg Tyr
        35                  40                  45

Thr Phe Thr Glu Tyr Thr Ile His Trp Val Arg Gln Ala Pro Gly Gln
    50                  55                  60

Arg Leu Glu Trp Ile Gly Gly Ile Asn Pro Asn Asn Gly Ile Pro Asn
65                  70                  75                  80

Tyr Asn Gln Lys Phe Lys Gly Arg Val Thr Ile Thr Val Asp Thr Ser
                85                  90                  95

Ala Ser Thr Ala Tyr Met Glu Leu Ser Ser Leu Arg Ser Glu Asp Thr
            100                 105                 110

Ala Val Tyr Tyr Cys Ala Arg Arg Ile Ala Tyr Gly Tyr Asp Glu
        115                 120                 125

Gly His Ala Met Asp Tyr Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Cys Thr Leu Pro Pro Ser Arg Glu
    370                 375                 380

Glu Met Thr Lys Asn Gln Val Ser Leu Ser Cys Ala Val Lys Gly Phe
385                 390                 395                 400

Tyr Pro Ser Asp Ile Ala Val Glu Trp Glu Ser Asn Gly Gln Pro Glu
```

```
                    405                 410                 415
Asn Asn Tyr Lys Thr Thr Pro Val Leu Asp Ser Asp Gly Ser Phe
            420                 425                 430

Phe Leu Val Ser Lys Leu Thr Val Asp Lys Ser Arg Trp Gln Gln Gly
                435                 440                 445

Asn Val Phe Ser Cys Ser Val Met His Glu Ala Leu His Asn His Tyr
            450                 455                 460

Thr Gln Lys Ser Leu Ser Leu Ser Pro Gly Lys Gly Gly Gly Gly Ser
465                 470                 475                 480

Asp Leu Lys Val Glu Met Met Ala Gly Gly Thr Gln Ile Thr Pro Leu
                485                 490                 495

Asn Asp Asn Val Thr Ile Phe Cys Asn Ile Phe Tyr Ser Gln Pro Leu
            500                 505                 510

Asn Ile Thr Ser Met Gly Ile Thr Trp Phe Trp Lys Ser Leu Thr Phe
            515                 520                 525

Asp Lys Glu Val Lys Val Phe Glu Phe Phe Gly Asp His Gln Glu Ala
530                 535                 540

Phe Arg Pro Gly Ala Ile Val Ser Pro Trp Arg Leu Lys Ser Gly Asp
545                 550                 555                 560

Ala Ser Leu Arg Leu Pro Gly Ile Gln Leu Glu Ala Gly Glu Tyr
            565                 570                 575

Arg Cys Glu Val Val Val Thr Pro Leu Lys Ala Gln Gly Thr Val Gln
            580                 585                 590

Leu Glu Trp Ala Ser Pro Ala Ser Arg Leu Leu Leu Asp Gln Val Gly
            595                 600                 605

Met Lys Glu Asn Glu Asp Lys Tyr Met Cys Glu Ser Ser Gly Phe Tyr
610                 615                 620

Pro Glu Ala Ile Asn Ile Thr Trp Glu Lys Gln Thr Gln Lys Phe Pro
625                 630                 635                 640

His Pro Ile Glu Ile Ser Glu Asp Val Ile Thr Gly Pro Thr Ile Lys
            645                 650                 655

Asn Met Asp Gly Thr Phe Asn Val Thr Ser Cys Leu Lys Leu Asn Ser
            660                 665                 670

Ser Gln Glu Asp Pro Gly Thr Val Tyr Gln Cys Trp Arg His Ala Ser
            675                 680                 685

Leu His Thr Pro Leu Arg Ser Asn Phe Thr Leu Thr Ala Ala Arg His
            690                 695                 700

Ser Leu Ser Glu Thr Glu Lys Thr Asp Asn Phe Ser
705                 710                 715

<210> SEQ ID NO 241
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gly Gly Gly Ser Gly Gly Gly Ser Gly Gly Gly Ser
1               5                   10

<210> SEQ ID NO 242
<211> LENGTH: 215
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 242

His Arg Arg Leu Asp Lys Ile Glu Asp Glu Arg Asn Leu His Glu Asp
1               5                   10                  15

Phe Val Phe Met Lys Thr Ile Gln Arg Cys Asn Thr Gly Glu Arg Ser
            20                  25                  30

Leu Ser Leu Leu Asn Cys Glu Glu Ile Lys Ser Gln Phe Glu Gly Phe
                35                  40                  45

Val Lys Asp Ile Met Leu Asn Lys Glu Glu Thr Lys Lys Glu Asn Ser
        50                  55                  60

Phe Glu Met Gln Lys Gly Asp Gln Asn Pro Gln Ile Ala Ala His Val
65                  70                  75                  80

Ile Ser Glu Ala Ser Ser Lys Thr Thr Ser Val Leu Gln Trp Ala Glu
                85                  90                  95

Lys Gly Tyr Tyr Thr Met Ser Asn Asn Leu Val Thr Leu Glu Asn Gly
                100                 105                 110

Lys Gln Leu Thr Val Lys Arg Gln Gly Leu Tyr Tyr Ile Tyr Ala Gln
            115                 120                 125

Val Thr Phe Cys Ser Asn Arg Glu Ala Ser Ser Gln Ala Pro Phe Ile
        130                 135                 140

Ala Ser Leu Cys Leu Lys Ser Pro Gly Arg Phe Glu Arg Ile Leu Leu
145                 150                 155                 160

Arg Ala Ala Asn Thr His Ser Ser Ala Lys Pro Cys Gly Gln Gln Ser
                165                 170                 175

Ile His Leu Gly Gly Val Phe Glu Leu Gln Pro Gly Ala Ser Val Phe
            180                 185                 190

Val Asn Val Thr Asp Pro Ser Gln Val Ser His Gly Thr Gly Phe Thr
        195                 200                 205

Ser Phe Gly Leu Leu Lys Leu
210                 215

MULTISPECIFIC AND MULTIFUNCTIONAL MOLECULES AND USES THEREOF

This application claims priority to U.S. Ser. No. 62/310,929 filed Mar. 21, 2016, and U.S. Ser. No. 62/310,899 filed Mar. 21, 2016, the contents of each of which is incorporated herein by reference in its entirety.

SEQUENCE LISTING

The instant application contains a Sequence Listing which has been filed electronically in ASCII format and is hereby incorporated by reference in its entirety. Said ASCII copy, created on Jul. 27, 2017, is named E2070-700010_SL.txt and is 501,495 bytes in size.

BACKGROUND

Multispecific molecules that include a tumor-targeting moiety; and one, two or all of: an immune cell engager, a cytokine molecule or a stromal modifier, and methods of using the same, are disclosed. Also disclosed herein are multifunctional molecules that include a stromal modifying moiety and a tumor-targeting moiety; and methods of using the same, are disclosed.

SUMMARY OF THE INVENTION

The disclosure relates, inter alia, to novel multispecific or multifunctional molecules that include (i) a tumor-targeting moiety; and one, two or all of: (ii) an immune cell engager (e.g., chosen from an NK cell engager, a T cell engager, a B cell engager, a dendritic cell engager, or a macrophage cell engager); (iii) a cytokine molecule; and/or (iv) a stromal modifying moiety. In some embodiments, the multispecific molecules include (i) a stromal modifying moiety and (ii) a tumor-targeting moiety (e.g., an antibody molecule, a ligand molecule, or a receptor molecule) that binds to a tumor antigen or a stromal antigen. The terms "multispecific" or "multifunctional" are used interchangeably herein.

Without wishing to be bound by theory, the multispecific or multifunctional molecules disclosed herein are expected to target (e.g., localize, bridge and/or activate) an immune cell (e.g., an immune effector cell chosen from an NK cell, a T cell, a B cell, a dendritic cell or a macrophage), at a cancer cell and/or alter the tumor stroma, e.g., alter the tumor microenvironment near the cancer site. Increasing the proximity and/or activity of the immune cell using the multispecific molecules described herein is expected to enhance an immune response against the cancer cell, thereby providing a more effective cancer therapy. Without being bound by theory, a targeted, localized immune response against the cancer cell is believed to reduce the effects of systemic toxicity of the multispecific molecules described herein. Accordingly, provided herein are, inter alia, multispecific molecules (e.g., multispecific or multifunctional antibody molecules) that include the aforesaid moieties, nucleic acids encoding the same, methods of producing the aforesaid molecules, and methods of treating a cancer using the aforesaid molecules.

Accordingly, in one aspect, the disclosure features a multispecific or multispecific molecule (e.g., polypeptide or nucleic acid encoding the same) that includes:

(i) a tumor-targeting moiety, e.g., a first tumor-targeting moiety, that binds to a cancer antigen; and
one, two or all of:
(ii) an immune cell engager chosen from an NK cell engager, a T cell engager, a B cell engager, a dendritic cell engager, or a macrophage cell engager;
(iii) a cytokine molecule; and
(iv) a stromal modifying moiety.

In some embodiments of the aforesaid molecules:
if (ii) and (iii) are absent, then (i) and (iv) are present,
if one (i) and one (ii) are present, then (iii) or (iv) or both are present, or
if one (i) and one (iii) are present, then (ii) or (iv) or both are present.

In some embodiments, the multispecific or multifunctional molecule includes (i), (ii) and one or both of (iii) and (iv).

In some embodiments, the multispecific or multifunctional molecule includes (i), (iii) and one or both of (ii) and (iv).

In some embodiments, the multispecific or multifunctional molecule includes (i), (ii) and (iii). In other embodiments, the multispecific or multifunctional molecule includes (i), (ii) and (iv).

In yet another embodiment, the multispecific or multifunctional molecule polypeptide includes (i), (ii), (iii) and (iv).

In another aspect, provided herein is a multispecific or multifunctional molecule polypeptide that includes:

(i) at least two tumor targeting moieties, e.g., a first and second tumor-targeting moiety, that bind to one or more cancer antigens; and
one, two or all of:
(ii) an immune cell engager chosen from an NK cell engager, a T cell engager, a B cell engager, a dendritic cell engager, or a macrophage cell engager;
(iii) a stromal modifying moiety; and
(iv) a cytokine molecule, e.g., that includes at least two non-contiguous polypeptides (e.g., a multichain cytokine).
In some embodiments, the cytokine molecule comprises two chains, e.g., an alpha and beta chain (e.g., IL-12).

In some embodiments, the at least two tumor targeting moieties, e.g., the first and second tumor-targeting moieties, bind to the same or a different cancer antigen.

In some embodiments, the multispecific or multifunctional molecule includes one or two immune cell engagers as described herein. In one embodiment, the one or two immune cell engagers include an antibody molecule that binds to and/or inhibits a checkpoint molecule chosen from one or two of CTLA4, PD1, PD-L1, PD-L2, TIM3, LAG3, CD160, 2B4, CD80, CD86, B7-H3 (CD276), B7-H4 (VTCN1), HVEM (TNFRSF14 or CD270), BTLA, KIR, MHC class I, MHC class II, GAL9, VISTA, BTLA, TIGIT, LAIR1, or A2aR. In one embodiment, the multispecific or multifunctional molecule includes two tumor-targeting moieties to one immune cell engager, e.g., a checkpoint binder. In one embodiment, the multispecific or multifunctional molecule includes two tumor-targeting moieties to two immune cell engagers, e.g., two checkpoint binder (e.g., the same or different checkpoint binder).

In some embodiments, the first tumor-targeting moiety binds to CD123, the second tumor-targeting moiety binds to CD47 and the T cell engager is or comprises a CD3 agonist.

In yet another aspect, the multifunctional (e.g., bifunctional) molecule includes a stromal modifying moiety and a tumor-targeting moiety (e.g., an antibody molecule, a ligand molecule, or a receptor molecule) that binds to a tumor antigen or a stromal antigen.

In embodiments of any of the aforesaid multispecific or multifunctional molecules, the molecules can further include comprising a second tumor-targeting moiety. In embodiments, the second tumor-targeting moiety binds to the same or a different cancer antigen as the first tumor-targeting moiety, e.g., the tumor-targeting moiety in (i). The second tumor-targeting moiety binds to a different epitope on the same cancer antigen as the first tumor-targeting moiety. In other embodiments, the second tumor-targeting moiety and the first tumor-targeting moiety bind to different cancer antigens. The different cancer antigens can be present on the same cell or tumor tissue, or can be present on different cells or tumor tissues.

Without wishing to be bound by theory, it is believed that systemic toxicity of an immune therapeutic, such as the multispecific molecules described herein, can be managed, e.g., reduced, by directing the immune therapeutic primarily to the tumor and/or stroma before eliciting an immunological response. This effect can be achieved by balancing the affinity of the tumor targeting moiety/moieties to be higher than the affinity for the immune cell engager(s) and/or cytokine(s). In some embodiments, the affinity, e.g., combined affinity, of the tumor-targeting moiety/moieties is at least a 10 fold higher toward the tumor and/or stroma cells compared to the affinity, e.g., combined affinity, of the multispecific molecule (e.g., the immune cell engager(s) and/or cytokine(s)) to the corresponding immune effector cells. The combined affinity can be measured using techniques known in the art. For example, using an SPR-based assay, which enables assessment of the binding activity of a bivalent-bispecific molecule in a single setup, e.g., as described in Meschendoerfer, W. et al. (2017) *J Pharm Biomed Anal.* 5; 132:141-147. doi: 10.1016/j.jpba.2016.09.028. Epub 2016 Sep. 26.

Thus, in some embodiments of the multispecific or multifunctional molecule, the affinity, e.g., the combined affinity, for the cancer antigens of the first tumor-targeting moiety and the second tumor-targeting moiety is equal to or greater than the affinity of (ii), (iii) or (iv) (either alone or as part of the multispecific molecule) for its corresponding binding member. For example, the affinity, e.g., the combined affinity, for the cancer antigens of the first tumor-targeting moiety and the second tumor-targeting moiety is at least 2, 5, 10, 20, 30, 40, 50, 75 or 100 times greater than the affinity of (ii), (iii) or (iv) (either alone or as part of the multispecific molecule) for its corresponding binding member.

In yet other embodiments of the multispecific or multifunctional molecule, the affinity, e.g., the combined affinity, of the first tumor-targeting moiety in and the second tumor-targeting moiety for the tumor, e.g., a cancer cell or a stromal cell, is equal to or greater than the affinity of a similar multispecific or multifunctional molecule polypeptide having only one of the tumor-targeting moiety or the second tumor-targeting moiety. For example, the affinity, e.g., the combined affinity, of the first tumor-targeting moiety and the second tumor-targeting moiety for the tumor, e.g., a cancer cell or a stromal cell, is at least 2, 5, 10, 20, 30, 40, 50, 75 or 100 times greater than the affinity of a similar multispecific or multifunctional molecule polypeptide having only one of the tumor-targeting moiety or the second tumor-targeting moiety.

In another aspect, provide herein is a multispecific or multifunctional molecule polypeptide that includes:

A, B-[dimerization module]-C, -D wherein:

(1) the dimerization module comprises an immunoglobulin constant domain, e.g., a heavy chain constant domain (e.g., a homodimeric or heterodimeric heavy chain constant region, e.g., an Fc region), or a constant domain of an immunoglobulin variable region (e.g., a Fab region); and (2) A, B, C, and D are independently absent; (i) a tumor-targeting moiety, e.g., a first and/or second tumor-targeting moiety; (ii) an immune cell engager chosen from an NK cell engager, a T cell engager, a B cell engager, a dendritic cell engager, or a macrophage cell engager; (iii) a cytokine molecule; or (iv) a stromal modifying moiety.

In some embodiments, said multispecific or multifunctional molecule polypeptide includes:

(i) the tumor-targeting moiety, e.g., a first tumor-targeting moiety, that binds to a cancer antigen; and one, two or all of:

(ii) an immune cell engager chosen from an NK cell engager, a T cell engager, a B cell engager, a dendritic cell engager, or a macrophage cell engager;

(iii) a cytokine molecule; and (iv) a stromal modifying moiety. In some embodiments,
if (ii) and (iii) are absent, then (i) and (iv) are present,
if one (i) and one (ii) are present, then (iii) or (iv) or both are present, or
if one (i) and one (iii) are present, then (ii) or (iv) or both are present.

Exemplary multispecific or multifunctional molecules include the following:

(i) A comprises a first tumor-targeting moiety, B comprises a second tumor-targeting moiety, C comprises a first immune cell engager, and D comprises a second immune cell engager (e.g., A and B comprise same or different targeting moieties, and C and D comprise same or different immune cell engagers);

(ii) A comprises a first tumor-targeting moiety, B comprises a second tumor-targeting moiety, C comprises a first cytokine molecule, and D comprises a second cytokine molecule (e.g., A and B comprise same or different targeting moieties, and C and D comprise same or different cytokine molecules);

(iii) A comprises a first tumor-targeting moiety, B comprises a second tumor-targeting moiety, C comprises a first stromal modifying moiety, and D comprises a second stromal modifying moiety (e.g., A and B comprise same or different targeting moieties, and C and D comprise same or different stromal modifying moieties);

(iv) A comprises a first tumor-targeting moiety, B comprises a second tumor-targeting moiety, C comprises an immune cell engager, and D comprises a cytokine molecule (e.g., A and B comprise same or different targeting moieties);

(v) A comprises a first tumor-targeting moiety, B comprises a second tumor-targeting moiety, C comprises a cytokine molecule, and D comprises an immune cell engager (e.g., A and B comprise same or different targeting moieties);

(vi) A comprises a first tumor-targeting moiety, B comprises a second tumor-targeting moiety, C comprises an immune cell engager, and D comprises a stromal modifying moiety (e.g., A and B comprise same or different targeting moieties);

(vii) A comprises a first tumor-targeting moiety, B comprises a second tumor-targeting moiety, C comprises a stromal modifying moiety, and D comprises an immune cell engager (e.g., A and B comprise same or different targeting moieties);

(viii) A comprises a first tumor-targeting moiety, B comprises a second tumor-targeting moiety, C comprises a cytokine molecule, and D comprises a stromal modifying moiety (e.g., A and B comprise same or different targeting moieties);

(ix) A comprises a first tumor-targeting moiety, B comprises a second tumor-targeting moiety, C comprises a stromal modifying moiety, and D comprises a cytokine molecule (e.g., A and B comprise same or different targeting moieties);

(x) A comprises a tumor-targeting moiety, and at least one, two, or three of B, C, and D comprises a second tumor-targeting moiety, an immune cell engager, a cytokine molecule, a stromal modifying moiety, or is absent, provided that if (ii) and (iii) are absent, then (i) and (iv) are present;

(xi) B comprises a tumor-targeting moiety, and at least one, two, or three of A, C, and D comprises a second tumor-targeting moiety, an immune cell engager, a cytokine molecule, a stromal modifying moiety, or is absent, provided that if (ii) and (iii) are absent, then (i) and (iv) are present;

(xii) C comprises a tumor-targeting moiety, and at least one, two, or three of A, B, and D comprises a second tumor-targeting moiety, an immune cell engager, a cytokine molecule, a stromal modifying moiety, or is absent, provided that if (ii) and (iii) are absent, then (i) and (iv) are present;

(xiii) D comprises a tumor-targeting moiety, and at least one, two, or three of A, B, and C comprises a second tumor-targeting moiety, an immune cell engager, a cytokine molecule, a stromal modifying moiety, or is absent, provided that if (ii) and (iii) are absent, then (i) and (iv) are present;

(xiv) A comprises a first tumor-targeting moiety, B comprises a second tumor-targeting moiety, C and D are an immune cell engager and absent, respectively;

(xv) A comprises a first tumor-targeting moiety, B comprises a second tumor-targeting moiety, C and D are absent and an immune cell engager, respectively;

(xvi) A comprises a first tumor-targeting moiety, B comprises a second tumor-targeting moiety, C and D are a cytokine molecule and absent, respectively;

(xvii) A comprises a first tumor-targeting moiety, B comprises a second tumor-targeting moiety, C and D are absent and a cytokine molecule, respectively;

(xviii) A comprises a first tumor-targeting moiety, B comprises a second tumor-targeting moiety, C and D are a stromal modifying moiety and absent, respectively;

(xix) A comprises a first tumor-targeting moiety, B comprises a second tumor-targeting moiety, C and D are absent and a stromal modifying moiety, respectively;

(xx) A comprises a tumor-targeting moiety, and one of B, C or D comprises a stromal modifying moiety;

(xxi) B comprises a tumor-targeting moiety, and one of A, C or D comprises a stromal modifying moiety;

(xxii) C comprises a tumor-targeting moiety, and one of A, B or D comprises a stromal modifying moiety;

(xxiii) D comprises a tumor-targeting moiety, and one of A, B or C comprises a stromal modifying moiety;

(xiv) A or B comprises a tumor-targeting moiety, and C comprises an immune cell engager, and D comprises a cytokine molecule;

(xv) A or B comprises a tumor-targeting moiety, and D comprises an immune cell engager, and C comprises a cytokine molecule;

(xvi) A and/or B comprises one or two immune cell engagers, and D comprises a tumor-targeting moiety, and C comprises a cytokine molecule;

(xvii) A and/or B comprises one or two immune cell engagers, and C comprises a tumor-targeting moiety, and D comprises a cytokine molecule;

(xviii) A and/or B comprises one or two cytokines, and D comprises a tumor-targeting moiety, and C comprises a immune cell engager; or (xix) A and/or B comprises one or two cytokines, and C comprises a tumor-targeting moiety, and D comprises a immune cell engager.

A selection of the exemplary molecules includes:

(i) A comprises a first tumor-targeting moiety, B comprises a second tumor-targeting moiety, C comprises an immune cell engager (e.g., dendritic cell engager), and D comprises a cytokine molecule (e.g., A and B comprise same or different targeting moieties);

(ii) A comprises a first tumor-targeting moiety, B comprises a second tumor-targeting moiety, C comprises a cytokine molecule, and D comprises an immune cell engager (e.g., A and B comprise same or different targeting moieties);

(iii) A comprises a first tumor-targeting moiety, B comprises a second tumor-targeting moiety, C and D are an immune cell engager and absent, respectively;

(iv) A comprises a first tumor-targeting moiety, B comprises a second tumor-targeting moiety, C and D are absent and an immune cell engager, e.g., a T cell engager, respectively;

(v) A comprises a first tumor-targeting moiety, B comprises a second tumor-targeting moiety, C and D are a cytokine molecule and absent, respectively;

(vi) A comprises a first tumor-targeting moiety, B comprises a second tumor-targeting moiety, C and D are absent and a cytokine molecule, respectively;

(vii) A comprises a first tumor-targeting moiety, B comprises a second tumor-targeting moiety, C and D are a stromal modifying moiety and absent, respectively;

(viii) A comprises a first tumor-targeting moiety, B comprises a second tumor-targeting moiety, C and D are absent and a stromal modifying moiety, respectively; or (ix) A comprises a tumor-targeting moiety, and one of B, C or D comprises a stromal modifying moiety.

In some embodiments of any of the aforesaid molecules, the first and second tumor targeting moieties bind to a different epitope on the same cancer antigen or to different cancer antigens.

In other embodiments, the different cancer antigens are present on the same cell or tumor tissue or on different cells or tumor tissues.

In other embodiments of any of the aforesaid molecules, the affinity, e.g., the combined affinity, for the cancer antigens of the first and the second tumor-targeting moiety is equal to or greater than the affinity of (ii), (iii) or (iv) (either alone or as part of the multispecific molecule) for its corresponding binding member. For example, the affinity, e.g., the combined affinity, for the cancer antigens of the first and the second tumor-targeting moiety is at least 2, 5, 10, 20, 30, 40, 50, 75 or 100 times greater than the affinity of (ii), (iii) or (iv) (either alone or as part of the multispecific molecule) for its corresponding binding member.

In yet other embodiments of any of the aforesaid molecules, the affinity, e.g., the combined affinity, of the first and the second tumor-targeting moiety for the tumor, e.g., a cancer cell or a stromal cell, is equal to or greater than the affinity of a similar multispecific or multifunctional molecule polypeptide having only one of the tumor-targeting moiety or the second tumor-targeting moiety. For example, the affinity, e.g., the combined affinity, of the first and the second tumor-targeting moiety for the tumor, e.g., a cancer cell or a stromal cell, is at least 2, 5, 10, 20, 30, 40, 50, 75 or 100 times greater than the affinity of a similar multispecific or multifunctional molecule polypeptide having only one of the tumor-targeting moiety or the second tumor-targeting moiety.

In some embodiments, the tumor-targeting moiety binds to, but does not activate or modulate the cancer antigen. In other embodiments, the tumor-targeting moiety binds to, and activates or modulates the cancer antigen.

In other embodiments, the immune cell engager binds to, but does not activate, an immune cell, e.g., an effector cell. In other embodiments, the immune cell engager binds to and activates an immune cell, e.g., an effector cell.

In other embodiments, the immune cell engager binds to, but does not activate, an immune cell, e.g., an effector cell. In other embodiments, the immune cell engager binds to and activates an immune cell, e.g., an effector cell.

In some embodiments, the immune cell engager comprises a T cell engager that binds to and activates a T cell. In other embodiments, the immune cell engager comprises a T cell engager that binds and does not activate a T cell.

In some embodiments, the immune cell engager comprises a dendritic cell engager that binds to and activates a dendritic cell. In other embodiments, the immune cell engager comprises a dendritic cell engager that binds and does not activate a dendritic cell.

In some embodiments, the immune cell engager comprises a macrophage cell engager that binds to and activates a macrophage cell. In other embodiments, the immune cell engager comprises a macrophage cell engager that binds and does not activate a macrophage cell.

In yet other embodiments, the immune cell engager and/or the tumor-targeting moiety binds to, but does not inhibit, a checkpoint inhibitor (e.g., a cell, e.g., an immune cell, expressing a checkpoint inhibitor). In other embodiments, the immune cell engager and/or the tumor-targeting moiety binds to, and inhibits, a checkpoint inhibitor (e.g., a cell, e.g., an immune cell, expressing a checkpoint inhibitor). Exemplary checkpoint molecules include, but are not limited to, CTLA4, PD1, PD-L1, PD-L2, TIM3, LAG3, CD160, 2B4, CD80, CD86, B7-H3 (CD276), B7-H4 (VTCN1), HVEM (TNFRSF14 or CD270), BTLA, KIR, MHC class I, MHC class II, GAL9, VISTA, BTLA, TIGIT, LAIR1, and A2aR. In one embodiment, the immune cell engager and/or the tumor-targeting moiety binds to, but does not inhibit, a PD1-PDL1 interaction. In another embodiment, the immune cell engager and/or the tumor-targeting moiety binds to and inhibits a PD1-PDL1 interaction.

In any of the embodiments disclosed herein, a multispecific molecule disclosed does not activate an immune cell when a component is presented individually, e.g., outside the context of the multispecific molecule (or in the context of a multispecific molecule having an individual component, e.g., an individual immune cell engager); but the multispecific molecule activates the immune cell when presented in the context of a multispecific molecule comprising two or more components, e.g., two or more immune cell engagers. For example, the multispecific molecule can become activated when binding the immune cell when two different receptors are bound by different moieties of the multispecific molecule or when two different epitopes on the same receptor of the effector cells are bound by the multispecific molecule (e.g. activation or inhibition of the corresponding receptor on the immune cell). The activity levels can be assessed by any of the assays described herein, e.g., by comparing the component presented individually, e.g., in the multispecific molecule to two or more components presented in combination in the multispecific molecule. Without wishing to be bound by theory, binding of two or more different moieties of the multispecific molecule is believed to trigger a change in physical state, e.g., conformation, clustering, which leads to regulated, targeted, activation of an immune response against the cancer cell; such regulated activation is believed to reduce the effects of systemic toxicity of the multispecific molecules described herein.

In other embodiments, the tumor-targeting moiety comprises an antibody molecule, a receptor molecule (e.g., a receptor, a receptor fragment or functional variant thereof), or a ligand molecule (e.g., a ligand, a ligand fragment or functional variant thereof), or a combination thereof, that binds to the cancer antigen. For example, the tumor-targeting moiety can binds to a cancer antigen present on a hematological cancer, a solid tumor, a metastatic cancer, soft tissue tumor, metastatic lesion, or a combination thereof. In other embodiments, the cancer antigen is a tumor antigen or stromal antigen, or a hematological antigen. The tumor antigen or stromal antigen can be present on a fibrotic or desmoplastic solid tumor. For example, the tumor antigen or stromal antigen is present on a tumor, e.g., a tumor of a class typified by having one or more of: limited tumor perfusion, compressed blood vessels, or fibrotic tumor interstitium.

Exemplary cancers that can be targeted include, but are not limited to the tumor, e.g., solid tumor, pancreatic (e.g., pancreatic adenocarcinoma), breast, colorectal, lung (e.g., small or non-small cell lung cancer), skin, ovarian, or liver cancer. The cancer can also be a hematological cancer including, but not limited to, B-cell or T cell malignancy, e.g., Hodgkin's lymphoma, Non-Hodgkin's lymphoma (e.g., B cell lymphoma, diffuse large B cell lymphoma, follicular lymphoma, chronic lymphocytic leukemia, mantle cell lymphoma, marginal zone B-cell lymphoma, Burkitt lymphoma, lymphoplasmacytic lymphoma, hairy cell leukemia), acute myeloid leukemia (AML), chronic myeloid leukemia, myelodysplastic syndrome, multiple myeloma, and acute lymphocytic leukemia.

In some embodiments, the cancer, e.g., solid tumor, antigen is chosen from: PDL1, CD47, mesothelin, ganglo-side 2 (GD2), prostate stem cell antigen (PSCA), prostate specific membrane antigen (PMSA), prostate-specific antigen (PSA), carcinoembryonic antigen (CEA), Ron Kinase, c-Met, Immature laminin receptor, TAG-72, BING-4, Calcium-activated chloride channel 2, Cyclin-B1, 9D7, Ep-CAM, EphA3, Her2/neu, Telomerase, SAP-1, Survivin, NY-ESO-1/LAGE-1, PRAME, SSX-2, Melan-A/MART-1, Gp100/pmel17, Tyrosinase, TRP-1/-2, MC1R, β-catenin, BRCA1/2, CDK4, CML66, Fibronectin, p53, Ras, TGF-B receptor, AFP, ETA, MAGE, MUC-1, CA-125, BAGE, GAGE, NY-ESO-1, β-catenin, CDK4, CDC27, CD47, α actinin-4, TRP1/gp75, TRP2, gp100, Melan-A/MART1, gangliosides, WT1, EphA3, Epidermal growth factor receptor (EGFR), CD20, MART-2, MART-1, MUC1, MUC2, MUM1, MUM2, MUMS, NA88-1, NPM, OA1, OGT, RCC, RUI1, RUI2, SAGE, TRG, TRP1, TSTA, Folate receptor alpha, L1-CAM, CAIX, EGFRvIII, gpA33, GD3, GM2, VEGFR, Intergrins (Integrin alphaVbeta3, Integrin alpha5Beta1), Carbohydrates (Le), IGF1R, EPHA3, TRAILR1, TRAILR2, or RANKL. In other embodiments, the cancer antigen is a stromal antigen can be chosen from fibroblast activating protease (FAP), TGF-beta, hyaluronic acid, collagen, e.g., collagen IV, tenascin C, or tenascin W. In embodiments where the cancer antigen is a hematological antigen, the cancer antigen can be chosen from CD19, CD33, CD47, CD123, CD20, CD99, CD30, BCMA, CD38, CD22, SLAMF7, or NY-ESO1.

In some embodiments of any of the multispecific or multifunctional molecules disclosed herein, the tumor-targeting moiety is chosen from an antibody molecule to a cancer antigen chosen from mesothelin, PDL1, HER3, IGF1R, FAP, CD47 or CD123. For example, the tumor-targeting moiety can include an antibody molecule (e.g., Fab or scFv) that binds to mesothelin or PDL1. In some embodiments, the tumor-targeting moiety binds to PDL1 and inhibits an interaction of PDL1 with PD1. In other embodiments, the tumor-targeting moiety binds to PDL1 and does not inhibit an interaction of PD L1 with PD1.

In embodiments, the multispecific or multifunctional molecule can include two or three antibody molecules to two or three cancer antigens chosen from mesothelin, PDL1, HER3, IGF1R, FAP, CD123 or CD47. For example, the first and second tumor targeting moieties are an anti-mesothelin antibody molecule and an anti-PDL1 antibody molecule, respectively; or the second and first tumor targeting moieties are an anti-mesothelin antibody molecule and an anti-PDL1 antibody molecule, respectively. Other combinations include, but are not limited to, the first and second tumor targeting moieties are an anti-FAP antibody molecule and an anti-PDL1 antibody molecule, respectively; or the second and first tumor targeting moieties are an anti-FAP antibody molecule and an anti-PDL1 antibody molecule, respectively. In other embodiments, the first and second tumor targeting moieties are an anti-HER3 antibody molecule and an anti-IGF1R antibody molecule, respectively; or the second and first tumor targeting moieties are an anti-HER3 antibody molecule and an anti-IGF1R antibody molecule, respectively. In other embodiments, the first and second tumor targeting moieties are an anti-CD123 antibody molecule and an anti-CD47 antibody molecule, respectively; or the second and first tumor targeting moieties are an anti-CD123 antibody molecule and an anti-CD47 antibody molecule, respectively.

In some embodiments, the multispecific or multifunctional molecule can include an immune cell engager is chosen from an NK cell engager, a T cell engager, a B cell engager, a dendritic cell engager, or a macrophage cell engager, or a combination thereof. In some embodiments, the immune cell engager comprises an NK cell engager that mediates binding to and activation of, an NK cell. In other embodiments, the immune cell engager comprises an NK cell engager that mediates binding to but not activation of, an NK cell. Exemplary NK cell engagers can be chosen from an antibody molecule, e.g., an antigen binding domain, or ligand that binds to (e.g., activates NKp30, NKp40, NKp44, NKp46, NKG2D, DNAM1, DAP10, CD16 (e.g., CD16a, CD16b, or both), CRTAM, CD27, PSGL1, CD96, CD100 (SEMA4D), NKp80, CD244 (also known as SLAMF4 or 2B4), SLAMF6, SLAMF7, KIR2DS2, KIR2DS4, KIR3DS1, KIR2DS3, KIR2DS5, KIR2DS1, CD94, NKG2C, NKG2E, or CD160. In some embodiments, the NK cell engager is an antibody molecule, e.g., an antigen binding domain that binds to NKp30 or NKp46.

In some embodiments, the immune cell engager comprises a T cell engager that mediates binding to and activation of, a T cell. In some embodiments, the immune cell engager comprises a T cell engager that mediates binding to but not activation of, a T cell.

In other embodiments of the multispecific or multifunctional molecule the NK cell engager is a ligand, optionally, the ligand further comprises an immunoglobulin constant region, e.g., an Fc region. For example, the ligand of NKp44 or NKp46 is a viral HA; the ligand of DAP10 is a coreceptor for NKG2D; the ligand of CD16 is a CD16a/b ligand, e.g., a CD16a/b ligand further comprising an antibody Fc region.

In other embodiments, the immune cell engager mediates binding to, or activation of, or both of, one or more of a B cell, T cell, a macrophage, and/or a dendritic cell.

In other embodiments of the multispecific or multifunctional molecule, the T cell engager is an agonist of CD3, TCRα, TCRβ, TCRγ, TCRξ, ICOS, CD28, CD27, HVEM, LIGHT, CD40, 4-1BB, OX40, DR3, GITR, CD30, TIM1, SLAM, CD2, or CD226. In other embodiments, the T cell engager binds to, but does not CD3, TCRα, TCRβ, TCRγ, TCRξ, ICOS, CD28, CD27, HVEM, LIGHT, CD40, 4-1BB, OX40, DR3, GITR, CD30, TIM1, SLAM, CD2, or CD226.

In some embodiments, the immune cell engager comprises a B cell, macrophage, and/or dendritic cell engager chosen from one or more of CD40 ligand (CD40L) or a CD70 ligand; an antibody molecule that binds to CD40 or CD70; an antibody molecule to OX40; an OX40 ligand (OX40L); an agonist of a Toll-like receptor (e.g., a TLR4, e.g., a constitutively active TLR4 (caTLR4) or a TLR9 agonist); a 41BB; a CD2 agonist; a CD47; or a STING agonist, or a combination thereof.

In some embodiments, the B cell engager is a CD40L, an OX40L, or a CD70 ligand, or an antibody molecule that binds to OX40, CD40 or CD70.

In other embodiments, the macrophage cell engager is a CD2 agonist; a CD40L; an OX40L; an antibody molecule that binds to OX40, CD40 or CD70; an agonist of a Toll-like receptor (TLR)(e.g., a TLR4, e.g., a constitutively active TLR4 (caTLR4) or a TLR9 agonist); CD47; or a STING agonist.

In yet other embodiments, the dendritic cell engager is a CD2 agonist, an OX40 antibody, an OX40L, 41BB agonist, a Toll-like receptor agonist or a fragment thereof (e.g., a TLR4, e.g., a constitutively active TLR4 (caTLR4)), CD47 agonist, or a STING agonist. For example, the STING agonist can include a cyclic dinucleotide, e.g., a cyclic di-GMP (cdGMP), a cyclic di-AMP (cdAMP), or a combination thereof, optionally with 2',5' or 3',5' phosphate linkages. The STING agonist can be covalently coupled to the multispecific or multifunctional molecule, e.g., by art known techniques.

In other embodiments, the multispecific or multifunctional molecule is chosen from interleukin-2 (IL-2), interleukin-7 (IL-7), interleukin-12 (IL-12), interleukin-15 (IL-15), interleukin-18 (IL-18), interleukin-21 (IL-21), or interferon gamma, or a fragment or variant thereof, or a combination of any of the aforesaid cytokines. The cytokine can be a monomer or a dimer. For example, the cytokine molecule can further include a receptor dimerizing domain, e.g., an IL15Ralpha dimerizing domain. In other embodiments, the cytokine molecule (e.g., IL-15) and the receptor dimerizing domain (e.g., an IL15Ralpha dimerizing domain) are not covalently linked, e.g., are non-covalently associated.

In other embodiments, the multispecific or multifunctional molecule can include a stromal modifying moiety that causes one or more of: decreases the level or production of a stromal or extracellular matrix (ECM) component; decreases tumor fibrosis; increases interstitial tumor transport; improves tumor perfusion; expands the tumor microvasculature; decreases interstitial fluid pressure (IFP) in a tumor; or decreases or enhances penetration or diffusion of an agent, e.g., a cancer therapeutic or a cellular therapy, into a tumor or tumor vasculature. For example, the stromal or ECM component decreased is chosen from a glycosaminoglycan or an extracellular protein, or a combination thereof. The glycosaminoglycan can be chosen from hyaluronan (also known as hyaluronic acid or HA), chondroitin sulfate, chondroitin, dermatan sulfate, heparan sulfate, heparin, entactin, tenascin, aggrecan or keratin sulfate. Exemplary extracellular proteins include, but are not limited to, from collagen, laminin, elastin, fibrinogen, fibronectin, or vitronectin.

In some embodiments, the multispecific or multifunctional molecule includes a stromal modifying moiety that comprises an enzyme molecule that degrades a tumor stroma or extracellular matrix (ECM). The enzyme molecule can be chosen from a hyaluronidase molecule, a collagenase molecule, a chondroitinase molecule, a matrix metalloproteinase molecule—(e.g., macrophage metalloelastase), or a variant (e.g., a fragment) of any of the aforesaid.

In some embodiments, the stromal modifying moiety decreases the level or production of hyaluronic acid. For example, the stromal modifying moiety comprises a hyaluronan degrading enzyme, an agent that inhibits hyaluronan synthesis, or an antibody molecule against hyaluronic acid.

In yet other embodiments, the hyaluronan degrading enzyme is a hyaluronidase molecule or a variant (e.g., fragment thereof) thereof. The hyaluronan degrading enzyme can be active in neutral or acidic pH, e.g., pH of about 4-5. In some embodiments, the hyaluronidase molecule is a mammalian hyaluronidase molecule, e.g., a recombinant human hyaluronidase molecule, or a variant thereof (e.g., a truncated form thereof). For example, the hyaluronidase molecule can be chosen from HYAL1, HYAL2, or PH-20/SPAM1, or a variant thereof (e.g., a truncated form thereof). In yet other embodiments, the truncated form lacks a C-terminal glycosylphosphatidylinositol (GPI) attachment site or a portion of the GPI attachment site.

In yet other embodiments, the hyaluronidase molecule is glycosylated, e.g., comprises at least one N-linked glycan.

In one embodiment, the hyaluronidase molecule includes the amino acid sequence of SEQ ID NO:61, or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 61.

In some embodiments, the hyaluronidase molecule comprises:

(i) the amino acid sequence of 36-464 of SEQ ID NO: 61;

(ii) the amino acid sequence of 36-481, 36-482, or 36-483 of PH20, wherein PH20 has the sequence of amino acids set forth in SEQ ID NO: 61; or (iii) an amino acid sequence having at least 95% to 100% sequence identity to the polypeptide or truncated form of sequence of amino acids set forth in SEQ ID NO: 61; or (iv) an amino acid sequence having 30, 20, 10, 5 or fewer amino acid substitutions to the amino acid sequence set forth in SEQ ID NO:61.

In some embodiments, the hyaluronidase molecule includes an amino acid sequence at least 95% (e.g., at least 95%, 96%, 97%, 98%, 99%, 100%) identical to the amino acid sequence of SEQ ID NO: 61; or is encoded by a nucleotide sequence at least 95% (e.g., at least 96%, 97%, 98%, 99%, 100%) identical to the nucleotide sequence of SEQ ID NO: 61.

In other embodiments, the hyaluronidase molecule is PH20, e.g., rHuPH20.

In one embodiment, the hyaluronidase molecule is HYAL1 and comprises the amino acid sequence:
SEQ ID NO: 62, or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 62.

In some embodiments, the hyaluronan degrading enzyme, e.g., the hyaluronidase molecule, further comprises a polymer, e.g., is conjugated to a polymer, e.g., PEG. For example, the hyaluronan-degrading enzyme can be a PEGylated PH20 enzyme (PEGPH20).

In some embodiments, the multispecific or multifunctional molecule polypeptide the hyaluronan degrading enzyme, e.g., the hyaluronidase molecule, further comprises an immunoglobulin chain constant region (e.g., Fc region) chosen from, e.g., the heavy chain constant regions of IgG1, IgG2, IgG3, and IgG4, more particularly, the heavy chain constant region of human IgG1, IgG2, IgG3, or IgG4.

In some embodiments, the immunoglobulin constant region (e.g., the Fc region) is linked, e.g., covalently linked to, the hyaluronan degrading enzyme, e.g., the hyaluronidase molecule. In some embodiments, the immunoglobulin chain constant region (e.g., Fc region) is altered, e.g., mutated, to increase or decrease one or more of: Fc receptor binding, antibody glycosylation, the number of cysteine residues, effector cell function, or complement function. In some embodiments, the hyaluronan degrading enzyme, e.g., the hyaluronidase molecule, forms a dimer.

In some embodiments, the stromal modifying moiety comprises an inhibitor of the synthesis of hyaluronan, e.g., an HA synthase. In some embodiments, the inhibitor comprises a sense or an antisense nucleic acid molecule against an HA synthase or is a small molecule drug. In some embodiments, the inhibitor is 4-methylumbelliferone (MU) or a derivative thereof (e.g., 6,7-dihydroxy-4-methyl coumarin or 5,7-dihydroxy-4-methyl coumarin), or leflunomide or a derivative thereof. In some embodiments, the stromal modifying moiety comprises a collagenase molecule, e.g., a mammalian collagenase molecule, or a variant (e.g., fragment) thereof. In some embodiments, the collagenase molecule is collagenase molecule IV, e.g., comprising the amino acid sequence of SEQ ID NO: 63, or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 63.

In some embodiments, the multispecific or multifunctional molecule polypeptide comprises two binding specificities or functions, e.g., it is a bispecific or a bifunctional molecule, e.g., which comprises: i) the tumor-targeting moiety and the immune cell engager, provided that when the multispecific molecule comprises the tumor-targeting moiety and the immune cell engager only, the immune cell engager is not an antibody molecule to an NK cell antigen; or ii) the tumor-targeting moiety and the stromal modifying moiety.

In some embodiments, the multispecific or multifunctional molecule polypeptide comprises three or four binding specificities or functions, e.g., is a trispecific or a tetraspecific molecule. In some embodiments, the multispecific or multifunctional molecule polypeptide comprises (i) at least two tumor-targeting moieties, the immune cell engager, and the cytokine molecule; (ii) the tumor-targeting moiety, the immune cell engager, and the stromal modifying moiety; or (iii) at least two tumor-targeting moieties that bind to two cancer antigens chosen from mesothelin, PDL1, HER3, Fibroblast Activation Protein (FAP), or insulin growth factor 1R (IGF1R), CD47 or CD123, provided that the two cancer antigens are not FAP and IGF1R; and a cytokine molecule.

In some embodiments, the multispecific or multifunctional molecule polypeptide comprises: (i) one tumor-targeting moiety; (ii) two immune cell engagers (e.g., same or different immune cell engagers); and one or both of: (iii) one cytokine molecule, or (iv) one stromal modifying moiety. In some embodiments, the multispecific or multifunctional molecule polypeptide comprises (i) two tumor-targeting moieties (e.g., same or different targeting moieties); (ii) one immune cell engager; and one or both of: (iii) one cytokine molecule, or (iv) one stromal modifying moiety. In some embodiments, the multispecific or multifunctional molecule polypeptide comprises (i) one tumor-targeting moiety; (ii) one immune cell engager; and one or both of: (iii) two cytokine molecules (e.g., same or different cytokine molecules).

In some embodiments, one of the two tumor targeting moieties binds PDL1; one of the two tumor targeting moieties binds mesothelin; the immune cell engager binds NKp46 or NKp30; and the cytokine molecule is IL2.

In some embodiments, the tumor-targeting moiety or the immune cell engager, or both, comprises (i) an antibody molecule, e.g., at least one immunoglobulin domain; and/or (ii) a receptor or a ligand, or a fragment thereof.

In some embodiments, the tumor-targeting antibody molecule binds to the solid tumor antigen and/or the stromal antigen with a dissociation constant of less than about 10 nM, and more typically, 10-100 pM.

In some embodiments, the immune cell engager antibody molecule binds to the NK cell antigen, the B cell antigen, the dendritic cell antigen, and/or the macrophage cell antigen with a dissociation constant of less than about 10 nM, and more typically, 10-100 pM.

In some embodiments, the tumor-targeting antibody molecule binds to a conformational or a linear epitope on the tumor antigen or the stromal antigen.

In some embodiments, the immune cell engager antibody molecule binds to a conformational or a linear epitope on the NK cell antigen, the B cell antigen, the dendritic cell antigen, and/or the macrophage cell antigen.

In some embodiments, the tumor-targeting antibody molecule is a monospecific antibody molecule, a bispecific antibody molecule, or a trispecific antibody molecule.

In some embodiments, the tumor-targeting antibody molecule is a monovalent antibody molecule, a bivalent antibody molecule, or a trivalent antibody molecule.

In some embodiments, the immune cell engager antibody molecule is a monospecific, a bispecific antibody molecule, or a trispecific antibody.

In some embodiments, the immune cell engager antibody molecule is a monovalent, a bivalent, or a trivalent antibody.

In some embodiments, the tumor targeting antibody molecule and/or immune cell engager antibody molecule is a full antibody (e.g., an antibody that includes at least one, and preferably two, complete heavy chains, and at least one, and preferably two, complete light chains), or an antigen-binding fragment (e.g., a Fab, $F(ab')_2$, Fv, a single chain Fv, a single domain antibody, a diabody (dAb), a bivalent antibody, or bispecific antibody or fragment thereof, a single domain variant thereof, or a camelid antibody).

In some embodiments, the tumor targeting antibody molecule and immune cell engager antibody molecule are, independently, a full antibody (e.g., an antibody that includes at least one, and preferably two, complete heavy chains, and at least one, and preferably two, complete light chains), or an antigen-binding fragment (e.g., a Fab, $F(ab')_2$, Fv, a single chain Fv fragment, a single domain antibody, a diabody (dAb), a bivalent antibody, or bispecific antibody or fragment thereof, a single domain variant thereof, or a camelid antibody).

In some embodiments, the tumor targeting antibody molecule and/or immune cell engager antibody molecule comprises a heavy chain constant region chosen from IgG1, IgG2, IgG3, or IgG4, or a fragment thereof.

In some embodiments, the tumor targeting antibody molecule and/or immune cell engager antibody molecule comprises a light chain constant region chosen from the light chain constant regions of kappa or lambda, or a fragment thereof.

In some embodiments, the tumor-targeting moiety or the immune cell engager, or both, comprises a receptor or receptor fragment, or a ligand or ligand fragment, that binds to the tumor antigen and/or the stromal antigen, or the NK cell antigen, the B cell antigen, the dendritic cell antigen, and/or the macrophage cell antigen.

In some embodiments, the multispecific or multifunctional molecule polypeptide further comprises an immunoglobulin constant region (e.g., Fc region) chosen from the heavy chain constant regions of IgG1, IgG2, and IgG4, more particularly, the heavy chain constant region of human IgG1, IgG2 or IgG4. In some embodiments, the immunoglobulin constant region (e.g., an Fc region) is linked, e.g., covalently linked to, one or more of the tumor-targeting moiety, the immune cell engager, or the cytokine molecule. In some embodiments, the immunoglobulin chain constant region (e.g., Fc region) is altered, e.g., mutated, to increase or decrease one or more of: Fc receptor binding, antibody glycosylation, the number of cysteine residues, effector cell function, or complement function.

In some embodiments, the multispecific or multifunctional polypeptide comprises at least two non-contiguous polypeptide chains.

In some embodiments, the tumor-targeting moiety or immune cell engager comprises a light chain constant region chosen from the light chain constant region of kappa or lambda, or a fragment thereof.

In some embodiments, the multispecific or multifunctional polypeptide comprises a first tumor-targeting moiety and a second tumor-targeting moiety, wherein the first tumor-targeting moiety comprises a kappa light chain constant region, or a fragment thereof, and the second tumor-targeting moiety comprises a lambda light chain constant region, or a fragment thereof.

In some embodiments, the multispecific or multifunctional polypeptide comprises a first tumor moiety and a second tumor-targeting moiety, wherein the first tumor-targeting moiety and the second tumor-targeting moiety comprise a common light chain variable region.

In some embodiments, the immunoglobulin constant region (e.g., an Fc region) is linked, e.g., covalently linked to, one or more of tumor-targeting moiety, the immune cell engager, the cytokine molecule, or the stromal modifying moiety.

In some embodiments, the multispecific or multifunctional polypeptide comprises an interface of a first and second immunoglobulin chain constant regions (e.g., Fc region) is altered, e.g., mutated, to increase or decrease dimerization, e.g., relative to a non-engineered interface.

In some embodiments, the dimerization of the immunoglobulin chain constant region (e.g., Fc region) is enhanced by providing an Fc interface of a first and a second Fc region with one or more of: a paired cavity-protuberance ("knob-in-a hole"), an electrostatic interaction, or a strand-exchange, such that a greater ratio of heteromultimer:homomultimer forms, e.g., relative to a non-engineered interface.

In some embodiments, the immunoglobulin chain constant region (e.g., Fc region) comprises an amino acid substitution at a position chosen from one or more of 347, 349, 350, 351, 366, 368, 370, 392, 394, 395, 397, 398, 399, 405, 407, or 409, e.g., of the Fc region of human IgG1.

In some embodiments, the immunoglobulin chain constant region (e.g., Fc region) comprises an amino acid substitution chosen from: T366S, L368A, or Y407V (e.g., corresponding to a cavity or hole), or T366W (e.g., corresponding to a protuberance or knob), or a combination thereof.

In some embodiments, the multispecific or multifunctional polypeptide further comprises a linker, e.g., a linker between one or more of: the targeting moiety and the cytokine molecule or the stromal modifying moiety, the targeting moiety and the immune cell engager, the cytokine molecule or the stromal modifying moiety, and the immune cell engager, the cytokine molecule or the stromal modifying moiety and the immunoglobulin chain constant region (e.g., the Fc region), the targeting moiety and the immunoglobulin chain constant region, or the immune cell engager and the immunoglobulin chain constant region.

In some embodiments, the linker is selected from: a cleavable linker, a non-cleavable linker, a peptide linker, a flexible linker, a rigid linker, a helical linker, or a non-helical linker. In some embodiments, the linker is a peptide linker. In some embodiments, the peptide linker comprises Gly and Ser.

In some embodiments, the multispecific or multifunctional polypeptide is a bispecific molecule comprising a first and a second non-contiguous polypeptides, wherein:

(i) the first polypeptide includes, e.g., in the N- to C-orientation, a tumor-targeting moiety, e.g., an antibody molecule (e.g., a first portion of a first antigen domain, e.g., a first VH-CH1 of a Fab molecule), that binds to, e.g., a cancer antigen, e.g., a solid tumor, a stromal or a hematological antigen, connected, optionally via a linker to, a cytokine molecule, a stromal modifying moiety, or an immune cell engager, e.g., an antibody molecule, e.g., a scFv that binds to an immune cell antigen; and (ii) the second polypeptide includes, e.g., in the N- to C-orientation, a second portion of the first antigen domain, e.g., a first VL-CL of the Fab, that binds to, e.g., a cancer antigen, e.g., a solid tumor, a stromal or a hematological antigen (e.g., the same tumor or stromal antigen bound by the first VH-CH1).

In some embodiments, the multispecific or multifunctional polypeptide is a bispecific molecule comprising a first and a second non-contiguous polypeptides, wherein:

(i) the first polypeptide includes, e.g., in the N- to C-orientation, a tumor-targeting moiety, e.g., an antibody molecule (e.g., a first portion of a first antigen domain, e.g., a first VH-CH1 of a Fab molecule), that binds to, e.g., a cancer antigen, e.g., a solid tumor, a stromal or a hematological antigen, connected, optionally, via a linker to, a first domain that promotes association between the first and the second polypeptide (e.g., a first immunoglobulin constant domain (e.g., a first Fc molecule as described herein);

(ii) the second polypeptide includes, e.g., in the N- to C-orientation, a cytokine molecule, a stromal modifying moiety, or an immune cell engager (e.g., an antibody molecule, e.g., a scFv, that binds to an immune cell antigen), connected, optionally, via a linker to, a second domain that promotes association between the first and the second polypeptide (e.g., a second immunoglobulin constant domain (e.g., a second Fc molecule as described herein); and (iii) the third polypeptide includes, e.g., in the N- to C-orientation, a second portion of the first antigen domain, e.g., a first VL-CL of the Fab, that binds to the cancer antigen.

In some embodiments, the multispecific or multifunctional polypeptide is a trispecific molecule comprising a first, a second and a third non-contiguous polypeptide, wherein:

(i) the first polypeptide includes, e.g., in the N- to C-orientation, a tumor-targeting moiety, e.g., an antibody molecule (e.g., a first portion of a first antigen domain, e.g., a first VH-CH1 of a Fab molecule), that binds to, e.g., a cancer antigen, connected, optionally, via a linker to, a first domain that promotes association between the first and the second polypeptide (e.g., a first immunoglobulin constant domain (e.g., a first Fc molecule as described herein);

(ii) the second polypeptide includes, e.g., in the N- to C-orientation, a cytokine molecule, a stromal modifying moiety, or an immune cell engager (e.g., an antibody molecule, e.g., a scFv, that binds to an immune cell antigen), connected, optionally, via a linker to, a second domain that promotes association between the first and the second polypeptide (e.g., a second immunoglobulin constant domain (e.g., a second Fc molecule as described herein); and (iii) the third polypeptide includes, e.g., in the N- to C-orientation, a second portion of the first antigen domain, e.g., a first VL-CL of the Fab, that binds to the cancer antigen, wherein either the first or the second polypeptide further comprise a cytokine molecule or an immune cell engager, optionally covalently linked to the C-terminus of the first or second immunoglobulin constant domain.

In some embodiments, the multispecific or multifunctional polypeptide is is a tetraspecific molecule comprising a first, a second and a third non-contiguous polypeptide, wherein:

(i) the first polypeptide includes, e.g., in the N- to C-orientation, a tumor-targeting moiety, e.g., an antibody molecule (e.g., a first portion of a first antigen domain, e.g., a first VH-CH1 of a Fab molecule), that binds to, e.g., a cancer antigen, connected, optionally, via a linker to, a first domain that promotes association between the first and the second polypeptide (e.g., a first immunoglobulin constant domain (e.g., a first Fc molecule as described herein);

(ii) the second polypeptide includes, e.g., in the N- to C-orientation, a cytokine molecule, a stromal modifying moiety, or an immune cell engager (e.g., an antibody molecule, e.g., a scFv, that binds to an immune cell antigen), connected, optionally, via a linker to, a second domain that promotes association between the first and the second polypeptide (e.g., a second immunoglobulin constant domain (e.g., a second Fc molecule as described herein); and (iii) the third polypeptide includes, e.g., in the N- to C-orientation, a second portion of the first antigen domain, e.g., a first VL-CL of the Fab, that binds to the cancer antigen, wherein the first and the second polypeptide further comprise a cytokine molecule and/or an immune cell engager, optionally covalently linked to the C-terminus of the first or second immunoglobulin constant domain.

In some embodiments, the multispecific or multifunctional polypeptide comprises a) a first polypeptide comprising: a domain that promotes association of the first and second polypeptide, e.g., an Fc molecule; and two polypeptides selected from: a tumor-targeting moiety; an immune cell engager; a stromal modifying moiety, and a cytokine molecule b) a second polypeptide comprising: a domain that promotes association of the first and second polypeptide, e.g., an Fc molecule; and two polypeptides selected from: a tumor-targeting moiety; an immune cell engager; and a cytokine molecule, wherein the multispecific or multifunctional molecule polypeptide comprises a tumor-targeting moiety; an immune cell engager; a stromal modifying moiety; and a cytokine molecule.

In some embodiments, the multispecific or multifunctional polypeptide comprises a tumor-targeting moiety; an immune cell engager; and two cytokine molecules or two stromal modifying moieties;

a tumor-targeting moiety; two immune cell engagers; and a cytokine molecule or a stromal modifying moiety; or two tumor targeting moieties; an immune cell engager; and a cytokine molecule or a stromal modifying moiety.

In some embodiments, the multispecific or multifunctional polypeptide comprises two tumor targeting moieties; an immune cell engager; and a cytokine molecule, wherein one of the two tumor-targeting moiety is an antibody molecule that binds PDL1; one of the two tumor-targeting moiety binds mesothelin; the immune cell engager binds NKp46 or NKp30; and the cytokine is IL2.

In some embodiments, the multispecific or multifunctional polypeptide comprises i) a first polypeptide comprises, e.g., in the N-C or C-N direction, a tumor-targeting moiety; a domain that promotes association of the first and second polypeptide, e.g., an Fc molecule; and an immune cell engager;

ii) a first polypeptide comprises, e.g., in the N-C or C-N direction, a tumor-targeting moiety; a domain that promotes association of the first and second polypeptide, e.g., an Fc molecule; and a cytokine molecule or a stromal modifying moiety; or iii) a first polypeptide comprises, e.g., in the N-C or C-N direction a cytokine; a domain that promotes association of the first and second polypeptide, e.g., an Fc molecule; and an immune cell engager; and iv) a second polypeptide comprises, e.g., in the N-C or C-N direction, a tumor-targeting moiety; a domain that promotes association of the first and second polypeptide, e.g., an Fc molecule; and an immune cell engager;

ii) a second polypeptide comprises, e.g., in the N-C or C-N direction, a tumor-targeting moiety; a domain that promotes association of the first and second polypeptide, e.g., an Fc molecule; and a cytokine molecule or a stromal modifying moiety; or iii) a second polypeptide comprises, e.g., in the N-C or C-N direction a cytokine; a domain that promotes association of the first and second polypeptide, e.g., an Fc molecule; and an immune cell engager.

In some embodiments, (i) the tumor-targeting moiety comprises:

(ia) an antibody molecule against a solid tumor antigen chosen from: PDL1, Mesothelin, HER3, IGF-1R, GD2, PMSA, CEA, Ron Kinase, or c-Met; and/or (ib) an antibody molecule against a stromal antigen is chosen from: FAP, hyaluronic acid, collagen IV, tenascin C, or tenascin W; or a combination of the antibody molecule against the solid tumor antigen and the antibody molecule against the stromal antigen; and (ii) one, two or all of:

(iia) the immune cell engager chosen from one, two, three, or all of a CD40L or a CD70 ligand; an antibody molecule that binds to CD40 or CD70; an antibody molecule to OX40; an OX40L; B7-H6, or a STING agonist, or a combination thereof;

(iib) the cytokine molecule chosen from IL-2, IL-12, IL-15, IL-18, or IL-21, fragment or variant thereof, or a combination of any of the aforesaid cytokine molecules;

(iic) the stromal modifying moiety chosen from hyaluronidase or gelatinase.

In some embodiments, the multispecific or multifunctional polypeptide comprises an antibody molecule to mesothelin, e.g., human mesothelin; a CD40L polypeptide; and an IL-15 or IL-2 molecule.

In some embodiments, the antibody molecule comprises a Fab against mesothelin having a light and a heavy chain.

In some embodiments, the heavy chain of the Fab against mesothelin further comprises the IL-15 or IL-2 molecule, e.g., human IL-15 molecule, optionally, wherein the Fab and the IL-15 or IL-2 molecule are linked, e.g., via a linker comprising Gly and Ser.

In some embodiments, the multispecific or multifunctional polypeptide has the following configuration: Heavy chain of the Fab (e.g., VH-CH1) against mesothelin to IL-15 or IL-2, from N- to C-terminus, optionally, comprising a Gly-Ser linker between the Fab and the IL-15 or IL-2.

In some embodiments, the light chain of the Fab to mesothelin further comprises a CD40L, optionally, wherein the Fab and the CD40L are linked, e.g., via a linker comprising Gly and Ser.

In some embodiments, the multispecific or multifunctional polypeptide has the following configuration: Light chain of the Fab (e.g., VL-CL1) to mesothelin fused to CD40L, from N- to C-terminus, optionally, comprising a Gly-Ser linker between the Fab and the CD40L.

In some embodiments, the multispecific or multifunctional molecule comprises an antibody molecule to FAP, e.g., human FAP, and an IL-15 or IL-2 molecule. In some embodiments, the antibody molecule comprises a Fab against FAP having a light and a heavy chain. In some embodiments, the heavy chain of the Fab to FAP further comprises a first Fc region having a member of a paired cavity-protuberance (knob-in-a hole) in the Fc interface of the first Fc region.

In some embodiments, the multifunctional or multispecific molecule has the following configuration: Heavy chain of the Fab (e.g., VH-CH1) of FAP fused to First Fc region (e.g., CH2 to CH3), from N- to C-terminus.

In some embodiments, the IL-15 or IL-2 molecule, e.g., human IL-15 or IL-2 molecule, further comprises a second Fc region having a second member of a paired cavity-protuberance (knob-in-a hole) in the Fc interface of the second Fc region, e.g., connected via a linker comprising Gly and Ser.

In some embodiments, the multispecific or multifunctional polypeptide has the following configuration: IL-15 or IL-2 molecule-Second Fc region (e.g., CH2 to CH3), from N- to C-terminus, e.g., wherein the IL-15 or IL-2 molecule and the second Fc region are connected via a linker comprising Gly and Ser.

In some embodiments, the multispecific or multifunctional polypeptide further comprises an immune cell engager. In some embodiments, the immune cell engager comprises a CD40 ligand. In some embodiments, the immune cell enhancer is linked, e.g., covalently linked, to the second Fc region having the second member of the paired cavity-protuberance (knob-in-a hole) and the IL-15 or IL-2 molecule, e.g., human IL-15 or IL-2 molecule, optionally comprising a linker comprising Gly and Ser between the IL-15 or IL-2 molecule and the second Fc region, and/or between the second Fc region and the immune cell enhancer.

In some embodiments, the multispecific or multifunctional polypeptide has the following configuration: IL-15 or IL-2 molecule-Second Fc region (e.g., CH2 to CH3)—Immune cell enhancer, from N- to C-terminus, optionally comprising a linker comprising Gly and Ser between the IL-15 or IL-2 molecule and the second Fc region, and/or between the second Fc region and the immune cell enhancer.

In some embodiments the multispecific or multifunctional polypeptide further comprises a second immune cell enhancer. In some embodiments, the second immune cell enhancer comprises a B7H6 molecule. In some embodiments, the second immune cell enhancer is linked, e.g., covalently linked, to the first Fc region having the first member of the paired cavity-protuberance (knob-in-a hole) in the Fc interface of the first Fc region and the heavy chain of the Fab, optionally comprising a linker comprising Gly and Ser between the B7H6 molecule and the first Fc region.

In some embodiments, the multispecific or multifunctional polypeptide comprises a targeting antibody molecule to a solid tumor antigen or a stromal antigen, and at least two immune cell enhancers. In some embodiments, the antibody molecule binds to mesothelin or FAP. In some embodiments, the immune cell enhancers are a TLR agonist (e.g., a TLR9 agonist) or a STING agonist and an antibody molecule against OX40. In some embodiments, the STING agonist comprises a cyclic dinucleotide, e.g., a cyclic di-GMP (cdGMP), a cyclic di-AMP (cdAMP), or a combination thereof, optionally with 2',5' or 3',5' phosphate linkages, and optionally, wherein the STING agonist is coupled (e.g., directly conjugated) to the targeting antibody or the immune cell enhancer. In some embodiments, the TLR agonist comprises an unmethylated CpG sequences In some embodiments, the multispecific or multifunctional polypeptide comprises a bispecific antibody having a first binding specificity for mesothelin or FAP, and a second binding specificity for OX40.

In some embodiments of any of the aforesaid multispecific molecules, the tumor targeting moiety is chosen from an antibody molecule to a cancer antigen chosen from mesothelin, PDL1, HER3, IGF1R or FAP. In some embodiments, the multispecific molecule comprises two or three antibody molecules to two or three cancer antigens chosen from mesothelin, PDL1, HER3, IGF1R or FAP. In some embodiments, the tumor targeting moiety binds to PD L1 and inhibits an interaction of PD L1 with its ligand, e.g., PD1. In other embodiments, the tumor targeting moiety binds to PD L1 and does not inhibit an interaction of PD L1 with its ligand, e.g., PD1.

In some embodiments, the first and second tumor targeting moieties are an anti-mesothelin antibody molecule and an anti-PDL1 antibody molecule, respectively. In some embodiments, the second and first tumor targeting moieties are an anti-mesothelin antibody molecule and an anti-PDL1 antibody molecule, respectively.

In some embodiments, the first and second tumor targeting moieties are an anti-FAP antibody molecule and an anti-PDL1 antibody molecule, respectively. In some embodiments, the second and first tumor targeting moieties are an anti-FAP antibody molecule and an anti-PDL1 antibody molecule, respectively.

In some embodiments, the first and second tumor targeting moieties are an anti-HER3 antibody molecule and an anti-IGF1R antibody molecule, respectively. In some embodiments, the second and first tumor targeting moieties are an anti-HER3 antibody molecule and an anti-IGF1R antibody molecule, respectively.

In some embodiments of any of the aforesaid multispecific molecules, the immune cell engager is chosen from an antibody molecule to NKp30, an antibody molecule to NKp46, CD40L, or 41BBL.

In some embodiments of any of the aforesaid multispecific molecules, the cytokine molecule is an IL-2 molecule (e.g., IL-2 or a functional variant thereof), an IL-15 molecule (e.g., IL-15 or a functional variant thereof), or an IL-21 molecule (e.g., IL-21 or a functional variant thereof).

In some embodiments of any of the aforesaid multispecific molecules, the stromal modifying molecule is chosen from a hyaluronidase (e.g., hyaluronidase 1), or a functional variant thereof, or gelatinase or a functional variant thereof.

In one embodiment, the multispecific molecule comprises an anti-mesothelin tumor targeting moiety (e.g., an anti-mesothelin Fab) and IL-2 (or functional variant thereof).

In one embodiment, the multispecific molecule comprises an anti-mesothelin tumor targeting moiety (e.g., an anti-mesothelin Fab), IL-2 (or functional variant thereof), and an anti-NKp30 NK cell engager moiety (e.g., an anti-NKp30 Fab or scFv).

In one embodiment, the multispecific molecule comprises an anti-mesothelin tumor targeting moiety (e.g., an anti-mesothelin Fab) and an anti-NKp30 NK cell engager moiety (e.g., an anti-NKp30 Fab or scFv).

In one embodiment, the multispecific molecule comprises an anti-mesothelin tumor targeting moiety (e.g., an anti-mesothelin Fab) and an anti-PDL1 tumor targeting moiety (e.g., an anti-PDL1 Fab)

In one embodiment, the multispecific molecule comprises an anti-mesothelin tumor targeting moiety (e.g., an anti-mesothelin Fab), an anti-PDL1 tumor targeting moiety (e.g., an anti-PDL1 Fab), and IL-2 (or functional variant thereof).

In one embodiment, the multispecific molecule comprises an anti-mesothelin tumor targeting moiety (e.g., an anti-mesothelin Fab), an anti-PDL1 tumor targeting moiety (e.g., an anti-PDL1 Fab), and an anti-NKp46 NK cell engager moiety (e.g., an anti-NKp46 Fab or scFv). In one embodiment, the multispecific molecule comprises an anti-mesothelin tumor targeting moiety (e.g., an anti-mesothelin Fab), an anti-PDL1 tumor targeting moiety (e.g., an anti-PDL1 Fab), an anti-NKp46 NK cell engager moiety (e.g., an anti-NKp46 Fab or scFv), and IL-2 (or functional variant thereof).

In one embodiment, the multispecific molecule comprises an anti-HER3 tumor targeting moiety (e.g., an anti-HER3 Fab), an anti-IGF1R tumor targeting moiety (e.g., an anti-IGF1R Fab), and IL-2 (or functional variant thereof).

In one embodiment, the multispecific molecule comprises an anti-HER3 tumor targeting moiety (e.g., an anti-HER3 Fab), an anti-IGF1R tumor targeting moiety (e.g., an anti-IGF1R Fab), an anti-NKp46 NK cell engager moiety (e.g., an anti-NKp46 Fab or scFv), and IL-2 (or functional variant thereof).

In one embodiment, the multispecific molecule comprises an anti-HER3 tumor targeting moiety (e.g., an anti-HER3 Fab) and an anti-IGF1R tumor targeting moiety (e.g., an anti-IGF1R Fab).

In one embodiment, the multispecific molecule comprises an anti-FAP tumor targeting moiety (e.g., an anti-FAP Fab) and hyaluronidase 1 (or functional variant thereof).

In one embodiment, the multispecific molecule comprises an anti-FAP tumor targeting moiety (e.g., an anti-FAP Fab), IL-2 (or functional variant thereof), and hyaluronidase 1 (or functional variant thereof).

In one embodiment, the multispecific molecule comprises an anti-FAP tumor targeting moiety (e.g., an anti-FAP Fab), an anti-PDL1 tumor targeting moiety (e.g., an anti-PDL1 Fab), and hyaluronidase 1 (or functional variant thereof).

In one embodiment, the multispecific molecule comprises an anti-FAP tumor targeting moiety (e.g., an anti-FAP Fab), an anti-PDL1 tumor targeting moiety (e.g., an anti-PDL1 Fab), IL-2 (or functional variant thereof), and hyaluronidase 1 (or functional variant thereof).

In one embodiment, the multispecific molecule comprises an anti-PDL1 tumor targeting moiety (e.g., an anti-PDL1 Fab), an anti-NKp46 NK cell engager moiety (e.g., an anti-NKp46 Fab or scFv), IL-2 (or functional variant thereof), and hyaluronidase 1 (or functional variant thereof).

In one embodiment, the multispecific molecule comprises an anti-FAP tumor targeting moiety (e.g., an anti-FAP Fab) and gelatinase (or functional variant thereof).

In one embodiment, the multispecific molecule comprises an anti-FAP tumor targeting moiety (e.g., an anti-FAP Fab), an anti-PDL1 tumor targeting moiety (e.g., an anti-PDL1 Fab), IL-2 (or functional variant thereof), and gelatinase (or functional variant thereof).

In one embodiment, the multispecific molecule comprises an anti-mesothelin tumor targeting moiety, IL-21 or a functional variant thereof, 41BB-L, and CD40L.

In one embodiment, the multispecific molecule comprises an anti-FAP tumor targeting moiety and CD40L.

In one embodiment, the multispecific molecule comprises an anti-FAP tumor targeting moiety and IL-15.

In one embodiment, the multispecific molecule comprises an anti-mesothelin tumor targeting moiety (e.g., an anti-mesothelin Fab) and IL-2 (or functional variant thereof).

In one embodiment, the multispecific molecule comprises an anti-mesothelin tumor targeting moiety (e.g., an anti-mesothelin Fab), IL-2 (or functional variant thereof), and an anti-NKp30 NK cell engager moiety (e.g., an anti-NKp30 Fab or scFv).

In one embodiment, the multispecific molecule comprises an anti-mesothelin tumor targeting moiety (e.g., an anti-mesothelin Fab) and an anti-NKp30 NK cell engager moiety (e.g., an anti-NKp30 Fab or scFv).

In one embodiment, the multispecific molecule comprises IL-2 (or functional variant thereof).

In one embodiment, the multispecific molecule comprises an anti-mesothelin tumor targeting moiety (e.g., an anti-mesothelin Fab) and an anti-PDL1 tumor targeting moiety (e.g., an anti-PDL1 Fab).

In one embodiment, the multispecific molecule comprises an anti-mesothelin tumor targeting moiety (e.g., an anti-mesothelin Fab), an anti-PDL1 tumor targeting moiety (e.g., an anti-PDL1 Fab), and IL-2 (or functional variant thereof).

In one embodiment, the multispecific molecule comprises an anti-mesothelin tumor targeting moiety (e.g., an anti-mesothelin Fab), an anti-PDL1 tumor targeting moiety (e.g., an anti-PDL1 Fab), and an anti-NKp46 NK cell engager moiety (e.g., an anti-NKp46 Fab or scFv).

In one embodiment, the multispecific molecule comprises an anti-mesothelin tumor targeting moiety (e.g., an anti-mesothelin Fab), an anti-PDL1 tumor targeting moiety (e.g., an anti-PDL1 Fab), an anti-NKp46 NK cell engager moiety (e.g., an anti-NKp46 Fab or scFv), and IL-2 (or functional variant thereof).

In one embodiment, the multispecific molecule comprises an anti-HER3 tumor targeting moiety (e.g., an anti-HER3 Fab), an anti-IGF1R tumor targeting moiety (e.g., an anti-IGF1R Fab), and IL-2 (or functional variant thereof).

In one embodiment, the multispecific molecule comprises an anti-HER3 tumor targeting moiety (e.g., an anti-HER3 Fab), an anti-IGF1R tumor targeting moiety (e.g., an anti-IGF1R Fab), and an anti-NKp46 NK cell engager moiety (e.g., an anti-NKp46 Fab or scFv).

In one embodiment, the multispecific molecule comprises an anti-HER3 tumor targeting moiety (e.g., an anti-HER3 Fab), an anti-IGF1R tumor targeting moiety (e.g., an anti-IGF1R Fab), and an anti-CD3 T cell engager moiety (e.g., an anti-CD3 Fab or scFv).

In one embodiment, the multispecific molecule comprises an anti-HER3 tumor targeting moiety (e.g., an anti-HER3 Fab), an anti-IGF1R tumor targeting moiety (e.g., an anti-IGF1R Fab), an anti-NKp46 NK cell engager moiety (e.g., an anti-NKp46 Fab or scFv), and IL-2 (or functional variant thereof).

In one embodiment, the multispecific molecule comprises an anti-HER3 tumor targeting moiety (e.g., an anti-HER3 Fab), an anti-IGF1R tumor targeting moiety (e.g., an anti-IGF1R Fab), an anti-CD3 T cell engager moiety (e.g., an anti-CD3 Fab or scFv), and IL-2 (or functional variant thereof).

In one embodiment, the multispecific molecule comprises an anti-HER3 tumor targeting moiety (e.g., an anti-HER3 Fab) and an anti-IGF1R tumor targeting moiety (e.g., an anti-IGF1R Fab).

In one embodiment, the multispecific molecule comprises an anti-HER3 tumor targeting moiety (e.g., an anti-HER3 Fab), an anti-IGF1R tumor targeting moiety (e.g., an anti-IGF1R Fab), and IL-7 (or functional variant thereof).

In one embodiment, the multispecific molecule comprises an anti-HER3 tumor targeting moiety (e.g., an anti-HER3 Fab), an anti-IGF1R tumor targeting moiety (e.g., an anti-IGF1R Fab), an anti-CD3 T cell engager moiety (e.g., an anti-CD3 Fab or scFv), and IL-7 (or functional variant thereof).

In one embodiment, the multispecific molecule comprises an anti-HER3 tumor targeting moiety (e.g., an anti-HER3 Fab), an anti-IGF1R tumor targeting moiety (e.g., an anti-IGF1R Fab), an anti-NKp46 NK cell engager moiety (e.g., an anti-NKp46 Fab or scFv), and IL-7 (or functional variant thereof).

In one embodiment, the multispecific molecule comprises an anti-FAP tumor targeting moiety (e.g., an anti-FAP Fab) and hyaluronidase 1 (or functional variant thereof).

In one embodiment, the multispecific molecule comprises an anti-FAP tumor targeting moiety (e.g., an anti-FAP Fab), IL-2 (or functional variant thereof), and hyaluronidase 1 (or functional variant thereof).

In one embodiment, the multispecific molecule comprises an anti-FAP tumor targeting moiety (e.g., an anti-FAP Fab), an anti-PDL1 tumor targeting moiety (e.g., an anti-PDL1 Fab), IL-2 (or functional variant thereof), and hyaluronidase 1 (or functional variant thereof).

In one embodiment, the multispecific molecule comprises an anti-FAP tumor targeting moiety (e.g., an anti-FAP Fab), an anti-PDL1 tumor targeting moiety (e.g., an anti-PDL1 Fab), and hyaluronidase 1 (or functional variant thereof).

In one embodiment, the multispecific molecule comprises an anti-PDL1 tumor targeting moiety (e.g., an anti-PDL1 Fab), an anti-NKp46 NK cell engager moiety (e.g., an anti-NKp46 Fab or scFv), IL-2 (or functional variant thereof), and hyaluronidase 1 (or functional variant thereof).

In one embodiment, the multispecific molecule comprises an anti-FAP tumor targeting moiety (e.g., an anti-FAP Fab) and gelatinase (or functional variant thereof).

In one embodiment, the multispecific molecule comprises an anti-FAP tumor targeting moiety (e.g., an anti-FAP Fab), an anti-PDL1 tumor targeting moiety (e.g., an anti-PDL1 Fab), IL-2 (or functional variant thereof), and gelatinase (or functional variant thereof).

In another aspect, the disclosure provides an isolated nucleic acid molecule encoding any multispecific or multifunctional molecule polypeptide described herein.

In another aspect, the disclosure provides an isolated nucleic acid molecule, which comprises the nucleotide sequence encoding any of the multispecific or multifunctional molecules described herein, or a nucleotide sequence substantially homologous thereto (e.g., at least 95% to 99.9% identical thereto).

In another aspect, the disclosure provides a vector, e.g., an expression vector, comprising one or more of any nucleic acid molecules described herein.

In another aspect, the disclosure provides a host cell comprising a nucleic acid molecule or a vector described herein.

In another aspect, the disclosure provides a method of making, e.g., producing, a multispecific or multifunctional molecule polypeptide described herein, comprising culturing a host cell described herein, under suitable conditions, e.g., conditions suitable for gene expression and/or homo- or heterodimerization.

In another aspect, the disclosure provides an pharmaceutical composition comprising a multispecific or multifunctional molecule polypeptide described herein and a pharmaceutically acceptable carrier, excipient, or stabilizer.

In another aspect, the disclosure provides a method of treating a cancer, comprising administering to a subject in need thereof a multispecific or multifunctional molecule polypeptide described herein, wherein the multispecific antibody is administered in an amount effective to treat the cancer.

In some embodiments, the cancer is a solid tumor cancer, or a metastatic lesion. In some embodiments, the solid tumor cancer is one or more of pancreatic (e.g., pancreatic adenocarcinoma), breast, colorectal, lung (e.g., small or non-small cell lung cancer), skin, ovarian, or liver cancer. In some embodiments, the cancer is a hematological cancer.

In some embodiments, the method further comprises administering a second therapeutic treatment. In some embodiments, second therapeutic treatment comprises a therapeutic agent (e.g., a chemotherapeutic agent, a biologic agent, hormonal therapy), radiation, or surgery. In some embodiments, therapeutic agent is selected from: a chemotherapeutic agent, or a biologic agent.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

Figures 1A, 1B, 1C:
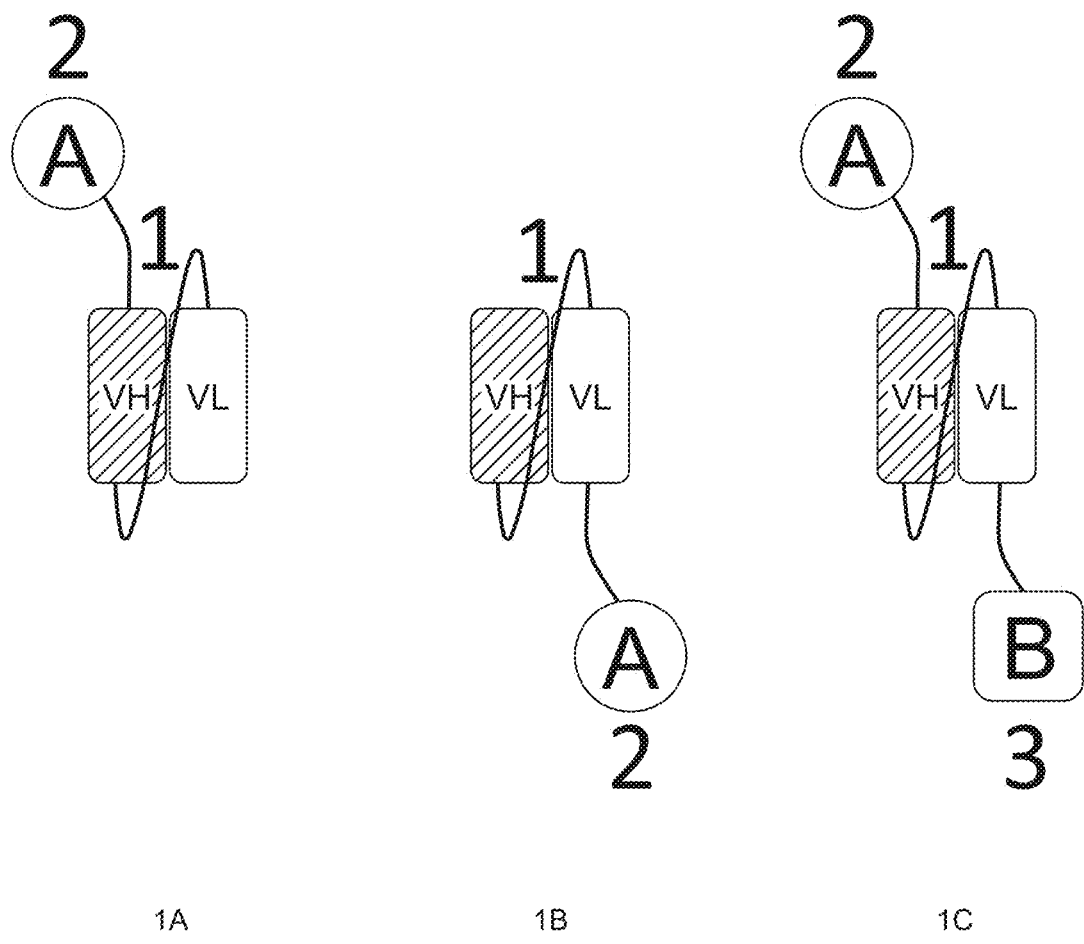
FIGS. 1A-1C depict schematic representations of multispecific molecules that include a single polypeptide chain, e.g., a scFv-based format. The bispecific and trispecific molecules can include a scFv core. Partner A can be connected to the N-terminal end of the VH or the C-terminal end of the VL (FIG. 1A or FIG. 1B, respectively), optionally connected by a linker, wherein partner A corresponds to binding moiety 2 in the bispecific format. Partner A can be an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, binding moiety 1 and binding moiety 2 can each be independently chosen from a tumor targeting moiety, a cytokine molecule, a T cell engager, an NK cell engager, a B cell engager, a dendritic cell engager, or a macrophage cell engager. In some embodiments, binding moiety 1 is a tumor targeting moiety as described herein, e.g., a scFv that binds to a cancer antigen; and partner A, corresponding to binding moiety 2, can be chosen from a cytokine molecule, a T cell engager, an NK cell engager, a B cell engager, a dendritic cell engager, or a macrophage cell engager, e.g., as described herein.

In embodiments of a trispecific format, partners A and B are connected, e.g., via a linker, to the scFv as binding moieties 2 and 3, respectively (FIG. 1C). Partner A and partner B can be, independently, an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, binding moiety 1, binding moiety 2 and binding moiety 3 can each be independently chosen from a tumor targeting moiety, a cytokine molecule, a T cell engager, an NK cell engager, a B cell engager, a dendritic cell engager, or a macrophage cell engager. In some embodiments, binding moiety 1 is a tumor targeting moiety as described herein, e.g., a scFv that binds to a cancer antigen; and partners A and B are each independently chosen from a cytokine molecule, a T cell engager, an NK cell engager, a B cell engager, a dendritic cell engager, or a macrophage cell engager, e.g., as described herein.

Partner A can be a stromal modifying moiety, e.g., as described herein. In some embodiments, binding moiety 1 is a tumor targeting moiety and binding moiety 2 is a stromal modifying moiety. In some embodiments, binding moiety 1 is a tumor targeting moiety as described herein, e.g., a scFv that binds to a cancer antigen; and partner A, corresponding to binding moiety 2, is a stromal modifying moiety, e.g., as described herein. In embodiments of a trispecific format, partners A and B are connected, e.g., via a linker, to the scFv as binding moieties 2 and 3, respectively (FIG. 1C). The trispecific molecule adds fusion partner B, binding moiety 3, which may be a cytokine molecule, a T cell engager, an NK cell engager, a B cell engager, a dendritic cell engager, or a macrophage cell engager. Fusion partners A and B may be on the heavy chain and light chain of the Fab or the light chain and heavy chain of the scFv, respectively. In some embodiments, Partner A is a stromal modifying moiety, e.g., as described herein. In some embodiments, binding moiety 1 is a tumor targeting moiety and binding moiety 2 is a stromal modifying moiety.

Figures 2A, 2B, 2C:
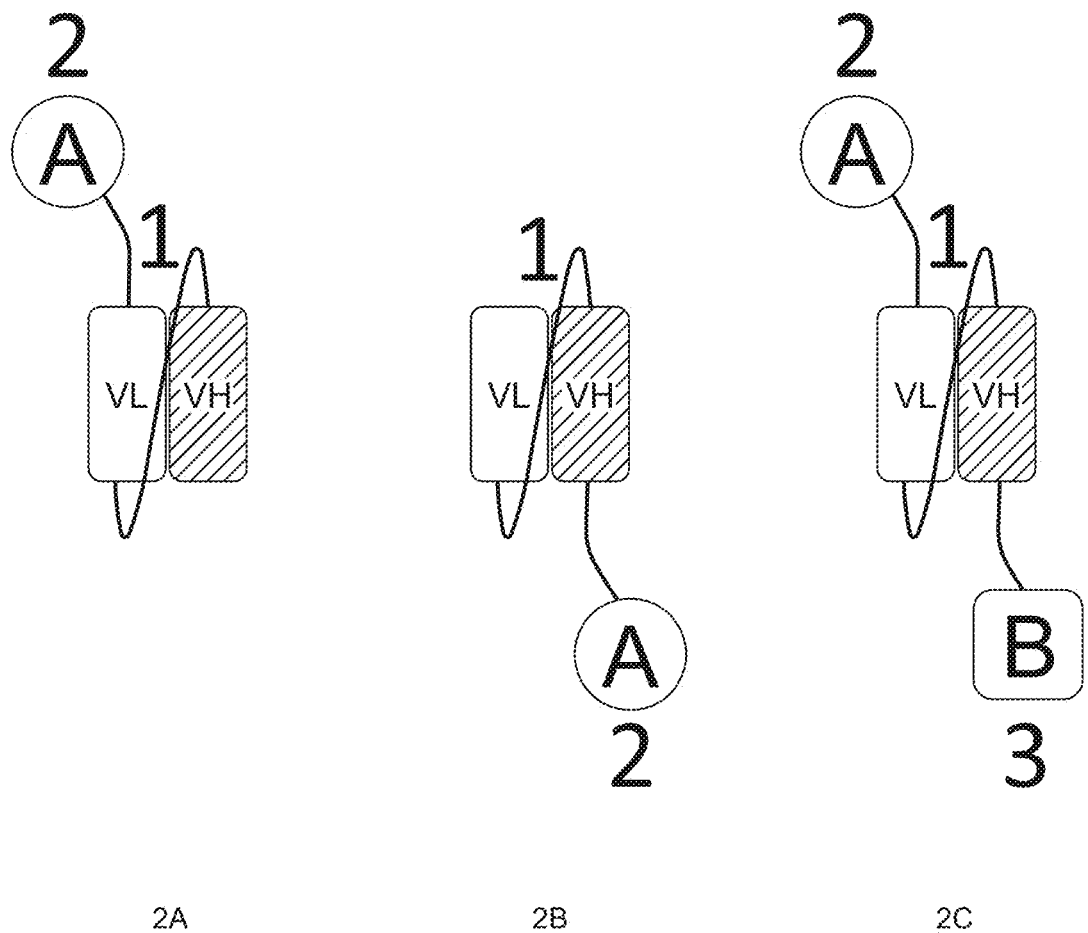

FIGS. 2A-2C depict schematic representations of multi-specific molecules that include a single polypeptide chain, e.g., a scFv-based format. The bispecific and trispecific molecules can include a scFv core. Partner A can be connected to the C terminal end of the VH or the N terminal end of the VL (FIG. 2A or FIG. 2B, respectively), optionally connected by a linker, wherein partner A corresponds to binding moiety 2 in the bispecific format. Partner A can be an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, binding moiety 1 is a tumor targeting moiety as described herein, e.g., a scFv that binds to a cancer antigen; and partner A, corresponding to binding moiety 2, is chosen from a cytokine, a T cell engager, an NK cell engager, a B cell engager, a dendritic cell engager, or a macrophage cell engager, e.g., as described herein. In some embodiments, binding moiety 1 and binding moiety 2 can each be independently chosen from a tumor targeting moiety, a cytokine molecule, a T cell engager, an NK cell engager, a B cell engager, a dendritic cell engager, or a macrophage cell engager.

In embodiments of a trispecific format, partners A and B are connected, e.g., via a linker, to the scFv as binding moieties 2 and 3, respectively (FIG. 1C). Partner A and partner B can be, independently, an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, binding moiety 1, binding moiety 2 and binding moiety 3 can each be independently chosen from a tumor targeting moiety, a cytokine molecule, a T cell engager, an NK cell engager, a B cell engager, a dendritic cell engager, or a macrophage cell engager. In some embodiments, binding moiety 1 is a tumor targeting moiety as described herein, e.g., a scFv that binds to a cancer antigen; and partners A and B are each independently chosen from a cytokine molecule, a T cell engager, an NK cell engager, a B cell engager, a dendritic cell engager, or a macrophage cell engager, e.g., as described herein.

Partner A can be connected to the C terminal end of the VH or the N terminal end of the VL (FIG. 2A or FIG. 2B, respectively), optionally connected by a linker, wherein partner A corresponds to binding moiety 2 in the bispecific format. In some embodiments, binding moiety 1 is a tumor targeting moiety and binding moiety 2 is a stromal modifying moiety. In some embodiments, binding moiety 1 is a tumor targeting moiety as described herein, e.g., a scFv that binds to a cancer antigen; and partner A, corresponding to binding moiety 2, is a stromal modifying moiety, e.g., as described herein. In embodiments of a trispecific format, partners A and B are connected, e.g., via a linker, to the scFv as binding moieties 2 and 3, respectively (FIG. 2C). The trispecific molecule adds fusion partner B, binding moiety 3, which may be a cytokine molecule, a T cell engager, an NK cell engager, a B cell engager, a dendritic cell engager, or a macrophage cell engager. Fusion partners A and B may be on the heavy chain and light chain of the Fab or the light chain and heavy chain of the scFv respectively. In some embodiments, Partner A is a stromal modifying moiety, e.g., as described herein. In some embodiments, binding moiety 1 is a tumor targeting moiety and binding moiety 2 is a stromal modifying moiety.

Figures 3A, 3B, 3C:
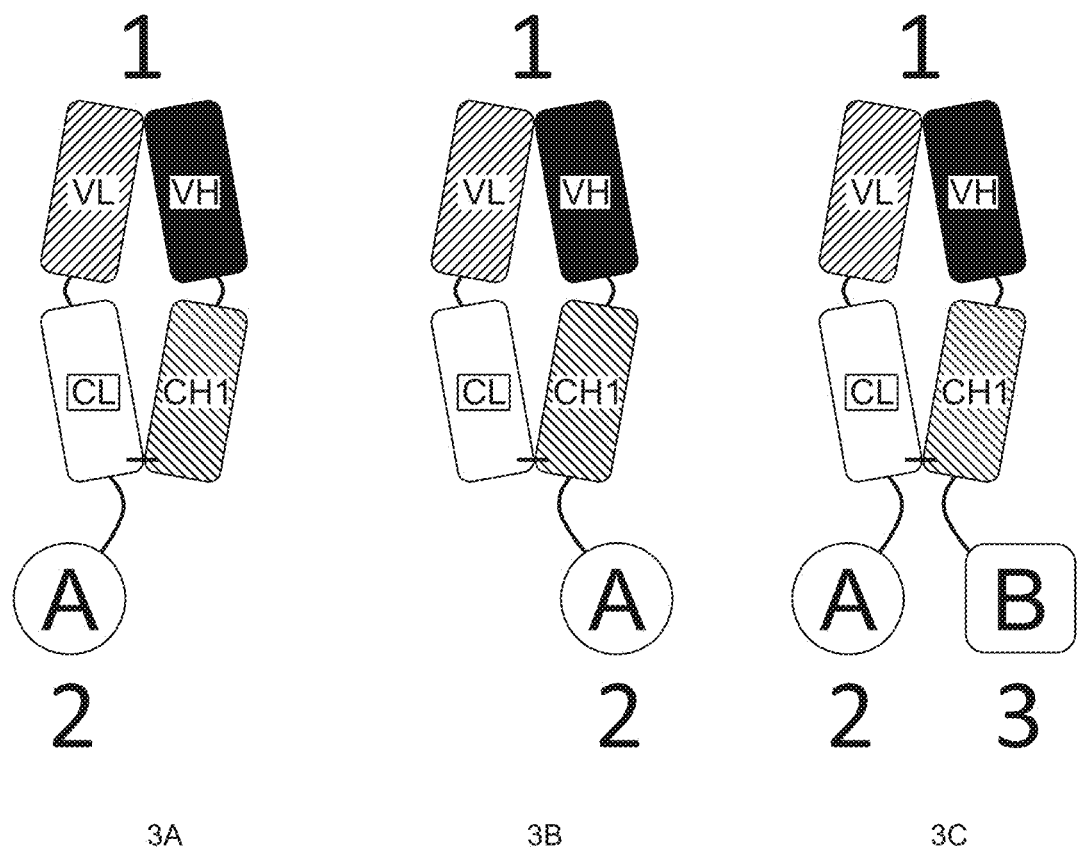

FIGS. 3A-3C depict schematic representations of multi-specific molecules that include a first and second polypeptide chains, e.g., an Fab-based format with a C-terminal fusion. The bispecific and trispecific molecules can include a Fab core. The VH and VL of the Fab can function as binding moiety 1 of the molecule. Partner A can be connected to the C-terminal end of either CL or CH1 (FIG. 3A or FIG. 3B, respectively), optionally connected by a linker, wherein partner A corresponds to binding moiety 2 in the bispecific format. Partner A can be an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, binding moiety 1 and binding moiety 2 can each be independently chosen from a tumor targeting moiety, a cytokine molecule, a T cell engager, an NK cell engager, a B cell engager, a dendritic cell engager, or a macrophage cell engager. In some embodiments, binding moiety 1 is a tumor targeting moiety as described herein, e.g., a Fab that binds to a cancer antigen; and partner A, corresponding to binding moiety 2, is chosen from a cytokine, a T cell engager, an NK cell engager, a B cell engager, a dendritic cell engager, or a macrophage cell engager, e.g., as described herein.

In embodiments of a trispecific format, partners A and B are connected, e.g., via a linker, to the C-terminus of the Fab as binding moieties 2 and 3, respectively (FIG. 3C). Partner A and partner B can each be, independently, an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, binding moiety 1, binding moiety 2 and binding moiety 3 can each be independently chosen from a tumor targeting moiety, a cytokine molecule, an NK cell engager, a B cell engager, a dendritic cell engager, or a macrophage cell engager. In some embodiments, binding moiety 1 is a tumor targeting moiety as described herein, e.g., a scFv that binds to a cancer antigen; and partners A and B are each independently chosen from a cytokine molecule, a T cell engager, an NK cell engager, a B cell engager, a dendritic cell engager, or a macrophage cell engager, e.g., as described herein.

The VH and VL of the Fab function as binding moiety 1 of the molecule. Fusion partner A, which can be fused to the C-terminal end of either CL or CH1 (FIG. 3A and FIG. 3B, respectively) connected by a linker, is binding moiety 2 in the bispecific format. In some embodiments of the bispecific format, binding moiety 1 is tumor targeting Fab and fusion partner A, binding moiety 2, is a stromal modifying molecule. The trispecific format can have fusion partners A and B on the C-terminus of the Fab as binding moieties 2 and 3 respectively (FIG. 3C). The trispecific molecule adds fusion partner B, binding moiety 3, which may be a cytokine molecule, a T cell engager, an NK cell engager, a B cell engager, a dendritic cell engager, or a macrophage cell engager. Fusion partners A and B may be on the heavy chain and light chain of the Fab or the light chain and heavy chain of the Fab respectively.

Figures 4A, 4B, 4C:
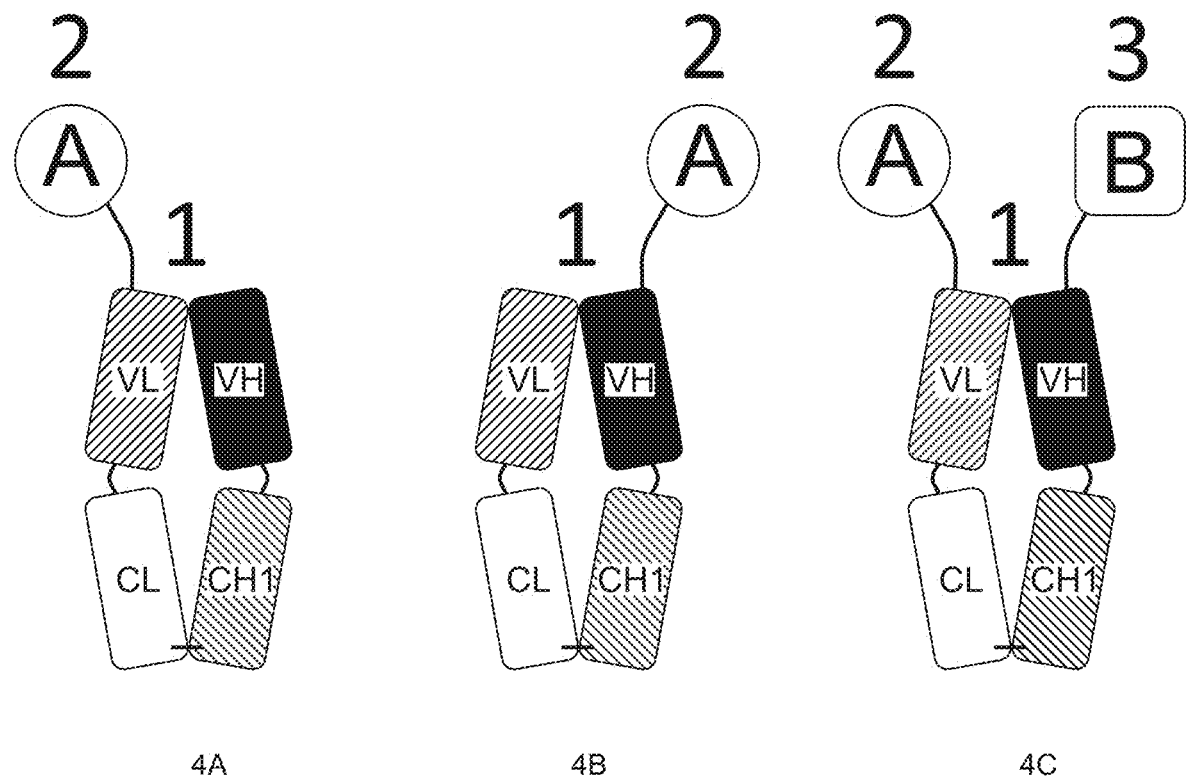

FIGS. 4A-4C depict schematic representations of multi-specific molecules that include a first and second polypeptide chains, e.g., an Fab-based format with an N-terminal fusion. The bispecific and trispecific molecules depicted include a Fab core. The VH and VL of the Fab can function as binding moiety 1 of the molecule. Partner A can be connected to the N-terminal end of either VL or VH (FIG. 4A or FIG. 4B, respectively), optionally connected by a linker, wherein partner A corresponds to binding moiety 2 in the bispecific format. Partner A can be an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, binding moiety 1 and binding moiety 2 can each be independently chosen from a tumor targeting moiety, a cytokine molecule, a T cell engager, an NK cell engager, a B cell engager, a dendritic cell engager, or a macrophage cell engager. In some embodiments, binding moiety 1 is a tumor targeting moiety as described herein, e.g., a Fab that binds to a cancer antigen; and partner A, corresponding to binding moiety 2, is chosen from a cytokine, a T cell engager, an NK cell engager, a B cell engager, a dendritic cell engager, or a macrophage cell engager, e.g., as described herein.

In embodiments of a trispecific format, partners A and B are connected, e.g., via a linker, to the N-terminus of the Fab as binding moieties 2 and 3, respectively (FIG. 4C). Partner A and partner B can be, independently, an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, binding moiety 1, binding moiety 2 and binding moiety 3 can each be independently chosen from a tumor targeting moiety, a cytokine molecule, a T cell engager, an NK cell engager, a B cell engager, a dendritic cell engager, or a macrophage cell engager. In some embodiments, binding moiety 1 is a tumor targeting moiety as described herein, e.g., a Fab that binds to a cancer antigen; and partner A and partner B, corresponding to binding moiety 2 and binding moiety 3, are each independently chosen from a cytokine, a T cell engager, an NK cell engager, a B cell engager, a dendritic cell engager, or a macrophage cell engager, e.g., as described herein.

The bispecific and trispecific molecules can include a Fab core. The VH and VL of the Fab can function as binding moiety 1 of the molecule. Fusion partner A, which can be fused to the N-terminal end of either CL or CH1 (FIG. 4A and FIG. 4B, respectively) connected by a linker, is binding moiety 2 in the bispecific format. In embodiments of the bispecific format, binding moiety 1 is tumor targeting Fab and fusion partner A, binding moiety 2, is a stromal modifying molecule. In embodiments, the trispecific format has fusion partners A and B on the C-terminus of the Fab as binding moieties 2 and 3 respectively (FIG. 4C). The trispecific molecule adds fusion partner B, binding moiety 3, which may be a cytokine molecule, a T cell engager, an NK cell engager, a B cell engager, a dendritic cell engager, or a macrophage cell engager. Fusion partners A and B may be on the heavy chain and light chain of the Fab or the light chain and heavy chain of the Fab respectively.

Figures 5A, 5B, 5C:
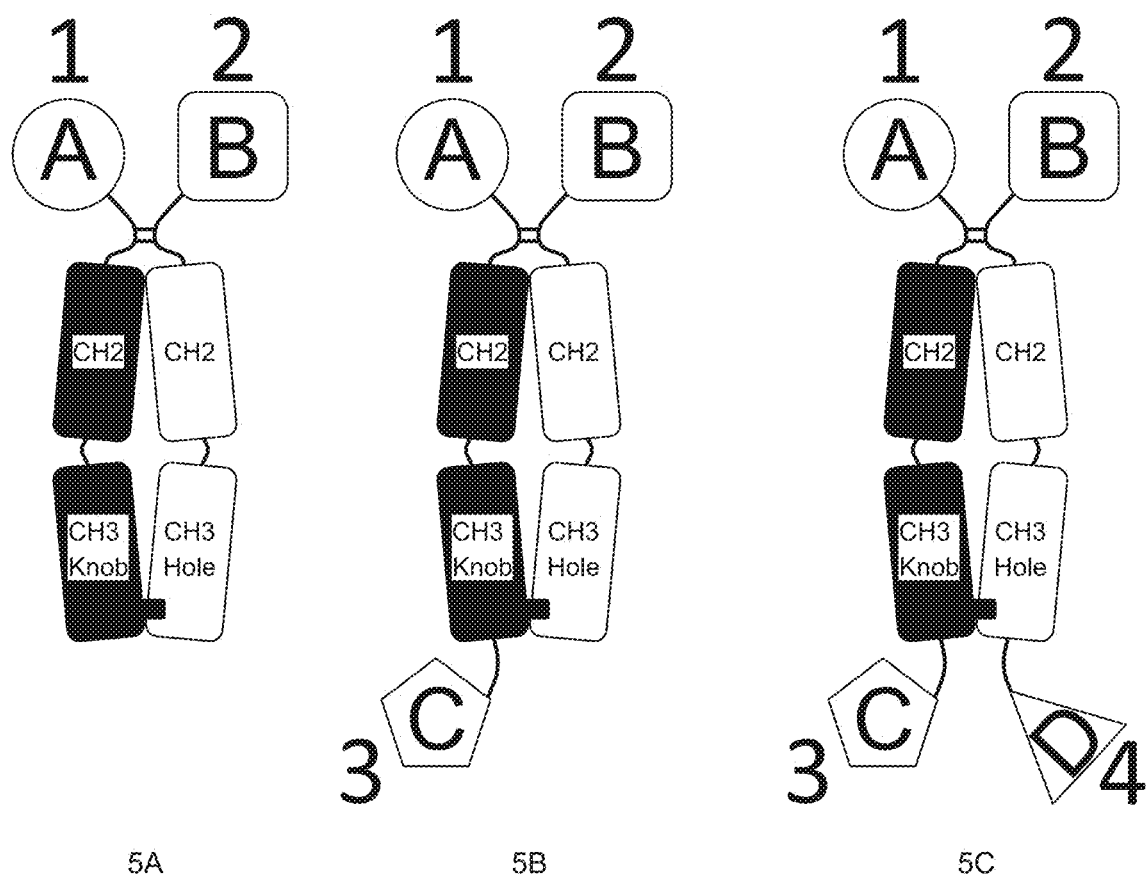

FIGS. 5A-5C depict schematic representations of multispecific molecules that include a first and a second polypeptide chains, e.g., an Fc-based format. In the embodiments shown, the multispecific molecules include a heterodimeric Fc core (knob-in-hole (KiH)). The bispecific molecule can have partner A and B, which are depicted as binding moieties 1 and 2, respectively (FIG. 5A). Partner A and partner B can be, each independently, an antibody molecule (e.g., a single chain antibody molecule (e.g., a scFv) or a Fab), a receptor molecule, a ligand molecule (e.g., a receptor ligand or a cytokine molecule), e.g., as described herein. Partner A and partner B may be connected to either first or second member, or each of the members, of the heterodimeric Fc core. In one embodiment, partner A is connected to the N-terminal end of a -CH2-CH3-region of the first Fc molecule, and partner B is connected to the N-terminal end of a -CH2-CH3-region of the second Fc molecule. Alternatively, partner A is connected to the C-terminal end of a -CH2-CH3-region of the first Fc molecule, and partner B is connected to the C-terminal end of a -CH2-CH3-region of the second Fc molecule. Alternatively, partner A may be connected to N-terminus of the first member of the heterodimeric Fc core, and partner B may be connected to C-terminus of the second member of the heterodimeric Fc core. In other embodiments, partner B may be connected to N-terminus of the first member of the heterodimeric Fc core, and Partner A may be connected to C-terminus of the second member of the heterodimeric Fc core. In some embodiments, binding moiety 1 and binding moiety 2 can each be independently chosen from a tumor targeting moiety, a cytokine molecule, a T cell engager, an NK cell engager, a B cell engager, a dendritic cell engager, or a macrophage cell engager. In some embodiments, binding moiety 1 is a tumor targeting moiety and binding moiety 2 is chosen from a cytokine molecule, a T cell engager, an NK cell engager, a B cell engager, a dendritic cell engager, or a macrophage cell engager.

Exemplary trispecific and tetraspecific molecules are depicted in FIGS. 5B and 5C, respectively. One or two additional partners C and D, respectively, which may be single or multiple binding moieties 3 and 4, can be added to the aforesaid molecules. Partner A, partner B, partner C and partner D can each be, independently, an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, partner C and partner D can be added to the C-terminus of either the first and second member of the Fc core, thus forming binding specificities 3 and 4, respectively. In some embodiments, Partners A-D (corresponding to binding specificities 1-4, respectively) are each independently chosen from a tumor targeting moiety, a cytokine molecule, a T cell engager, an NK cell engager, a B cell engager, a dendritic cell engager, or a macrophage cell engager, e.g., as described herein. In one embodiment, partner A. In embodiments, partner A is a tumor targeting moiety and partner B, partners C and D are each independently chosen from a cytokine molecule, a T cell engager, an NK cell engager, a B cell engager, a dendritic cell engager, or a macrophage cell engager.

The bispecific molecule can have partner A and B, which are depicted as binding moieties 1 and 2, respectively (FIG. 5A). Partner A and partner B can be, each independently, a stromal modifying moiety, an enzyme molecule, an antibody molecule (e.g., a single chain antibody molecule (e.g., a scFv) or a Fab), a receptor molecule, a ligand molecule (e.g., a receptor ligand or a cytokine molecule), e.g., as described herein. Partner A and partner B may be connected to either first or second member, or each of the members, of the heterodimeric Fc core. In one embodiment, partner A is connected to the N-terminal end of a -CH2-CH3-region of the first Fc molecule, and partner B is connected to the N-terminal end of a -CH2-CH3-region of the second Fc molecule. Alternatively, partner A is connected to the C-terminal end of a -CH2-CH3-region of the first Fc molecule, and partner B is connected to the C-terminal end of a -CH2-CH3-region of the second Fc molecule. Alternatively, partner A may be connected to N-terminus of the first member of the heterodimeric Fc core, and partner B may be connected to C-terminus of the second member of the heterodimeric Fc core. In other embodiments, partner B may be connected to N-terminus of the first member of the heterodimeric Fc core, and Partner A may be connected to C-terminus of the second member of the heterodimeric Fc core. In some embodiments, binding moiety 1 is a tumor targeting moiety and binding moiety 2 is a stromal modifying moiety. In other embodiments, binding moiety 2 is a tumor targeting moiety and binding moiety 1 is a stromal modifying moiety.

Exemplary trispecific and tetraspecific molecules are depicted in FIGS. 5B and 5C, respectively. One or two additional partners C and D, respectively, which may be single or multiple binding moieties 3 and 4, can be added to the aforesaid molecules. Partner A, partner B, partner C and partner D can each be, independently, an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, partner C and partner D can be added to the C-terminus of either the first and second member of the Fc core, thus forming binding specificities 3 and 4, respectively. In some embodiments, Partners A-D (corresponding to binding specificities 1-4, respectively) are each independently chosen from a tumor targeting moiety, a cytokine molecule, a T cell engager, an NK cell engager, a B cell engager, a dendritic cell engager, or a macrophage cell engager, or a stromal modifying moiety, e.g., as described herein. In some embodiment, one of partner A, B, C, or D is a stromal modifying moiety, one of partner A, B, C, or D is a tumor targeting moiety, and the two remaining partners are each independently chosen from a tumor targeting moiety, a cytokine molecule, a T cell engager, an NK cell engager, a B cell engager, a dendritic cell engager, or a macrophage cell engager.

Figure 6:
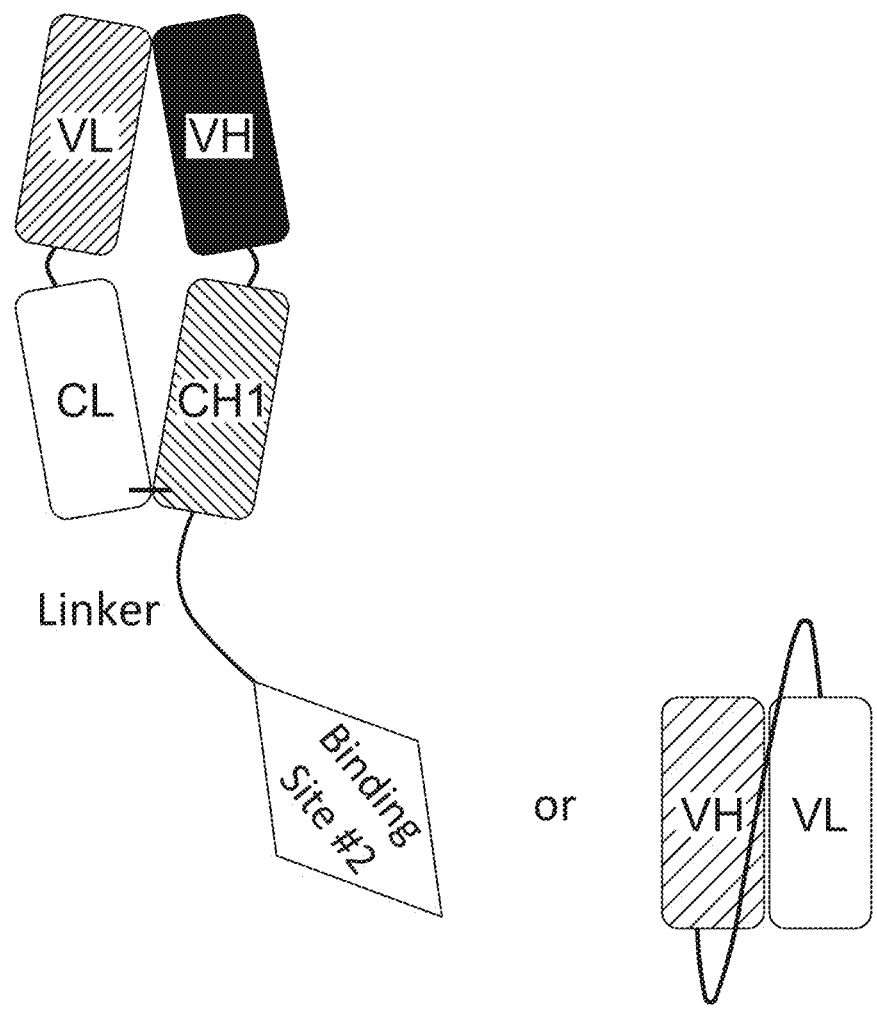

FIG. 6 depicts an exemplary schematic of a bispecific molecule that includes a Fab corresponding to binding site #1 fused to a binding site #2. In embodiments, binding site #1 is a tumor targeting moiety, e.g., binds to a cancer antigen, e.g., a tumor or stromal antigen; and binding site #2 is chosen from a cytokine molecule, or a ligand molecule or a scFv that is an immune cell engager, e.g., binds to an immune cell antigen. In embodiments, the bispecific molecule comprises two non-contiguous polypeptides, wherein the first polypeptide has the following configuration from N-to-C: VH-CH1 of the Fab that binds to, e.g., a tumor or stromal antigen, fused optionally, via a linker to, the binding site #2; and the second polypeptide has the following configuration from N-to-C: VL-CL of the Fab that binds to, e.g., a tumor or stromal antigen.

Figure 7:
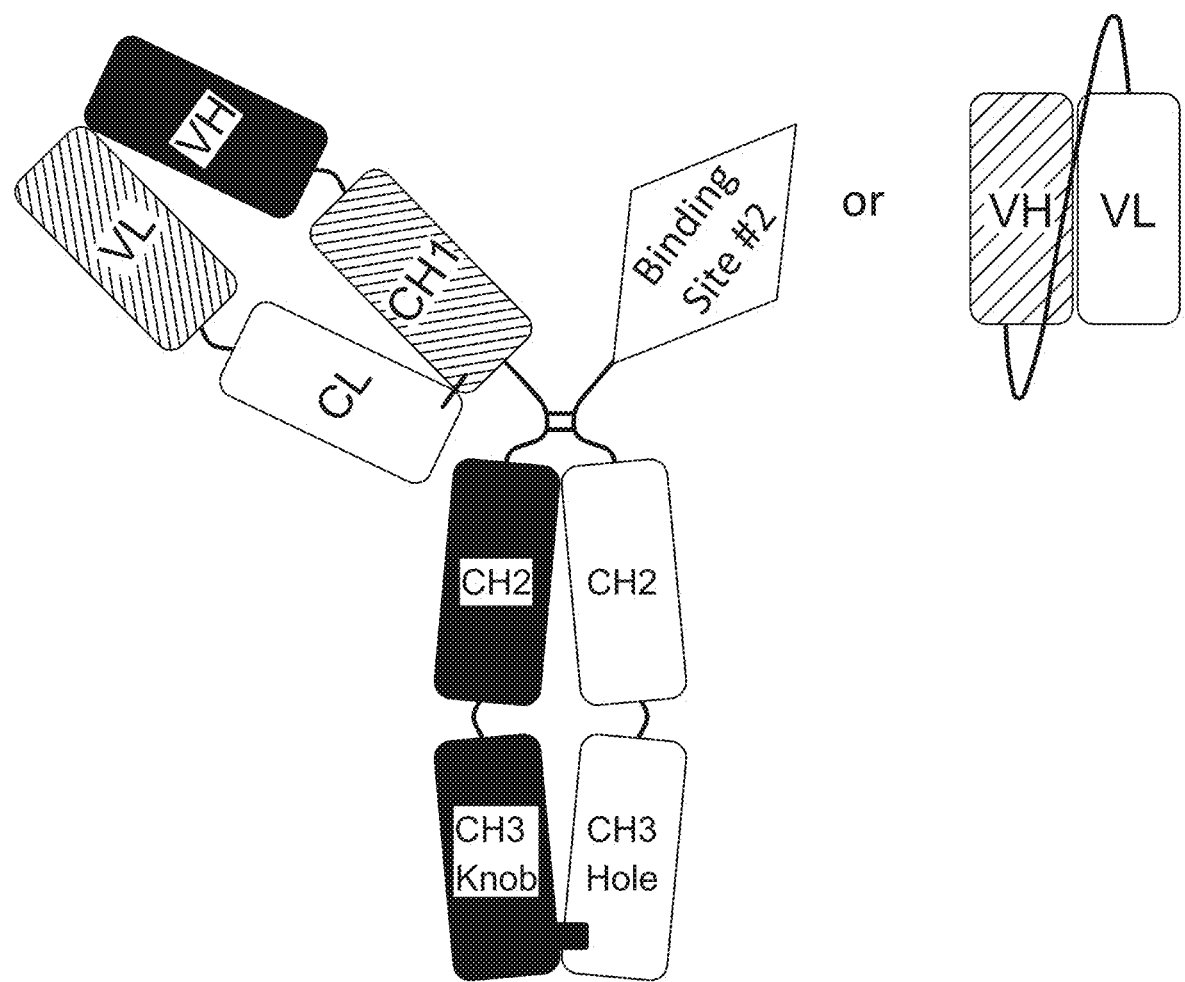

FIG. 7 depicts an exemplary schematic of a bispecific molecule that includes a Fab corresponding to binding site #1 connected, optionally via a liker, to a first member of an immunoglobulin constant region, e.g., a first Fc molecule; and a binding site #2 connected, optionally via a liker, to a second member of the Fc molecule. In embodiments, binding site #1 is a tumor targeting moiety, e.g., binds to a tumor or stromal antigen; and binding site #2 is chosen from a cytokine molecule, or an immune cell engager, e.g., a ligand molecule, or a scFv that binds to an immune cell antigen. In embodiments, the bispecific molecule comprises three non-contiguous polypeptides, wherein the first polypeptide has the following configuration from N-to-C: VH-CH1 of the Fab that binds to, e.g., a tumor or stromal antigen, optionally connected via a linker to, the first member of the Fc molecule (e.g., a first CH2-CH3 region, optionally, comprising a protuberance or knob); the second polypeptide has the following configuration from N-to-C: VL-CL of the Fab that binds to, e.g., a tumor or stromal antigen; and the third polypeptide has the following configuration from N-to-C: binding site #2 (e.g., a cytokine molecule, a ligand molecule, or a scFv that binds to, e.g., an immune cell antigen), connected, optionally, via a linker to, the second member of the Fc molecule (e.g., a second CH2-CH3 region, optionally, comprising a hole or cavity). In embodiments, the first and second members of the Fc molecule promote heterodimerization of the bispecific molecule.

Figure 8A:
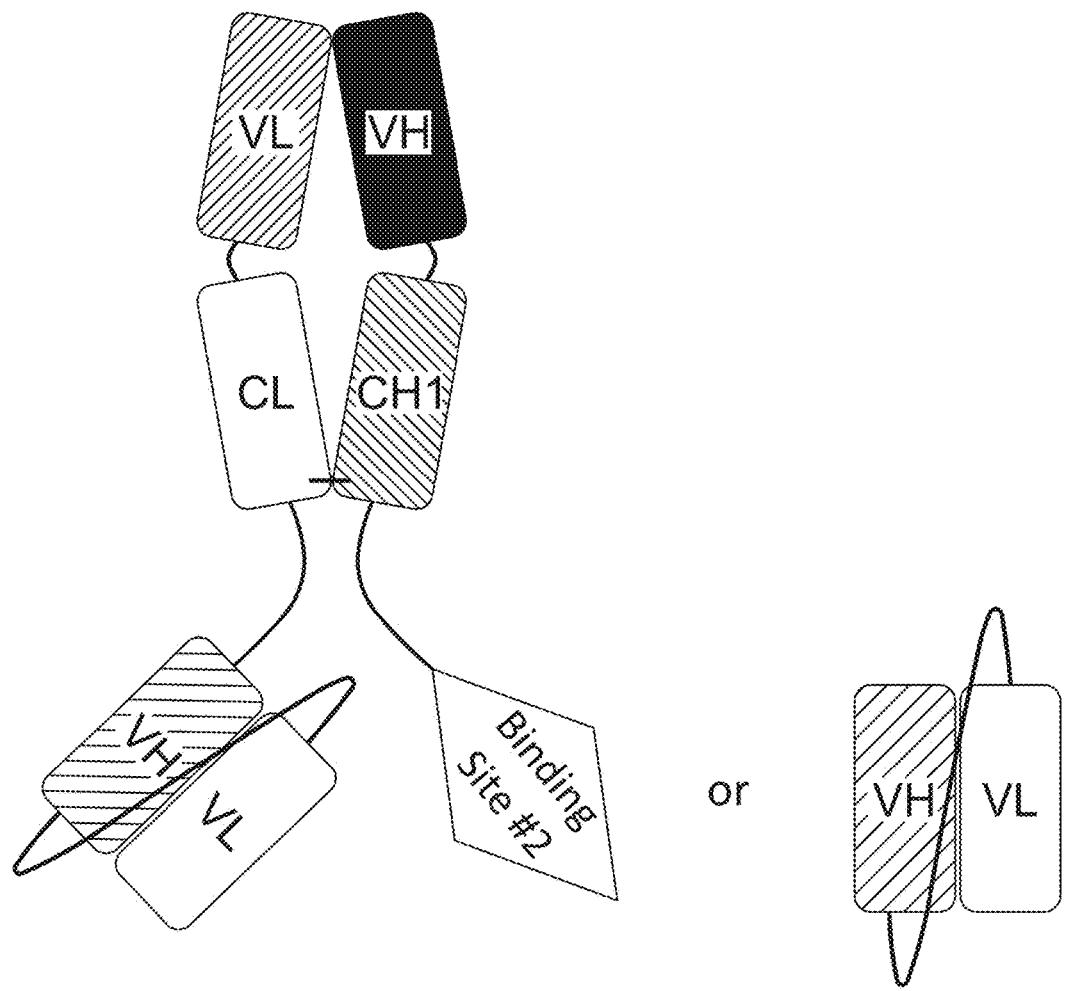
Figure 8B:
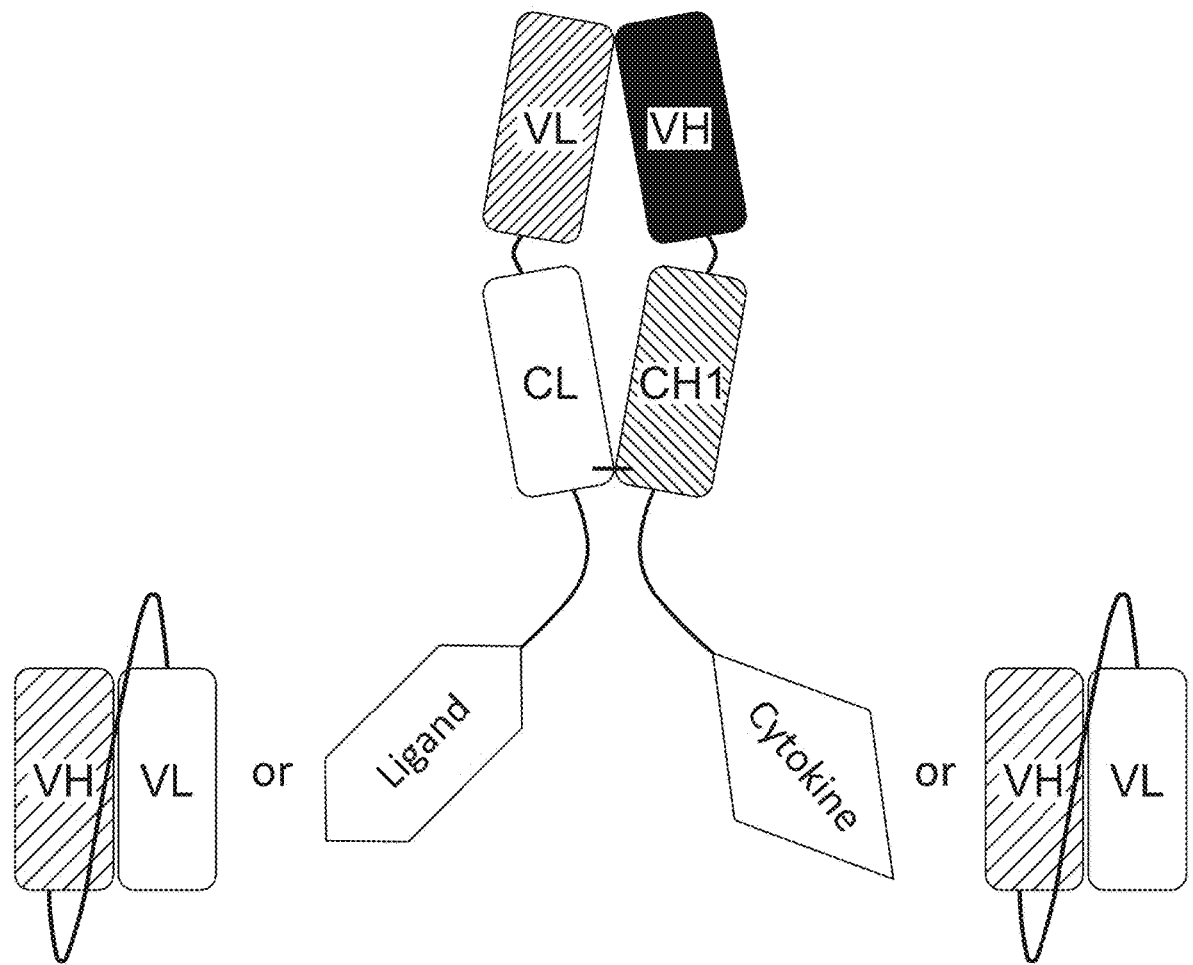
Figure 8C:
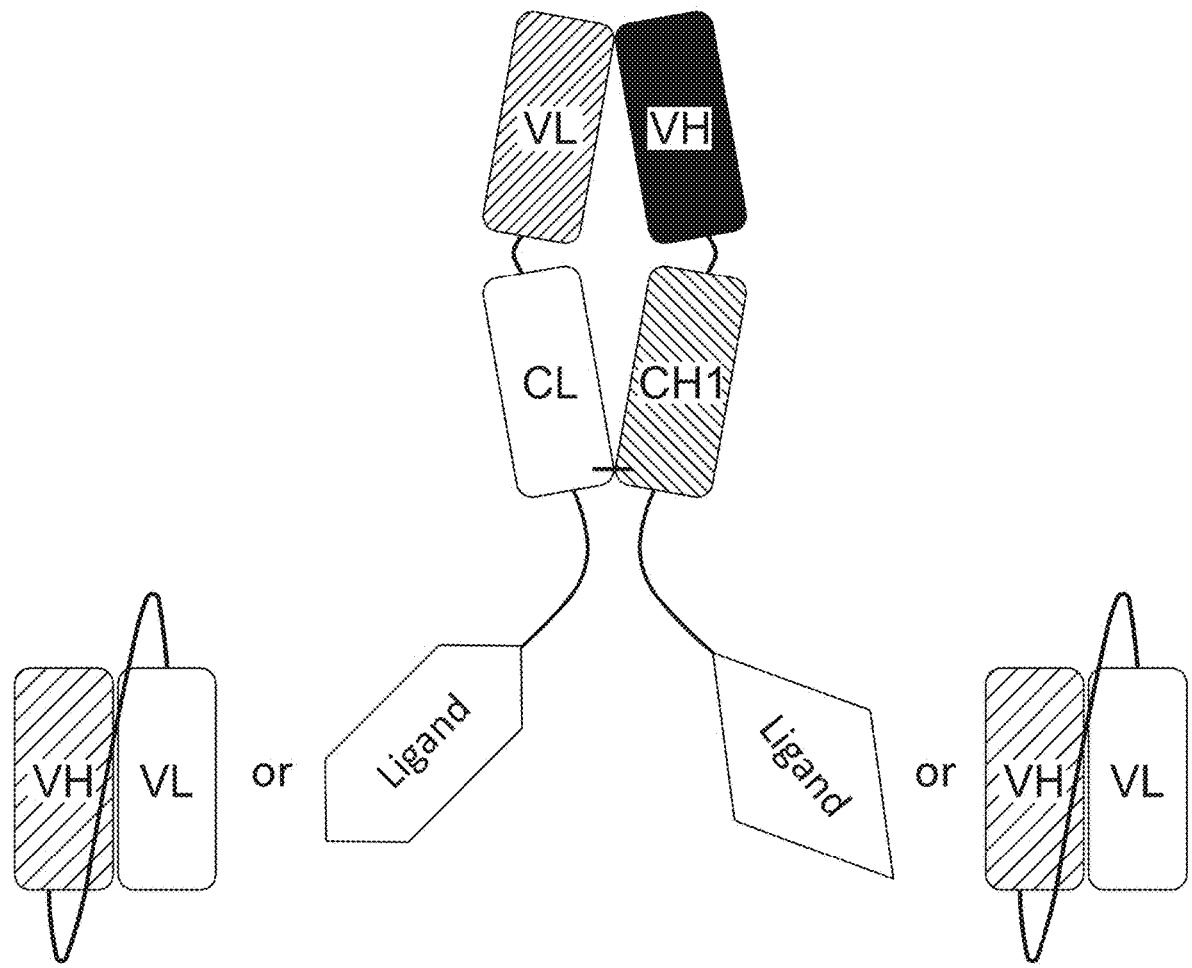

FIGS. 8A-8C depict exemplary schematics of a trispecific molecule that includes a Fab corresponding to binding site #1 fused to a binding site #2 and a binding site #3. In embodiments, binding site #1 is a tumor targeting moiety, e.g., binds to a tumor or stromal antigen; and binding sites #2 and #3 are independently chosen from a cytokine molecule, or an immune cell engager, e.g., a ligand molecule or a scFv that binds to an immune cell antigen. In embodiments, the trispecific molecule comprises two non-contiguous polypeptides in FIG. 8A, wherein the first polypeptide has the following configuration from N-to-C: VH-CH1 of the Fab that binds to, e.g., a tumor or stromal antigen, connected, optionally, via a linker to, the binding site #3 (e.g., chosen from a cytokine molecule, a ligand or a scFv); and the second polypeptide having the following configuration from N-to-C: VL-CL of the Fab that binds to, e.g., a tumor or stromal antigen, fused to a scFv (e.g., a VH-VL of the scFv from N-to-C) that binds to, e.g., an immune cell antigen. FIG. 8B depicts an alternative configuration, wherein the first polypeptide has the following configuration from N-to-C: VH-CH1 of the Fab that binds to, e.g., a tumor or stromal antigen, connected, optionally via a linker, to a cytokine molecule; and the second polypeptide has the following configuration from N-to-C: VL-CL of the Fab that binds to, e.g., a tumor or stromal antigen, connected to a ligand or a scFv (e.g., a ligand or a scFv that binds to, e.g., an immune cell). FIG. 8C depicts an alternative configuration, wherein the first polypeptide has the following configuration from N-to-C: VH-CH1 of the Fab that binds to, e.g., a tumor or stromal antigen, connected, optionally via a linker to, the ligand or the scFv that binds to, e.g., a first immune cell; and the second polypeptide has the following configuration from N-to-C: VL-CL of the Fab that binds to, e.g., a tumor or stromal antigen, connected, optionally via a linker to, to the ligand or the scFv that binds to, e.g., a second immune cell.

Figure 9A:
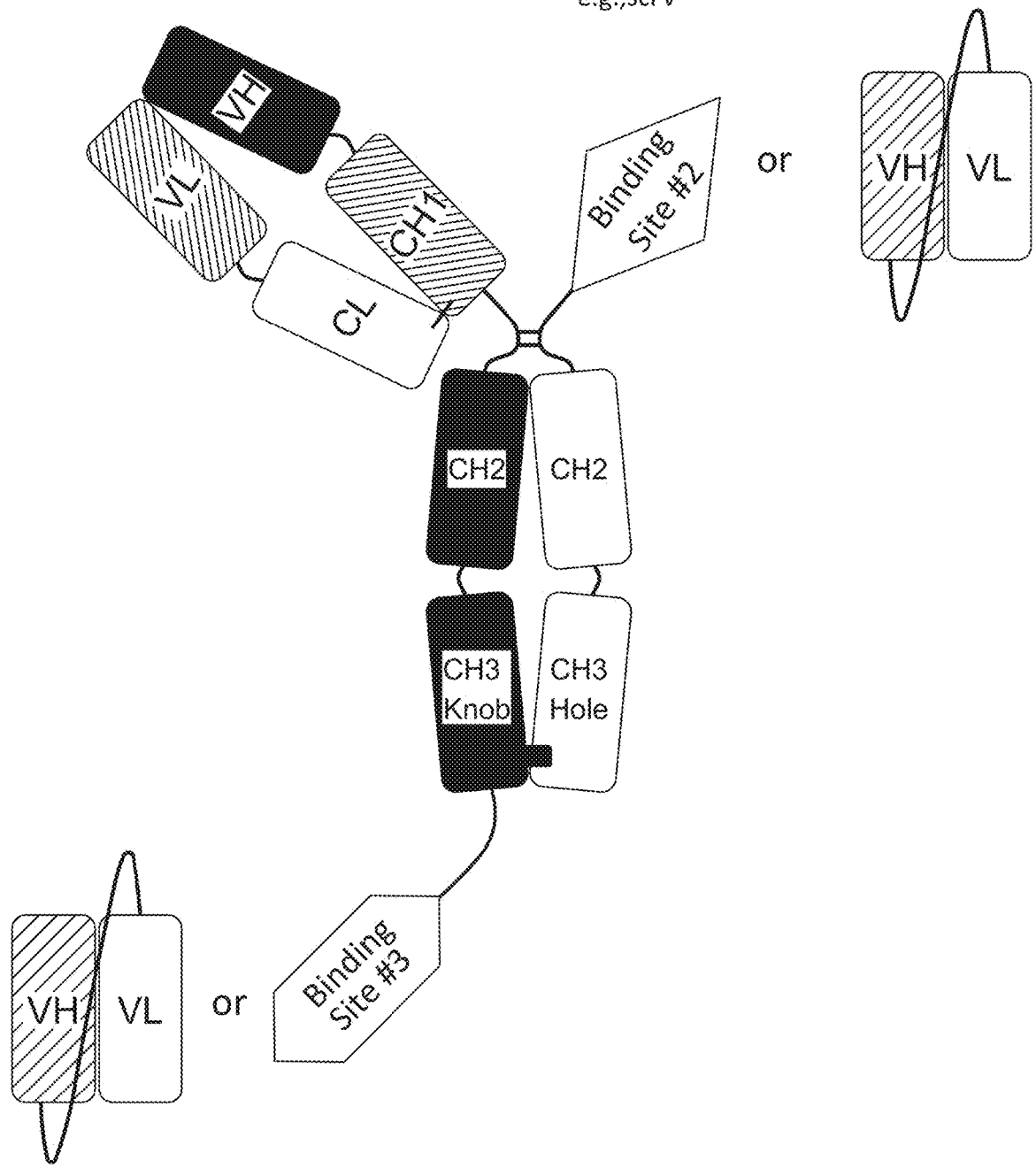
Figure 9B:
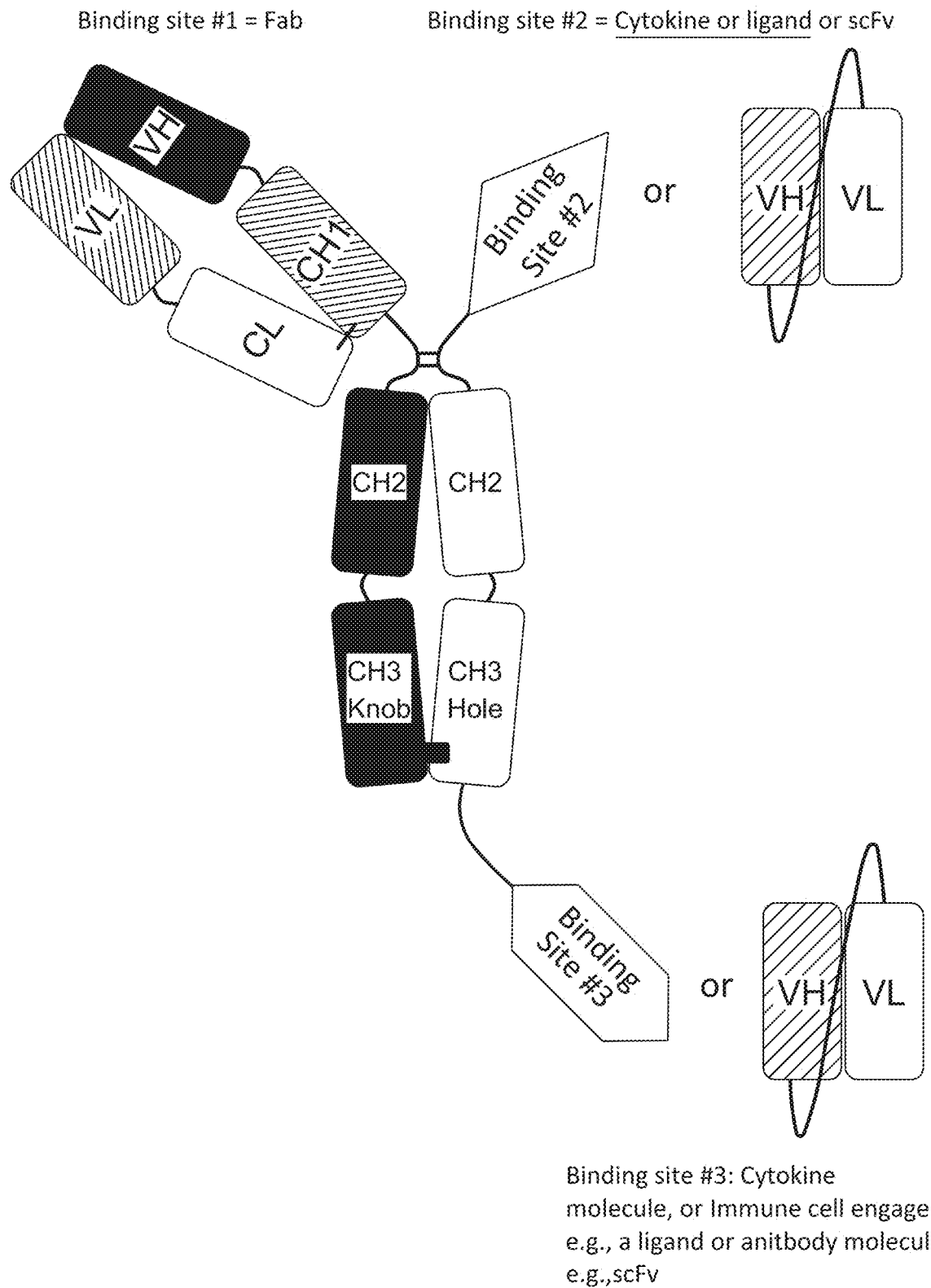

FIGS. 9A-9B depict exemplary schematics of a trispecific molecule that includes a Fab corresponding to binding site #1, a binding site #2, a binding site #3, each of which is connected, e.g., via a linker, to a first and second member of an immunoglobulin binding domain, e.g., first and second Fc molecule. In embodiments, the trispecific molecule comprises three non-contiguous polypeptides shown in FIGS. 9A-9B. In the embodiments shown in FIG. 9A, the first polypeptide has the following configuration from N-to-C: VH-CH1 of the Fab that binds to, e.g., a tumor or stromal antigen, connected, e.g., via a linker, to a first member of an Fc molecule (e.g., the N-terminus of the CH2-CH3 region of the first Fc molecule, optionally, comprising a protuberance or cavity), which first member can, optionally further include binding site #3 connected, optionally via a linker, to the C-terminus of the first Fc molecule; the second polypeptide includes from N-to-C orientation a binding site #2 connected, e.g., via a linker, to a second member of an Fc molecule (e.g., the N-terminus of the CH2-CH3 region of the second Fc molecule, optionally, comprising a protuberance or cavity); and the third polypeptide includes from N-to-C: the VL-CL of the Fab that binds to, e.g., a tumor or stromal antigen. In the embodiments shown in FIG. 9B, the first polypeptide has the following configuration from N-to-C: VH-CH1 of the Fab that binds to, e.g., a tumor or stromal antigen, connected, e.g., via a linker, to a first member of an Fc molecule (e.g., the N-terminus of the CH2-CH3 region of the first Fc molecule, optionally, comprising a protuberance or cavity); the second polypeptide includes from N-to-C orientation a binding site #2 connected, e.g., via a linker, to a second member of an Fc molecule (e.g., the N-terminus of the CH2-CH3 region of the second Fc molecule, optionally, comprising a protuberance or cavity) which second member can, optionally further include binding site #3 connected, optionally via a linker, to the C-terminus of the second Fc molecule); and the third polypeptide includes from N-to-C: the VL-CL of the Fab that binds to, e.g., a tumor or stromal antigen. In the aforesaid embodiments, binding site #1 binds to a tumor or stromal antigen; and binding sites #2 and #3 are independently chosen from a cytokine molecule, or an immune cell engager, e.g., a ligand molecule or a scFv that binds to an immune cell antigen. In embodiments, the first and second members of the Fc molecule promote heterodimerization of the trispecific molecule.

Figure 10A:
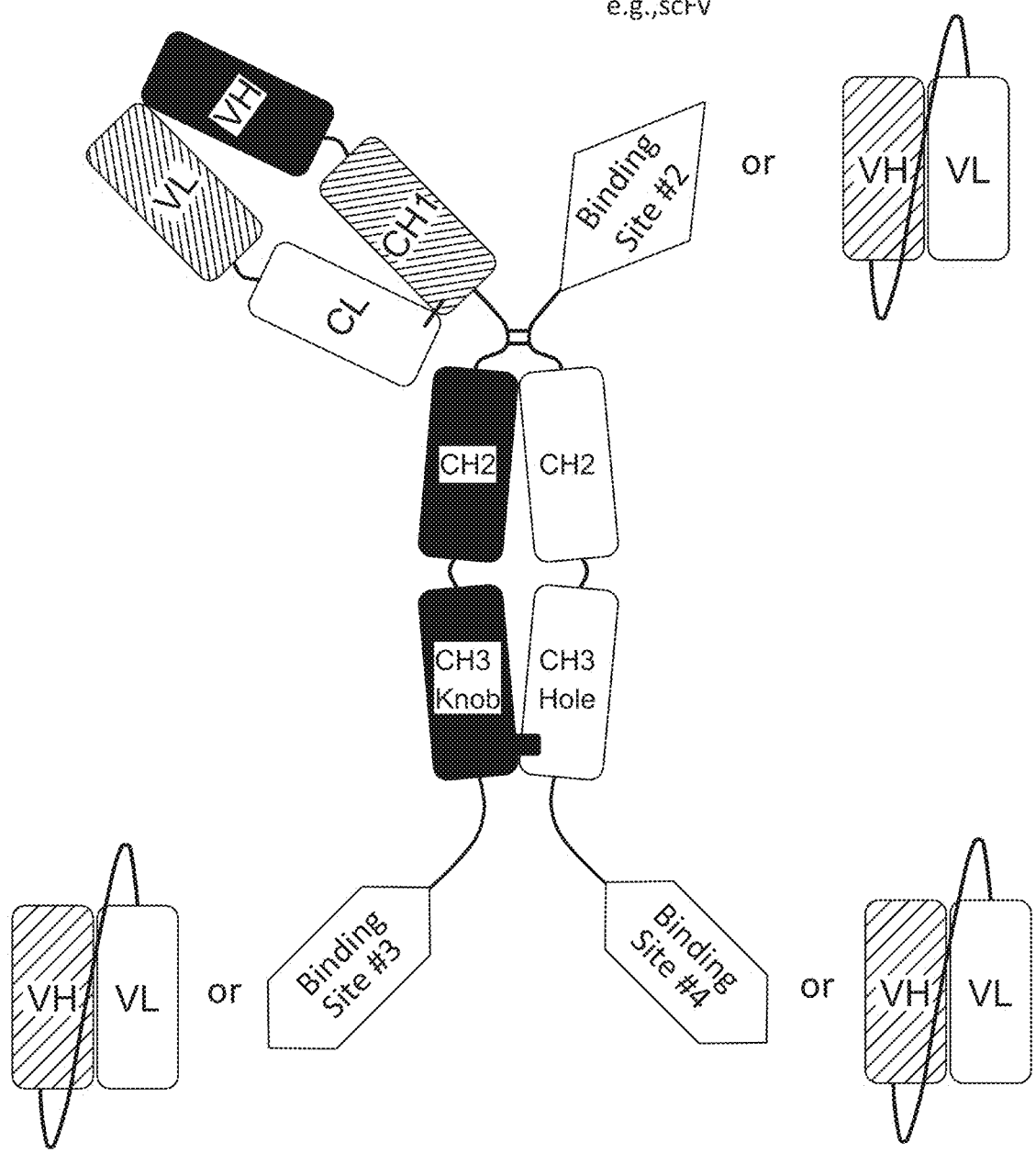
Figure 10B:
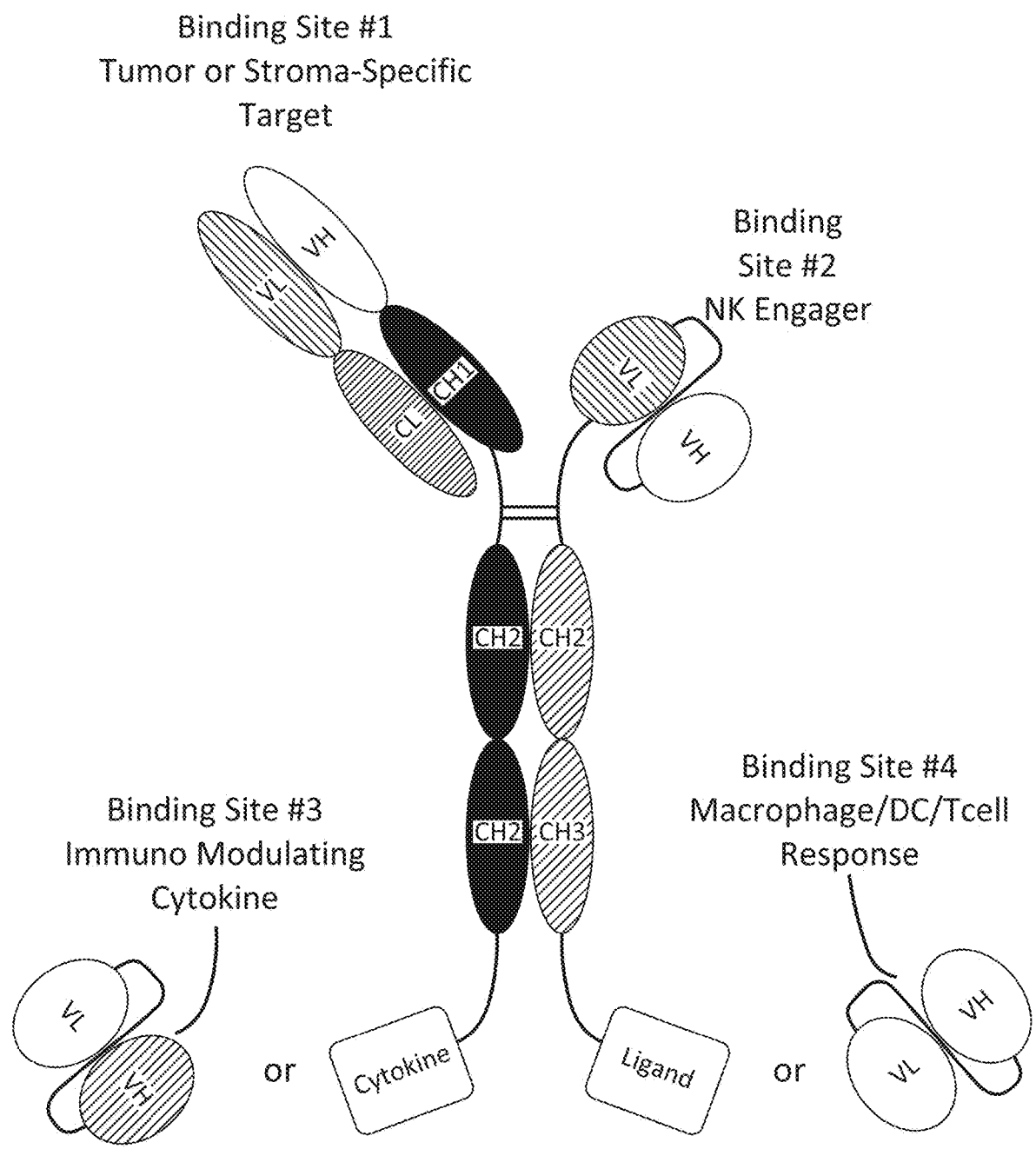
Figure 10C:
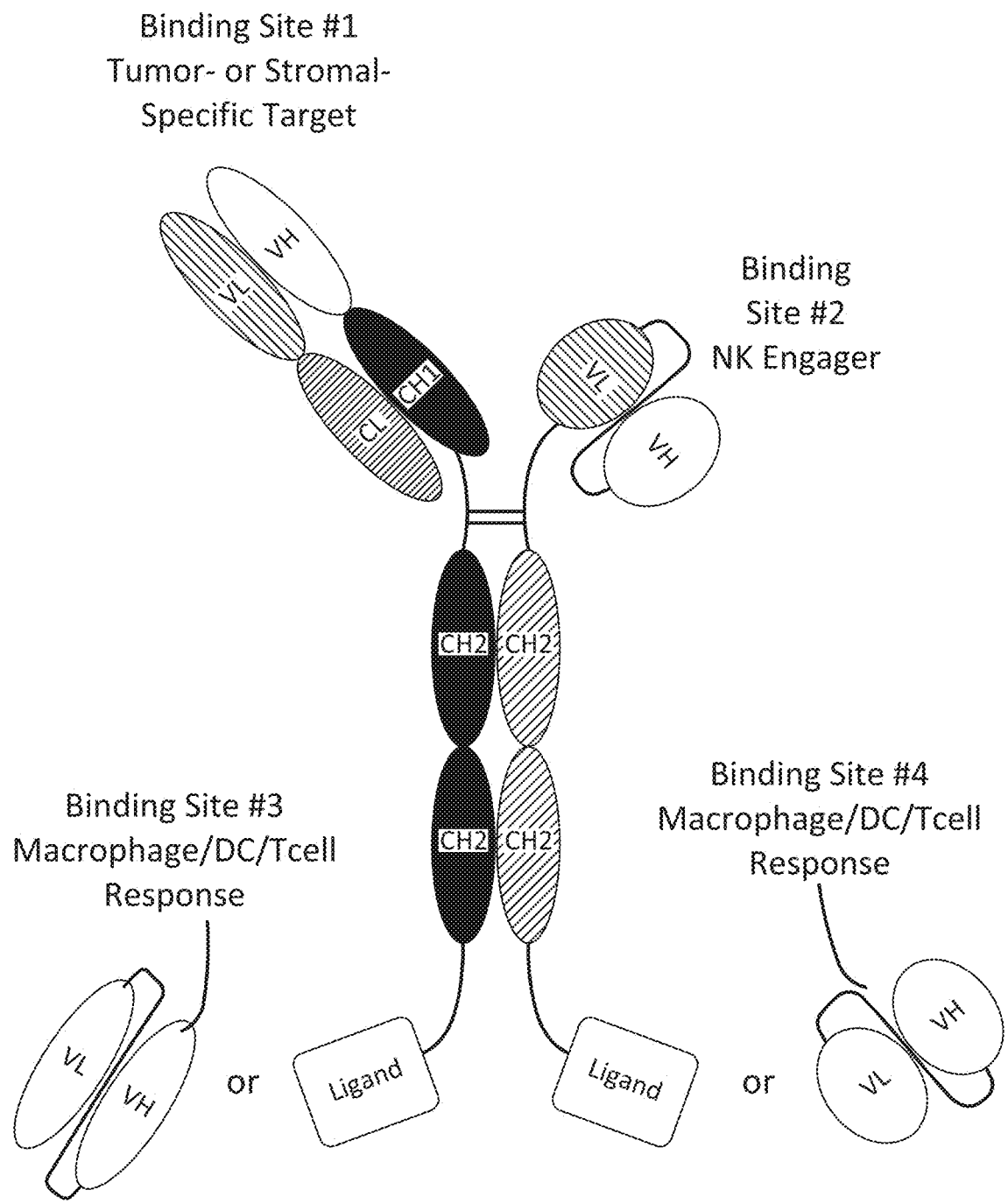

FIGS. 10A-10C depict exemplary schematics of a tetraspecific molecule that includes a Fab corresponding to binding site #1, a binding site #2, a binding site #3, and a binding site #4, each of which is connected, e.g., via a linker, to a first and second member of an immunoglobulin constant region, e.g., a first and a second Fc molecule. In embodiments, the tetraspecific molecule comprises three non-contiguous polypeptides shown in FIGS. 10A-10C. In the embodiments shown in FIG. 10A, the first polypeptide has the following configuration from N-to-C: VH-CH1 of the Fab that binds to, e.g., a tumor or stromal antigen, connected, e.g., via a linker, to a first member of an Fc molecule (e.g., the N-terminus of the CH2-CH3 region of the first Fc molecule, optionally, comprising a protuberance or cavity), which first member can, optionally further include binding site #3 connected, optionally via a linker, to the C-terminus of the first Fc molecule); the second polypeptide includes from N-to-C orientation a binding site #2 connected, e.g., via a linker, to a second member of an Fc molecule (e.g., the N-terminus of the CH2-CH3 region of the second Fc molecule, optionally, comprising a protuberance or cavity) which second member can, optionally further include binding site #4 connected, optionally via a linker, to the C-terminus of the second Fc molecule); and the third polypeptide includes from N-to-C: the VL-CL of the Fab that binds to, e.g., a tumor or stromal antigen. In the embodiments depicted in FIG. 10A, binding site #1 binds to a tumor or stromal antigen; and binding sites #2, #3 and 4 are independently chosen from a cytokine molecule, a ligand molecule, or a scFv that binds to, e.g., an immune cell antigen. In the embodiments depicted in FIG. 10A, binding site #1 binds to a tumor or stromal antigen; and binding sites #2, #3 and 4 are independently chosen from a cytokine molecule, a ligand molecule, or a scFv that binds to, e.g., an immune cell antigen. In the embodiments depicted in FIG. 10B, binding site #1 binds to a tumor or stromal antigen; binding site #2 depicts an NK cell engager, e.g., a scFv, e.g., in a VH-VL orientation from N- to C-terminus, connected to the N-terminus of the second Fc member, e.g., via a linker; binding site #3 depicts a cytokine molecule or an immune cell engager, e.g., a scFv, connected to the C-terminus of the first Fc member, e.g., via a linker; and binding site #4 are depicts a ligand molecule, or a scFv that binds to, e.g., an immune cell antigen, connected to the C-terminus of the second Fc member, e.g., via a linker. In the embodiments depicted in FIG. 10C, binding site #1 binds to a tumor or stromal antigen; binding site #2 depicts an NK cell engager, e.g., a scFv, e.g., in a VH-VL orientation from N- to C-terminus, connected to the N-terminus of the second Fc member, e.g., via a linker; binding site #3 depicts a ligand molecule or an immune cell engager, e.g., a scFv, connected to the C-terminus of the first Fc member, e.g., via a linker; and binding site #4 are depicts a ligand molecule, or a scFv that binds to, e.g., an immune cell antigen, connected to the C-terminus of the second Fc member, e.g., via a linker. In embodiments of any of the aforesaid tetraspecific molecules, the first and second members of the Fc molecule promote heterodimerization of the tetraspecific molecule.

FIGS. 11A-11C depict an exemplary trispecific molecule. FIG. 11A shows a schematic representation of the trispecific molecule including a Fab molecule directed to the mesothelin tumor antigen, wherein first polypeptide includes the heavy chain VH-CH1 of the Fab connected via a linker to an IL-15 cytokine, and the second polypeptide of the Fab includes the light chain VL-CL connected via a linker to CD40 ligand (CD40L). FIG. 11B provides, from N- to C-orientation, the amino acid sequence of an optional signal peptide (shown in italics), followed by the heavy chain VH-CH1 of the Fab (shown in underline and bold for VH and CH1, respectively), connected via a Gly-Ser linker (shown in dashed underline), to a human IL-15 cytokine (shown in regular font) (SEQ. ID NO: 238). FIG. 11C provides, from N- to C-orientation, the amino acid sequence of an optional signal peptide (shown in italics), followed by the kappa light chain VL-CL of the Fab (shown in underline and bold for VL and CL, respectively), connected via a Gly-Ser linker (shown in dashed underline), to a human CD40L (shown in regular font) (SEQ. ID NO: 235).

FIGS. 12A-12D depict an exemplary bispecific molecule that includes a Fab to a stromal target and a cytokine molecule, each of which is connected, e.g., via a linker, to a first and second member of an immunoglobulin constant region, e.g., a first and a second Fc molecule. FIG. 12A shows a schematic representation of the bispecific molecule including a Fab molecule directed to the stromal antigen, wherein the first polypeptide includes the heavy chain VH-CH1 of the Fab to the stromal antigen connected to the first Fc molecule having a cavity; the second polypeptide includes the IL-15 cytokine connected to the second Fc molecule having a protuberance; and the third polypeptide includes a light chain VL-CL of the Fab to the stromal antigen. FIG. 12B provides, from N- to C-orientation, the amino acid sequence of an optional signal peptide (shown in italics), followed by the human IL-15 cytokine (shown in underline), and further including an optional Gly-Ser linker (shown in dashed underline) connected to the second Fc molecule having a protuberance (shown in regular font) (SEQ. ID NO: 233). FIG. 12C provides, from N- to C-orientation, the amino acid sequence of an optional signal peptide (shown in italics), followed by the followed by the heavy chain VH-CH1 of the Fab to the stromal antigen FAP (shown in underline and bold for VH and CH1, respectively), connected to the first Fc molecule having a cavity (shown in regular font) (SEQ. ID NO: 55). FIG. 12D provides, from N- to C-orientation, the amino acid sequence of an optional signal peptide (shown in italics), followed by the kappa light chain VL-CL of the Fab to the stromal antigen FAP (shown in underline and bold for VL and CL, respectively) (SEQ. ID NO: 239).

FIGS. 13A-13D depict an exemplary tetraspecific molecule that includes a Fab to a stromal target two immune cell engagers, and a cytokine molecule, each of which is connected, e.g., via a linker, to a first and second member of an immunoglobulin constant region, e.g., a first and a second Fc molecule. FIG. 13A shows a schematic representation of the tetraspecific molecule including a Fab molecule directed to the stromal antigen, wherein the first polypeptide includes the heavy chain VH-CH1 of the Fab to the stromal antigen connected to the first Fc molecule having a cavity, and further includes a first immune cell engager, e.g., B7H6; the second polypeptide includes the IL-15 cytokine connected, optionally via a Gly-Ser linker, to the second Fc molecule having a protuberance, and further includes, e.g., via a Gly-Ser linker, a second immune cell engager, e.g., CD40L; and the third polypeptide includes a light chain VL-CL of the Fab to the stromal antigen. FIG. 13B provides, from N- to C-orientation, the amino acid sequence of an optional signal peptide (shown in italics), followed by the human IL-15 cytokine (shown in underline), further including an optional Gly-Ser linker (shown in dashed underline) connected to the second Fc molecule having a protuberance (shown in bold), which further includes, e.g., an optional Gly-Ser linker (shown in dashed underline, connected to the human CD40L amino acid sequence (shown in regular font) (SEQ. ID NO: 58). FIG. 13C provides, from N- to C-orientation, the amino acid sequence of an optional signal peptide (shown in italics), followed by the followed by the heavy chain VH-CH1 of the Fab to the stromal antigen FAP (shown in underline and bold for VH and CH1, respectively), connected to the first Fc molecule having a cavity (shown in regular font), which further includes, e.g., an optional Gly-Ser linker (shown in dashed underline, connected to the human B7H6 amino acid sequence (shown in underline) (SEQ. ID NO: 240). FIG. 13D provides, from N- to C-orientation, the amino acid sequence of an optional signal peptide (shown in italics), followed by the kappa light chain VL-CL of the Fab to the stromal antigen FAP (shown in underline and regular font for VL and CL, respectively) (SEQ. ID NO: 60).

FIG. 14A-14B depicts an exemplary tetraspecific molecule that includes a Fab to a mesothelin (molecule A), two immune cell engagers, 41BB-ligand (molecule C) and CD40 ligand (molecule D), and a cytokine molecule (molecule B), each of which is connected, e.g., via a linker, to a first and second member of an immunoglobulin constant region, e.g., a first and a second Fc molecule (knob-in-hole, KiH, Fc first member and Fc hole second member). FIG. 14A-14B shows a schematic representation of the tetraspecific molecule including a Fab molecule directed to the mesothelin antigen, wherein the first polypeptide includes the heavy chain VH-CH1 of the Fab to the mesothelin antigen connected to the first Fc molecule having a protuberance (knob) in the CH3 region, and further includes a first immune cell engager, e.g., 41BB-ligand; the second polypeptide includes the IL-21 cytokine connected, optionally via a Gly-Ser linker, to the second Fc molecule having a cavity (hole), and further includes, e.g., via a Gly-Ser linker, a second immune cell engager, e.g., CD40L; and the third polypeptide includes a light chain VL-CL of the Fab to the mesothelin antigen (molecule A). The following amino acid sequences are shown:

(i) Molecule A corresponding to the heavy chain (SEQ. ID NO: 1) and light chain (SEQ. ID NO: 80), respectively, of the mesothelin binding Fab (a_hMeso_SS1_Fab);

(ii) Molecule B corresponding to human IL-21 (SEQ. ID NO: 22);

(iii) Linker between the Molecule B and second Fc region (Molecule B to KiH_Fc linker) (SEQ. ID NO: 43);

(iv) Linker between the first Fc region and Molecule C (KiH_Fc to Molecule C linker) (SEQ. ID NO: 241);

(v) Molecule C corresponding to human 41BB ligand (SEQ. ID NO: 38);

(vi) Linker between the second Fc region and Molecule D (KiH_Fc to Molecule D linker) (SEQ. ID NO: 44);

(vii) Molecule C corresponding to human CD40L (SEQ. ID NO: 242);

(viii) first member Fc region (Fc Knob), including from N to C orientation, the VH of the mesothelin Fab, the CH2-CH3 amino acid sequence including a substitution of S for C at position 354 and W for T at position 366, followed by a Gly-Ser linker and the human 41BB ligand; and (ix) second member Fc region (Fc Hole), including from N to C orientation, the human IL-21, a Gly-Ser linker, the CH2-CH3 amino acid sequence including a substitution of C for Y at position 349, S for T at position 366, A for L at position 368, V for Y at position 407, followed by a Gly-Ser linker and the human CD40L.

Figure 15E:
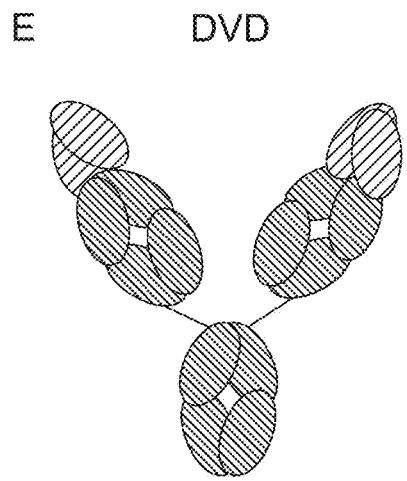
Figure 15F:
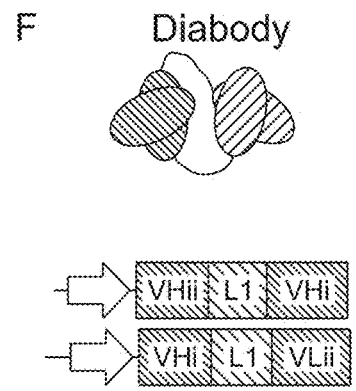
Figure 15G:
Figure 15H:
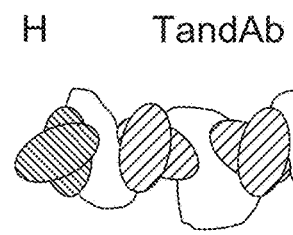

FIGS. 15A-15J are schematic representations of exemplary bispecific antibody molecules. FIG. 15A is a schematic representation of a bispecific antibody utilizing "knob-in-hole" heterodimerization. FIG. 15B is a schematic representation of a bispecific antibody utilizing a common light chain. FIG. 15C is a schematic representation of an IgG-Fab bispecific antibody. FIG. 15D is a schematic representation of an IgG-dsscFv2 bispecific antibody. FIG. 15E is a schematic representation of a DVD bispecific antibody. FIG. 15F is a schematic representation of a diabody. FIG. 15G is a schematic representation of a DART bispecific antibody. FIG. 15H is a schematic representation of a TandAb bispecific antibody. FIG. 15I is a schematic representation of a Fab-scFv2 bispecific antibody. FIG. 15J is a schematic representation of a Fab-scFv bispecific antibody. The corresponding mRNA that encode each of the building blocks for molecules depicted in FIG. 15A-15J are depicted below the antibody molecule.

Figure 16:
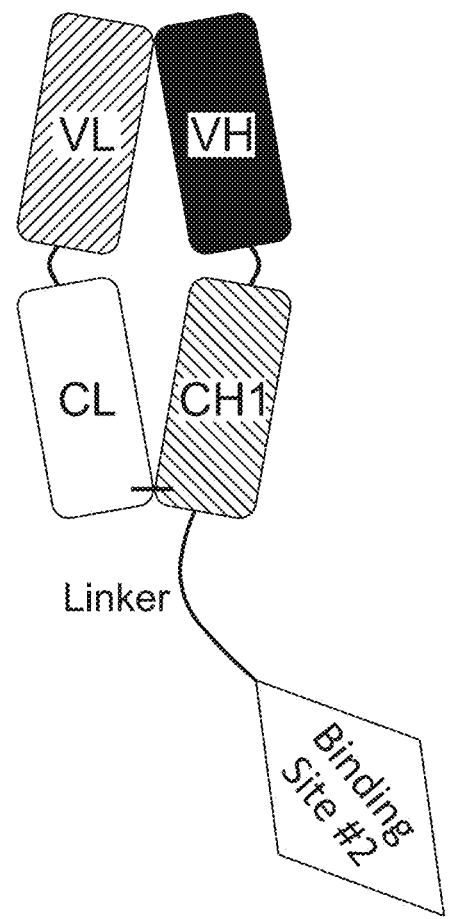

FIG. 16 depicts an exemplary schematic of a bispecific molecule that includes a Fab corresponding to binding site #1 fused to a binding site #2. In embodiments, binding site #1 is a tumor targeting moiety, e.g., binds to a cancer antigen, e.g., a tumor or stromal antigen; and binding site #2 is a stromal modifying moiety. In embodiments, the bispecific molecule comprises two non-contiguous polypeptides, wherein the first polypeptide has the following configuration from N-to-C: VH-CH1 of the Fab that binds to, e.g., a cancer antigen, fused optionally, via a linker to, the binding site #2; and the second polypeptide has the following configuration from N-to-C: VL-CL of the Fab that binds to, e.g., a cancer antigen, e.g., a tumor or stromal antigen.

Figure 17:
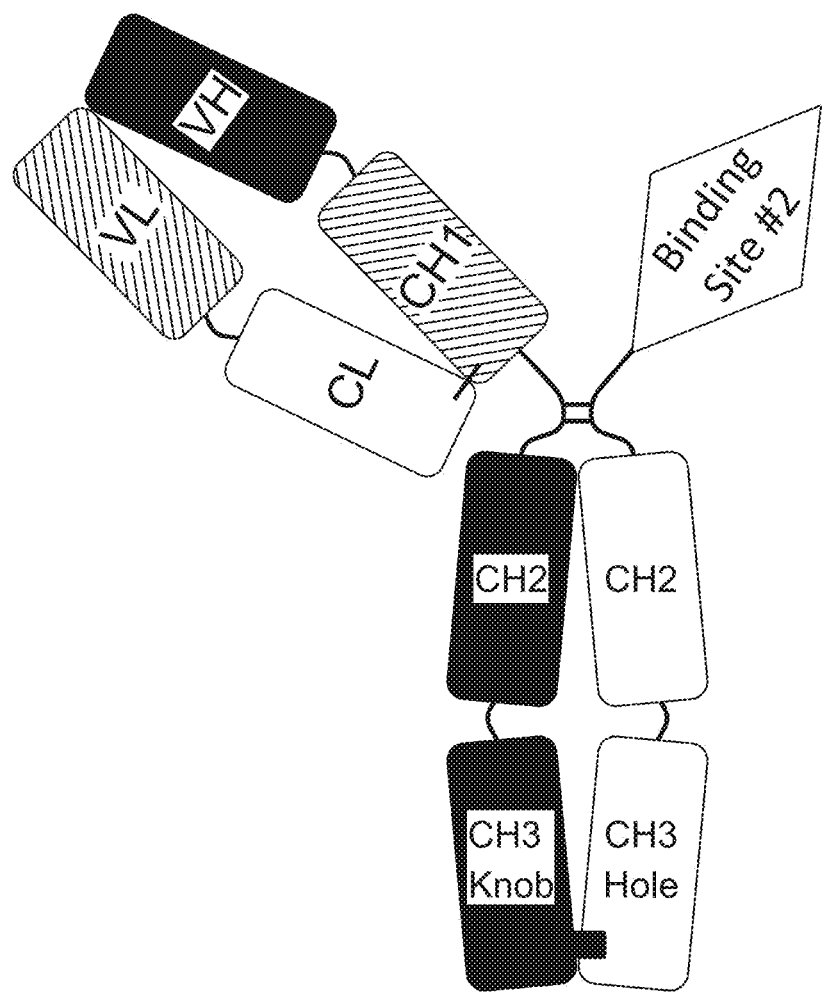

FIG. 17 depicts an exemplary schematic of a bispecific molecule that includes a Fab corresponding to binding site #1 connected, optionally via a liker, to a first member of an immunoglobulin constant region, e.g., a first Fc molecule; and a binding site #2 connected, optionally via a liker, to a second member of the Fc molecule. In embodiments, binding site #1 is a tumor targeting moiety, e.g., binds to a tumor or stromal antigen; and binding site #2 is a stromal modifying moiety. In embodiments, the bispecific molecule comprises three non-contiguous polypeptides, wherein the first polypeptide has the following configuration from N-to-C: VH-CH1 of the Fab that binds to, e.g., a tumor or stromal antigen, optionally connected via a linker to, the first member of the Fc molecule (e.g., a first CH2-CH3 region, optionally, comprising a protuberance or knob); the second polypeptide has the following configuration from N-to-C: VL-CL of the Fab that binds to, e.g., a tumor or stromal antigen; and the third polypeptide has the following configuration from N-to-C: binding site #2 (a stromal modifying moiety), connected, optionally, via a linker to, the second member of the Fc molecule (e.g., a second CH2-CH3 region, optionally, comprising a hole or cavity). In embodiments, the first and second members of the Fc molecule promote heterodimerization of the bispecific molecule.

Figure 18:
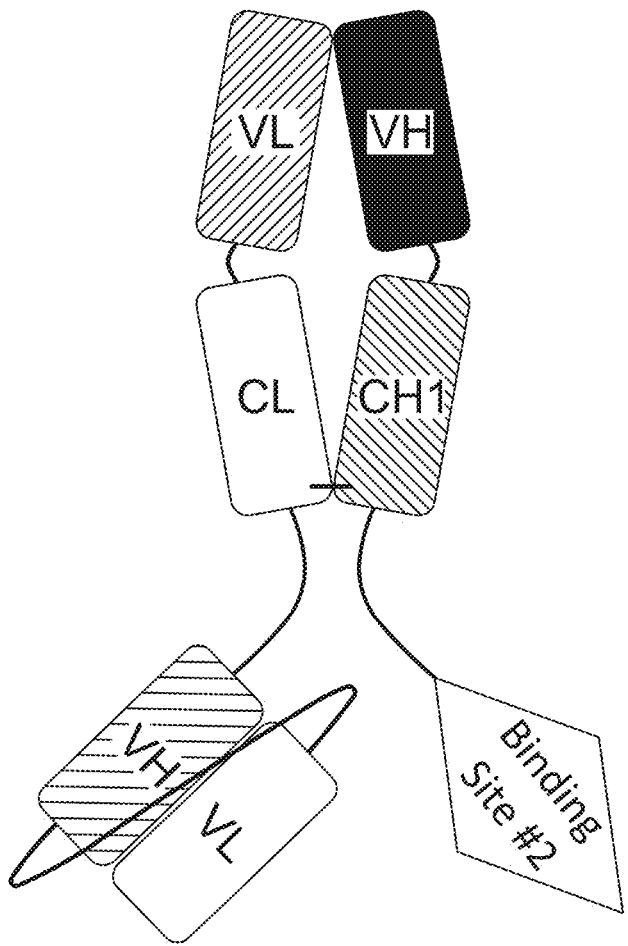

FIG. 18 depict exemplary schematics of a trispecific molecule that includes a Fab corresponding to binding site #1 fused to a binding site #2 and a binding site #3. In embodiments, binding site #1 is a tumor targeting moiety, e.g., binds to a tumor or stromal antigen; binding sites #2 is chosen from a cytokine molecule, or an immune cell engager, e.g., a ligand molecule or a scFv that binds to an immune cell antigen; and binding site 3 is a stromal modifying moiety. In embodiments, the trispecific molecule comprises two non-contiguous polypeptides in FIG. 18, wherein the first polypeptide has the following configuration from N-to-C: VH-CH1 of the Fab that binds to, e.g., a tumor or stromal antigen, connected, optionally, via a linker to, the binding site #3 (a stromal modifying moiety); and the second polypeptide having the following configuration from N-to-C: VL-CL of the Fab that binds to, e.g., a tumor or stromal antigen, fused to a scFv (e.g., a VH-VL of the scFv from N-to-C) that binds to, e.g., an immune cell antigen.

Figure 19A:
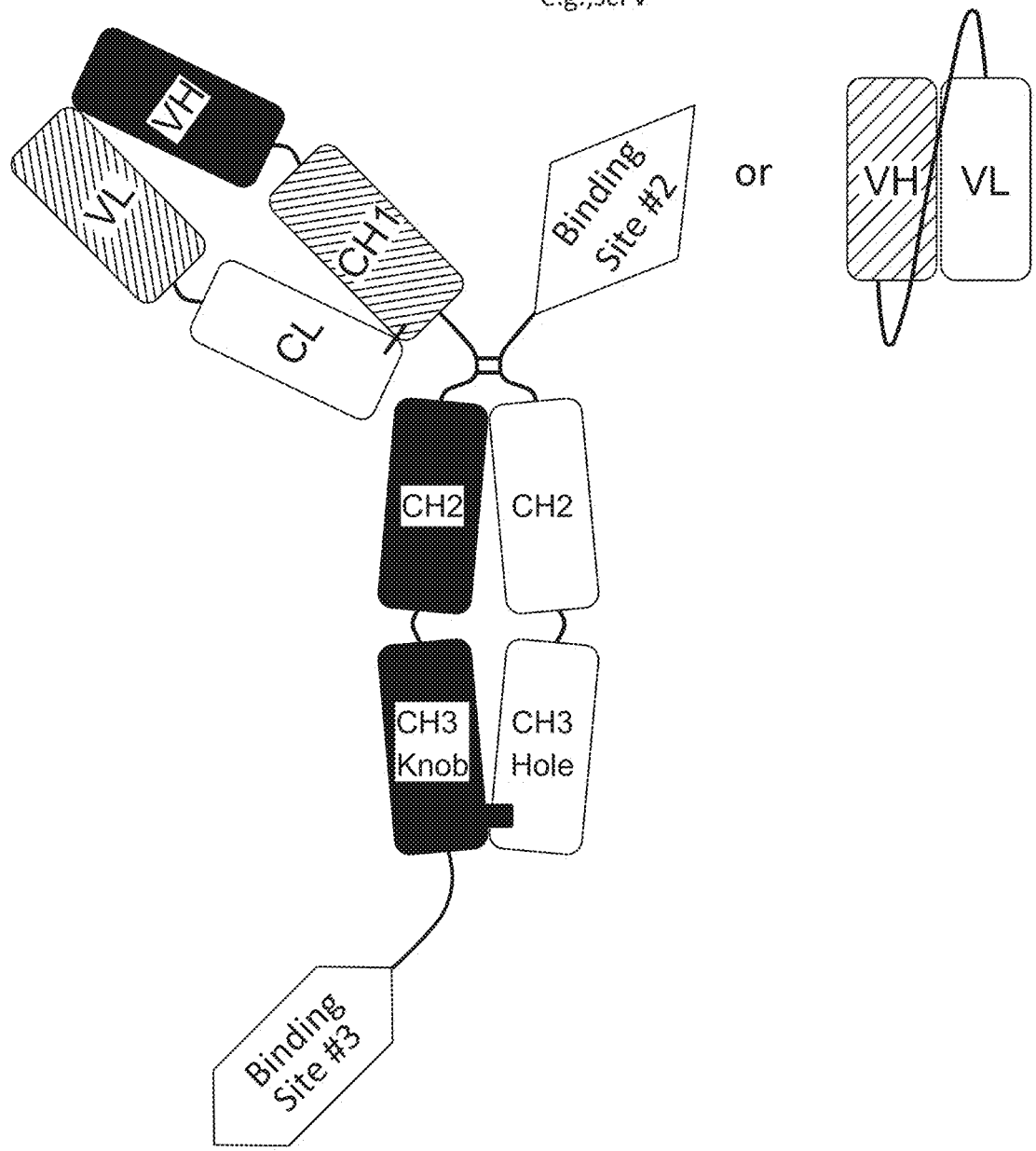
Figure 19B:
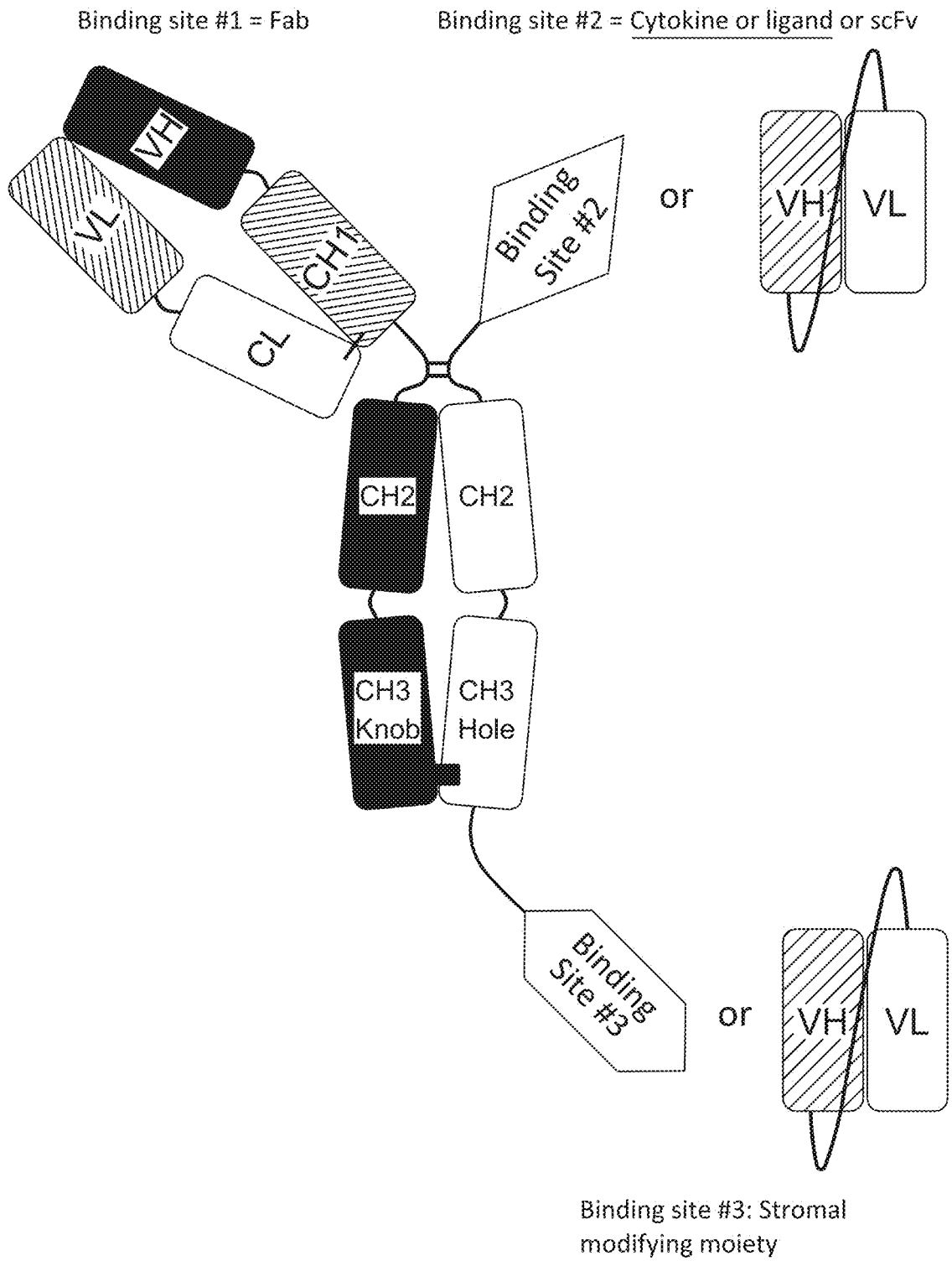

FIGS. 19A-19B depict exemplary schematics of a trispecific molecule that includes a Fab corresponding to binding site #1, a binding site #2, a binding site #3, each of which is connected, e.g., via a linker, to a first and second member of an immunoglobulin binding domain, e.g., first and second Fc molecule. In embodiments, the trispecific molecule comprises three non-contiguous polypeptides shown in FIGS. 19A-19B. In the embodiments shown in FIG. 19A, the first polypeptide has the following configuration from N-to-C: VH-CH1 of the Fab that binds to, e.g., a tumor or stromal antigen, connected, e.g., via a linker, to a first member of an Fc molecule (e.g., the N-terminus of the CH2-CH3 region of the first Fc molecule, optionally, comprising a protuberance or cavity), which first member can, optionally further include binding site #3 connected, optionally via a linker, to the C-terminus of the first Fc molecule; the second polypeptide includes from N-to-C orientation a binding site #2 connected, e.g., via a linker, to a second member of an Fc molecule (e.g., the N-terminus of the CH2-CH3 region of the second Fc molecule, optionally, comprising a protuberance or cavity); and the third polypeptide includes from N-to-C: the VL-CL of the Fab that binds to, e.g., a tumor or stromal antigen. In the embodiments shown in FIG. 19B, the first polypeptide has the following configuration from N-to-C: VH-CH1 of the Fab that binds to, e.g., a tumor or stromal antigen, connected, e.g., via a linker, to a first member of an Fc molecule (e.g., the N-terminus of the CH2-CH3 region of the first Fc molecule, optionally, comprising a protuberance or cavity); the second polypeptide includes from N-to-C orientation a binding site #2 connected, e.g., via a linker, to a second member of an Fc molecule (e.g., the N-terminus of the CH2-CH3 region of the second Fc molecule, optionally, comprising a protuberance or cavity) which second member can, optionally further include binding site #3 connected, optionally via a linker, to the C-terminus of the second Fc molecule); and the third polypeptide includes from N-to-C: the VL-CL of the Fab that binds to, e.g., a tumor or stromal antigen. In the aforesaid embodiments, binding site #1 binds to a tumor or stromal antigen; binding site #2 is chosen from a cytokine molecule, or an immune cell engager, e.g., a ligand molecule or a scFv that binds to an immune cell antigen; and binding site #3 is a stromal modifying moiety. In embodiments, the first and second members of the Fc molecule promote heterodimerization of the trispecific molecule.

Figure 20:
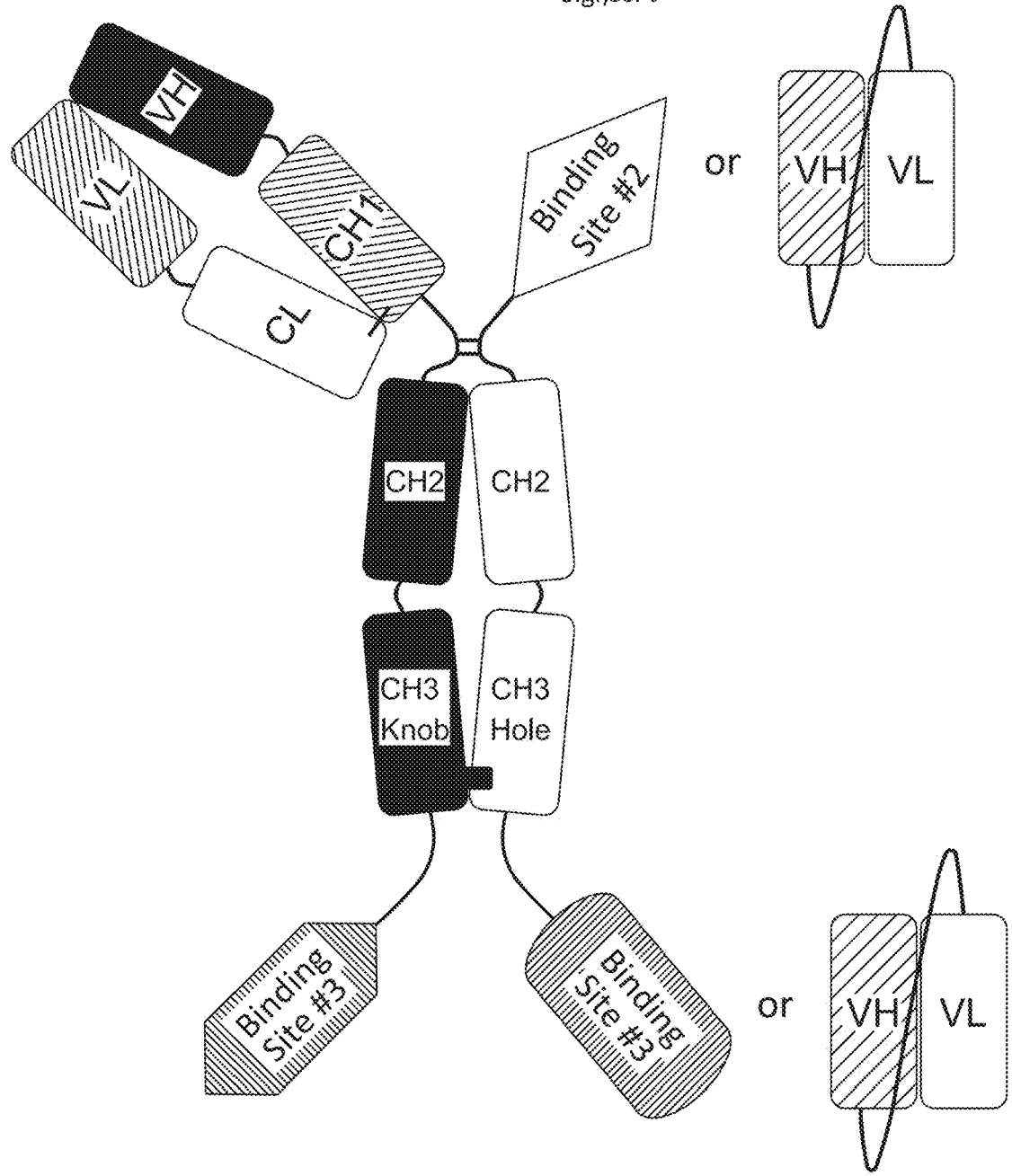

FIG. 20 depict an exemplary schematic of a tetraspecific molecule that includes a Fab corresponding to binding site #1, a binding site #2, a binding site #3, and a binding site #4, each of which is connected, e.g., via a linker, to a first and second member of an immunoglobulin constant region, e.g., a first and a second Fc molecule. In embodiments, the tetraspecific molecule comprises three non-contiguous polypeptides. In the embodiments, the first polypeptide has the following configuration from N-to-C: VH-CH1 of the Fab that binds to, e.g., a tumor or stromal antigen, connected, e.g., via a linker, to a first member of an Fc molecule (e.g., the N-terminus of the CH2-CH3 region of the first Fc molecule, optionally, comprising a protuberance or cavity), which first member can, optionally further include binding site #3 connected, optionally via a linker, to the C-terminus of the first Fc molecule); the second polypeptide includes from N-to-C orientation a binding site #2 connected, e.g., via a linker, to a second member of an Fc molecule (e.g., the N-terminus of the CH2-CH3 region of the second Fc molecule, optionally, comprising a protuberance or cavity) which second member can, optionally further include binding site #4 connected, optionally via a linker, to the C-terminus of the second Fc molecule); and the third polypeptide includes from N-to-C: the VL-CL of the Fab that binds to, e.g., a tumor or stromal antigen. In the embodiments depicted in FIG. 10, binding site #1 binds to a tumor or stromal antigen; binding sites #2 and #4 are independently chosen from a cytokine molecule, a ligand molecule, or a scFv that binds to, e.g., an immune cell antigen; and binding site #3 is a stromal modifying moiety.

Figure 21:
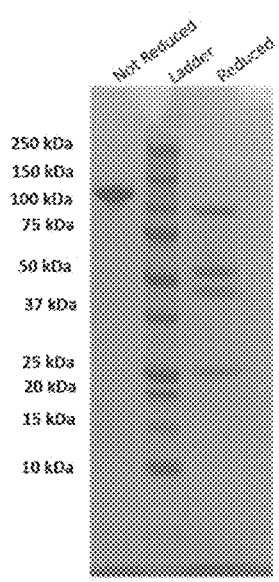
Figure 22:
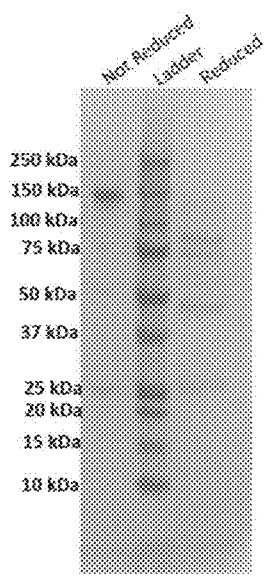
Figure 23:
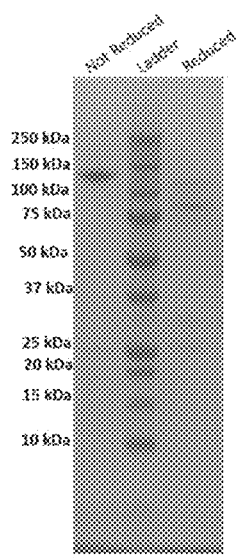
Figure 24:
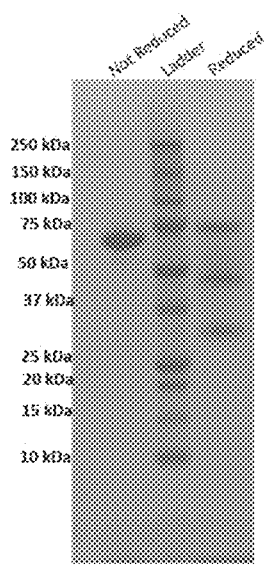
Figure 25:
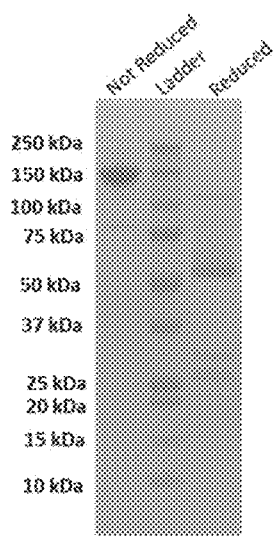
Figure 26:
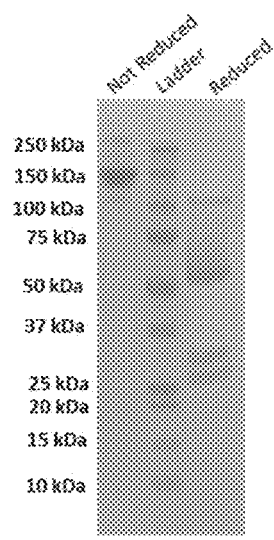
Figure 27:
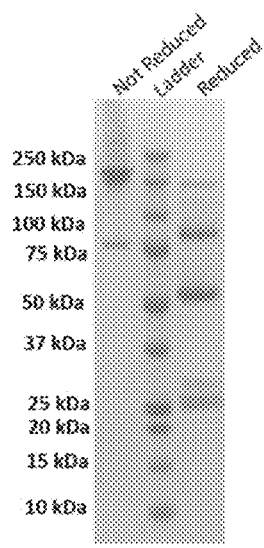
Figure 28:
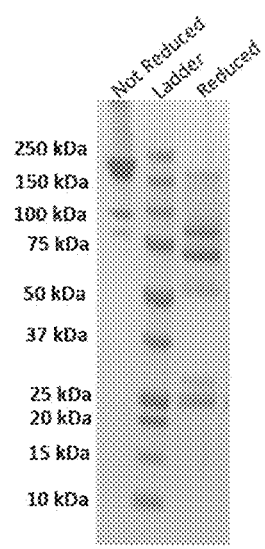
Figure 29:
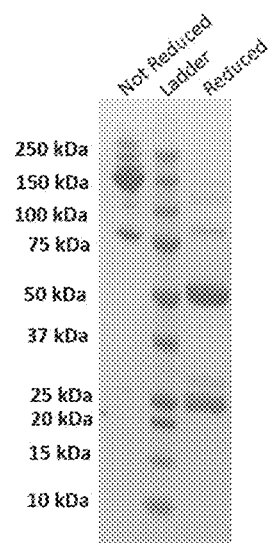
Figure 30:
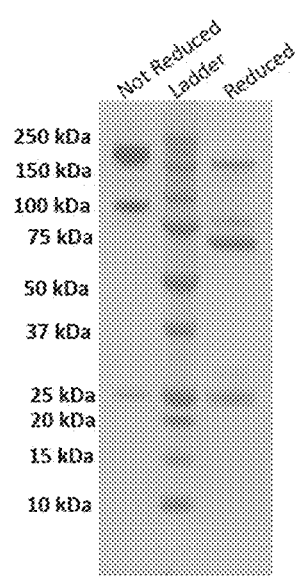
Figure 31:
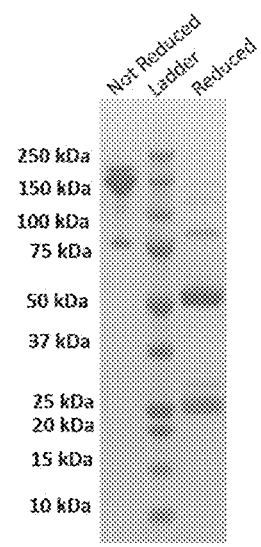
Figure 32:
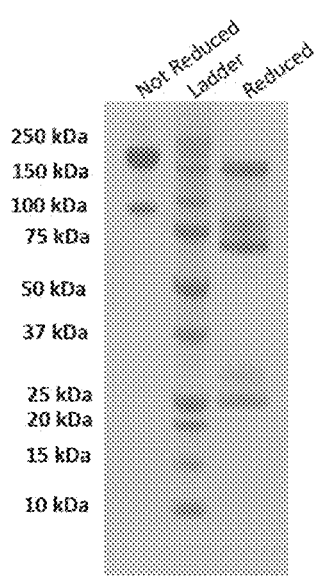
Figure 33:
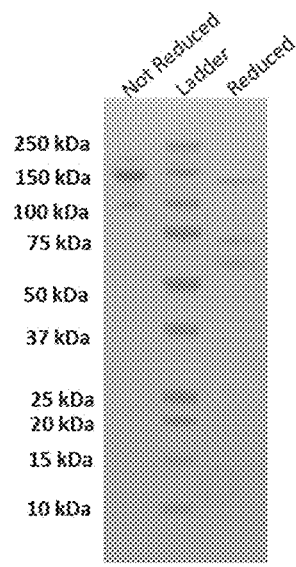
Figure 34:
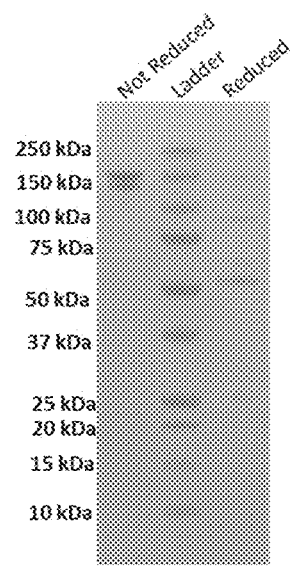
Figure 35:
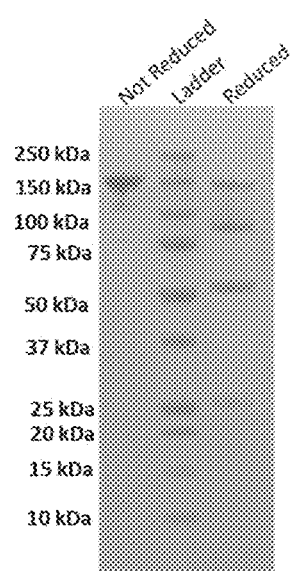
Figure 36:
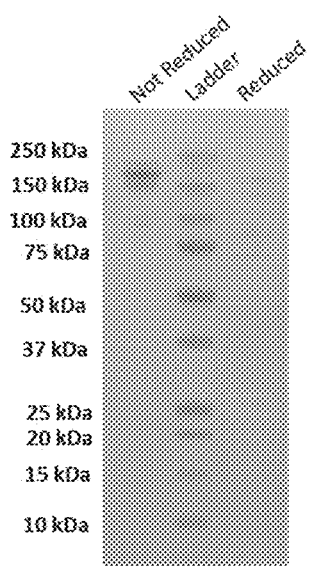
Figure 37:
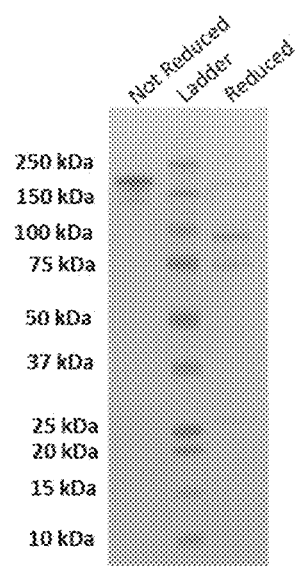
Figure 38:
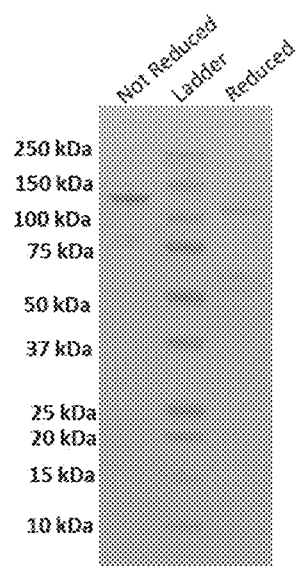
Figure 39:
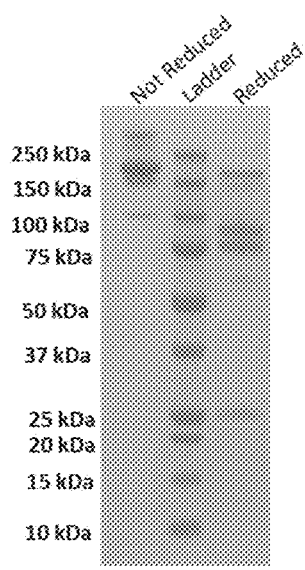
Figure 40:
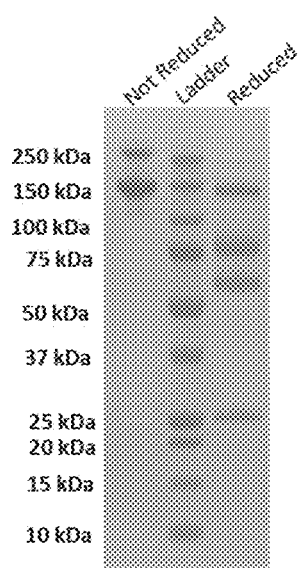
Figure 41:
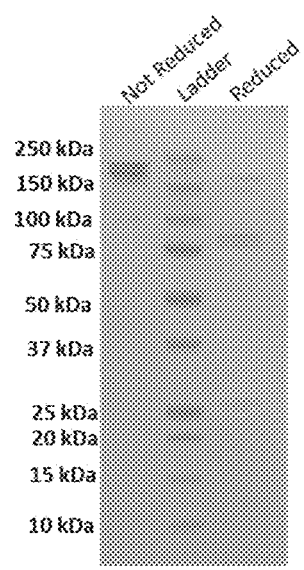
Figure 42:
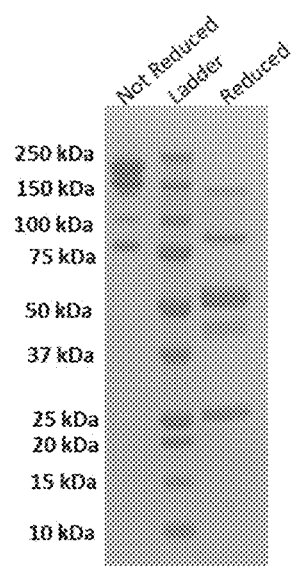
Figure 43:
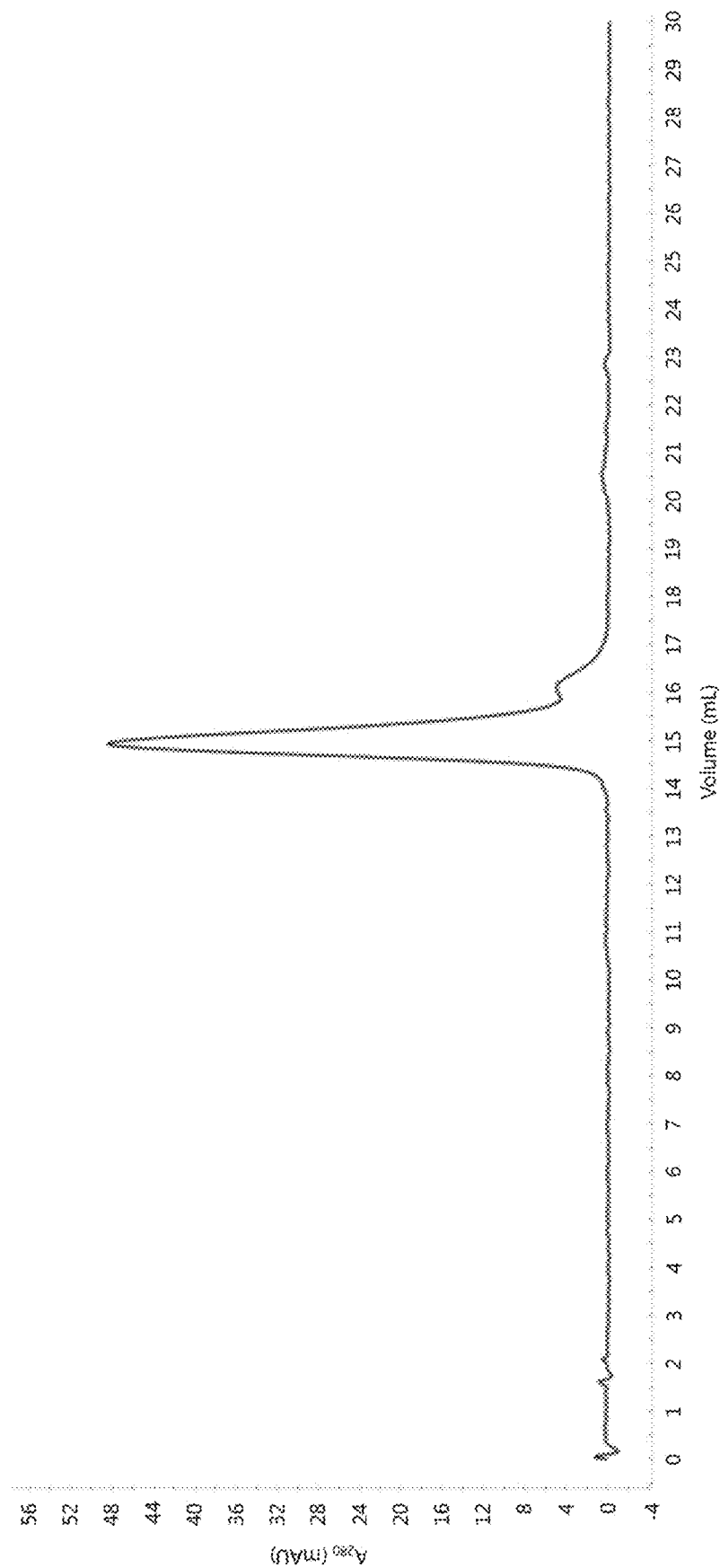
Figure 44:
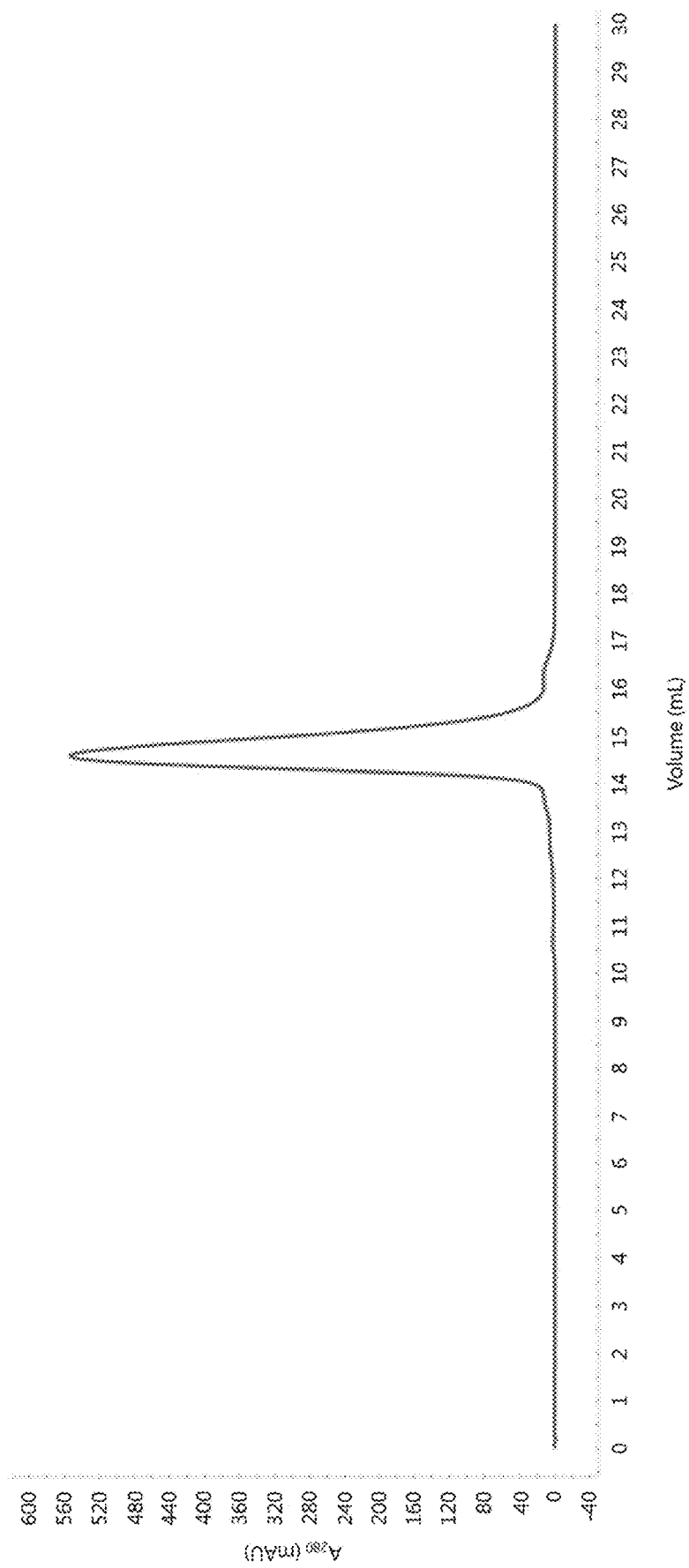
Figure 45:
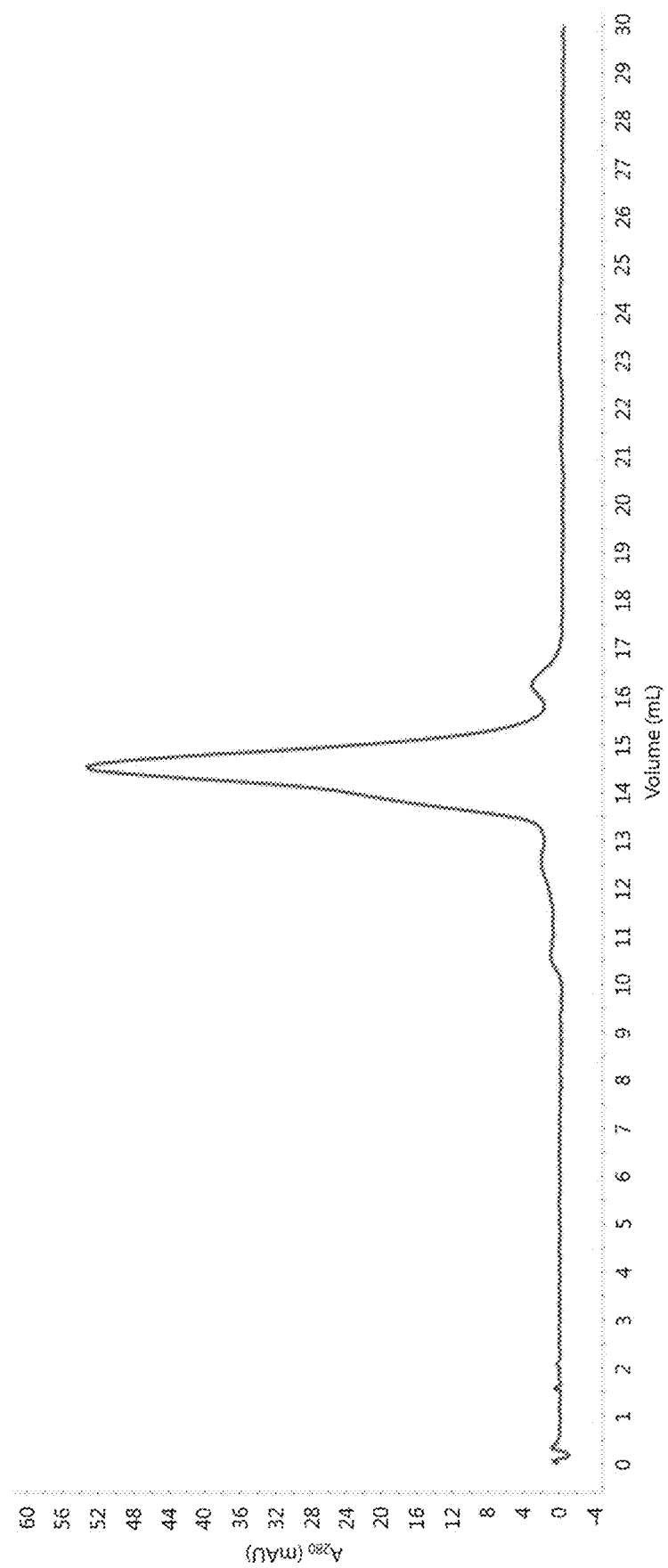
Figure 46:
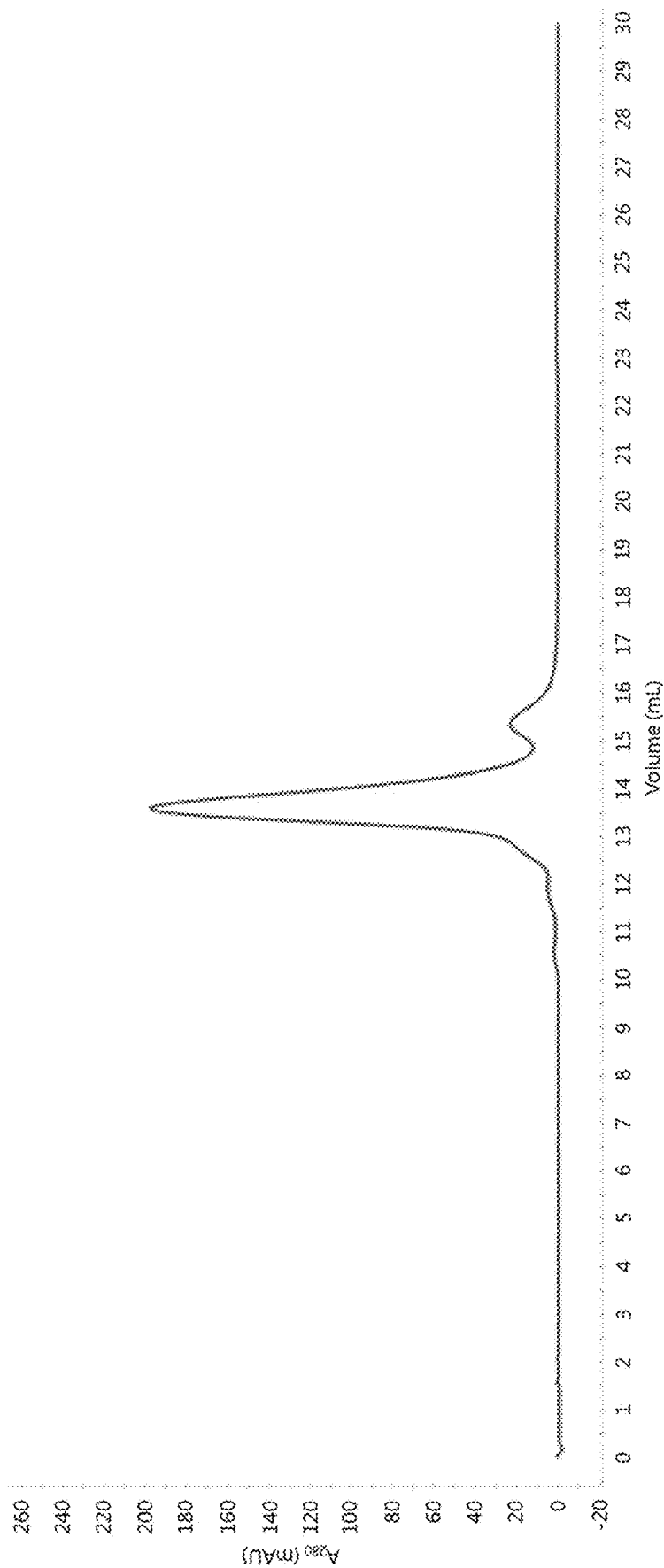
Figure 47:
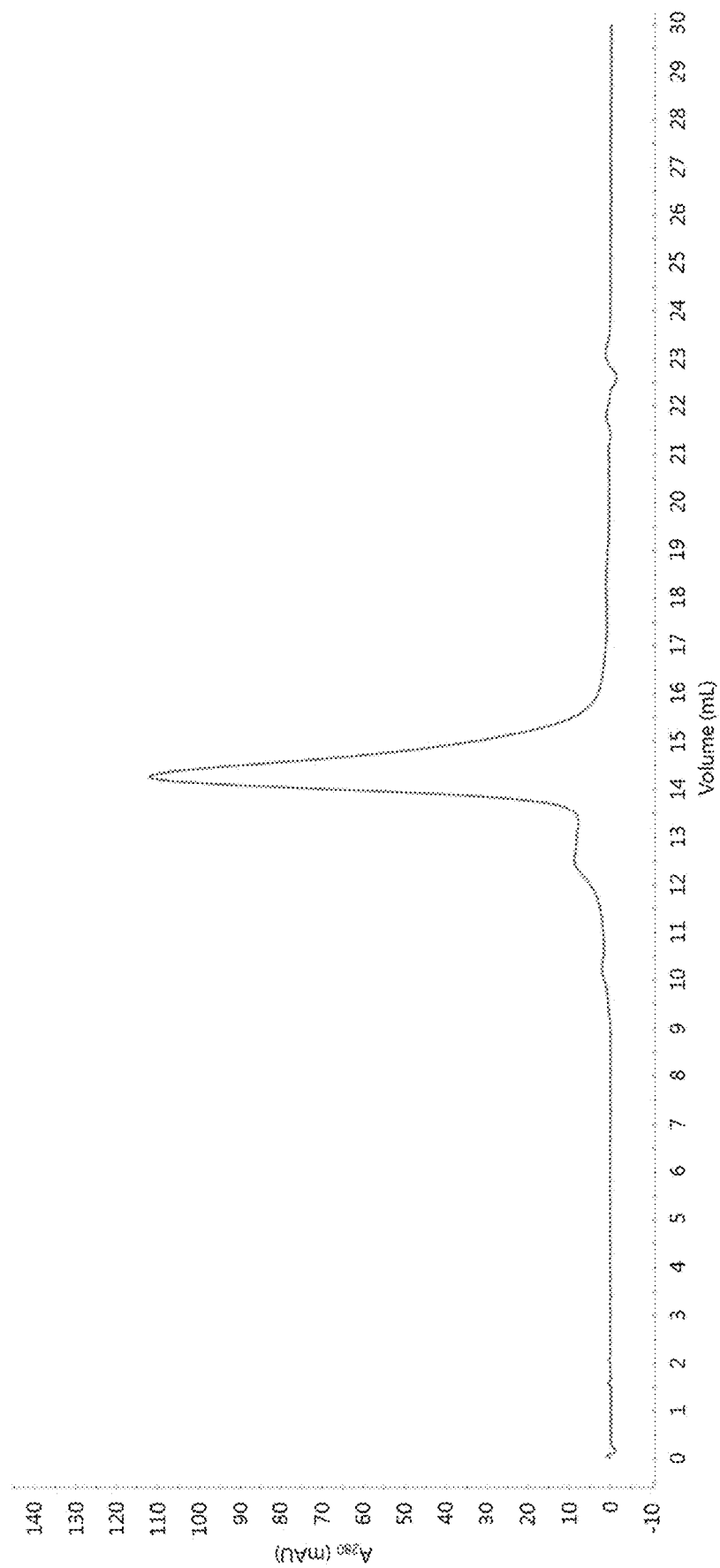
Figure 48:
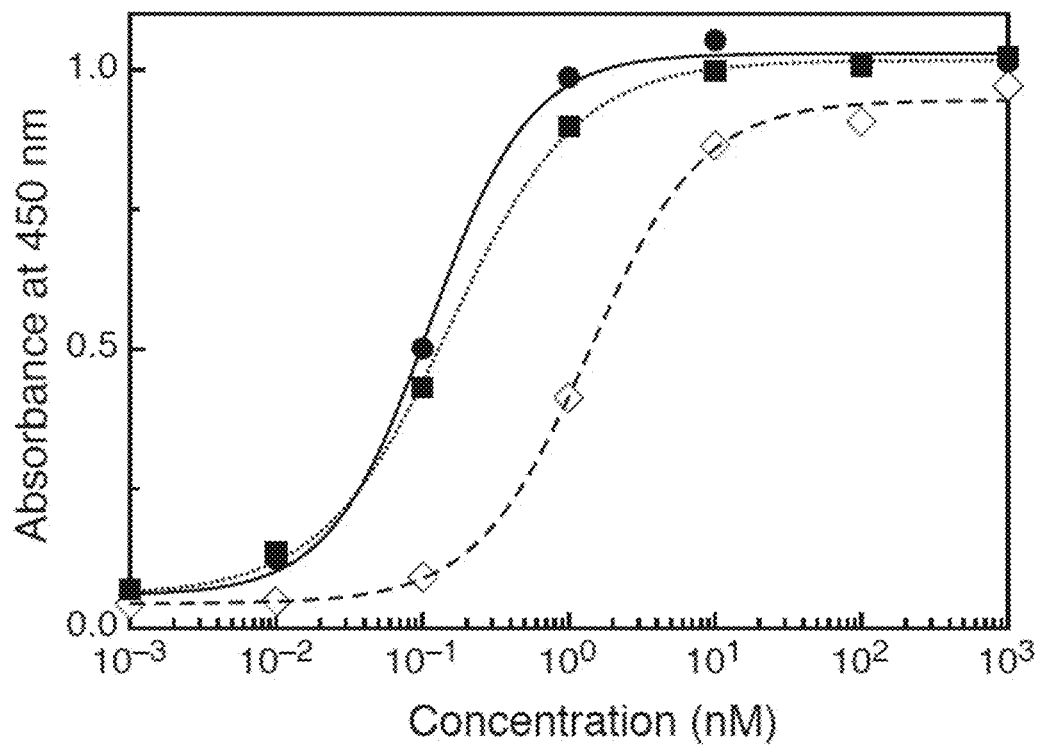
Figure 49:
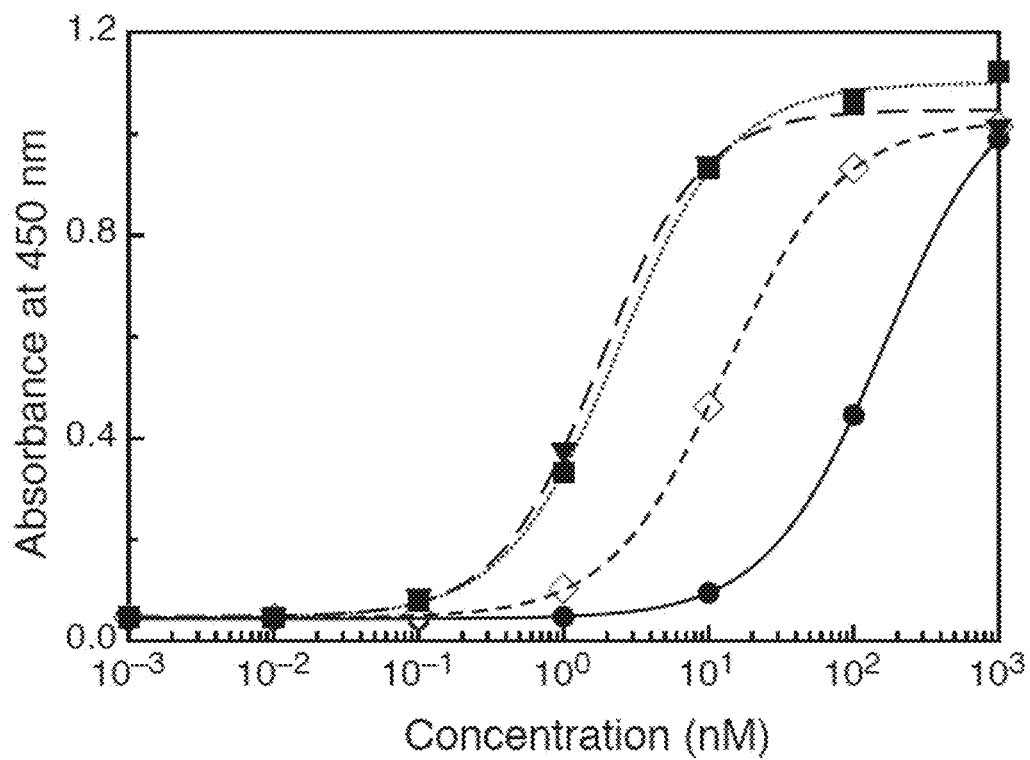

FIG. 21. Gel of multispecific molecule 1.
FIG. 22. Gel of multispecific molecule 2.
FIG. 23. Gel of multispecific molecule 3.
FIG. 24. Gel of multispecific molecule 4.
FIG. 25. Gel of multispecific molecule 5.
FIG. 26. Gel of multispecific molecule 6.
FIG. 27. Gel of multispecific molecule 7.
FIG. 28. Gel of multispecific molecule 8.
FIG. 29. Gel of multispecific molecule 9.
FIG. 30. Gel of multispecific molecule 10.
FIG. 31. Gel of multispecific molecule 11.
FIG. 32. Gel of multispecific molecule 12.
FIG. 33. Gel of multispecific molecule 13.
FIG. 34. Gel of multispecific molecule 14.
FIG. 35. Gel of multispecific molecule 15.
FIG. 36. Gel of multispecific molecule 16.
FIG. 37. Gel of multispecific molecule 17.
FIG. 38. Gel of multispecific molecule 18.
FIG. 39. Gel of multispecific molecule 19.
FIG. 40. Gel of multispecific molecule 20.
FIG. 41. Gel of multispecific molecule 21.
FIG. 42. Gel of multispecific molecule 22.
FIG. 43. Size exclusion chromatogram of multispecific molecule 1.
FIG. 44. Size exclusion chromatogram of multispecific molecule 5.
FIG. 45. Size exclusion chromatogram of multispecific molecule 11.
FIG. 46. Size exclusion chromatogram of multispecific molecule 12.
FIG. 47. Size exclusion chromatogram of multispecific molecule 13.
FIG. 48. ELISA of multispecific molecule 1 (circles, solid line), multispecific molecule 2 (diamonds, dashed line), and multispecific molecule 3 (squares, dotted line) binding to human mesothelin (generated from SEQ ID NO: 181).
FIG. 49. ELISA of multispecific molecule 5 (circles, solid line), multispecific molecule 6 (diamonds, short dash line), multispecific molecule 7 (squares, dotted line), and multispecific molecule 8 (triangles, long dash line) binding to human mesothelin (generated from SEQ ID NO: 181).

Figure 50:
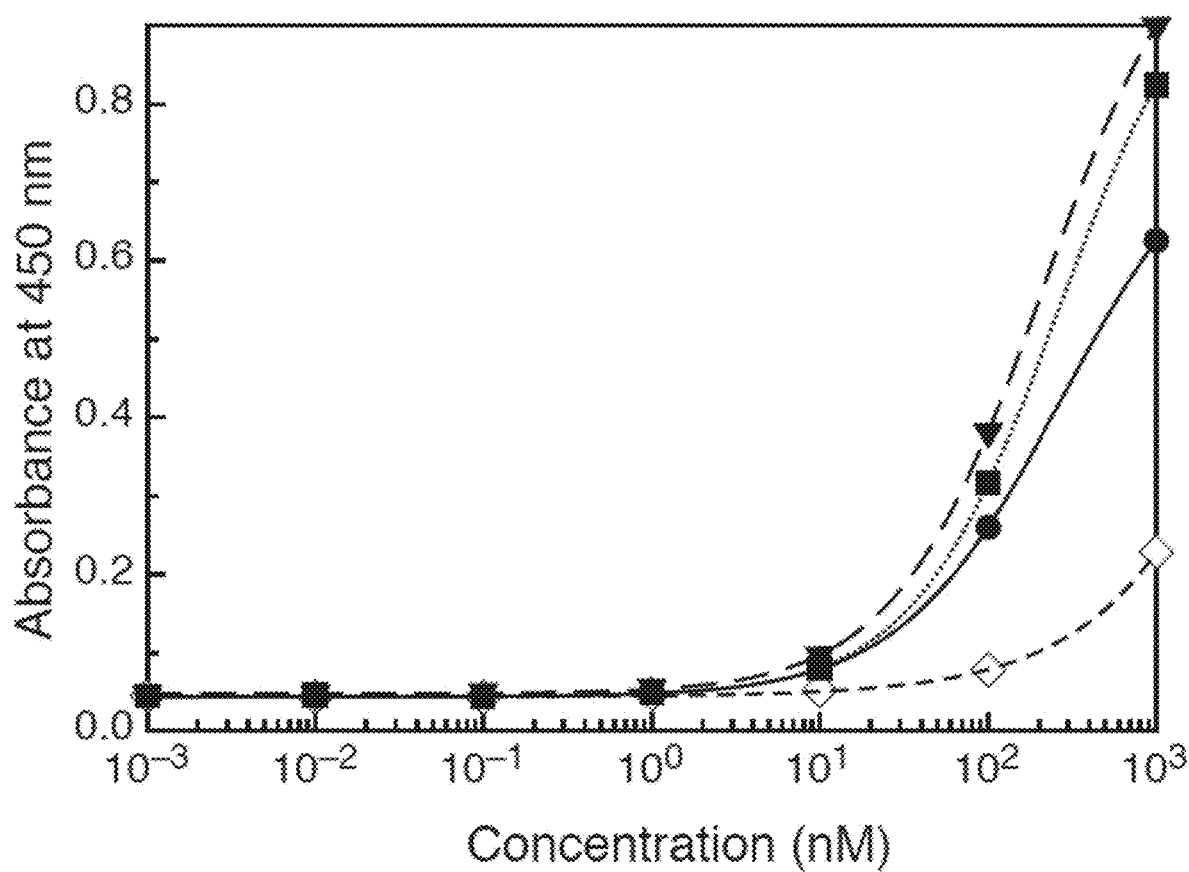

FIG. 50. ELISA of multispecific molecule 9 (circles, solid line), multispecific molecule 11 (diamonds, short dash line), multispecific molecule 10 (squares, dotted line), and multispecific molecule 12 (triangles, long dash line) binding to human mesothelin (generated from SEQ ID NO: 181).

Figure 51:
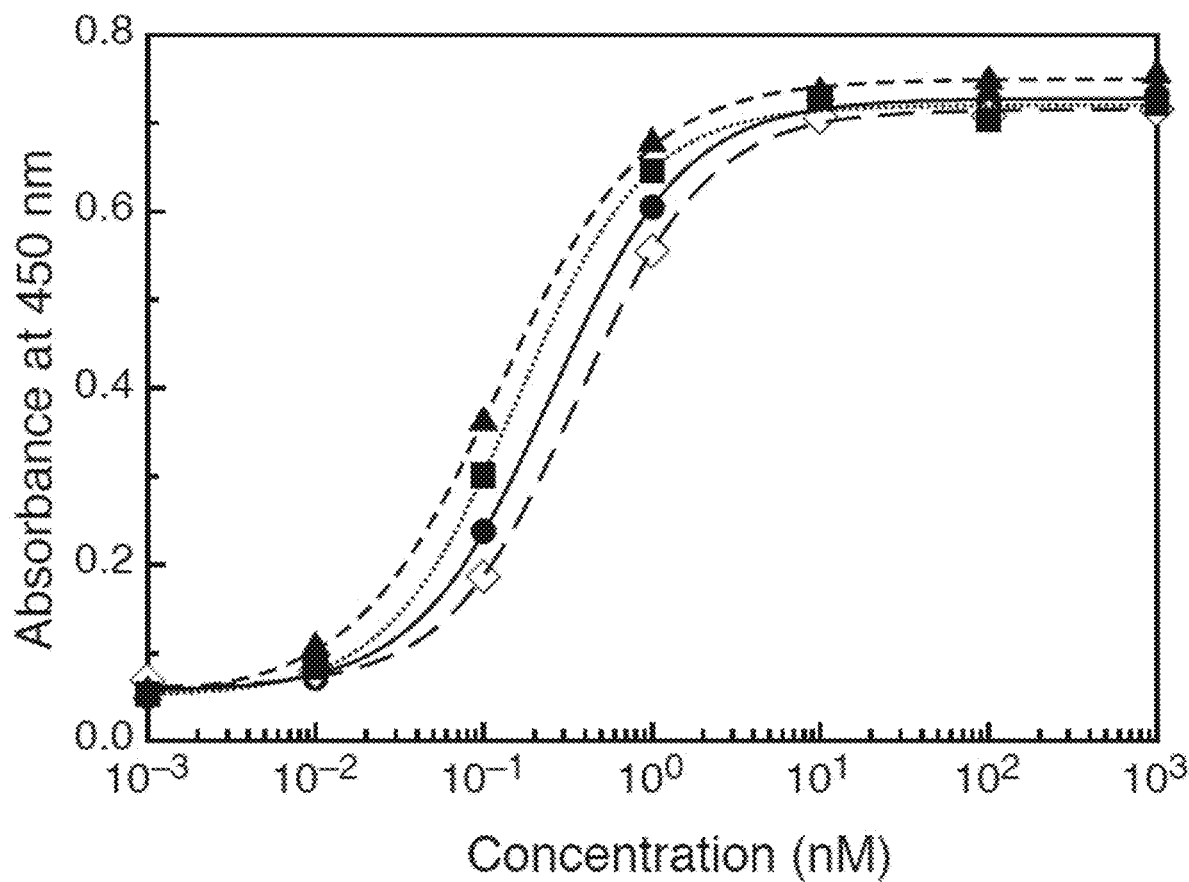

FIG. 51. ELISA of multispecific molecule 5 (circles, solid line), multispecific molecule 6 (diamonds, long dash line), multispecific molecule 7 (squares, dotted line), and multispecific molecule 9 (triangles, short dash line) binding to human PD1L1 (generated from SEQ ID NO: 178).

Figure 52:
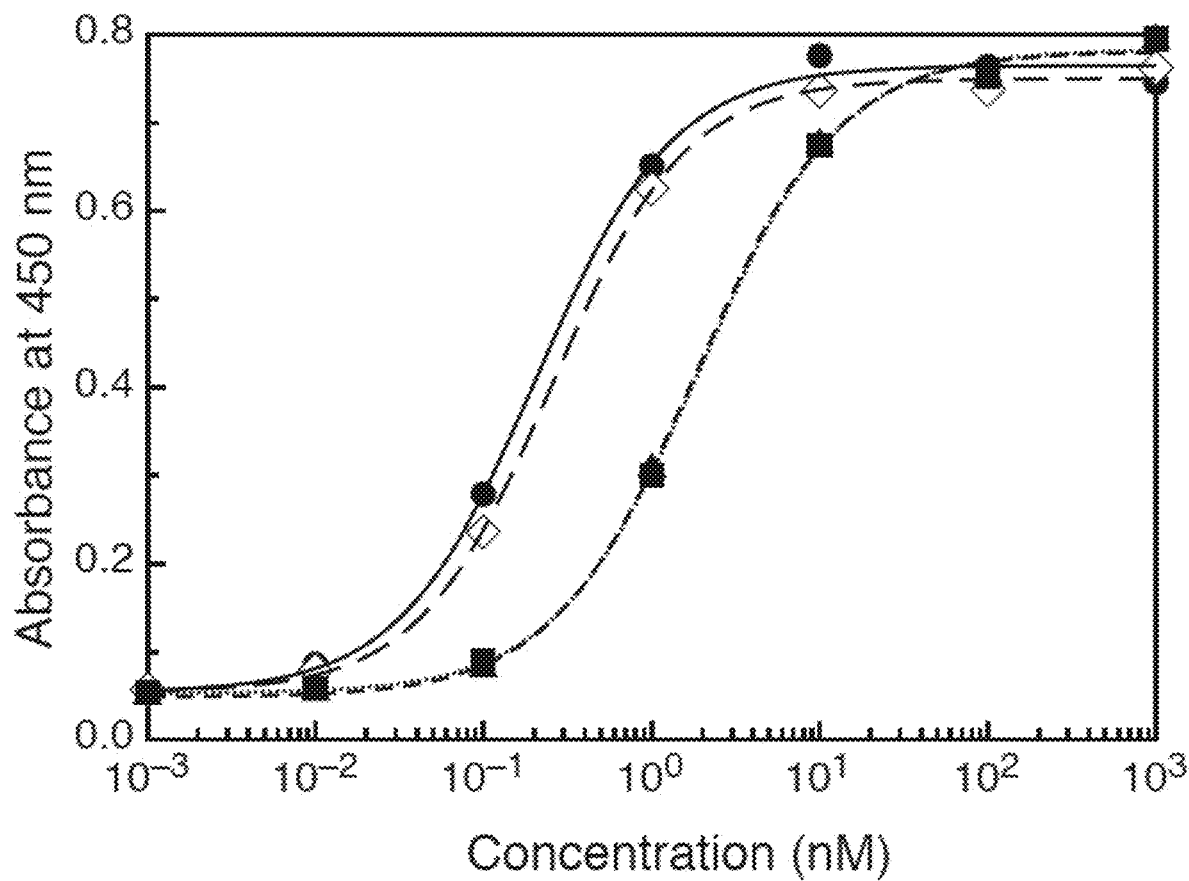

FIG. 52. ELISA of multispecific molecule 11 (circles, solid line), multispecific molecule 8 (diamonds, long dash line), multispecific molecule 10 (squares, dotted line), and multispecific molecule 12 (triangles, short dash line) binding to human PD1L1 (generated from SEQ ID NO: 178).

Figure 53:
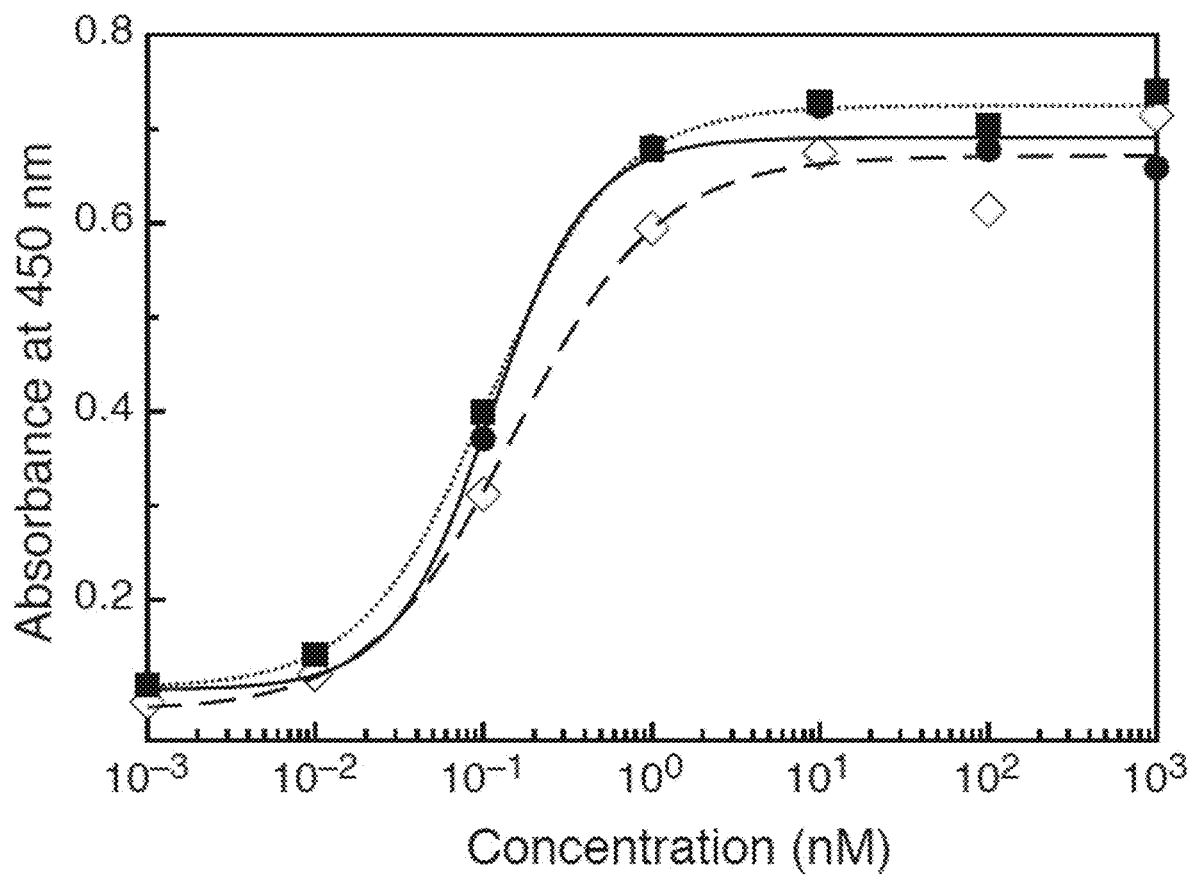

FIG. 53. ELISA of multispecific molecule 1 (circles, solid line), multispecific molecule 2 (diamonds, dashed line), and multispecific molecule 4 (squares, dotted line) binding to human IL2Rα (generated from SEQ ID NO: 182).

Figure 54:
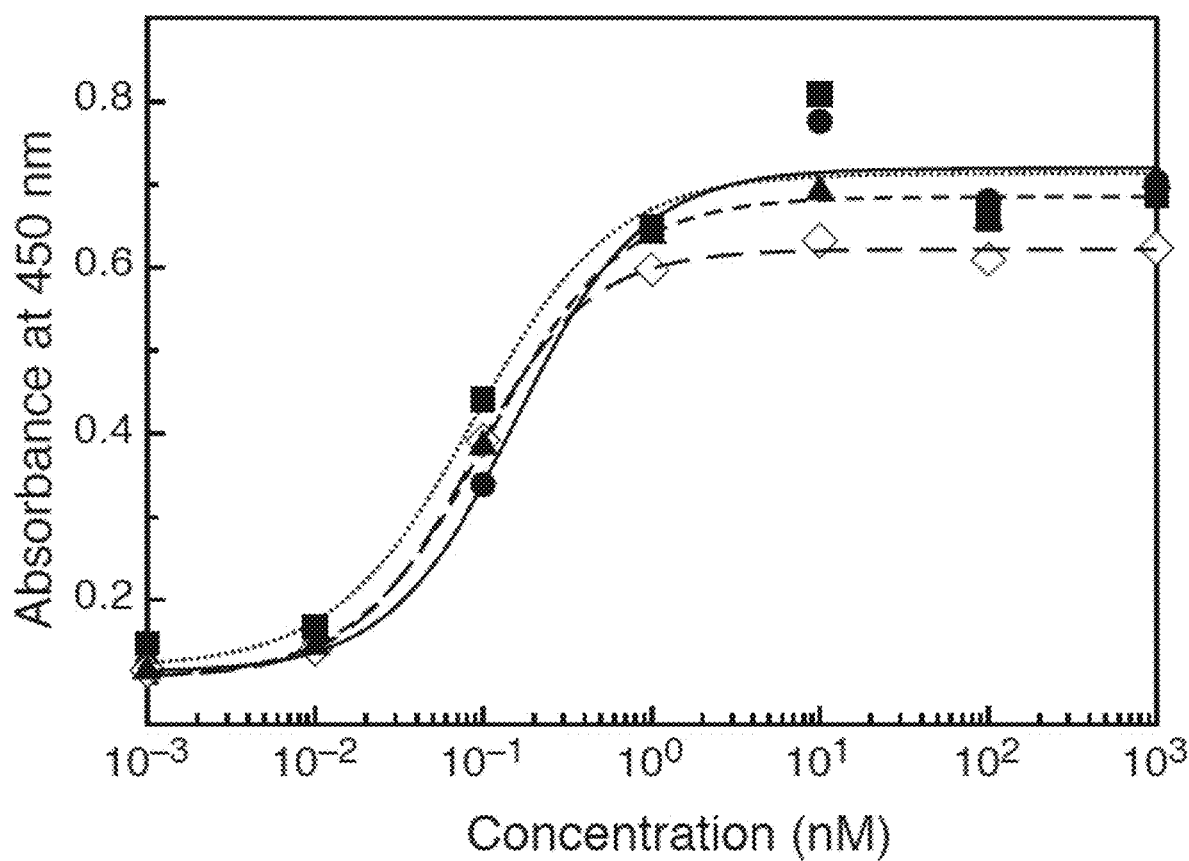

FIG. 54. ELISA of multispecific molecule 6 (circles, solid line), multispecific molecule 8 (diamonds, long dash line), multispecific molecule 10 (squares, dotted line), and multispecific molecule 12 (triangles, short dash line) binding to human IL2Rα (generated from SEQ ID NO: 182).

Figure 55:
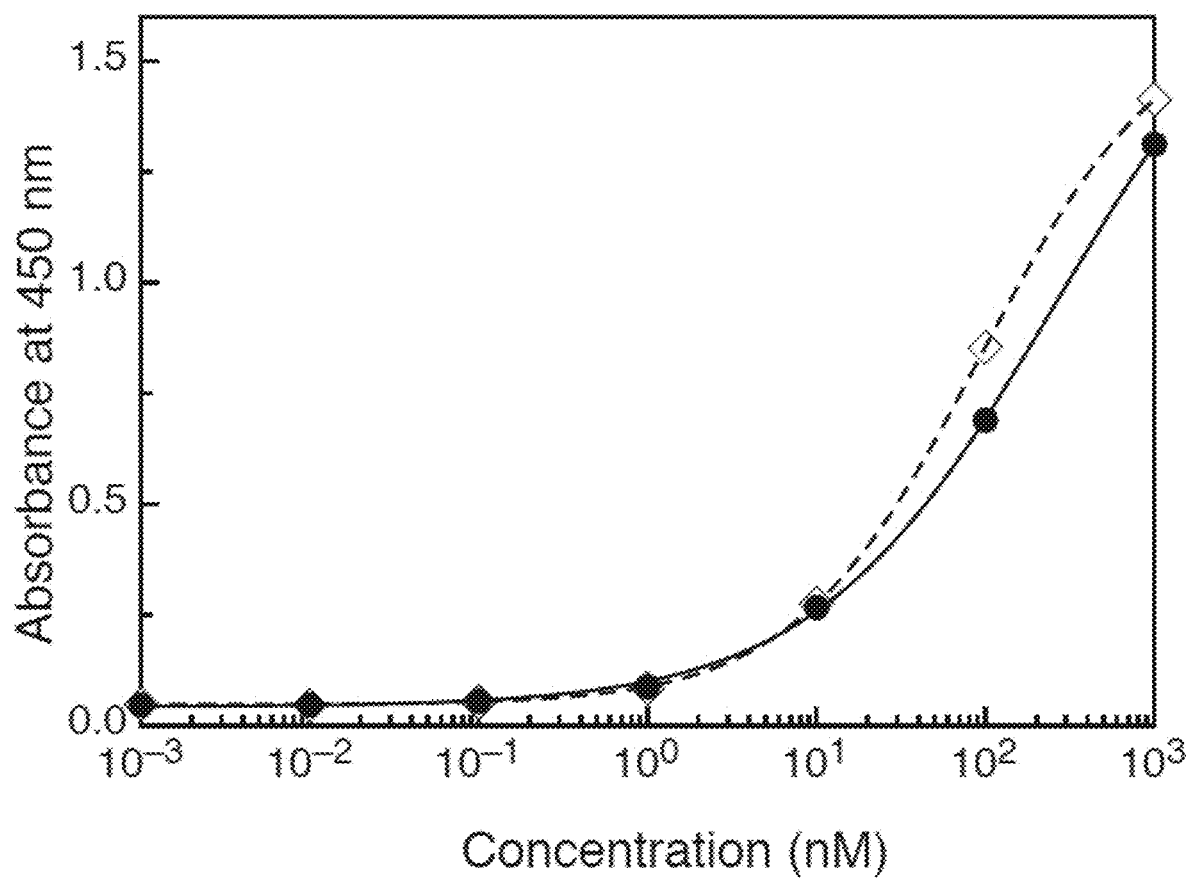

FIG. 55. ELISA of multispecific molecule 2 (circles, solid line) and multispecific molecule 3 (diamonds, dashed line) with human NKp30 (generated from SEQ ID NO: 180).

Figure 56:
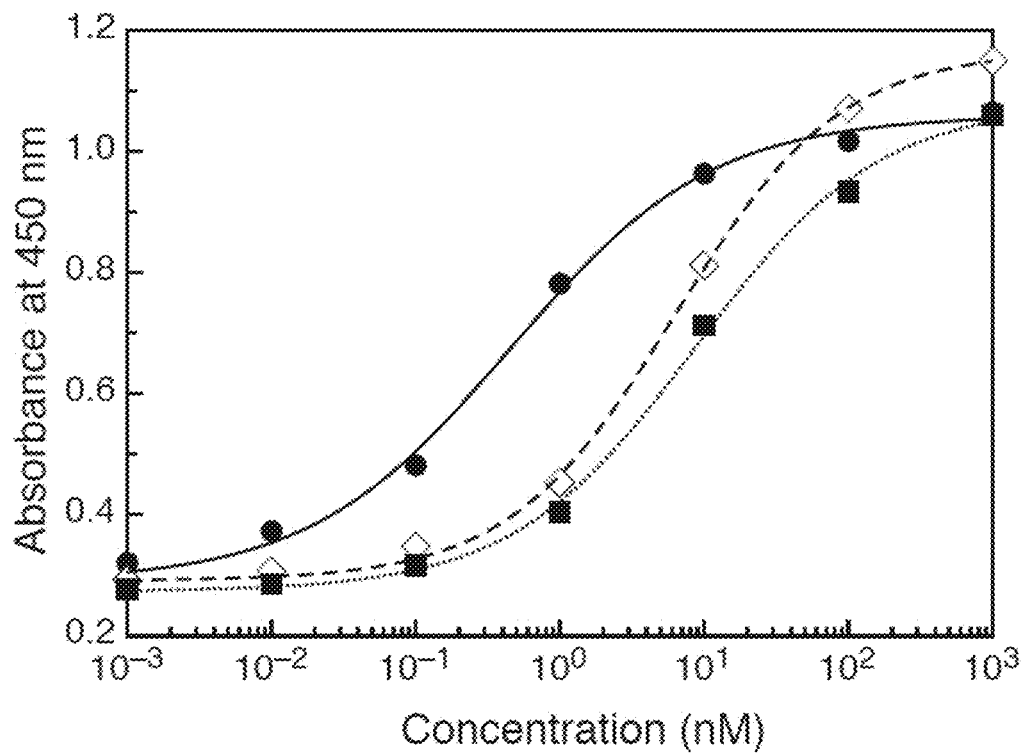

FIG. 56. ELISA of multispecific molecule 7 (circles, solid line), multispecific molecule 9 (diamonds, dashed line), and multispecific molecule 11 (squares, dotted line) with human NKp46 (generated from SEQ ID NO: 179).

Figure 57:
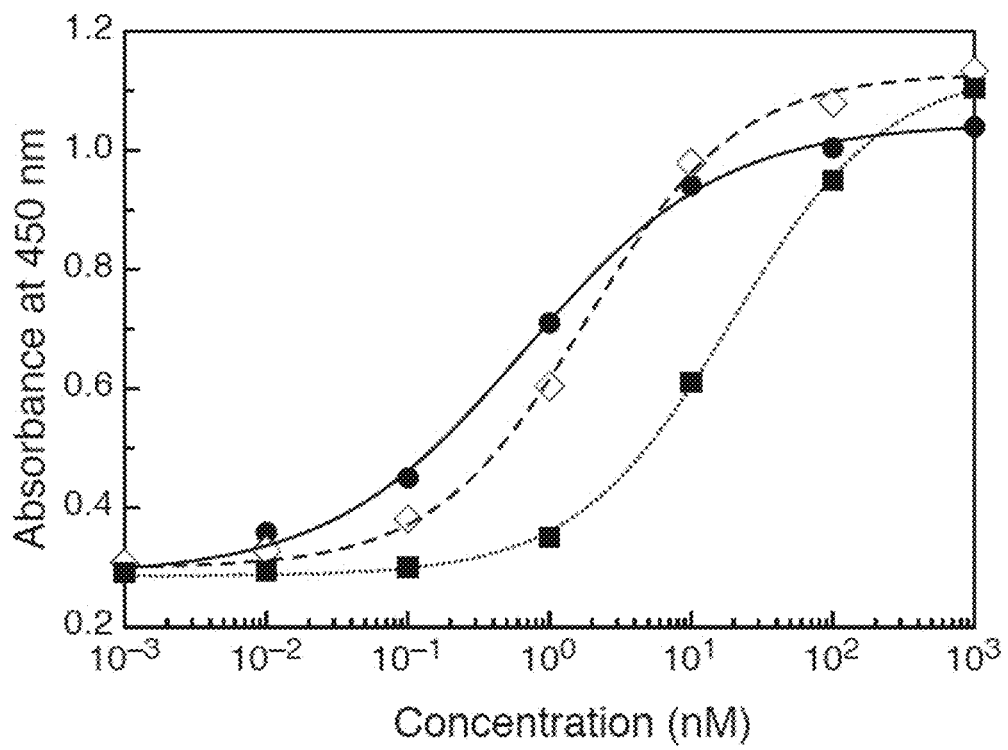

FIG. 57. ELISA of multispecific molecule 8 (circles, solid line), multispecific molecule 10 (diamonds, dashed line), and multispecific molecule 11 (squares, dotted line) with human NKp46 (generated from SEQ ID NO: 179).

Figure 58:
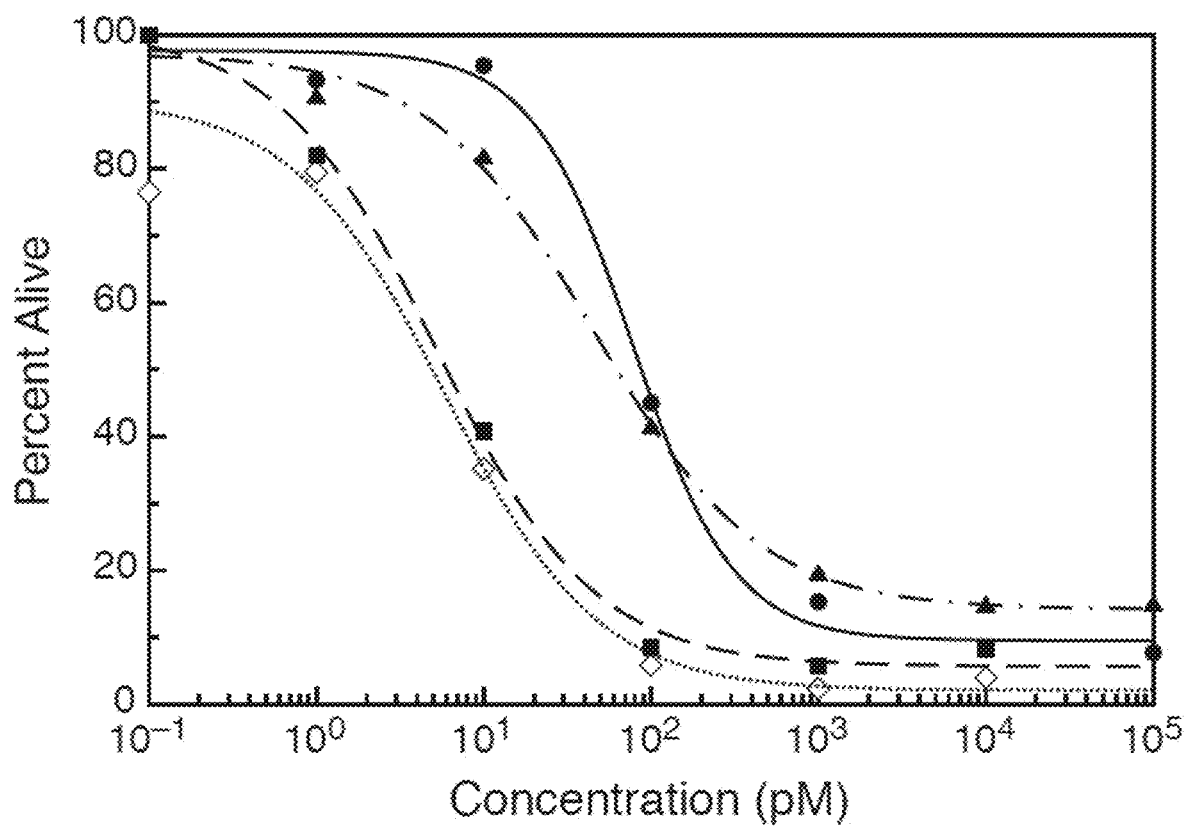

FIG. 58. Cell-killing curves for multispecific molecule 1 (circles, solid line), multispecific molecule 2 (diamonds, dotted line), multispecific molecule 3 (squares, dashed line), and multispecific molecule 4 (triangles, dashed and dotted line).

Figure 59:
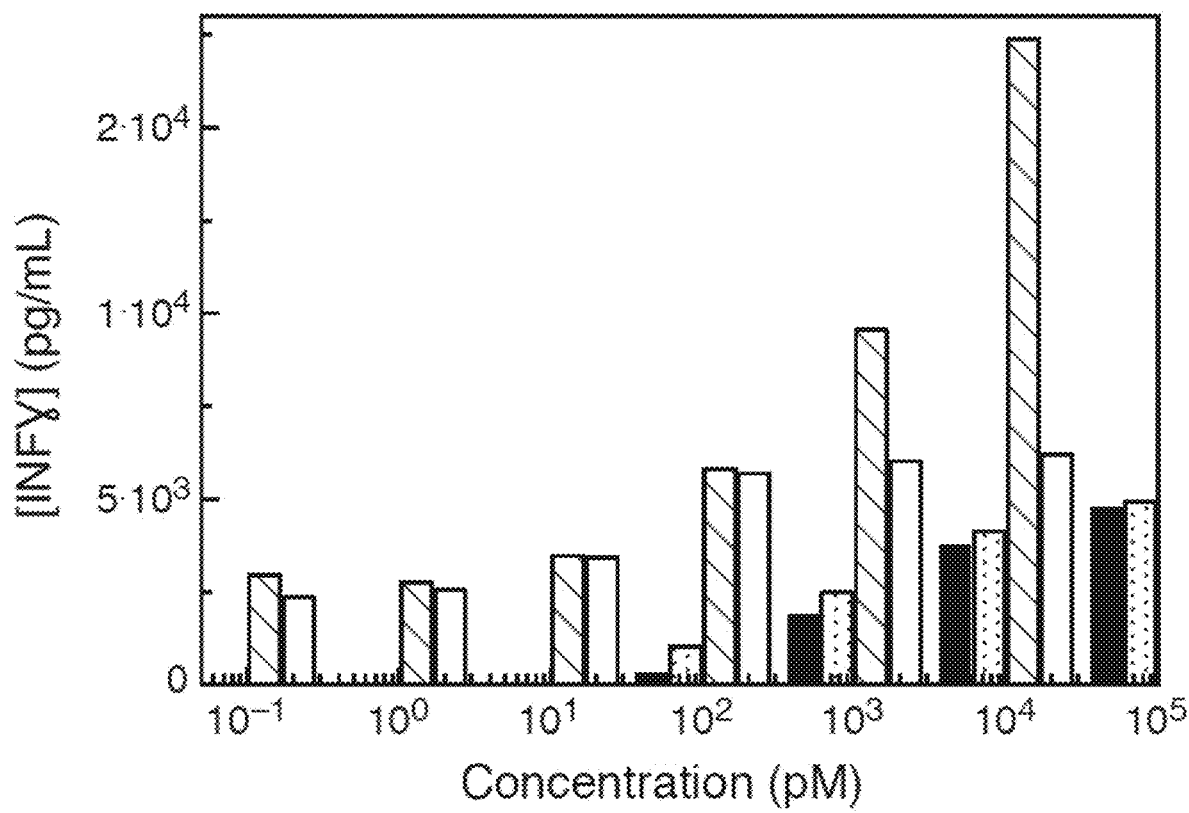

FIG. 59. Cytokine release of IFNγ for multispecific molecule 1 (solid black), multispecific molecule 2 (diagonal line), multispecific molecule 3 (white), and multispecific molecule 4 (dotted).

Figure 60:
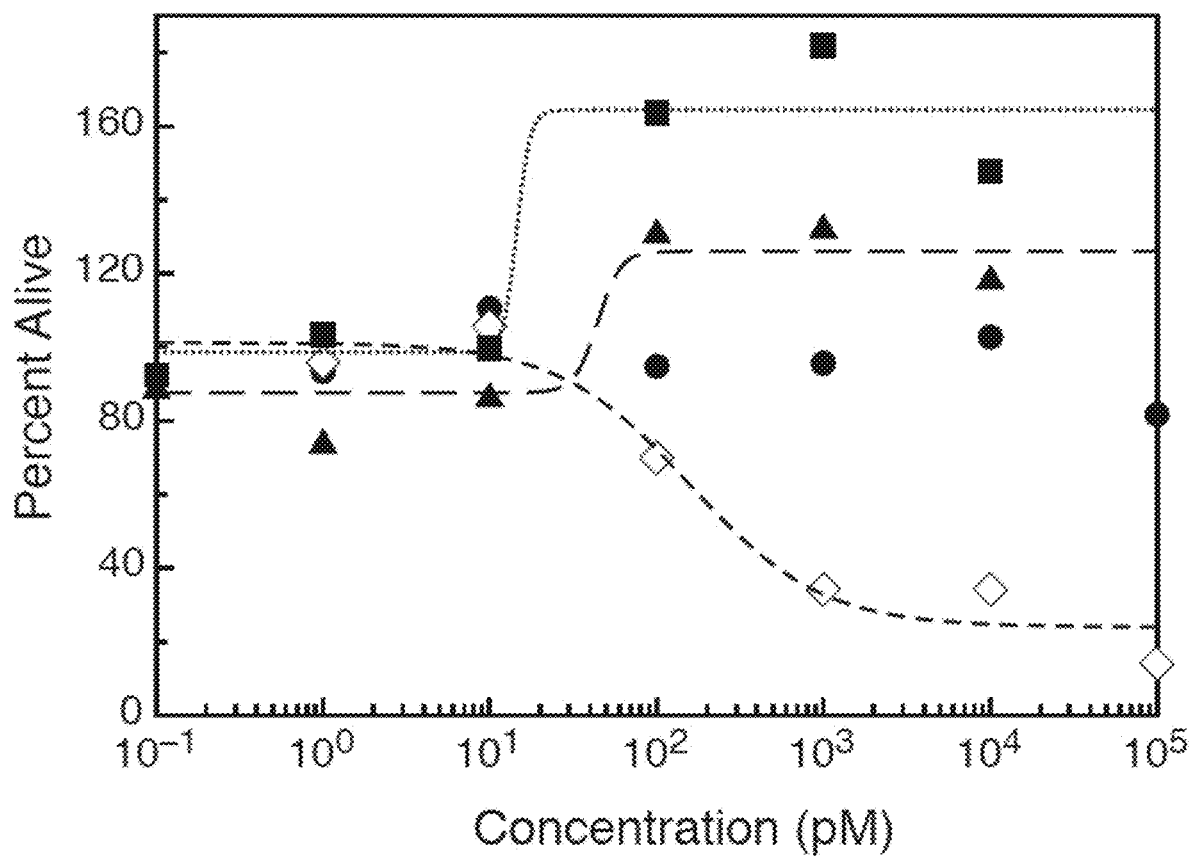

FIG. 60. Cell-killing curves for multispecific molecule 5 (circles), multispecific molecule 6 (diamonds, short dash line), multispecific molecule 7 (squares, dotted line), and multispecific molecule 8 (triangles, long dash line).

Figure 61:
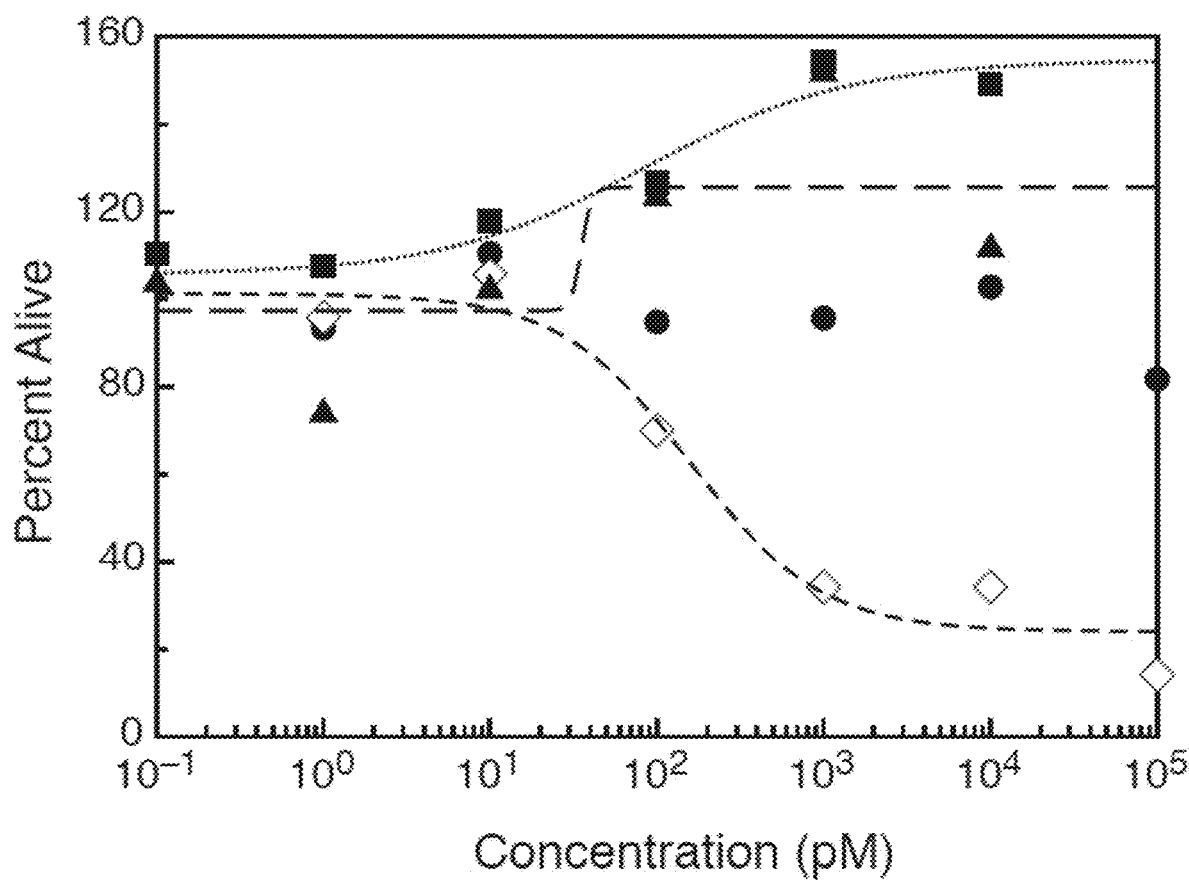

FIG. 61. Cell-killing curves for multispecific molecule 5 (circles), multispecific molecule 6 (diamonds, short dash line), multispecific molecule 9 (squares, dotted line), and multispecific molecule 10 (triangles, long dash line).

Figure 62:
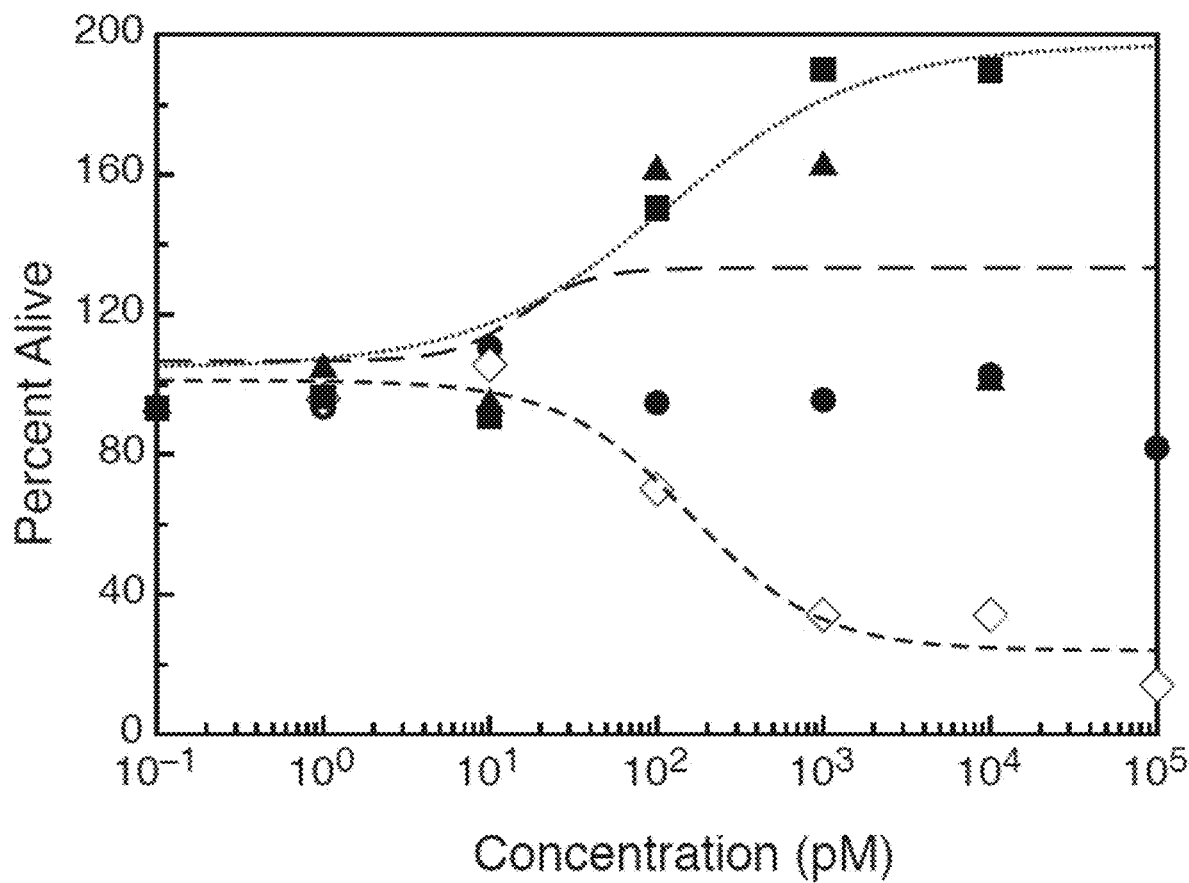

FIG. 62. Cell-killing curves for multispecific molecule 5 (circles), multispecific molecule 6 (diamonds, short dash line), multispecific molecule 11 (squares, dotted line), and multispecific molecule 12 (triangles, long dash line).

Figure 63:
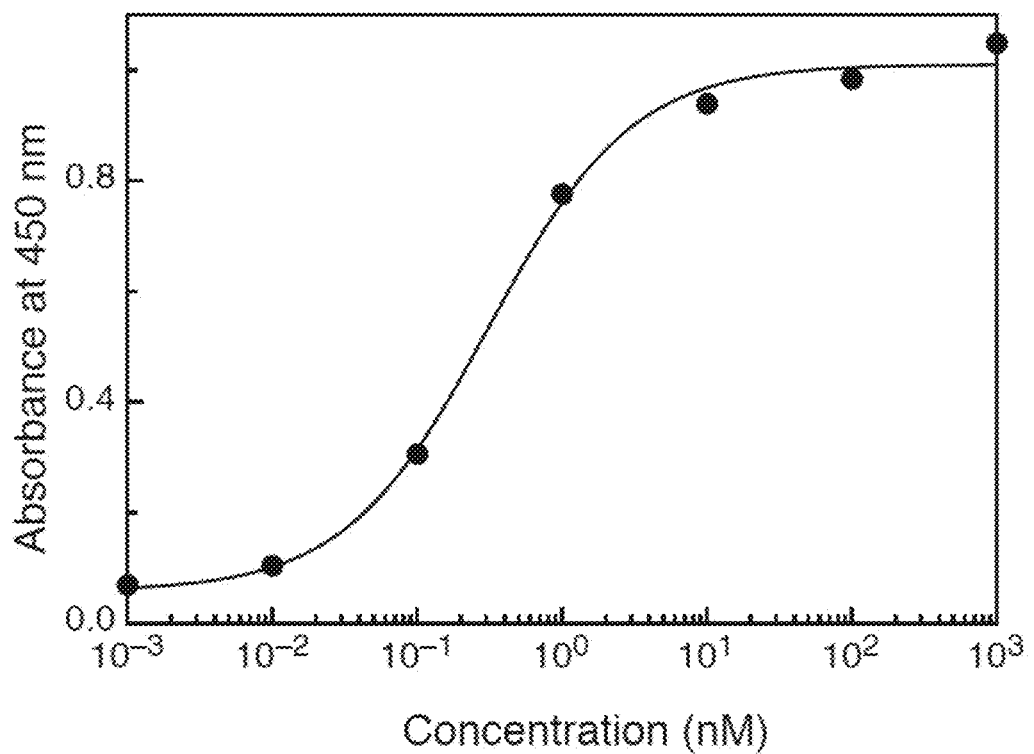

FIG. 63. Binding of multispecific molecule 22 to human mesothelin (from SEQ ID NO: 181).

Figure 64:
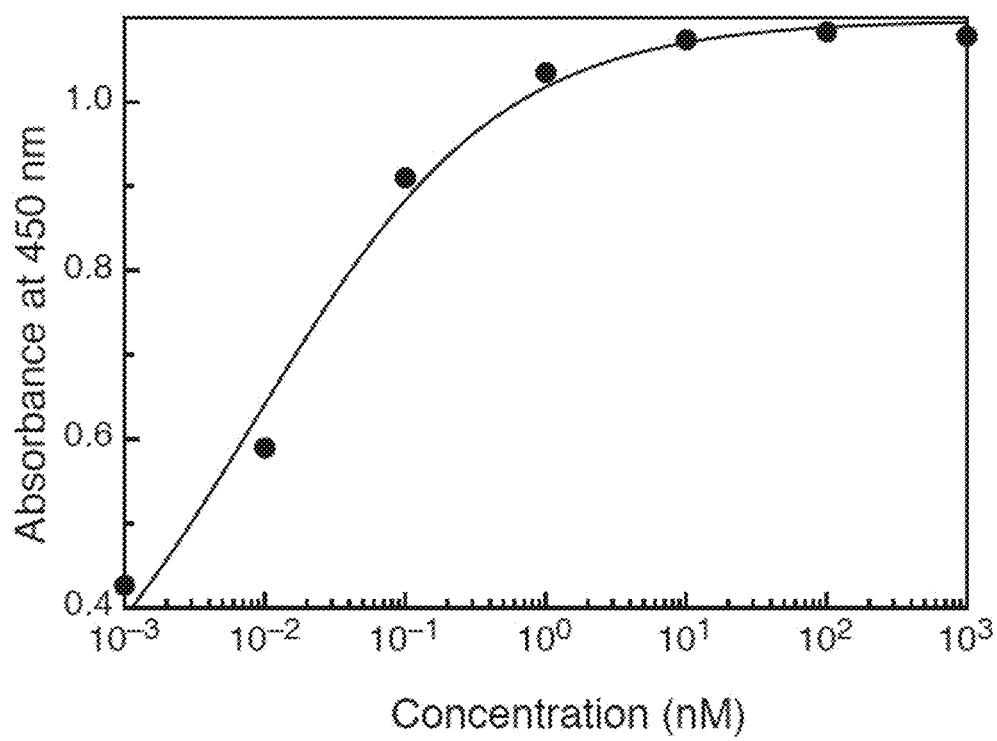

FIG. 64. Binding of multispecific molecule 22 to human PD1L1 (from SEQ ID NO: 178).

Figure 65:
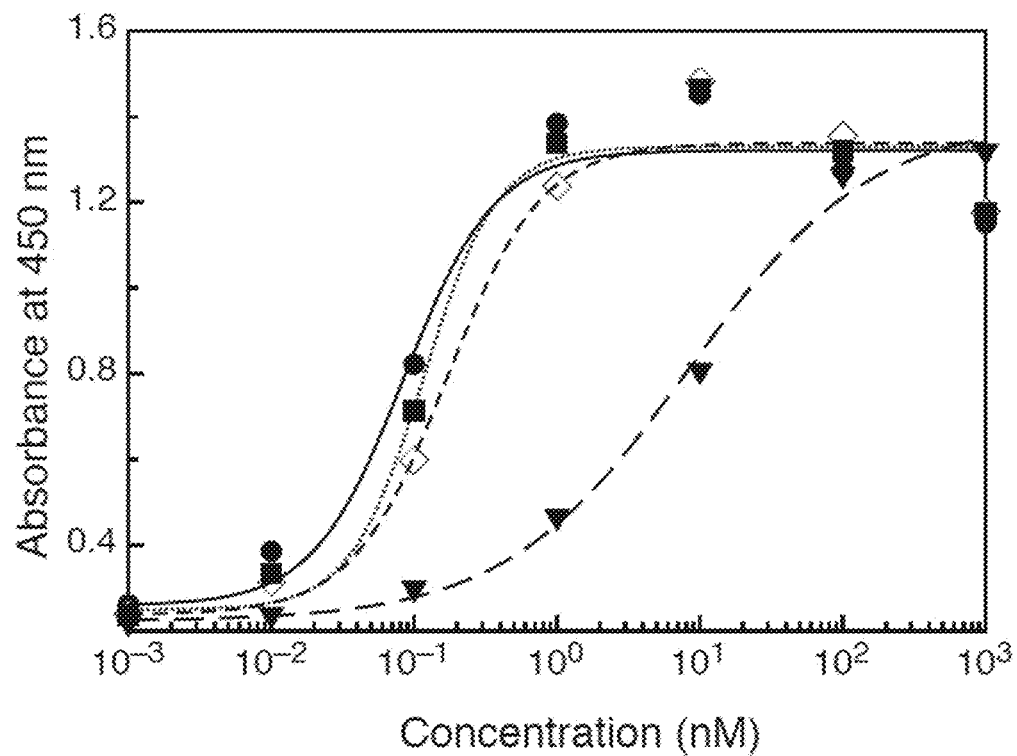

FIG. 65. ELISA of multispecific molecule 13 (circles, solid line), multispecific molecule 16 (diamonds, short dash line), multispecific molecule 17 (squares, dotted line), and multispecific molecule 22 (triangles, long dash line) binding to human IL2Rα (generated from SEQ ID NO: 182).

Figure 66:
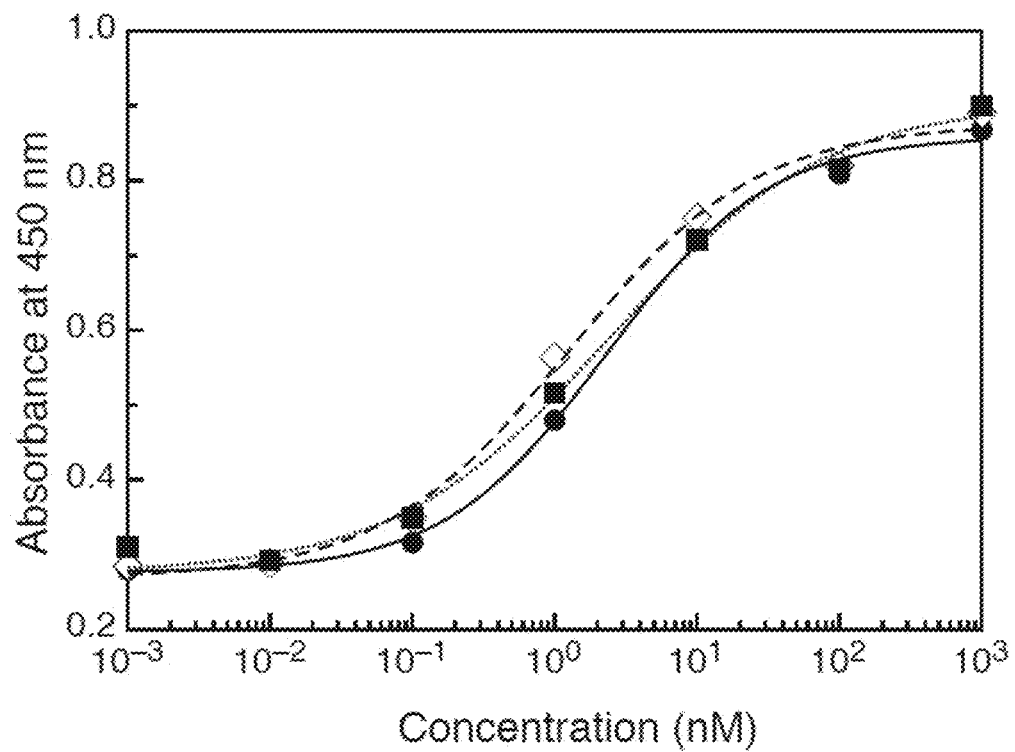

FIG. 66. ELISA of multispecific molecule 14 (circles, solid line), multispecific molecule 21 (diamonds, short dash line), and multispecific molecule 22 (squares, dotted line) binding to human NKp46 (generated from SEQ ID NO: 179).

Figure 67:
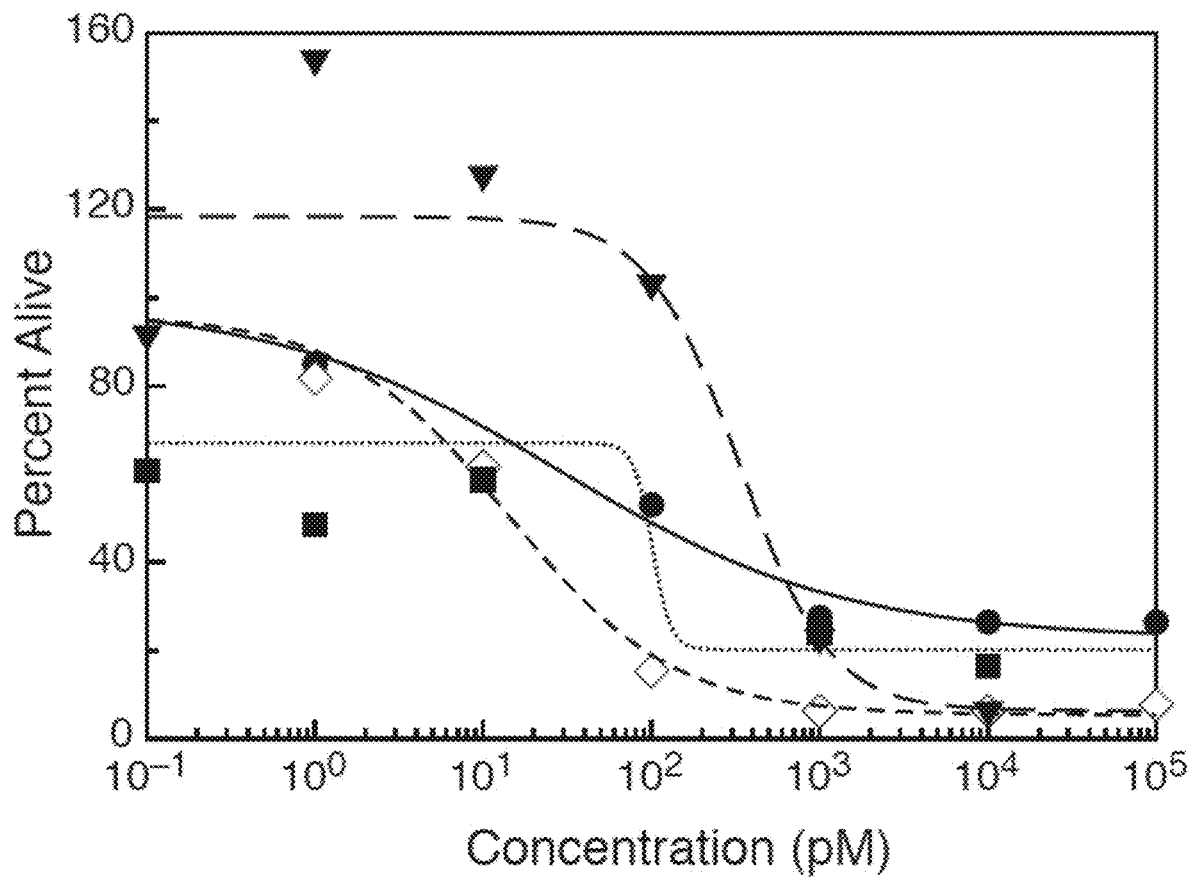

FIG. 67. Cell-killing curves for multispecific molecule 18 (circles, solid line), multispecific molecule 13 (diamonds, short dash line), multispecific molecule 14 (squares, dotted line), and multispecific molecule 16 (triangles, long dash line).

Figure 68:
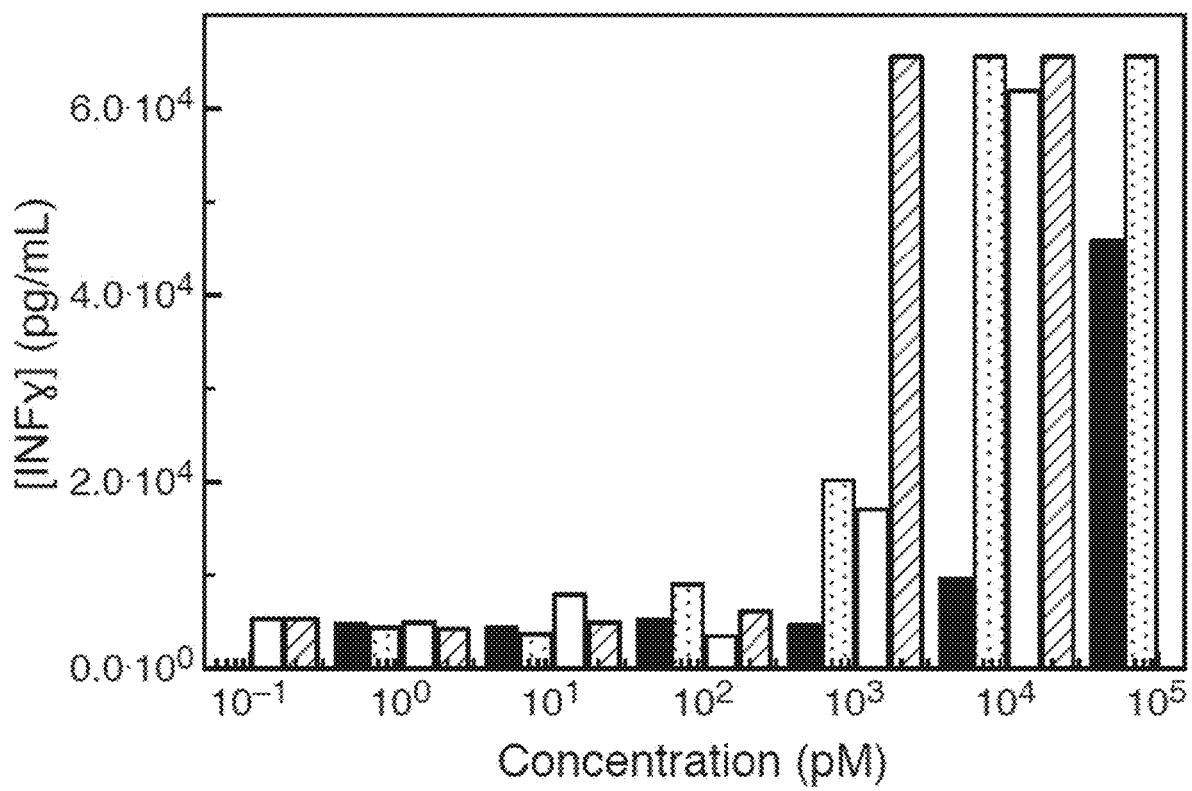

FIG. 68. Cytokine release of IFNγ for multispecific molecule 18 (solid black), multispecific molecule 13 (dotted), multispecific molecule 14 (white), and multispecific molecule 16 (diagonal lines).

Figure 69:
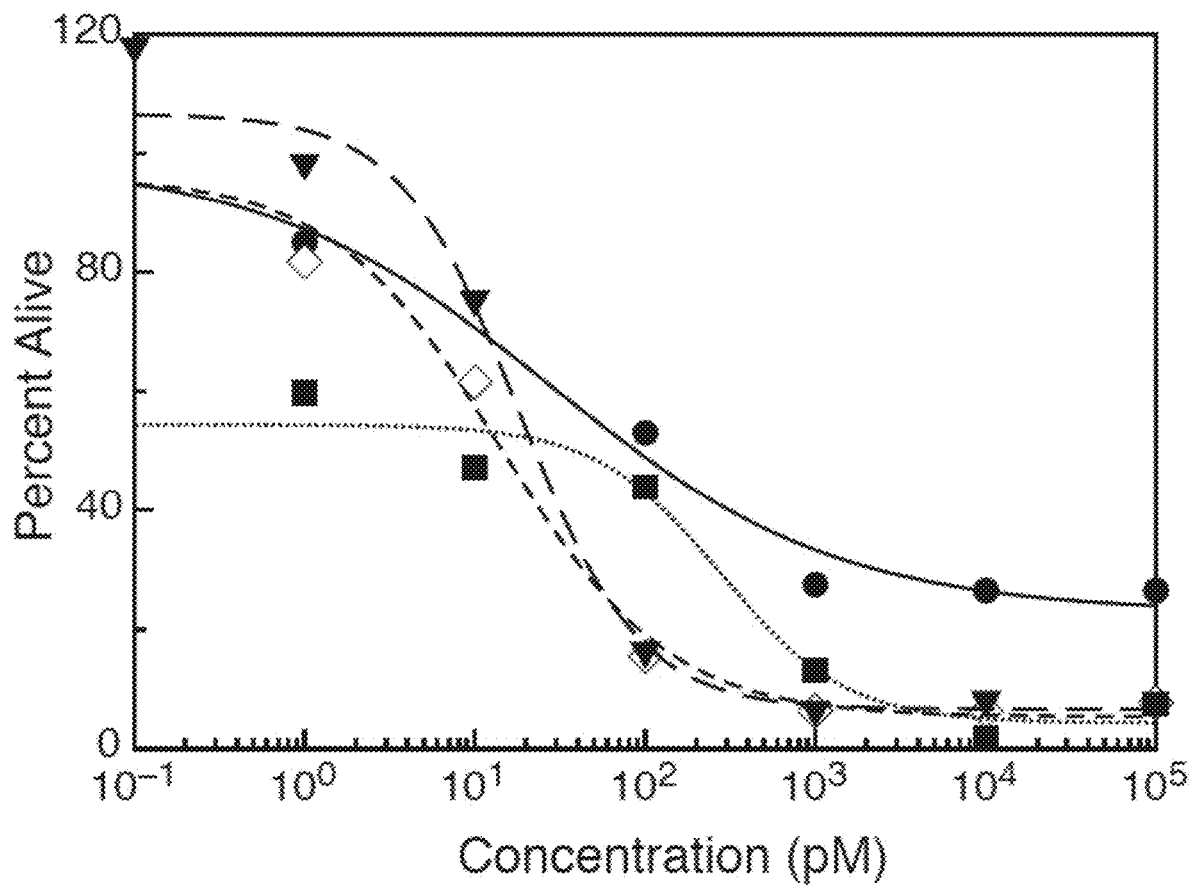

FIG. 69. Cell-killing curves for multispecific molecule 18 (circles, solid line), multispecific molecule 13 (diamonds, short dash line), multispecific molecule 15 (squares, dotted line), and multispecific molecule 17 (triangles, long dash line).

Figure 70:
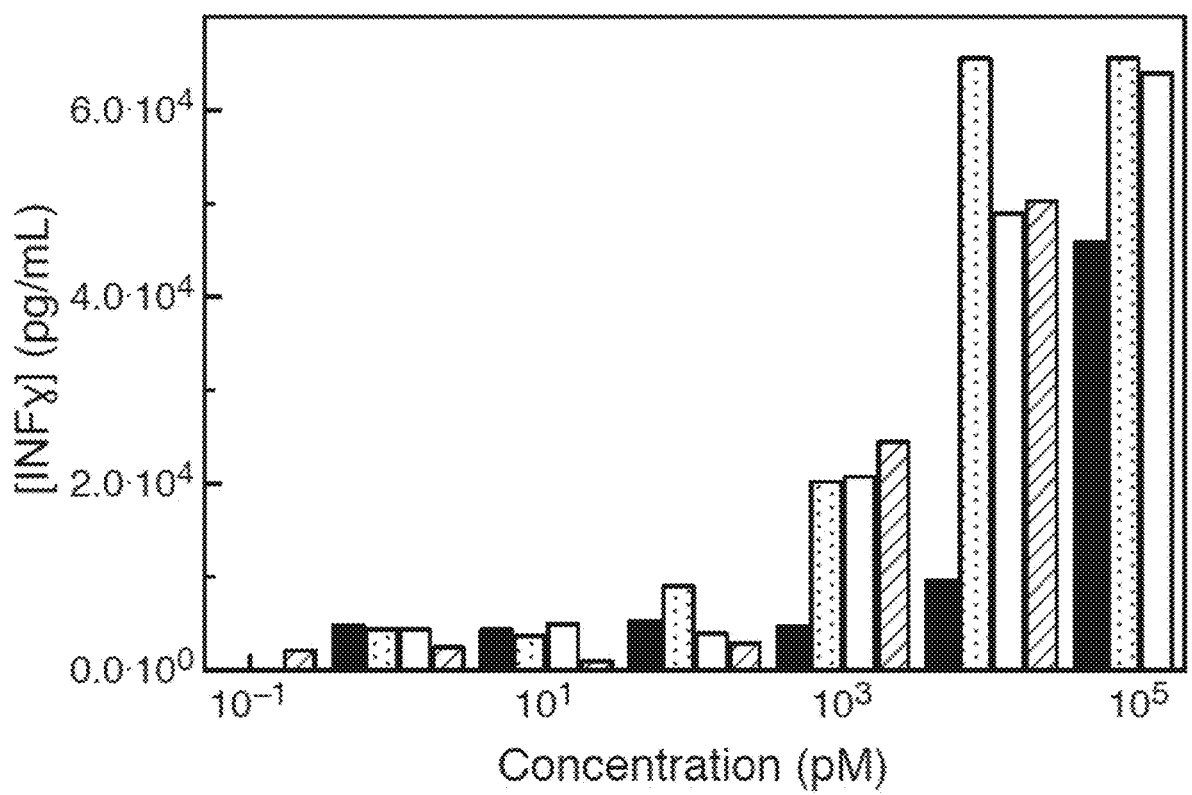

FIG. 70. Cytokine release of IFNγ for multispecific molecule 18 (solid black), multispecific molecule 13 (dotted), multispecific molecule 15 (white), and multispecific molecule 17 (diagonal lines).

Figure 71:
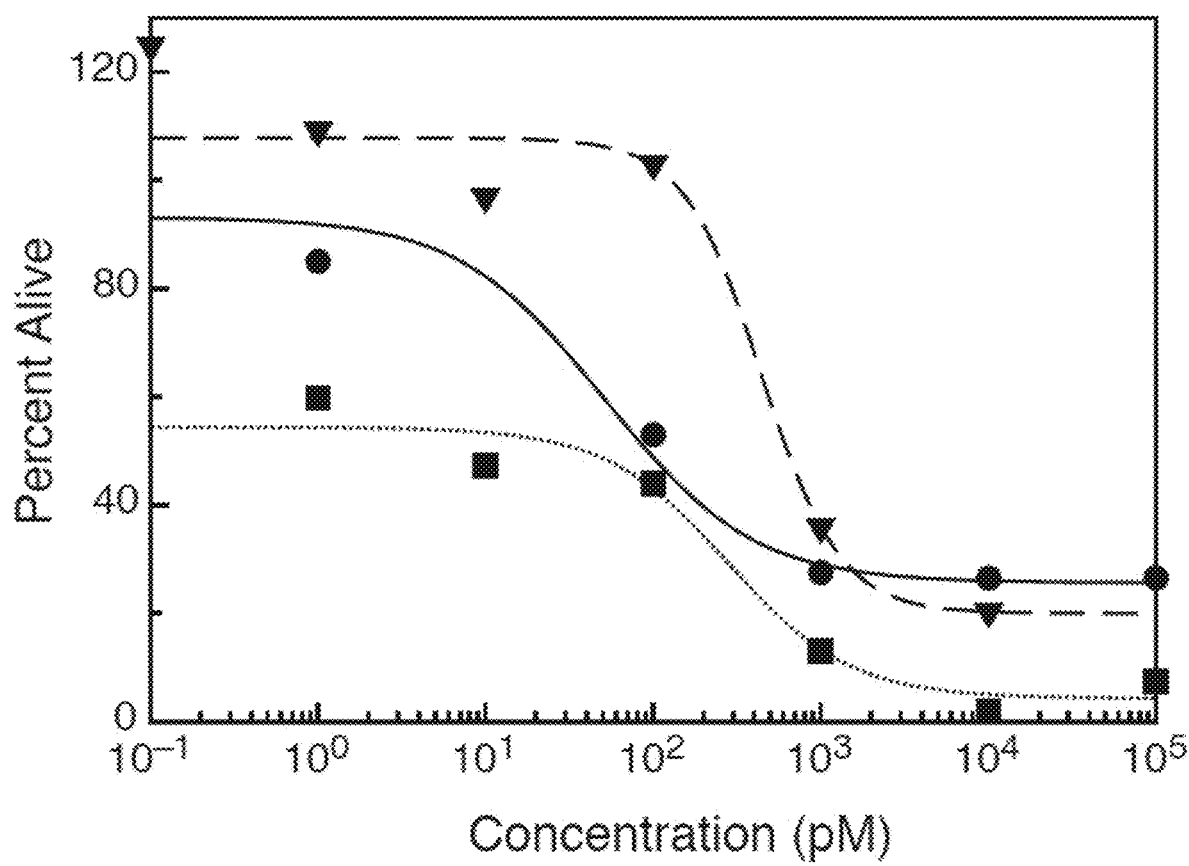

FIG. 71. Cell-killing curves for multispecific molecule 18 (circles, solid line), multispecific molecule 15 (squares, dotted line), and multispecific molecule 20 (triangles, long dash line).

Figure 72:
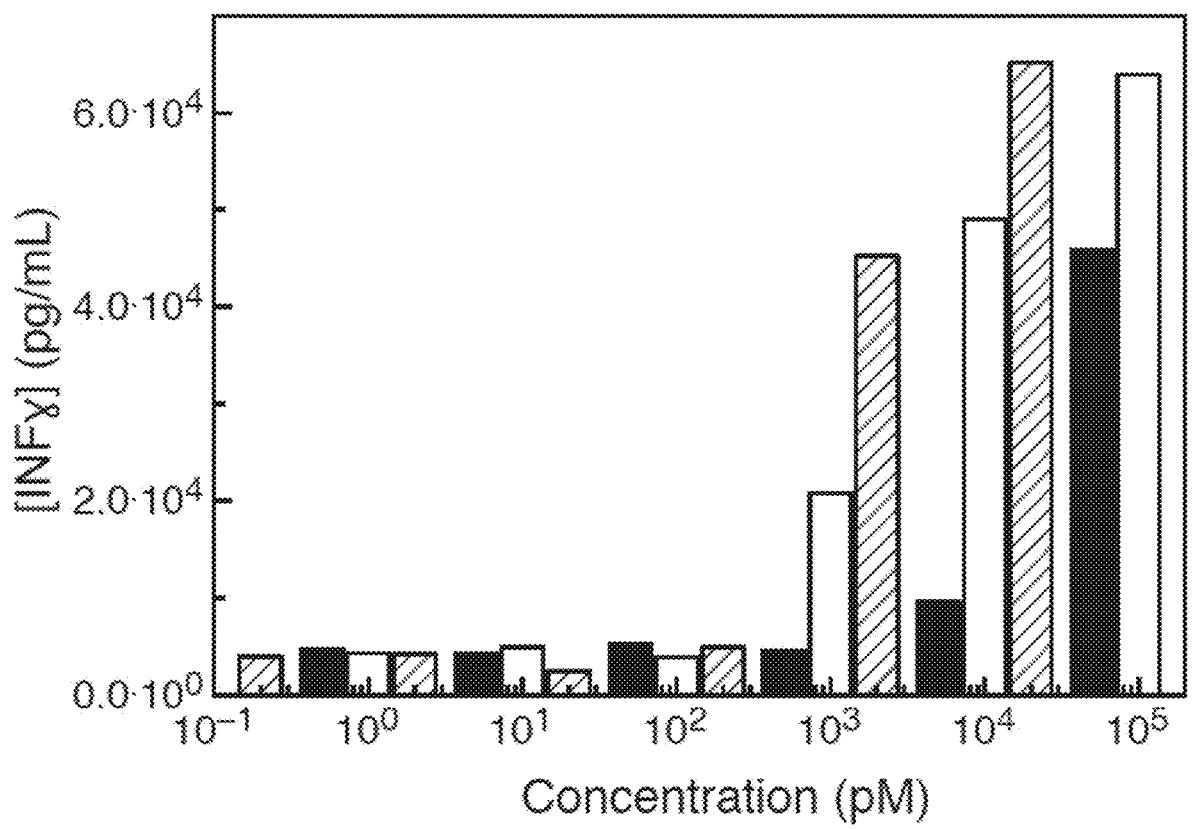

FIG. 72. Cytokine release of IFNγ for multispecific molecule 18 (solid black), multispecific molecule 15 (white), and multispecific molecule 20 (diagonal lines).

Figure 73:
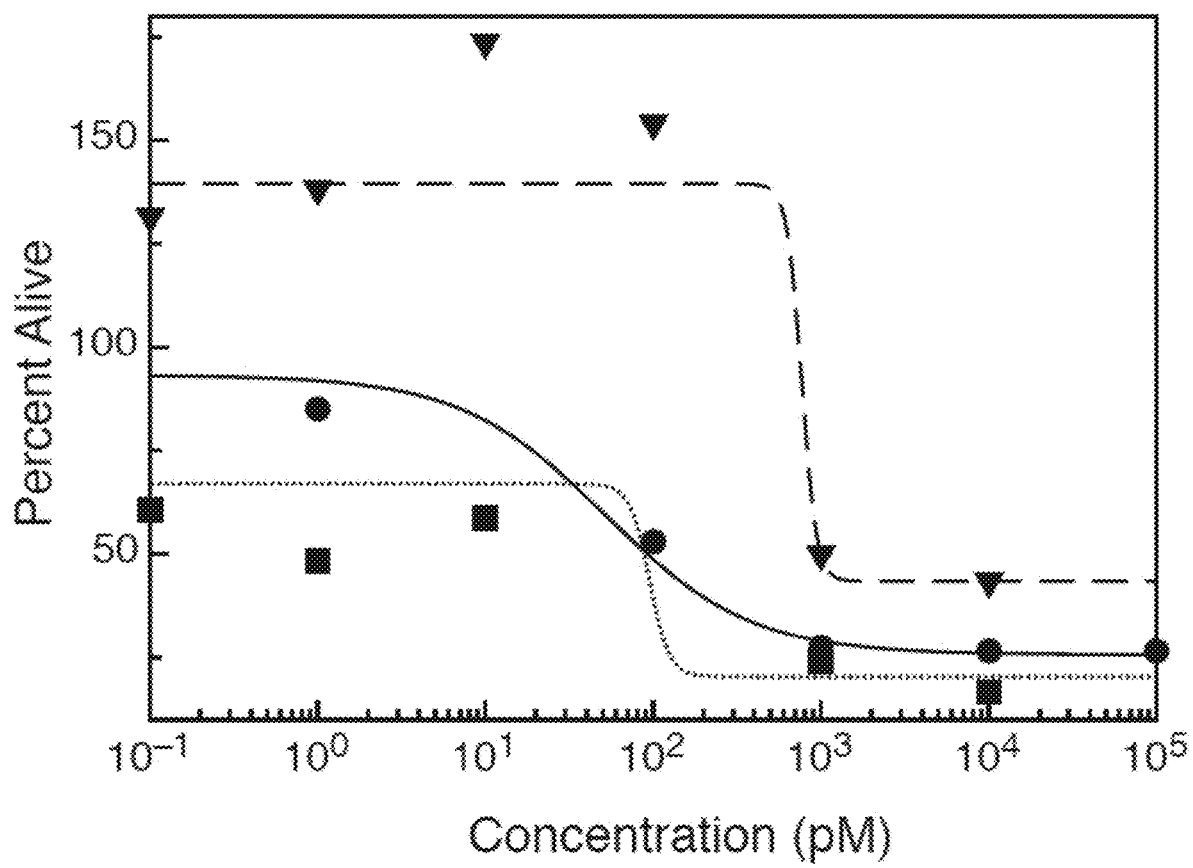

FIG. 73. Cell-killing curves for multispecific molecule 18 (circles, solid line), multispecific molecule 14 (squares, dotted line), and multispecific molecule 21 (triangles, long dash line).

Figure 74:
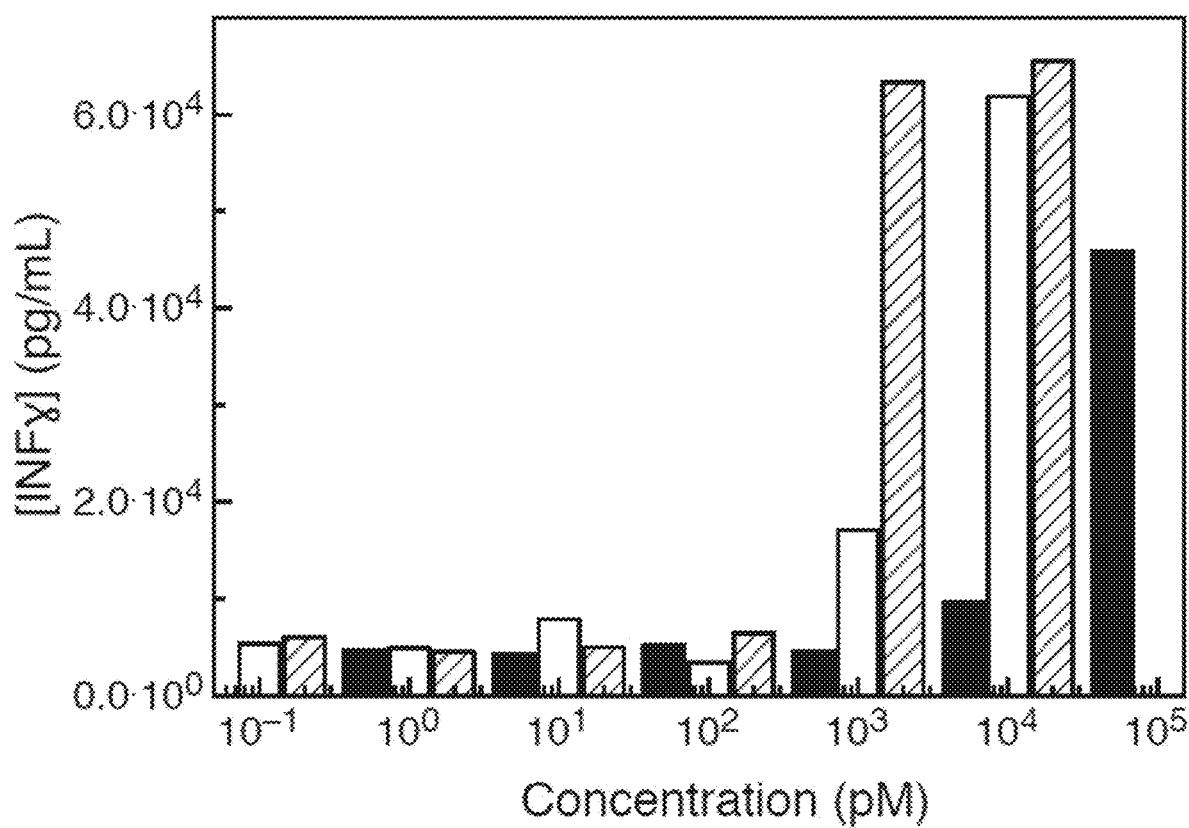

FIG. 74. Cytokine release of IFNγ for multispecific molecule 18 (solid black), multispecific molecule 14 (white), and multispecific molecule 21 (diagonal lines).

Figure 75:
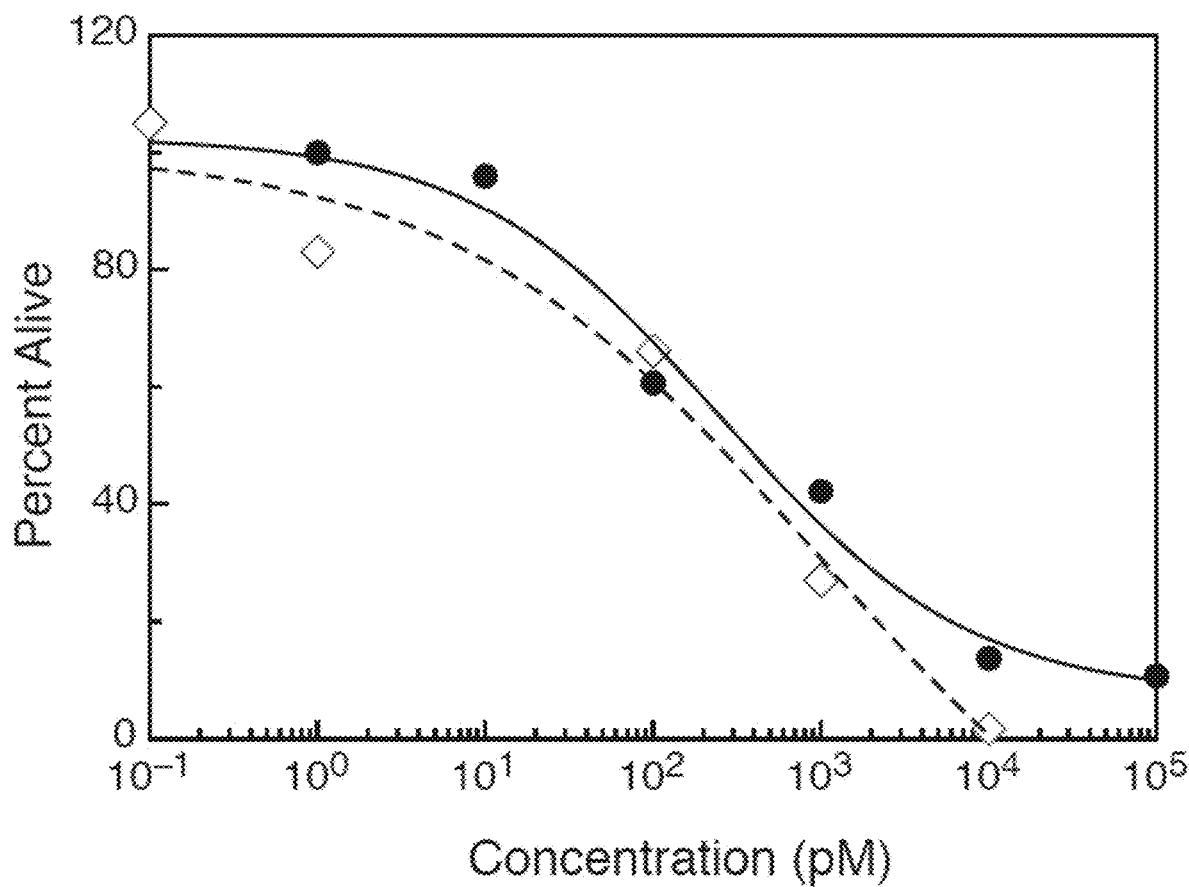

FIG. 75. Cell-killing curves for multispecific molecule 23 (circles, solid line) and multispecific molecule 22 (diamonds, dashed line).

Figure 76:
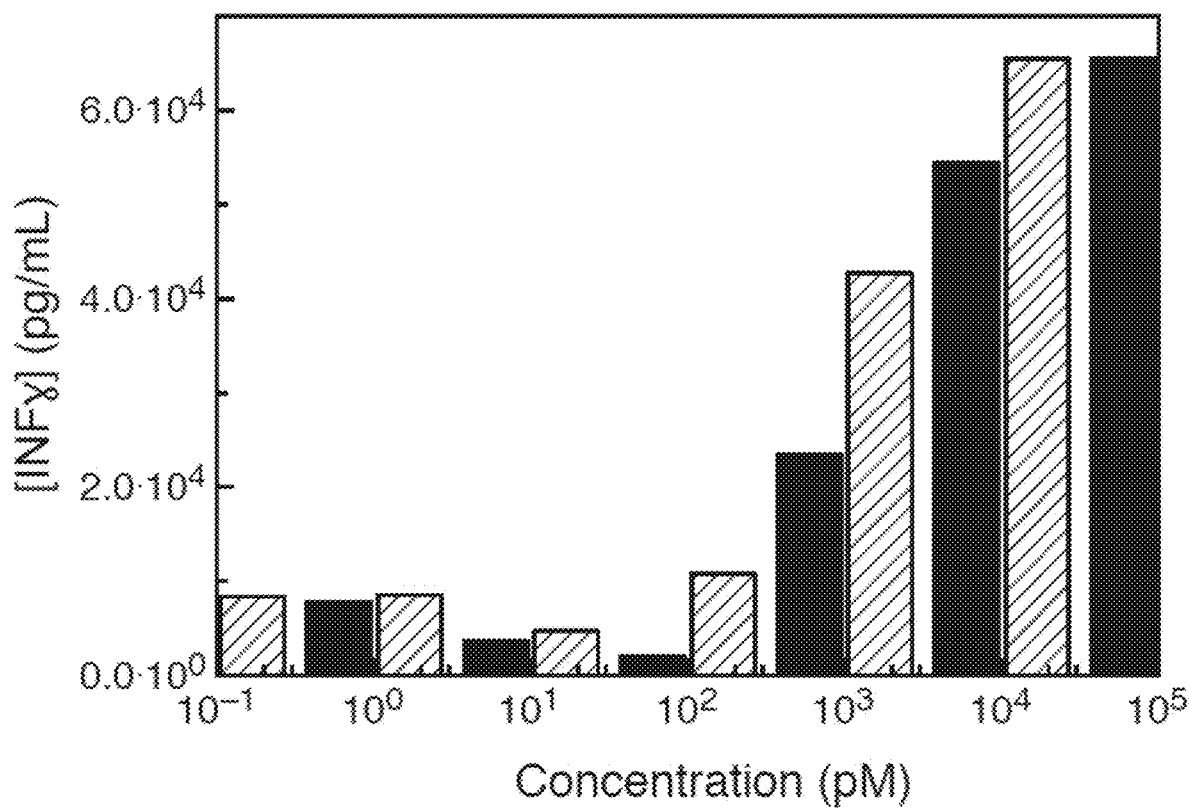

FIG. 76. Cytokine release of IFNγ for multispecific molecule 23 (solid black) and multispecific molecule 22 (diagonal lines).

Figure 77:
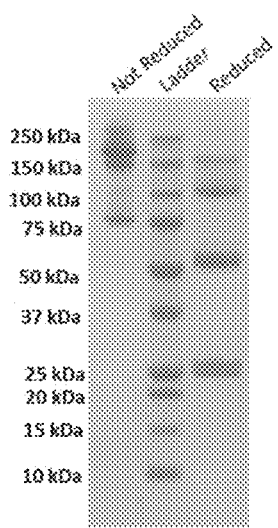
Figure 78:
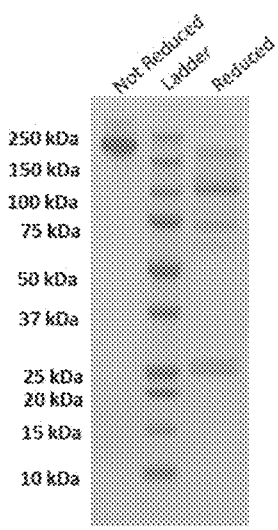
Figure 79:
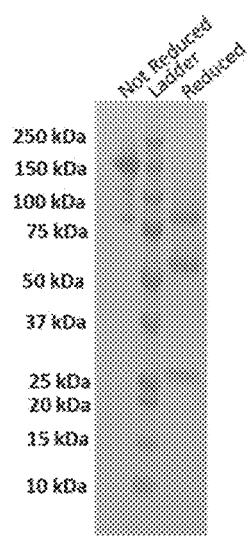
Figure 80:
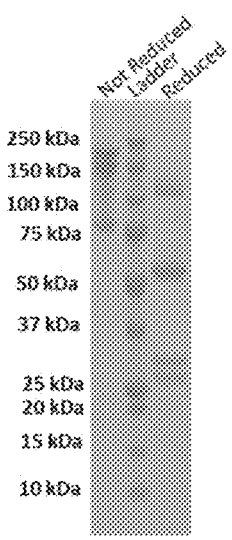
Figure 81:
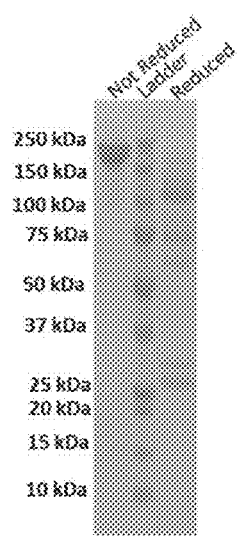
Figure 82:
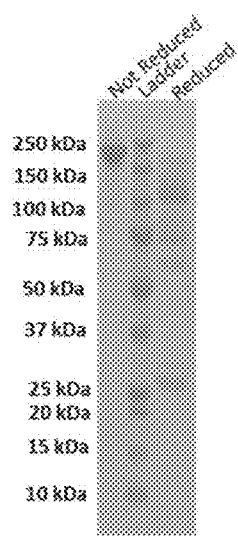
Figure 83:
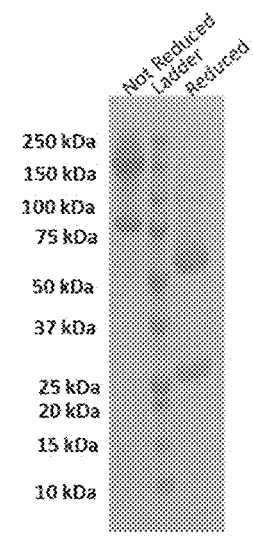
Figure 84:
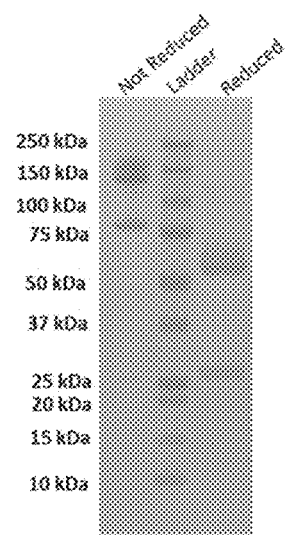
Figure 85:
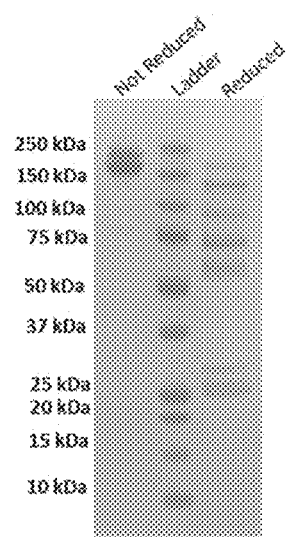
Figure 86:
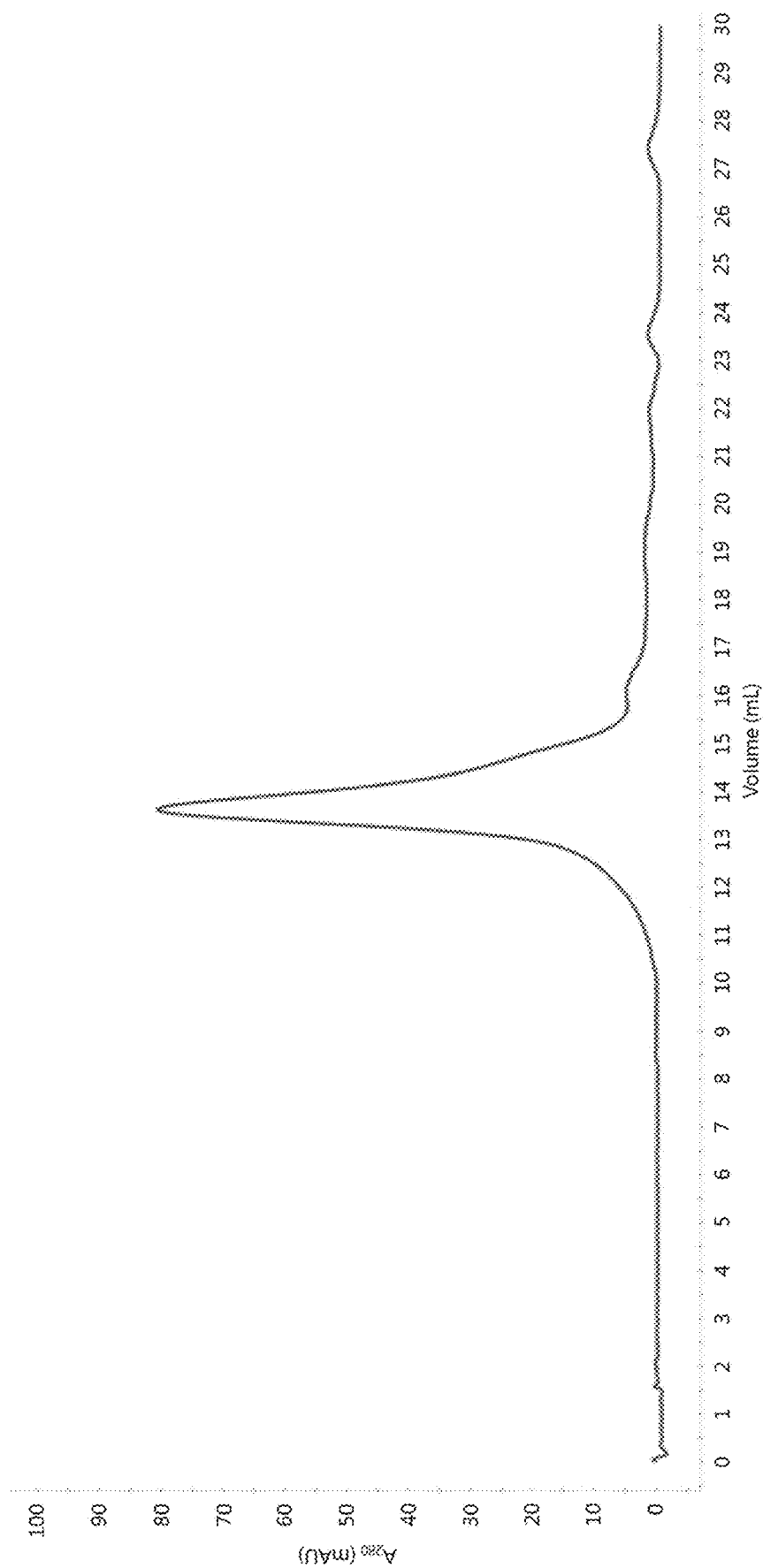
Figure 87:
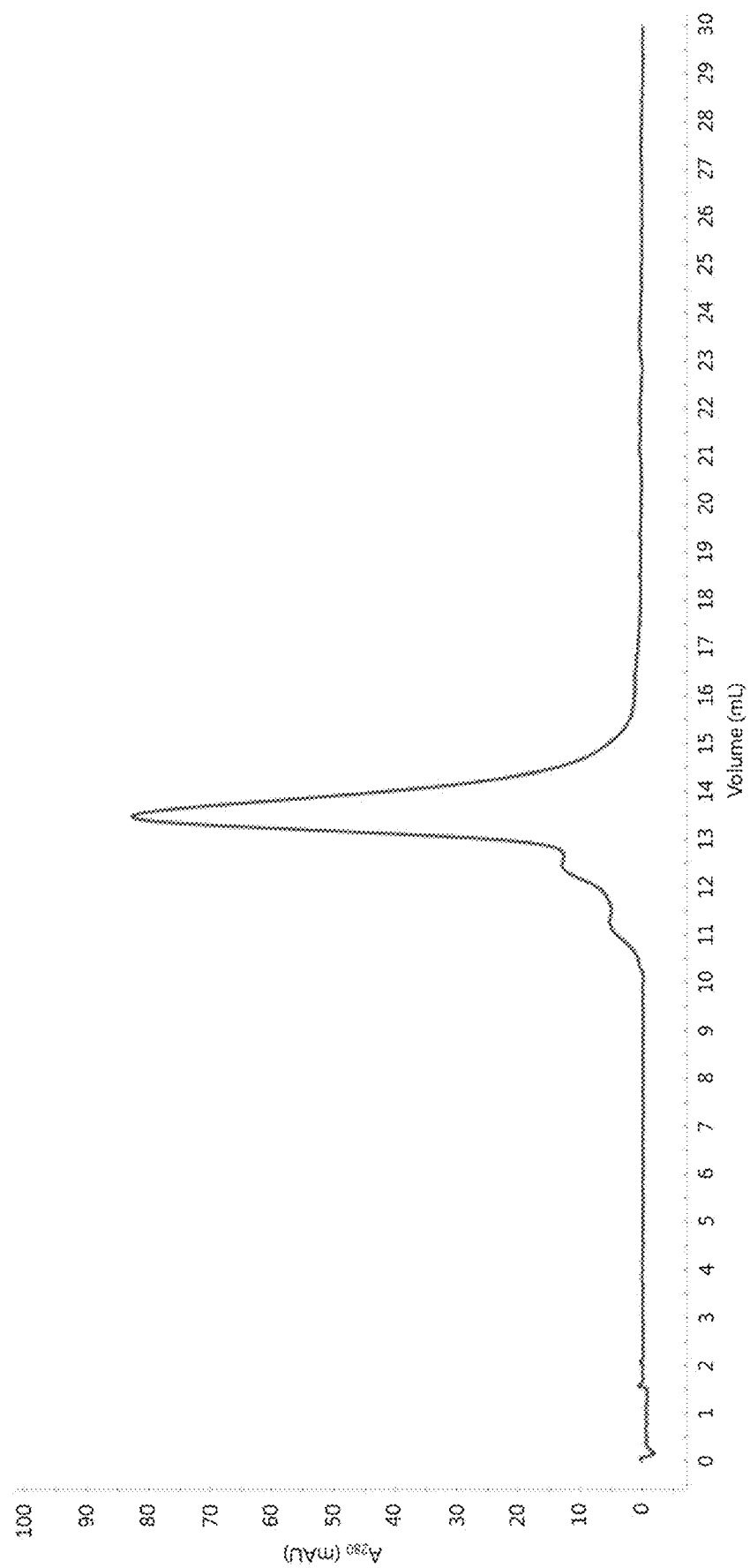
Figure 88:
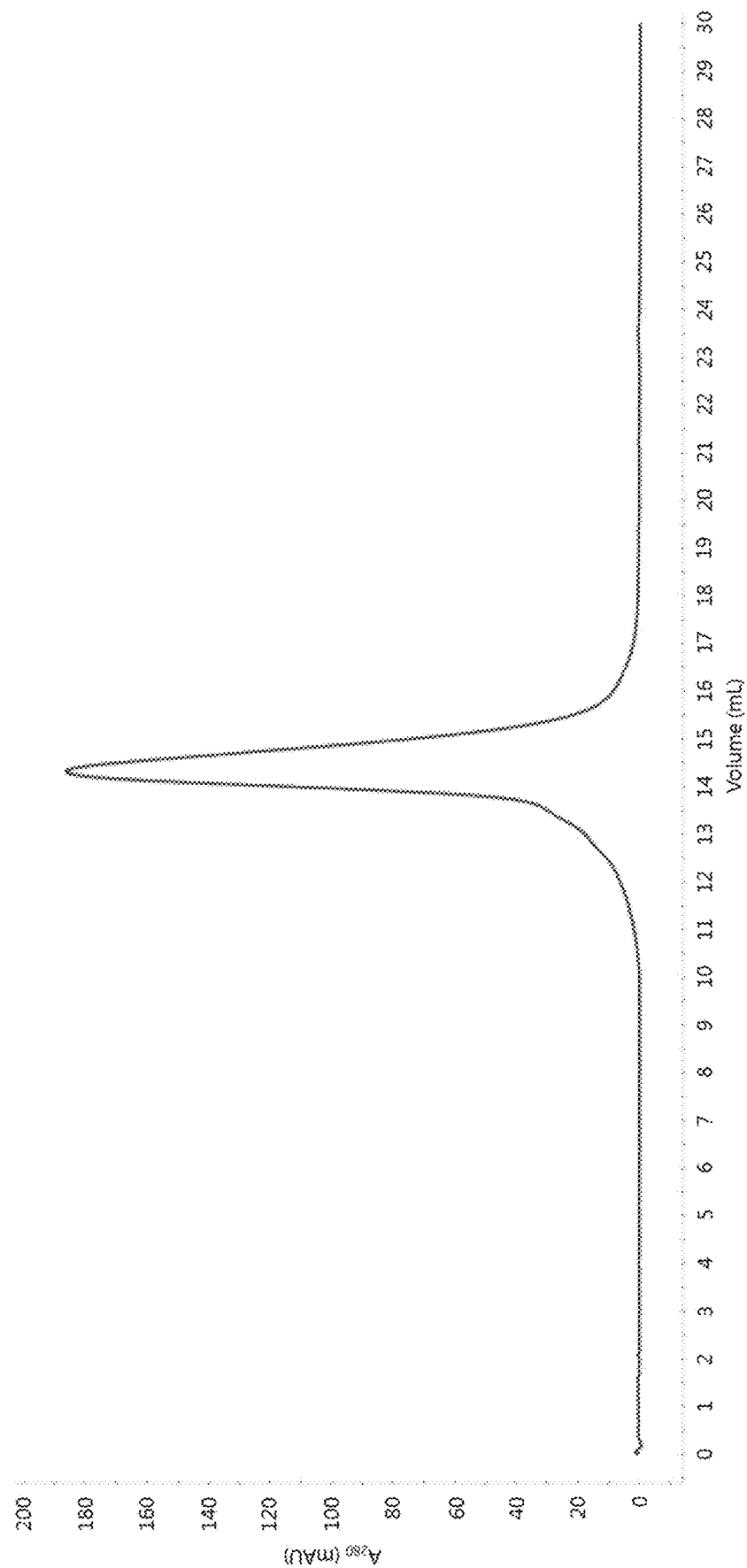
Figure 89:
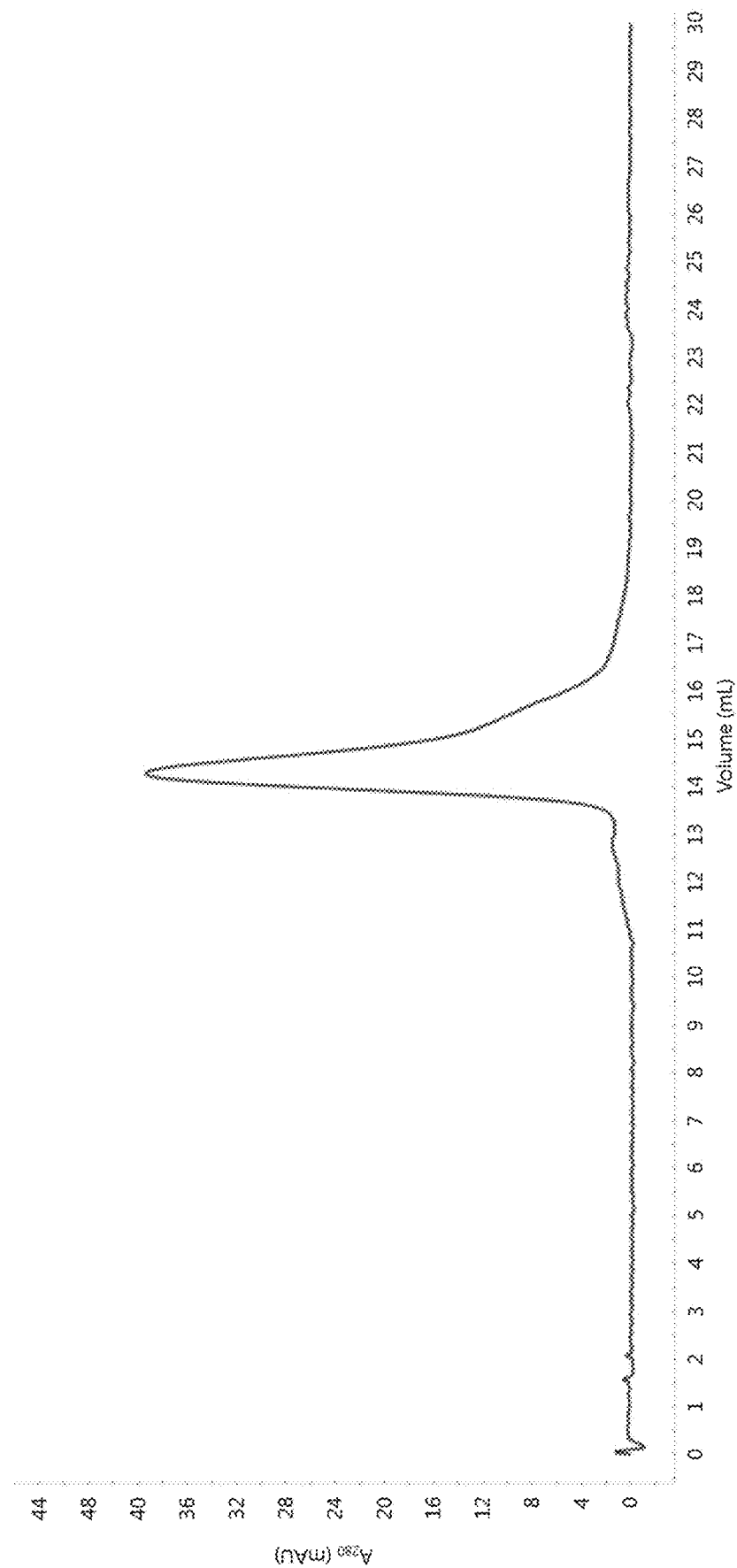
Figure 90:
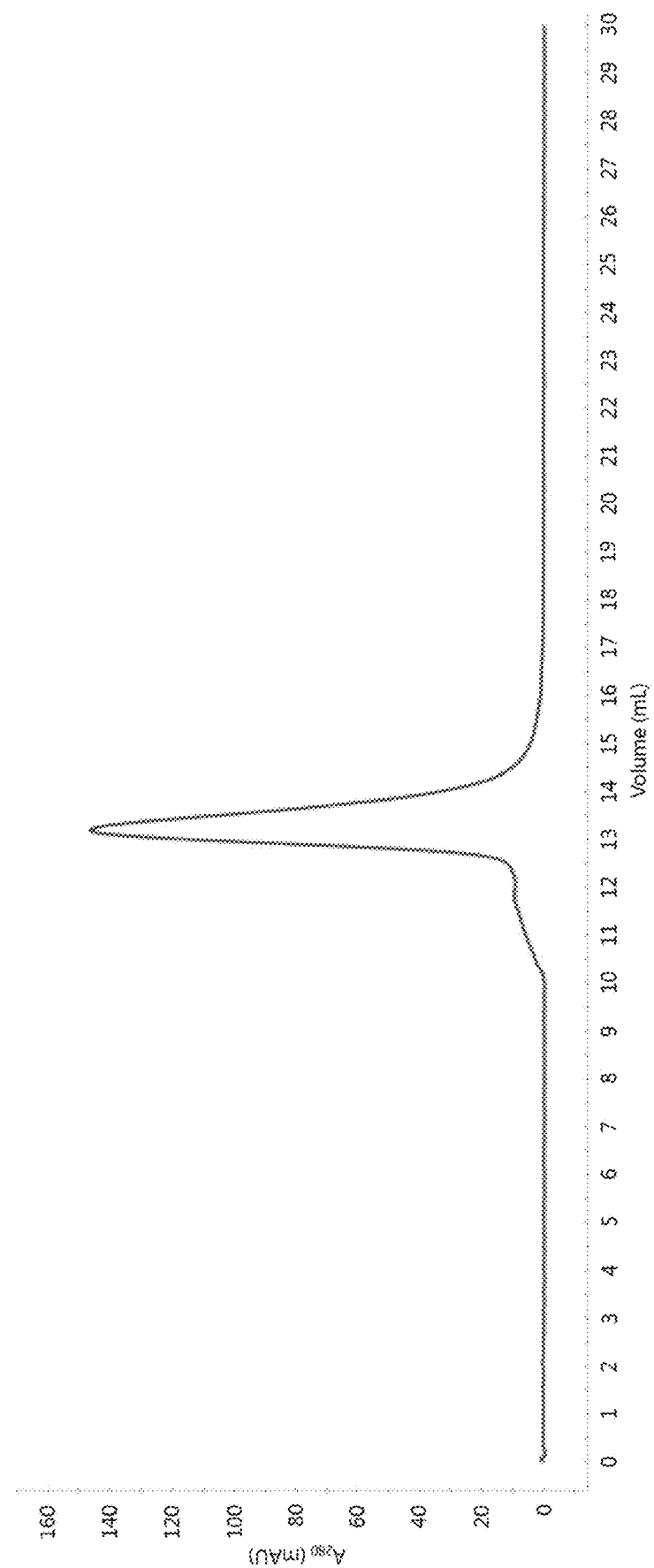
Figure 91:
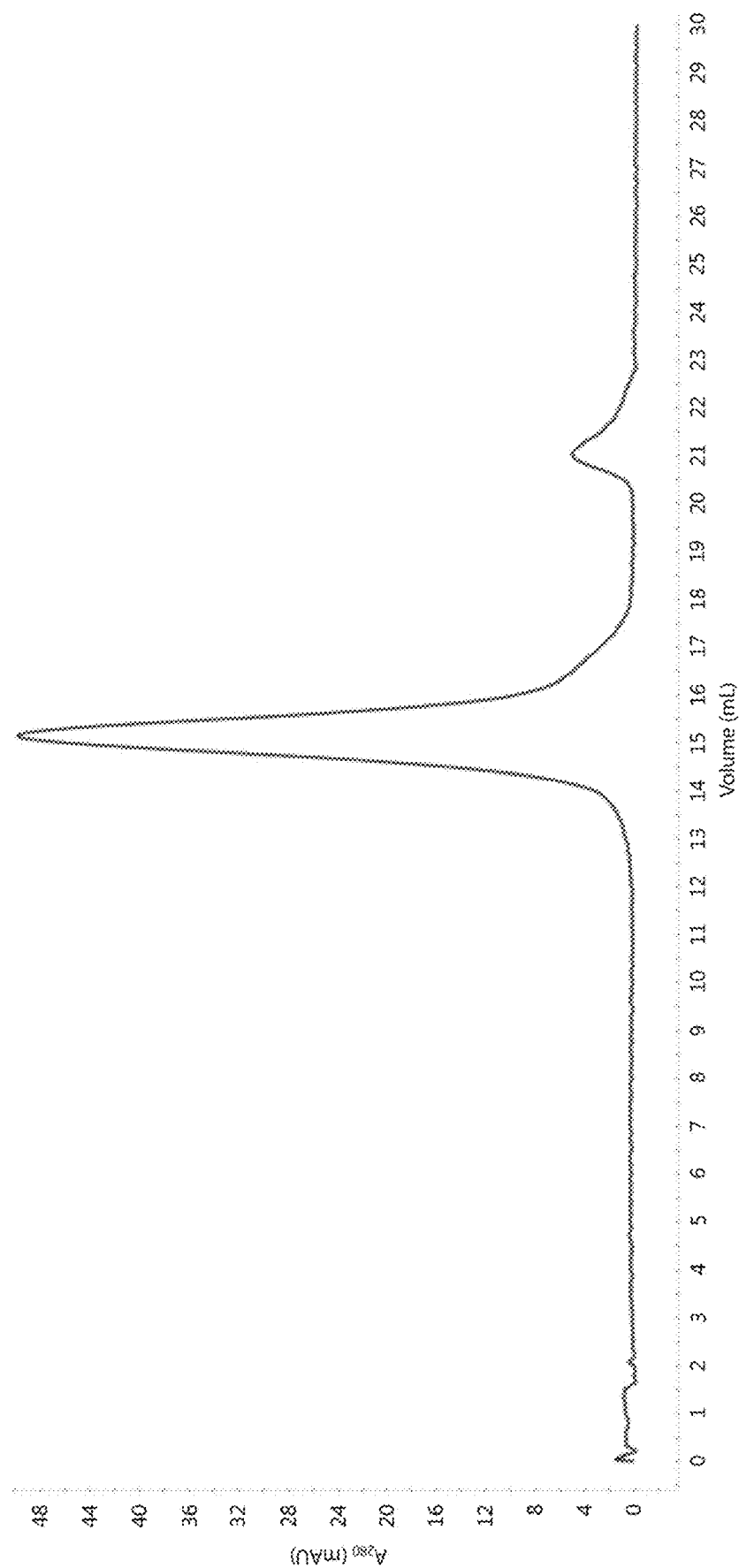
Figure 92:
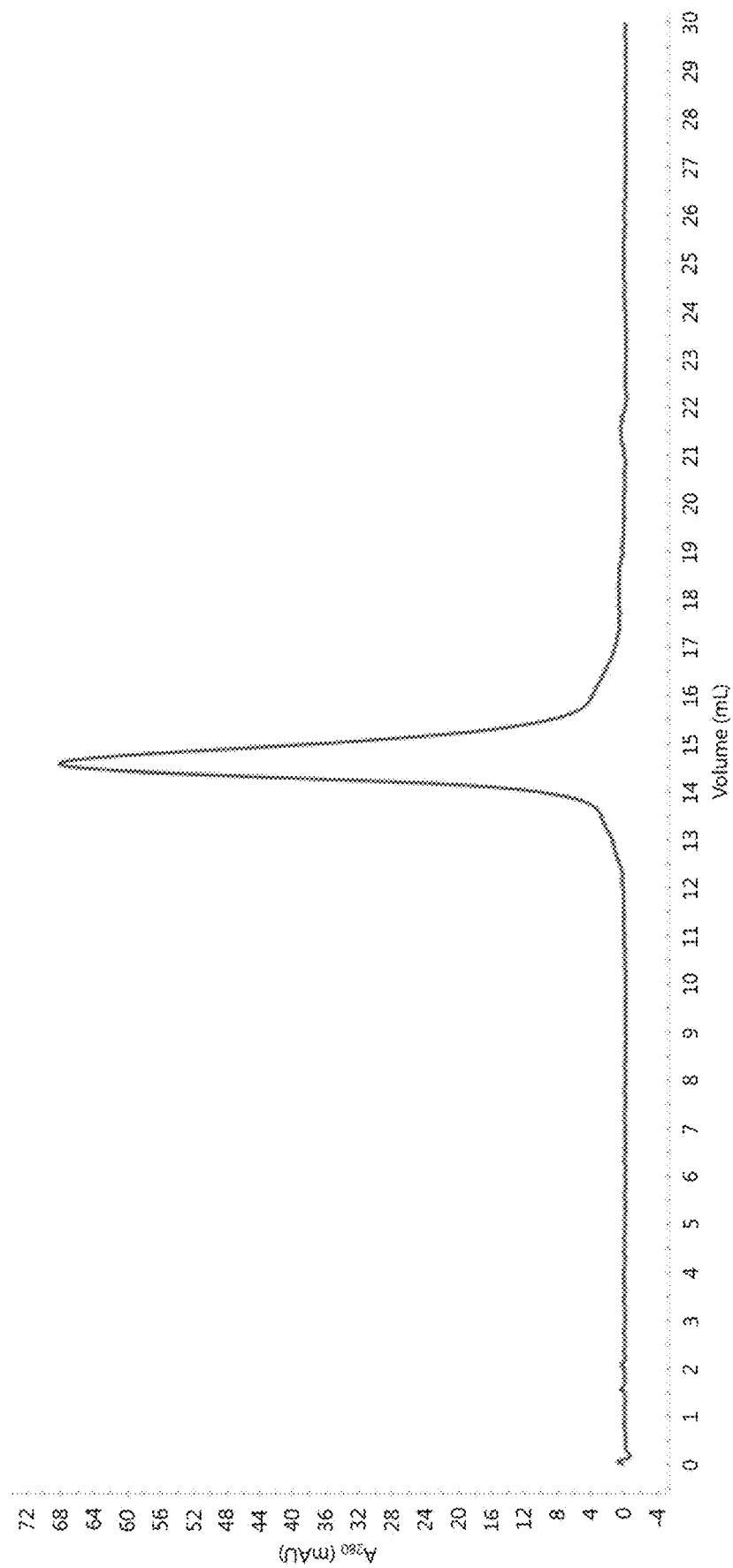

FIG. 77. Gel of multispecific molecule 24.
FIG. 78. Gel of multispecific molecule 25.
FIG. 79. Gel of multispecific molecule 26.
FIG. 80. Gel of multispecific molecule 27.
FIG. 81. Gel of multispecific molecule 28.
FIG. 82. Gel of multispecific molecule 29.
FIG. 83. Gel of multispecific molecule 30.
FIG. 84. Gel of multispecific molecule 31.
FIG. 85. Gel of multispecific molecule 32.
FIG. 86. Size exclusion chromatogram of multispecific molecule 24.
FIG. 87. Size exclusion chromatogram of multispecific molecule 25.
FIG. 88. Size exclusion chromatogram of multispecific molecule 26.
FIG. 89. Size exclusion chromatogram of multispecific molecule 28.
FIG. 90. Size exclusion chromatogram of multispecific molecule 29.
FIG. 91. Size exclusion chromatogram of multispecific molecule 30.
FIG. 92. Size exclusion chromatogram of multispecific molecule 31.

Figure 93:
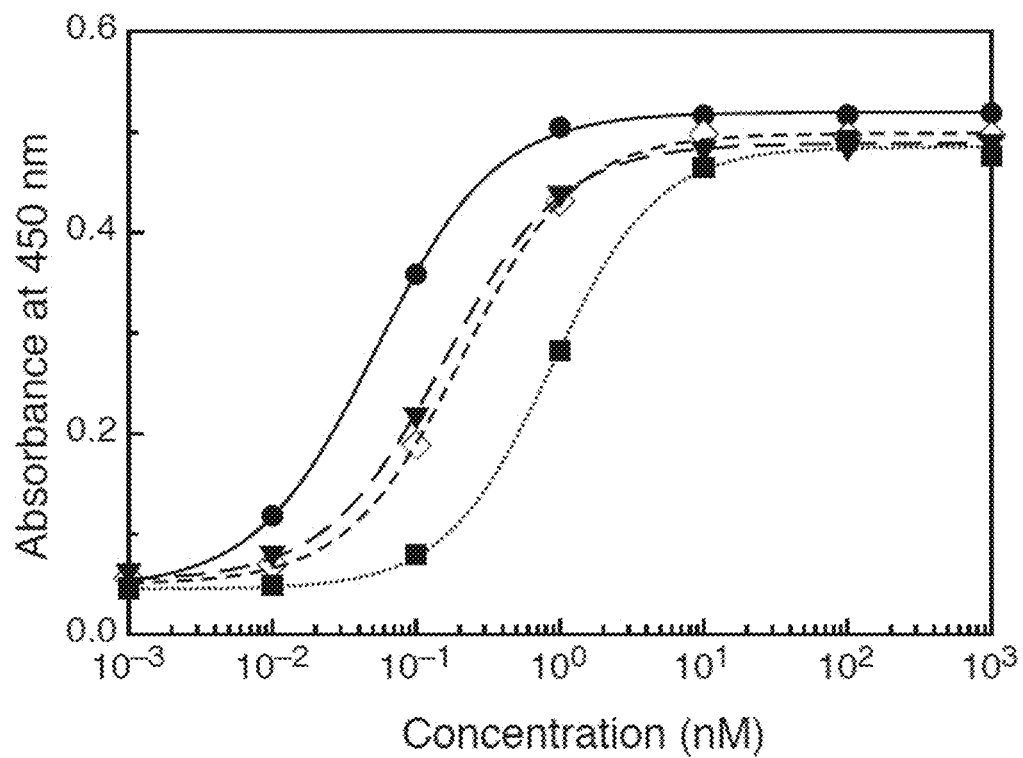

FIG. 93. ELISA of multispecific molecule 27 (circles, solid line), multispecific molecule 28 (diamonds, short dash line), multispecific molecule 29 (squares, dotted line), and multispecific molecule 32 (triangles, long dash line) with human PDL1 from SEQ ID NO: 178.

Figure 94:
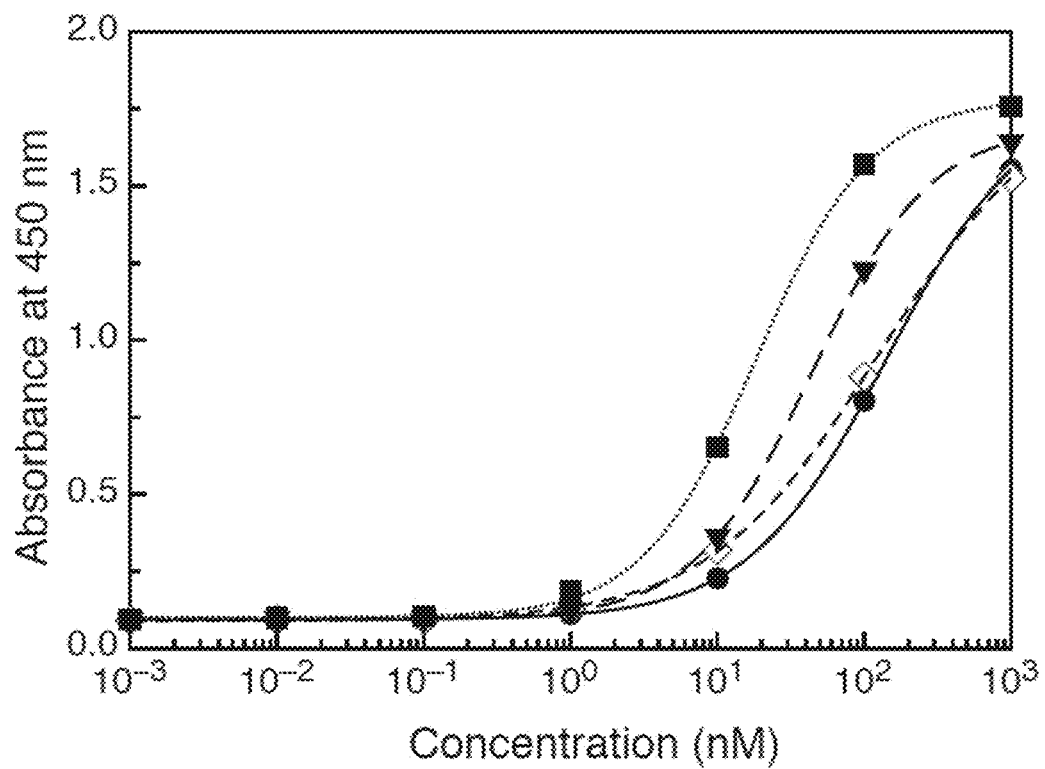

FIG. 94. ELISA of multispecific molecule 24 (circles, solid line), multispecific molecule 25 (diamonds, short dash line), multispecific molecule 26 (squares, dotted line), and multispecific molecule 27 (triangles, long dash line) with human FAP from SEQ ID NO: 225.

Figure 95:
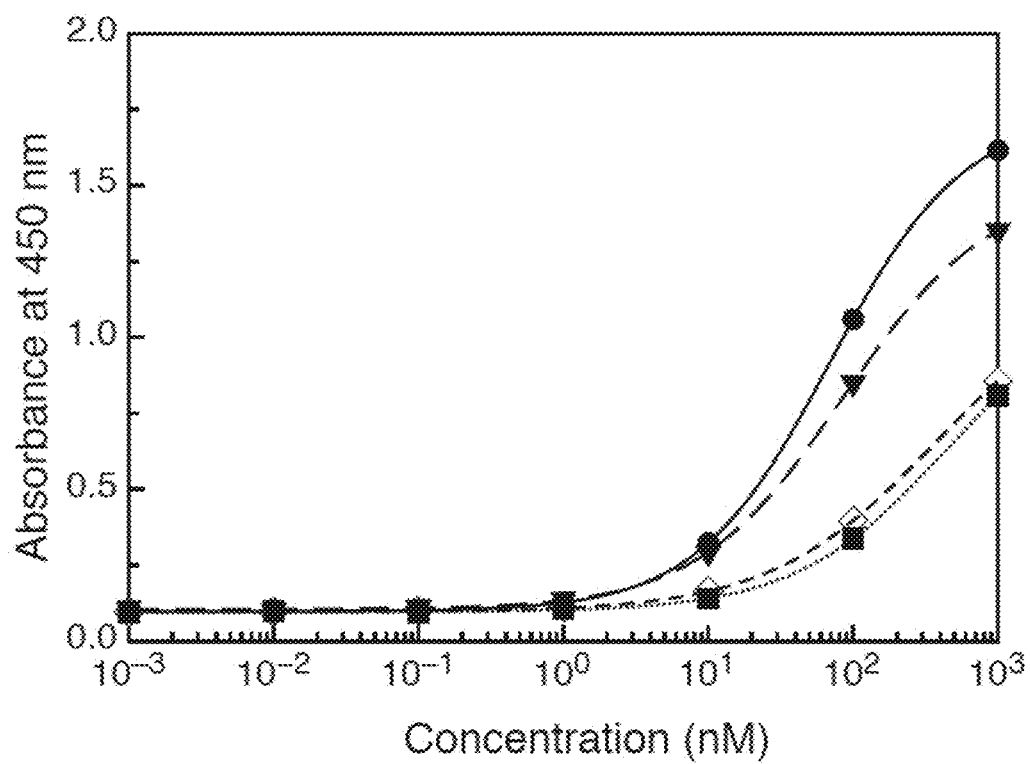

FIG. 95. ELISA of multispecific molecule 28 (circles, solid line), multispecific molecule 30 (diamonds, short dash line), multispecific molecule 31 (squares, dotted line), and multispecific molecule 32 (triangles, long dash line) with human FAP from SEQ ID NO: 225.

Figure 96:
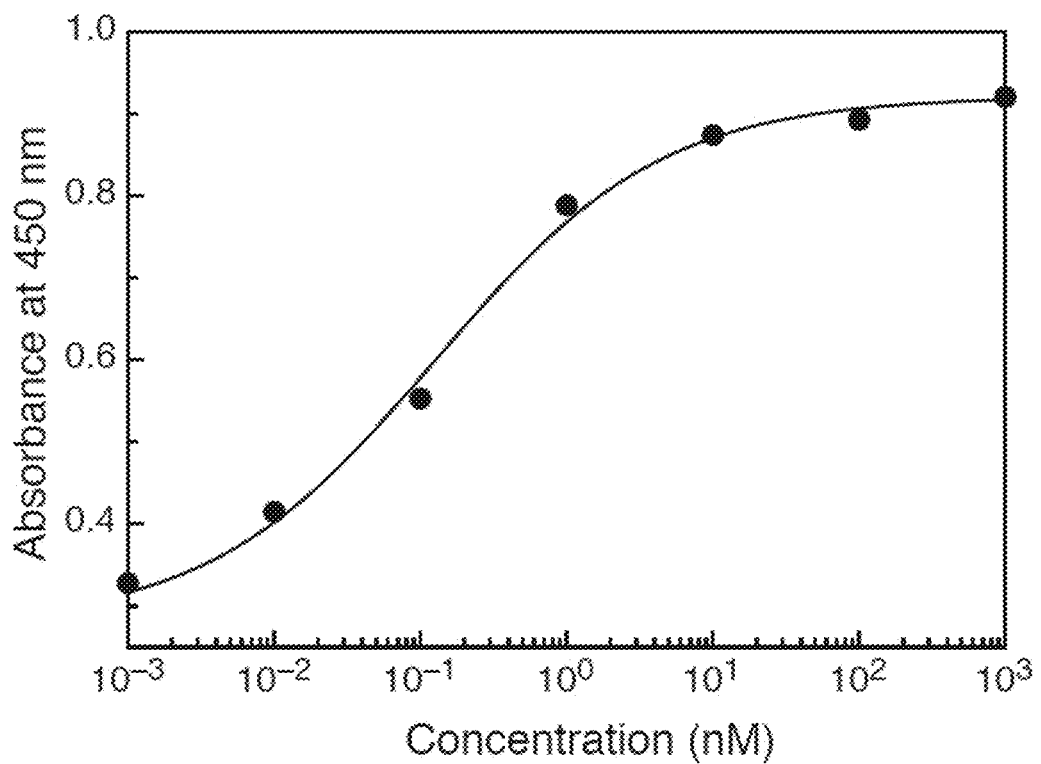

FIG. 96. Binding of multispecific molecule 29 to human NKp46 generated from SEQ ID NO: 179.

Figure 97:
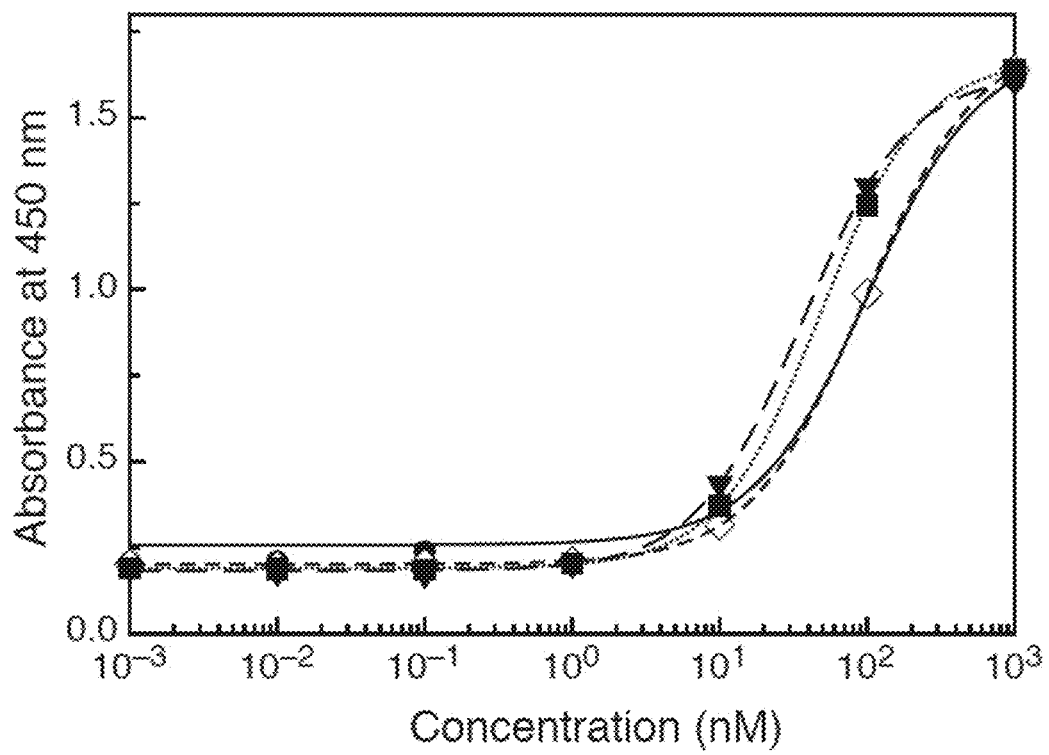

FIG. 97. ELISA of multispecific molecule 25 (circles, solid line), multispecific molecule 28 (diamonds, short dash line), multispecific molecule 29 (squares, dotted line), and multispecific molecule 32 (triangles, long dash line) with human IL2Rα from SEQ ID NO: 182.

Figure 98:
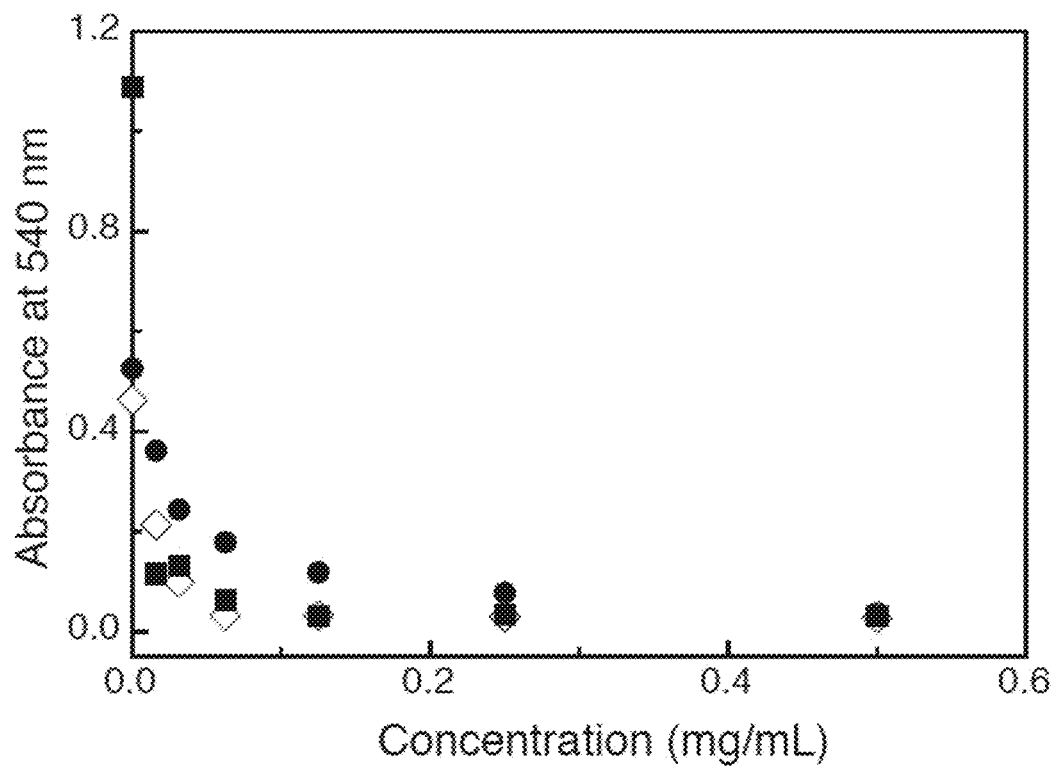

FIG. 98. Turbidimetric enzyme assay for hyaluronidase activity of multispecific molecule 24 (circles), multispecific molecule 25 (diamonds), and multispecific molecule 26 (squares), where degradation of hyaluronic acid results in a decrease in absorbance.

Figure 99:
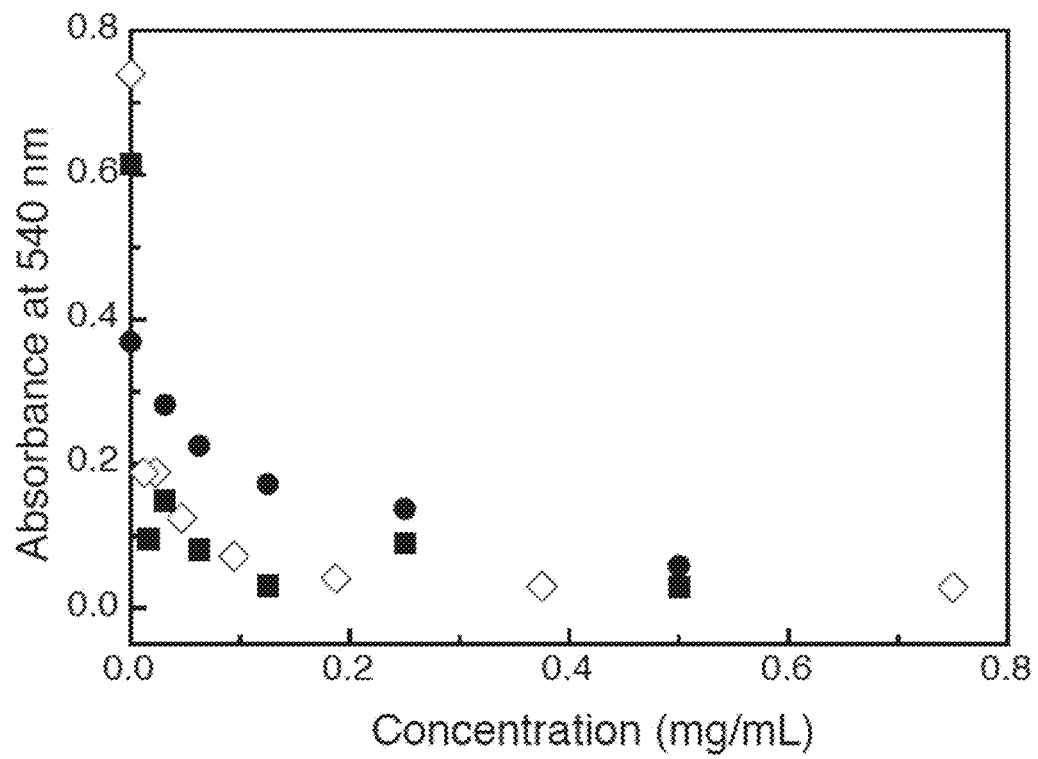

FIG. 99. Turbidimetric enzyme assay for hyaluronidase activity of multispecific molecule 27 (circles), multispecific molecule 28 (diamonds), and multispecific molecule 29 (squares), where degradation of hyaluronic acid results in a decrease in absorbance.

Figure 100:
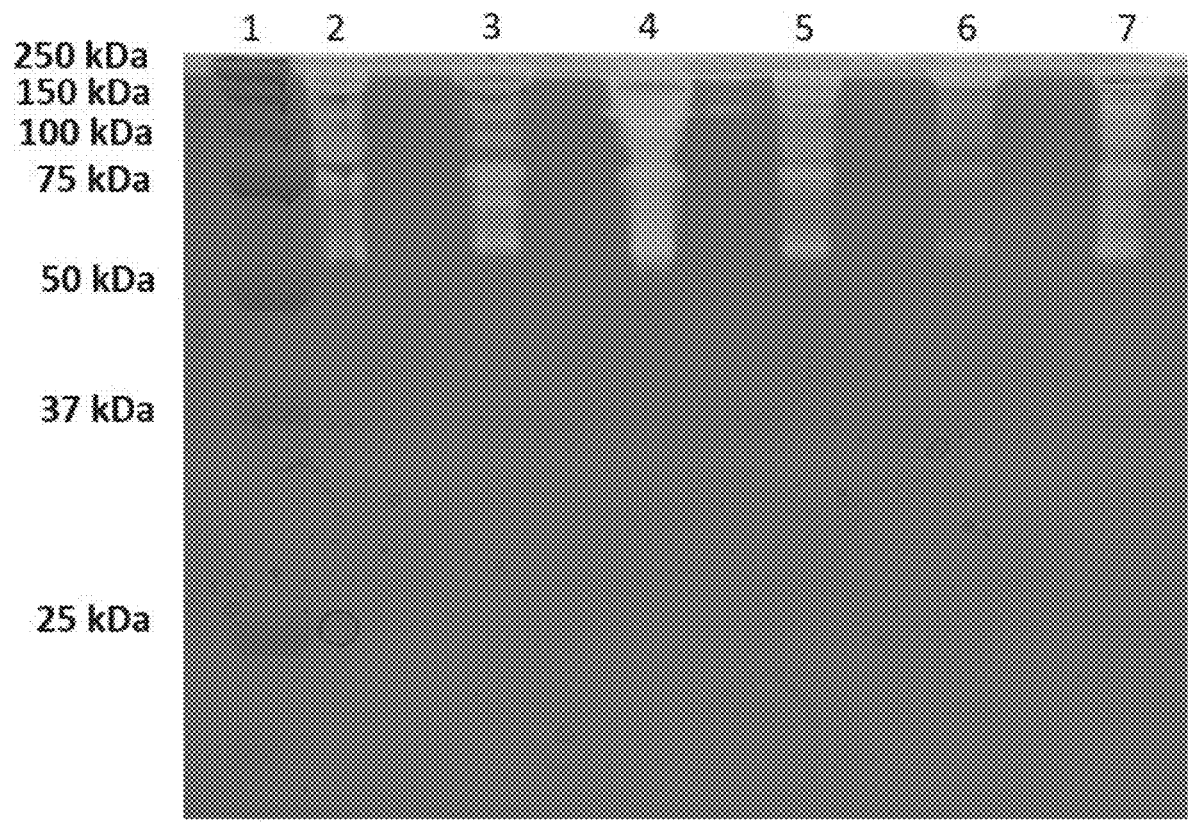

FIG. 100. Gel-based assay for hyaluronidase activity, where the white bands represent degraded hyaluronic acid. Lane 1 is the ladder, lane 2 is multispecific molecule 24, lane 3 is multispecific molecule 25, lane 4 is multispecific molecule 26, lane 5 is multispecific molecule 27, lane 6 is multispecific molecule 28, and lane 7 is multispecific molecule 29.

Figure 101:
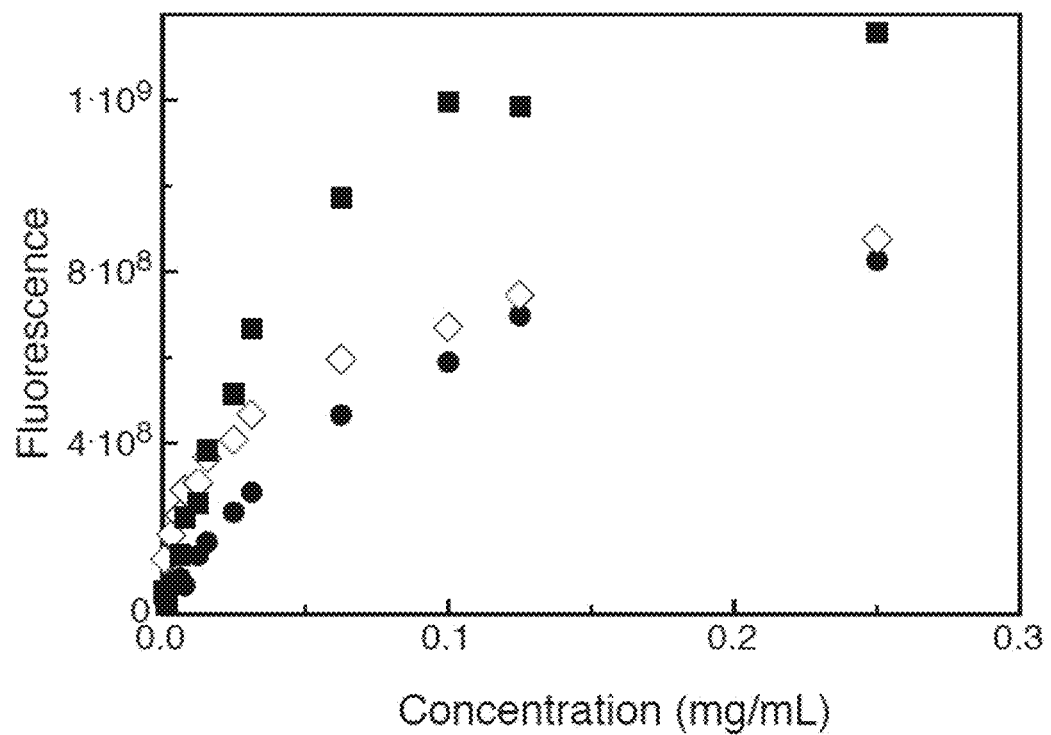

FIG. 101. Type IV collagenase activity of multispecific molecule 30 (circles), multispecific molecule 31 (diamonds), and multispecific molecule 32 (squares), where degradation of gelatinase results in an increase in the fluorescence.

DETAILED DESCRIPTION OF THE INVENTION

Disclosed herein are multispecific molecules (also referred to herein as "multifunctional molecules") that include a plurality (e.g., two or more) binding specificities (or functionalities), wherein a first binding specificity selectively localizes to a cancer cell, e.g., it includes a tumor-targeting moiety; and the second (or third, or fourth) binding specificity includes one or both of: an immune cell engager (e.g., chosen from one, two, three, or all of a T cell engager, NK cell engager, a B cell engager, a dendritic cell engager, or a macrophage cell engager); and/or a cytokine molecule. In an embodiment, the multispecific molecule is a bispecific (or bifunctional) molecule, a trispecific (or trifunctional) molecule, or a tetraspecific (or tetrafunctional) molecule. Without being bound by theory, the multispecific molecules disclosed herein are expected to localize (e.g., bridge) and/or activate an immune cell (e.g., an immune effector cell chosen from an NK cell, a B cell, a dendritic cell or a macrophage), in the presence of the cancer cell. Increasing the proximity and/or activity of the immune cell, in the presence of the cancer cell, using the multispecific molecules described herein is expected to enhance an immune response against the target cancer cell, thereby providing a more effective cancer therapy. Accordingly, provided herein are, inter alia, multispecific molecules (e.g., multispecific antibody molecules) that include the aforesaid moieties, nucleic acids encoding the same, methods of producing the aforesaid molecules, and methods of treating a cancer using the aforesaid molecules.

Novel multifunctional, e.g., multispecific, molecules that include (i) a stromal modifying moiety and (ii) a tumor-targeting moiety (e.g., an antibody molecule, a ligand molecule, or a receptor molecule) are disclosed. Without being bound by theory, the multifunctional molecules disclosed herein are believed to inter alia target (e.g., localize to) a cancer site, and alter the tumor stroma, e.g., alter the tumor microenvironment near the cancer site. The multifunctional molecules can further include one or both of: an immune cell engager (e.g., chosen from one, two, three, or all of a T cell engager, NK cell engager, a B cell engager, a dendritic cell engager, or a macrophage cell engager); and/or a cytokine molecule. Accordingly, provided herein are, inter alia, multifunctional, e.g., multispecific, molecules, that include the aforesaid moieties, nucleic acids encoding the same, methods of producing the aforesaid molecules, and methods of treating a cancer using the aforesaid molecules.

Also disclosed herein are Novel multifunctional, e.g., multispecific, molecules that include (i) a stromal modifying moiety and (ii) a tumor-targeting moiety (e.g., an antibody molecule, a ligand molecule, or a receptor molecule) are disclosed. Without being bound by theory, the multifunctional molecules disclosed herein are believed to inter alia target (e.g., localize to) a cancer site, and alter the tumor stroma, e.g., alter the tumor microenvironment near the cancer site. The multifunctional molecules can further include one or both of: an immune cell engager (e.g., chosen from one, two, three, or all of a T cell engager, an NK cell engager, a B cell engager, a dendritic cell engager, or a macrophage cell engager); and/or a cytokine molecule. Accordingly, provided herein are, inter alia, multifunctional, e.g., multispecific molecules, that include the aforesaid moieties, nucleic acids encoding the same, methods of producing the aforesaid molecules, and methods of treating a cancer using the aforesaid molecules.

Definitions

In some embodiments, the multispecific molecule includes a tumor-targeting moiety. A "tumor-targeting moiety," as used herein, refers to a binding agent that recognizes or associates with, e.g., binds to, a target in a cancer cell. The tumor-targeting moiety can be an antibody molecule, a receptor molecule (e.g., a full length receptor, receptor fragment, or fusion thereof (e.g., a receptor-Fc fusion)), or a ligand molecule (e.g., a full length ligand, ligand fragment, or fusion thereof (e.g., a ligand-Fc fusion)) that binds to the cancer antigen (e.g., the tumor and/or the stromal antigen). In embodiments, the tumor-targeting moiety specifically binds to the target tumor, e.g., binds preferentially to the target tumor. For example, when the tumor-targeting moiety is an antibody molecule, it binds to the cancer antigen (e.g., the tumor antigen and/or the stromal antigen) with a dissociation constant of less than about 10 nM, and more typically, 10-100 pM.

In some embodiments, the multispecific molecule includes an immune cell engager. "An immune cell engager" refers to one or more binding specificities that bind and/or activate an immune cell, e.g., a cell involved in an immune response. In embodiments, the immune cell is chosen from a T cell, an NK cell, a B cell, a dendritic cell, and/or the macrophage cell. The immune cell engager can be an antibody molecule, a receptor molecule (e.g., a full length receptor, receptor fragment, or fusion thereof (e.g., a receptor-Fc fusion)), or a ligand molecule (e.g., a full length ligand, ligand fragment, or fusion thereof (e.g., a ligand-Fc fusion)) that binds to the immune cell antigen (e.g., the NK cell antigen, the B cell antigen, the dendritic cell antigen, and/or the macrophage cell antigen). In embodiments, the immune cell engager specifically binds to the target immune cell, e.g., binds preferentially to the target immune cell. For example, when the immune cell engager is an antibody molecule, it binds to the immune cell antigen (e.g., the NK cell antigen, the B cell antigen, the dendritic cell antigen, and/or the macrophage cell antigen) with a dissociation constant of less than about 10 nM, and more typically, 10-100 pM.

In some embodiments, the multispecific molecule includes a cytokine molecule. As used herein, a "cytokine molecule" refers to full length, a fragment or a variant of a cytokine; a cytokine further comprising a receptor domain, e.g., a cytokine receptor dimerizing domain; or an agonist of a cytokine receptor, e.g., an antibody molecule (e.g., an agonistic antibody) to a cytokine receptor, that elicits at least one activity of a naturally-occurring cytokine. In some embodiments the cytokine molecule is chosen from interleukin-2 (IL-2), interleukin-7 (IL-7), interleukin-12 (IL-12), interleukin-15 (IL-15), interleukin-18 (IL-18), interleukin-21 (IL-21), or interferon gamma, or a fragment or variant thereof, or a combination of any of the aforesaid cytokines. The cytokine molecule can be a monomer or a dimer. In embodiments, the cytokine molecule can further include a cytokine receptor dimerizing domain. In other embodiments, the cytokine molecule is an agonist of a cytokine receptor, e.g., an antibody molecule (e.g., an agonistic antibody) to a cytokine receptor chosen from an IL-15Ra or IL-21R.

As used herein, the term "molecule" as used in, e.g., antibody molecule, cytokine molecule, receptor molecule, includes full-length, naturally-occurring molecules, as well as variants, e.g., functional variants (e.g., truncations, fragments, mutated (e.g., substantially similar sequences) or derivatized form thereof), so long as at least one function and/or activity of the unmodified (e.g., naturally-occurring) molecule remains.

In some embodiments, the multifunctional molecule includes a stromal modifying moiety. A "stromal modifying moiety," as used herein refers to an agent, e.g., a protein (e.g., an enzyme), that is capable of altering, e.g., degrading a component of, the stroma. In embodiments, the component of the stroma is chosen from, e.g., an ECM component, e.g., a glycosaminoglycan, e.g., hyaluronan (also known as hyaluronic acid or HA), chondroitin sulfate, chondroitin, dermatan sulfate, heparin sulfate, heparin, entactin, tenascin, aggrecan and keratin sulfate; or an extracellular protein, e.g., collagen, laminin, elastin, fibrinogen, fibronectin, and vitronectin.

The term "functional variant" refers to polypeptides that have a substantially identical amino acid sequence to the naturally-occurring sequence, or are encoded by a substantially identical nucleotide sequence, and are capable of having one or more activities of the naturally-occurring sequence.

Certain terms are defined below.

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values.

"Antibody molecule" as used herein refers to a protein, e.g., an immunoglobulin chain or fragment thereof, comprising at least one immunoglobulin variable domain sequence. An antibody molecule encompasses antibodies (e.g., full-length antibodies) and antibody fragments. In an embodiment, an antibody molecule comprises an antigen binding or functional fragment of a full length antibody, or a full length immunoglobulin chain. For example, a full-length antibody is an immunoglobulin (Ig) molecule (e.g., an IgG antibody) that is naturally occurring or formed by normal immunoglobulin gene fragment recombinatorial processes). In embodiments, an antibody molecule refers to an immunologically active, antigen-binding portion of an immunoglobulin molecule, such as an antibody fragment. An antibody fragment, e.g., functional fragment, is a portion of an antibody, e.g., Fab, Fab', F(ab')$_2$, F(ab)$_2$, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full length antibodies and antibody fragments, e.g., dAb (domain antibody), single chain, Fab, Fab', and F(ab')$_2$ fragments, and single chain variable fragments (scFvs).

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

In embodiments, an antibody molecule is monospecific, e.g., it comprises binding specificity for a single epitope. In some embodiments, an antibody molecule is multispecific, e.g., it comprises a plurality of immunoglobulin variable domain sequences, where a first immunoglobulin variable domain sequence has binding specificity for a first epitope and a second immunoglobulin variable domain sequence has binding specificity for a second epitope. In some embodiments, an antibody molecule is a bispecific antibody molecule. "Bispecific antibody molecule" as used herein refers to an antibody molecule that has specificity for more than one (e.g., two, three, four, or more) epitope and/or antigen.

"Antigen" (Ag) as used herein refers to a molecule that can provoke an immune response, e.g., involving activation of certain immune cells and/or antibody generation. Any macromolecule, including almost all proteins or peptides, can be an antigen. Antigens can also be derived from genomic recombinant or DNA. For example, any DNA comprising a nucleotide sequence or a partial nucleotide sequence that encodes a protein capable of eliciting an immune response encodes an "antigen." In embodiments, an antigen does not need to be encoded solely by a full length nucleotide sequence of a gene, nor does an antigen need to be encoded by a gene at all. In embodiments, an antigen can be synthesized or can be derived from a biological sample, e.g., a tissue sample, a tumor sample, a cell, or a fluid with other biological components. As used, herein a "tumor antigen" or interchangeably, a "cancer antigen" includes any molecule present on, or associated with, a cancer, e.g., a cancer cell or a tumor microenvironment that can provoke an immune response. As used, herein an "immune cell antigen" includes any molecule present on, or associated with, an immune cell that can provoke an immune response.

The "antigen-binding site," or "binding portion" of an antibody molecule refers to the part of an antibody molecule, e.g., an immunoglobulin (Ig) molecule, that participates in antigen binding. In embodiments, the antigen binding site is formed by amino acid residues of the variable (V) regions of the heavy (H) and light (L) chains. Three highly divergent stretches within the variable regions of the heavy and light chains, referred to as hypervariable regions, are disposed between more conserved flanking stretches called "framework regions," (FRs). FRs are amino acid sequences that are naturally found between, and adjacent to, hypervariable regions in immunoglobulins. In embodiments, in an antibody molecule, the three hypervariable regions of a light chain and the three hypervariable regions of a heavy chain are disposed relative to each other in three dimensional space to form an antigen-binding surface, which is complementary to the three-dimensional surface of a bound antigen. The three hypervariable regions of each of the heavy and light chains are referred to as "complementarity-determining regions," or "CDRs." The framework region and CDRs have been defined and described, e.g., in Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917. Each variable chain (e.g., variable heavy chain and variable light chain) is typically made up of three CDRs and four FRs, arranged from amino-terminus to carboxy-terminus in the amino acid order: FR1, CDR1, FR2, CDR2, FR3, CDR3, and FR4.

"Cancer" as used herein can encompass all types of oncogenic processes and/or cancerous growths. In embodiments, cancer includes primary tumors as well as metastatic tissues or malignantly transformed cells, tissues, or organs. In embodiments, cancer encompasses all histopathologies and stages, e.g., stages of invasiveness/severity, of a cancer. In embodiments, cancer includes relapsed and/or resistant cancer. The terms "cancer" and "tumor" can be used interchangeably. For example, both terms encompass solid and liquid tumors. As used herein, the term "cancer" or "tumor" includes premalignant, as well as malignant cancers and tumors.

As used herein, an "immune cell" refers to any of various cells that function in the immune system, e.g., to protect against agents of infection and foreign matter. In embodiments, this term includes leukocytes, e.g., neutrophils, eosinophils, basophils, lymphocytes, and monocytes. Innate leukocytes include phagocytes (e.g., macrophages, neutrophils, and dendritic cells), mast cells, eosinophils, basophils, and natural killer cells. Innate leukocytes identify and eliminate pathogens, either by attacking larger pathogens through contact or by engulfing and then killing microorganisms, and are mediators in the activation of an adaptive immune response. The cells of the adaptive immune system are special types of leukocytes, called lymphocytes. B cells and T cells are important types of lymphocytes and are derived from hematopoietic stem cells in the bone marrow. B cells are involved in the humoral immune response, whereas T cells are involved in cell-mediated immune response. The term "immune cell" includes immune effector cells.

"Immune effector cell," as that term is used herein, refers to a cell that is involved in an immune response, e.g., in the promotion of an immune effector response. Examples of immune effector cells include, but are not limited to, T cells, e.g., alpha/beta T cells and gamma/delta T cells, B cells, natural killer (NK) cells, natural killer T (NK T) cells, and mast cells.

The term "effector function" or "effector response" refers to a specialized function of a cell. Effector function of a T cell, for example, may be cytolytic activity or helper activity including the secretion of cytokines.

The compositions and methods of the present invention encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence, e.g., a sequence provided herein.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS*, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid (e.g., SEQ ID NO: 1) molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used. See http://www.ncbi.nlm.nih.gov.

It is understood that the molecules of the present invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Various aspects of the invention are described in further detail below. Additional definitions are set out throughout the specification.

Antibody Molecules

In one embodiment, the antibody molecule binds to a cancer antigen, e.g., a tumor antigen or a stromal antigen. In some embodiments, the cancer antigen is, e.g., a mammalian, e.g., a human, cancer antigen. In other embodiments, the antibody molecule binds to an immune cell antigen, e.g., a mammalian, e.g., a human, immune cell antigen. For example, the antibody molecule binds specifically to an epitope, e.g., linear or conformational epitope, on the cancer antigen or the immune cell antigen.

In an embodiment, an antibody molecule is a monospecific antibody molecule and binds a single epitope. E.g., a monospecific antibody molecule having a plurality of immunoglobulin variable domain sequences, each of which binds the same epitope.

In an embodiment an antibody molecule is a multispecific antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable domain. In an embodiment, a multispecific antibody molecule is a bispecific antibody molecule, a trispecific antibody molecule, or a tetraspecific antibody molecule.

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv or a Fab, or fragment thereof, have binding specificity for a first epitope and a scFv or a Fab, or fragment thereof, have binding specificity for a second epitope.

In an embodiment, an antibody molecule comprises a diabody, and a single-chain molecule, as well as an antigen-binding fragment of an antibody (e.g., Fab, F(ab')$_2$, and Fv). For example, an antibody molecule can include a heavy (H) chain variable domain sequence (abbreviated herein as VH), and a light (L) chain variable domain sequence (abbreviated herein as VL). In an embodiment an antibody molecule comprises or consists of a heavy chain and a light chain (referred to herein as a half antibody). In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The a preparation of antibody molecules can be monoclonal or polyclonal. An antibody molecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

Antibody molecules include intact molecules as well as functional fragments thereof. Constant regions of the antibody molecules can be altered, e.g., mutated, to modify the properties of the antibody (e.g., to increase or decrease one or more of: Fc receptor binding, antibody glycosylation, the number of cysteine residues, effector cell function, or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains*. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) *JMB* 273,927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia, the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3).

Each VH and VL typically includes three CDRs and four FRs, arranged from amino-terminus to carboxy-terminus in the following order: FR1, CDR1, FR2, CDR2, FR3, CDR3, FR4.

The antibody molecule can be a polyclonal or a monoclonal antibody.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

The antibody can be recombinantly produced, e.g., produced by phage display or by combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody molecule can be one in which the variable region, or a portion thereof, e.g., the CDRs, are generated in a non-human organism, e.g., a rat or mouse. Chimeric, CDR-grafted, and humanized antibodies are within the invention. Antibody molecules generated in a non-human organism, e.g., a rat or mouse, and then modified, e.g., in the variable framework or constant region, to decrease antigenicity in a human are within the invention.

An "effectively human" protein is a protein that does substantially not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.,* 32:180-190 (1990)) and also because of potential allergic reactions (see, e.g., LoBuglio et al., *Hybridoma,* 5:5117-5123 (1986)).

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No.

4,816,567; Cabilly et al., European Patent Application 125, 023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding to the antigen. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody molecule can be humanized by methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibody molecules can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibody molecules in which specific amino acids have been substituted, deleted or added. Criteria for selecting amino acids from the donor are described in U.S. Pat. No. 5,585,089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Multispecific Antibody Molecules

Exemplary structures of multispecific and multifunctional molecules defined herein are described throughout. Exemplary structures are further described in: Weidle U et al. (2013) The Intriguing Options of Multispecific Antibody Formats for Treatment of Cancer. *Cancer Genomics & Proteomics* 10: 1-18 (2013); and Spiess C et al. (2015) Alternative molecular formats and therapeutic applications for bispecific antibodies. *Molecular Immunology* 67: 95-106; the full contents of each of which is incorporated by reference herein).

In embodiments, multispecific antibody molecules can comprise more than one antigen-binding site, where different sites are specific for different antigens. In embodiments, multispecific antibody molecules can bind more than one (e.g., two or more) epitopes on the same antigen. In embodiments, multispecific antibody molecules comprise an antigen-binding site specific for a target cell (e.g., cancer cell) and a different antigen-binding site specific for an immune effector cell. In one embodiment, the multispecific antibody molecule is a bispecific antibody molecule. Bispecific antibody molecules can be classified into five different structural groups: (i) bispecific immunoglobulin G (BsIgG); (ii) IgG appended with an additional antigen-binding moiety; (iii) bispecific antibody fragments; (iv) bispecific fusion proteins; and (v) bispecific antibody conjugates.

BsIgG is a format that is monovalent for each antigen. Exemplary BsIgG formats include but are not limited to crossMab, DAF (two-in-one), DAF (four-in-one), DutaMab, DT-IgG, knobs-in-holes common LC, knobs-in-holes assembly, charge pair, Fab-arm exchange, SEEDbody, triomab, LUZ-Y, Fcab, κλ-body, orthogonal Fab. See Spiess et al. Mol. Immunol. 67(2015):95-106. Exemplary BsIgGs include catumaxomab (Fresenius Biotech, Trion Pharma, Neopharm), which contains an anti-CD3 arm and an anti-EpCAM arm; and ertumaxomab (Neovii Biotech, Fresenius Biotech), which targets CD3 and HER2. In some embodiments, BsIgG comprises heavy chains that are engineered for heterodimerization. For example, heavy chains can be engineered for heterodimerization using a "knobs-into-holes" strategy, a SEED platform, a common heavy chain (e.g., in κλ-bodies), and use of heterodimeric Fc regions. See Spiess et al. Mol. Immunol. 67(2015):95-106. Strategies that have been used to avoid heavy chain pairing of homodimers in BsIgG include knobs-in-holes, duobody, azymetric, charge pair, HA-TF, SEEDbody, and differential protein A affinity. See Id. BsIgG can be produced by separate expression of the component antibodies in different host cells and subsequent purification/assembly into a BsIgG. BsIgG can also be produced by expression of the component antibodies in a single host cell. BsIgG can be purified using affinity chromatography, e.g., using protein A and sequential pH elution.

IgG appended with an additional antigen-binding moiety is another format of bispecific antibody molecules. For example, monospecific IgG can be engineered to have bispecificity by appending an additional antigen-binding unit onto the monospecific IgG, e.g., at the N- or C-terminus of either the heavy or light chain. Exemplary additional antigen-binding units include single domain antibodies (e.g., variable heavy chain or variable light chain), engineered protein scaffolds, and paired antibody variable domains (e.g., single chain variable fragments or variable fragments). See Id. Examples of appended IgG formats include dual variable domain IgG (DVD-Ig), IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, zybody, and DVI-IgG (four-in-one). See Spiess et al. Mol. Immunol. 67(2015):95-106. An example of an IgG-scFv is MM-141 (Merrimack Pharmaceuticals), which binds IGF-1R and HERS. Examples of DVD-Ig include ABT-981 (AbbVie), which binds IL-1α and IL-1β; and ABT-122 (AbbVie), which binds TNF and IL-17A.

Bispecific antibody fragments (BsAb) are a format of bispecific antibody molecules that lack some or all of the antibody constant domains. For example, some BsAb lack an Fc region. In embodiments, bispecific antibody fragments include heavy and light chain regions that are connected by a peptide linker that permits efficient expression of the BsAb in a single host cell. Exemplary bispecific antibody fragments include but are not limited to nanobody, nanobody-HAS, BiTE, Diabody, DART, TandAb, scDiabody, scDiabody-CH3, Diabody-CH3, triple body, miniantibody, minibody, TriBi minibody, scFv-CH3 KIH, Fab-scFv, scFv-CH-CL-scFv, F(ab')2, F(ab')2-scFv2, scFv-KIH, Fab-scFv-Fc, tetravalent HCAb, scDiabody-Fc, Diabody-Fc, tandem scFv-Fc, and intrabody. See Id. For example, the BiTE format comprises tandem scFvs, where the component scFvs bind to CD3 on T cells and a surface antigen on cancer cells Bispecific fusion proteins include antibody fragments linked to other proteins, e.g., to add additional specificity and/or functionality. An example of a bispecific fusion protein is an immTAC, which comprises an anti-CD3 scFv linked to an affinity-matured T-cell receptor that recognizes HLA-presented peptides. In embodiments, the dock-and-lock (DNL) method can be used to generate bispecific antibody molecules with higher valency. Also, fusions to albumin binding proteins or human serum albumin can be extend the serum half-life of antibody fragments. See Id.

In embodiments, chemical conjugation, e.g., chemical conjugation of antibodies and/or antibody fragments, can be used to create BsAb molecules. See Id. An exemplary bispecific antibody conjugate includes the CovX-body format, in which a low molecular weight drug is conjugated site-specifically to a single reactive lysine in each Fab arm or an antibody or fragment thereof. In embodiments, the conjugation improves the serum half-life of the low molecular weight drug. An exemplary CovX-body is CVX-241 (NCT01004822), which comprises an antibody conjugated to two short peptides inhibiting either VEGF or Ang2. See Id.

The antibody molecules can be produced by recombinant expression, e.g., of at least one or more component, in a host system. Exemplary host systems include eukaryotic cells (e.g., mammalian cells, e.g., CHO cells, or insect cells, e.g., SF9 or S2 cells) and prokaryotic cells (e.g., *E. coli*). Bispecific antibody molecules can be produced by separate expression of the components in different host cells and subsequent purification/assembly. Alternatively, the antibody molecules can be produced by expression of the components in a single host cell. Purification of bispecific antibody molecules can be performed by various methods such as affinity chromatography, e.g., using protein A and sequential pH elution. In other embodiments, affinity tags can be used for purification, e.g., histidine-containing tag, myc tag, or streptavidin tag.

CDR-Grafted Scaffolds

In embodiments, the antibody molecule is a CDR-grafted scaffold domain. In embodiments, the scaffold domain is based on a fibronectin domain, e.g., fibronectin type III domain. The overall fold of the fibronectin type III (Fn3) domain is closely related to that of the smallest functional antibody fragment, the variable domain of the antibody heavy chain. There are three loops at the end of Fn3; the positions of BC, DE and FG loops approximately correspond to those of CDR1, 2 and 3 of the VH domain of an antibody. Fn3 does not have disulfide bonds; and therefore Fn3 is stable under reducing conditions, unlike antibodies and their fragments (see, e.g., WO 98/56915; WO 01/64942; WO 00/34784). An Fn3 domain can be modified (e.g., using CDRs or hypervariable loops described herein) or varied, e.g., to select domains that bind to an antigen/marker/cell described herein.

In embodiments, a scaffold domain, e.g., a folded domain, is based on an antibody, e.g., a "minibody" scaffold created by deleting three beta strands from a heavy chain variable domain of a monoclonal antibody (see, e.g., Tramontano et al., 1994, J Mol. Recognit. 7:9; and Martin et al., 1994, EMBO J. 13:5303-5309). The "minibody" can be used to present two hypervariable loops. In embodiments, the scaffold domain is a V-like domain (see, e.g., Coia et al. WO 99/45110) or a domain derived from tendamistatin, which is a 74 residue, six-strand beta sheet sandwich held together by two disulfide bonds (see, e.g., McConnell and Hoess, 1995, J Mol. Biol. 250:460). For example, the loops of tendamistatin can be modified (e.g., using CDRs or hypervariable loops) or varied, e.g., to select domains that bind to a marker/antigen/cell described herein. Another exemplary scaffold domain is a beta-sandwich structure derived from the extracellular domain of CTLA-4 (see, e.g., WO 00/60070).

Other exemplary scaffold domains include but are not limited to T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin, and heat shock proteins; and intracellular signaling domains (such as SH2 and SH3 domains). See, e.g., US 20040009530 and U.S. Pat. No. 7,501,121, incorporated herein by reference.

In embodiments, a scaffold domain is evaluated and chosen, e.g., by one or more of the following criteria: (1) amino acid sequence, (2) sequences of several homologous domains, (3) 3-dimensional structure, and/or (4) stability data over a range of pH, temperature, salinity, organic solvent, oxidant concentration. In embodiments, the scaffold domain is a small, stable protein domain, e.g., a protein of less than 100, 70, 50, 40 or 30 amino acids. The domain may include one or more disulfide bonds or may chelate a metal, e.g., zinc.

Antibody-Based Fusions

A variety of formats can be generated which contain additional binding entities attached to the N or C terminus of antibodies. These fusions with single chain or disulfide stabilized Fvs or Fabs result in the generation of tetravalent molecules with bivalent binding specificity for each antigen. Combinations of scFvs and scFabs with IgGs enable the production of molecules which can recognize three or more different antigens.

Antibody-Fab Fusion

Antibody-Fab fusions are bispecific antibodies comprising a traditional antibody to a first target and a Fab to a second target fused to the C terminus of the antibody heavy chain. Commonly the antibody and the Fab will have a common light chain. Antibody fusions can be produced by (1) engineering the DNA sequence of the target fusion, and (2) transfecting the target DNA into a suitable host cell to express the fusion protein. It seems like the antibody-scFv fusion may be linked by a (Gly)-Ser linker between the C-terminus of the CH3 domain and the N-terminus of the scFv, as described by Coloma, J. et al. (1997) *Nature Biotech* 15:159.

Antibody-scFv Fusion

Antibody-scFv Fusions are bispecific antibodies comprising a traditional antibody and a scFv of unique specificity fused to the C terminus of the antibody heavy chain. The scFv can be fused to the C terminus through the Heavy Chain of the scFv either directly or through a linker peptide. Antibody fusions can be produced by (1) engineering the DNA sequence of the target fusion, and (2) transfecting the target DNA into a suitable host cell to express the fusion protein. It seems like the antibody-scFv fusion may be linked by a (Gly)-Ser linker between the C-terminus of the CH3 domain and the N-terminus of the scFv, as described by Coloma, J. et al. (1997) *Nature Biotech* 15:159.

Variable Domain Immunoglobulin DVD

A related format is the dual variable domain immunoglobulin (DVD), which are composed of VH and VL domains of a second specificity place upon the N termini of the V domains by shorter linker sequences.

Other exemplary multispecific antibody formats include, e.g., those described in the following US20160114057A1, US20130243775A1, US20140051833, US20130022601, US20150017187A1, US20120201746A1, US201501336-38A1, US20130266568A1, US20160145340A1, WO-2015127158A1, US20150203591A1, US20140322221A1, US20130303396A1, US20110293613, US20130017200A1, US20160102135A1, WO2015197598A2, WO20151975-82A1, U.S. Pat. No. 9,359,437, US20150018529, WO2016115274A1, WO2016087416A1, US20080069820-A1, U.S. Pat. Nos. 9,145,588B, 7,919,257, and US20150232560A1. Exemplary multispecific molecules utilizing a full antibody-Fab/scFab format include those described in the following, U.S. Pat. No. 9,382,323B2, US20140072581A1, US20140308285A1, US201301656-38A1, US20130267686A1, US20140377269A1, U.S. Pat. No. 7,741,446B2, and WO1995009917A1. Exemplary multispecific molecules utilizing a domain exchange format include those described in the following, US-20150315296A1, WO2016087650A1, US20160075785A1, WO2016016299A1, US20160130347A1, US20150166670, U.S. Pat. No. 8,703,132B2, US20100316645, U.S. Pat. No. 8,227,577B2, US20130078249.

Fc-Containing Entities (Mini-Antibodies)

Fc-containing entities, also known as mini-antibodies, can be generated by fusing scFv to the C-termini of constant heavy region domain 3 (CH3-scFv) and/or to the hinge region (scFv-hinge-Fc) of an antibody with a different specificity. Trivalent entities can also be made which have disulfide stabilized variable domains (without peptide linker) fused to the C-terminus of CH3 domains of IgGs.

Fc-Containing Multispecific Molecules

In some embodiments, the multispecific molecules disclosed herein includes an immunoglobulin constant region (e.g., an Fc region). Exemplary Fc regions can be chosen from the heavy chain constant regions of IgG1, IgG2, IgG3 or IgG4; more particularly, the heavy chain constant region of human IgG1, IgG2, IgG3, or IgG4.

In some embodiments, the immunoglobulin chain constant region (e.g., the Fc region) is altered, e.g., mutated, to increase or decrease one or more of: Fc receptor binding, antibody glycosylation, the number of cysteine residues, effector cell function, or complement function.

In other embodiments, an interface of a first and second immunoglobulin chain constant regions (e.g., a first and a second Fc region) is altered, e.g., mutated, to increase or decrease dimerization, e.g., relative to a non-engineered interface, e.g., a naturally-occurring interface. For example, dimerization of the immunoglobulin chain constant region (e.g., the Fc region) can be enhanced by providing an Fc interface of a first and a second Fc region with one or more of: a paired protuberance-cavity ("knob-in-a hole"), an electrostatic interaction, or a strand-exchange, such that a greater ratio of heteromultimer to homomultimer forms, e.g., relative to a non-engineered interface.

In some embodiments, the multispecific molecules include a paired amino acid substitution at a position chosen from one or more of 347, 349, 350, 351, 366, 368, 370, 392, 394, 395, 397, 398, 399, 405, 407, or 409, e.g., of the Fc region of human IgG1 For example, the immunoglobulin chain constant region (e.g., Fc region) can include a paired an amino acid substitution chosen from: T366S, L368A, or Y407V (e.g., corresponding to a cavity or hole), and T366W (e.g., corresponding to a protuberance or knob).

In other embodiments, the multifunctional molecule includes a half-life extender, e.g., a human serum albumin or an antibody molecule to human serum albumin.

Heterodimerized Antibody Molecules & Methods of Making

Various methods of producing multispecific antibodies have been disclosed to address the problem of incorrect heavy chain pairing. Exemplary methods are described below. Exemplary multispecific antibody formats and methods of making said multispecific antibodies are also disclosed in e.g., Speiss et al. Molecular Immunology 67 (2015) 95-106; and Klein et al mAbs 4:6, 653-663; November/December 2012; the entire contents of each of which are incorporated by reference herein.

Heterodimerized bispecific antibodies are based on the natural IgG structure, wherein the two binding arms recognize different antigens. IgG derived formats that enable defined monovalent (and simultaneous) antigen binding are generated by forced heavy chain heterodimerization, combined with technologies that minimize light chain mispairing (e.g., common light chain). Forced heavy chain heterodimerization can be obtained using, e.g., knob-in-hole OR strand exchange engineered domains (SEED).

Knob-in-Hole

Knob-in-Hole as described in U.S. Pat. Nos. 5,731,116, 7,476,724 and Ridgway, J. et al. (1996) *Prot. Engineering* 9(7): 617-621, broadly involves: (1) mutating the CH3 domain of one or both antibodies to promote heterodimerization; and (2) combining the mutated antibodies under conditions that promote heterodimerization. "Knobs" or "protuberances" are typically created by replacing a small amino acid in a parental antibody with a larger amino acid (e.g., T366Y or T366W); "Holes" or "cavities" are created by replacing a larger residue in a parental antibody with a smaller amino acid (e.g., Y407T, T366S, 11368A and/or Y407\$^7$).

For bispecific antibodies including an Fc domain, introduction of specific mutations into the constant region of the heavy chains to promote the correct heterodimerization of the Fc portion can be utilized. Several such techniques are reviewed in Klein et al. (mAbs (2012) 4:6, 1-11), the contents of which are incorporated herein by reference in their entirety. These techniques include the "knobs-into-holes" (KiH) approach which involves the introduction of a bulky residue into one of the CH3 domains of one of the antibody heavy chains. This bulky residue fits into a complementary "hole" in the other CH3 domain of the paired heavy chain so as to promote correct pairing of heavy chains (see e.g., U.S. Pat. No. 7,642,228).

Exemplary KiH mutations include S354C, T366W in the "knob" heavy chain and Y349C, T366S, L368A, Y407V in the "hole" heavy chain. Other exemplary KiH mutations are provided in Table 1, with additional optional stabilizing Fc cysteine mutations.

TABLE 19

Exemplary Fc KiH mutations and optional Cysteine mutations

| Position | Knob Mutation | Hole Mutation |
|---|---|---|
| T366 | T366W | T366S |
| L368 | — | L368A |
| Y407 | — | Y407V |

| Additional Cysteine Mutations to form a stabilizing disulfide bridge | | |
|---|---|---|
| Position | Knob CH3 | Hole CH3 |
| S354 | S354C | — |
| Y349 | — | Y349C |

Other Fc mutations are provided by Igawa and Tsunoda who identified 3 negatively charged residues in the CH3 domain of one chain that pair with three positively charged residues in the CH3 domain of the other chain. These specific charged residue pairs are: E356-K439, E357-K370, D399-K409 and vice versa. By introducing at least two of the following three mutations in chain A: E356K, E357K and D399K, as well as K370E, K409D, K439E in chain B, alone or in combination with newly identified disulfide bridges, they were able to favor very efficient heterodimerization while suppressing homodimerization at the same time (Martens T et al. A novel one-armed antic-Met antibody inhibits glioblastoma growth in vivo. Clin Cancer Res 2006; 12:6144-52; PMID:17062691). Xencor defined 41 variant pairs based on combining structural calculations and sequence information that were subsequently screened for maximal heterodimerization, defining the combination of S364H, F405A (HA) on chain A and Y349T, T394F on chain B (TF) (Moore G L et al. A novel bispecific antibody format enables simultaneous bivalent and monovalent co-engagement of distinct target antigens. MAbs 2011; 3:546-57; PMID: 22123055).

Other exemplary Fc mutations to promote heterodimerization of multispecific antibodies include those described in the following references, the contents of each of which is incorporated by reference herein, WO-2016071377A1, US20140079689A1, US20160194389A1, US20160257763, WO2016071376A2, WO2015107026A1, WO2015107025A1, WO2015107015A1, US201503536-36A1, US20140199294A1, U.S. Pat. No. 7,750,128B2, US20160229915A1, US20150344570A1, U.S. Pat. No. 8,003,774A1, US20150337049A1, US20150175707A1, US20140242075A1, US20130195849A1, US201201498-76A1, US20140200331A1, U.S. Pat. No. 9,309,311B2, U.S. Pat. No. 8,586,713, US20140037621A1, US201301786-05A1, US20140363426A1, US20140051835A1 and US20110054151A1.

Stabilizing cysteine mutations have also been used in combination with KiH and other Fc heterodimerization promoting variants, see e.g., U.S. Pat. No. 7,183,076. Other exemplary cysteine modifications include, e.g., those disclosed in US20140348839A1, U.S. Pat. No. 7,855,275B2, and U.S. Pat. No. 9,000,130B2.

Strand Exchange Engineered Domains (SEED)

Heterodimeric Fc platform that support the design of bispecific and asymmetric fusion proteins by devising strand-exchange engineered domain (SEED) C(H)3 heterodimers are known. These derivatives of human IgG and IgA C(H)3 domains create complementary human SEED C(H)3 heterodimers that are composed of alternating segments of human IgA and IgG C(H)3 sequences. The resulting pair of SEED C(H)3 domains preferentially associates to form heterodimers when expressed in mammalian cells. SEEDbody (Sb) fusion proteins consist of [IgG1 hinge]-C(H)2-[SEED C(H)3], that may be genetically linked to one or more fusion partners (see e.g., Davis J H et al. SEEDbodies: fusion proteins based on strand exchange engineered domain (SEED) CH3 heterodimers in an Fc analogue platform for asymmetric binders or immunofusions and bispecific antibodies. Protein Eng Des Sel 2010; 23:195-202; PMID:20299542 and U.S. Pat. No. 8,871,912. The contents of each of which are incorporated by reference herein).

Duobody

"Duobody" technology to produce bispecific antibodies with correct heavy chain pairing are known. The DuoBody technology involves three basic steps to generate stable bispecific human IgG1 antibodies in a post-production exchange reaction. In a first step, two IgG1s, each containing single matched mutations in the third constant (CH3) domain, are produced separately using standard mammalian recombinant cell lines. Subsequently, these IgG1 antibodies are purified according to standard processes for recovery and purification. After production and purification (post-production), the two antibodies are recombined under tailored laboratory conditions resulting in a bispecific antibody product with a very high yield (typically >95%) (see e.g., Labrijn et al, PNAS 2013; 110(13):5145-5150 and Labrijn et al. Nature Protocols 2014; 9(10):2450-63, the contents of each of which are incorporated by reference herein).

Electrostatic Interactions

Methods of making multispecific antibodies using CH3 amino acid changes with charged amino acids such that homodimer formation is electrostatically unfavorable are disclosed. EP1870459 and WO 2009089004 describe other strategies for favoring heterodimer formation upon co-expression of different antibody domains in a host cell. In these methods, one or more residues that make up the heavy chain constant domain 3 (CH3), CH3-CH3 interfaces in both CH3 domains are replaced with a charged amino acid such that homodimer formation is electrostatically unfavorable and heterodimerization is electrostatically favorable. Additional methods of making multispecific molecules using electrostatic interactions are described in the following references, the contents of each of which is incorporated by reference herein, include US20100015133, U.S. Pat. No. 8,592,562B2, U.S. Pat. No. 9,200,060B2, US20140154254A1, and U.S. Pat. No. 9,358,286A1.

Common Light Chain

Light chain mispairing needs to be avoided to generate homogenous preparations of bispecific IgGs. One way to achieve this is through the use of the common light chain principle, i.e. combining two binders that share one light chain but still have separate specificities. An exemplary method of enhancing the formation of a desired bispecific antibody from a mixture of monomers is by providing a common variable light chain to interact with each of the heteromeric variable heavy chain regions of the bispecific antibody. Compositions and methods of producing bispecific antibodies with a common light chain as disclosed in, e.g., U.S. Pat. No. 7,183,076B2, US20110177073A1, EP284-7231A1, WO2016079081A1, and EP3055329A1, the contents of each of which is incorporated by reference herein.

CrossMab

Another option to reduce light chain mispairing is the CrossMab technology which avoids non-specific L chain mispairing by exchanging CH1 and CL domains in the Fab of one half of the bispecific antibody. Such crossover variants retain binding specificity and affinity, but make the two arms so different that L chain mispairing is prevented. The CrossMab technology (as reviewed in Klein et al. Supra) involves domain swapping between heavy and light chains so as to promote the formation of the correct pairings. Briefly, to construct a bispecific IgG-like CrossMab antibody that could bind to two antigens by using two distinct light chain-heavy chain pairs, a two-step modification process is applied. First, a dimerization interface is engineered into the C-terminus of each heavy chain using a heterodimerization approach, e.g., Knob-into-hole (KiH) technology, to ensure that only a heterodimer of two distinct heavy chains from one antibody (e.g., Antibody A) and a second antibody (e.g., Antibody B) is efficiently formed. Next, the constant heavy 1 (CH1) and constant light (CL) domains of one antibody are exchanged (Antibody A), keeping the variable heavy (VH) and variable light (VL) domains consistent. The exchange of the CH1 and CL domains ensured that the modified antibody (Antibody A) light chain would only efficiently dimerize with the modified antibody (antibody A) heavy chain, while the unmodified antibody (Antibody B) light chain would only efficiently dimerize with the unmodified antibody (Antibody B) heavy chain; and thus only the desired bispecific CrossMab would be efficiently formed (see e.g., Cain, C. SciBX 4(28); doi:10.1038/scibx.2011.783, the contents of which are incorporated by reference herein).

Common Heavy Chain

An exemplary method of enhancing the formation of a desired bispecific antibody from a mixture of monomers is by providing a common variable heavy chain to interact with each of the heteromeric variable light chain regions of the bispecific antibody. Compositions and methods of producing bispecific antibodies with a common heavy chain are disclosed in, e.g., US20120184716, US20130317200, and US20160264685A1, the contents of each of which is incorporated by reference herein.

Amino Acid Modifications

Alternative compositions and methods of producing multispecific antibodies with correct light chain pairing include various amino acid modifications. For example, Zymeworks describes heterodimers with one or more amino acid modifications in the CH1 and/or CL domains, one or more amino acid modifications in the VH and/or VL domains, or a combination thereof, which are part of the interface between the light chain and heavy chain and create preferential pairing between each heavy chain and a desired light chain such that when the two heavy chains and two light chains of the heterodimer pair are co-expressed in a cell, the heavy chain of the first heterodimer preferentially pairs with one of the light chains rather than the other (see e.g., WO2015181805). Other exemplary methods are described in WO2016026943 (Argen-X), US20150211001, US20140072581A1, US20160039947A1, and US20150368352.

Lambda/Kappa Formats

Multispecific molecules (e.g., multispecific antibody molecules) that include the lambda light chain polypeptide and a kappa light chain polypeptides, can be used to allow for heterodimerization. Methods for generating bispecific antibody molecules comprising the lambda light chain polypeptide and a kappa light chain polypeptides are disclosed in U.S. Ser. No. 62/399,319 filed on Sep. 23, 2016, incorporated herein by reference in its entirety.

In embodiments, the multispecific molecules includes a multispecific antibody molecule, e.g., an antibody molecule comprising two binding specificities, e.g., a bispecific antibody molecule. The multispecific antibody molecule includes:

a lambda light chain polypeptide 1 (LLCP1) specific for a first epitope;

a heavy chain polypeptide 1 (HCP1) specific for the first epitope;

a kappa light chain polypeptide 2 (KLCP2) specific for a second epitope; and a heavy chain polypeptide 2 (HCP2) specific for the second epitope.

"Lambda light chain polypeptide 1 (LLCP1)", as that term is used herein, refers to a polypeptide comprising sufficient light chain (LC) sequence, such that when combined with a cognate heavy chain variable region, can mediate specific binding to its epitope and complex with an HCP1. In an embodiment it comprises all or a fragment of a CH1 region. In an embodiment, an LLCP1 comprises LC-CDR1, LC-CDR2, LC-CDR3, FR1, FR2, FR3, FR4, and CH1, or sufficient sequence therefrom to mediate specific binding of its epitope and complex with an HCP1. LLCP1, together with its HCP1, provide specificity for a first epitope (while KLCP2, together with its HCP2, provide specificity for a second epitope). As described elsewhere herein, LLCP1 has a higher affinity for HCP1 than for HCP2.

"Kappa light chain polypeptide 2 (KLCP2)", as that term is used herein, refers to a polypeptide comprising sufficient light chain (LC) sequence, such that when combined with a cognate heavy chain variable region, can mediate specific binding to its epitope and complex with an HCP2. In an embodiments it comprises all or a fragment of a CH1 region. In an embodiment, a KLCP2 comprises LC-CDR1, LC-CDR2, LC-CDR3, FR1, FR2, FR3, FR4, and CH1, or sufficient sequence therefrom to mediate specific binding of its epitope and complex with an HCP2. KLCP2, together with its HCP2, provide specificity for a second epitope (while LLCP1, together with its HCP1, provide specificity for a first epitope).

"Heavy chain polypeptide 1 (HCP1)", as that term is used herein, refers to a polypeptide comprising sufficient heavy chain (HC) sequence, e.g., HC variable region sequence, such that when combined with a cognate LLCP1, can mediate specific binding to its epitope and complex with an HCP1. In an embodiments it comprises all or a fragment of a CH1 region. In an embodiment, it comprises all or a fragment of a CH2 and/or CH3 region. In an embodiment an HCP1 comprises HC-CDR1, HC-CDR2, HC-CDR3, FR1, FR2, FR3, FR4, CH1, CH2, and CH3, or sufficient sequence therefrom to: (i) mediate specific binding of its epitope and complex with an LLCP1, (ii) to complex preferentially, as described herein to LLCP1 as opposed to KLCP2; and (iii) to complex preferentially, as described herein, to an HCP2, as opposed to another molecule of HCP1. HCP1, together with its LLCP1, provide specificity for a first epitope (while KLCP2, together with its HCP2, provide specificity for a second epitope).

"Heavy chain polypeptide 2 (HCP2)", as that term is used herein, refers to a polypeptide comprising sufficient heavy chain (HC) sequence, e.g., HC variable region sequence, such that when combined with a cognate LLCP1, can mediate specific binding to its epitope and complex with an HCP1. In an embodiments it comprises all or a fragment of a CH1 region. In an embodiments it comprises all or a fragment of a CH2 and/or CH3 region. In an embodiment an HCP1 comprises HC-CDR1, HC-CDR2, HC-CDR3, FR1, FR2, FR3, FR4, CH1, CH2, and CH3, or sufficient sequence therefrom to: (i) mediate specific binding of its epitope and complex with an KLCP2, (ii) to complex preferentially, as described herein to KLCP2 as opposed to LLCP1; and (iii) to complex preferentially, as described herein, to an HCP1, as opposed to another molecule of HCP2. HCP2, together with its KLCP2, provide specificity for a second epitope (while LLCP1, together with its HCP1, provide specificity for a first epitope).

In some embodiments of the multispecific antibody molecule disclosed herein:

LLCP1 has a higher affinity for HCP1 than for HCP2; and/or

KLCP2 has a higher affinity for HCP2 than for HCP1.

In embodiments, the affinity of LLCP1 for HCP1 is sufficiently greater than its affinity for HCP2, such that under preselected conditions, e.g., in aqueous buffer, e.g., at pH 7, in saline, e.g., at pH 7, or under physiological conditions, at least 75%, 80, 90, 95, 98, 99, 99.5, or 99.9% of the multispecific antibody molecule molecules have a LLCP1 complexed, or interfaced with, a HCP1.

In some embodiments of the multispecific antibody molecule disclosed herein:

the HCP1 has a greater affinity for HCP2, than for a second molecule of HCP1; and/or the HCP2 has a greater affinity for HCP1, than for a second molecule of HCP2.

In embodiments, the affinity of HCP1 for HCP2 is sufficiently greater than its affinity for a second molecule of HCP1, such that under preselected conditions, e.g., in aqueous buffer, e.g., at pH 7, in saline, e.g., at pH 7, or under physiological conditions, at least 75%, 80, 90, 95, 98, 99 99.5 or 99.9% of the multispecific antibody molecule molecules have a HCP1 complexed, or interfaced with, a HCP2.

In another aspect, disclosed herein is a method for making, or producing, a multispecific antibody molecule. The method includes:

(i) providing a first heavy chain polypeptide (e.g., a heavy chain polypeptide comprising one, two, three or all of a first heavy chain variable region (first VH), a first CH1, a first heavy chain constant region (e.g., a first CH2, a first CH3, or both));

(ii) providing a second heavy chain polypeptide (e.g., a heavy chain polypeptide comprising one, two, three or all of a second heavy chain variable region (second VH), a second CH1, a second heavy chain constant region (e.g., a second CH2, a second CH3, or both));

(iii) providing a lambda chain polypeptide (e.g., a lambda light variable region (VLX), a lambda light constant chain (VLX), or both) that preferentially associates with the first heavy chain polypeptide (e.g., the first VH); and (iv) providing a kappa chain polypeptide (e.g., a lambda light variable region (VLK), a lambda light constant chain (VLK), or both) that preferentially associates with the second heavy chain polypeptide (e.g., the second VH), under conditions where (i)-(iv) associate.

In embodiments, the first and second heavy chain polypeptides form an Fc interface that enhances heterodimerization.

In embodiments, (i)-(iv) (e.g., nucleic acid encoding (i)-(iv)) are introduced in a single cell, e.g., a single mammalian cell, e.g., a CHO cell. In embodiments, (i)-(iv) are expressed in the cell.

In embodiments, (i)-(iv) (e.g., nucleic acid encoding (i)-(iv)) are introduced in different cells, e.g., different mammalian cells, e.g., two or more CHO cell. In embodiments, (i)-(iv) are expressed in the cells.

In one embodiments, the method further comprises purifying a cell-expressed antibody molecule, e.g., using a lambda- and/or-kappa-specific purification, e.g., affinity chromatography.

In embodiments, the method further comprises evaluating the cell-expressed multispecific antibody molecule. For example, the purified cell-expressed multispecific antibody molecule can be analyzed by techniques known in the art, include mass spectrometry. In one embodiment, the purified cell-expressed antibody molecule is cleaved, e.g., digested with papain to yield the Fab moieties and evaluated using mass spectrometry.

In embodiments, the method produces correctly paired kappa/lambda multispecific, e.g., bispecific, antibody molecules in a high yield, e.g., at least 75%, 80, 90, 95, 98, 99 99.5 or 99.9%.

In other embodiments, the multispecific, e.g., a bispecific, antibody molecule that includes:

(i) a first heavy chain polypeptide (HCP1) (e.g., a heavy chain polypeptide comprising one, two, three or all of a first heavy chain variable region (first VH), a first CH1, a first heavy chain constant region (e.g., a first CH2, a first CH3, or both)), e.g., wherein the HCP1 binds to a first epitope;

(ii) a second heavy chain polypeptide (HCP2) (e.g., a heavy chain polypeptide comprising one, two, three or all of a second heavy chain variable region (second VH), a second CH1, a second heavy chain constant region (e.g., a second CH2, a second CH3, or both)), e.g., wherein the HCP2 binds to a second epitope;

(iii) a lambda light chain polypeptide (LLCP1) (e.g., a lambda light variable region (VL1), a lambda light constant chain (VL1), or both) that preferentially associates with the first heavy chain polypeptide (e.g., the first VH), e.g., wherein the LLCP1 binds to a first epitope; and (iv) a kappa light chain polypeptide (KLCP2) (e.g., a lambda light variable region (VLk), a lambda light constant chain (VLk), or both) that preferentially associates with the second heavy chain polypeptide (e.g., the second VH), e.g., wherein the KLCP2 binds to a second epitope.

In embodiments, the first and second heavy chain polypeptides form an Fc interface that enhances heterodimerization. In embodiments, the multispecific antibody molecule has a first binding specificity that includes a hybrid VL1-CL1 heterodimerized to a first heavy chain variable region connected to the Fc constant, CH2-CH3 domain (having a knob modification) and a second binding specificity that includes a hybrid VLk-CLk heterodimerized to a second heavy chain variable region connected to the Fc constant, CH2-CH3 domain (having a hole modification).

Exemplary Multispecific Configurations:

In some embodiments, the multispecific molecule includes a first and a second non-contiguous polypeptide, wherein:

(i) the first polypeptide includes, e.g., in the N- to C-orientation, a tumor targeting moiety, e.g., an antibody molecule (e.g., a first portion of a first antigen domain, e.g., a first VH-CH1 of a Fab molecule), that binds to, e.g., a cancer antigen, e.g., a solid tumor, a stromal or a hematological antigen, connected, optionally, via a linker to, a cytokine molecule or an immune cell engager, e.g., an antibody molecule, e.g., a scFv that binds to an immune cell antigen; and (ii) the second polypeptide includes, e.g., in the N- to C-orientation, a second portion of the first antigen domain, e.g., a first VL-CL of the Fab, that binds to, e.g., a tumor or stromal antigen (e.g., the same tumor or stromal antigen bound by the first VH-CH1). In some embodiments, the multispecific molecule includes a Fab molecule connected, optionally, via a linker to, a scFv. In embodiments, the multispecific molecule is a bispecific molecule.

In other embodiments, the multispecific molecule includes a first, a second and a third non-contiguous polypeptide, wherein:

(i) the first polypeptide includes, e.g., in the N- to C-orientation, a tumor targeting moiety, e.g., an antibody molecule (e.g., a first portion of a first antigen domain, e.g., a first VH-CH1 of a Fab molecule), that binds to, e.g., a tumor or a stromal antigen, connected, optionally, via a linker to, a first domain that promotes association between the first and the second polypeptide (e.g., a first immunoglobulin constant domain (e.g., a first Fc molecule as described herein);

(ii) the second polypeptide includes, e.g., in the N- to C-orientation, a cytokine molecule or an immune cell engager (e.g., an antibody molecule, e.g., a scFv, that binds to an immune cell antigen), connected, optionally, via a linker to, a second domain that promotes association between the first and the second polypeptide (e.g., a second immunoglobulin constant domain (e.g., a second Fc molecule as described herein); and (iii) the third polypeptide includes, e.g., in the N- to C-orientation, a second portion of the first antigen domain, e.g., a first VL-CL of the Fab, that binds to, e.g., a tumor or stromal antigen (e.g., the same tumor or stromal antigen bound by the first VH-CH1). In some embodiments, the multispecific molecule includes a Fab molecule connected, optionally, via a linker to, a first Fc molecule, a cytokine or immune cell engager (e.g., a scFv), connected, optionally, via a linker to, a second Fc molecule. In embodiments, the multispecific molecule is a bispecific molecule.

In other embodiments, the multispecific molecule includes a first, a second and a third non-contiguous polypeptide, wherein:

(i) the first polypeptide includes, e.g., in the N- to C-orientation, a tumor targeting moiety, e.g., an antibody molecule (e.g., a first portion of a first antigen domain, e.g., a first VH-CH1 of a Fab molecule), that binds to, e.g., a cancer antigen, connected, optionally, via a linker to, a first domain that promotes association between the first and the second polypeptide (e.g., a first immunoglobulin constant domain (e.g., a first Fc molecule as described herein);

(ii) the second polypeptide includes, e.g., in the N- to C-orientation, a cytokine molecule or an immune cell engager (e.g., an antibody molecule, e.g., a scFv, that binds to an immune cell antigen), connected, optionally, via a linker to, a second domain that promotes association between the first and the second polypeptide (e.g., a second immunoglobulin constant domain (e.g., a second Fc molecule as described herein); and (iii) the third polypeptide includes, e.g., in the N- to C-orientation, a second portion of the first antigen domain, e.g., a first VL-CL of the Fab, that binds to, e.g., a tumor or stromal antigen (e.g., the same tumor or stromal antigen bound by the first VH-CH1). In some embodiments, the multispecific molecule includes a Fab molecule connected, optionally, via a linker to, a first Fc molecule, a cytokine or immune cell engager (e.g., a scFv), connected, optionally, via a linker to, a second Fc molecule,
wherein either the first or the second polypeptide further comprise a cytokine molecule or an immune cell engager, optionally covalently linked to the C-terminus of the first or second immunoglobulin constant domain. In embodiments, the multispecific molecule is a trispecific molecule.

In other embodiments, the multispecific molecule includes a first, a second and a third non-contiguous polypeptide, wherein:
(i) the first polypeptide includes, e.g., in the N- to C-orientation, a tumor targeting moiety, e.g., an antibody molecule (e.g., a first portion of a first antigen domain, e.g., a first VH-CH1 of a Fab molecule), that binds to, e.g., a tumor or a stromal antigen, connected, optionally, via a linker to, a first domain that promotes association between the first and the second polypeptide (e.g., a first immunoglobulin constant domain (e.g., a first Fc molecule as described herein);
(ii) the second polypeptide includes, e.g., in the N- to C-orientation, a cytokine molecule or an immune cell engager (e.g., an antibody molecule, e.g., a scFv, that binds to an immune cell antigen), connected, optionally, via a linker to, a second domain that promotes association between the first and the second polypeptide (e.g., a second immunoglobulin constant domain (e.g., a second Fc molecule as described herein); and
(iii) the third polypeptide includes, e.g., in the N- to C-orientation, a second portion of the first antigen domain, e.g., a first VL-CL of the Fab, that binds to, e.g., a tumor or stromal antigen (e.g., the same tumor or stromal antigen bound by the first VH-CH1). In some embodiments, the multispecific molecule includes a Fab molecule connected, optionally, via a linker to, a first Fc molecule, a cytokine or immune cell engager (e.g., a scFv), connected, optionally, via a linker to, a second Fc molecule,
wherein either the first and the second polypeptide further comprise a cytokine molecule, an immune cell engager or both, optionally covalently linked to the C-terminus of the first or second immunoglobulin constant domain. In embodiments, the multispecific molecule is a tetraspecific molecule.

In other embodiments, the multispecific molecule comprises a first and a second polypeptide, wherein the first polypeptide comprises, e.g., in the N to C direction:
a tumor targeting moiety;
(optionally) a domain that promotes association of the first and second polypeptide, e.g., an Fc molecule; and
a first polypeptide comprising an immune cell engager or a cytokine molecule; and, wherein the second polypeptide comprises, e.g., in the N to C direction:
a tumor targeting moiety, or subunit thereof;
(optionally) a domain that promotes association of the first and second polypeptide, e.g., an Fc molecule; and
a second polypeptide comprising an immune cell engager or a cytokine molecule,
wherein the first and second polypeptide are different.

In embodiments, the tumor targeting moiety of the first polypeptide comprises a light chain variable domain of a tumor targeting molecule (e.g., Fab); and the tumor targeting moiety of the second polypeptide comprises a heavy chain variable domain of a tumor targeting molecule (e.g., Fab).

In other embodiments, the first tumor targeting moiety of the first polypeptide comprises a heavy chain variable domain of a tumor targeting molecule (e.g., Fab); and the second tumor targeting moiety of the second polypeptide comprises a light chain variable domain of a tumor targeting molecule (e.g., Fab).

In other embodiments, the first tumor targeting moiety of the first polypeptide comprises a light chain variable domain of a tumor targeting molecule (e.g., Fab); and the second tumor targeting moiety of the second polypeptide comprises a heavy chain variable domain of a tumor targeting molecule (e.g., Fab).

In other embodiments, the tumor targeting moiety of the first polypeptide comprises a tumor targeting scFv; and the tumor targeting moiety of the second polypeptide comprises a tumor targeting scFv.

In other embodiments, the multispecific molecule comprises:
a) a first polypeptide comprising:
a first domain that promotes association of the first and second polypeptide, e.g., a first Fc molecule; and
two polypeptides chosen from: a tumor targeting moiety; an immune cell engager; or a cytokine molecule; and
b) a second polypeptide comprising:
a second domain that promotes association of the first and second polypeptide, e.g., an second Fc molecule; and
two polypeptides chosen from: a tumor targeting moiety; an immune cell engager; or a cytokine molecule,
wherein the multispecific molecule comprises a tumor targeting moiety; an immune cell engager; and a cytokine molecule. In embodiments, the multispecific molecule includes one of the following:
(i) a tumor targeting moiety; an immune cell engager; and two cytokine molecules;
(ii) a tumor targeting moiety; two immune cell engagers; and a cytokine molecules; or
(iii) two tumor targeting moieties; an immune cell engager; and a cytokine molecule.

In other embodiments, the multispecific molecule includes a first polypeptide and a second polypeptide, wherein:
i) the first polypeptide comprises, e.g., in the N-C or C-N direction, a tumor targeting moiety; a first domain that promotes association of the first and second polypeptide, e.g., a first Fc molecule; and an immune cell engager;
ii) a first polypeptide comprises, e.g., in the N-C or C-N direction, a tumor targeting moiety; a first domain that promotes association of the first and second polypeptide, e.g., a first Fc molecule; and a cytokine molecule; or
iii) a first polypeptide comprises, e.g., in the N-C or C-N direction a cytokine; a first domain that promotes association of the first and second polypeptide, e.g., a first Fc molecule; and an immune cell engager; and
iv) the second polypeptide comprises, e.g., in the N-C or C-N direction, a tumor targeting moiety; a second domain that promotes association of the first and second polypeptide, e.g., a second Fc molecule; and an immune cell engager;
ii) the second polypeptide comprises, e.g., in the N-C or C-N direction, a tumor targeting moiety; a second domain that promotes association of the first and second polypeptide, e.g., a second Fc molecule; and a cytokine molecule; or
iii) a second polypeptide comprises, e.g., in the N-C or C-N direction a cytokine; a second domain that promotes association of the first and second polypeptide, e.g., a second Fc molecule; and an immune cell engager.

Additional features and embodiments of the application include one or more of the following.

In another aspect, the invention features a multispecific (e.g., bi- or trispecific) molecule comprising the following formula in an N terminal to C terminal orientation:
R1-(optionally L1)-R2-(optionally L2)-R3;
R1-(optionally L1)-R3-(optionally L2)-R2;

R2-(optionally L1)-R1-(optionally L2)-R3;
R2-(optionally L1)-R3-(optionally L2)-R1;
R3-(optionally L1)-R1-(optionally L2)-R2; or
R3-(optionally L1)-R2-(optionally L2)-R1;
wherein:

(i) R1 is an tumor targeting moiety as described herein, wherein R1 can be 0 only when R2 and R3 are present, or R1 comprises 1, 2 or more tumor targeting moieties (e.g., the same or different tumor targeting moieties);

(ii) R2 is an immune cell engager as described herein, wherein R2 can be 0 only when R1 and R3 are present, or R2 comprises 1, 2 or more immune cell engagers (e.g., the same or different immune cell engagers);

(iii) R3 is a cytokine molecule as described herein, wherein R3 can be 0 only when R1 and R2 are present, or R3 comprises 1, 2 or more cytokine molecules (e.g., the same or different cytokine molecules); and (iv) optionally, L1 and/or L2 are any of the linkers described herein.

In some embodiments, R1 and/or R2 is a full antibody (e.g., an antibody that includes at least one, and preferably two, complete heavy chains, and at least one, and preferably two, complete light chains), or an antigen-binding fragment (e.g., a Fab, F(ab')$_2$, Fv, a single chain Fv fragment, a single domain antibody, a diabody (dAb), a bivalent antibody, or bispecific antibody or fragment thereof, a single domain variant thereof, or a camelid antibody)

In other embodiments, R1 and R2 is chosen from a common light chain bispecific IgG; a dual acting Fab (DAF), a CrossMab, an IgG-dssc-Fv2, a DVD (dual variable domain), an IgG-dsFv, an IgG-scFab, a scFab-dsscFv, an Fv2-Fc, a Fab-scFv2, a Fab-scFv, a scFv-scFv, a whole antibody-Fab, a whole antibody-scFv, a diabody, a DART (dual affinity retargeting molecule), or a TandAb.

In other embodiments, the multispecific molecule further includes R4, wherein R4 is a second tumor targeting moiety; a second immune cell engager (e.g., an NK cell engager, a B cell engager, a dendritic cell engager, or a macrophage cell engager); or a second cytokine molecule.

In other embodiments, the multispecific molecule can further include L3, wherein L3 is a linker (e.g., a linker described herein).

In some embodiments, R4 is a full antibody (e.g., an antibody that includes at least one, and preferably two, complete heavy chains, and at least one, and preferably two, complete light chains), or an antigen-binding fragment (e.g., a Fab, F(ab')$_2$, Fv, a single chain Fv fragment, a single domain antibody, a diabody (dAb), a bivalent antibody, or bispecific antibody or fragment thereof, a single domain variant thereof, or a camelid antibody).

In other embodiments, R1 and R4 is a common light chain bispecific IgG; a dual acting Fab (DAF), a CrossMab, an IgG-dssc-Fv2, a DVD (dual variable domain), an IgG-dsFv, an IgG-scFab, a scFab-dsscFv, an Fv2-Fc, a Fab-scFv2, a Fab-scFv, a scFv-scFv, a whole antibody-Fab, a whole antibody-scFv, a diabody, a DART (dual affinity retargeting molecule), or a TandAb.

In other embodiments, R2 and R4 is a common light chain bispecific IgG; a dual acting Fab (DAF), a CrossMab, an IgG-dssc-Fv2, a DVD (dual variable domain), an IgG-dsFv, an IgG-scFab, a scFab-dsscFv, an Fv2-Fc, a Fab-scFv2, a Fab-scFv, a scFv-scFv, a whole antibody-Fab, a whole antibody-scFv, a diabody, a DART (dual affinity retargeting molecule), or a TandAb.

In another aspect, the invention features a multispecific molecule, comprising R1 and R2, wherein:

(i) R1 is the tumor targeting moiety described herein, e.g., R1 comprises 1, 2 or more tumor targeting moieties (e.g., the same or different tumor targeting moieties);

(ii) R2 is the cytokine molecule described herein, e.g., R2 comprises 1, 2 or more cytokine molecules (e.g., the same or different cytokine molecules); and (iii) optionally, L1 and/or L2 are the linkers described herein.

In some embodiments, R1 is an anti-FAP Fab and R2 is an IL-15 polypeptide. In some embodiments, R1 and R2 are dimerized via a knob-in-hole Fc dimer (e.g., as shown in Fig. XA), e.g., comprising a first and second Fc. In some embodiments, the first Fc comprises an amino acid substitution selected from: T366S; L368A; or Y407V. In some embodiments, the second Fc comprises an amino acid substitution selected from: T366W.

In another aspect, the invention features a multispecific molecule comprising R1, R2, and R3, wherein:

(i) R1 is the tumor targeting moiety described herein, e.g., R1 comprises 1, 2 or more tumor targeting moieties (e.g., the same or different tumor targeting moieties);

(ii) R2 is the immune cell engager described herein, e.g., R2 comprises 1, 2 or more immune cell engagers (e.g., the same or different immune cell engagers);

(iii) R3 is the cytokine molecule described herein, e.g., R3 comprises 1, 2 or more cytokine molecules (e.g., the same or different cytokine molecules); and (iv) optionally, L1 and/or L2 are the linkers described herein.

In some embodiments, R1 is an anti-mesothelin Fab, R2 is an IL-15 polypeptide, and R3 is a CD40L polypeptide. In some embodiments, R1 and R2 are dimerized via a knob-in-hole Fc, e.g., comprising a first and second Fc. In some embodiments, the first Fc comprises an amino acid substitution at position 366, 368 and/or 407, e.g., selected from: T366S; L368A; or Y407V. In some embodiments, the second Fc comprises an amino acid substitution at position 366, e.g., T366W.

In another aspect, the invention features a multispecific molecule comprising: R1, R2, R3, and R4, wherein:

(i) R1 is the tumor targeting moiety described herein;

(ii) R2 and R4 are each a first and second immune cell engager described herein;

(iii) R3 is the cytokine molecule described herein; and (iv) optionally, L1 and/or L2 are the linkers described herein.

In some embodiments, R1 is an anti-FAP Fab, R3 is an IL-15 polypeptide, R2 is a CD40L polypeptide, and R4 is a B7H6 polypeptide. In some embodiments, R1, R2, R3, and R4 are dimerized via an Fc dimer. In some embodiments, the Fc comprises an amino acid substitution selected from: T366S; L368A; or Y407V. In some embodiments, the Fc comprises an amino acid substitution selected from: T366W.

Tumor-Targeting Moieties

The present disclosure provides, inter alia, multispecific (e.g., bi-, tri-, tetra-specific) molecules, that include, e.g., are engineered to contain, one or more tumor specific targeting moieties that direct the molecule to a tumor cell.

In certain embodiments, the multispecific molecules disclosed herein include a tumor-targeting moiety. The tumor targeting moiety can be chosen from an antibody molecule (e.g., an antigen binding domain as described herein), a receptor or a receptor fragment, or a ligand or a ligand fragment, or a combination thereof. In some embodiments, the tumor targeting moiety associates with, e.g., binds to, a tumor cell (e.g., a molecule, e.g., antigen, present on the surface of the tumor cell). In certain embodiments, the tumor targeting moiety targets, e.g., directs the multispecific molecules disclosed herein to a cancer (e.g., a cancer or tumor cells). In some embodiments, the cancer is chosen from a hematological cancer, a solid cancer, a metastatic cancer, or a combination thereof.

In some embodiments, the multispecific molecule, e.g., the tumor-targeting moiety, binds to a solid tumor antigen or a stromal antigen. The solid tumor antigen or stromal antigen can be present on a solid tumor, or a metastatic lesion thereof. In some embodiments, the solid tumor is chosen from one or more of pancreatic (e.g., pancreatic adenocarcinoma), breast, colorectal, lung (e.g., small or non-small cell lung cancer), skin, ovarian, or liver cancer. In one embodiment, the solid tumor is a fibrotic or desmoplastic solid tumor. For example, the solid tumor antigen or stromal antigen can be present on a tumor, e.g., a tumor of a class typified by having one or more of: limited tumor perfusion, compressed blood vessels, or fibrotic tumor interstitium.

In certain embodiments, the solid tumor antigen is chosen from one or more of: PDL1, CD47, mesothelin, ganglioside 2 (GD2), prostate stem cell antigen (PSCA), prostate specific membrane antigen (PMSA), prostate-specific antigen (PSA), carcinoembryonic antigen (CEA), Ron Kinase, c-Met, Immature laminin receptor, TAG-72, BING-4, Calcium-activated chloride channel 2, Cyclin-B1, 9D7, Ep-CAM, EphA3, Her2/neu, Telomerase, SAP-1, Survivin, NY-ESO-1/LAGE-1, PRAME, SSX-2, Melan-A/MART-1, Gp100/pmel17, Tyrosinase, TRP-1/-2, MC1R, β-catenin, BRCA1/2, CDK4, CML66, Fibronectin, p53, Ras, TGF-B receptor, AFP, ETA, MAGE, MUC-1, CA-125, BAGE, GAGE, NY-ESO-1, β-catenin, CDK4, CDC27, CD47, α actinin-4, TRP1/gp75, TRP2, gp100, Melan-A/MART1, gangliosides, WT1, EphA3, Epidermal growth factor receptor (EGFR), CD20, MART-2, MART-1, MUC1, MUC2, MUM1, MUM2, MUM3, NA88-1, NPM, OA1, OGT, RCC, RUI1, RUI2, SAGE, TRG, TRP1, TSTA, Folate receptor alpha, L1-CAM, CAIX, EGFRvIII, gpA33, GD3, GM2, VEGFR, Intergrins (Integrin alphaVbeta3, Integrin alpha5Beta1), Carbohydrates (Le), IGF1R, EPHA3, TRAILR1, TRAILR2, or RANKL.

In some embodiments, the solid tumor antigen is chosen from: PDL1, Mesothelin, CD47, GD2, PMSA, PSCA, CEA, Ron Kinase, or c-Met.

In one embodiment, the tumor-targeting moiety includes an antibody molecule (e.g., Fab or scFv) that binds to mesothelin. In some embodiments, the antibody molecule to mesothelin comprises one, two, three CDRs from the heavy chain variable domain sequence of: QVQLQQSGPELEKPGASVKISCKASGYSFTGYTMNWVKQSHGKSLEWIGLITPYNGASS YNQKFRGKATLTVDKSSSTAYMDLLSLTSEDSAVYFCARGGYDGRGFDYWGQGTTVT VSS (SEQ ID NO: 1), or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 1.

In some embodiments, the antibody molecule to mesothelin comprises one, two, three CDRs selected from GYSFTGYTMN (SEQ ID NO: 2); LITPYNGASSYNQKFRG (SEQ ID NO: 3); and GGYDGRGFDY (SEQ ID NO: 4), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin consists of three CDRs, wherein CDR1 comprises GYSFTGYTMN (SEQ ID NO: 2); CDR2 comprises: LITPYNGASSYNQKFRG (SEQ ID NO: 3); and CDR3 comprises GGYDGRGFDY (SEQ ID NO: 4), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin consists of three CDRs, wherein CDR1 consists of GYSFTGYTMN (SEQ ID NO: 2); CDR2 consists of LITPYNGASSYNQKFRG (SEQ ID NO: 3); and CDR3 consists of GGYDGRGFDY (SEQ ID NO: 4), or a closely related CDR, e.g., CDRs which have at least one amino acid alteration, but not more than two, three or four alterations (e.g., substitutions, deletions, or insertions, e.g., conservative substitutions).

In embodiments, the antibody molecule to mesothelin includes the heavy chain variable domain sequence of: QVQLQQSGPELEKPGASVKISCKASGYSFTGYTMNWVKQSHGKSLEWIGLITPYNGASSYNQKFRGKATLTVDKSSSTAYMDLLSLTSEDSAVYFCARGGYDGRGFDYWGQGTTVT VSS (SEQ ID NO: 1), or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 1.

In embodiments, the antibody molecule to mesothelin is a Fab and further comprises a heavy chain constant region (CH1) having the amino acid sequence:

(SEQ ID NO: 5)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHT, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 5. In some embodiments, the antibody molecule further comprises a signal peptide, e.g., a signal peptide comprising the amino acid sequence:

(SEQ ID NO: 6)
MEFGLSWVFLVALFRGVQC.

Alternatively, or in combination with the heavy chain to mesothelin disclosed herein, the antibody molecule to mesothelin comprises one, two, three CDRs from the light chain variable domain sequence of: DIELTQSPAIMSASPGEKVTMTCSASSSVSYMHWYQQKSGTSPKRWIYDTSKLASGVPG RFSGSGSGNSYSLTISSVEAEDDATYYCQQWSGYPLTFGAGTKLEIK (SEQ ID NO: 7), or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 7.

In some embodiments, the antibody molecule to mesothelin comprises one, two, three CDRs from SASSSVSYMH (SEQ ID NO: 8); DTSKLAS (SEQ ID NO: 9); and QQWSGYPLT (SEQ ID NO: 10), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin consists of three CDRs, wherein CDR1 comprises SASSSVSYMH (SEQ ID NO: 8); CDR2 comprises: DTSKLAS (SEQ ID NO: 9); and CDR3 comprises QQWSGYPLT (SEQ ID NO: 10), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin consists of three CDRs, wherein CDR1 consists of SASSSVSYMH (SEQ ID NO: 8); CDR2 consists of DTSKLAS (SEQ ID NO: 9); and CDR3 consists of QQWSGYPLT (SEQ ID NO: 10), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin comprises the light chain variable domain sequence of: DIELTQSPAIMSASPGEKVTMTCSASSSVSY-MHWYQQKSGTSPKRWIYDTSKLASGVPG RFSGS-GSGNSYSLTISSVEAEDDATYYCQQWSGYPLTFG-AGTKLEIK (SEQ ID NO: 7), or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7.

In some embodiments, the antibody molecule to mesothelin is a Fab and further comprises a light chain constant region (CL1) having the amino acid sequence:

```
                                        (SEQ ID NO: 11)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC,
``` or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 11. In embodiments, the antibody molecule further comprises a signal peptide, e.g., a signal peptide comprising the amino acid sequence: MKYLL-PTAAAGLLLLAAQPAMA (SEQ ID NO: 12).

In other embodiments, the multispecific molecule, e.g., the tumor-targeting moiety, binds to a stromal antigen. In embodiments, the stromal antigen is chosen from one or more of: fibroblast activating protease (FAP), TGF-beta, hyaluronic acid, collagen, e.g., collagen IV, tenascin C, or tenascin W.

In one embodiment, the tumor-targeting moiety includes an antibody molecule (e.g., Fab or scFv) that binds to FAP, e.g., human FAP. In some embodiments, the antibody molecule to FAP comprises one, two, three CDRs from the heavy chain variable domain sequence depicted in underline in FIG. 12C (SEQ ID NO: 13), or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 13. In some embodiments, the antibody molecule to FAP includes the heavy chain variable domain sequence depicted in underline in FIG. 12C (SEQ ID NO: 13), or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 13.

In embodiments, the antibody molecule to FAP is a Fab and further comprises a heavy chain constant region (CH1) having the amino acid sequence: ASTKGPSVFPLA-PSSKSTSGGTAALGCLVKDYFPEPVTVSWNSGALT-SGVHTFPAVLQSS GLYSLSSVVTVPSSSLGTQTYI-CNVNHKPSNTKVDKRVEPKSC (SEQ ID NO: 14), or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 14. In embodiments, the antibody molecule further comprises a signal peptide, e.g., a signal peptide comprising the amino acid sequence: MEFGLSWVFLVALFRG-VQCEV (SEQ ID NO: 15).

Alternatively, or in combination with the heavy chain to FAP disclosed herein, the antibody molecule to FAP comprises one, two, three CDRs from the light chain variable domain sequence depicted in underline in FIG. 12D (SEQ ID NO: 16), or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 16. In some embodiments, the antibody molecule to FAP includes the light chain variable domain sequence depicted in underline in FIG. 12D (SEQ ID NO: 16), or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 16.

In embodiments, the antibody molecule to FAP is a Fab and further comprises a light chain constant region (CL1) having the amino acid sequence:

```
                                        (SEQ ID NO: 11)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC,
``` or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 11. In some embodiments, the antibody molecule further comprises a signal peptide, e.g., a signal peptide comprising the amino acid sequence:

```
                                        (SEQ ID NO: 12)
MKYLLPTAAAGLLLLAAQPAMA.
```

In other embodiments, the multispecific molecule, e.g., the tumor-targeting moiety, binds to a molecule, e.g., antigen, present on the surface of a hematological cancer, e.g., a leukemia or a lymphoma. In some embodiments, the hematological cancer is a B-cell or T cell malignancy. In some embodiments, the hematological cancer is chosen from one or more of a Hodgkin's lymphoma, Non-Hodgkin's lymphoma (e.g., B cell lymphoma, diffuse large B cell lymphoma, follicular lymphoma, chronic lymphocytic leukemia, mantle cell lymphoma, marginal zone B-cell lymphoma, Burkitt lymphoma, lymphoplasmacytic lymphoma, hairy cell leukemia), acute myeloid leukemia (AML), chronic myeloid leukemia, myelodysplastic syndrome (MDS), multiple myeloma, or acute lymphocytic leukemia. In embodiments, the cancer is other than acute myeloid leukemia (AML) or myelodysplastic syndrome (MDS). In embodiments, the hematological antigen is chosen from CD19, CD33, CD123, or CD20. In embodiments, the hematological antigen is other than CD33. CD19, In embodiments, the hematological antigen is chosen from CD19, CD20, CD33, CD47, CD123, CD20, CD99, CD30, BCMA, CD38, CD22, SLAMF7, or NY-ESO1.

Cytokine Molecules

The cytokines are generally polypeptides that influence cellular activity, for example, through signal transduction pathways. Accordingly, a cytokine of the multispecific or multifunctional polypeptide is useful and can be associated with receptor-mediated signaling that transmits a signal from outside the cell membrane to modulate a response within the cell. Cytokines are proteinaceous signaling compounds that are mediators of the immune response. They control many different cellular functions including proliferation, differentiation and cell survival/apoptosis; cytokines are also involved in several pathophysiological processes including viral infections and autoimmune diseases. Cytokines are synthesized under various stimuli by a variety of cells of both the innate (monocytes, macrophages, dendritic cells) and adaptive (T- and B-cells) immune systems. Cytokines can be classified into two groups: pro- and anti-inflammatory. Pro-inflammatory cytokines, including IFNγ, IL-1, IL-6 and TNF-alpha, are predominantly derived from the innate immune cells and Th1 cells. Anti-inflammatory cytokines, including IL-10, IL-4, IL-13 and IL-5, are synthesized from Th2 immune cells.

The present disclosure provides, inter alia, multi-specific (e.g., bi-, tri-, quad-specific) proteins, that include, e.g., are engineered to contain, one or more cytokine molecules, e.g., immunomodulatory (e.g., proinflammatory) cytokines and variants, e.g., functional variants, thereof. Accordingly, in some embodiments, the cytokine molecule is an interleukin or a variant, e.g., a functional variant thereof. In some embodiments the interleukin is a proinflammatory interleukin. In some embodiments the interleukin is chosen from interleukin-2 (IL-2), interleukin-12 (IL-12), interleukin-15 (IL-15), interleukin-18 (IL-18), interleukin-21 (IL-21), interleukin-7 (IL-7), or interferon gamma. In some embodiments, the cytokine molecule is a proinflammatory cytokine.

In certain embodiments, the cytokine is a single chain cytokine. In certain embodiments, the cytokine is a multichain cytokine (e.g., the cytokine comprises 2 or more (e.g., 2) polypeptide chains. An exemplary multichain cytokine is IL-12.

Examples of useful cytokines include, but are not limited to, GM-CSF, IL-1α, IL-1β, IL-2, IL-3, IL-4, IL-5, IL-6, IL-7, IL-8, IL-10, IL-12, IL-21, IFN-α, IFN-β, IFN-γ, MIP-1α, MIP-1β, TGF-β, TNF-α, and TNFβ. In one embodiment the cytokine of the multispecific or multifunctional polypeptide is a cytokine selected from the group of GM-CSF, IL-2, IL-7, IL-8, IL-10, IL-12, IL-15, IL-21, IFN-α, IFN-γ, MIP-1α, MP-1β and TGF-β. In one embodiment the cytokine of the i the multispecific or multifunctional polypeptide is a cytokine selected from the group of IL-2, IL-7, IL-10, IL-12, IL-15, IFN-α, and IFN-γ. In certain embodiments the cytokine is mutated to remove N- and/or O-glycosylation sites. Elimination of glycosylation increases homogeneity of the product obtainable in recombinant production.

In one embodiment, the cytokine of the multispecific or multifunctional polypeptide is IL-2. In a specific embodiment, the IL-2 cytokine can elicit one or more of the cellular responses selected from the group consisting of: proliferation in an activated T lymphocyte cell, differentiation in an activated T lymphocyte cell, cytotoxic T cell (CTL) activity, proliferation in an activated B cell, differentiation in an activated B cell, proliferation in a natural killer (NK) cell, differentiation in a NK cell, cytokine secretion by an activated T cell or an NK cell, and NK/lymphocyte activated killer (LAK) antitumor cytotoxicity. In another particular embodiment the IL-2 cytokine is a mutant IL-2 cytokine having reduced binding affinity to the .alpha.-subunit of the IL-2 receptor. Together with the .beta.- and .gamma.-subunits (also known as CD122 and CD132, respectively), the .alpha.-subunit (also known as CD25) forms the heterotrimeric high-affinity IL-2 receptor, while the dimeric receptor consisting only of the β- and γ-subunits is termed the intermediate-affinity IL-2 receptor. As described in PCT patent application number PCT/EP2012/051991, which is incorporated herein by reference in its entirety, a mutant IL-2 polypeptide with reduced binding to the .alpha.-subunit of the IL-2 receptor has a reduced ability to induce IL-2 signaling in regulatory T cells, induces less activation-induced cell death (AICD) in T cells, and has a reduced toxicity profile in vivo, compared to a wild-type IL-2 polypeptide. The use of such an cytokine with reduced toxicity is particularly advantageous in a multispecific or multifunctional polypeptide according to the invention, having a long serum half-life due to the presence of an Fc domain. In one embodiment, the mutant IL-2 cytokine of the multispecific or multifunctional polypeptide according to the invention comprises at least one amino acid mutation that reduces or abolishes the affinity of the mutant IL-2 cytokine to the .alpha.-subunit of the IL-2 receptor (CD25) but preserves the affinity of the mutant IL-2 cytokine to the intermediate-affinity IL-2 receptor (consisting of the β and γ subunits of the IL-2 receptor), compared to the non-mutated IL-2 cytokine. In one embodiment the one or more amino acid mutations are amino acid substitutions. In a specific embodiment, the mutant IL-2 cytokine comprises one, two or three amino acid substitutions at one, two or three position(s) selected from the positions corresponding to residue 42, 45, and 72 of human IL-2. In a more specific embodiment, the mutant IL-2 cytokine comprises three amino acid substitutions at the positions corresponding to residue 42, 45 and 72 of human IL-2. In an even more specific embodiment, the mutant IL-2 cytokine is human IL-2 comprising the amino acid substitutions F42A, Y45A and L72G. In one embodiment the mutant IL-2 cytokine additionally comprises an amino acid mutation at a position corresponding to position 3 of human IL-2, which eliminates the O-glycosylation site of IL-2. Particularly, said additional amino acid mutation is an amino acid substitution replacing a threonine residue by an alanine residue. A particular mutant IL-2 cytokine useful in the invention comprises four amino acid substitutions at positions corresponding to residues 3, 42, 45 and 72 of human IL-2. Specific amino acid substitutions are T3A, F42A, Y45A and L72G. As demonstrated in PCT patent application number PCT/EP2012/051991 and in the appended Examples, said quadruple mutant IL-2 polypeptide (IL-2 qm) exhibits no detectable binding to CD25, reduced ability to induce apoptosis in T cells, reduced ability to induce IL-2 signaling in T.sub.reg cells, and a reduced toxicity profile in vivo. However, it retains ability to activate IL-2 signaling in effector cells, to induce proliferation of effector cells, and to generate IFN-γ as a secondary cytokine by NK cells.

The IL-2 or mutant IL-2 cytokine according to any of the above embodiments may comprise additional mutations that provide further advantages such as increased expression or stability. For example, the cysteine at position 125 may be replaced with a neutral amino acid such as alanine, to avoid the formation of disulfide-bridged IL-2 dimers. Thus, in certain embodiments the IL-2 or mutant IL-2 cytokine of the multispecific or multifunctional polypeptide according to the invention comprises an additional amino acid mutation at a position corresponding to residue 125 of human IL-2. In one embodiment said additional amino acid mutation is the amino acid substitution C125A.

In a specific embodiment the IL-2 cytokine of the multispecific or multifunctional polypeptide comprises the polypeptide sequence of SEQ ID NO: 227 [APTSSSTK KTQLQLEHLLLDLQMILNGINN YKNPKLTRMLTFKF YMPKKATELKHLQCLEEELKPLEEVLNLAQSKNFHL RPRDLISNINVIVLELKGSETTFMCEYADETATIVE-FLNRWITFAQSIISTLT]. In another specific embodiment the IL-2 cytokine of the multispecific or multifunctional polypeptide comprises the polypeptide sequence of SEQ ID NO: 228 [APASSSTKKT QLQLEHLLLD LQMILNGINN YKNPKLTRMLTAKFAMPKKATELKHLQCLE EELKP LEEVLNGAQSKNFHL RPRDLISNIN VIVLELKG-SETTFMCEYADETATIVEFLNRWITFAQSIISTLT].

In another embodiment the cytokine of the multispecific or multifunctional polypeptide is IL-12. In a specific embodiment said IL-12 cytokine is a single chain IL-12 cytokine. In an even more specific embodiment the single chain IL-12 cytokine comprises the polypeptide sequence of SEQ ID NO: 229 [IWELKKDVYVVELDWYPDAPGEMV VLTCDTPEEDGITWTLDQSSEVLGSGKTLTIQVKEF G DAGQYTCHKGGEVLSHSLLLLHKKEDGIWSTDIL KDQKEPKNKTFLRCEAKNYSGR FTCWWLTTISTDL TFSVKSSRGSSDPQGVTCGAATLSAERVRGDNKEY-EYSVECQEDSA CPAAEESLPIEVMVDAVHKLKYEN YTSSFFIRDIIKPDPPKNLQLKPLKNSRQVEVSWEY PDTWSTPHSYFSLTFCVQVQGKSKREKKDRVFTDKT-SATVICRKNASISVRAQDRYYSS SWSEWASVPCS GG GGSGGGGSGGGGSRNLPVATPDGMFPCLHH SQN LLRAVSNMLQ KARQTLEFYPCTSEEIDHEDITKDKT-STVEACLPLELTKNESCLNSRETSFITNGSCLASRK-TSFMMALCLSSIYEDLKMYQVEFKTMNAKLLMDP-KRQIFLDQNMLAVIDELMQALNFNSETVPQKSSLEE-PDFYKTKIKLCILLHAFRIRAVTIDRVMSYLNAS]. In one embodiment, the IL-12 cytokine can elicit one or more of the cellular responses selected from the group consisting of: proliferation in a NK cell, differentiation in a NK cell, proliferation in a T cell, and differentiation in a T cell.

In another embodiment the cytokine of the multispecific or multifunctional polypeptide is IL-10. In a specific embodiment said IL-10 cytokine is a single chain IL-10 cytokine. In an even more specific embodiment the single chain IL-10 cytokine comprises the polypeptide sequence of SEQ ID NO: 230 [SPGQGTQSENSCTHFPGN- LPNM LRDLRDAFSRVKTFFQMKDQLDNLLLKESLLEDFKG YLGCQALSEMIQFYLEEVMPQAENQDPDIKAHV-NSL- GENLKTLRLRLRRCHRFLPCENK SKAVEQVKN AFNKLQEKGIYKAMSEFDIFINYIEAYMTMKIRNG GGGSGGGGSGGGGS GGGGSSPGQGTQSENSCTHFP GNLPNMLRDLRDAFSRVKTFFQMKDQLDNLLLKE SLLE DFKGYLGCQALSEMIQFYLEEVMPQAENQD PDIKAHVNSLGENLKTLRLRLRRCHRFLP CENKSK A VEQVKNAFNKLQEKGIYKAMSEFDIFINYIEAYMTM-KIRN]. In another specific embodiment the IL-10 cytokine is a monomeric IL-10 cytokine. In a more specific embodiment the monomeric IL-10 cytokine comprises the polypeptide sequence of SEQ ID NO: 231 [SPGQGTQSEN-SCTHFPGNLPNMLRDLRDAFSRVKTFFQMKDQLD NLLLKESLLEDFKG YLGCQALSEMIQFYLEEVMPQ AENQDPDIKAHVNSLGENLKTLRLRLRRCHR FLP CENG GGSGGKSKAVEQVKNAFNKLQEKGIYKAMSE FDIFINYIEAYMTMKIRN]. In one embodiment, the IL-10 cytokine can elicit one or more of the cellular responses selected from the group consisting of: inhibition of cytokine secretion, inhibition of antigen presentation by antigen presenting cells, reduction of oxygen radical release, and inhibition of T cell proliferation. A multispecific or multifunctional polypeptide according to the invention wherein the cytokine is IL-10 is particularly useful for downregulation of inflammation, e.g. in the treatment of an inflammatory disorder.

In another embodiment, the cytokine of the multispecific or multifunctional polypeptide is IL-15. In a specific embodiment said IL-15 cytokine is a mutant IL-15 cytokine having reduced binding affinity to the α-subunit of the IL-15 receptor. Without wishing to be bound by theory, a mutant IL-15 polypeptide with reduced binding to the .alpha.-subunit of the IL-15 receptor has a reduced ability to bind to fibroblasts throughout the body, resulting in improved pharmacokinetics and toxicity profile, compared to a wild-type IL-15 polypeptide. The use of an cytokine with reduced toxicity, such as the described mutant IL-2 and mutant IL-15 effector moieties, is particularly advantageous in a multispecific or multifunctional polypeptide according to the invention, having a long serum half-life due to the presence of an Fc domain. In one embodiment the mutant IL-15 cytokine of the multispecific or multifunctional polypeptide according to the invention comprises at least one amino acid mutation that reduces or abolishes the affinity of the mutant IL-15 cytokine to the .alpha.-subunit of the IL-15 receptor but preserves the affinity of the mutant IL-15 cytokine to the intermediate-affinity IL-15/IL-2 receptor (consisting of the .beta.- and .gamma.-subunits of the IL-15/IL-2 receptor), compared to the non-mutated IL-15 cytokine. In one embodiment the amino acid mutation is an amino acid substitution. In a specific embodiment, the mutant IL-15 cytokine comprises an amino acid substitution at the position corresponding to residue 53 of human IL-15. In a more specific embodiment, the mutant IL-15 cytokine is human IL-15 comprising the amino acid substitution E53A. In one embodiment the mutant IL-15 cytokine additionally comprises an amino acid mutation at a position corresponding to position 79 of human IL-15, which eliminates the N-glycosylation site of IL-15. Particularly, said additional amino acid mutation is an amino acid substitution replacing an asparagine residue by an alanine residue. In an even more specific embodiment the IL-15 cytokine comprises the polypeptide sequence of SEQ ID NO: 232 [NWVNVISDLK-KIEDLIQSMHIDATLYTESDVHPSCKVTAMKCFL-LELQVISLASGDASIH DTVENLIILANNSLSSN GAVTESGCKECEELEEKNIKEFLQSFVHIVQMFINTS]. In one embodiment, the IL-15 cytokine can elicit one or more of the cellular responses selected from the group consisting of: proliferation in an activated T lymphocyte cell, differentiation in an activated T lymphocyte cell, cytotoxic T cell (CTL) activity, proliferation in an activated B cell, differentiation in an activated B cell, proliferation in a natural killer (NK) cell, differentiation in a NK cell, cytokine secretion by an activated T cell or an NK cell, and NK/lymphocyte activated killer (LAK) antitumor cytotoxicity.

Mutant cytokine molecules useful as effector moieties in the multispecific or multifunctional polypeptide can be prepared by deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing. Substitution or insertion may involve natural as well as non-natural amino acid residues. Amino acid modification includes well known methods of chemical modification such as the addition or removal of glycosylation sites or carbohydrate attachments, and the like.

In one embodiment, the cytokine, particularly a single-chain cytokine, of the multispecific or multifunctional polypeptide is GM-CSF. In a specific embodiment, the GM-CSF cytokine can elicit proliferation and/or differentiation in a granulocyte, a monocyte or a dendritic cell. In one embodiment, the cytokine, particularly a single-chain cytokine, of the multispecific or multifunctional polypeptide is IFN-α. In a specific embodiment, the IFN-α cytokine can elicit one or more of the cellular responses selected from the group consisting of: inhibiting viral replication in a virus-infected cell, and upregulating the expression of major histocompatibility complex I (MHC I). In another specific embodiment, the IFN-α cytokine can inhibit proliferation in a tumor cell. In one embodiment the cytokine, particularly a single-chain cytokine, of the multispecific or multifunctional polypeptide is IFNγ. In a specific embodiment, the IFN-γ cytokine can elicit one or more of the cellular responses selected from the group of: increased macrophage activity, increased expression of MHC molecules, and increased NK cell activity. In one embodiment the cytokine, particularly a single-chain cytokine, of the multispecific or multifunctional polypeptide is IL-7. In a specific embodiment, the IL-7 cytokine can elicit proliferation of T and/or B lymphocytes. In one embodiment, the cytokine, particularly a single-chain cytokine, of the multispecific or multifunctional polypeptide is IL-8. In a specific embodiment, the IL-8 cytokine can elicit chemotaxis in neutrophils. In one embodiment, the cytokine, particularly a single-chain cytokine, of the multispecific or multifunctional polypeptide, is MIP-1α. In a specific embodiment, the MIP-1α cytokine can elicit chemotaxis in monocytes and T lymphocyte cells. In one embodiment, the cytokine, particularly a single-chain cytokine, of the multispecific or multifunctional polypeptide is MIP-1β. In a specific embodiment, the MIP-1β cytokine can elicit chemotaxis in monocytes and T lymphocyte cells. In one embodiment, the cytokine, particularly a single-chain cytokine, of the multispecific or multifunctional polypeptide is TGF-β. In a specific embodiment, the TGF-β cytokine can elicit one or more of the cellular responses selected from the group consisting of: chemotaxis in monocytes, chemotaxis in macrophages, upregulation of IL-1 expression in activated macrophages, and upregulation of IgA expression in activated B cells.

In one embodiment, the multispecific or multifunctional polypeptide of the invention binds to an cytokine receptor with a dissociation constant ($K_D$) that is at least about 1, 1.5, 2, 2.5, 3, 3.5, 4, 4.5, 5, 5.5, 6, 6.5, 7, 7.5, 8, 8.5, 9, 9.5 or 10 times greater than that for a control cytokine. In another embodiment, the multispecific or multifunctional polypeptide binds to an cytokine receptor with a $K_D$ that is at least 2, 3, 4, 5, 6, 7, 8, 9, or 10 times greater than that for a corresponding multispecific or multifunctional polypeptide comprising two or more effector moieties. In another embodiment, the multispecific or multifunctional polypeptide binds to an cytokine receptor with a dissociation constant $K_D$ that is about 10 times greater than that for a corresponding the multispecific or multifunctional polypeptide comprising two or more cytokines.

In some embodiments, the multispecific molecules disclosed herein include a cytokine molecule. In embodiments, the cytokine molecule includes a full length, a fragment or a variant of a cytokine; a cytokine receptor domain, e.g., a cytokine receptor dimerizing domain; or an agonist of a cytokine receptor, e.g., an antibody molecule (e.g., an agonistic antibody) to a cytokine receptor.

In some embodiments the cytokine molecule is chosen from IL-2, IL-12, IL-15, IL-18, IL-7, IL-21, or interferon gamma, or a fragment or variant thereof, or a combination of any of the aforesaid cytokines. The cytokine molecule can be a monomer or a dimer. In embodiments, the cytokine molecule can further include a cytokine receptor dimerizing domain.

In other embodiments, the cytokine molecule is an agonist of a cytokine receptor, e.g., an antibody molecule (e.g., an agonistic antibody) to a cytokine receptor chosen from an IL-15Ra or IL-21R.

In one embodiment, the cytokine molecule is IL-15, e.g., human IL-15 (e.g., comprising the amino acid sequence: NWVNVISDLKKIEDLIQSMHIDATLYTESDVHPSCKV-TAMKCFLLELQVISLESGDASIH DTVENLIILAN- NS LSSNGNVTESGCKECEELEEKNIKEFLQSFVHIVQM-FINTS (SEQ ID NO: 17), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 17.

In some embodiments, the cytokine molecule comprises a receptor dimerizing domain, e.g., an IL15Ralpha dimerizing domain. In one embodiment, the IL15Ralpha dimerizing domain comprises the amino acid sequence: MAPR-RARGCRTLGLPALLLLLLLRPPATRGITCPPPMSVE-HADIWVKSYSLYSRERYICN SGFKRKAGTSSLTECVL (SEQ ID NO: 18), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 18. In some embodiments, the cytokine molecule (e.g., IL-15) and the receptor dimerizing domain (e.g., an IL15Ralpha dimerizing domain) of the multispecific molecule are covalently linked, e.g., via a linker (e.g., a Gly-Ser linker, e.g., a linker comprising the amino acid sequence SGGSG GGGSGGGSGGGGSLQ (SEQ ID NO: 19). In other embodiments, the cytokine molecule (e.g., IL-15) and the receptor dimerizing domain (e.g., an IL15Ralpha dimerizing domain) of the multispecific molecule are not covalently linked, e.g., are non-covalently associated.

In other embodiments, the cytokine molecule is IL-2, e.g., human IL-2 (e.g., comprising the amino acid sequence: APTSSSTKKTQLQLEHLLLDLQMILNGINNYKNPKL-TRMLTFKFYMPKKATELKHLQCL EEELKPLEEVLN-LAQSKNFHLRPRDLISNINVIVLELKGSETTFMCEYA-DETATIVEFLNR WITFCQSIISTLT (SEQ ID NO: 20), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO:20).

In other embodiments, the cytokine molecule is IL-18, e.g., human IL-18 (e.g., comprising the amino acid sequence: YFGKLESKLSVIRNLNDQVLFIDQGNRPLF EDMTDSDCRDNAPRTIFIISMYKDSQPRGM AVTIS VKCEKISTLSCENKIISFKEMNPPDNIKDTKSDIIFFQ RSVPGHDNKMQFESSSY EGYFLACEKERDLFKLI LKKEDELGDRSIMFTVQNED (SEQ ID NO: 21), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 21).

In other embodiments, the cytokine molecule is IL-21, e.g., human IL-21 (e.g., comprising the amino acid sequence: QGQDRHMIRMRQLIDIVDQLKNYVNDLV PEFLPAPEDVETNCEWSAFSCFQKAQLKSA NTGNNE RIINVSIKKLKRKPPSTNAGRRQKHRLTCPSCDSYE KKPPKEFLERFKSLLQKMI HQHLSSRTHGSEDS (SEQ ID NO: 22), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 22).

In yet other embodiments, the cytokine molecule is interferon gamma, e.g., human interferon gamma (e.g., comprising the amino acid sequence: QDPYVKEAENLKK YFNAGHSDVADNGTLFLGILKNWKEESDRKIMQSQI-VSFYFKLFK NFKDDQSIQKSVETIKEDMNVKFFN SNKKKRDDFEKLTNYSVTDLNVQRKAIHELIQVM AELSPAAKTGKRKRSQMLFRG (SEQ ID NO: 23), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 23).

Immune Cell Engagers

The immune cell engagers of the multispecific molecules disclosed herein can mediate binding to, and/or activation of, an immune cell, e.g., an immune effector cell. In some embodiments, the immune cell is chosen from an NK cell, a B cell, a dendritic cell, or a macrophage cell engager, or a combination thereof. In some embodiments, the immune cell engager is chosen from one, two, three, or all of a a T cell engager, NK cell engager, a B cell engager, a dendritic cell engager, or a macrophage cell engager, or a combination thereof. The immune cell engager can be an agonist of the immune system. In some embodiments, the immune cell engager can be an antibody molecule, a ligand molecule (e.g., a ligand that further comprises an immunoglobulin constant region, e.g., an Fc region), a small molecule, a nucleotide molecule.

Natural Killer Cell Engagers

Natural Killer (NK) cells recognize and destroy tumors and virus-infected cells in an antibody-independent manner. The regulation of NK cells is mediated by activating and inhibiting receptors on the NK cell surface. One family of activating receptors is the natural cytotoxicity receptors (NCRs) which include NKp30, NKp44 and NKp46. The NCRs initiate tumor targeting by recognition of heparan sulfate on cancer cells. NKG2D is a receptor that provides both stimulatory and costimulatory innate immune responses on activated killer (NK) cells, leading to cytotoxic activity. DNAM1 is a receptor involved in intercellular adhesion, lymphocyte signaling, cytotoxicity and lymphokine secretion mediated by cytotoxic T-lymphocyte (CTL) and NK cell. DAP10 (also known as HCST) is a transmembrane adapter protein which associates with KLRK1 to form an activation receptor KLRK1-HCST in lymphoid and myeloid cells; this receptor plays a major role in triggering cytotoxicity against target cells expressing cell surface ligands such as MHC class I chain-related MICA and MICB, and U(optionally L1)6-binding proteins (ULBPs); it KLRK1-HCST receptor plays a role in immune surveillance against tumors and is required for cytolysis of tumors cells; indeed, melanoma cells that do not express KLRK1 ligands escape from immune surveillance mediated by NK cells. CD16 is a receptor for the Fc region of IgG, which binds complexed or aggregated IgG and also monomeric IgG and thereby mediates antibody-dependent cellular cytotoxicity (ADCC) and other antibody-dependent responses, such as phagocytosis.

In some embodiments, the NK cell engager is a viral hemagglutinin (HA), HA is a glycoprotein found on the surface of influenza viruses. It is responsible for binding the virus to cells with sialic acid on the membranes, such as cells in the upper respiratory tract or erythrocytes. HA has at least 18 different antigens. These subtypes are named H1 through H18. NCRs can recognize viral proteins. NKp46 has been shown to be able to interact with the HA of influenza and the HA-NA of Paramyxovirus, including Sendai virus and Newcastle disease virus. Besides NKp46, NKp44 can also functionally interact with HA of different influenza subtypes.

The present disclosure provides, inter alia, multi-specific (e.g., bi-, tri-, quad-specific) proteins, that are engineered to contain one or more NK cell engager that mediate binding to and/or activation of an NK cell. Accordingly, in some embodiments, the NK cell engager is selected from an antigen binding domain or ligand that binds to (e.g., activates): NKp30, NKp40, NKp44, NKp46, NKG2D, DNAM1, DAP10, CD16 (e.g., CD16a, CD16b, or both), CRTAM, CD27, PSGL1, CD96, CD100 (SEMA4D), NKp80, CD244 (also known as SLAMF4 or 2B4), SLAMF6, SLAMF7, KIR2DS2, KIR2DS4, KIR3DS1, KIR2DS3, KIR2DS5, KIR2DS1, CD94, NKG2C, NKG2E, or CD160.

In one embodiment, the NK cell engager is a ligand of NKp30 is a B7-6, e.g., comprises the amino acid sequence of: DLKVEMMAGGTQITPLNDNVTIFCNIFYSQPL NI TSMGITWFWKSLTFDKEVKVFEFFGD HQEAFRPGA IVSPWRLKSGDASLRLPGIQLEEAGEYRCEVVVTPL KAQGTVQLEVVASP ASRLLLDQVGMKENEDKYMC ESSGFYPEAINITWEKQTQKFPHPIEISEDVITGPTIK NM DGTFNVTSCLKLNSSQEDPGTVYQCVVRHASL HTPLRSNFTLTAARHSLSETEKTDNFS (SEQ ID NO: 24), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 24.

In other embodiments, the NK cell engager is a ligand of NKp44 or NKp46, which is a viral HA. Viral hemagglutinins (HA) are glyco proteins which are on the surface of viruses. HA proteins allow viruses to bind to the membrane of cells via sialic acid sugar moieties which contributes to the fusion of viral membranes with the cell membranes (see e.g., Eur J Immunol. 2001 September; 31(9):2680-9 "Recognition of viral hemagglutinins by NKp44 but not by NKp30"; and Nature. 2001 Feb. 22; 409(6823):1055-60 "Recognition of haemagglutinins on virus-infected cells by NKp46 activates lysis by human NK cells" the contents of each of which are incorporated by reference herein).

In other embodiments, the NK cell engager is a ligand of NKG2D chosen from MICA, MICB, or ULBP1, e.g., wherein:

(i) MICA comprises the amino acid sequence: EPHSLRYNLTVLSWDGSVQSGFLTEVHLDGQPFLRCD RQ KCRAKPQGQWAEDVLGNK TWDRETRDLTGNGK DLRMTLAHIKDQKEGLHSLQEIRVCEIHEDNSTR SSQHFYYDGEL FLSQNLETKEWTMPQSSRAQTLAMNVRNFLKEDAMKTKTHYHAMHADCLQELRRYLK SGVVLRRTVPPMVNVTRSEASEGNITVTCRA SGFYPWNITLSWRQDGVSLSHDTQQWG DVLPDG NGTYQTWVATRICQGEEQRFTCYMEHSGNHSTHP VPSGKVLVLQSHW (SEQ ID NO: 25), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 25;

(ii) MICB comprises the amino acid sequence: AEPHSLRYNLMVLSQDESVQSGFLAEGHLDGQPFLRYDRQ KRRAKPQGQWAEDVLGA KTWDTETEDLTENGQDL RRTLTHIKDQKGGLHSLQEIRVCEIHEDSSTRGS RHFYYDGEL FLSQNLETQESTVPQSSRAQTLAMNV TNFWKEDAMKTKTHYRAMQADCLQKLQRYLK SGVAIRRTVPPMVNVTCSEVSEGNITVTCRASSFYPRNITLTWRQDGVSLSHNTQQWGD VLPDGNGTYQTWVATRIRQGEEQRFTCYMEHSGNHGTHPVPSGKV LVLQSQRTD (SEQ ID NO: 26), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 26; or (iii) ULBP1 comprises the amino acid sequence: GWVDTHCLCYDFIITPKSRPEPQWCEVQGLVDERPFLHYDCVNHKAKAFASLGKKVNV TKTWEEQTET LRDVVDFLKGQLLDIQVENLIPIEPLTLQARMSCEHEAHGHGRGSWQFL FNGQKFLLLFDSNNRKW TAL HPGAKKMTEKWEKNRDVTMFFQKISLGDCKMW LEEFL MYWEQMLDPTKPPSLAPG (SEQ ID NO: 27), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 27.

In other embodiments, the NK cell engager is a ligand of DNAM1 chosen from NECTIN2 or NECL5, e.g., wherein:

(i) NECTIN2 comprises the amino acid sequence: QDVRVQVLPEVRGQLGGTVELPCHLLPPVPGLYISLVTWQRPDAPANHQNVAAFHPKM GPSFPSPKPGSERLSFVSAKQSTGQDTEAELQDATLALHGLTVEDEGNYTCEFATFPKGS VRGMTWLRVIAKPKNQAEA QKVTFSQDPTTVALCISKEGRPPARISWLSSLDWEAKETQ VSGTLAGTVTVTSRFTLVPSGRADGVTVTCKV EHESFEEPALIPVTLSVRYPPEVSISGYD DNWYLGRTDATLSCDVRSNPEPTGYDWSTTSGTFPTSAVAQGS QLVIHAVDSLFNTTFV CTVTNAVGMGRAEQVIFVR ETPNTAGAGATGG (SEQ ID NO: 28), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 28; or (ii) NECL5 comprises the amino acid sequence: WPPPGTGDVVVQAPTQVPGFLGDSVTLPCYLQVPNMEVTHVSQLTWARHGESGSMAV FHQTQGPSYSESKRLEFVAARLGAELRNASLRMFGLRVEDEGNYTCLFVTFPQGSRSVD IWLRVLAKPQNTAEVQKVQLT GEPVPMARCVSTGGRPPAQITWHSDLGGMPNTS QVPG FLSGTVTVTSLWILVPSSQVDGKNVTCKVEHESFEKPQLLTVNLTVYYPPEVSISGYDNN WYLGQ NEATLTCDARSNPEPTGYNWSTTMGPLPPFAVAQ GAQLLIRPVDKPINTTLICN VTNALGARQAELTVQV KEGPPSEHSGISRN (SEQ ID NO: 29), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 29.

In yet other embodiments, the NK cell engager is a ligand of DAP10, which is an adapter for NKG2D (see e.g., Proc Natl Acad Sci USA. 2005 May 24; 102(21): 7641-7646; and Blood, 15 Sep. 2011 Volume 118, Number 11, the full contents of each of which is incorporated by reference herein).

In other embodiments, the NK cell engager is a ligand of CD16, which is a CD16a/b ligand, e.g., a CD16a/b ligand further comprising an antibody Fc region (see e.g., Front Immunol. 2013; 4: 76 discusses how antibodies use the Fc to trigger NK cells through CD16, the full contents of which are incorporated herein).

In other embodiments, the NK cell engager is a ligand of CRTAM, which is NECL2, e.g., wherein NECL2 comprises the amino acid sequence: QNLFTKDVTVIEGEVATISCQVNKSDDSVIQLLNPNRQTIYFRDFRPLKDSRF QLLNFSSS ELKVSLTNVSISDEGRYFCQLYTDPPQESYTTITVLVPPRNLMIDIQKDTAVEGEEIEVNC TAMA SKPATTIRWFKGNTELKGKSEVEEWSDMYTVTSQL MLKVHKEDDGVPVICQVE HPAVTGNLQTQRYLEV QYKPQVHIQMTYPLQGLTREGDALELTCEAIGK PQPVMVTWV RVDDEMPQHAVLSGPNLFINNL NKTD NGTYRCEASNIVGKAHSDYMLYVYDPPTTIPPP TTTTTTTTTTTTTILTIITDSRAGEEGSIRAVDH (SEQ ID NO: 30), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 30.

In other embodiments, the NK cell engager is a ligand of CD27, which is CD70, e.g., wherein CD70 comprises the amino acid sequence: QRFAQAQQQLPLESLGWDVAELQLNHTGPQQDPRLYWQGGPALGRSFLHGPELDKGQ LRIHRDGIYMVHIQVTLAICSSTTASRHHPTTLAVGICSPASRSISLLRLSFHQGCTIASQR LTPLARGDTLCT NLTGTLLPSRNTDETFFGVQWVRP (SEQ ID NO: 31), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 31.

In other embodiments, the NK cell engager is a ligand of PSGL1, which is L-selectin (CD62L), e.g., wherein L-selectin comprises the amino acid sequence: WTYHYSEKPMNWQRARRFCRDNYTDLVAIQNKAEIEYLEKTLPFSRSYYWIGIRKIGGI WTWVGTNKSL TEEAENWGDGEPNNKKNKEDCVEIYIKRNKDAGKWNDDACHKLKAA LCYTASCQPWSCSGHG ECVEIINNYTCNCDVGYYGPQCQFVIQCEPLEAPELGTMDCTH PLGNFSFSSQCAFSCSEGTNLTGIE ETTCGPFGNWSSPEPTCQVIQCEPLSAPDLGIMNCSH PLASFSFTSACTFICSEGTELIGKKKTICESSGIWSNP SPICQKLDKSFSMIKEGDYN (SEQ ID NO: 32), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 32.

In other embodiments, the NK cell engager is a ligand of CD96, which is NECL5, e.g., wherein NECL5 comprises the amino acid sequence: WPPPGTGDVVV QAPTQVPGFLGDSVTLPCYLQVPNMEVTHVSQLTWARHGESGSMAV FHQTQGPSYSESKRLEFVAARLGAELRNASLRMFGLRVEDEGNYTCLFVTFP QG SR SVD IWLRVLAKPQNTAEVQKVQLTGEPVPMARC VSTGGRPPAQITWHSDLGGMPNTSQVPG FLSGTVT VTSLWILVPSSQVDGKNVTCKVEHESFEKPQLL TVNLTVYYPPEVSISGYDNN WYLGQNEATLTCDARS NPEPTGYNWSTTMGPLPPFAVAQGAQLLIRPVDKPINITTLICN VTNALGARQAELTVQVKEGPPSEHSGISRN (SEQ ID NO: 29), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 30.

In other embodiments, the NK cell engager is a ligand of CD100 (SEMA4D), which is CD72, e.g., wherein CD72 comprises the amino acid sequence: RYLQVSQQL QQTNRVLEVTNSSLRQQLRLKITQLGQSAEDLQGSRRELAQSQEALQVEQ RAHQAAEGQLQACQAD RQK TKETLQSEEQQRRALEQKLSNMENRLKPFFTCGS ADTCC PSGWIMHQKSCFYISLTSKNWQESQKQCETL SSKLATFSEIYPQSHSYYFLNSLLPNGGS GNSYWT GLSSNKDWKLTDDTQRTRTYAQSSKCNKVHKTWS WWT LESESCRSSLPYICE MTAFRFPD (SEQ ID NO: 33), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 33.

In other embodiments, the NK cell engager is a ligand of NKp80, which is CLEC2B (AICL), e.g., wherein CLEC2B (AICL) comprises the amino acid sequence: KLTRDSQSLCPYDWIGFQNKCYYFSKEEGDWNSSK YNCSTQHADLTIIDNIEEMNFLRR YKCSSDHWIGLKMAKNRTGQWVDGATFTKSFGMRGSEGCAYLSDDGAATARCYTER KWICRKRIH (SEQ ID NO: 34), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 34.

In other embodiments, the NK cell engager is a ligand of CD244, which is CD48, e.g., wherein CD48 comprises the amino acid sequence: QGHLVHMTVVSGSNVTLNISESLPENYKQLTWFYTFDQKIVEWDSRKSKYFESKFKGR VRLDPQSGALYISKVQKEDNSTYIMRVLKKTGNEQ EWKIKLQVLDPVPKPVIKIEKIEDM DDNCYLKLS CVIPGESVNYTWYGDKRPFPKELQNSVLETTLMPHNYSRCYTCQVSNSVS SKNGTVCLSPPCTLARS (SEQ ID NO: 35), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 35.

T Cell Engagers

The present disclosure provides, inter alia, multi-specific (e.g., bi-, tri-, quad-specific) proteins, that are engineered to contain one or more T cell engager that mediate binding to and/or activation of a T cell. Accordingly, in some embodiments, the T cell engager is selected from an antigen binding domain or ligand that binds to (e.g., and in some embodiments activates) one or more of CD3, TCRα, TCRβ, TCRγ, TCRξ, ICOS, CD28, CD27, HVEM, LIGHT, CD40, 4-1BB, OX40, DR3, GITR, CD30, TIM1, SLAM, CD2, or CD226. In other embodiments, the T cell engager is selected from an antigen binding domain or ligand that binds to and does not activate one or more of CD3, TCRα, TCRβ, TCRγ, TCRξ, ICOS, CD28, CD27, HVEM, LIGHT, CD40, 4-1BB, OX40, DR3, GITR, CD30, TIM1, SLAM, CD2, or CD226. In some embodiments, the T cell engager binds to CD3.

B Cell, Macrophage & Dendritic Cell Engagers

Broadly, B cells, also known as B lymphocytes, are a type of white blood cell of the lymphocyte subtype. They function in the humoral immunity component of the adaptive immune system by secreting antibodies. Additionally, B cells present antigen (they are also classified as professional antigen-presenting cells (APCs)) and secrete cytokines. Macrophages are a type of white blood cell that engulfs and digests cellular debris, foreign substances, microbes, cancer cells via phagocytosis. Besides phagocytosis, they play important roles in nonspecific defense (innate immunity) and also help initiate specific defense mechanisms (adaptive immunity) by recruiting other immune cells such as lymphocytes. For example, they are important as antigen presenters to T cells. Beyond increasing inflammation and stimulating the immune system, macrophages also play an important anti-inflammatory role and can decrease immune reactions through the release of cytokines. Dendritic cells (DCs) are antigen-presenting cells that function in processing antigen material and present it on the cell surface to the T cells of the immune system.

The present disclosure provides, inter alia, multi-specific (e.g., bi-, tri-, quad-specific) proteins, that include, e.g., are engineered to contain, one or more B cell, macrophage, and/or dendritic cell engager that mediate binding to and/or activation of a B cell, macrophage, and/or dendritic cell.

Accordingly, in some embodiments, the immune cell engager comprises a B cell, macrophage, and/or dendritic cell engager chosen from one or more of CD40 ligand (CD40L) or a CD70 ligand; an antibody molecule that binds to CD40 or CD70; an antibody molecule to OX40; an OX40 ligand (OX40L); an agonist of a Toll-like receptor (e.g., as described herein, e.g., a TLR4, e.g., a constitutively active TLR4 (caTLR4), or a TLR9 agonists); a 41BB; a CD2; a CD47; or a STING agonist, or a combination thereof.

In some embodiments, the B cell engager is a CD40L, an OX40L, or a CD70 ligand, or an antibody molecule that binds to OX40, CD40 or CD70.

In some embodiments, the macrophage engager is a CD2 agonist. In some embodiments, the macrophage engager is an antigen binding domain that binds to: CD40L or antigen binding domain or ligand that binds CD40, a Toll like receptor (TLR) agonist (e.g., as described herein), e.g., a TLR9 or TLR4 (e.g., caTLR4 (constitutively active TLR4), CD47, or a STING agonist. In some embodiments, the STING agonist is a cyclic dinucleotide, e.g., cyclic di-GMP (cdGMP) or cyclic di-AMP (cdAMP). In some embodiments, the STING agonist is biotinylated.

In some embodiments, the dendritic cell engager is a CD2 agonist. In some embodiments, the dendritic cell engager is a ligand, a receptor agonist, or an antibody molecule that binds to one or more of: OX40L, 41BB, a TLR agonist (e.g., as described herein) (e.g., TLR9 agonist, TLR4 (e.g., caTLR4 (constitutively active TLR4)), CD47, or and a STING agonist. In some embodiments, the STING agonist is a cyclic dinucleotide, e.g., cyclic di-GMP (cdGMP) or cyclic di-AMP (cdAMP). In some embodiments, the STING agonist is biotinylated.

In other embodiments, the immune cell engager mediates binding to, or activation of, one or more of a B cell, a macrophage, and/or a dendritic cell. Exemplary B cell, macrophage, and/or dendritic cell engagers can be chosen from one or more of CD40 ligand (CD40L) or a CD70 ligand; an antibody molecule that binds to CD40 or CD70; an antibody molecule to OX40; an OX40 ligand (OX40L); a Toll-like receptor agonist (e.g., a TLR4, e.g., a constitutively active TLR4 (caTLR4) or a TLR9 agonist); a 41BB agonist; a CD2; a CD47; or a STING agonist, or a combination thereof.

In some embodiments, the B cell engager is chosen from one or more of a CD40L, an OX40L, or a CD70 ligand, or an antibody molecule that binds to OX40, CD40 or CD70.

In other embodiments, the macrophage cell engager is chosen from one or more of a CD2 agonist; a CD40L; an OX40L; an antibody molecule that binds to OX40, CD40 or CD70; a Toll-like receptor agonist or a fragment thereof (e.g., a TLR4, e.g., a constitutively active TLR4 (caTLR4)); a CD47 agonist; or a STING agonist.

In other embodiments, the dendritic cell engager is chosen from one or more of a CD2 agonist, an OX40 antibody, an OX40L, 41BB agonist, a Toll-like receptor agonist or a fragment thereof (e.g., a TLR4, e.g., a constitutively active TLR4 (caTLR4)), CD47 agonist, or a STING agonist.

In one embodiment, the OX40L comprises the amino acid sequence: QVSHRYPRIQSIKVQFTEYKKEKGFILTSQ KEDEIMKVQNNSVIINCDGFYLISLKGYFSQ EVNISLHYQKDEEPLFQLKKVRSVNSLMVASLTYKDKVY LNVTTDNTSLDDFHVNGGE LILIHQNPGEFCVL (SEQ ID NO: 36), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 36.

In another embodiment, the CD40L comprises the amino acid sequence: MQKGDQNPQIAAHVISEASSKTTSVLQ WAEKGYYTMSNNLVTLENGKQLTVKRQGLY YIYA QVTFCSNREASSQAPFIASLCLKSPGRFERILLRAA NTHSSAKPCGQQSIHLGGVFE LQPGASVFVNVTDP-SQVSHGTGFTSFGLLKL (SEQ ID NO: 37), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 37.

In yet other embodiments, the STING agonist comprises a cyclic dinucleotide, e.g., a cyclic di-GMP (cdGMP), a cyclic di-AMP (cdAMP), or a combination thereof, optionally with 2',5' or 3',5' phosphate linkages.

In one embodiment, the immune cell engager includes 41BB ligand, e.g., comprising the amino acid sequence: ACPWAVSGARASPGSAASPRLREGPELSPDDPAGL LDLRQGMFAQLVAQNVLLIDGPLS WYSDPGLA GV SLTGGLSYKEDTKELVVAKAGVYYVFFQLELRRVV AGEGSGSVSLALH LQPLRSAAGAAALALTVDLPPAS-SEARNSAFGFQGRLLHLSAGQRLGVHLHTEARARH AWQLTQGATVLGLFRVTPEIPAGLPSPRSE (SEQ ID NO: 38), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 38.

Toll-Like Receptors

Toll-Like Receptors (TLRs) are evolutionarily conserved receptors are homologues of the *Drosophila* Toll protein, and recognize highly conserved structural motifs known as pathogen-associated microbial patterns (PAMPs), which are exclusively expressed by microbial pathogens, or danger-associated molecular patterns (DAMPs) that are endogenous molecules released from necrotic or dying cells. PAMPs include various bacterial cell wall components such as lipopolysaccharide (LPS), peptidoglycan (PGN) and lipopeptides, as well as flagellin, bacterial DNA and viral double-stranded RNA. DAMPs include intracellular proteins such as heat shock proteins as well as protein fragments from the extracellular matrix. Stimulation of TLRs by the corresponding PAMPs or DAMPs initiates signaling cascades leading to the activation of transcription factors, such as AP-1, NF-κB and interferon regulatory factors (IRFs). Signaling by TLRs results in a variety of cellular responses, including the production of interferons (IFNs), pro-inflammatory cytokines and effector cytokines that direct the adaptive immune response. TLRs are implicated in a number of inflammatory and immune disorders and play a role in cancer (Rakoff-Nahoum S. & Medzhitov R., 2009. Toll-like receptors and cancer. Nat Revs Cancer 9:57-63.)

TLRs are type I transmembrane proteins characterized by an extracellular domain containing leucine-rich repeats (LRRs) and a cytoplasmic tail that contains a conserved region called the Toll/IL-1 receptor (TIR) domain. Ten human and twelve murine TLRs have been characterized, TLR1 to TLR10 in humans, and TLR1 to TLR9, TLR11, TLR12 and TLR13 in mice, the homolog of TLR10 being a pseudogene. TLR2 is essential for the recognition of a variety of PAMPs from Gram-positive bacteria, including bacterial lipoproteins, lipomannans and lipoteichoic acids. TLR3 is implicated in virus-derived double-stranded RNA. TLR4 is predominantly activated by lipopolysaccharide. TLR5 detects bacterial flagellin and TLR9 is required for response to unmethylated CpG DNA. Finally, TLR7 and TLR8 recognize small synthetic antiviral molecules, and single-stranded RNA was reported to be their natural ligand.

TLR11 has been reported to recognize uropathogenic *E. coli* and a profilin-like protein from *Toxoplasma gondii*. The repertoire of specificities of the TLRs is apparently extended by the ability of TLRs to heterodimerize with one another. For example, dimers of TLR2 and TLR6 are required for responses to diacylated lipoproteins while TLR2 and TLR1 interact to recognize triacylated lipoproteins. Specificities of the TLRs are also influenced by various adapter and accessory molecules, such as MD-2 and CD14 that form a complex with TLR4 in response to LPS.

TLR signaling consists of at least two distinct pathways: a MyD88-dependent pathway that leads to the production of inflammatory cytokines, and a MyD88-independent pathway associated with the stimulation of IFN-β and the maturation of dendritic cells. The MyD88-dependent pathway is common to all TLRs, except TLR3 (Adachi O. et al., 1998. Targeted disruption of the MyD88 gene results in loss of IL-1- and IL-18-mediated function. Immunity. 9(1):143-50). Upon activation by PAMPs or DAMPs, TLRs hetero- or homodimerize inducing the recruitment of adaptor proteins via the cytoplasmic TIR domain. Individual TLRs induce different signaling responses by usage of the different adaptor molecules. TLR4 and TLR2 signaling requires the adaptor TIRAP/Mal, which is involved in the MyD88-dependent pathway. TLR3 triggers the production of IFN-β in response to double-stranded RNA, in a MyD88-independent manner, through the adaptor TRIF/TICAM-1. TRAM/TICAM-2 is another adaptor molecule involved in the MyD88-independent pathway which function is restricted to the TLR4 pathway.

TLR3, TLR7, TLR8 and TLR9 recognize viral nucleic acids and induce type I IFNs. The signaling mechanisms leading to the induction of type I IFNs differ depending on the TLR activated. They involve the interferon regulatory factors, IRFs, a family of transcription factors known to play a critical role in antiviral defense, cell growth and immune regulation. Three IRFs (IRF3, IRF5 and IRF7) function as direct transducers of virus-mediated TLR signaling. TLR3 and TLR4 activate IRF3 and IRF7, while TLR7 and TLR8 activate IRF5 and IRF7 (Doyle S. et al., 2002. IRF3 mediates a TLR3/TLR4-specific antiviral gene program. Immunity. 17(3):251-63). Furthermore, type I IFN production stimulated by TLR9 ligand CpG-A has been shown to be mediated by PI(3)K and mTOR (Costa-Mattioli M. & Sonenberg N. 2008. RAPping production of type I interferon in pDCs through mTOR. Nature Immunol. 9: 1097-1099).

TLR-9

TLR9 recognizes unmethylated CpG sequences in DNA molecules. CpG sites are relatively rare (~1%) on vertebrate genomes in comparison to bacterial genomes or viral DNA. TLR9 is expressed by numerous cells of the immune system such as B lymphocytes, monocytes, natural killer (NK) cells, and plasmacytoid dendritic cells. TLR9 is expressed intracellularly, within the endosomal compartments and functions to alert the immune system of viral and bacterial infections by binding to DNA rich in CpG motifs. TLR9 signals leads to activation of the cells initiating pro-inflammatory reactions that result in the production of cytokines such as type-I interferon and IL-12.

TLR Agonists

A TLR agonist can agonize one or more TLR, e.g., one or more of human TLR-1, 2, 3, 4, 5, 6, 7, 8, 9, or 10. In some embodiments, an adjunctive agent described herein is a TLR agonist. In some embodiments, the TLR agonist specifically agonizes human TLR-9. In some embodiments, the TLR-9 agonist is a CpG moiety. As used herein, a CpG moiety, is a linear dinucleotide having the sequence: 5'-C-phosphate-G-3', that is, cytosine and guanine separated by only one phosphate.

In some embodiments, the CpG moiety comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more CpG dinucleotides. In some embodiments, the CpG moiety consists of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 CpG dinucleotides. In some embodiments, the CpG moiety has 1-5, 1-10, 1-20, 1-30, 1-40, 1-50, 5-10, 5-20, 5-30, 10-20, 10-30, 10-40, or 10-50 CpG dinucleotides.

In some embodiments, the TLR-9 agonist is a synthetic ODN (oligodeoxynucleotides). CpG ODNs are short synthetic single-stranded DNA molecules containing unmethylated CpG dinucleotides in particular sequence contexts (CpG motifs). CpG ODNs possess a partially or completely phosphorothioated (PS) backbone, as opposed to the natural phosphodiester (PO) backbone found in genomic bacterial DNA. There are three major classes of CpG ODNs: classes A, B and C, which differ in their immunostimulatory activities. CpG-A ODNs are characterized by a PO central CpG-containing palindromic motif and a PS-modified 3' poly-G string. They induce high IFN-α production from pDCs but are weak stimulators of TLR9-dependent NF-κB signaling and pro-inflammatory cytokine (e.g. IL-6) production. CpG-B ODNs contain a full PS backbone with one or more CpG dinucleotides. They strongly activate B cells and TLR9-dependent NF-κB signaling but weakly stimulate IFN-α secretion. CpG-C ODNs combine features of both classes A and B. They contain a complete PS backbone and a CpG-containing palindromic motif. C-Class CpG ODNs induce strong IFN-α production from pDC as well as B cell stimulation.

Stromal Modifying Moieties

Solid tumors have a distinct structure that mimics that of normal tissues and comprises two distinct but interdependent compartments: the parenchyma (neoplastic cells) and the stroma that the neoplastic cells induce and in which they are dispersed. All tumors have stroma and require stroma for nutritional support and for the removal of waste products. In the case of tumors which grow as cell suspensions (e.g., leukemias, ascites tumors), the blood plasma serves as stroma (Connolly J L et al. Tumor Structure and Tumor Stroma Generation. In: Kufe D W et al., editors. Holland-Frei *Cancer Medicine*. 6th edition. Hamilton: BC Decker; 2003). The stroma includes a variety of cell types, including fibroblasts/myofibroblasts, glial, epithelial, fat, vascular, smooth muscle, and immune cells along with extracellular matrix (ECM) and extracellular molecules (Li Hanchen et al. Tumor Microenvironment: The Role of the Tumor Stroma in Cancer. *J of Cellular Biochemistry* 101: 805-815 (2007)).

Stromal modifying moieties described herein include moieties (e.g., proteins, e.g., enzymes) capable of degrading a component of the stroma, e.g., an ECM component, e.g., a glycosaminoglycan, e.g., hyaluronan (also known as hyaluronic acid or HA), chondroitin sulfate, chondroitin, dermatan sulfate, heparin sulfate, heparin, entactin, tenascin, aggrecan and keratin sulfate; or an extracellular protein, e.g., collagen, laminin, elastin, fibrinogen, fibronectin, and vitronectin.

Stromal Modifying Enzymes

In some embodiments, the stromal modifying moiety is an enzyme. For example, the stromal modifying moiety can include, but is not limited to a hyaluronidase, a collagenase, a chondroitinase, a matrix metalloproteinase (e.g., macrophage metalloelastase).

Hyaluronidases

Hyaluronidases are a group of neutral- and acid-active enzymes found throughout the animal kingdom. Hyaluronidases vary with respect to substrate specificity, and mechanism of action. There are three general classes of hyaluronidases: (1) Mammalian-type hyaluronidases, (EC 3.2.1.35) which are endo-beta-N-acetylhexosaminidases with tetrasaccharides and hexasaccharides as the major end products. They have both hydrolytic and transglycosidase activities, and can degrade hyaluronan and chondroitin sulfates; (2) Bacterial hyaluronidases (EC 4.2.99.1) degrade hyaluronan and, and to various extents, chondroitin sulfate and dermatan sulfate. They are endo-beta-N-acetylhexosaminidases that operate by a beta elimination reaction that yields primarily disaccharide end products; (3) Hyaluronidases (EC 3.2.1.36) from leeches, other parasites, and crustaceans are endo-beta-glucuronidases that generate tetrasaccharide and hexasaccharide end products through hydrolysis of the beta 1-3 linkage.

Mammalian hyaluronidases can be further divided into two groups: (1) neutral active and (2) acid active enzymes. There are six hyaluronidase-like genes in the human genome, HYAL1, HYAL2, HYAL3 HYAL4 HYALP1 and PH20/SPAM1. HYALP1 is a pseudogene, and HYAL3 has not been shown to possess enzyme activity toward any known substrates. HYAL4 is a chondroitinase and lacks activity towards hyaluronan. HYAL1 is the prototypical acid-active enzyme and PH20 is the prototypical neutral-active enzyme. Acid active hyaluronidases, such as HYAL1 and HYAL2 lack catalytic activity at neutral pH. For example, HYAL1 has no catalytic activity in vitro over pH 4.5 (Frost and Stern, "A Microtiter-Based Assay for Hyaluronidase Activity Not Requiring Specialized Reagents", Analytical Biochemistry, vol. 251, pp. 263-269 (1997). HYAL2 is an acid active enzyme with a very low specific activity in vitro.

In some embodiments the hyaluronidase is a mammalian hyaluronidase. In some embodiments the hyaluronidase is a recombinant human hyaluronidase. In some embodiments, the hyaluronidase is a neutral active hyaluronidase. In some embodiments, the hyaluronidase is a neutral active soluble hyaluronidase. In some embodiments, the hyaluronidase is a recombinant PH20 neutral-active enzyme. In some embodiments, the hyaluronidase is a recombinant PH20 neutral-active soluble enzyme. In some embodiments the hyaluronidase is glycosylated. In some embodiments, the hyaluronidase possesses at least one N-linked glycan. A recombinant hyaluronidase can be produced using conventional methods known to those of skill in the art, e.g., U.S. Pat. No. 7,767,429, the entire contents of which are incorporated by reference herein.

In some embodiments the hyaluronidase is rHuPH20 (also referred to as Hylenex®; presently manufactured by Halozyme; approved by the FDA in 2005 (see e.g., Scodeller P (2014) Hyaluronidase and other Extracellular Matrix Degrading Enzymes for Cancer Therapy: New Uses and Nano-Formulations. *J Carcinog Mutage* 5:178; U.S. Pat. Nos. 7,767,429; 8,202,517; 7,431,380; 8,450,470; 8,772,246; 8,580,252, the entire contents of each of which is incorporated by reference herein). rHuPH20 is produced by genetically engineered CHO cells containing a DNA plasmid encoding for a soluble fragment of human hyaluronidase PH20. In some embodiments the hyaluronidase is glycosylated. In some embodiments, the hyaluronidase possesses at least one N-linked glycan. A recombinant hyaluronidase can be produced using conventional methods known to those of skill in the art, e.g., U.S. Pat. No. 7,767,429, the entire contents of which are incorporated by reference herein. In some embodiments, rHuPH20 has a sequence at least 95% (e.g., at least 96%, 97%, 98%, 99%, 100%) identical to the amino acid sequence of

```
                                        (SEQ ID NO: 39)
LNFRAPPVIPNVPFLWAWNAPSEFCLGKFDEPLDMSLFSFIGSPRINATG

QGVTIFYVDRLGYYPYIDSITGVTVNGGIPQKISLQDHLDKAKKDITFYM

PVDNLGMAVIDWEEWRPTWARNWKPKDVYKNRSIELVQQQNVQLSLTEAT

EKAKQEFEKAGKDFLVETIKLGKLLRPNHLWGYYLFPDCYNHHYKKPGYN

GSCFNVEIKRNDDLSWLWNESTALYPSIYLNTQQSPVAATLYVRNRVREA

IRVSKIPDAKSPLPVFAYTRIVFTDQVLKFLSQDELVYTFGETVALGASG

IVIWGTLSIMRSMKSCLLLDNYMETILNPYIINVTLAAKMCSQVLCQEQG

VCIRKNWNSSDYLHLNPDNFAIQLEKGGKFTVRGKPTLEDLEQFSEKFYC

SCYSTLSCKEKADVKDTDAVDVCIADGVCIDAFLKPPMETEEPQIFYNAS

PSTLS.
```

In any of the methods provided herein, the anti-hyaluronan agent can be an agent that degrades hyaluronan or can be an agent that inhibits the synthesis of hyaluronan. For example, the anti-hyaluronan agent can be a hyaluronan degrading enzyme. In another example, the anti-hyaluronan agent or is an agent that inhibits hyaluronan synthesis. For example, the anti-hyaluronan agent is an agent that inhibits hyaluronan synthesis such as a sense or antisense nucleic acid molecule against an HA synthase or is a small molecule drug. For example, an anti-hyaluronan agent is 4-methylumbelliferone (MU) or a derivative thereof, or leflunomide or a derivative thereof. Such derivatives include, for example, a derivative of 4-methylumbelliferone (MU) that is 6,7-dihydroxy-4-methyl coumarin or 5,7-dihydroxy-4-methyl coumarin.

In further examples of the methods provided herein, the hyaluronan degrading enzyme is a hyaluronidase. In some examples, the hyaluronan-degrading enzyme is a PH20 hyaluronidase or truncated form thereof to lacking a C-terminal glycosylphosphatidylinositol (GPI) attachment site or a portion of the GPI attachment site. In specific examples, the hyaluronidase is a PH20 selected from a human, monkey, bovine, ovine, rat, mouse or guinea pig PH20. For example, the hyaluronan-degrading enzyme is a human PH20 hyaluronidase that is neutral active and N-glycosylated and is selected from among (a) a hyaluronidase polypeptide that is a full-length PH20 or is a C-terminal truncated form of the PH20, wherein the truncated form includes at least amino acid residues 36-464 of SEQ ID NO: 39, such as 36-481, 36-482, 36-483, where the full-length PH20 has the sequence of amino acids set forth in SEQ ID NO: 39; or (b) a hyaluronidase polypeptide comprising a sequence of amino acids having at least 85%, 86%, 87%, 88%, 89%, 90%, 91%, 92%, 93%, 94%, 95%, 96%, 97%, 98%, 99% or more sequence identity with the polypeptide or truncated form of sequence of amino acids set forth in SEQ ID NO: 39; or (c) a hyaluronidase polypeptide of (a) or (b) comprising amino acid substitutions, whereby the hyaluronidase polypeptide has a sequence of amino acids having at least 85%, 86%, 87%, 88%, 89%, 90%, 91%, 92%, 93%, 94%, 95%, 96%, 97%, 98%, 99% or more sequence identity with the polypeptide set forth in SEQ ID NO: 39 or the with the corresponding truncated forms thereof. In exemplary examples, the hyaluronan-degrading enzyme is a PH20 that comprises a composition designated rHuPH20.

In other examples, the anti-hyaluronan agent is a hyaluronan degrading enzyme that is modified by conjugation to a polymer. The polymer can be a PEG and the anti-hyaluronan agent a PEGylated hyaluronan degrading enzyme. Hence, in some examples of the methods provided herein the hyaluronan-degrading enzyme is modified by conjugation to a polymer. For example, the hyaluronan-degrading enzyme is conjugated to a PEG, thus the hyaluronan degrading enzyme is PEGylated. In an exemplary example, the hyaluronan-degrading enzyme is a PEGylated PH20 enzyme (PEGPH20). In the methods provided herein, the corticosteroid can be a glucocorticoid that is selected from among cortisones, dexamethasones, hydrocortisones, methylprednisolones, prednisolones and prednisones.

Chondroitinases

Chondroitinases are enzymes found throughout the animal kingdom which degrade glycosaminoglycans, specifically chondroitins and chondroitin sulfates, through an endoglycosidase reaction. In some embodiments the chondroitinase is a mammalian chondroitinase. In some embodiments the chondroitinase is a recombinant human chondroitinase. In some embodiments the chondroitinase is HYAL4. Other exemplary chondroitinases include chondroitinase ABC (derived from *Proteus vulgaris*; Japanese Patent Application Laid-open No 6-153947, T. Yamagata et al. J. Biol. Chem., 243, 1523 (1968), S. Suzuki et al, J. Biol. Chem., 243, 1543 (1968)), chondroitinase AC (derived from *Flavobacterium heparinum*; T. Yamagata et al., J. Biol. Chem., 243, 1523 (1968)), chondroitinase AC II (derived from *Arthrobacter aurescens*; K. Hiyama, and S. Okada, J. Biol. Chem., 250, 1824 (1975), K. Hiyama and S. Okada, J. Biochem. (Tokyo), 80, 1201 (1976)), Hyaluronidase ACIII (derived from *Flavobacterium* sp. Hp102; Hirofumi Miyazono et al., Seikagaku, 61, 1023 (1989)), chondroitinase B (derived from *Flavobacterium heparinum*; Y. M. Michelacci and C. P. Dietrich, Biochem. Biophys. Res. Commun., 56, 973 (1974), Y. M. Michelacci and C. P. Dietrich, Biochem. J., 151, 121 (1975), Kenichi Maeyama et al, Seikagaku, 57, 1189 (1985)), chondroitinase C (derived from *Flavobacterium* sp. Hp102; Hirofumi Miyazono et al, Seikagaku, 61, 1023 (1939)), and the like.

Matrix Metalloproteinases

Matrix metalloproteases (MMPs) are zinc-dependent endopeptidases that are the major proteases involved in extracellular matrix (ECM) degradation. MMPs are capable of degrading a wide range of extracellular molecules and a number of bioactive molecules. Twenty-four MMP genes have been identified in humans, which can be organized into six groups based on domain organization and substrate preference: Collagenases (MMP-1, -8 and -13), Gelatinases (MMP-2 and MMP-9), Stromelysins (MMP-3, -10 and -11), Matrilysin (MMP-7 and MMP-26), Membrane-type (MT)-MMPs (MMP-14, -15, -16, -17, -24 and -25) and others (MMP-12, -19, -20, -21, -23, -27 and -28). In some embodiments, the stromal modifying moiety is a human recombinant MMP (e.g., MMP-1, -2, -3, -4, -5, -6, -7, -8, -9, 10, -11, -12, -13, -14, 15, -15, -17, -18, -19, 20, -21, -22, -23, or -24).

Collagenases

The three mammalian collagenases (MMP-1, -8, and -13) are the principal secreted endopeptidases capable of cleaving collagenous extracellular matrix. In addition to fibrillar collagens, collagenases can cleave several other matrix and non-matrix proteins including growth factors. Collagenases are synthesized as inactive pro-forms, and once activated, their activity is inhibited by specific tissue inhibitors of metalloproteinases, TIMPs, as well as by non-specific proteinase inhibitors (Ala-aho R et al. *Biochimie*. Collagenases in cancer. 2005 March-April; 87(3-4):273-86). In some embodiments, the stromal modifying moiety is a collagenase. In some embodiments, the collagenase is a human recombinant collagenase. In some embodiments, the collagenase is MMP-1. In some embodiments, the collagenase is MMP-8. In some embodiments, the collagenase is MMP-13.

Macrophage Metalloelastase

Macrophage metalloelastase (MME), also known as MMP-12, is a member of the stromelysin subgroup of MMPs and catalyzes the hydrolysis of soluble and insoluble elastin and a broad selection of matrix and nonmatrix substrates including type IV collagen, fibronectin, laminin, vitronectin, entactin, heparan, and chondroitin sulfates (Erja Kerkelä et al. Journal of Investigative Dermatology (2000) 114, 1113-1119; doi:10.1046/j.1523-1747.2000.00993). In some embodiments, the stromal modifying moiety is a MME. In some embodiments, the MME is a human recombinant MME. In some embodiments, the MME is MMP-12.

Exemplary Multispecific Molecules

The disclosure relates, inter alia, to novel multispecific molecules that include (i) a tumor-targeting moiety; and one or both of: (ii) an immune cell engager (e.g., chosen from one, two, three, or all of an NK cell engager, a B cell engager, a dendritic cell engager, or a macrophage cell engager); and/or (iii) a cytokine molecule. Without being bound by theory, the multispecific molecules disclosed herein are expected to target (e.g., localize, bridge and/or activate) an immune cell (e.g., an immune effector cell chosen from an NK cell, a B cell, a dendritic cell or a macrophage), at a cancer cell. Increasing the proximity and/or activity of the immune cell using the multispecific molecules described herein is expected to enhance an immune response against the cancer cell, thereby providing a more effective cancer therapy. Accordingly, provided herein are, inter alia, multispecific molecules (e.g., multispecific antibody molecules) that include the aforesaid moieties, nucleic acids encoding the same, methods of producing the aforesaid molecules, and methods of treating a cancer using the aforesaid molecules.

Accordingly, in one aspect, the disclosure features a multispecific molecule that includes:

(i) a tumor-targeting moiety, e.g., that binds to a cancer antigen (e.g., a solid tumor antigen, a stromal antigen, or a hematological antigen); and one or two of the following:

(ii) an immune cell engager, e.g., chosen from one, two, three, or all of an NK cell engager, a T cell engager, a B cell engager, a dendritic cell engager, or a macrophage cell engager; or (iii) a cytokine molecule.

In one embodiment, the multispecific molecule includes two binding specificities or functions, e.g., it is a bispecific or a bifunctional molecule, e.g., which includes:

i) the tumor-targeting moiety and the cytokine molecule; or ii) the tumor-targeting moiety and the immune cell engager.

In other embodiments, the multispecific molecule includes three or four binding specificities or functions, e.g., it is a trispecific or a tetraspecific molecule. Exemplary trispecific and tetraspecific molecules include:

(i) one tumor-targeting moiety, one immune cell engager, and one cytokine molecule;

(ii) one tumor-targeting moiety and two immune cell engagers (e.g., same or different immune cell engagers);

(iii) one tumor-targeting moiety and two cytokines (e.g., same or different cytokines);

(iv) one tumor-targeting moiety, two immune cell engagers (e.g., same or different immune cell engagers), and one cytokine molecule;

(v) one tumor-targeting moiety, one immune cell engager, and two cytokine molecules (e.g., same or different cytokine molecules);

(vi) one tumor-targeting moiety and three immune cell engagers (e.g., same or different immune cell engagers);

(vii) one tumor-targeting moiety and three cytokine molecules (e.g., same or different cytokine molecules);

(viii) two tumor-targeting moieties (e.g., same or different targeting moieties) and one immune cell engager;

(ix) two tumor-targeting moieties (e.g., same or different targeting moieties) and one cytokine molecule; and (ix) two tumor-targeting moieties (e.g., same or different targeting moieties), one immune cell engager, and one cytokine molecule.

In some embodiments, the multispecific molecule includes a single chain antibody molecule, e.g., a single domain antibody, a scFv, a camelid, or a shark antibody, and a second moiety. In some embodiments, the multispecific molecule comprises a VH to VL from N to C orientation, of the scFv connected, optionally via a linker, to the second moiety (e.g., as shown in FIGS. 1A and 1B); the scFv can form the first binding specificity (depicted as binding moiety "1" in FIGS. 1A-1B). In some embodiments, the second moiety (depicted as partner A in FIGS. 1A-1B) is located before the VH region of the scFv from an N- to C-orientation (e.g., as shown in FIG. 1A), or after the VL region of the scFv from an N- to C-orientation (e.g., as shown in FIG. 1B); the second moiety can form the second binding specificity (depicted as binding moiety "2" in FIGS. 1A-1B). In other embodiments, the multispecific molecule comprises a VL to VH from N to C orientation, of the scFv connected, optionally via a linker, to the second moiety (e.g., as shown in FIGS. 2A and 2B); the scFv can form the first binding specificity (depicted as binding moiety "1" in FIGS. 2A-2B). In some embodiments, the second moiety (depicted as partner A in FIGS. 2A-2B) is located before the VL region of the scFv from an N- to C-orientation (e.g., as shown in FIG. 2A), or after the VH region of the scFv from an N- to C-orientation (e.g., as shown in FIG. 2B); the second moiety can form the second binding specificity (depicted as binding moiety "2" in FIGS. 2A-2B). In embodiments, the scFv can be a tumor targeting moiety (e.g., binds to a cancer antigen, e.g., a solid tumor, stromal, or hematological antigen), or can be an immune cell engager (e.g., binds to an immune cell antigen). In other embodiments, the second moiety (e.g., depicted as partner A in FIG. 1A-1B or 2A-2B) is a tumor targeting moiety (e.g., in embodiments where the scFv is not the tumor targeting moiety), an immune cell engager (e.g., in embodiments where the scFv is not the immune cell engager), or a cytokine molecule (e.g., as described herein). In embodiments, partner A can be an antibody molecule (e.g., a single chain antibody molecule (e.g., a scFv) or a Fab), a receptor molecule, a ligand molecule (e.g., a receptor ligand or a cytokine molecule), e.g., as described herein. In one embodiment, the tumor-targeting moiety is a scFv to a cancer cell antigen, and the second moiety is chosen from a cytokine molecule or an immune cell engager. In some embodiments, the second moiety is a second antibody molecule (e.g., a second scFv or Fab), a receptor molecule, a ligand molecule (e.g., a receptor ligand or a cytokine molecule).

In other embodiments, the multispecific molecule is a trispecific or trifunctional that includes, or consists of, a single chain polypeptide, e.g., a contiguous single polypeptide chain. For example, the multispecific molecule can include a tumor targeting moiety (e.g., a first binding specificity to a cancer antigen, e.g., a solid tumor, stromal, or hematological antigen as described herein), a cytokine molecule as described herein, and an immune cell engager (e.g., a second binding specificity to an immune cell antigen as described herein), or any combination of at least 2 of any of the aforesaid.

In some embodiments, the multispecific molecule includes a single chain antibody molecule, e.g., a single domain antibody, a scFv, a camelid, or a shark antibody, and a second moiety. In some embodiments, the multispecific molecule comprises a VH to VL from N to C orientation, of the scFv connected, optionally via a linker, to a second moiety and/or a third moiety (e.g., as shown in FIG. 1C); the scFv can form the first binding specificity (depicted as binding moiety "1" in FIG. 1C). In some embodiments, the second or third moieties (depicted as partners A and B in FIG. 1C) is located before the VH region of the scFv from an N- to C-orientation (e.g., as shown in FIG. 1C) and the third moiety (partner B) after the VL region of the scFv from an N- to C-orientation (e.g., as shown in FIG. 1C), respectively; the second and third moieties can form the second and third binding specificities (depicted as binding moiety "2" and binding moiety "3," respectively, in FIG. 1C). In other embodiments, the multispecific molecule comprises a VL to VH from N to C orientation, of the scFv connected, optionally via a linker, to a second moiety and/or a third moiety (e.g., as shown in FIG. 2C). In some embodiments, the second moiety (depicted as partner A in FIG. 2C) is located before the VL region of the scFv from an N- to C-orientation (e.g., as shown in FIG. 2C), and the third moiety (partner B) after the VH region of the scFv from an N- to C-orientation (e.g., as shown in FIG. 2C); the second and third moieties can form the second and third binding specificities (depicted as binding moiety "2" and binding moiety "3," respectively, in FIG. 2C). In embodiments, the scFv of any of the aforesaid multispecific molecules can be a tumor targeting moiety (e.g., bind to a cancer antigen, e.g., a solid tumor, stromal or hematological antigen) or can be an immune cell engager (e.g., bind to an immune cell antigen). In embodiments, the second moiety and third moiety (e.g., depicted as partner A and partner B in FIG. 1C or 2C) is independently chosen from a tumor targeting moiety, an immune cell engager, or a cytokine molecule (e.g., as described herein). In embodiments, partner A and/or partner B can be an antibody molecule (e.g., a single chain antibody molecule (e.g., a scFv or a Fab), a receptor molecule, or a ligand molecule (e.g., a receptor ligand or a cytokine molecule), e.g., as described herein. In one embodiment, the tumor-targeting moiety is a scFv to a cancer cell antigen, and the second moiety and third moiety is independently chosen from a cytokine molecule or an immune cell engager. In some embodiments, the second and third moiety is independently chosen from a second antibody molecule (e.g., a second scFv or Fab), a receptor molecule, or a ligand molecule (e.g., a receptor ligand or a cytokine molecule).

In some embodiments, the multispecific molecule does not consist of a single chain polypeptide of an NK cell engager (i.e., a scFv) that binds to CD16 (FcγRIII), and a tumor targeting moiety, i.e., a scFv targeting CD33. In other embodiments, the multispecific molecule does not consist of a single chain polypeptide of the scFv that binds to CD16, an IL-15 cytokine, and the scFv targeting CD33.

In embodiments, the multispecific molecule is a bispecific or bifunctional molecule, wherein the first and second polypeptides (i) and (ii) are non-contiguous, e.g., are two separate polypeptide chains. In embodiments, the first and second polypeptides have a configuration as shown in FIGS. 3A-3B or FIGS. 4A-4B. In embodiments, the first and second polypeptides form a first binding specificity, e.g., an antigen binding domain (e.g., depicted as binding moiety "1" in FIGS. 3A-3B and FIGS. 4A-4B). In embodiments, a second moiety (depicted as partner A) is connected, e.g., via a linker, to either the first polypeptide or the second polypeptide. In embodiments, the second moiety forms a second binding specificity (e.g., depicted as binding moiety "2" in FIGS. 3A-3B and FIGS. 4A-4B).

In one embodiment depicted in FIGS. 3A-3B, the second moiety (e.g., partner A) is connected, e.g., via a linker, to the C-terminus of the second polypeptide (e.g., the C-terminus of the CL region of the second polypeptide) (e.g., as shown in FIG. 3A). In other embodiments, the second moiety (e.g., partner A) is connected, e.g., via a linker, to the C-terminus of the first polypeptide (e.g., C-terminus of the CH1 region of the first polypeptide) (e.g., as shown in FIG. 3B).

In another embodiment depicted in FIGS. 4A-4B, the second moiety (e.g., partner A) is connected, e.g., via a linker, to the N-terminus of the second polypeptide (e.g., the N-terminus of the VL region of the second polypeptide) (e.g., as shown in FIG. 4A). In other embodiments, the second moiety (e.g., partner A) is connected, e.g., via a linker, to the N-terminus of the first polypeptide (e.g., the N-terminus of the VH region of the first polypeptide) (e.g., as shown in FIG. 4B).

In embodiments, the first and second polypeptide (e.g., the VH and VL regions) can form a binding moiety (e.g., binding moiety 1 in FIGS. 3A-3B and 4A-4B); for example, the first and second polypeptide can be a tumor targeting moiety (e.g., bind to a cancer antigen, e.g., a solid tumor, a stromal or hematological antigen) or can be an immune cell engager (e.g., bind to an immune cell antigen). In embodiments, the second moiety (e.g., depicted as partner A in FIGS. 3A-3B and 4A-4B) forms a second binding moiety, e.g., it is chosen from a tumor targeting moiety, an immune cell engager, or a cytokine molecule (e.g., as described herein). In embodiments, the second moiety, e.g., partner A, can be an antibody molecule (e.g., a single chain antibody molecule (e.g., a scFv) or a Fab), a receptor molecule, or a ligand molecule (e.g., a receptor ligand or a cytokine molecule), e.g., as described herein. In one embodiment, the multispecific molecule includes a Fab molecule and the second moiety is chosen from a second antibody molecule (e.g., a scFv or a second Fab), a receptor molecule, or a ligand molecule (e.g., a cytokine molecule). In one embodiment, the tumor-targeting moiety is a Fab to a cancer cell antigen, and the second moiety is chosen from a cytokine molecule or an immune cell engager. In some embodiments, the second moiety is a second antibody molecule (e.g., a second scFv or Fab), a receptor molecule, or a receptor ligand molecule, or a cytokine molecule.

In embodiments, the multispecific molecule is a bispecific or bifunctional molecule, wherein the first and second polypeptides (i) and (ii) are non-contiguous, e.g., are two separate polypeptide chains. In embodiments, the first and second polypeptides have a configuration as shown in FIGS. 3A-3B or FIGS. 4A-4B. In embodiments, a second moiety (depicted as partner A) is connected, e.g., via a linker, to either the first polypeptide or the second polypeptide (e.g., either the N-terminus or the C-terminus of the first polypeptide or the second polypeptide).

In one embodiment of the bispecific or bifunctional molecule depicted in FIGS. 3A-3B, the second moiety (e.g., partner A) is connected, e.g., via a linker, to the CL region (e.g., C-terminus of the CL region) of the second polypeptide (e.g., as shown in FIG. 3A). In other embodiments, the second moiety (e.g., partner A) is connected, e.g., via a linker, to the CH1 region (e.g., C-terminus of the CH1 region) of the first polypeptide (e.g., as shown in FIG. 3B).

In another embodiment of the bispecific or bifunctional molecule depicted in FIGS. 4A-4B, the second moiety (e.g., partner A) is connected, e.g., via a linker, to the VL region (e.g., N-terminus of the VL region) of the second polypeptide (e.g., as shown in FIG. 4A). In other embodiments, the second moiety (e.g., partner A) is connected, e.g., via a linker, to the VH region (e.g., N-terminus of the VH region) of the first polypeptide (e.g., as shown in FIG. 4B).

In embodiments of the bispecific or bifunctional molecule, the first and second polypeptide (e.g., the VH and VL regions) can form a binding moiety (e.g., binding moiety 1 in FIGS. 3A-3B and 4A-4B); for example, the first and second polypeptide can be a tumor targeting moiety (e.g., bind to a cancer antigen, e.g., a tumor, a stromal or a hematological antigen) or can be an immune cell engager (e.g., bind to an immune cell antigen). In embodiments, the second moiety (e.g., depicted as partner A in FIGS. 3A-3B and 4A-4B) forms a second binding moiety, e.g., it is chosen from a tumor targeting moiety, an immune cell engager, or a cytokine molecule (e.g., as described herein). In embodiments, the second moiety, e.g., partner A, can be an antibody molecule (e.g., a single chain antibody molecule (e.g., a scFv) or a Fab), a receptor molecule, or a ligand molecule (e.g., a receptor ligand or a cytokine molecule), e.g., as described herein. In one embodiment, the multispecific molecule includes a Fab molecule and the second moiety is chosen from a second antibody molecule (e.g., a scFv or a second Fab), a receptor molecule, or a ligand molecule (e.g., a cytokine molecule). In one embodiment, the tumor-targeting moiety is a Fab to a cancer cell antigen, and the second moiety is chosen from a cytokine molecule or an immune cell engager. In some embodiments, the second moiety is a second antibody molecule (e.g., a second scFv or Fab), a receptor molecule, a receptor ligand molecule, or a cytokine molecule.

In other embodiments, the multispecific molecule is a trispecific or a trifunctional molecule, wherein the first and second polypeptides (i) and (ii) are non-contiguous, e.g., are two separate polypeptide chains. In embodiments, the first and second polypeptides have a configuration as shown in FIGS. 3C and 4C. In embodiments, a second moiety and a third moiety (depicted as partners A and B, respectively) are connected, e.g., via a linker, to the C-terminus, the N-terminus, or both of the first polypeptide and the second polypeptide, respectively. In one embodiment, the second moiety and third moieties are connected to C-terminus of the second and first polypeptides (or the first and second polypeptides), respectively. In another embodiment, the second moiety and third moieties are connected to N-terminus of the second and first polypeptides (or the first and second polypeptides), respectively. In one embodiment, the second moiety and third moiety are connected to N- and C-terminus of the second and first polypeptides (or the first and second polypeptides), respectively. Any configuration is intended by the present disclosure, including those exemplified in FIGS. 3C and 4C.

In one embodiment of the trispecific or trifunctional molecule depicted in FIGS. 3C-4C, the second moiety (e.g., partner A corresponding to the second binding specificity "2") is connected, e.g., via a linker, to the C-terminus of the second polypeptide (e.g., the C-terminus of the CL region of the second polypeptide) (e.g., as shown in FIG. 3C), and the third moiety (e.g., partner B corresponding to the third binding specificity "3") is connected, e.g., via a linker, to the C-terminus of the first polypeptide (e.g., the C-terminus of the CH1 region of the first polypeptide) (e.g., as shown in FIG. 3C).

In another embodiment of the trispecific or trifunctional molecule depicted in FIGS. 3C-4C, the second moiety (e.g., partner A corresponding to the second binding specificity "2") is connected, e.g., via a linker, to the N-terminus of the second polypeptide (e.g., the N-terminus of the VL region of the second polypeptide) (e.g., as shown in FIG. 4C), and the third moiety (e.g., partner B corresponding to the third binding specificity "3") is connected, e.g., via a linker, to the N-terminus of the first polypeptide (e.g., the N-terminus of the VH region of the first polypeptide) (e.g., as shown in FIG. 4C).

In another embodiment of the trispecific or trifunctional molecule, the second moiety (e.g., partner A corresponding to the second binding specificity "2") is connected, e.g., via a linker, to the N-terminus of the second polypeptide (e.g., the N-terminus of the VL region of the second polypeptide), and the third moiety (e.g., partner B corresponding to the third binding specificity "3") is connected, e.g., via a linker, to the C-terminus of the first polypeptide (e.g., the C-terminus of the CH1 region of the first polypeptide).

In another embodiment of the trispecific or trifunctional molecule, the second moiety (e.g., partner A corresponding to the second binding specificity "2") is connected, e.g., via a linker, to the C-terminus of the second polypeptide (e.g., the N-terminus of the CL region of the second polypeptide), and the third moiety (e.g., partner B corresponding to the third binding specificity "3") is connected, e.g., via a linker, to the N-terminus of the first polypeptide (e.g., the N-terminus of the VH region of the first polypeptide).

In embodiments of the trispecific or trifunctional molecule, the first and second polypeptides (e.g., the VH and VL regions) can form a first binding specificity (e.g., binding moiety "1" in FIGS. 3C and 4C); for example, the first and second polypeptide can be a tumor targeting moiety (e.g., bind to a cancer antigen, e.g., a solid tumor, a stromal or a hematological antigen) or can be an immune cell engager (e.g., bind to an immune cell antigen). In embodiments, the second moiety and the third moiety (e.g., depicted as partners A and B in FIGS. 3C and 4C) form a second and a third binding specificity, e.g., it is independently chosen from a tumor targeting moiety, an immune cell engager, or a cytokine molecule (e.g., as described herein). In embodiments, the second and a third binding specificity, e.g., partners A and B, can be, independently, an antibody molecule (e.g., a single chain antibody molecule (e.g., a scFv) or a Fab), a receptor molecule, a ligand molecule (e.g., a receptor ligand or a cytokine molecule), e.g., as described herein. In one embodiment, the multispecific molecule includes a Fab molecule and the second moiety and third moiety is, independently, chosen from a second antibody molecule (e.g., a scFv or a second Fab), a receptor molecule, or a ligand molecule (e.g., a receptor ligand or a cytokine molecule). In some embodiments, the first binding specificity, the second binding specificity and the third binding specificity can each be independently chosen from a tumor targeting moiety, a cytokine molecule, an NK cell engager, a T cell engager, a B cell engager, a dendritic cell engager, or a macrophage cell engager. In one embodiment, the tumor-targeting moiety is a Fab to a cancer cell antigen, and the second and third moiety is independently chosen from a cytokine molecule or an immune cell engager. In one embodiment, the tumor-targeting moiety is a Fab to a cancer cell antigen; the second moiety is a cytokine molecule; and the third moiety is an immune cell engager.

In one embodiment, the multispecific molecule includes at least two or at least three or at least four non-contiguous polypeptides, wherein:

(i) the first polypeptide includes from N- to C-orientation a first immunoglobulin constant region (e.g., a CH2 connected to a CH3 region) (e.g., a first Fc region); and (ii) the second polypeptide includes from N- to C-orientation a second immunoglobulin constant region (e.g., a CH2 connected to a CH3 region) (e.g., a second Fc region).

In embodiments, the multispecific molecule is a bispecific or bifunctional molecule, wherein the first and second polypeptides (i) and (ii) are non-contiguous, e.g., are two separate polypeptide chains. In some embodiments, the first and second polypeptides (i) and (ii) include a paired amino acid substitution at a position chosen from one or more of 347, 349, 350, 351, 366, 368, 370, 392, 394, 395, 397, 398, 399, 405, 407, or 409, e.g., of the Fc region of human IgG1 For example, the first immunoglobulin chain constant region (e.g., the first Fc region) can include an amino acid substitution chosen from: T366S, L368A, or Y407V (e.g., corresponding to a cavity or hole), and the second immunoglobulin chain constant region (e.g., the second Fc region) includes a T366W (e.g., corresponding to a protuberance or knob). In some embodiments, the first and second polypeptides are a first and second member of a heterodimeric first and second Fc region.

In embodiments, the first and second polypeptides form a bispecific molecule. In some embodiments, the first polypeptide includes a first binding specificity (e.g., partner A or binding specificity 1 in FIG. 5A), and the second polypeptide includes a second binding specificity (e.g., partner B or binding specificity 2 in FIG. 5A). In embodiments, the first and second binding specificities (partner A and partner B, respectively) is each independently chosen from an antibody molecule (e.g., a single chain antibody molecule (e.g., a scFv) or a Fab), a receptor molecule, a ligand molecule (e.g., a receptor ligand or a cytokine molecule), e.g., as described herein. In embodiments, the first and second binding specificities are connected to either the first or the second polypeptide, or each of the polypeptides, (e.g., one or both members of a heterodimeric Fc molecule). In one embodiment, the first binding specificity (e.g., partner A) is connected to the N-terminal end of the first polypeptide (e.g., a -CH2-CH3-region of the first Fc molecule), and the second binding specificity (e.g., partner B) is connected to the N-terminal end of the second polypeptide (e.g., a -CH2-CH3-region of the second Fc molecule). Alternatively, the first binding specificity (e.g., partner A) is connected to the C-terminal end of the first polypeptide (e.g., a -CH2-CH3-region of the first Fc molecule), and the second binding specificity (e.g., partner B) is connected to the C-terminal end of the second polypeptide (e.g., a -CH2-CH3-region of the second Fc molecule). Alternatively, the first binding specificity (e.g., partner A) is connected to the N-terminal end of the first polypeptide (e.g., a -CH2-CH3-region of the first Fc molecule), and the second binding specificity (e.g., partner B) is connected to the C-terminal end of the second polypeptide (e.g., a -CH2-CH3-region of the second Fc molecule). In other embodiments, the second binding specificity (e.g., partner B) is connected to N-terminus of the first polypeptide (e.g., the -CH2-CH3-region of the first Fc molecule), and the first binding specificity (e.g., partner A)

is connected to the C-terminal end of the second polypeptide (e.g., a -CH2-CH3-region of the second Fc molecule). In one embodiment, the first -CH2-CH3 region includes a protuberance or knob, and the second -CH2-CH3 region includes a cavity or hole, e.g., as depicted in FIG. 5A).

In some embodiments, the first and second binding specificities (binding moiety 1 and binding moiety 2) of the bispecific molecule can each be independently chosen from a tumor targeting moiety, a cytokine molecule, a T cell engager, an NK cell engager, a B cell engager, a dendritic cell engager, or a macrophage cell engager. In some embodiments, the first binding specificity is a tumor targeting moiety and the second binding specificity is chosen from a cytokine molecule, an NK cell engager, a T cell engager, a B cell engager, a dendritic cell engager, or a macrophage cell engager.

In some embodiments shown in FIG. 5A, the bispecific molecule can have partner A and B, which are depicted as first and second binding specificities (binding moieties 1 and 2), respectively (FIG. 5A). The first and second binding specificities can be, each independently, an antibody molecule (e.g., a single chain antibody molecule (e.g., a scFv) or a Fab), a receptor molecule, a ligand molecule (e.g., a receptor ligand or a cytokine molecule), e.g., as described herein. In some embodiments, the first binding specificity is a tumor targeting moiety and the second binding specificity is chosen from a cytokine molecule, an NK cell engager, a T cell engager, a B cell engager, a dendritic cell engager, or a macrophage cell engager.

In embodiments, the first and second polypeptides form a trispecific or tetraspecific molecule (e.g., as depicted in FIGS. 5B-5C, respectively).

In some embodiments of the trispecific molecule, the first polypeptide includes a first binding specificity (e.g., partner A or binding moiety 1 in FIG. 5B), and the second polypeptide includes a second binding specificity (e.g., partner B or binding specificity 2 in FIG. 5B), wherein either the first or the second polypeptide further includes a third binding specificity (e.g., partner C or binding moiety 3 in FIG. 5B). In embodiments, the first and second binding specificities are connected to either the first or the second polypeptide, or each of the polypeptides, (e.g., one or both members of a heterodimeric Fc molecule). In one embodiment, the first and second binding specificities are connected, e.g., via a linker, to the N-terminus of the first and the second polypeptide, respectively, and the third binding specificity is connected, e.g., via a linker, to the C-terminal end of either the first or the second polypeptide. In one embodiment, the third binding specificity is connected, e.g., via a linker, to the C-terminal end of the first polypeptide (e.g., the C-terminal end of the first -CH2-CH3 region depicted in FIG. 5B). In one embodiment, the third binding specificity is connected, e.g., via a linker, to the C-terminal end of the second polypeptide (e.g., the C-terminal end of the second -CH2-CH3 region). In one embodiment, the first -CH2-CH3 region includes a protuberance or knob, and the second -CH2-CH3 region includes a hole or cavity, e.g., as depicted in FIG. 5B).

In embodiments, the first, second and third binding specificities (partner A, partner B, and partner C respectively) is each independently chosen from an antibody molecule (e.g., a single chain antibody molecule (e.g., a scFv) or a Fab), a receptor molecule, a ligand molecule (e.g., a receptor ligand or a cytokine molecule), e.g., as described herein. In one embodiment, the first binding specificity (e.g., partner A) is connected to the N-terminal end of the first polypeptide (e.g., a -CH2-CH3-region of the first Fc molecule); the second binding specificity (e.g., partner B) is connected to the N-terminal end of the second polypeptide (e.g., a -CH2-CH3-region of the second Fc molecule); and the third binding specificity (e.g., partner C) is connected to the C-terminal end of the first polypeptide (e.g., a -CH2-CH3-region of the second Fc molecule). In other embodiments, the first binding specificity (e.g., partner A) is connected to the N-terminal end of the first polypeptide (e.g., a -CH2-CH3-region of the first Fc molecule); the second binding specificity (e.g., partner B) is connected to the N-terminal end of the second polypeptide (e.g., a -CH2-CH3-region of the first Fc molecule); and the third binding specificity (e.g., partner C) is connected to the C-terminal end of the second polypeptide (e.g., a -CH2-CH3-region of the second Fc molecule). The first, second and third binding specificities can each be, independently, an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, the first, second and third binding specificities (partners A-C, corresponding to binding moieties 1-3, respectively) are each independently chosen from a tumor targeting moiety, a cytokine molecule, an NK cell engager, a T cell engager, a B cell engager, a dendritic cell engager, or a macrophage cell engager, e.g., as described herein. In embodiments, the first binding specificity is a tumor targeting moiety and the second and third binding specificity are each independently chosen from a cytokine molecule, an NK cell engager, a T cell engager, a B cell engager, a dendritic cell engager, or a macrophage cell engager.

In some embodiments of the tetraspecific molecule, the first polypeptide includes a first binding specificity (e.g., partner A or binding moiety 1 in FIG. 5C) and a third binding specificity (e.g., partner C or binding moiety 3 in FIG. 5C), and the second polypeptide includes a second binding specificity (e.g., partner B or binding specificity 2 in FIG. 5C) and a fourth binding specificity (e.g., partner D or binding moiety 4 in FIG. 5C). In one embodiment, the first and second binding specificities are connected, e.g., via a linker, to the N-terminus of the first and the second polypeptide, respectively, and the third and fourth binding specificities are connected, e.g., via a linker, to the C-terminal end of the first and the second polypeptide, respectively. Any permutation of binding specificity to the N- or C-terminus of the first or second polypeptide is encompassed by the present disclosure. In one embodiment, the first binding specificity (e.g., partner A) is connected, e.g., via a linker, to the N-terminal end of the first polypeptide (e.g., the N-terminal end of the first -CH2-CH3 region depicted in FIG. 5C); the second binding specificity (e.g., partner B) is connected, e.g., via a linker, to the N-terminal end of the second polypeptide (e.g., the N-terminal end of the second -CH2-CH3 region depicted in FIG. 5C); the third binding specificity (e.g., partner C) is connected, e.g., via a linker, to the C-terminal end of the first polypeptide (e.g., the C-terminal end of the first -CH2-CH3 region depicted in FIG. 5C); and the fourth binding specificity (e.g., partner D) is connected, e.g., via a linker, to the C-terminal end of the second polypeptide (e.g., the C-terminal end of the second -CH2-CH3 region). In one embodiment, the first -CH2-CH3 region includes a protuberance or knob, and the second -CH2-CH3 region includes a cavity or hole, e.g., as depicted in FIG. 5C). In embodiments, the first, second, third and fourth binding specificities (partner A, partner B, partner C and partner D, respectively) is each independently chosen from an antibody molecule (e.g., a single chain antibody molecule (e.g., a scFv) or a Fab), a receptor molecule, a ligand molecule (e.g., a receptor ligand or a cytokine molecule), e.g., as described herein. The first, second, third and fourth binding specificities can each be, independently, an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, the first, second, third and fourth binding specificities (partners A-D, corresponding to binding moieties 1-4, respectively) are each independently chosen from a tumor targeting moiety, a cytokine molecule, an NK cell engager, a T cell engager, a B cell engager, a dendritic cell engager, or a macrophage cell engager, e.g., as described herein. In embodiments, the first binding specificity is a tumor targeting moiety and the second, third and fourth binding specificities are each independently chosen from a cytokine molecule, an NK cell engager, a T cell engager, a B cell engager, a dendritic cell engager, or a macrophage cell engager.

In one embodiment, the multispecific molecule is a bispecific molecule that includes two non-contiguous first and second polypeptides. In embodiments, the first and second polypeptides, include, respectively, a first and a second binding sites, which are independently chosen from an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, the first and second binding specificities (binding sites 1-2, respectively) are each independently chosen from a tumor targeting moiety, a cytokine molecule, an NK cell engager, a T cell engager, a B cell engager, a dendritic cell engager, or a macrophage cell engager, e.g., as described herein. In some embodiments, the first polypeptide has the following configuration from N-to-C: a first portion of a first antigen domain, e.g., a first VH-CH1 of a Fab molecule, that binds to, e.g., a tumor or stromal antigen (e.g., binding site #1), connected, optionally, via a linker to, a second binding specificity (e.g., a binding site #2); and the second polypeptide has the following configuration from N-to-C: a second portion of a first antigen domain, e.g., a first VL-CL of the Fab, that binds to, e.g., a cancer antigen (e.g., the same cancer antigen bound by the first VH-CH1, e.g., binding site #1) (e.g., an example of this configuration is depicted in FIG. 6). In one embodiment, the bispecific molecule that includes a Fab corresponding to the first binding specificity (binding site #1) connected, optionally via a linker, to the second binding specificity (e.g., binding site #2). In some embodiments, the first binding specificity (e.g., binding site #1 in FIG. 6) is a tumor targeting moiety, e.g., binds to a cancer antigen, e.g., a tumor or stromal antigen; and the second binding specificity (e.g., binding site #2 in FIG. 6) is chosen from a cytokine molecule, or an immune cell engager, e.g., chosen from a receptor, a receptor ligand molecule or an antibody molecule (e.g., a scFv) that binds to an immune cell antigen. In embodiments where the antibody molecule is a scFV, the scFv may be connected to the C-terminus of the first polypeptide in a VH-VL or a VL-VH configuration.

In another embodiment, the multispecific molecule is a bispecific molecule that includes two or at least three non-contiguous first and second polypeptides, wherein:

(i) the first polypeptide includes from N- to C-orientation a first binding specificity, e.g., a first antibody molecule, connected, optionally via a linker, to a first immunoglobulin constant region (e.g., a CH2 connected to a CH3 region) (e.g., a first Fc region);

(ii) the second polypeptide includes from N- to C-orientation a second immunoglobulin constant region (e.g., a CH2 connected to a CH3 region) (e.g., a second Fc region); and (optionally) (iii) a third polypeptide comprising a portion of the first antibody molecule or a second antibody molecule.

In embodiments, the first and second polypeptides, include, respectively, a first and a second binding specificities (e.g., sites), which are independently chosen from an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, the first and second binding specificities (binding sites 1-2, respectively) are each independently chosen from a tumor targeting moiety, a cytokine molecule, an NK cell engager, a T cell engager, a B cell engager, a dendritic cell engager, or a macrophage cell engager, e.g., as described herein.

In some embodiments, the first polypeptide has the following configuration from N-to-C:

(a) a first portion of a first antigen domain, e.g., a first VH-CH1 of a Fab molecule, that binds to, e.g., a cancer antigen, e.g., a solid tumor, stromal or hematological antigen (e.g., binding site #1), connected, optionally via a linker to, the first immunoglobulin constant region (e.g., the CH2 connected to the CH3 region) (e.g., a first Fc region);

(b) a second binding specificity (e.g., a second binding site), which is chosen from a cytokine molecule, or an immune cell engager, connected, optionally, via a linker to, the second immunoglobulin constant region (e.g., the CH2 connected to the CH3 region) (e.g., the second Fc region); and (c) the third polypeptide has the following configuration from N-to-C: a second portion of the first antigen domain, e.g., a first VL-CL of the Fab, that binds to, e.g., a cancer antigen, e.g., a solid tumor, stromal or hematological antigen (e.g., the same cancer antigen bound by the first VH-CH1, e.g., binding site #1) (e.g., an example of this configuration is depicted in FIG. 7).

In one embodiment, the bispecific molecule that includes a Fab corresponding to the first binding specificity (binding site #1) connected, optionally via a linker, to the first Fc region, and the second binding specificity (e.g., binding site #2) connected, optionally via a linker, to the second Fc region. In some embodiments, the first binding specificity (e.g., binding site #1 in FIG. 7) is a tumor targeting moiety, e.g., binds to a cancer antigen, e.g., a tumor or stromal antigen; and the second binding specificity (e.g., binding site #2 in FIG. 7) is chosen from a cytokine molecule, or an immune cell engager, e.g., chosen from a receptor, a ligand molecule or an antibody molecule (e.g., a scFv) that binds to an immune cell antigen. In embodiments where the antibody molecule is a scFV, the scFv may be connected to the C-terminus of the first polypeptide in a VH-VL or a VL-VH configuration.

In embodiments, the first immunoglobulin constant region (e.g., the first CH2-CH3 region) includes a protuberance or knob, e.g., as described herein.

In embodiments, the second immunoglobulin constant region (e.g., the second CH2-CH3 region) includes a cavity or hole. In embodiments, the first and second immunoglobulin constant region promote heterodimerization of the bispecific molecule.

In one embodiment, the multispecific molecule is a trispecific molecule that includes two non-contiguous first and second polypeptides. In embodiments, the first and second polypeptides, include, respectively, a first, a second and a third binding specificities, which are independently chosen from an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, the first, second and third binding specificities (binding sites 1-3, respectively) are each independently chosen from a tumor targeting moiety, a cytokine molecule, an NK cell engager, a T cell engager, a B cell engager, a dendritic cell engager, or a macrophage cell engager, e.g., as described herein.

In some embodiments, the first polypeptide has the following configuration from N-to-C:

(i) a first portion of a first antigen domain, e.g., a first VH-CH1 of a Fab molecule, that binds to, e.g., a tumor or stromal antigen (e.g., binding site #1), connected, optionally, via a linker to, a second binding specificity (e.g., a binding site #3, e.g., a cytokine, a ligand or a second antibody molecule, e.g., a scFv); and (ii) the second polypeptide has the following configuration from N-to-C: a second portion of a first antigen domain, e.g., a first VL-CL of the Fab, that binds to, e.g., a tumor or stromal antigen (e.g., the same tumor or stromal antigen bound by the first VH-CH1, e.g., binding site #1), connected, optionally, via a linker to, a third binding specificity (e.g., a binding site #2, e.g., a cytokine, a ligand or a second antibody molecule, e.g., a scFv) (e.g., an example of this configuration is depicted in FIGS. 8A-8C).

In one embodiment, the bispecific molecule that includes a Fab corresponding to the first binding specificity (binding site #1) connected, optionally via a linker, to the second and third binding specificities (e.g., binding sites #2 and #3). In some embodiments, the first binding specificity (e.g., binding site #1 in FIGS. 8A-8C) is a tumor targeting moiety, e.g., binds to a cancer antigen, e.g., a tumor, stromal or hematological antigen; and the second and third binding specificity (e.g., binding sites #2 and #3 in FIGS. 8A-8C) are independently chosen from a cytokine molecule, or an immune cell engager, e.g., chosen from a receptor, a ligand molecule or an antibody molecule (e.g., a scFv) that binds to an immune cell antigen. In one embodiment, the first binding specificity (e.g., binding site #1 in FIG. 8A) is a tumor targeting moiety, e.g., binds to a cancer antigen, e.g., a tumor, stromal or hematological antigen; the second binding specificity (e.g., binding site #3 in FIG. 8A) is chosen from a cytokine molecule, or an immune cell engager, e.g., chosen from a receptor, a ligand molecule or an antibody molecule (e.g., a scFv) that binds to an immune cell antigen; and the third binding specificity (e.g., binding site #2 in FIG. 8A) is an antibody molecule (e.g., a scFv) that binds to an immune cell antigen. In other embodiments, the first binding specificity (e.g., binding site #1 in FIG. 8B) is a tumor targeting moiety, e.g., binds to a cancer antigen, e.g., a tumor, stromal or hematological antigen; the second binding specificity (e.g., binding site #3 in FIG. 8B) is chosen from a cytokine molecule, or an immune cell engager, e.g., chosen from a receptor, a ligand molecule or an antibody molecule (e.g., a scFv) that binds to an immune cell antigen; and the third binding specificity (e.g., binding site #2 in FIG. 8B) is a ligand or an antibody molecule (e.g., a scFv) that binds to an immune cell antigen. In other embodiments, the first binding specificity (e.g., binding site #1 in FIG. 8C) is a tumor targeting moiety, e.g., binds to a cancer antigen, e.g., a tumor, stromal or hematological antigen; the second binding specificity (e.g., binding site #3 in FIG. 8C) is an immune cell engager, e.g., chosen from a receptor, a ligand molecule or an antibody molecule (e.g., a scFv) that binds to an immune cell antigen; and the third binding specificity (e.g., binding site #2 in FIG. 8C) is a ligand or an antibody molecule (e.g., a scFv) that binds to an immune cell antigen. In embodiments where the antibody molecule is a scFV, the scFv may be connected to the C-terminus of the first polypeptide in a VH-VL or a VL-VH configuration.

In another embodiment, the multispecific molecule is a trispecific molecule that includes two or at least three non-contiguous first and second polypeptides, wherein:

(i) the first polypeptide includes from N- to C-orientation a first binding specificity, e.g., a first antibody molecule, connected, optionally via a linker, to a first immunoglobulin constant region (e.g., a CH2 connected to a CH3 region) (e.g., a first Fc region);

(ii) the second polypeptide includes from N- to C-orientation a second binding specificity connected, optionally via a linker, to a second immunoglobulin constant region (e.g., a CH2 connected to a CH3 region) (e.g., a second Fc region); and (optionally) (iii) a third polypeptide comprising a portion of the first antibody molecule or a second antibody molecule, wherein either the first or the second polypeptide further includes a third binding specificity.

In embodiments, the first and second polypeptides, include, respectively, a first, a second, and a third binding specificities (e.g., sites), which are independently chosen from an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, the first, second and third binding specificities (binding sites 1-3, respectively) are each independently chosen from a tumor targeting moiety, a cytokine molecule, an NK cell engager, a T cell engager, a B cell engager, a dendritic cell engager, or a macrophage cell engager, e.g., as described herein.

In some embodiments, the first polypeptide has the following configuration from N-to-C:

(a) a first portion of a first antigen domain, e.g., a first VH-CH1 of a Fab molecule, that binds to, e.g., a tumor or stromal antigen (e.g., binding site #1), connected, optionally, via a linker to, the first immunoglobulin constant region (e.g., the CH2 connected to the CH3 region) (e.g., a first Fc region);

(b) a second binding specificity (e.g., a second binding site), which is chosen from a cytokine molecule, or an immune cell engager, connected, optionally, via a linker to, the second immunoglobulin constant region (e.g., the CH2 connected to the CH3 region) (e.g., the second Fc region); and (c) the third polypeptide has the following configuration from N-to-C: a second portion of the first antigen domain, e.g., a first VL-CL of the Fab, that binds to, e.g., a tumor or stromal antigen (e.g., the same tumor or stromal antigen bound by the first VH-CH1, e.g., binding site #1), wherein either the first or the second polypeptide further includes a third binding specificity, which is connected, optionally, via a linker to, the first or second immunoglobulin constant region (e.g., the CH2 connected to the CH3 region) (e.g., the first or second Fc region). In one embodiment, the third binding specificity is connected, optionally, via a linker to, the first immunoglobulin constant region (e.g., the CH2 connected to the CH3 region) (e.g., the first Fc region). In another embodiment, the third binding specificity is connected, optionally, via a linker to, the second immunoglobulin constant region (e.g., the CH2 connected to the CH3 region) (e.g., the second Fc region). Examples of these configurations are depicted in FIGS. 9A-9B.

In one embodiment, the trispecific molecule includes a Fab corresponding to the first binding specificity (binding site #1) connected, optionally via a linker, to the first Fc region; and the second binding specificity (e.g., binding site #2) connected, optionally via a linker, to the second Fc region, which further includes the third binding specificity (e.g., binding site #3) (e.g., as depicted in FIG. 9A). In other embodiments, the trispecific molecule includes a Fab corresponding to the first binding specificity (binding site #1) connected, optionally via a linker, to the first Fc region, which further includes the third binding specificity (e.g., binding site #3); and the second binding specificity (e.g., binding site #2) connected, optionally via a linker, to the second Fc region (e.g., as depicted in FIG. 9B).

In some embodiments, (a) the first binding specificity (e.g., binding site #1 in FIGS. 9A-9B) is a tumor targeting moiety, e.g., binds to a cancer antigen, e.g., a tumor or stromal antigen; (b) the second binding specificity (e.g., binding site #2 in FIGS. 9A-9B) is chosen from a cytokine molecule, or an immune cell engager, e.g., chosen from a receptor, a ligand molecule or an antibody molecule (e.g., a scFv) that binds to an immune cell antigen; and (c) the third binding specificity (e.g., binding site #3 in FIGS. 9A-9B) is chosen from a cytokine molecule, or an immune cell engager, e.g., chosen from a receptor, a ligand molecule or an antibody molecule (e.g., a scFv) that binds to an immune cell antigen. In embodiments where the antibody molecule is a scFV, the scFv may be connected to the C-terminus of the first polypeptide in a VH-VL or a VL-VH configuration.

In embodiments, the first immunoglobulin constant region (e.g., the first CH2-CH3 region) includes a protuberance or knob, e.g., as described herein.

In embodiments, the second immunoglobulin constant region (e.g., the second CH2-CH3 region) includes a cavity or hole. In embodiments, the first and second immunoglobulin constant region promote heterodimerization of the bispecific molecule.

In another embodiment, the multispecific molecule is a tetraspecific molecule that includes two or at least three non-contiguous first and second polypeptides, wherein:

(i) the first polypeptide includes from N- to C-orientation a first binding specificity, e.g., a first antibody molecule, connected, optionally via a linker, to a first immunoglobulin constant region (e.g., a CH2 connected to a CH3 region) (e.g., a first Fc region);

(ii) the second polypeptide includes from N- to C-orientation a second binding specificity connected, optionally via a linker, to a second immunoglobulin constant region (e.g., a CH2 connected to a CH3 region) (e.g., a second Fc region); and (optionally) (iii) a third polypeptide comprising a portion of the first antibody molecule or a second antibody molecule, wherein the first or the second polypeptide further includes a third and a fourth binding specificities.

In embodiments, the first and second polypeptides, include, respectively, a first, a second, a third and a fourth binding specificities (e.g., sites), which are independently chosen from an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, the first, second, third and fourth binding specificities (binding sites 1-4, respectively) are each independently chosen from a tumor targeting moiety, a cytokine molecule, an NK cell engager, a T cell engager, a B cell engager, a dendritic cell engager, or a macrophage cell engager, e.g., as described herein.

In some embodiments, the first polypeptide has the following configuration from N-to-C:

(a) a first portion of a first antigen domain, e.g., a first VH-CH1 of a Fab molecule, that binds to, e.g., a tumor or stromal antigen (e.g., binding site #1), connected, optionally, via a linker to, the first immunoglobulin constant region (e.g., the CH2 connected to the CH3 region) (e.g., a first Fc region);

(b) a second binding specificity (e.g., a second binding site), which is chosen from a cytokine molecule, or an immune cell engager, connected, optionally, via a linker to, the second immunoglobulin constant region (e.g., the CH2 connected to the CH3 region) (e.g., the second Fc region); and (c) the third polypeptide has the following configuration from N-to-C: a second portion of the first antigen domain, e.g., a first VL-CL of the Fab, that binds to, e.g., a tumor or stromal antigen (e.g., the same tumor or stromal antigen bound by the first VH-CH1, e.g., binding site #1), wherein the first and the second polypeptide further includes a third and a fourth binding specificity, respectively, each of which is connected, optionally, via a linker to, the first and second immunoglobulin constant region (e.g., the CH2 connected to the CH3 region) (e.g., the first and second Fc region). In one embodiment, the third binding specificity is connected, optionally, via a linker to, the second immunoglobulin constant region (e.g., the CH2 connected to the CH3 region) (e.g., the second Fc region); and the fourth binding specificity is connected, optionally, via a linker to, the first immunoglobulin constant region (e.g., the CH2 connected to the CH3 region) (e.g., the firstFc region). Examples of these configurations are depicted in FIGS. 10A-10C.

In one embodiment, the tetraspecific molecule includes a Fab corresponding to the first binding specificity (binding site #1) connected, optionally via a linker, to the first Fc region, which further includes a fourth binding specificity (e.g., binding site #4); and the second binding specificity (e.g., binding site #2) connected, optionally via a linker, to the second Fc region, which further includes the third binding specificity (e.g., binding site #3) (e.g., as depicted in FIG. 10A). In other embodiments, the tetraspecific molecule includes a Fab corresponding to the first binding specificity (binding site #1) connected, optionally via a linker, to the first Fc region, which further includes a third binding specificity (e.g., binding site #3); and the second binding specificity (e.g., binding site #2) connected, optionally via a linker, to the second Fc region, which further includes the fourth binding specificity (e.g., binding site #4).

In some embodiments, (a) the first binding specificity (e.g., binding site #1 in FIGS. 10A-10C) is a tumor targeting moiety, e.g., binds to a cancer antigen, e.g., a tumor, stromal or hematological antigen; and the second, third and fourth binding specificities (e.g., binding sites #2-4 in FIG. 10A) are each independently chosen from a cytokine molecule, or an immune cell engager, e.g., chosen from a receptor, a ligand molecule or an antibody molecule (e.g., a scFv) that binds to an immune cell antigen. In embodiments where the antibody molecule is a scFV, the scFv may be connected to the C-terminus of the first polypeptide in a VH-VL or a VL-VH configuration.

In one embodiment, (a) the first binding specificity (e.g., binding site #1 in FIG. 10B) is a tumor targeting moiety, e.g., binds to a cancer antigen, e.g., a tumor, stromal or hematological antigen; (b) the second binding specificity (e.g., binding site #2 in FIG. 10B) is an immune cell engager (e.g., an NK cell engager) chosen from a receptor, a ligand molecule or an antibody molecule (e.g., a scFv) that binds to an immune cell antigen; (c) the third binding specificity (e.g., binding site #3 in FIG. 10B) is a cytokine molecule or an immune cell engager; and (d) the fourth binding specificity (e.g., binding site #4 in FIG. 10B) is an immune cell engager (e.g., a macrophage or a dendritic cell engager) chosen from a ligand molecule or an antibody molecule (e.g., a scFv) that binds to an immune cell antigen. In embodiments where the antibody molecule is a scFV, the scFv may be connected to the C-terminus of the first polypeptide in a VH-VL or a VL-VH configuration.

In one embodiment, (a) the first binding specificity (e.g., binding site #1 in FIG. 10C) is a tumor targeting moiety, e.g., binds to a cancer antigen, e.g., a tumor or stromal antigen; (b) the second binding specificity (e.g., binding site #2 in FIG. 10C) is an immune cell engager (e.g., an NK cell engager) chosen from a receptor, a ligand molecule or an antibody molecule (e.g., a scFv) that binds to an immune cell antigen; (c) the third binding specificity (e.g., binding site #3 in FIG. 10C) is an immune cell engager (e.g., a macrophage or a dendritic cell engager) chosen from a ligand molecule or an antibody molecule (e.g., a scFv) that binds to an immune cell antigen; and (d) the fourth binding specificity (e.g., binding site #4 in FIG. 10C) is an immune cell engager (e.g., a macrophage or a dendritic cell engager) chosen from a ligand molecule or an antibody molecule (e.g., a scFv) that binds to an immune cell antigen. In embodiments where the antibody molecule is a scFV, the scFv may be connected to the C-terminus of the first polypeptide in a VH-VL or a VL-VH configuration.

In embodiments, the first immunoglobulin constant region (e.g., the first CH2-CH3 region) includes a protuberance or knob, e.g., as described herein.

In embodiments, the second immunoglobulin constant region (e.g., the second CH2-CH3 region) includes a cavity or hole. In embodiments, the first and second immunoglobulin constant region promote heterodimerization of the bispecific molecule.

Tumor-Targeting Moieties

In one embodiment, the tumor-targeting moiety includes an antibody molecule (e.g., Fab or scFv) that binds to mesothelin. In some embodiments, the antibody molecule to mesothelin comprises one, two, three CDRs from the heavy chain variable domain sequence of: QVQLQQSGPELEKPGASVKISCKASGYSFTGYTMNWVKQSHGKSLEWIGLITPYNGASS YNQKFRGKATLTVDKSSSTAYMDLLSLTSEDSAVYFCARGGYDGRGFDYWGQGTTVT VSS (SEQ ID NO: 1), or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 1.

In some embodiments, the antibody molecule to mesothelin comprises one, two, three CDRs selected from GYSFTGYTMN (SEQ ID NO: 2); LITPYNGASSYNQKFRG (SEQ ID NO: 3); and GGYDGRGFDY (SEQ ID NO: 4), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin consists of three CDRs, wherein CDR1 comprises GYSFTGYTMN (SEQ ID NO: 2); CDR2 comprises: LITPYNGASSYNQKFRG (SEQ ID NO: 3); and CDR3 comprises GGYDGRGFDY (SEQ ID NO: 4), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin consists of three CDRs, wherein CDR1 consists of GYSFTGYTMN (SEQ ID NO: 2); CDR2 consists of LITPYNGASSYNQKFRG (SEQ ID NO: 3); and CDR3 consists of GGYDGRGFDY (SEQ ID NO: 4), or a closely related CDR, e.g., CDRs which have at least one amino acid alteration, but not more than two, three or four alterations (e.g., substitutions, deletions, or insertions, e.g., conservative substitutions).

In embodiments, the antibody molecule to mesothelin includes the heavy chain variable domain sequence of: QVQLQQSGPELEKPGASVKISCKASGYSFTGYTM NWVKQSHGKSLEWIGLITPYNGASS YNQKFRGKAT LTVDKSSSTAYMDLLSLTSEDSAVYFCARGGYDGR GFDYWGQGTTVT VSS (SEQ ID NO: 1), or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 1. In embodiments, the antibody molecule to mesothelin is a Fab and further comprises a heavy chain constant region (CH1) having the amino acid sequence:

```
                                         (SEQ ID NO: 5)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHT,
``` or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 5. In some embodiments, the antibody molecule further comprises a signal peptide, e.g., a signal peptide comprising the amino acid sequence:

```
                          (SEQ ID NO: 6)
           MEFGLSWVFLVALFRGVQC.
```

Alternatively, or in combination with the heavy chain to mesothelin disclosed herein, the antibody molecule to mesothelin comprises one, two, three CDRs from the light chain variable domain sequence of: DIELTQSPAIMSASPG EKVTMTCSASSSVSYMHWYQQKSGTSPKRWIYDTS KLASGVPG RFSGSGSGNSYSLTISSVEAEDDATYYC QQWSGYPLTFGAGTKLEIK (SEQ ID NO: 7), or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 7.

In some embodiments, the antibody molecule to mesothelin comprises one, two, three CDRs from SASSSVSYMH (SEQ ID NO: 8); DTSKLAS (SEQ ID NO: 9); and QQWSGYPLT (SEQ ID NO: 10), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin consists of three CDRs, wherein CDR1 comprises SASSSVSYMH (SEQ ID NO: 8); CDR2 comprises: DTSKLAS (SEQ ID NO: 9); and CDR3 comprises QQWSGYPLT (SEQ ID NO: 10), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin consists of three CDRs, wherein CDR1 consists of SASSSVSYMH (SEQ ID NO: 8); CDR2 consists of DTSKLAS (SEQ ID NO: 9); and CDR3 consists of QQWSGYPLT (SEQ ID NO: 10), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin comprises the light chain variable domain sequence of: DIELTQSPAIMSASPGEKVTMTCSASSSVS YMH WYQQKSGTSPKRWIYDTSKLASGVPG RFSGSGSGN-SYSLTISSVEAEDDATYYCQQWSGYPLTFGAGT KLEIK (SEQ ID NO: 7), or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7.

In some embodiments, the antibody molecule to mesothelin is a Fab and further comprises a light chain constant region (CL1) having the amino acid sequence:

```
                                         (SEQ ID NO: 11)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC,
``` or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 11. In embodiments, the antibody molecule further comprises a signal peptide, e.g., a signal peptide comprising the amino acid sequence: MKYLLPT AAAGLLLLAAQPAMA (SEQ ID NO: 12).

In other embodiments, the multispecific molecule, e.g., the tumor-targeting moiety, binds to a stromal antigen. In embodiments, the stromal antigen is chosen from one or more of: fibroblast activating protease (FAP), TGF-beta, hyaluronic acid, collagen, e.g., collagen IV, tenascin C, or tenascin W.

In one embodiment, the tumor-targeting moiety includes an antibody molecule (e.g., Fab or scFv) that binds to FAP, e.g., human FAP. In some embodiments, the antibody molecule to FAP comprises one, two, three CDRs from the heavy chain variable domain sequence depicted in underline in FIG. 12C (SEQ ID NO: 13), or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 13. In some embodiments, the antibody molecule to FAP includes the heavy chain variable domain sequence depicted in underline in FIG. 12C (SEQ ID NO: 13), or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 13.

In embodiments, the antibody molecule to FAP is a Fab and further comprises a heavy chain constant region (CH1) having the amino acid sequence: ASTKGPSVFPLA PSSKSTSGGTAALGCLVKDYFPEPVTVSWNSGALT-SGVHTFPAVLQSS GLYSLSSVVTVPSSSLGTQTYI CNVNHKPSNTKVDKRVEPKSC (SEQ ID NO: 14), or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 14. In embodiments, the antibody molecule further comprises a signal peptide, e.g., a signal peptide comprising the amino acid sequence: MEFGLSWVFLVAL-FRGVQCEV (SEQ ID NO: 15).

Alternatively, or in combination with the heavy chain to FAP disclosed herein, the antibody molecule to FAP comprises one, two, three CDRs from the light chain variable domain sequence depicted in underline in FIG. 12D (SEQ ID NO: 16), or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 16. In some embodiments, the antibody molecule to FAP includes the light chain variable domain sequence depicted in underline in FIG. 12D (SEQ ID NO: 16), or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 16.

In embodiments, the antibody molecule to FAP is a Fab and further comprises a light chain constant region (CL1) having the amino acid sequence:

```
                                         (SEQ ID NO: 11)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC,
``` or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 11. In some embodiments, the antibody molecule further comprises a signal peptide, e.g., a signal peptide comprising the amino acid sequence:

```
                                         (SEQ ID NO: 12)
         MKYLLPTAAAGLLLLAAQPAMA.
```

Immune Cell Engagers

In one embodiment, the NK cell engager is a ligand of NKp30 is a B7-6, e.g., comprises the amino acid sequence of: DLKVEMMAGGTQITPLNDNVTIFCNIFYSQPL NITSMGITWFWKSLTFDKEVKVFEFFGD HQEAFRP-GAIVSPWRLKSGDASLRLPGIQLEEAGEYRCEVVV TPLKAQGTVQLEVVASP ASRLLLDQVGMKENEDKY MCESSGFYPEAINITWEKQTQKFPHPIEISEDVITGP-TIKNM DGTFNVTSCLKLNSSQEDPGTVYQCVVRH ASL HTPLRSNFTLTAARHSLSETEKTDNFS (SEQ ID NO: 24), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 24.

In other embodiments, the NK cell engager is a ligand of NKG2D chosen from MICA, MICB, or ULBP1, e.g., wherein:

(i) MICA comprises the amino acid sequence: EPHSL-RYNLTVLSWDGSVQSGFLTEVHLDGQPFLRCDR QK CRAKPQGGWAEDVLGNK TWDRETRDLTGNGKDL RMTLAHIKDQKEGLHSLQEIRVCEIHEDNSTRSSQ H FYYDGEL FLSQNLETKEWTMPQSSRAQTLAMN VR NFLKEDAMKTKTHYHAMHADCLQELRRYLK SGVV LRRTVPPMVNVTRSEASEGNITVTCRASGFYPWNI TLSWRQDGVSLSHDTQQWG DVLPDGNGTYQTW-VATRICQGEEQRFTCYMEHSGNHSTHPVPSGKV LVLQSHW (SEQ ID NO: 25), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 25;

(ii) MICB comprises the amino acid sequence: AEPHSL-RYNLMVLSQDESVQSGFLAEGHLDGQPFLRYDRQ KRRAKPQGQWAEDVLGA KTWDTETEDLTENGQDL RRTLTHIKDQKGGLHSLQEIRVCEIHEDSSTRGSRH FYYDGEL FLSQNLETQESTVPQSSRAQTLAMNVT NFWKEDAMKTKTHYRAMQADCLQKLQRYLK SGV AIRRTVPPMVNVTCSEVSEGNITVTCRASSFYPRNI-TLTWRQDGVSLSHNTQQWGD VLPDGNGTYQTWVA TRIRQGEEQRFTCYMEHSGNHGTHPVPSGKVLV LQSQRTD (SEQ ID NO: 26), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 26; or (iii) ULBP1 comprises the amino acid sequence: GW VDTHCLCYDFIITPKSRPEPQWCEVQGLVDERPFLH YDCVNHKAKAFASLGKKVNV TKTWEEQTETLR DVVDFLKGQLLDIQVENLIPIEPLTLQARMSCEHEA HGHGRGSWQFL FNGQKFLLFDSNNRKWTALHPG AKKMTEKWEKNRDVTMFFQKISLGDCKMWLEEFL MYWEQMLDPTKPPSLAPG (SEQ ID NO: 27), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 27.

In other embodiments, the NK cell engager is a ligand of DNAM1 chosen from NECTIN2 or NECL5, e.g., wherein:

(i) NECTIN2 comprises the amino acid sequence: QDVRVQVLPEVRGQLGGTVELPCHLLPPVPGLYIS-LVTWQRPDAPANHQNVAAFHPKM GPSFPSPKPG-SERLSFVSAKQSTGQDTEAELQDATLALHGLTVEDE-GNYTCEFATFPKGS VRGMTWLRVIAKPKNQAEA QK-VTFSQDPTTVALCISKEGRPPARISWLSSLDWEAKE TQ VSGTLAGTVTVTSRFTLVPSGRADGVTVTCKVE-HESFEEPALIPVTLSVRYPPEVSISGYD DNWYLGRT-DATLSCDVRSNPEPTGYDWSTTSGTFPTSAVAQG SQLVIHAVDSLFNTTFV CTVTNAVGMGRAEQVIFVR ETPNTAGAGATGG (SEQ ID NO: 28), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 28; or (ii) NECL5 comprises the amino acid sequence: WPPPGTGDVVVQAPTQVPGFLGDSVTLPCYLQVPN-MEVTHVSQLTWARHGESGSMAV FHQTQGPSYSES KRLEFVAARLGAELRNASLRMFGLRVEDEGNYTCL FVTFPQGSRSVD IWLRVLAKPQNTAEVQKVQLTGE PV PMARCVSTGGRPPAQITWHSDLGGMPNTSQVPG FLSGTVTVTSLWILVPSSQVDGKNVTCKVEHESFE KPQLLTVNLTVYYPPEVSISGYDNN WYLGQNE ATLTCDARSNPEPTGYNWSTTMGPLPPFAVAQGAQL-LIRPVDKPINTTLICN VTNALGARQAELTVQVKEG-PPSEHSGISRN (SEQ ID NO: 29), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 29.

In yet other embodiments, the NK cell engager is a ligand of DAP10, which is an adapter for NKG2D (see e.g., Proc Natl Acad Sci USA. 2005 May 24; 102(21): 7641-7646; and Blood, 15 Sep. 2011 Volume 118, Number 11, the full contents of each of which is incorporated by reference herein).

In other embodiments, the NK cell engager is a ligand of CD16, which is a CD16a/b ligand, e.g., a CD16a/b ligand further comprising an antibody Fc region (see e.g., Front Immunol. 2013; 4: 76 discusses how antibodies use the Fc to trigger NK cells through CD16, the full contents of which are incorporated herein).

In other embodiments, the NK cell engager is a ligand of CRTAM, which is NECL2, e.g., wherein NECL2 comprises the amino acid sequence: QNLFTKDVTVIEGEVATIS CQVNKSDDSVIQLLNPNRQTIYFRDFRPLKDSRFQ LLNFSSS ELKVSLTNVSISDEGRYFCQLYTDPPQESY TTITVLVPPRNLMIDIQKDTAVEGEEIEVNC TAMASK PATTIRWFKGNTELKGKSEVEEWSDMYTVTSQL ML KVHKEDDGVPVICQVE HPAVTGNLQTQRYLEVQY KPQVHIQMTYPLQGLTREGDALELTCEAIGKPQP VMVTWV RVDDEMPQHAVLSGPNLFINNLNKTDNG-TYRCEASNIVGKAHSDYMLYVYDPPTTIPPP TTTT TTTTTTTTTILTIITDSRAGEEGSIRAVDH (SEQ ID NO: 30), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 30.

In other embodiments, the NK cell engager is a ligand of CD27, which is CD70, e.g., wherein CD70 comprises the amino acid sequence: QRFAQAQQQLPLESLGWDVAEL-QLNHTGPQQDPRLYWQGGPALGRSFLHGPELDKGQ LRIHRDGIYMVHIQVTLAICSSTTASRHHPTTLAVG-ICSPASRSISLLRLSFHQGCTIASQR LTPLARGDTLCT NLT GTLLPSRNTDETFFGVQWVRP (SEQ ID NO: 31), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 31.

In other embodiments, the NK cell engager is a ligand of PSGL1, which is L-selectin (CD62L), e.g., wherein L-selectin comprises the amino acid sequence: WTYHYSEKPMNWQRARRFCRDNYTDLVAIQNKAEIEYLEK TLPFSRSYYWIGIRKIGGI WTWVGTNKSLTEEAENW GDGEPNNKKNKEDCVEIYIKRNKDAGKWNDDAC HKLKAA LCYTASCQPWSCSGHGECVEIINNYTCNC DVGYYGPQCQFVIQCEPLEAPELGTMDCTH PLGNF SFSSQCAFSCSEGTNLTGIEETTCGPFGNWSSPEPTC QVIQCEPLSAPDLGIMNCSH PLASFSFTSACTFICS EG TELIGKKKTICESSGIWSNPSPICQKLDKSFSMIKEGDYN (SEQ ID NO: 32), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 32.

In other embodiments, the NK cell engager is a ligand of CD96, which is NECL5, e.g., wherein NECL5 comprises the amino acid sequence: WPPPGTGDVVVQ APTQVPGFLGDSVTLPCYLQVPNMEVTHVSQLTWARHGESGSMAV FHQTQGPSYSESKRLEFVAARLGAELRNASLRMFGLRVEDEGNYTCLFVTFPQ GSRSVD IWLRVLAKPQNTAEVQKVQLTGEPVPMARCVSTGGRPPAQITWHSDLGGMPNTSQVPG FLS GTVTVTSLWILVPSSQVDGKNVTCKVEHESFEKPQ LLTVNLTVYYPPEVSISGYDNN WYLGQNEATLTCDA RSNPEPTGYNWSTTMGPLPPFAVAQGAQLLIRPVDK-PINTTLICN VTNALGARQAELTVQVKEGPPSEHS-GISRN (SEQ ID NO: 29), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 29.

In other embodiments, the NK cell engager is a ligand of CD100 (SEMA4D), which is CD72, e.g., wherein CD72 comprises the amino acid sequence: RYLQVSQQL QQTNRVLEVTNSSLRQQLRLKITQLGQSAEDLQGSRRELAQSQEALQVEQ RAHQAAEGQLQACQADRQ KTKETLQSEEQQRRALEQKLSNMENRLKPFFTCGS ADTCC PSGWIMHQKSCFYISLTSKNWQESQKQCETL SSKLATFSEIYPQSHSYYFLNSLLPNGGS GNSYWTGL SSNKDWKLTDDTQRTRTYAQSSKCNKVHKTWSWW TLES ESCRSSLPYICE MTAFRFPD (SEQ ID NO: 33), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 33.

In other embodiments, the NK cell engager is a ligand of NKp80, which is CLEC2B (AICL), e.g., wherein CLEC2B (AICL) comprises the amino acid sequence: KLTRDS QSLCPYDWIGFQNKCYYFSKEEGDWNSSKYNC-STQHADLTIIDNIEEMNFLRR YKCSSDHWIGLK-MAKNRTGQWVDGATFTKSFGMRGSEGCAYLSDD-GAATARCYTER KWICRKRIH (SEQ ID NO: 34), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 34.

In other embodiments, the NK cell engager is a ligand of CD244, which is CD48, e.g., wherein CD48 comprises the amino acid sequence: QGHLVHMTVVSGSNVTLNISESL-PENYKQLTWFYTFDQKIVEWDSRKSKYFESKFKGR VRLDPQSGALYISKVQKEDNSTYIMRVLKKTGNEQE WKIKLQVLDPVPKPVIKIEKIEDM DDNCYLKLSCVI PGESVNYTWYGDKRPFPKELQNSVLETTLMPHNYS RCYTCQVSNSVS SKNGTVCLSPPCTLARS (SEQ ID NO: 35), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 35.

In other embodiments, the dendritic cell engager is chosen from one or more of a CD2 agonist, an OX40 antibody, an OX40L, 41BB agonist, a Toll-like receptor agonist or a fragment thereof (e.g., a TLR4, e.g., a constitutively active TLR4 (caTLR4)), CD47 agonist, or a STING agonist.

In one embodiment, the OX40L comprises the amino acid sequence: QVSHRYPRIQSIKVQFTEYKKEKGFILTSQK E DEIMKVQNNSVIINCDGFYLISLKGYFSQ EVNISL HYQKDEEPLFQLKKVRSVNSLMVASLTYKDKVYLN VTTDNTSLDDFHVNGGE LILIHQNPGEFCVL (SEQ ID NO: 36), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 36.

In another embodiment, the CD40L comprises the amino acid sequence: MQKGDQNPQIAAHVISEASSKTTSV LQWAEKGYYTMSNNLVTLENGKQLTVKRQGLY YIY AQVTFCSNREASSQAPFIASLCLKSPGRFERILLRA ANTHSSAKPCGQQSIHLGGVFE LQPGASVFVNVT DPSQVSHGTGFTSFGLLKL (SEQ ID NO: 37), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 37.

In yet other embodiments, the STING agonist comprises a cyclic dinucleotide, e.g., a cyclic di-GMP (cdGMP), a cyclic di-AMP (cdAMP), or a combination thereof, optionally with 2',5' or 3',5' phosphate linkages.

In one embodiment, the immune cell engager includes 41BB ligand, e.g., comprising the amino acid sequence: ACPWAVSGARASPGSAASPRLREGPELSPDDPAGLL DLRQGMFAQLVAQNVLLIDGPLS WYSDPGLAGV SLTGGLSYKEDTKELVVAKAGVYYVFFQLELRRVV AGEGSGSVSLALH LQPLRSAAGAAALALTVDLPPAS-SEARNSAFGFQGRLLHLSAGQRLGVHLHTEARARH AWQLTQGATVLGLFRVTPEIPAGLPSPRSE (SEQ ID NO: 38), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 38.

Cytokine Molecules

In some embodiments, the multispecific molecules disclosed herein include a cytokine molecule. In embodiments, the cytokine molecule includes a full length, a fragment or a variant of a cytokine; a cytokine receptor domain, e.g., a cytokine receptor dimerizing domain; or an agonist of a cytokine receptor, e.g., an antibody molecule (e.g., an agonistic antibody) to a cytokine receptor. In some embodiments, the cytokine is a single chain. In some embodiments, the cytokine comprises 2 or 2 or more polypeptide chains. An exemplary multichain cytokine molecule is IL12.

In some embodiments the cytokine molecule is chosen from interleukin-2 (IL-2), interleukin-12 (IL-12), interleukin-15 (IL-15), interleukin-18 (IL-18), interleukin-21 (IL-21), interleukin-7 (IL-7), or interferon gamma, or a fragment or variant thereof, or a combination of any of the aforesaid cytokines. The cytokine molecule can be a monomer or a dimer. In embodiments, the cytokine molecule can further include a cytokine receptor dimerizing domain.

In other embodiments, the cytokine molecule is an agonist of a cytokine receptor, e.g., an antibody molecule (e.g., an agonistic antibody) to a cytokine receptor chosen from an IL-15Ra or IL-21R.

In one embodiment, the cytokine molecule is IL-15, e.g., human IL-15 (e.g., comprising the amino acid sequence: NWVNVISDLKKIEDLIQSMHIDATLYTESDVHPSCK VTAMKCFLLELQVISLESGDASIH DTVENLIILAN NSLSSNGNVTESGCKECEELEEKNIKEFLQSFVH IVQMFINTS (SEQ ID NO: 17), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 17.

In some embodiments, the cytokine molecule comprises a receptor dimerizing domain, e.g., an IL15Ralpha dimerizing domain. In one embodiment, the IL15Ralpha dimerizing domain comprises the amino acid sequence: MAPR-RARGCRTLGLPALLLLLLLRPPATRGITCPPPMSVE-HADIWVKSYSLYSRERYICN SGFKRKAGTSSLTECVL (SEQ ID NO: 40), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 40. In some embodiments, the cytokine molecule (e.g., IL-15) and the receptor dimerizing domain (e.g., an IL15Ralpha dimerizing domain) of the multispecific molecule are covalently linked, e.g., via a linker (e.g., a Gly-Ser linker, e.g., a linker comprising the amino acid sequence SGGSGGGGSGGGSGGGGSLQ (SEQ ID NO: 19). In other embodiments, the cytokine molecule (e.g., IL-15) and the receptor dimerizing domain (e.g., an IL15Ralpha dimerizing domain) of the multispecific molecule are not covalently linked, e.g., are non-covalently associated.

In other embodiments, the cytokine molecule is IL-2, e.g., human IL-2 (e.g., comprising the amino acid sequence: APTSSSTKKTQLQLEHLLLDLQMILNGINNYKNPKL-TRMLTFKFYMPKKATELKHLQCL EEELKPLEEVLN-LAQSKNFHLRPRDLISNINVIVLELKGSETTFMCEYA-DETATIVEFLNR WITFCQSIISTLT (SEQ ID NO: 20), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 20).

In other embodiments, the cytokine molecule is IL-18, e.g., human IL-18 (e.g., comprising the amino acid sequence: YFGKLESKLSVIRNLNDQVLFIDQGNR-PLFEDMTDSDCRDNAPRTIFIISMYKDSQPRGM AVTISVKCEKISTLSCENKIISFKEMNPPDNIKDTKS-DIIFFQRSVPGHDNKMQFESSSY EGYFLACEKER-DLFKLILKKEDELGDRSIMFTVQNED (SEQ ID NO: 41), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 41).

In other embodiments, the cytokine molecule is IL-21, e.g., human IL-21 (e.g., comprising the amino acid sequence: QGQDRHMIRMRQLIDIVDQLKNYVN DLVPEFLPAPEDVETNCEWSAFSCFQKAQLKSA NTGNNERIINVSIKKLKRKPPSTNAGRRQKHRLTCP-SCDSYEKKPPKEFLERFKSLLQKMI HQHLSSRT HGSEDS (SEQ ID NO: 22), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 22).

In yet other embodiments, the cytokine molecule is interferon gamma, e.g., human interferon gamma (e.g., comprising the amino acid sequence: QDPYVKEAENLKKYFNAG HSDVADNGTLFLGILKNWKEESDRKIMQSQIVSFYF KLFK NFKDDQSIQKSVETIKEDMNVKFFNSNKKKRD DFEKLTNYSVTDLNVQRKAIHELIQVM AELSPAA KTGKRKRSQMLFRG (SEQ ID NO: 23), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 23).

Linkers

The multispecific molecule disclosed herein can further include a linker, e.g., a linker between one or more of: the targeting moiety and the cytokine molecule, the targeting moiety and the immune cell engager, the cytokine molecule and the immune cell engager, the cytokine molecule and the immunoglobulin chain constant region (e.g., the Fc region), the targeting moiety and the immunoglobulin chain constant region, or the immune cell engager and the immunoglobulin chain constant region. In embodiments, the linker chosen from: a cleavable linker, a non-cleavable linker, a peptide linker, a flexible linker, a rigid linker, a helical linker, or a non-helical linker, or a combination thereof.

In one embodiment, the multispecific molecule can include one, two, three or four linkers, e.g., a peptide linker. In one embodiment, the peptide linker includes Gly and Ser. Exemplary peptide linkers are depicted in the figures disclosed herein (e.g., FIGS. 11B-11C, 12B, 13B-C, 14A-B), e.g., a peptide linker chosen from: GGGGS (SEQ ID NO: 42); GGGGSGGGGS (SEQ ID NO: 43); GGGGSGGGGSGGGGS (SEQ ID NO: 44); or DVPSGPGGGGSGGGGS (SEQ ID NO: 45).

Exemplary Multispecific Configurations:

In some embodiments, any of the multispecific molecules disclosed herein can include:

(I) a tumor-targeting moiety that comprises:

(a) an antibody molecule against a solid tumor antigen chosen from: Mesothelin, GD2, PMSA, CEA, Ron Kinase, or c-Met; and/or (b) an antibody molecule against a stromal antigen is chosen from: FAP, hyaluronic acid, collagen IV, tenascin C, or tenascin W; or (c) a combination of the antibody molecule against the solid tumor antigen and the antibody molecule against the stromal antigen; and (II) one or both of:

(a) an immune cell engager chosen from one, two, three, or all of a CD40L or a CD70 ligand; an antibody molecule that binds to CD40 or CD70; an antibody molecule to OX40; an OX40L; B7H6, 41BB ligand (41BBL), or a STING agonist, or a combination thereof; or (b) the cytokine molecule chosen from IL-2, IL-12, IL-15, IL-18, IL-7, or IL-21, fragment or variant thereof, or an antibody molecule to a cytokine receptor (e.g., an antibody (e.g., an agonistic antibody) to IL-15Ra, or IL-21R), or a combination of any of the aforesaid.

In some embodiments, the tumor targeting moiety is an antibody molecule that binds to mesothelin, PSCA or FAP. In some embodiments, the immune cell engager is an antibody molecule that binds to NKp30 or CD16. In other embodiments, the immune cell engager is chosen from a CD40 ligand (CD40L), B7H6 or 41BB ligand (41BBL). In other embodiments, the cytokine molecule is chosen from IL-15 or IL-21, or an agonist of a cytokine receptor, e.g., an antibody molecule (e.g., an agonistic antibody) to an IL-15Ra or IL-21R.

In some embodiments, the bispecific molecule is chosen from: (i) an antibody molecule to mesothelin and an antibody molecule to NKp30; (ii) an antibody molecule to mesothelin and an antibody molecule to CD16; (iii) an antibody molecule to PSCA and an antibody molecule to NKp30; (iv) an antibody molecule to PSCA and an antibody molecule to CD16; (v) an antibody molecule to FAP and an antibody molecule to NKp30; (vi) an antibody molecule to FAP and an antibody molecule to CD16; (vii) an antibody molecule to FAP and an IL-15 molecule; (viii) an antibody molecule to FAP and an antibody molecule (e.g., an agonistic antibody) to an IL-15Ra; (ix) an antibody molecule to FAP and an antibody molecule (e.g., an agonistic antibody) to an IL-21; or (x) an antibody molecule to FAP and an antibody molecule (e.g., an agonistic antibody) to an IL-21R.

In other embodiments, the trispecific molecule includes a tumor targeting moiety chosen from an antibody molecule to mesothelin, antibody molecule to PSCA or an antibody molecule to FAP; an immune cell engager, e.g., an NK cell engager, chosen from an antibody molecule to NKp30 or an antibody molecule to CD16; or a macrophage cell engager chosen from a CD40L, OX40L, or an antibody molecule to CD40 or an antibody molecule to OX40; and a cytokine molecule chosen from an IL-15, IL-21, an antibody to IL-15Ra or an antibody to IL-21R. Exemplary combinations include but are not limited to: (i) an antibody molecule to mesothelin; a CD40L polypeptide; and an IL-15 molecule; (ii) an antibody molecule to mesothelin; a CD40L polypeptide; and an IL-15 molecule; (iii) an antibody molecule to mesothelin; an antibody molecule that binds to NKp30; and an IL-15 molecule; (iv) an antibody molecule to mesothelin; an antibody molecule that binds to CD16; and an IL-15 molecule; (v) an antibody molecule to PSCA; an antibody molecule that binds to NKp30; and an IL-15 molecule; (vi) an antibody molecule to PSCA; an antibody molecule that binds to CD16; and an IL-15 molecule; (vii) an antibody molecule to PSCA; an antibody molecule that binds to CD16; and an IL-21 molecule; or (viii) an antibody molecule to mesothelin; an antibody molecule that binds to CD16; and an IL-21 molecule.

In other embodiments, the tetraspecific molecule includes (i) an antibody molecule to mesothelin, e.g., human mesothelin; a CD40L polypeptide; an IL-15 molecule; and B7H6; (ii) an antibody molecule to FAP, e.g., human mesothelin; a CD40L polypeptide; an IL-15 molecule; and B7H6; or (iii) an antibody molecule to mesothelin, e.g., human mesothelin; a CD40L polypeptide; an IL-21 molecule; and 41BBL.

In some embodiments, the multispecific molecule includes an antibody molecule to mesothelin, e.g., human mesothelin; a CD40L polypeptide; and an IL-15 molecule. In one embodiment, the antibody molecule includes a Fab against mesothelin having a light and a heavy chain. In embodiments, the heavy chain of the Fab against mesothelin further comprises the IL-15 molecule, e.g., human IL-15 molecule, optionally, wherein the Fab and the IL-15 molecule are linked, e.g., via a linker comprising Gly and Ser. In some embodiments, the multispecific molecule has the following configuration: Heavy chain of the Fab (e.g., VH-CH1) against mesothelin to IL-15, from N- to C-terminus, optionally, comprising a Gly-Ser linker between the Fab and the IL-15. In some embodiments, the multispecific molecule includes the amino acid sequence: QVQLQQSGPELEKPGASVKISCKASGYSFTGYTMNWVKQSHGKS LEWIGLITPYNGASS YNQKFRGKATLTVDKSSSTAY MDLLSLTSEDSAVYFCARGGYDGRGFDYWGQ GTTVT VSSASTKGPSVFPLAPSSKSTSGGTAALGCLV KDYFPEPVTVSWNSGALTSGVHTFPAVL QSSGLYSLSSVVTVPSSSLGTQTYICNVNHKPSNTKVDKRVEPKSCDKTHTGGGGSGGG GSGGGGSNWVNVISDLKKIEDLIQSMHIDATLYTESDVHPSCKVTAMKCFLLEL QVISLE SGDASIHDTVENLIILANNSLSSNGNVTESG CKECEELEEKNIKEFLQSFVHIVQMFINTS, (SEQ ID NO: 46), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 46.

In embodiments, the light chain of the Fab to mesothelin further comprises a CD40L, optionally, wherein the Fab and the CD40L are linked, e.g., via a linker comprising Gly and Ser. In one embodiment, the multispecific molecule has the following configuration: Light chain of the Fab (e.g., VL-CL1) to mesothelin fused to CD40L, from N- to C-terminus, optionally, comprising a Gly-Ser linker between the Fab and the CD40L. In embodiments, the multispecific molecule includes the amino acid sequence: DIELTQSPAIMSASPGEKVTMTCSASSSVSYMHWYQQKSGTSPKRWIYDTSKLASGVPG RFSGSGSGNSYSLTISSVEAEDDATYYCQQWSGYPLTFGAGTKLEIKRTVAAPSVFIF PPS DEQLKSGTASVVCLLNNFYPREAKVQWKVDNALQSGNSQESVTEQDSKDSTYSLSSTL TLSKADY EKHKVYACEVTHQGLSSPVTKSFNRGECDVPSGP GGGG GSGGGGSMQKGD QNPQIAAHVISEASSKT TSVLQWAEKGYYTMSNNLVTLENGKQLTVKRQGLYYIYAQV TFCSNREASSQAPFIASLCLKSPGRFERILLRAANTHSSAKPCGQQSIHLGGVFELQPGAS VFVNVTDPSQVSHGTGFTSFGLLKL, (SEQ ID NO: 47), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 47.

In other embodiments, the multispecific molecule includes an antibody molecule to FAP, e.g., human FAP, and an IL-15 molecule. In some embodiments, the antibody molecule includes a Fab against FAP having a light and a heavy chain. The heavy chain of the Fab to FAP can further include a first Fc region having a member of a paired cavity-protuberance (knob-in-a hole) in the Fc interface of the first Fc region. For example, the multispecific molecule can have the following configuration: Heavy chain of the Fab (e.g., VH-CH1) of FAP fused to First Fc region (e.g., CH2 to CH3), from N- to C-terminus, e.g., includes the amino acid sequence: QVQLVQSGAEVKKP-GASVKVSCKTSRYTFTEYTIHWVRQAPGQRLEWIG-GINPNNGIPN YNQKFKGRVTITVDTSASTAYME LSSLRSEDTAVYYCARRRIAYGYDEGHAMDYWGQ GTLVTVSSASTKGPSVFPLAPSSKSTSGGTAAL-GCLVKDYFPEPVTVSWNSGALTSGVHT FPAVLQSSG-LYSLSSVVTVPSSSLGTQTYICNVNHKPSNTKVDKR VEPKSCDKTHTCPPC PAPELLGGPSVFLFPPKP KDTLMISRTPEVTCVVVDVSHEDPEVKFNWYVDGV EVHNAK TKPREEQYNSTYRVVSVLTVLHQDWLNG KEYK CKVSNKALPAPIEKTISKAKGQPREPQ VCTLP PSREEMTKNQVSLSCAVKGFYPSDIAVEWESNGQ-PENNYKTTPPVLDSDGSFFL VSKLTVDKSRWQ QGNVFSCSVMHEALHNHYTQKSLSLSPGK, (SEQ ID NO: 48), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 48.

In embodiments, the light chain of the Fab to FAP includes the amino acid sequence: DIVMTQSPD-SLAVSLGERATINCKSSQSLLYSRNQKNYLAWY QQ KP GQPPKLLIFWAST RESGVPDRFSGSGFGTDF TLTISSLQAEDVAVYYCQQYFSYPLTFGQGTKVEI KRTVAAP SVFIFPPSDEQLKSGTASVVCLLNNFYPR EA KVQWKVDNALQSGNSQESVTEQDSKDST YSLSS TLTLSKADYEKHKVYACEVTHQGLSSPVTKSFNR GEC, (SEQ ID NO: 49), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 49.

In embodiments, the IL-15 molecule, e.g., human IL-15 molecule, further includes a second Fc region having a second member of a paired cavity-protuberance (knob-in-a hole) in the Fc interface of the second Fc region, e.g., connected via a linker comprising Gly and Ser. In one embodiment, the multispecific molecule has the following configuration: IL-15 molecule-Second Fc region (e.g., CH2 to CH3), from N- to C-terminus, e.g., wherein the IL-15 molecule and the Second Fc region are connected via a linker comprising Gly and Ser, e.g., includes the amino acid sequence: NWVNVISDLKKIEDLIQSMHIDATLYTESD VHPSCKVTAMKCFLLELQVISLESGDASIH DTVEN-LIILANNSLSSNGNVTESGCKECEELEEKNIKEFLQ SFVHIVQMFINTSGGGGSDK THTCPPCPAPELLGG PSVFLFPPKPKDTLMISRTPEVTCVVVDVSHEDPE-VKFNWYVDG VEVHNAKTKPREEQYNSTYRVSV LTVLHQDWLNGKEYKCKVSNKALPAPIEKTISKA KGQPREPQVYTLPPCREEMTKNQVSLWCLVKGFY PSDIAVEWESNGQPENNYKTTPPV LDSDGSFFLYSK-LTVDKSRWQQGNVFSCSVMHEALHNHYTQKSLSL-SPGK, (SEQ ID NO: 50), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 50.

In other embodiments, the multispecific molecule that includes the antibody molecule to FAP, e.g., human FAP, and the IL-15 molecule, further includes an immune cell engager, e.g., as described herein (e.g., a CD40 ligand). In some embodiments, the immune cell enhancer is linked, e.g., covalently linked, to the second Fc region having the second member of the paired cavity-protuberance (knob-in-a hole) and the IL-15 molecule, e.g., human IL-15 molecule, optionally comprising a linker comprising Gly and Ser between the IL-15 molecule and the second Fc region, and/or between the second Fc region and the immune cell enhancer. In embodiments, the multispecific molecule has the following configuration: IL-15 molecule-Second Fc region (e.g., CH2 to CH3)—Immune cell enhancer, from N- to C-terminus, optionally comprising a linker comprising Gly and Ser between the IL-15 molecule and the second Fc region, and/or between the second Fc region and the immune cell enhancer, e.g., it includes the amino acid sequence: NWVNVISDLKKIEDLIQSMHIDATLYTESDVHPSC KVTAMKCFLLELQVISLESGDASIH DTVENLIILA NNSLSSNGNVTESGCKECEELEEKNIKEFLQSFVHI VQMFINTSGGGGSDK THTCPPCPAPELLGGPS VFLFP PKPKDTLMISRTPEVTCVVVDVSHEDPEVKFNWYV DG VEVHNAKTKPREEQYNSTYRVVSVLTVLHQ DWLNGKEYKCKVSNKALPAPIEKTISKA KGQPREPQ VYTLPPCREEMTKNQVSLWCLVKGFYPSDIAVEWE SNGQPENNYKTTPPV LDSDGSFFLYSKLTVDKSRW QQGNVFSCSVMHEALHNHYTQKSLSLSPGKGGGG SMQ KGDQNPQIAAHVISEASSKTTSVLQWAE KGY YT MSNNLVTLENGKQLTVKRQGLYYIY AQVTFCSN-REASSQAPFIASLCLKSPGRFERILLRAANTHSSAK-PCGQQSIHLGGVFELQP GAS VFVNVTDPSQVSH GTGFTSFGLLKL, (SEQ ID NO: 51), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 51.

In other embodiments, the multispecific molecule that includes the antibody molecule to FAP, e.g., human FAP, the IL-15 molecule, and the CD40 ligand, further includes a second immune cell enhancer, e.g., a B7H6 molecule. In some embodiments, the second immune cell enhancer is linked, e.g., covalently linked, to the first Fc region having the first member of the paired cavity-protuberance (knob-in-a hole) in the Fc interface of the first Fc region and the heavy chain of the Fab, optionally comprising a linker comprising Gly and Ser between the B7H6 molecule and the first Fc region. In embodiments, the multispecific molecule has the following configuration: Heavy chain of the Fab (e.g., VH-CH1) to FAP fused to—First Fc region (e.g., CH2 to CH3) fused to—B7H6 molecule, from N- to C-terminus, optionally comprising a linker comprising Gly and Ser between the first Fc region and the B7H6 molecule, e.g., includes the amino acid sequence: QVQLVQSGAEVKKP-GASVKVSCKTSRYTFTEYTIHWVRQAPGQRLEWIG-GINPNNGIPN YNQKFKGRVTITVDTSASTAYMELSS LRS EDTAVYYCARRRIAYGYDEGHAMDYWGQ GTLVTVSSASTKGPSVFPLAPSSKSTSGGTAALGCL VK DYFPEPVTVSWNSGALTSGVHT FPAVLQSSGLYS-LSSVVTVPSSSLGTQTYICNVNHKPSNTKVDKRVE-PKSCDKTHTCPPC PAPELLGGPSVFLFPPKPKDTLMIS RTPEVTCVVVDVSHEDPEVKFNWYVDGVEVHNAK TKPREEQYNSTYRVVSVLTVLHQDWLNGKEYKCKV SN KALPAPIEKTISKAKGQPREPQ VCTLPPSREEMT-KNQVSLSCAVKGFYPSDIAVEWESNGQPENNYKT TPPVLDSDGSFFL VSKLTVDKSRWQQGNVFSC SVMHEALHNHYTQKSLSLSPGKGGGGSDLKVEM-MAGG TQITPLNDNVTIFCNIFYSQPLNITSMGIT-WFWKSLTFDKEVKVFEFFGD HQEAFRPGAIVS PWRLKSGDASLRLPGIQLEEAGEYRCEVVVTPLK AQGTVQLEVVASP ASRLLLDQVGMKENEDKYM CESS GFYPEAINITWEKQTQKFPHPIEISEDVITGP-TIKNM DGTFNVTSCLKLNSSQEDPGTVYQCVVRH ASLH TPLRSNFTLTAARHSLSETEKTDNFS, (SEQ ID NO: 52), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 52).

In another aspect, the invention features a multispecific molecule comprising:

a first amino acid sequence comprising: NWVNVISDLK-KIEDLIQSMHIDATLYTESDVHPSCKVTAMKCFLLE LQVISLESGDASIH DTVENLIILANNSLSSNGNVTE SGCKECEELEEKNIKEFLQSFVHIVQMFINTSGGG GSDK THTCPPCPAPELLGGPSVFLFPPKPKDTLMIS-RTPEVTCVVVDVSHEDPEVKFNWYVDG VEVHN AKTKPREEQYNSTYRVVSVLTVLHQDWLNGKEYKC KVSNKALPAPIEKTISKA KGQPREPQVYTLPPCREE MTKNQVSLWCLVKGFYPSDIAVEWESNGQPENNY KTTPPV LDSDGSFFLYSKLTVDKSRWQQGNVFS CSVMHEALHNHYTQKSLSLSPGK (SEQ ID NO: 50) or an amino acid sequence substantially homologous thereto, wherein the amino acid sequence comprises an IL-15 polypeptide, a linker, and an immunoglobulin Fc;

a second amino acid sequence comprising:

(SEQ ID NO: 53)
QVQLVQSGAEVKKPGASVKVSCKTSRYTFTEYTIHWVRQAPGQRLEWIGG

INPNNGIPNYNQKFKGRVTITVDTSASTAYMELSSLRSEDTAVYYCARRR

IAYGYDEGHAMDYWGQGTLVTVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKRVEPKSCDKTHTCPPCPAPELLGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVCTLPPSREEMTKNQVSLSCAVKGFYPSDIAVEWESNGQPENNYKT

TPPVLDSDGSFFLVSKLTVDKSRWQQGNVFSCSVMHEALHNHYTQKSLSL

SPGKGGGGS or an amino acid sequence substantially homologous thereto, wherein the amino acid sequence comprises an anti-FAP heavy chain of a Fab and an immunoglobulin Fc; and a a third amino acid sequence comprising:

(SEQ ID NO: 54)
DIVMTQSPDSLAVSLGERATINCKSSQSLLYSRNQKNYLAWYQQKPGQPP

KLLIFWASTRESGVPDRFSGSGFGTDFTLTISSLQAEDVAVYYCQQYFSY

PLTFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC or an amino acid sequence substantially homologous thereto), wherein the amino acid sequence comprises a human kappa light chain of anti-FAP Fab, In some embodiments, the first amino acid sequence further comprises: MEFGLSWVFLVALFRGVQC (SEQ ID NO: 6) or an amino acid sequence substantially homologous thereto. In some embodiments, the second amino acid sequence further comprises: MEFGLSWVFLVAL-FRGVQCEV (SEQ ID NO: 15) or an amino acid sequence substantially homologous thereto. In some embodiments, the third amino acid sequence further comprises: MKYLLPTAAAGLLLLAAQPAMA (SEQ ID NO: 12) or an amino acid sequence substantially homologous thereto.

In another aspect, the invention features a multispecific molecule comprising:

a first amino acid sequence comprising: MEFGLSWVFLVALFRGVQC NWVNVISDLKKIEDLI QSMHIDATLYTESDVHPSCKVTAMKCFLLELQVIS LESGDASIH DTVENLIILANNSLSSNGNVTESGCKE-CEELEEKNIKEFLQSFVHIVQMFINTSGGGGSDK THTCPPCPAPELLGGPSVFLFPPKPKDTLMISRTPE-VTCVVVDVSHEDPEVKFNWYVDG VEVHNA KTK PRE EQYNSTYRVVSVLTVLHQDWLNGKEYK CKV SNKALPAPIEKTISKA KGQPREPQVYTLPPCREEMT-KNQVSLWCLVKGFYPSDIAVEWESNGQPENNYK TTPPV LDSDGSFFLYSKLTVDKSRWQQGNVFSCSVM HEALHNHYTQKSLSLSPGK (SEQ ID NO: 50) or an amino acid sequence substantially homologous thereto, wherein the amino acid sequence comprises a leader peptide, IL-15, a linker, and immunoglobulin Fc;

a second amino acid sequence comprising: MEFGLS WVFLVALFRGVQCEVQVQLVQSGAEVKKPGAS VKVS CKTSRYTFTEYTIHWV RQAPGQRLEWIGGI NPNNGIPNYNQKFKGRVTITVDTSASTAYMELSSL RSEDTAVYYC ARRRIAYGYDEGHAMDYWGQG TLV TVSS ASTKGPSVFPLAPSSKSTSGGTAALGCLVKDY FPEPVTVSWNSGALTSGVHTFPAVLQSS GLYSLSSV VTVPSSSLGTQTYICNVNHKPSNTKVDKRVEPKSC DKTHTCPPCPAPELLGG PSVFLFPPKPKDTLMISRT-PEVTCVVVDVSHEDPEVKFNWYVDGVEVHNA KTKPREEQY NSTYRVVSVLTVLHQDWLNGKEYKC KVSNKALPAPIEKTISKAKGQPREPQVCTLPPSR EEMTKNQVSLSCAVKGFYPSDIAVEWESNGQPEN-NYKTTPPVLDSDGSFFLVSKLTVDK SRWQQGNVFSCSV MHEALHNHYTQKSLSLSPGK (SEQ ID NO: 55) or an amino acid sequence substantially homologous thereto, wherein the amino acid sequence comprises a leader peptide, an anti-FAP heavy chain of a Fab and immunoglobulin Fc; and a a third amino acid sequence comprising: DIVMTQSPD-SLAVSLGERATINCKSSQSLLYSRNQKNYLAWYQQK PGQPPKLLIFWAST RESGVPDRFSGSGFGTDFTLTI SSLQAEDVAVYYCQQYFSYPLTFGQGTKVEIKRTVA AP SVFIFPPSDEQLKSGTASVVCLLNNFYPREAKVQ WKVDNALQSGNSQESVTEQDSKDST YSLSSTLTL- SKADYEKHKVYACEVTHQGLSSPVTKSFNRGEC (SEQ ID NO: 49) or an amino acid sequence substantially homologous thereto, wherein the amino acid sequence comprises a leader peptide and human kappa light chain of anti-FAP Fab.

In another aspect, the invention features a multispecific molecule comprising:

a first amino acid sequence comprising: QVQLQQSGPELEKPGASVKISCKASGYSFTGYTMNWVKQSHGKSLE WIGLITPYNGASS YNQKFRGKATLTVDKSSST AY MD LL SLTSEDSAVYFCARGGYDGRGFDYW GQGTTVT VSSASTKGPSVFPLAPSSKSTSGGTAALGCLVKDYFPEPVTVSWNSGALTSGVHTFPAVL QSSGLYSLSSVVTVPSSSLGTQTYICNVNHKPSNTKVDKRV EPKSCDKTHTGGGGSGG GSGGGGSNWVNVISDL KKIEDLIQSMHIDATLYTESDVHPSCKVTAMKCFLL ELQVISLE SGDASIHDTVENLIILANNSLSSNGNV TESGCKECEELEEKNIKEFLQSFVHIVQMFINTS (SEQ ID NO: 46) or an amino acid sequence substantially homologous thereto, wherein the amino acid sequence comprises an anti-mesothelin heavy chain of a Fab, a linker, and an IL-15; and a second amino acid sequence comprising:

(SEQ ID NO: 56)
DIELTQSPAIMSASPGEKVTMTCSASSSVSYMHWYQQKSGTSPKRWIYDT

SKLASGVPGRFSGSGSGNSYSLTISSVEAEDDATYYCQQWSGYPLTFGAG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGECDVPSGPGGGGSGGGGSMQKGDQNPQIAAHVISEASS

KTTSVLQWAEKGYYTMSNNLVTLENGKQLTVKRQGLYYIYAQVTFCSNRE

ASSQAPFIASLCLKSPGRFERILLRAANTHSSAKPCGQQSIHLGGVFELQ

PGASVFVNVTDPSQVSHGTGFTSFGLLKL or an amino acid sequence substantially homologous thereto, wherein the amino acid sequence comprises a human kappa light chain of anti-mesothelin Fab, a linker, and a CD40L.

In some embodiments, the first amino acid sequence further comprises: MEFGLSWVFLVALFRGVQC (SEQ ID NO: 6) or an amino acid sequence substantially homologous thereto. In some embodiments, the second amino acid sequence further comprises: MKYLLPTAAAGLLLLAAQPAMA (SEQ ID NO: 12) or an amino acid sequence substantially homologous thereto.

In another aspect, the invention features a multispecific molecule comprising:

a first amino acid sequence comprising: MEFGLSWVFLVALFRGVQCQVQLQQSGPELEKPGASVKISCKASGYSFTGYTMNWVK QSHGKSLEWIGLITPYNGAS-SYNQKFRGKATLTVDKSSSTAYMDLLSLTSEDSAV YFCARGGYDGRGFDYWGQGTTVTVSSASTKGPSVFPLAPSSKSTSGGTAALGCLVKDYFPEPV TVSWNS GA LTSGVHTFPAVLQSSGLYSLSSVVTVPSSSLGTQTYIC NVNHKPSNTKVDK RVEPKSCDKTHTGGGGS GGG GSGGGGSNWVNVISDLKKIEDLIQSMHIDATLYTES DVH PSCKVTAMKCFLLELQVISLESGDASIHDTVENLIILANNSLSSNGNVTESGCKECEELEE KNIKEFLQSFVHIVQMFINTS (SEQ ID NO: 234) or an amino acid sequence substantially homologous thereto, wherein the amino acid sequence comprises a leader peptide, an anti-mesothelin heavy chain of a Fab, a linker, and an IL-15; and a second amino acid sequence comprising: MKYLLPTAAAGLLLLAAQPAMA DIELTQSPAIMSAS PGEKVTMTCSASSSVSYMHWYQQKSGTSPKRWI YDTSKLASGVPG RFSGSGSGNSYSLTISSVEAEDDA TYYCQQWSGYPLTFGAGTKLEIKRTVAAPSVFIFPPS DEQLKSGTASVVCLLNNFYPREAKVQWKVDNAL QSGNSQESVTEQDSKDSTYSLSSTL TLSKADYEKHK VYACEVTHQGLSSPVTKSFNRGECDVPSGPGGGGG SGG GGSMQKGD QNPQIAAHVISEASSKTTSVL QWAEKGYYTMSNNLVTLENGKQLTVKRQGLYYI-YAQV TFCSNREASSQAPFIASLCLKSPGRFERILLR A ANTHSSAKPCGQQSIHLGGVFELQPGAS VFVNVT DPSQVSHGTGFTSFGLLKL (SEQ ID NO: 235) or an amino acid sequence substantially homologous thereto, wherein the amino acid sequence comprises a leader peptide, a human kappa light chain of anti-mesothelin Fab, a linker, and a CD40L.

In another aspect, the invention features a multispecific molecule comprising:

a first amino acid sequence comprising: NWVNVISDLKKIEDLIQSMHIDATLYTESDVHPSCKVTAMKCFLLE LQVISLESGDASIH DTVENLIILANNSLSSNGNVT ES GCKECEELEEKNIKEFLQSFVHIVQMFINTS GGGG S DKTHTCPPCPAPELLGGPSVFLFPPKPK DTLMISRTP EVTCVVVDVSHEDPEVKF NWYVDGVEVHNA KTK PREEQYNSTYRVVSVLTVLHQDWLNGKEYKCKVS NKALPAPI EKTISKAKGQPREPQVYTLPPCREEMTK NQVSLWCLVKGFYPSDIAVEWESNGQPENNY KTT PP VLDSDGSFFLYSKLTVDKSRWQQGNVFSCSVMHEA LHN HYTQKSLSLSPGKGG GGSMQKGDQNPQIAAH VISEASSKTTSVLQWAEKGYYTMSNNLVTLENGK QLTVKRQ GLYYIYAQVTFCSNREASSQAPFIASLCLK SPGRFERILLRAANTHSSAKPCGQQSIFILGG VFELQ PGASVFVNVTDPSQVSHGTGFTSFGLLKL (SEQ ID NO: 51) or an amino acid sequence substantially homologous thereto, wherein the amino acid sequence comprises IL-15, a linker, and immunoglobulin Fc, a linker, and CD40L;

a second amino acid sequence comprising: QVQLVQSGAEVKKPGASVKVSCKTSRYTFTEYTIHWVRQAPGQ RLEWIGGINPNNGIPN YNQKFKGRVTITVDTSASTAY MELSSLRSEDTAVYYCARRRIAYGYDEGHAMDYW G Q GTLVTVSSASTKGPSVFPLAPSSKSTSGGTAALGC-LVKDYFPEPVTVSWNSGALTSGVHT FPAVLQSSGLY-SLSSVVTVPSSSLGTQTYICNVNHKPSNTKVDKRV EPKSCDKTHTCPPC PAPELLGGPSVFLFPPKPKDTL MISR TPEVTCVVVDVSHEDPEVKFNWYVDGVEV HNAK TKPREEQYNSTYRVVSVLTVLHQDWLNGKEY KCK VSNKALPAPIEKTISKAKGQPREPQ VCTLPPSREEMTKNQVSLSCAVKGFYPSDIAVEWESNGQPEN-NYKTTPPVLDSDGSFFL VSKLTVDKSRWQQGNVFSC SVMHEALHNHYTQKSLSLSPGKGGGGS DLKVEMM AGGTQITPLNDNVTIFCNIFYSQPLNITSMGITWFW-KSLTFDKEVKVFEFFGD HQEAFRPGAIVSPWRLKSG-DASLRLPGIQLEEAGEYRCEVVVTPLKAQGTVQLE-VVASP ASRLLLDQVGMKENEDKYMCESSGFYPEAI-NITWEKQTQKFPHPIEISEDVITGPTIKNM DGTFNVT-SCLKLNSSQEDPGTVYQCVVRHASLHTPLRSNFTL-TAARHSLSETEKTDNFS (SEQ ID NO: 52) or an amino acid sequence substantially homologous thereto, wherein the amino acid sequence comprises an anti-B7H6 heavy chain of a Fab and immunoglobulin Fc, a linker, and B7H6; and a third amino acid sequence comprising:

(SEQ ID NO: 57)
DIVMTQSPDSLAVSLGERATINCKSSQSLLYSRNQKNYLAWYQQKPGQPP

KLLIFWASTRESGVPDRFSGSGFGTDFTLTISSLQAEDVAVYYCQQYFSY

PLTFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC or an amino acid sequence substantially homologous thereto, wherein the amino acid sequence comprises a human kappa light chain of anti-FAP Fab.

In some embodiments, the first amino acid sequence further comprises: MEFGLSWVFLVALFRGVQC (SEQ ID NO: 6) or an amino acid sequence substantially homologous thereto. In some embodiments, the second amino acid sequence further comprises: MEFGLSWVFLVALFR GVQCEV (SEQ ID NO: 15) or an amino acid sequence substantially homologous thereto. In some embodiments, the third amino acid sequence further comprises: MK YLLPTAAAGLLLLAAQPAMA (SEQ ID NO: 12) or an amino acid sequence substantially homologous thereto.

In another aspect, the invention features a multispecific molecule comprising:

a first amino acid sequence comprising: MEFGL SWVFLVALFRGVQCNWVNVISDLKKIEDLIQSMHI-DATLYTESDVHPSCKVTAM KCFLLELQVISLESGDA SIHDTVENLIILANNSLSSNGNVTESGCKECEELEE KNIKEFLQS FVHIVQMFINTSGGGGSDKTHTCPPCPA-PELLGGPSVFLFPPKPKDTLMISRTPEVTCVVVDVS-HEDPEVKFNWYVDGVEVHNAKTKPREEQYNSTYR-VVSVLTVLHQDWLNGKEYK CKVSNKALPAPIEKTI-SKAKGQPREPQVYTLPPCREEMTKNQVSLWCLV-KGFYPSDIAVE WESNGQPENNYKTTPPVLDSDGSFF-LYSKLTVDKSRWQQGNVFSCSVMHEALHNHYT QK-SLSLSPGKGGGGSMQKGDQNPQIAAHVISEASSK-TTSVLQWAEKGYYTMSNNLVTL ENGKQLTVKRQG-LYYIYAQVTFCSNREASSQAPFIASLCLKSPGRFER-ILLRAANTHSSA KPCGQQSIHLGGVFELQPGASVF-VNVTDPSQVSHGTGFTSFGLLKL (SEQ ID NO: 58) or an amino acid sequence substantially homologous thereto, wherein the amino acid sequence comprises a leader peptide, IL-15, a linker, and immunoglobulin Fc, a linker, and CD40L;

a second amino acid sequence comprising (or substantially homologous thereto): MEFGLSWVFLVALFRGVQ-CEVQVQLVQSGAEVKKPGASVKVSCKTSRYTFTEY-TIHWV RQAPGQRLEWIGGINPNNGIPNYNQKFK-GRVTITVDTSASTAYMELSSLRSEDTAVYYC ARRRI-AYGYDEGHAMDYWGQGTLVTVSSASTKGPSVF-PLAPSSKSTSGGTAALGCLVK DYFPEPVTVSWNS-GALTSGVHTFPAVLQSSGLYSLSSVVTVPSSSL-GTQTYICNVNHKPS NTKVDKRVEPKSCDKTHTCP-PCPAPELLGGPSVFLFPPKPKDTLMISRTPEVTCVVV-DVS HEDPEVKFNWYVDGVEVHNAKTKPREEQYN-STYRVVSVLTVLHQDWLNGKEYKCKV SNKALPAPI-EKTISKAKGQPREPQVCTLPPSREEMTKNQVSLSCA-VKGFYPSDIAVEWES NGQPENNYKTTPPVLDSDGSF-FLVSKLTVDKSRWQQGNVFSCSVMHEALHNHYTQ-KSL SLSPGKGGGGSDLKVEMMAGGTQITPLNDNV-TIFCNIFYSQPLNITSMGITWFWKSLTFD KEVKVFEF-FGDHQEAFRPGAIVSPWRLKSGDASLRLPGIQLEE-AGEYRCEVVVTPLKAQ GTVQLEVVASPASRLLLDQ VGMKENEDKYMCESSGFYPEAINTITWEKQTQK-FPHPIEISEDVITGPTIKNMDGTFNVTSCLKLNSSQE DPGT VYQCVVRHASLHTPLRSNFTLTAARHSL SETE KTDNFS (SEQ ID NO: 59) or an amino acid sequence substantially homologous thereto, wherein the amino acid sequence comprises a leader peptide, anti-FAP heavy chain of a Fab and immunoglobulin Fc, a linker, and B7H6; and a third amino acid sequence comprising: MKYLLPTAAA AGLLLLAAQPAMADIVMTQSPDSLAVSLGERATINC KSSQSLLYSRNQKN YLAWYQQKPGQPPKLLIFWAST-RESGVPDRFSGSGFGTDFTLTISSLQAEDVAVYYCQQ YFSYPLTFGQGTKVEIKRTVAAPSVFIFPPSDEQLKSG-TASVVCLLNNFYPREAKVQWKV DNALQSGNSQES VTEQDSKDSTYSLSSTLTLSKADYEKHKVYACEVT HQGLSSPVTKSF NRGEC (SEQ ID NO: 60) or an amino acid sequence substantially homologous thereto, wherein the amino acid sequence comprises a leader peptide and human kappa light chain of anti-FAP Fab.

An exemplary trispecific molecule includes a Fab molecule directed to the mesothelin tumor antigen, wherein first polypeptide includes the heavy chain VH-CH1 of the Fab connected via a linker to an IL-15 cytokine, and the second polypeptide of the Fab includes the light chain VL-CL connected via a linker to CD40 ligand (CD40L) (FIG. 11A-C). FIG. 11B provides, from N- to C-orientation, the amino acid sequence of an optional signal peptide (shown in italics), followed by the heavy chain VH-CH1 of the Fab (shown in underline and bold for VH and CH1, respectively), connected via a Gly-Ser linker (shown in italics), to a human IL-15 cytokine (shown in regular font). FIG. 11C provides, from N- to C-orientation, the amino acid sequence of an optional signal peptide (shown in italics), followed by the kappa light chain VL-CL of the Fab (shown in underline and bold for VL and CL, respectively), connected via a Gly-Ser linker (shown in italics), to a human CD40L (shown in orange).

An exemplary bispecific molecule includes a Fab molecule directed to the stromal antigen, wherein the first polypeptide includes the heavy chain VH-CH1 of the Fab to the stromal antigen connected to the first Fc molecule having a cavity; the second polypeptide includes the IL-15 cytokine connected to the second Fc molecule having a protuberance; and the third polypeptide includes a light chain VL-CL of the Fab to the stromal antigen (FIG. 12A). FIG. 12B provides, from N- to C-orientation, the amino acid sequence of an optional signal peptide (shown in italics), followed by the human IL-15 cytokine (shown in regular font), and further including an optional Gly-Ser linker (shown in italics) connected to the second Fc molecule having a protuberance (shown in italics). FIG. 12C provides, from N- to C-orientation, the amino acid sequence of an optional signal peptide (shown in italics), followed by the followed by the heavy chain VH-CH1 of the Fab to the stromal antigen FAP (shown in underline and bold for VH and CH1, respectively), connected to the first Fc molecule having a cavity (shown in regular font). FIG. 12D provides, from N- to C-orientation, the amino acid sequence of an optional signal peptide (shown in italics), followed by the kappa light chain VL-CL of the Fab to the stromal antigen FAP (shown in underline and bold for VL and CL, respectively).

An exemplary tetraspecific molecule includes a Fab molecule directed to the mesothelin antigen, wherein the first polypeptide includes the heavy chain VH-CH1 of the Fab to the mesothelin antigen connected to the first Fc molecule having a protuberance (knob) in the CH3 region, and further includes a first immune cell engager, e.g., 41BB-ligand; the second polypeptide includes the IL-21 cytokine connected, optionally via a Gly-Ser linker, to the second Fc molecule having a cavity (hole), and further includes, e.g., via a Gly-Ser linker, a second immune cell engager, e.g., CD40L; and the third polypeptide includes a light chain VL-CL of the Fab to the mesothelin antigen (molecule A) (FIG. 14A-14B). The following amino acid sequences are included: (i) Molecule A corresponding to the heavy chain and light chain, respectively, of the mesothelin Fab (hMeso_SS1_Fab); (ii) Molecule B corresponding to human IL-21; (iii) Linker between the Molecule B and second Fc region (Molecule B to KiH_Fc linker); (iv) Linker between the first Fc region and Molecule C (KiH_Fc to Molecule C linker); (v) Molecule C corresponding to human 41BB ligand; (vi) Linker between the second Fc region and Molecule D (KiH_Fc to Molecule D linker); (vii) Molecule C corresponding to human CD40L; (viii) first member Fc region (Fc Knob), including from N to C orientation, the VH of the mesothelin Fab, the CH2-CH3 amino acid sequence including a substitution of T for W at position 366, followed by a Gly-Ser linker and the human 41BB ligand; and (ix) second member Fc region (Fc Hole), including from N to C orientation, the human IL-21, a Gly-Ser linker, the CH2-CH3 amino acid sequence including a substitution of T for S at position 366, L for A at position 368, Y for V at position 407, followed by a Gly-Ser linker and the human CD40L An exemplary tetraspecific molecule includes a Fab molecule directed to the stromal antigen, wherein the first polypeptide includes the heavy chain VH-CH1 of the Fab to the stromal antigen connected to the first Fc molecule having a cavity, and further includes a first immune cell engager, B7H6; the second polypeptide includes the IL-15 cytokine connected, optionally via a Gly-Ser linker, to the second Fc molecule having a protuberance, and further includes, e.g., via a Gly-Ser linker, a second immune cell engager, CD40L; and the third polypeptide includes a light chain VL-CL of the Fab to the stromal antigen (FIG. 13A). FIG. 13B provides, from N- to C-orientation, the amino acid sequence of an optional signal peptide (shown in italics), followed by the human IL-15 cytokine (shown in regular font), further including an optional Gly-Ser linker (shown in italics) connected to the second Fc molecule having a protuberance (shown in regular font), which further includes, e.g., an optional Gly-Ser linker (shown in italics, connected to the human CD40L amino acid sequence (shown in italics). FIG. 13C provides, from N- to C-orientation, the amino acid sequence of an optional signal peptide (shown in italics), followed by the followed by the heavy chain VH-CH1 of the Fab to the stromal antigen FAP (shown in underline and bold for VH and CH1, respectively), connected to the first Fc molecule having a cavity (shown in regular font), which further includes, e.g., an optional Gly-Ser linker (shown in italics, connected to the human B7H6 amino acid sequence (shown in blue). FIG. 13D provides, from N- to C-orientation, the amino acid sequence of an optional signal peptide (shown in italics), followed by the kappa light chain VL-CL of the Fab to the stromal antigen FAP (shown in underline and bold for VL and CL, respectively).

Exemplary Multispecific Molecules Comprising Stromal Modifying Moiety

The disclosure relates, inter alia, to novel multifunctional, e.g., multispecific, molecules that include (i) a stromal modifying moiety and (ii) a tumor-targeting moiety (e.g., an antibody molecule, a ligand molecule, or a receptor molecule) that binds to a tumor antigen or a stromal antigen. Without being bound by theory, the multifunctional molecules disclosed herein are believed to inter alia target (e.g., localize to) a cancer site, and alter the tumor stroma, e.g., alter the tumor microenvironment near the cancer site. The multifunctional molecules can further include one or both of: an immune cell engager (e.g., chosen from one, two, three, or all of an NK cell engager, a T cell engager, a B cell engager, a dendritic cell engager, or a macrophage cell engager); and/or a cytokine molecule. Accordingly, provided herein are, inter alia, multifunctional, e.g., multispecific molecules, that include the aforesaid moieties, nucleic acids encoding the same, methods of producing the aforesaid molecules, and methods of treating a cancer using the aforesaid molecules.

Accordingly, in one aspect, the disclosure features a multifunctional (e.g., bifunctional) molecule that includes a stromal modifying moiety and a tumor-targeting moiety (e.g., an antibody molecule, a ligand molecule, or a receptor molecule), e.g., that binds to a cancer antigen (e.g., a solid tumor antigen, a stromal antigen, or a hematological antigen).

In some embodiments, the multifunctional molecule further includes one or two of the following:
(i) an immune cell engager, e.g., chosen from one, two, three, or all of an NK cell engager, a T cell engager, a B cell engager, a dendritic cell engager, or a macrophage cell engager; or
(ii) a cytokine molecule.

In other embodiments, the multifunctional molecule includes three or four binding specificities or functions, e.g., it is a trispecific or a tetraspecific molecule. Exemplary trispecific and tetraspecific molecules include:
(i) one tumor-targeting moiety, one stromal modifying moiety and one immune cell engager;
(ii) one tumor-targeting moiety, one stromal modifying moiety and one cytokine molecule;
(iii) one tumor-targeting moiety, one stromal modifying moiety and two immune cell engagers (e.g., same or different immune cell engagers);
(iv) one tumor-targeting moiety, one stromal modifying moiety and two cytokines (e.g., same or different cytokines);
(v) one tumor-targeting moiety, one stromal modifying moiety, one immune cell engager, and one cytokine molecule;
(vi) two tumor-targeting moieties (e.g., same or different targeting moieties) and one stromal modifying moiety;
(vii) one tumor-targeting moiety and two stromal modifying moieties (e.g., same or different stromal modifying moieties);
(viii) two tumor-targeting moieties (e.g., same or different targeting moieties), one stromal modifying moiety and one immune cell engager;
(ix) two tumor-targeting moieties (e.g., same or different targeting moieties), one stromal modifying moiety and one cytokine molecule;
(x) one tumor-targeting moiety, two stromal modifying moieties (e.g., same or different stromal modifying moieties) and one immune cell engager; and
(xi) one tumor-targeting moiety, two stromal modifying moieties (e.g., same or different stromal modifying moieties) and one cytokine molecule.

Stromal Modifying Moieties

In some embodiments, the stromal modifying moiety causes one or more of: decreases the level or production of a stromal or extracellular matrix (ECM) component; decreases tumor fibrosis; increases interstitial tumor transport; improves tumor perfusion; expands the tumor microvasculature; decreases interstitial fluid pressure (IFP) in a tumor; or decreases or enhances penetration or diffusion of an agent, e.g., a cancer therapeutic or a cellular therapy, into a tumor or tumor vasculature.

In some embodiments, the stromal or ECM component decreased is chosen from a glycosaminoglycan or an extracellular protein, or a combination thereof. In some embodiments, the glycosaminoglycan is chosen from hyaluronan (also known as hyaluronic acid or HA), chondroitin sulfate, chondroitin, dermatan sulfate, heparin, heparin sulfate, entactin, tenascin, aggrecan and keratin sulfate. In some embodiments, the extracellular protein is chosen from collagen, laminin, elastin, fibrinogen, fibronectin, or vitronectin. In some embodiments, the stromal modifying moiety includes an enzyme molecule that degrades a tumor stroma or extracellular matrix (ECM). In some embodiments, the enzyme molecule is chosen from a hyaluronidase molecule, a collagenase molecule, a chondroitinase molecule, a matrix metalloproteinase molecule (e.g., macrophage metalloelastase), or a variant (e.g., a fragment) of any of the aforesaid. The term "enzyme molecule" includes a full length, a fragment or a variant of the enzyme, e.g., an enzyme variant that retains at least one functional property of the naturally-occurring enzyme.

In some embodiments, the stromal modifying moiety decreases the level or production of hyaluronic acid. In other embodiments, the stromal modifying moiety comprises a hyaluronan degrading enzyme, an agent that inhibits hyaluronan synthesis, or an antibody molecule against hyaluronic acid.

In some embodiments, the hyaluronan degrading enzyme is a hyaluronidase molecule, e.g., a full length or a variant (e.g., fragment thereof) thereof. In some embodiments, the hyaluronan degrading enzyme is active in neutral or acidic pH, e.g., pH of about 4-5. In some embodiments, the hyaluronidase molecule is a mammalian hyaluronidase molecule, e.g., a recombinant human hyaluronidase molecule, e.g., a full length or a variant (e.g., fragment thereof, e.g., a truncated form) thereof. In some embodiments, the hyaluronidase molecule is chosen from HYAL1, HYAL2, or PH-20/SPAM1, or a variant thereof (e.g., a truncated form thereof). In some embodiments, the truncated form lacks a C-terminal glycosylphosphatidylinositol (GPI) attachment site or a portion of the GPI attachment site. In some embodiments, the hyaluronidase molecule is glycosylated, e.g., comprises at least one N-linked glycan.

In some embodiments, the hyaluronidase molecule comprises the amino acid sequence: LNFRAPPVIPNVPFL-WAWNAPSEFCLGKFDEPLDMSLFSFIGSPRINATGQG VTIFYVDR LGYYPYIDSITGVTVNGGIPQKISLQDHL DKAKKDITFYMPVDNLGMAVIDWEEWRPTWARN WKPKDVYKNRSIELVQQQNVQLSLTEATEKAK QE FEKAGKDFLVETIKLGKLLRP NHLWGYYLFPDCYN-HHYKKPGYNGSCFNVEIKRNDDLSWLWNESTALY PSIYLNTQQS PVAATLYVRNRVREAIRVSKIPDAKSPL PVFAYTRIVFTDQVLKFLSQDELVYTFGETVA LGAS-GIVIWGTLSIMRSMKSCLLLDNYMETILNPYIINVT-LAAKMCSQVLCQEQGVCIRK NWNSSDYLHLNPDN-FAIQLEKGGKFTVRGKPTLEDLEQFSEKFYCSCYST-LSCKEKADV KDTDAVDVCIADGVCIDAFLKPPME-TEEPQIFYNASPSTLS (SEQ ID NO:61), or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 61.

In some embodiments, the hyaluronidase molecule comprises:

(i) the amino acid sequence of 36-464 of SEQ ID NO: 61;

(ii) the amino acid sequence of 36-481, 36-482, or 36-483 of wherein P 20 has the sequence of amino acids set forth in SEQ ID NO: 61; or (iii) an amino acid sequence having at least 95% to 100% sequence identity to the polypeptide or truncated form of sequence of amino acids set forth in SEQ ID NO: 61; or (iv) an amino acid sequence having 30, 20, 10, 5 or fewer amino acid substitutions to the amino acid sequence set forth in SEQ ID NO: 61. In some embodiments, the hyaluronidase molecule comprises an amino acid sequence at least 95% (e.g., at least 95%, 96%, 97%, 98%, 99%, 100%) identical to the amino acid sequence of SEQ ID NO: 61. In some embodiments, the hyaluronidase molecule is encoded by a nucleotide sequence at least 95% (e.g., at least 96%, 97%, 98%, 99%, 100%) identical to the nucleotide sequence of SEQ ID NO: 61.

In some embodiments, the hyaluronidase molecule is PH20, e.g., rHuPH20. In some embodiments, the hyaluronidase molecule is HYAL1 and comprises the amino acid sequence: FRGPLLPNRPFTTVWNANTQWCLERHGVD VDVSVFDVVANPGQTFRGPDMTWYSSQG TYPYY TP TGEPVFGGLPQNASLIAHLARTFQDILAAIPAPDFS GL AVIDWEAWRPRWAFN WDTKDIYRQRSRALVQ AQH PDWPAPQVEAVAQDQFQGAARAWMAGTLQLGRA LRPR GLWGFYGFPDCYNYDFLSPNYTGQCPSGIRAQ NDQLGWLWGQSRALYPSIYMPAVLEG TGKSQMYV QHRVAEAFRVAVAAGDPNLPVLPYVQIFYDTTNHF LPLDELEHSLGESAA QGAAGVVLWVSWENTRTKE SCQAIKEYMDTTLGPFILNVTSGALLCSQALCSGH GRCV RRTSHPKALLLLNPASFSIQLTPGGGPLSLR-GALSLEDQAQMAVEFKCRCYPGWQAPWC ERKSMW (SEQ ID NO: 62), or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 62.

In some embodiments, the hyaluronan degrading enzyme, e.g., the hyaluronidase molecule, further comprises a polymer, e.g., is conjugated to a polymer, e.g., PEG. In some embodiments, the hyaluronan-degrading enzyme is a PEGylated PH20 enzyme (PEGPH20). In some embodiments, the hyaluronan degrading enzyme, e.g., the hyaluronidase molecule, further comprises an immunoglobulin chain constant region (e.g., Fc region) chosen from, e.g., the heavy chain constant regions of IgG1, IgG2, IgG3, and IgG4, more particularly, the heavy chain constant region of human IgG1, IgG2, IgG3, or IgG4. In some embodiments, the immunoglobulin constant region (e.g., the Fc region) is linked, e.g., covalently linked to, the hyaluronan degrading enzyme, e.g., the hyaluronidase molecule. In some embodiments, the immunoglobulin chain constant region (e.g., Fc region) is altered, e.g., mutated, to increase or decrease one or more of: Fc receptor binding, antibody glycosylation, the number of cysteine residues, effector cell function, or complement function. In some embodiments, the hyaluronan degrading enzyme, e.g., the hyaluronidase molecule forms a dimer.

In some embodiments, the stromal modifying moiety comprises an inhibitor of the synthesis of hyaluronan, e.g., an HA synthase. In some embodiments, the inhibitor comprises a sense or an antisense nucleic acid molecule against an HA synthase or is a small molecule drug. In some embodiments, the inhibitor is 4-methylumbelliferone (MU) or a derivative thereof (e.g., 6,7-dihydroxy-4-methyl coumarin or 5,7-dihydroxy-4-methyl coumarin), or leflunomide or a derivative thereof.

In some embodiments, the stromal modifying moiety comprises antibody molecule against hyaluronic acid.

In some embodiments, the stromal modifying moiety comprises a collagenase molecule, e.g., a mammalian collagenase molecule, or a variant (e.g., fragment) thereof. In some embodiments, the collagenase molecule is collagenase molecule IV, e.g., comprising the amino acid sequence of: YNFFPRKPKWDKNQITYRIIGYTPDLDPETVDDAFA RAFQVWSDVTPLRFSRIHDGEADI MINFGRWEHGD GYPFDGKDGLLAHAFAPGTGVGGDSHFDDDELW TLGEGQVVRVKY GNADGEYCKFPFLFNGKEYNSCT DTGRSDGFLWCSTTYNFEKDGKYGFCPHEALFTMG GNAEGQPCKFPFRFQGTSYDSCTTEGRTDGYRW CGTTEDYDRDKKYGFCPETAMSTVG GNSEGAPC VFPFTFLGNKYESCTSAGRSDGKMWCATTANYDD- DRKWGFCPDQGYSLF LVAAHEFGHAMGLEHSQDP- GALMAPIYTYTKNFRLSQDDIKGIQELYGASPDI DLGTGP TPTLGPVTPEICKQDIVFDGIAQ IRGEI FFF KDRFIWRTVTPRDKPMGPLLVATFWPELPEK IDAV- YEAPQEEKAVFFAGNEYWIYSASTLERGYPKPLT- SLGLPPDVQRVDAAFNWSKNK KTYIFAGDKFWRY- NEVKKKMDPGFPKLIADAWNAIPDNLDAVVDLQG GGHSYFFKGA YYLKLENQSLKSVKFGSIKSDWLGC (SEQ ID NO: 63), or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 63.

Tumor-Targeting Moieties

In some embodiments, the tumor-targeting moiety comprises an antibody molecule (e.g., Fab or scFv) that binds to mesothelin. In some embodiments, the antibody molecule to mesothelin comprises one, two, three CDRs from the heavy chain variable domain sequence of: QVQLQQSGPELEKP- GASVKISCKASGYSFTGYTMNWVKQSHGKSLEWIG- LITPYNGASS YNQKFRGKATLTVDKSSSTAYMDLLS LT SEDSAVYFCARGGYDGRGFDYWGQGTTVT VSS (SEQ ID NO: 1), or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 1.

In some embodiments, the antibody molecule to mesothelin comprises one, two, three CDRs from GYSFTGYTMN (SEQ ID NO: 2); LITPYNGASSYN- QKFRG (SEQ ID NO: 3); and GGYDGRGFDY (SEQ ID NO: 4), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin consists of three CDRs, wherein CDR1 comprises GYSFTGYTMN (SEQ ID NO: 2); CDR2 comprises: LITPYNGASSYNQKFRG (SEQ ID NO: 3); and CDR3 comprises GGYDGRGFDY (SEQ ID NO: 4), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin consists of three CDRs, wherein CDR1 consists of GYSFTGYTMN (SEQ ID NO: 2); CDR2 consists of LITPYNGASSYNQKFRG (SEQ ID NO: 3); and CDR3 consists of GGYDGRGFDY (SEQ ID NO: 4), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin comprises the heavy chain variable domain sequence of: QVQLQQSGPELEKPGASVKISCKASGYSFTGYT MNWVKQSHGKSLEWIGLITPYNGASS YNQKFRGK ATLTVDKSSSTAYMDLLSLTSEDSAVYFCARGGYDG RGFDYWGQGTTVT VSS (SEQ ID NO: 1), or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 1.

In some embodiments, the antibody molecule to mesothelin is a Fab and further comprises a heavy chain constant region (CH1) having the amino acid sequence:

(SEQ ID NO: 5)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHT, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 5.

In some embodiments, the antibody molecule further comprises a signal peptide, e.g., a signal peptide comprising the amino acid sequence: MEFGLSWVFLVALFRGVQC (SEQ ID NO: 6).

In some embodiments, the antibody molecule to mesothelin comprises one, two, three CDRs from the light chain variable domain sequence of: DIELTQSPAIMSASPG EKVTMTCSASSSVSYMHWYQQKSGTSPKRWIYD- TSKLASGVPG RFSGSGSGNSYSLTISSVEAEDDATYY- CQQWSGYPLTFGAGTKLEIK (SEQ ID NO: 7), or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 7.

In some embodiments, the antibody molecule to mesothelin comprises one, two, three CDRs from SASSSVS- YMH (SEQ ID NO: 8); DTSKLAS (SEQ ID NO: 9); and QQWSGYPLT (SEQ ID NO: 10), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin consists of three CDRs, wherein CDR1 comprises SASSSVSYMH (SEQ ID NO: 8); CDR2 comprises: DTSK- LAS (SEQ ID NO: 9); and CDR3 comprises QQWSGYPLT (SEQ ID NO: 10), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin consists of three CDRs, wherein CDR1 consists of SASSSVSYMH (SEQ ID NO: 8); CDR2 consists of DTSKLAS (SEQ ID NO: 9); and CDR3 consists of QQWSGYPLT (SEQ ID NO: 10), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to mesothelin comprises the light chain variable domain sequence of: DIELTQSPAIMSASPGEKVTMTCSASSSVSYMHW YQQKSGTSPKRWIYDTSKLASGVPG RFSGSGSGNS YSLTISSVEAEDDATYYCQQWSGYPLTFGAGTKLEIK (SEQ ID NO: 7), or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 7.

In some embodiments, the antibody molecule to mesothelin is a Fab and further comprises a light chain constant region (CL1) having the amino acid sequence:

```
                                        (SEQ ID NO: 11)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC,
``` or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 11.

In some embodiments, the antibody molecule further comprises a signal peptide, e.g., a signal peptide comprising the amino acid sequence: MKYLLPTAAAGLLLLAAQ-PAMA (SEQ ID NO: 12). In some embodiments, the signal peptide comprises the amino acid sequence of SEQ ID NO: 12. In some embodiments, the signal peptide comprises the amino acid sequence: METDTLLLWVLLLWVPGSTG (SEQ ID NO: 64). In some embodiments, the signal peptide comprises the amino acid sequence: MEFGLSWVFLVAL-FRGVQC (SEQ ID NO: 6).

In some embodiments, the tumor-targeting moiety comprises an antibody molecule (e.g., Fab or scFv) that binds to FAP.

In some embodiments, the antibody molecule to FAP comprises one, two, three CDRs from the heavy chain variable domain sequence of: QVQLVQSGAEVKKP-GASVKVSCKTSRYTFTEYTIHWVRQAPGQRLEWIG-GINPNNGIPNYNQKFKGRVTITVDTSASTAYMELSSL-RSEDTAVYYCARRRIAYGYDEGHAMDYWGQGTLV-TVSS (SEQ ID NO: 65), or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 65.

In some embodiments, the antibody molecule to FAP comprises one, two, three CDRs selected from SRYT-FTEYTIH (SEQ ID NO: 66); GINPNNGIPNYNQKFKG (SEQ ID NO: 67); and RRIAYGYDEGHAMDY (SEQ ID NO: 68), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to FAP consists of three CDRs, wherein CDR1 comprises SRYTFTEYTIH (SEQ ID NO: 66); CDR2 comprises: GINPNNGIPNYNQKFKG (SEQ ID NO: 67); and CDR3 comprises RRIAYGYDEGHAMDY (SEQ ID NO: 68), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to FAP consists of three CDRs, wherein CDR1 consists of SRYTFTEYTIH (SEQ ID NO: 66); CDR2 consists of GINPNNGIPNYNQKFKG (SEQ ID NO: 67); and CDR3 consists of RRIAYGYDEGHAMDY (SEQ ID NO: 68), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to FAP comprises the heavy chain variable domain sequence of: QVQLVQSGAEVKKPGASVKVSCKTSRYTFTEYTIH-WVRQAPGQRLEWIGGINPNNGIPNYNQKFKGRV-TITVDTSASTAYMELSSLRSEDTAVYYCARRRIAYGY-DEGHAMDYWGQ GTLVTVSS (SEQ ID NO: 65), or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 65.

In some embodiments, the antibody molecule to FAP is a Fab and further comprises a heavy chain constant region (CH1) having the amino acid sequence: ASTKGPSVF-PLAPSSKSTSGGTAALGCLVKDYFPEPVTVSWNSG-ALTSGVHTFPAVLQSSGLYSLSSVVTVPSSSLGTQT-YICNVNHKPSNTKVDKRVEPKSC (SEQ ID NO: 14), or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 14.

In some embodiments, the antibody molecule further comprises a signal peptide, e.g., a signal peptide comprising the amino acid sequence: MKYLLPTAAAGLLLLAAQ-PAMA (SEQ ID NO: 12). In some embodiments, the signal peptide comprises the amino acid sequence of SEQ ID NO: 12. In some embodiments, the signal peptide comprises the amino acid sequence: METDTLLLWVLLLWVPGSTG (SEQ ID NO: 16). In some embodiments, the signal peptide comprises the amino acid sequence: MEFGLSWVFLVAL-FRGVQC (SEQ ID NO: 6), In some embodiments, the antibody molecule to FAP comprises one, two, three CDRs from the light chain variable domain sequence of: DI-VMTQSPDSLAVSLGERATINCKSSQSLLYSRNQKNY-LAWYQQKPGQPPKLLIFWAST RESGVPDRFSGSG-FGTDFTLTISSLQAEDVAVYYCQQYFSYPLTFGQGT-KVEIK (SEQ ID NO: 69), or a closely related CDR, e.g., CDRs which have at least one amino acid alteration, but not more than two, three or four alterations (e.g., substitutions, deletions, or insertions, e.g., conservative substitutions) from the CDR sequence of SEQ ID NO: 69.

In some embodiments, the antibody molecule to FAP comprises one, two, three CDRs selected from KSSQSLLYSRNQKNYLA (SEQ ID NO: 70); WASTRES (SEQ ID NO: 71); and QQYFSYPLT (SEQ ID NO: 72), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to FAP consists of three CDRs, wherein CDR1 comprises KSSQSLLYSRNQKNYLA (SEQ ID NO: 70); CDR2 comprises: WASTRES (SEQ ID NO: 71); and CDR3 comprises QQYFSYPLT (SEQ ID NO: 72), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to FAP consists of three CDRs, wherein CDR1 consists of KSSQSLLYSRNQKNYLA (SEQ ID NO: 70); CDR2 consists of WASTRES (SEQ ID NO: 71); and CDR3 consists of QQYFSYPLT (SEQ ID NO: 72), or a closely related CDR, e.g., CDRs which have at least one amino acid alteration, but not more than two, three or four alterations (e.g., substitutions, deletions, or insertions, e.g., conservative substitutions).

In some embodiments, the antibody molecule to FAP comprises the light chain variable domain sequence of: DIVMTQSPDSLAVSLGERATINCKSSQSLLYSRNQKNYLAWYQQKPGQPPKLLIFWAST RESGVPDRFS- GSGFGTDFTLTISSLQAEDVAVYYCQQYFSYPLTFGQGTKVEIK (SEQ ID NO: 69), or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 69.

In some embodiments, the antibody molecule to FAP is a Fab and further comprises a light chain constant region (CL1) having the amino acid sequence:

```
                                    (SEQ ID NO: 11)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC,
``` or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 11.

In some embodiments, the antibody molecule further comprises a signal peptide, e.g., a signal peptide comprising the amino acid sequence: MKYLLPTAAAGLLLLAAQPAMA (SEQ ID NO: 12). In some embodiments, the signal peptide comprises the amino acid sequence of SEQ ID NO: 12. In some embodiments, the signal peptide comprises the amino acid sequence: METDTLLLWVLLLWVPGSTG (SEQ ID NO: 16). In some embodiments, the signal peptide comprises the amino acid sequence: MEFGLSWVFLVALFRGVQC (SEQ ID NO: 6).

Immune Cell Engagers

In some embodiments, the ligand of NKp30 is a B7-6, e.g., comprises the amino acid sequence of: DLKVEMMAGGTQITPLNDNVTIFCNIFYSQPLNITSMGIT- WFWKSLTFDKEVKVFEFFGD HQEAFRPGAIVSPW- RLKSGDASLRLPGIQLEEAGEYRCEVVVTPLKA- QGTVQLEVVASP ASRLLLDQVGMKENEDKYMCE- SSGFYPEAINITWEKQTQKFPHPIEISEDVITGPTIKNM DGTFNVTSCLKLNSSQEDPGTVYQCVVRHASLHTP- LRSNFTLTAARHSLSETEKTDNFS (SEQ ID NO: 24), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 24.

In some embodiments, the ligand of NKp44 or NKp46 is a viral HA.

In some embodiments, the ligand of DAP10 is a coreceptor for NKG2D.

In some embodiments, the ligand of CD16 is a CD16a/b ligand, e.g., a CD16a/b ligand further comprising an antibody Fc region.

In some embodiments, the ligand of NKG2D is chosen from MICA, MICB, or ULBP1, e.g., wherein: (i) MICA includes the amino acid sequence: EPHSLRYNLTVLSWDGSVQSGFLTEVHLDGQPFLRCDRQKCRAK- PQGQWAEDVLGNK TWDRETRDLTGNGKDLRMT- LAHIKDQKEGLHSLQEIRVCEIHEDNSTRSSQHFYYD- GEL FLSQNLETKEWTMPQSSRAQTLAMNVRN- FLK- EDAMKTKTHYHAMHADCLQELRRYLK SGVVLRR- TVPPMVNVTRSEASEGNITVTCRASGFYPWNITLS- WRQDGVSLSHDTQQWG DVLPDGNGTYQTWVAT- RICQGEEQRFTCYMEHSGNHSTHPVPSGKVLVL- QSHW (SEQ ID NO: 25), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 25;

(ii) MICB includes the amino acid sequence: AEPHSLRYNLMVLSQDESVQSGFLAEGHLDGQPFLRYD- QKRRAKPQGQWAEDVLGA KTWDTETEDLTENGQD- LRRTLTHIKDQKGGLHSLQEIRVCEIHEDSSTRGSRH- FYYDGEL FLSQNLETQESTVPQSSRAQTLAMNVT- NFWKEDAMKTKTHYRAMQADCLQKLQRYLK SG- VAIRRTVPPMVNVTCSEVSEGNITVTCRASSFYPRNI- TLTWRQDGVSLSHNTQQWGD VLPDGNGTYQTW- VATRIRQGEEQRFTCYMEHSGNHGTH- PVPSGKVLVLQSQRTD (SEQ ID NO: 26), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 26; or (iii) ULBP1 includes the amino acid sequence: GWVDTHCLCYDFIITPKSRPEPQWCEVQGLVDERP- FLHYDCVNHKAKAFASLGKKVNV TKTWEEQTETL- RDVVDFLKGQLLDIQVENLIPIEPLTLQARMSCE- HEAHGHGRGSWQFL FNGQKFLLFDSNNRKWTA LH PGAKKMTEKWEKNRDVTMFFQKISLGDCK MWLEEFL MYWEQMLDPTKPPSLAPG (SEQ ID NO: 27), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 27.

In some embodiments, the ligand of DNAM1 is chosen from NECTIN2 or NECL5, e.g., wherein:

(i) NECTIN2 includes the amino acid sequence: QDVRVQVLPEVRGQLGGTVELPCHLLPPVPGLYISLVTWQRPDAPANHQNVAAFHPKM GPSFPSPKPGSERLSFVSAKQSTGQDTEAELQDATLALHGLTVEDEGNYTCEFATFPKGS VRGMTWLRVIAKPKNQAEAQKVT FSQDPTTVALCISKEGRPPARISWLSSLDWEAKETQ VS GTLAGTVTVTSRFTLVPSGRADGVTVTCKVEHESFEEPALIPVTLSVRYPPEVSISGYD DNWYLGRTDATLSCDVRSNPEPTGYDWSTTSGTFPTSAVAQGSQLVIHAVDSLFNTTFV CTVTNAVGMGRAEQVIFVRETPNTAGAGATGG (SEQ ID NO: 28), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 28; or (ii) NECL5 includes the amino acid sequence: WPPPGTGDVVVQAPTQVPGFLGDSVTLPCYLQVPNMEVTHVSQLTWARHGESGSMAVFHQTQGPSYSESKRLEFVAARLGAELRNASLRMFGLRVEDEGNYTCLFVTFPQGSRSVD IWLRVLAKPQNTAEVQKVQLTGEPVPMARCVSTGGRPPAQITWHSDLGGMPNTSQVPGFLSGTVTVTSLWILVPSSQVDGKNVTCKVEHESFEKPQLLTVNLTVYYPPEVSISGYDNNWYLGQNEATLTCDARSNPEPTGYNWSTTMGPLPPFAVAQGAQLLIRPVDKPINTTLICNVTNALGARQAELTVQVKEGPPSEHSGISRN (SEQ ID NO: 29), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 29.

In some embodiments, the ligand of CRTAM is NECL2, e.g., wherein NECL2 includes the amino acid sequence: QNLFTKDVTVIEGEVATISCQVNKSDDSVIQLLNPNRQTIYFRDFRPLKDSRFQLLNFSSS ELKVSLTNVSISDEGRYFCQLYTDPPQESYTTITVLVPPRNLMIDIQKDTAVEGEEIEVNC TAMASKPATTIRWFKGNTELKGKSEVEEWSDMYTVTSQLMLKVHKEDDGVPVICQVEHPAVTGNLQTQRYLEVQYKPQVHIQMTYPLQGLTREGDALELTCEAIGKPQPVMVTWV RVDDEMPQHAVLSGPNLFINNLNKTDNGTYRCEASNIVGKAHSDYMLYVYDPPTTIPPP TTTTTTTTTTTTTILTIITDSRAGEEGSIRAVDH (SEQ ID NO: 30), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 30.

In some embodiments, the ligand of CD27 is CD70, e.g., wherein CD70 includes the amino acid sequence: QRFAQAQQQLPLESLGWDVAELQLNHTGPQQDPRLYWQGGPALGRSFLHGPELDKGQ LRIHRDGIYMVHIQVTLAICSSTTASRHHPTTLAVGICSPASRSISLLRLSFHQGCTIASQR LTPLARGDTLCTNLTGTLLPSRNTDETFFGVQWVRP (SEQ ID NO: 31), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 31.

In some embodiments, the ligand of PSGL1 is L-selectin (CD62L), e.g., wherein L-selectin includes the amino acid sequence: WTYHYSEKPMNWQRARRFCRDNYTDLVAIQNKAEIEYLEKTLPFSRSYYWIGIRKIGGI WTWVGTNKSLTEEAENWGDGEPNNKKNKEDCVEIYIKRNKDAGKWNDDACHKLKAA LCYTASCQPWSCSGHGECVEIINNYTCNCDVGYYGPQCQFVIQCEPLEAPELGTMDCTH PLGNFSFSSQCAFSCSEGTNLTGIEETTCGPFGNWSSPEPTCQVIQCEPLSAPDLGIMNCSH PLASFSFTSACTFICSEGTELIGKKKTICESSGIWSNPSPICQKLDKSFSMIKEGDYN (SEQ ID NO: 32), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 32.

In some embodiments, the ligand of CD96 is NECL5, e.g., wherein NECL5 includes the amino acid sequence: WPPPGTGDVVVQAPTQVPGFLGDSVTLPCYLQVPNMEVTHVSQLTWARHGESGSMAV FHQTQGPSYSESKRLEFVAARLGAELRNASLRMFGLRVEDEGNYTCLFVTFPQGSRSVD IWLRVLAKPQNTAEVQKVQLTGEPVPMARCVSTGGRPPAQITWHSDLGGMPNTSQVPGFLSGTVTVTSLWILVPSSQVDGKNVTCKVEHESFEKPQLLTVNLTVYYPPEVSISGYDNNWYLGQN EATLTCDARSNPEPTGYNWSTTMGPLPPFAVAQ- G- AQLLIRPVDKPINTTLICN VTNALGARQAELTVQ- VKEGPPSEHSGISRN (SEQ ID NO: 29), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 29.

In some embodiments, the ligand of CD100 (SEMA4D) is CD72, e.g., wherein CD72 includes the amino acid sequence: RYLQVSQQLQQTNRVLEVTNSSLRQQLRLKIT- QLGQSAEDLQGSRRELAQSQEALQVEQ RAHQAAEGQLQACQADRQKTKETLQSEEQQRRALEQKLSNMENRLKPFFTCGSADTCC PSGWIMHQKSCFYISLTSKNWQESQKQCETLSSKLATFSEIYPQSHSYYFLNSLLPNGGS GNSYWTGLSSNKDWKLTDDTQRTRTYAQSSKCNKVHKTWSWWTLESESCRSSLPYICE MTAFRFPD (SEQ ID NO: 33), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 33.

In some embodiments, the ligand of NKp80 is CLEC2B (AICL), e.g., wherein CLEC2B (AICL) includes the amino acid sequence: KLTRDSQSLCPYDWIGFQNKCYYFSKEEGDWNSSKYNCSTQHADLTIIDNIEEMNFLRR YKCSSDHWIGLKMAKNRTGQWVDGATFTKSFGM- RGSEGCAYLSDDGAATARCYTER KWICRKRIH (SEQ ID NO: 34), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 34.

In some embodiments, the ligand of CD244 is CD48, e.g., wherein CD48 includes the amino acid sequence: QGHLVHMTVVSGSNVTLNISESLPENYKQLTWFY TFDQKIVEWDSRKSKYFESKFKGR VRLDPQSGALYISKVQKEDNSTYIMRVLKKTGNEQEWKIKLQV LDPVPKPVIKIEKIEDM DDNCYLKLSCVIPGESVNYT WYGDKRPFPKELQNSVLETTLMPHNYSRCYTCQV SNSVS SKNGTVCLSPPCTLARS (SEQ ID NO: 35), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 35.

In some embodiments, the immune cell engager mediates binding to, or activation of, one or more of a B cell, a macrophage, and/or a dendritic cell. In some embodiments, the immune cell engager comprises a B cell, macrophage, and/or dendritic cell engager chosen from one or more of CD40 ligand (CD40L) or a CD70 ligand; an antibody molecule that binds to CD40 or CD70; an antibody molecule to OX40; an OX40 ligand (OX40L); a Toll-like receptor agonist (e.g., a TLR4, e.g., a constitutively active TLR4 (caTLR4) or a TLR9 agonist); a 41BB agonist; a CD2 agonist; a CD47 agonist; or a STING agonist, or a combination thereof. In some embodiments, the B cell engager is a CD40L, an OX40L, or a CD70 ligand, or an antibody molecule that binds to OX40, CD40 or CD70. In some embodiments, the macrophage cell engager is a CD2 agonist; a CD40L; an OX40L; an antibody molecule that binds to OX40, CD40 or CD70; a Toll-like receptor agonist or a fragment thereof (e.g., a TLR4, e.g., a constitutively active TLR4 (caTLR4) or TLR9); CD47; or a STING agonist. In some embodiments, the dendritic cell engager is a CD2 agonist, an OX40 antibody, an OX40L, 41BB agonist, a Toll-like receptor agonist (e.g., a TLR4, e.g., a constitutively active TLR4 (caTLR4) or a TLR9 agonist); a CD47 agonist, or a STING agonist.

In some embodiments, the OX40L comprises the amino acid sequence: QVSHRYPRIQSIKVQFTEYKKEKGFILTSQKEDEIMKVQNNSVIINCDGFYLISLKGYFSQ EVNISLHYQKDEEPLFQLKKVRSVNSLMVASLTYKDKVY LNVTT DNTSLDDFHVNGGE LILIHQNPGEFCVL (SEQ ID NO: 36), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 36.

In some embodiments, the CD40L comprises the amino acid sequence: MQKGDQNPQIAAHVISEASSKTTSVL QWAEKGYYTMSNNLVTLENGKQLTVKRQGLYYIY AQVTFCSNREASSQAPFIASLCLKSPGRFERILLRA ANTHSSAKPCGQQSIHLGGVFE LQPGASVFVNVTDP SQVSHGTGFTSFGLLKL (SEQ ID NO: 37), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 37.

In some embodiments, the STING agonist comprises a cyclic dinucleotide, e.g., a cyclic di-GMP (cdGMP), a cyclic di-AMP (cdAMP), or a combination thereof, optionally with 2',5' or 3',5' phosphate linkages.

In one embodiment, the immune cell engager includes 41BB ligand, e.g., comprising the amino acid sequence: ACPWAVSGARASPGSAASPRLREGPELSPDDPAGLL DLRQGMFAQLVAQNVLLIDGPLSWYSDPGLAGVSL TGGLSYKEDTKELVVAKAGVYYVFFQLELRRVVAGEGSGSVSLALH LQPLRSAAGAAALALTVDLPPASSEARNSAFGFQGRLLHLSAGQRLGVHLHTEARARH AWQLTQGATVLGLFRVTPEIPAGLPSPRSE (SEQ ID NO: 38), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 38.

Cytokine Molecules

In one embodiment, the cytokine molecule is IL-15, e.g., human IL-15 (e.g., comprising the amino acid sequence: NWVNVISDLKKIEDLIQSMHIDATLYTESDVHPSC KVTAMKCFLLELQVISLESGDASIHDTVENLIILANN S LSSNGNVTESGCKECEELEEKNIKEFLQSFVHIV QMFINTS (SEQ ID NO: 17), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 17.

In some embodiments, the cytokine molecule comprises a receptor dimerizing domain, e.g., an IL15Ralpha dimerizing domain. In one embodiment, the IL15Ralpha dimerizing domain comprises the amino acid sequence: MAPRRARGCRTLGLPALLLLLLRPPATRGITCPPPMSVEHADIWVKSYSLYSRERYICN SGFKRKAGTSSLTECVL (SEQ ID NO: 73), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 73. In some embodiments, the cytokine molecule (e.g., IL-15) and the receptor dimerizing domain (e.g., an IL15Ralpha dimerizing domain) of the multispecific molecule are covalently linked, e.g., via a linker (e.g., a Gly-Ser linker, e.g., a linker comprising the amino acid sequence SGGSGGGGSGGGSGGGGSLQ (SEQ ID NO: 19). In other embodiments, the cytokine molecule (e.g., IL-15) and the receptor dimerizing domain (e.g., an IL15Ralpha dimerizing domain) of the multispecific molecule are not covalently linked, e.g., are non-covalently associated.

In other embodiments, the cytokine molecule is IL-2, e.g., human IL-2 (e.g., comprising the amino acid sequence: APTSSSTKKTQLQLEHLLLDLQMILNGINNYKNPKLTRMLTFKFYMPKKATELKHLQCL EEELKPLEEVLNLAQSKNFHLRPRDLISNINVIVLELKGSETTFMCEYADETATIVEFLNR WITFCQSIISTLT (SEQ ID NO: 20), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 20).

In other embodiments, the cytokine molecule is IL-18, e.g., human IL-18 (e.g., comprising the amino acid sequence: YFGKLESKLSVIRNLNDQVLFIDQGNRPLFEDMTDSDCRDNAPRTIFIISMYKDSQPRGM AVTISVKCEKISTLSCENKIISFKEMNPPDNIKDTKSDIIFFQRSVPGHDNKMQFESSSY EGYFLACEKERDLFKLILKKEDELGDRSIMFTVQNED (SEQ ID NO: 74), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 74).

In other embodiments, the cytokine molecule is IL-21, e.g., human IL-21 (e.g., comprising the amino acid sequence: QGQDRHMIRMRQLIDIVDQLKNYVNDLV-PEFLPAPEDVETNCEWSAFSCFQKAQLKSA NTGNNE-RIINVSIKKLKRKPPSTNAGRRQKHRLTCPSCDSY-EKKPPKEFLERFKSLLQKMI HQHLSSRTHGSEDS (SEQ ID NO: 22), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 22).

In yet other embodiments, the cytokine molecule is interferon gamma, e.g., human interferon gamma (e.g., comprising the amino acid sequence: QDPYVKEAENLKKYFN-AGHSDVADNGTLFLGILKNWKEESDRKIMQSQIVS-FYFKLFKNFKDDQSIQKSVETIKEDMNVKFFNSNK-KKRDDFEKLTNYSVTDLNVQRKAIHELIQVMAELS-PAAKTGKRKRSQMLFRG (SEQ ID NO: 23), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 23).

Linkers

In some embodiments, the multifunctional molecule further comprises a linker, e.g., a linker between the tumor targeting moiety and the stromal modifying moiety, the cytokine molecule and the immunoglobulin chain constant region (e.g., the Fc region), the targeting moiety and the immunoglobulin chain constant region, or the immune cell engager and the immunoglobulin chain constant region.

In some embodiments, the linker is selected from: a cleavable linker, a non-cleavable linker, a peptide linker, a flexible linker, a rigid linker, a helical linker, or a non-helical linker. In some embodiments, the linker is a peptide linker. In some embodiments, the peptide linker comprises Gly and Ser. In some embodiments, the peptide linker is selected from GGGGS (SEQ ID NO: 42); GGGGSGGGGSGGGGS (SEQ ID NO: 44); and DVPSGPGGGGSGGGGS (SEQ ID NO: 45). In some embodiments, the peptide linker is a A(EAAAK)nA family of linkers (e.g., as described in Protein Eng. (2001) 14 (8): 529-532). These are stiff helical linkers with n ranging from 2-5. In some embodiments, the peptide linker is selected from

AEAAAKEAAAKAAA; (SEQ ID NO: 75)

AEAAAKEAAAKEAAAKAAA; (SEQ ID NO: 76)

AEAAAKEAAAKEAAAKEAAAKAAA; (SEQ ID NO: 77)
and

AEAAAKEAAAKEAAAKEAAAKEAAAKAAA. (SEQ ID NO: 78)

Configurations of the Multifunctional Molecules

In some embodiments, the multifunctional molecule includes a single chain antibody molecule, e.g., a single domain antibody, a scFv, a camelid, or a shark antibody, and a second moiety. In some embodiments, the multifunctional molecule comprises a VH to VL from N to C orientation, of the scFv connected, optionally via a linker, to the second moiety (e.g., as shown in FIGS. 1A and 1B); the scFv can form the first binding specificity (depicted as binding moiety "1" in FIGS. 1A-1B). In some embodiments, the second moiety (depicted as partner A in FIGS. 1A-1B) is located before the VH region of the scFv from an N- to C-orientation (e.g., as shown in FIG. 1A), or after the VL region of the scFv from an N- to C-orientation (e.g., as shown in FIG. 1B); the second moiety can form the second binding specificity (depicted as binding moiety "2" in FIGS. 1A-1B). In other embodiments, the multifunctional molecule comprises a VL to VH from N to C orientation, of the scFv connected, optionally via a linker, to the second moiety (e.g., as shown in FIGS. 2A and 2B); the scFv can form the first binding specificity (depicted as binding moiety "1" in FIGS. 2A-2B). In some embodiments, the second moiety (depicted as partner A in FIGS. 2A-2B) is located before the VL region of the scFv from an N- to C-orientation (e.g., as shown in FIG. 2A), or after the VH region of the scFv from an N- to C-orientation (e.g., as shown in FIG. 2B); the second moiety can form the second binding specificity (depicted as binding moiety "2" in FIGS. 2A-2B). In embodiments, the scFv can be a tumor targeting moiety (e.g., binds to a cancer antigen, e.g., a solid tumor, stromal, or hematological antigen), or can be an immune cell engager (e.g., binds to an immune cell antigen). In other embodiments, the second moiety (e.g., depicted as partner A in FIG. 1A-1B or 2A-2B) is a stromal modifying, e.g., as described herein.

In other embodiments, the multifunctional molecule is a trispecific or trifunctional that includes, or consists of, a single chain polypeptide, e.g., a contiguous single polypeptide chain. For example, the multifunctional molecule can include a tumor targeting moiety (e.g., a first binding specificity to a cancer antigen, e.g., a solid tumor, stromal, or hematological antigen as described herein), a stromal modifying, e.g., as described herein, and one of: a cytokine molecule as described herein, and an immune cell engager (e.g., a second binding specificity to an immune cell antigen as described herein), or any combination of any of the aforesaid.

In some embodiments, the multifunctional molecule includes a single chain antibody molecule, e.g., a single domain antibody, a scFv, a camelid, or a shark antibody, and a second moiety. In some embodiments, the multifunctional molecule comprises a VH to VL from N to C orientation, of the scFv connected, optionally via a linker, to a second moiety and/or a third moiety (e.g., as shown in FIG. 1C); the scFv can form the first binding specificity (depicted as binding moiety "1" in FIG. 1C). In some embodiments, the second or third moieties (depicted as partners A and B in FIG. 1C) is located before the VH region of the scFv from an N- to C-orientation (e.g., as shown in FIG. 1C) and the third moiety (partner B) after the VL region of the scFv from an N- to C-orientation (e.g., as shown in FIG. 1C), respectively; the second and third moieties can form the second and third binding specificities (depicted as binding moiety "2" and binding moiety "3," respectively, in FIG. 1C). In other embodiments, the multifunctional molecule comprises a VL to VH from N to C orientation, of the scFv connected, optionally via a linker, to a second moiety and/or a third moiety (e.g., as shown in FIG. 2C). In some embodiments, the second moiety (depicted as partner A in FIG. 2C) is located before the VL region of the scFv from an N- to C-orientation (e.g., as shown in FIG. 2C), and the third moiety (partner B) after the VH region of the scFv from an N- to C-orientation (e.g., as shown in FIG. 2C); the second and third moieties can form the second and third binding specificities (depicted as binding moiety "2" and binding moiety "3," respectively, in FIG. 2C). In embodiments, the scFv of any of the aforesaid multifunctional molecules can be a tumor targeting moiety (e.g., bind to a cancer antigen, e.g., a solid tumor, stromal or hematological antigen) or can be an immune cell engager (e.g., bind to an immune cell antigen). In embodiments, the second moiety or the third moiety (e.g., depicted as partner A and partner B in FIG. 1C or 2C) include a stromal modifying, e.g., as described herein, with the remaining moiety being chosen from a second tumor targeting moiety, an immune cell engager, or a cytokine molecule (e.g., as described herein). In embodiments, partner A and/or partner B can be an antibody molecule (e.g., a single chain antibody molecule (e.g., a scFv or a Fab), a stromal modifying moiety, receptor molecule, or a ligand molecule (e.g., a receptor ligand or a cytokine molecule), e.g., as described herein. In one embodiment, the tumor-targeting moiety is a scFv to a cancer cell antigen, the second moiety is a stromal modifying, e.g., as described herein, and third moiety is independently chosen from a cytokine molecule or an immune cell engager. In some embodiments, the second and third moiety is independently chosen from a stromal modifying moiety, a second antibody molecule (e.g., a second scFv or Fab), a receptor molecule, or a ligand molecule (e.g., a receptor ligand or a cytokine molecule).

In embodiments, the multifunctional molecule is a bispecific or bifunctional molecule, wherein the first and second polypeptides (i) and (ii) are non-contiguous, e.g., are two separate polypeptide chains. In embodiments, the first and second polypeptides have a configuration as shown in FIGS. 3A-3B or FIGS. 4A-4B. In embodiments, the first and second polypeptides form a first binding specificity, e.g., an antigen binding domain (e.g., depicted as binding moiety "1" in FIGS. 3A-3B and FIGS. 4A-4B). In embodiments, a second moiety (depicted as partner A) is connected, e.g., via a linker, to either the first polypeptide or the second polypeptide. In embodiments, the second moiety forms a second binding specificity (e.g., depicted as binding moiety "2" in FIGS. 3A-3B and FIGS. 4A-4B).

In one embodiment depicted in FIGS. 3A-3B, the second moiety (e.g., partner A) is connected, e.g., via a linker, to the C-terminus of the second polypeptide (e.g., the C-terminus of the CL region of the second polypeptide) (e.g., as shown in FIG. 3A). In other embodiments, the second moiety (e.g., partner A) is connected, e.g., via a linker, to the C-terminus of the first polypeptide (e.g., C-terminus of the CH1 region of the first polypeptide) (e.g., as shown in FIG. 3B).

In another embodiment depicted in FIGS. 4A-4B, the second moiety (e.g., partner A) is connected, e.g., via a linker, to the N-terminus of the second polypeptide (e.g., the N-terminus of the VL region of the second polypeptide) (e.g., as shown in FIG. 4A). In other embodiments, the second moiety (e.g., partner A) is connected, e.g., via a linker, to the N-terminus of the first polypeptide (e.g., the N-terminus of the VH region of the first polypeptide) (e.g., as shown in FIG. 4B).

In embodiments, the first and second polypeptide (e.g., the VH and VL regions) can form a binding moiety (e.g., binding moiety 1 in FIGS. 3A-3B and 4A-4B); for example, the first and second polypeptide can be a tumor targeting moiety (e.g., bind to a cancer antigen, e.g., a solid tumor, a stromal or hematological antigen) or can be an immune cell engager (e.g., bind to an immune cell antigen). In embodiments, the second moiety (e.g., depicted as partner A in FIGS. 3A-3B and 4A-4B) includes a stromal modifying moiety, e.g., a stromal modifying moiety as described herein.

In embodiments, the multispecific molecule is a bispecific or bifunctional molecule, wherein the first and second polypeptides (i) and (ii) are non-contiguous, e.g., are two separate polypeptide chains. In embodiments, the first and second polypeptides have a configuration as shown in FIGS. 3A-3B or FIGS. 4A-4B. In embodiments, a second moiety (depicted as partner A) is connected, e.g., via a linker, to either the first polypeptide or the second polypeptide (e.g., either the N-terminus or the C-terminus of the first polypeptide or the second polypeptide).

In one embodiment of the bispecific or bifunctional molecule depicted in FIGS. 3A-3B, the second moiety (e.g., partner A) is connected, e.g., via a linker, to the CL region (e.g., C-terminus of the CL region) of the second polypeptide (e.g., as shown in FIG. 3A). In other embodiments, the second moiety (e.g., partner A) is connected, e.g., via a linker, to the CH1 region (e.g., C-terminus of the CH1 region) of the first polypeptide (e.g., as shown in FIG. 3B).

In another embodiment of the bispecific or bifunctional molecule depicted in FIGS. 4A-4B, the second moiety (e.g., partner A) is connected, e.g., via a linker, to the VL region (e.g., N-terminus of the VL region) of the second polypeptide (e.g., as shown in FIG. 4A). In other embodiments, the second moiety (e.g., partner A) is connected, e.g., via a linker, to the VH region (e.g., N-terminus of the VH region) of the first polypeptide (e.g., as shown in FIG. 4B).

In embodiments of the bispecific or bifunctional molecule, the first and second polypeptide (e.g., the VH and VL regions) can form a binding moiety (e.g., binding moiety 1 in FIGS. 3A-3B and 4A-4B); for example, the first and second polypeptide can be a tumor targeting moiety (e.g., bind to a cancer antigen, e.g., a tumor, a stromal or a hematological antigen) or can be an immune cell engager (e.g., bind to an immune cell antigen). In embodiments, the second moiety (e.g., depicted as partner A in FIGS. 3A-3B and 4A-4B) includes a stromal modifying moiety, e.g., as described herein.

In one embodiment, the multispecific molecule includes a Fab molecule and the second moiety is chosen from a stromal modifying moiety, or a second antibody molecule (e.g., a scFv or a second Fab), a receptor molecule, or a ligand molecule (e.g., a cytokine molecule). In one embodiment, the tumor-targeting moiety is a Fab to a cancer cell antigen, and the second moiety includes a stromal modifying moiety, optionally further including a cytokine molecule or an immune cell engager. In some embodiments, the second moiety is a second antibody molecule (e.g., a second scFv or Fab), a stromal modifying moiety, a receptor molecule, a receptor ligand molecule, or a cytokine molecule.

In other embodiments, the multispecific molecule is a trispecific or a trifunctional molecule, wherein the first and second polypeptides (i) and (ii) are non-contiguous, e.g., are two separate polypeptide chains. In embodiments, the first and second polypeptides have a configuration as shown in FIGS. 3C and 4C. In embodiments, a second moiety and a third moiety (depicted as partners A and B, respectively) are connected, e.g., via a linker, to the C-terminus, the N-terminus, or both of the first polypeptide and the second polypeptide, respectively. In one embodiment, the second moiety and third moieties are connected to C-terminus of the second and first polypeptides (or the first and second polypeptides), respectively. In another embodiment, the second moiety and third moieties are connected to N-terminus of the second and first polypeptides (or the first and second polypeptides), respectively. In one embodiment, the second moiety and third moiety are connected to N- and C-terminus of the second and first polypeptides (or the first and second polypeptides), respectively. Any configuration is intended by the present disclosure, including those exemplified in FIGS. 3C and 4C.

In one embodiment of the trispecific or trifunctional molecule depicted in FIGS. 3C-4C, the second moiety (e.g., partner A corresponding to the second binding specificity "2") is connected, e.g., via a linker, to the C-terminus of the second polypeptide (e.g., the C-terminus of the CL region of the second polypeptide) (e.g., as shown in FIG. 3C), and the third moiety (e.g., partner B corresponding to the third binding specificity "3") is connected, e.g., via a linker, to the C-terminus of the first polypeptide (e.g., the C-terminus of the CH1 region of the first polypeptide) (e.g., as shown in FIG. 3C).

In another embodiment of the trispecific or trifunctional molecule depicted in FIGS. 3C-4C, the second moiety (e.g., partner A corresponding to the second binding specificity "2") is connected, e.g., via a linker, to the N-terminus of the second polypeptide (e.g., the N-terminus of the VL region of the second polypeptide) (e.g., as shown in FIG. 4C), and the third moiety (e.g., partner B corresponding to the third binding specificity "3") is connected, e.g., via a linker, to the N-terminus of the first polypeptide (e.g., the N-terminus of the VH region of the first polypeptide) (e.g., as shown in FIG. 4C).

In another embodiment of the trispecific or trifunctional molecule, the second moiety (e.g., partner A corresponding to the second binding specificity "2") is connected, e.g., via a linker, to the N-terminus of the second polypeptide (e.g., the N-terminus of the VL region of the second polypeptide), and the third moiety (e.g., partner B corresponding to the third binding specificity "3") is connected, e.g., via a linker, to the C-terminus of the first polypeptide (e.g., the C-terminus of the CH1 region of the first polypeptide).

In another embodiment of the trispecific or trifunctional molecule, the second moiety (e.g., partner A corresponding to the second binding specificity "2") is connected, e.g., via a linker, to the C-terminus of the second polypeptide (e.g., the N-terminus of the CL region of the second polypeptide), and the third moiety (e.g., partner B corresponding to the third binding specificity "3") is connected, e.g., via a linker, to the N-terminus of the first polypeptide (e.g., the N-terminus of the VH region of the first polypeptide).

In embodiments of the trispecific or trifunctional molecule, the first and second polypeptides (e.g., the VH and VL regions) can form a first binding specificity (e.g., binding moiety "1" in FIGS. 3C and 4C); for example, the first and second polypeptide can be a tumor targeting moiety (e.g., bind to a cancer antigen, e.g., a solid tumor, a stromal or a hematological antigen) or can be an immune cell engager (e.g., bind to an immune cell antigen). In embodiments, the second moiety or the third moiety (e.g., depicted as partners A and B in FIGS. 3C and 4C) includes a stromal modifying moiety, e.g., a stromal modifying moiety as described herein, and the remaining moiety is chosen from a tumor targeting moiety, an immune cell engager, or a cytokine molecule (e.g., as described herein). In embodiments, the second and a third binding specificity, e.g., partners A and B, can be, independently, a stromal modifying moiety, an enzyme molecule, an antibody molecule (e.g., a single chain antibody molecule (e.g., a scFv) or a Fab), a receptor molecule, a ligand molecule (e.g., a receptor ligand or a cytokine molecule), e.g., as described herein. In one embodiment, the multifunctional molecule includes a Fab molecule and the second moiety or third moiety includes a stromal modifying moiety, and the remaining moiety is chosen from a second antibody molecule (e.g., a scFv or a second Fab), a receptor molecule, or a ligand molecule (e.g., a receptor ligand or a cytokine molecule). In some embodiments, the first binding specificity, the second binding specificity and the third binding specificity can each be independently chosen from a tumor targeting moiety, a stromal modifying moiety, a cytokine molecule, an NK cell engager, a T cell engager, a B cell engager, a dendritic cell engager, or a macrophage cell engager. In one embodiment, the tumor-targeting moiety is a Fab to a cancer cell antigen, and the second or third moiety is a stromal modifying moiety, and the remaining moiety is chosen from a cytokine molecule or an immune cell engager.

In one embodiment, the multifunctional molecule includes at least two, at least three, or at least four non-contiguous polypeptides, wherein:

(i) the first polypeptide includes from N- to C-orientation a first immunoglobulin constant region (e.g., a CH2 connected to a CH3 region) (e.g., a first Fc region); and (ii) the second polypeptide includes from N- to C-orientation a second immunoglobulin constant region (e.g., a CH2 connected to a CH3 region) (e.g., a second Fc region).

In embodiments, the multifunctional molecule is a bispecific or bifunctional molecule, wherein the first and second polypeptides (i) and (ii) are non-contiguous, e.g., are two separate polypeptide chains. In some embodiments, the first and second polypeptides (i) and (ii) include a paired amino acid substitution at a position chosen from one or more of 347, 349, 350, 351, 366, 368, 370, 392, 394, 395, 397, 398, 399, 405, 407, or 409, e.g., of the Fc region of human IgG1 For example, the first immunoglobulin chain constant region (e.g., the first Fc region) can include an amino acid substitution chosen from: T366S, L368A, or Y407V (e.g., corresponding to a cavity or hole), and the second immunoglobulin chain constant region (e.g., the second Fc region) includes a T366W (e.g., corresponding to a protuberance or knob). In some embodiments, the first and second polypeptides are a first and second member of a heterodimeric first and second Fc region.

In embodiments, the first and second polypeptides form a bifunctional, e.g., a bispecific, molecule. In some embodiments, the first polypeptide includes a first binding and/or functional specificity (e.g., partner A or binding specificity 1 in FIG. 5A), and the second polypeptide includes a second binding and/or functional specificity (e.g., partner B or binding specificity 2 in FIG. 5A). In embodiments, the first and second binding and/or functional specificities (partner A and partner B, respectively) is each independently chosen from a stromal modified moiety, an enzyme molecule, an antibody molecule (e.g., a single chain antibody molecule (e.g., a scFv) or a Fab), a receptor molecule, a ligand molecule (e.g., a receptor ligand or a cytokine molecule), e.g., as described herein. In embodiments, the first and second binding specificities are connected to either the first or the second polypeptide, or each of the polypeptides, (e.g., one or both members of a heterodimeric Fc molecule). In one embodiment, the first binding specificity (e.g., partner A) is connected to the N-terminal end of the first polypeptide (e.g., a -CH2-CH3-region of the first Fc molecule), and the second binding specificity (e.g., partner B) is connected to the N-terminal end of the second polypeptide (e.g., a -CH2-CH3-region of the second Fc molecule). Alternatively, the first binding and/or functional specificity (e.g., partner A) is connected to the C-terminal end of the first polypeptide (e.g., a -CH2-CH3-region of the first Fc molecule), and the second binding and/or functional specificity (e.g., partner B) is connected to the C-terminal end of the second polypeptide (e.g., a -CH2-CH3-region of the second Fc molecule). Alternatively, the first binding specificity (e.g., partner A) is connected to the N-terminal end of the first polypeptide (e.g., a -CH2-CH3-region of the first Fc molecule), and the second binding specificity (e.g., partner B) is connected to the C-terminal end of the second polypeptide (e.g., a -CH2-CH3-region of the second Fc molecule). In other embodiments, the second binding and/or functional specificity (e.g., partner B) is connected to N-terminus of the first polypeptide (e.g., the -CH2-CH3-region of the first Fc molecule), and the first binding and/or functional specificity (e.g., partner A) is connected to the C-terminal end of the second polypeptide (e.g., a -CH2-CH3-region of the second Fc molecule). In one embodiment, the first CH2-CH3 region includes a protuberance or knob, and the second -CH2-CH3 region includes a cavity or hole, e.g., as depicted in FIG. 5A).

In some embodiments, the first and second binding and/or functional specificities (binding moiety 1 and binding moiety 2) of the bifunctional molecule can each be independently chosen from a stromal modifying moiety, a tumor targeting moiety, a cytokine molecule, an NK cell engager, a T cell engager, a B cell engager, a dendritic cell engager, or a macrophage cell engager. In some embodiments, the first binding and/or functional specificity is a tumor targeting moiety and the second binding and/or functional specificity is a stromal modifying moiety. In other embodiments, the first binding and/or functional specificity is an immune cell engager and the second binding and/or functional specificity is a stromal modifying moiety, e.g., wherein the immune cell engager is chosen from a cytokine molecule, an NK cell engager, a T cell engager, a B cell engager, a dendritic cell engager, or a macrophage cell engager.

In some embodiments shown in FIG. 5A, the bispecific molecule can have partner A and B, which are depicted as first and second binding and/or functional specificities (binding moieties 1 and 2), respectively (FIG. 5A). The first and second binding and/or functional specificities can be, each independently, a stromal modifying moiety, an enzyme molecule, an antibody molecule (e.g., a single chain antibody molecule (e.g., a scFv) or a Fab), a receptor molecule, a ligand molecule (e.g., a receptor ligand or a cytokine molecule), e.g., as described herein. In some embodiments, the first binding and/or functional specificity is a tumor targeting moiety and the second binding and/or functional specificity is a stromal modifying moiety. In other embodiments, the first binding and/or functional specificity is an immune cell engager and the second binding and/or functional specificity is a stromal modifying moiety, e.g., wherein the immune cell engager is chosen from a cytokine molecule, an NK cell engager, a T cell engager, a B cell engager, a dendritic cell engager, or a macrophage cell engager.

In embodiments, the first and second polypeptides form a trifunctional, e.g., a trispecific, or a tetrafunctional, e.g., a tetraspecific, molecule (e.g., as depicted in FIGS. 5B-5C, respectively).

In some embodiments of the trifunctional, e.g., the trispecific, molecule, the first polypeptide includes a first binding and/or functional specificity (e.g., partner A or binding moiety 1 in FIG. 5B), and the second polypeptide includes a second binding and/or functional specificity (e.g., partner B or binding specificity 2 in FIG. 5B), wherein either the first or the second polypeptide further includes a third binding and/or functional specificity (e.g., partner C or binding moiety 3 in FIG. 5B). In embodiments, the first and second binding and/or functional specificities are connected to either the first or the second polypeptide, or each of the polypeptides, (e.g., one or both members of a heterodimeric Fc molecule). In one embodiment, the first and second binding and/or functional specificities are connected, e.g., via a linker, to the N-terminus of the first and the second polypeptide, respectively, and the third binding and/or functional specificity is connected, e.g., via a linker, to the C-terminal end of either the first or the second polypeptide. In one embodiment, the third binding and/or functional specificity is connected, e.g., via a linker, to the C-terminal end of the first polypeptide (e.g., the C-terminal end of the first -CH2-CH3 region depicted in FIG. 5B). In one embodiment, the third binding and/or functional specificity is connected, e.g., via a linker, to the C-terminal end of the second polypeptide (e.g., the C-terminal end of the second -CH2-CH3 region). In one embodiment, the first -CH2-CH3 region includes a protuberance or knob, and the second -CH2-CH3 region includes a hole or cavity, e.g., as depicted in FIG. 5B).

In embodiments, the first, second and third binding and/or functional specificities (partner A, partner B, and partner C respectively) is each independently chosen from a stromal modifying moiety, an enzyme molecule, an antibody molecule (e.g., a single chain antibody molecule (e.g., a scFv) or a Fab), a receptor molecule, a ligand molecule (e.g., a receptor ligand or a cytokine molecule), e.g., as described herein. In one embodiment, the first binding and/or functional specificity (e.g., partner A) is connected to the N-terminal end of the first polypeptide (e.g., a -CH2-CH3-region of the first Fc molecule); the second binding and/or functional specificity (e.g., partner B) is connected to the N-terminal end of the second polypeptide (e.g., a -CH2-CH3-region of the second Fc molecule); and the third binding and/or functional specificity (e.g., partner C) is connected to the C-terminal end of the first polypeptide (e.g., a -CH2-CH3-region of the second Fc molecule). In other embodiments, the first binding and/or functional specificity (e.g., partner A) is connected to the N-terminal end of the first polypeptide (e.g., a -CH2-CH3-region of the first Fc molecule); the second binding and/or functional specificity (e.g., partner B) is connected to the N-terminal end of the second polypeptide (e.g., a -CH2-CH3-region of the first Fc molecule); and the third binding and/or functional specificity (e.g., partner C) is connected to the C-terminal end of the second polypeptide (e.g., a -CH2-CH3-region of the second Fc molecule). The first, second and third binding and/or functional specificities can each be, independently, a stromal modifying moiety, an enzyme molecule, an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, the first, second and third binding and/or functional specificities (partners A-C, corresponding to binding moieties 1-3, respectively) are each independently chosen from a tumor targeting moiety, a stomal modifying moiety, a cytokine molecule, an NK cell engager, a T cell engager, a B cell engager, a dendritic cell engager, or a macrophage cell engager, e.g., as described herein. In embodiments, the first binding and/or functional specificity is a tumor targeting moiety, the second binding and/or functional specificity is a stromal modifying moiety, and the third binding and/or functional specificity is chosen from a cytokine molecule, an NK cell engager, a T cell engager, a B cell engager, a dendritic cell engager, or a macrophage cell engager.

In some embodiments of the tetrafunctional, e.g., the tetraspecific, molecule, the first polypeptide includes a first binding and/or functional specificity (e.g., partner A or binding moiety 1 in FIG. 5C) and a third binding and/or functional specificity (e.g., partner C or binding moiety 3 in FIG. 5C), and the second polypeptide includes a second binding and/or functional specificity (e.g., partner B or binding specificity 2 in FIG. 5C) and a fourth binding and/or functional specificity (e.g., partner D or binding moiety 4 in FIG. 5C). In one embodiment, the first and second binding specificities are connected, e.g., via a linker, to the N-terminus of the first and the second polypeptide, respectively, and the third and fourth binding specificities are connected, e.g., via a linker, to the C-terminal end of the first and the second polypeptide, respectively. Any permutation of binding and/or functional specificity to the N- or C-terminus of the first or second polypeptide is encompassed by the present disclosure. In one embodiment, the first binding and/or functional specificity (e.g., partner A) is connected, e.g., via a linker, to the N-terminal end of the first polypeptide (e.g., the N-terminal end of the first -CH2-CH3 region depicted in FIG. 5C); the second binding and/or functional specificity (e.g., partner B) is connected, e.g., via a linker, to the N-terminal end of the second polypeptide (e.g., the N-terminal end of the second -CH2-CH3 region depicted in FIG. 5C); the third binding and/or functional specificity (e.g., partner C) is connected, e.g., via a linker, to the C-terminal end of the first polypeptide (e.g., the C-terminal end of the first -CH2-CH3 region depicted in FIG. 5C); and the fourth binding and/or functional specificity (e.g., partner D) is connected, e.g., via a linker, to the C-terminal end of the second polypeptide (e.g., the C-terminal end of the second -CH2-CH3 region). In one embodiment, the first -CH2-CH3 region includes a protuberance or knob, and the second -CH2-CH3 region includes a cavity or hole, e.g., as depicted in FIG. 5C. In embodiments, the first, second, third and fourth binding and/or functional specificities (partner A, partner B, partner C and partner D, respectively) is each independently chosen from a stromal modifying moiety, an enzyme molecule, an antibody molecule (e.g., a single chain antibody molecule (e.g., a scFv) or a Fab), a receptor molecule, a ligand molecule (e.g., a receptor ligand or a cytokine molecule), e.g., as described herein. The first, second, third and fourth binding and/or functional specificities can each be, independently, a stromal modifying moiety, an enzyme molecule, an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, the first, second, third and fourth binding and/or functional specificities (partners A-D, corresponding to binding moieties 1-4, respectively) are each independently chosen from a tumor targeting moiety, a stromal modifying moiety, a cytokine molecule, an NK cell engager, a T cell engager, a B cell engager, a dendritic cell engager, or a macrophage cell engager, e.g., as described herein. In embodiments, the first binding and/or functional specificity is a tumor targeting moiety, the second binding and/or functional specificity is a stromal modifying moiety, and the third and fourth binding and/or functional specificities are each independently chosen from a cytokine molecule, an NK cell engager, a T cell engager, a B cell engager, a dendritic cell engager, or a macrophage cell engager.

In one embodiment, the multifunctional molecule is a bispecific molecule that includes two non-contiguous first and second polypeptides. In embodiments, the first and second polypeptides, include, respectively, a first and a second binding sites, which are independently chosen from a stromal modifying moiety, an enzyme molecule, an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, the first and second binding and/or functional specificities (binding sites 1-2, respectively) are each independently chosen from a stromal modifying moiety, a tumor targeting moiety, a cytokine molecule, an NK cell engager, a T cell engager, a B cell engager, a dendritic cell engager, or a macrophage cell engager, e.g., as described herein. In some embodiments, the first polypeptide has the following configuration from N-to-C: a first portion of a first antigen domain, e.g., a first VH-CH1 of a Fab molecule, that binds to, e.g., a cancer antigen (e.g., binding site #1), connected, optionally, via a linker to, a second binding and/or functional specificity (e.g., a binding site #2, e.g., a stromal modifying moiety, e.g., as described herein); and the second polypeptide has the following configuration from N-to-C: a second portion of a first antigen domain, e.g., a first VL-CL of the Fab, that binds to, e.g., a cancer antigen (e.g., the same cancer antigen bound by the first VH-CH1, e.g., binding site #1) (e.g., an example of this configuration is depicted in FIG. 16). In one embodiment, the bispecific molecule that includes a Fab corresponding to the first binding and/or functional specificity (binding site #1) connected, optionally via a linker, to the second binding and/or functional specificity (e.g., binding site #2, e.g., a stromal modifying moiety, e.g., as described herein). In some embodiments, the first binding and/or functional specificity (e.g., binding site #1 in FIG. 16) is a tumor targeting moiety, e.g., binds to a cancer antigen, e.g., a tumor or stromal antigen; and the second binding and/or functional specificity (e.g., binding site #2 in FIG. 16) is a stromal modifying moiety, e.g., as described herein.

In another embodiment, the multifunctional molecule is a bifunctional, e.g., a bispecific, molecule that includes two or at least three non-contiguous first and second polypeptides, wherein:

(i) the first polypeptide includes from N- to C-orientation a first binding and/or functional specificity, e.g., a first antibody molecule, connected, optionally via a linker, to a first immunoglobulin constant region (e.g., a CH2 connected to a CH3 region) (e.g., a first Fc region);

(ii) the second polypeptide includes from N- to C-orientation a second immunoglobulin constant region (e.g., a CH2 connected to a CH3 region) (e.g., a second Fc region); and (optionally) (iii) a third polypeptide comprising a portion of the first antibody molecule or a second antibody molecule.

In embodiments, the first and second polypeptides, include, respectively, a first and a second binding and/or functional specificities (e.g., sites), which are independently chosen from a stromal modifying moiety, an enzyme molecule, an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, the first and second binding and/or functional specificities (binding sites 1-2, respectively) are a tumor targeting moiety and a stromal modifying moiety, e.g., as described herein.

In some embodiments, the first polypeptide has the following configuration from N-to-C:

(a) a first portion of a first antigen domain, e.g., a first VH-CH1 of a Fab molecule, that binds to, e.g., a cancer antigen, e.g., a solid tumor, stromal or hematological antigen (e.g., binding site #1), connected, optionally, via a linker to, the first immunoglobulin constant region (e.g., the CH2 connected to the CH3 region) (e.g., a first Fc region);

(b) a second binding and/or functional specificity (e.g., a second binding site), which is a stromal modifying moiety, connected, optionally, via a linker to, the second immunoglobulin constant region (e.g., the CH2 connected to the CH3 region) (e.g., the second Fc region); and (c) the third polypeptide has the following configuration from N-to-C: a second portion of the first antigen domain, e.g., a first VL-CL of the Fab, that binds to, e.g., a cancer antigen, e.g., a solid tumor, stromal or hematological antigen (e.g., the same cancer antigen bound by the first VH-CH1, e.g., binding site #1) (e.g., an example of this configuration is depicted in FIG. 7).

In one embodiment, the bifunctional, e.g., bispecific, molecule that includes a Fab corresponding to the first binding and/or functional specificity (binding site #1) connected, optionally via a linker, to the first Fc region, and the second binding and/or functional specificity (e.g., binding site #2, e.g., a stromal modifying moiety, e.g., as described herein) connected, optionally via a linker, to the second Fc region.

In some embodiments, the first binding and/or functional specificity (e.g., binding site #1 in FIG. 17) is a tumor targeting moiety, e.g., binds to a cancer antigen, e.g., a tumor or stromal antigen; and the second binding and/or functional specificity (e.g., binding site #2 in FIG. 17) is a stromal modifying moiety, e.g., as described herein.

In embodiments, the first immunoglobulin constant region (e.g., the first CH2-CH3 region) includes a protuberance or knob, e.g., as described herein.

In embodiments, the second immunoglobulin constant region (e.g., the second CH2-CH3 region) includes a cavity or hole. In embodiments, the first and second immunoglobulin constant region promote heterodimerization of the bispecific molecule.

In one embodiment, the multifunctional molecule is a trifunctional, e.g., a trispecific, molecule that includes two non-contiguous first and second polypeptides. In embodiments, the first and second polypeptides, include, respectively, a first, a second and a third binding and/or functional specificities, which are independently chosen from a stromal modifying moiety, an enzyme molecule, an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, the first, second and third binding and/or functional specificities (binding sites 1-3, respectively) are each independently chosen from a tumor targeting moiety, a stromal modifying moiety, a cytokine molecule, an NK cell engager, a T cell engager, a B cell engager, a dendritic cell engager, or a macrophage cell engager, e.g., as described herein. In some embodiments, the first binding and/or functional specificity (binding site 1) is a tumor targeting moiety, the second binding and/or functional specificity (binding site 2) is a stromal modifying moiety, and the third binding and/or functional specificities (binding site 3) is chosen from a tumor targeting moiety, a stromal modifying moiety, a cytokine molecule, an NK cell engager, a T cell engager, a B cell engager, a dendritic cell engager, or a macrophage cell engager, e.g., as described herein.

In some embodiments, the first polypeptide has the following configuration from N-to-C:

(i) a first portion of a first antigen domain, e.g., a first VH-CH1 of a Fab molecule, that binds to, e.g., a cancer antigen (e.g., binding site #1), connected, optionally, via a linker to, a second binding and/or functional specificity (e.g., a binding site #3, e.g., a cytokine, a ligand or a second antibody molecule, e.g., a scFv); and (ii) the second polypeptide has the following configuration from N-to-C: a second portion of a first antigen domain, e.g., a first VL-CL of the Fab, that binds to, e.g., a tumor or stromal antigen (e.g., the same tumor or stromal antigen bound by the first VH-CH1, e.g., binding site #1), connected, optionally, via a linker to, a third binding and/or functional specificity (e.g., a binding site #2, e.g., a stromal modifying moiety) (e.g., an example of this configuration is depicted in FIG. 18.

In one embodiment, the bifunctional, e.g., bispecific, molecule includes a Fab corresponding to the first binding and/or functional specificity (binding site #1) connected, optionally via a linker, to the second and third binding and/or functional specificities (e.g., binding sites #2 and #3). In some embodiments, the first binding and/or functional specificity (e.g., binding site #1 in FIG. 18) is a tumor targeting moiety, e.g., binds to a cancer antigen, e.g., a tumor, stromal or hematological antigen; the second binding and/or functional specificity (e.g., binding site #2 in FIG. 18) is chosen from a cytokine molecule, or an immune cell engager, e.g., chosen from a receptor, a ligand molecule or an antibody molecule (e.g., a scFv) that binds to an immune cell antigen; and the third binding and/or functional specificity (e.g., binding site #3) is a stromal modifying moiety. In embodiments where the antibody molecule is a scFV, the scFv may be connected to the C-terminus of the first polypeptide in a VH-VL or a VL-VH configuration.

In another embodiment, the multifunctional molecule is a trifunctional, e.g., a trispecific, molecule that includes two or at least three non-contiguous first and second polypeptides, wherein:

(i) the first polypeptide includes from N- to C-orientation a first binding specificity, e.g., a first antibody molecule, connected, optionally via a linker, to a first immunoglobulin constant region (e.g., a CH2 connected to a CH3 region) (e.g., a first Fc region);

(ii) the second polypeptide includes from N- to C-orientation a second binding specificity connected, optionally via a linker, to a second immunoglobulin constant region (e.g., a CH2 connected to a CH3 region) (e.g., a second Fc region); and (optionally) (iii) a third polypeptide comprising a portion of the first antibody molecule or a second antibody molecule, wherein either the first or the second polypeptide further includes a third binding and/or functional specificity.

In embodiments, the first and second polypeptides, include, respectively, a first, a second, and a third binding and/or functional specificities (e.g., sites), which are independently chosen from a stromal modifying moiety, an enzyme molecule, an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, the first, second and third binding and/or functional specificities (binding sites 1-3, respectively) are each independently chosen from a tumor targeting moiety, a stromal modifying moiety, a cytokine molecule, an NK cell engager, a T cell engager, a B cell engager, a dendritic cell engager, or a macrophage cell engager, e.g., as described herein. In one embodiment, the first binding and/or functional specificity (binding site #1) is a tumor targeting moiety, the second binding and/or functional specificity (binding site #2) is an immune cell engager or a cytokine molecule, and the third binding and/or functional specificity (binding site #3) is a stromal modifying moiety, e.g., as shown in FIG. 19A or 19B.

In some embodiments, the first polypeptide has the following configuration from N-to-C:

(a) a first portion of a first antigen domain, e.g., a first VH-CH1 of a Fab molecule, that binds to, e.g., a tumor or stromal antigen (e.g., binding site #1), connected, optionally, via a linker to, the first immunoglobulin constant region (e.g., the CH2 connected to the CH3 region) (e.g., a first Fc region);

(b) a second binding and/or functional specificity (e.g., a second binding site), which is chosen from a cytokine molecule, or an immune cell engager, connected, optionally, via a linker to, the second immunoglobulin constant region (e.g., the CH2 connected to the CH3 region) (e.g., the second Fc region); and (c) the third polypeptide has the following configuration from N-to-C: a second portion of the first antigen domain, e.g., a first VL-CL of the Fab, that binds to, e.g., a tumor or stromal antigen (e.g., the same tumor or stromal antigen bound by the first VH-CH1, e.g., binding site #1), wherein either the first or the second polypeptide further includes a third binding and/or functional specificity, which is connected, optionally, via a linker to, the first or second immunoglobulin constant region (e.g., the CH2 connected to the CH3 region) (e.g., the first or second Fc region). In one embodiment, the third binding specificity is connected, optionally, via a linker to, the first immunoglobulin constant region (e.g., the CH2 connected to the CH3 region) (e.g., the first Fc region). In another embodiment, the third binding specificity is connected, optionally, via a linker to, the second immunoglobulin constant region (e.g., the CH2 connected to the CH3 region) (e.g., the second Fc region). Examples of these configurations are depicted in FIGS. 19A-19B.

In one embodiment, the trifunctional, e.g., trispecific, molecule includes a Fab corresponding to the first binding and/or functional specificity (binding site #1) connected, optionally via a linker, to the first Fc region; and the second binding and/or functional specificity (e.g., binding site #2) connected, optionally via a linker, to the second Fc region, which further includes the third binding and/or functional specificity (e.g., binding site #3) (e.g., as depicted in FIG. 19A). In other embodiments, the trifunctional, e.g., trispecific, molecule includes a Fab corresponding to the first binding and/or functional specificity (binding site #1) connected, optionally via a linker, to the first Fc region, which further includes the third binding and/or functional specificity (e.g., binding site #3); and the second binding and/or functional specificity (e.g., binding site #2) connected, optionally via a linker, to the second Fc region (e.g., as depicted in FIG. 19B).

In some embodiments, (a) the first binding and/or functional specificity (e.g., binding site #1 in FIGS. 19A-19B) is a tumor targeting moiety, e.g., binds to a cancer antigen, e.g., a tumor or stromal antigen; (b) the second binding and/or functional specificity (e.g., binding site #2 in FIGS. 19A-19B) is chosen from a cytokine molecule, or an immune cell engager, e.g., chosen from a receptor, a ligand molecule or an antibody molecule (e.g., a scFv) that binds to an immune cell antigen; and (c) the third binding and/or functional specificity (e.g., binding site #3 in FIGS. 19A-19B) is a stromal modifying moiety. In embodiments where the antibody molecule is a scFV, the scFv may be connected to the C-terminus of the first polypeptide in a VH-VL or a VL-VH configuration.

In embodiments, the first immunoglobulin constant region (e.g., the first CH2-CH3 region) includes a protuberance or knob, e.g., as described herein.

In embodiments, the second immunoglobulin constant region (e.g., the second CH2-CH3 region) includes a cavity or hole. In embodiments, the first and second immunoglobulin constant region promote heterodimerization of the bispecific molecule.

In another embodiment, the multifunctional molecule is a tetrafunctional, e.g., tetraspecific, molecule that includes two or at least three non-contiguous first and second polypeptides, wherein:

(i) the first polypeptide includes from N- to C-orientation a first binding and/or functional specificity, e.g., a first antibody molecule, connected, optionally via a linker, to a first immunoglobulin constant region (e.g., a CH2 connected to a CH3 region) (e.g., a first Fc region);

(ii) the second polypeptide includes from N- to C-orientation a second binding and/or functional specificity connected, optionally via a linker, to a second immunoglobulin constant region (e.g., a CH2 connected to a CH3 region) (e.g., a second Fc region); and (optionally) (iii) a third polypeptide comprising a portion of the first antibody molecule or a second antibody molecule, wherein the first or the second polypeptide further includes a third and a fourth binding and/or functional specificities.

In embodiments, the first and second polypeptides, include, respectively, a first, a second, a third and a fourth binding and/or functional specificities (e.g., sites), which are independently chosen from a stromal modifying moiety, an enzyme molecule, an antibody molecule (e.g., a single chain antibody molecule (e.g., a scFv) or a Fab), a receptor molecule, a ligand molecule (e.g., a receptor ligand, or a cytokine molecule), e.g., as described herein. In some embodiments, the first, second, third and fourth binding and/or functional specificities (binding sites 1-4, respectively) are each independently chosen from a tumor targeting moiety, a stromal modifying moiety, a cytokine molecule, an NK cell engager, a T cell engager, a B cell engager, a dendritic cell engager, or a macrophage cell engager, e.g., as described herein.

In some embodiments, the first polypeptide has the following configuration from N-to-C:

(a) a first portion of a first antigen domain, e.g., a first VH-CH1 of a Fab molecule, that binds to, e.g., a tumor or stromal antigen (e.g., binding site #1), connected, optionally, via a linker to, the first immunoglobulin constant region (e.g., the CH2 connected to the CH3 region) (e.g., a first Fc region);

(b) a second binding and/or functional specificity (e.g., a second binding site), which is chosen from a cytokine molecule, or an immune cell engager, connected, optionally, via a linker to, the second immunoglobulin constant region (e.g., the CH2 connected to the CH3 region) (e.g., the second Fc region); and (c) the third polypeptide has the following configuration from N-to-C: a second portion of the first antigen domain, e.g., a first VL-CL of the Fab, that binds to, e.g., a tumor or stromal antigen (e.g., the same tumor or stromal antigen bound by the first VH-CH1, e.g., binding site #1), wherein the first and the second polypeptide further includes a third and a fourth binding and/or functional specificity, respectively, each of which is connected, optionally, via a linker to, the first and second immunoglobulin constant region (e.g., the CH2 connected to the CH3 region) (e.g., the first and second Fc region). In one embodiment, the third binding and/or functional specificity is connected, optionally, via a linker to, the second immunoglobulin constant region (e.g., the CH2 connected to the CH3 region) (e.g., the second Fc region); and the fourth binding and/or functional specificity is connected, optionally, via a linker to, the first immunoglobulin constant region (e.g., the CH2 connected to the CH3 region) (e.g., the first Fc region). Examples of these configurations are depicted in FIG. 20.

In one embodiment, the tetrafunctional, e.g., tetraspecific, molecule includes a Fab corresponding to the first binding and/or functional specificity (binding site #1) connected, optionally via a linker, to the first Fc region, which further includes a fourth binding and/or functional specificity (e.g., binding site #4); and the second binding and/or functional specificity (e.g., binding site #2) connected, optionally via a linker, to the second Fc region, which further includes the third binding and/or functional specificity (e.g., binding site #3) (e.g., as depicted in FIG. 20). In other embodiments, the tetrafunctional, e.g., tetraspecific, molecule includes a Fab corresponding to the first binding and/or functional specificity (binding site #1) connected, optionally via a linker, to the first Fc region, which further includes a third binding and/or functional specificity (e.g., binding site #3); and the second binding and/or functional specificity (e.g., binding site #2) connected, optionally via a linker, to the second Fc region, which further includes the fourth binding and/or functional specificity (e.g., binding site #4).

In some embodiments, (a) the first binding and/or functional specificity (e.g., binding site #1 in FIG. 20) is a tumor targeting moiety, e.g., binds to a cancer antigen, e.g., a tumor, stromal or hematological antigen; the second and fourth binding and/or functional specificities (e.g., binding sites #2 and 4 in FIG. 20) are each independently chosen from a cytokine molecule, or an immune cell engager, e.g., chosen from a receptor, a ligand molecule or an antibody molecule (e.g., a scFv) that binds to an immune cell antigen; and the third binding and/or functional specificity (e.g., binding site #3 in FIG. 20) is a stromal modifying moiety. In embodiments where the antibody molecule is a scFV, the scFv may be connected to the C-terminus of the first polypeptide in a VH-VL or a VL-VH configuration.

In another embodiment, (a) the first binding and/or functional specificity is a tumor targeting moiety, e.g., binds to a cancer antigen, e.g., a tumor, stromal or hematological antigen; (b) the second binding and/or functional specificity is an immune cell engager (e.g., an NK cell engager) chosen from a receptor, a ligand molecule or an antibody molecule (e.g., a scFv) that binds to an immune cell antigen; (c) the third binding and/or functional specificity is a cytokine molecule or an immune cell engager; and (d) the fourth binding and/or functional specificity is a stromal modifying moiety. In embodiments where the antibody molecule is a scFV, the scFv may be connected to the C-terminus of the first polypeptide in a VH-VL or a VL-VH configuration.

In one embodiment, (a) the first binding and/or functional specificity is a tumor targeting moiety, e.g., binds to a cancer antigen, e.g., a tumor or stromal antigen; (b) the second binding and/or functional specificity is a stromal modifying moiety; (c) the third binding and/or functional specificity is an immune cell engager (e.g., a macrophage or a dendritic cell engager) chosen from a ligand molecule or an antibody molecule (e.g., a scFv) that binds to an immune cell antigen; and (d) the fourth binding and/or functional specificity is an immune cell engager (e.g., a macrophage or a dendritic cell engager) chosen from a ligand molecule or an antibody molecule (e.g., a scFv) that binds to an immune cell antigen. In embodiments where the antibody molecule is a scFV, the scFv may be connected to the C-terminus of the first polypeptide in a VH-VL or a VL-VH configuration.

In embodiments, the first immunoglobulin constant region (e.g., the first CH2-CH3 region) includes a protuberance or knob, e.g., as described herein.

In embodiments, the second immunoglobulin constant region (e.g., the second CH2-CH3 region) includes a cavity or hole. In embodiments, the first and second immunoglobulin constant region promote heterodimerization of the bispecific molecule.

In some embodiments, the multifunctional molecule comprises the following formula in an N terminal to C terminal orientation:

R1-(optionally L1)-R2;

R2-(optionally L1)-R1;

wherein:
(i) R1 comprises 1, 2 or more stromal modifying moieties, e.g., the same or different stromal modifying moieties as described herein;
(ii) R2 comprises 1, 2 or more tumor targeting moieties, e.g., the same or different tumor targeting moieties as described herein; and
(iii) optionally, L1 is the linker (e.g., a linker described herein).

In some embodiments, the multifunctional molecule further comprises R3, wherein R3 comprises 1, 2 or more cytokine molecules, e.g., a cytokine molecule described herein.

In some embodiments, the multifunctional molecule further comprises R4, wherein R4 comprises 1, 2 or more immune cell engagers (e.g., an NK cell engager, a T cell engager, a B cell engager, a dendritic cell engager, or a macrophage cell engager described herein).

In some embodiments, the invention describes a multifunctional molecule comprising an R1, R2, R3, and R4 described herein.

In some embodiments, the multifunctional molecule comprises the following formula in an N terminal to C terminal orientation:

R1-(optionally L1)-R2-(optionally L2)-R3/R4;

R1-(optionally L1)-R3/R4-(optionally L2)-R2;

R2-(optionally L1)-R1-(optionally L2)-R3/R4;

R2-(optionally L1)-R3/R4-(optionally L2)-R1;

R3/R4-(optionally L1)-R1-(optionally L2)-R2; or

R3/R4-(optionally L1)-R2-(optionally L2)-R1;

wherein:
(i) R1 comprises 1, 2 or more of the stromal modifying moieties (e.g., a moiety described herein) (e.g., the same or different stromal modifying moieties);

(ii) R2 comprises 1, 2 or more of the tumor targeting moieties (e.g., a moiety described herein) (e.g., the same or different tumor targeting moieties);

(iii) R3 comprises 1, 2 or more cytokine molecules, e.g., a cytokine molecule (e.g., a cytokine molecule described herein) (e.g., the same or different cytokine molecules);

(iv) R4 comprises 1, 2 or more immune cell engagers (e.g., an NK cell engager, a T cell engager, a B cell engager, a dendritic cell engager, or a macrophage cell engager (e.g., an immune cell engager described herein)); and wherein:

R3 and R4 are both present;

R3 is present and R4 is absent;

R4 is present and R3 is absent; and optionally, L1 and/or L2 is the linker (e.g., a linker described herein).

In some embodiments, the multifunctional molecule has the following configuration:

(i) Stromal modifying moiety connected to the heavy chain of the Fab that bind to tumor or stromal antigen (e.g., VH-CH1), from N- to C-terminus, optionally, comprising a Gly-Ser linker between the Fab and the stromal modifying moiety; and/or (ii) Light chain of the Fab (e.g., VL-CL1), from N- to C-terminus.

In other embodiments, the Fab (e.g., VH-CH1) against mesothelin is coupled to a hyaluronidase molecule or collagenase molecule IV, e.g., comprising the Fab amino acid sequence: QVQLQQSGPELEKPGASVKISCKASGYSF-TGYTMNWVKQSHGKSLEWIGLITPYNGASS YNQ-KFRGKATLTVDKSSSTAYMDLLSLTSEDSAVYFCA-RGGYDGRGFDYWGQGTTVT VSSASTKGPSVFPLA-PSSKSTSGGTAALGCLVKDYFPEPVTVSWNSGALT-SGVHTFPAVL QSSGLYSLSSVVTVPSSSLGTQTYICN-VNHKPSNTKVDKRVEPKSCDKTHT (SEQ ID NO: 79) a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 79; and one or both of hyaluronidase molecule or collagenase molecule IV, e.g., comprising:

(i) the hyaluronidase molecule amino acid sequence of: FRGPLLPNRPFTTVWNANTQWCLERHGVDVDVSV-FDVVANPGQTFRGPDMTIFYSSQG TYPYYTPTGEPV-FGGLPQNASLIAHLARTFQDILAAIPAPDFSGLAVI-DWEAWRPRWAFN WDTKDIYRQRSRALVQAQHPD-WPAPQVEAVAQDQFQGAARAWMAGTLQLGRAL-RPR GLWGFYGFPDCYNYDFLSPNYTGQCPSGIRAQ-NDQLGWLWGQSRALYPSIYMPAVLEG TGKSQMYV-QHRVAEAFRVAVAAGDPNLPVLPYVQIFYDTTNH-FLPLDELEHSLGESAA QGAAGVVLWVSWENTRTK-ESCQAIKEYMDTTLGPFILNVTSGALLCSQALCSGH-GRCV RRTSHPKALLLLNPASFSIQLTPGGGPLSLR-GALSLEDQAQMAVEFKCRCYPGWQAPWC ERKSMW (SEQ ID NO: 62), or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 62; or (ii) the collagenase molecule amino acid sequence of SEQ ID NO: 63, or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 63, optionally, comprising a Gly-Ser linker between the Fab and the hyaluronidase molecule or collagenase molecule IV.

In some embodiments, the second polypeptide comprises a light chain of the Fab (e.g., VL-CL1) to the tumor or stromal antigen. In some embodiments, the light chain of the Fab binds to mesothelin, e.g., comprises the amino acid sequence: DIELTQSPAIMSASPGEKVTMTCSASSSVSY-MHWYQQKSGTSPKRWIYDTSKLASGVPGRFSGSGS-GNSYSLTISSVEAEDDATYYCQQWSGYPLTFGAGT-KLEIKRTVAAPSVFIFPPS DEQLKSGTASVVCLLNN-FYPREAKVQWKVDNALQSGNSQESVTEQDSKDS-TYSLSSTL TLSKADYEKHKVYACEVTHQGLSSPVT-KSFNRGEC (SEQ ID NO: 80), or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 80.

In other embodiments, the Fab (e.g., VH-CH1) against FAP coupled to a hyaluronidase molecule or collagenase molecule IV, e.g., comprising the Fab amino acid sequence: QVQLVQSGAEVKKPGASVKVSCKTSRYTFTEYTIH-WVRQAPGQRLEWIGGINPNNGIPN YNQKFKGRVTI-TVDTSASTAYMELSSLRSEDTAVYYCARRRIAYGY-DEGHAMDYWGQ GTLVTVSSASTKGPSVFPLAPSS-KSTSGGTAALGCLVKDYFPEPVTVSWNSGALTSG-VHT FPAVLQSSGLYSLSSVVTVPSSSLGTQTYICNV-NHKPSNTKVDKRVEPKSC (SEQ ID NO: 81), or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 81; and one or both of hyaluronidase molecule or collagenase molecule IV, e.g., comprising:

(i) the hyaluronidase molecule amino acid sequence of: FRGPLLPNRPFTTVWNANTQWCLERHGVDVDVSVF-DVVANPGQTFRGPDMTIFYSSQG TYPYYTPTGEPV-FGGLPQNASLIAHLARTFQDILAAIPAPDFSGLAVID-WEAWRPRWAFN WDTKDIYRQRSRALVQAQHPDW-PAPQVEAVAQDQFQGAARAWMAGTLQLGRALRPR GLWGFYGFPDCYNYDFLSPNYTGQCPSGIRAQND-QLGWLWGQSRALYPSIYMPAVLEG TGKSQMYVQH-RVAEAFRVAVAAGDPNLPVLPYVQIFYDTTNHF-LPLDELEHSLGESAA QGAAGVVLWVSWENTRTKES-CQAIKEYMDTTLGPFILNVTSGALLCSQALCSGHG-RCV RRTSHPKALLLLNPASFSIQLTPGGGPLSLRGAL-SLEDQAQMAVEFKCRCYPGWQAPWC ERKSMW (SEQ ID NO: 62), or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 62; or (ii) the collagenase molecule amino acid sequence of SEQ ID NO: 63, or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 63, optionally, comprising a Gly-Ser linker between the Fab and the hyaluronidase molecule or collagenase IV molecule. The amino acid sequence for the VH is underlined and the amino acid sequence for CH1 is shown without the underline.

In some embodiments, the second polypeptide comprises a light chain of the Fab (e.g., VL-CL1) to FAP. In some embodiments, the light chain of the Fab binds to FAP, e.g., comprises the amino acid sequence: DIVMTQSPDSLAVSLGERATINCKSSQSLLYSRNQKNYLAWYQQKPGQPPKLLIFWAST RESGVPDRFSGSGFGTDFTLTISSLQAEDVAVYYCQQYFSYPLTFGQGTKVEIKRTVAAP SVFIFPPSDEQLKSGTASVVCLLNNFYPREAKVQWKVDNALQSGNSQESVTEQDSKDST YSLSSTLTLSKADYEKHKVYACEVTHQGLSSPVTKSFNRGEC (SEQ ID NO: 49), or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 49. The amino acid sequence for the VL is underlined and the amino acid sequence for CL1 is shown without the underline.

In some embodiments, the multifunctional molecule further comprises a first and second domain that promote association of the first and the second polypeptide, e.g., a first and second immunoglobulin chain constant regions (e.g., a first and second Fc regions).

In some embodiments, (i) the first polypeptide has the following configuration: Heavy chain of the Fab (e.g., VH-CH1) to first Fc region (e.g., CH2 to CH3), from N- to C-terminus; and (ii) the second polypeptide has the following configuration: Light chain of the Fab (e.g., VH-CH1) to second Fc region (e.g., CH2 to CH3), from N- to C-terminus.

In some embodiments, the first immunoglobulin chain constant regions (e.g., a first Fc region) comprises the amino acid sequence: DKTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKTIS KAKGQPREPQVCTLPPSREEMTKNQVSLSCAVKGFYPSDIAVEWESNGQPENNYKTTPP VLDSDGSFFLVSKLTVDKSRWQQGNVFSCSVMHEALHNHYTQKSLSLSPGK (SEQ ID NO: 82), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 82.

In some embodiments, the second immunoglobulin chain constant regions (e.g., a second Fc region) comprises the amino acid sequence: DKTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEKTIS KAKGQPREPQVYTLPPCREEMTKNQVSLWCLVKGFYPSDIAVEWESNGQPENNYKTTP PVLDSDGSFFLYSKLTVDKSRWQQGNVFSCSVMHEALHNHYTQKSLSLSPGK, (SEQ ID NO: 83), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 83.

In some embodiments, the multifunctional molecule further comprises at least one cytokine molecule (e.g., R3) and/or at least one immune cell engager (e.g., R4) (e.g., an NK cell engager, a T cell engager, a B cell engager, a dendritic cell engager, or a macrophage cell engager). In some embodiments, the stromal modifying moiety (e.g., R1), the tumor-targeting moiety (e.g., R2), and one or both of the cytokine molecule (e.g., R3) and/or the immune cell engager (e.g., R4) are in the same polypeptide, e.g., wherein, e.g., in the N- to C-direction, the stromal modifying moiety is a first polypeptide, the tumor-targeting moiety is a second polypeptide, and one or both of the cytokine molecule and/or the immune cell engager, optionally connected via a linker.

In some embodiments, the stromal modifying moiety (e.g., R1), the tumor-targeting moiety (e.g., R2), and one or both of the cytokine molecule (e.g., R3) and/or the immune cell engager (e.g., R4) are in the same polypeptide, e.g., wherein, e.g., in the N- to C-direction, the tumor-targeting moiety is a first polypeptide, the stromal modifying moiety is a second polypeptide, and one or both of the cytokine molecule and/or the immune cell engager, optionally connected via a linker. In some embodiments, the stromal modifying moiety, the tumor-targeting moiety, and one or both of the cytokine molecule (e.g., R3) and/or the immune cell engager (e.g., R4) are in different polypeptides, e.g., a first and a second polypeptide not covalently linked.

In some embodiments, 1) the first polypeptide comprises, e.g., in the N- to C-direction, the first tumor-targeting moiety (e.g., R2), the stromal modifying moiety (e.g., R1), and optionally, a first domain that promotes association of the first and second polypeptide, e.g., a first immunoglobulin chain constant region (e.g., a first Fc region); 2) the second polypeptide comprises, e.g., in the N- to C-direction, the second tumor-targeting moiety (e.g., R2), and optionally, a second domain that promotes association of the first and second polypeptide, e.g., a second immunoglobulin chain constant region (e.g., a second Fc region); and 3) either or both the first and/or second polypeptide, e.g., in the N- to C-direction, further comprise the cytokine molecule (e.g., R3) and/or the immune cell engager (e.g., R4).

In some embodiments, the first tumor targeting moiety comprises a heavy chain variable domain of the tumor targeting antibody molecule (e.g., Fab); and the second tumor targeting moiety comprises a light chain variable domain of the tumor targeting antibody molecule (e.g., Fab). In some embodiments, the first tumor targeting moiety comprises a light chain variable domain of a tumor targeting antibody; and the tumor targeting moiety of the second polypeptide comprises a heavy chain variable domain of a tumor targeting antibody.

In some embodiments, the multifunctional molecule comprises a) a first polypeptide comprising: a domain that promotes association of the first and second polypeptide, e.g., an Fc molecule; and two polypeptides, one comprising a tumor targeting moiety and the other comprising a stromal modifying moiety; b) a second polypeptide comprising: a domain that promotes association of the first and second polypeptide, e.g., an Fc molecule; and two polypeptides selected from: a tumor targeting moiety; an immune cell engager; and a cytokine molecule, wherein the multifunctional molecule comprises the tumor targeting moiety and the stromal modifying moiety; and one or both of the immune cell engager or the cytokine molecule.

In some embodiments, the multifunctional molecule comprises: a tumor targeting moiety; a stromal modifying moiety; and an immune cell engager; a tumor targeting moiety; a stromal modifying moiety; and a cytokine molecule; a tumor targeting moiety; a stromal modifying moiety; an immune cell engager; and a cytokine molecule; a tumor targeting moiety; a stromal modifying moiety; and two immune cell engagers; a tumor targeting moiety; a stromal modifying moiety; and two cytokine molecules; two tumor targeting moieties; a stromal modifying moiety; and an immune cell engager; or a tumor targeting moiety; a stromal modifying moiety; and two immune cell engagers.

In some embodiments, the multifunctional molecule comprises: i) a first polypeptide comprises, e.g., in the N-C or C-N direction, a tumor targeting moiety; a domain that promotes association of the first and second polypeptide, e.g., an Fc molecule; and a stromal modifying moiety; ii) a first polypeptide comprises, e.g., in the N-C or C-N direction, a tumor targeting moiety; a domain that promotes association of the first and second polypeptide, e.g., an Fc molecule; and a cytokine molecule and/or an immune cell engager; or iii) a first polypeptide comprises, e.g., in the N-C or C-N direction a cytokine; a domain that promotes association of the first and second polypeptide, e.g., an Fc molecule; and an immune cell engager; and iv) a second polypeptide comprises, e.g., in the N-C or C-N direction, a tumor targeting moiety; a domain that promotes association of the first and second polypeptide, e.g., an Fc molecule; and a stromal modifying moiety; ii) a second polypeptide comprises, e.g., in the N-C or C-N direction, a tumor targeting moiety; a domain that promotes association of the first and second polypeptide, e.g., an Fc molecule; and a cytokine molecule and/or an immune cell engager; or iii) a second polypeptide comprises, e.g., in the N-C or C-N direction a cytokine; a domain that promotes association of the first and second polypeptide, e.g., an Fc molecule; and a stromal modifying moiety.

In some embodiments, the tumor targeting moiety is specific for mesothelin or FAP; the stromal modifying moiety comprises hyaluronidase molecule or collagenase IV molecule, or a fragment or variant thereof; the cytokine molecule comprising an IL-15 molecule; the immune cell engager comprising a CD40L molecule; and the immune cell engager comprising a B7H6 molecule.

Exemplary Multispecific and Multifunctional Molecules and Corresponding Nucleic Acid and Amino Acid Sequences

TABLE 1

Nucleic acid sequences.

| Sequence ID | Description | Nucleic Acid Sequence |
|---|---|---|
| SEQ ID NO: 85 | αMesothelin Ab237 VH | CAGGTCCAGCTGCAGGAAAGCGGCCCTGGACTGGTCAAGCCT AGCCAGACCCTGAGCCTGACCTGTACCGTGTCCGGCGGCAGCA TCAACAACAACAATTACTACTGGACATGGATCCGGCAGCACCC CGGCAAGGGCCTGGAATGGATCGGCTACATCTACTACAGCGG CTCCACCTTCTACAACCCCAGCCTGAAGTCCAGAGTGACCATC AGCGTGGACACCAGCAAGACCCAGTTCTCCCTGAAGCTGAGC AGCGTGACAGCCGCCGACACAGCCGTGTACTACTGCGCCAGA GAAGATACCATGACCGGCCTGGATGTGTGGGGCCAGGGCACC ACAGTGACAGTGTCTAGC |
| SEQ ID NO: 86 | αMesothelin Ab237 VL | GATATCCAGATGACACAGAGCCCTAGCAGCCTGAGCGCCAGC GTGGGCGATAGAGTGACCATCACCTGTCGGGCCAGCCAGAGC ATCAACAACTACCTGAACTGGTATCAGCAGAAGCCCGGCAAG GCCCCTACCCTGCTGATCTATGCCGCTTCTAGCCTGCAGAGCG GCGTGCCCAGCAGATTTTCTGGCAGCAGATCCGGCACCGACTT CACCCTGACAATCAGCAGCCTGCAGCCCGAGGACTTCGCCGCC TACTTCTGCCAGCAGACCTACAGCAATCCCACCTTCGGCCAGG GCACCAAGGTGGAAGTGAAG |
| SEQ ID NO: 87 | Human IL2 | GCCCCTACCAGCAGCAGCACCAAGAAAACCCAGCTCCAGCTC GAGCACCTCCTGCTGGACCTGCAGATGATCCTGAACGGCATCA ACAACTACAAGAACCCCAAGCTGACCCGGATGCTGACCTTCA AGTTCTACATGCCCAAGAAGGCCACCGAGCTGAAGCACCTCC AGTGCCTGGAAGAGGAACTGAAGCCCCTGGAAGAAGTGCTGA ACCTGGCCCAGAGCAAGAACTTCCACCTGAGGCCCAGGGACC TGATCAGCAACATCAACGTGATCGTGCTGGAACTGAAAGGCA GCGAGACAACCTTCATGTGCGAGTACGCCGACGAGACAGCCA CCATCGTGGAATTTCTGAACCGGTGGATCACCTTCTGCCAGAG CATCATCAGCACCCTGACA |
| SEQ ID NO: 88 | 2x4GS linker | GGCGGCGGAGGATCTGGCGGAGGCGGCAGC |
| SEQ ID NO: 89 | Human CH2, CH3 knob | GATAAGACCCACACCTGTCCTCCATGTCCTGCCCCTGAGCTGC TGGGCGGACCTAGCGTGTTCCTGTTCCCTCCAAAGCCCAAGGA CACCCTGATGATCAGCCGGACCCCTGAAGTGACCTGCGTGGTG GTGGATGTGTCCCACGAGGATCCCGAAGTGAAGTTCAATTGGT ACGTGGACGGCGTGGAAGTGCACAACGCCAAGACCAAGCCCA GAGAGGAACAGTACAACAGCACCTACCGGGTGGTGTCCGTGC TGACCGTGCTGCACCAGGACTGGCTGAACGGCAAAGAGTACA AGTGCAAGGTGTCCAACAAGGCCCTGCCTGCCCCTATCGAGAA AACCATCAGCAAGGCCAAGGGCCAGCCCCGCGAACCTCAGGT GTACACACTGCCTCCCTGCCGGGAAGAGATGACCAAGAACCA GGTGTCCCTGTGGTGCCTGGTCAAGGGCTTCTACCCCTCCGAT ATCGCCGTGGAATGGGAGAGCAACGGCCAGCCCGAGAACAAC TACAAGACCACCCCTCCCGTGCTGGACAGCGACGGCAGCTTCT TCCTGTACTCCAAACTGACCGTGGACAAGAGCCGGTGGCAGC |

TABLE 1-continued

Nucleic acid sequences.

| Sequence ID | Description | Nucleic Acid Sequence |
| --- | --- | --- |
| | | AGGGCAATGTGTTCAGCTGTAGCGTGATGCACGAGGCCCTGCA<br>CAACCACTACACCCAGAAGTCTCTGAGCCTGAGCCCCGGCAA<br>GTAATGA |
| SEQ ID NO: 90 | Human CH2, CH3 hole | GATAAGACCCACACCTGTCCTCCATGTCCTGCCCCTGAGCTGC<br>TGGGCGGACCTAGCGTGTTCCTGTTCCCTCCAAAGCCCAAGGA<br>CACCCTGATGATCAGCCGGACCCCTGAAGTGACCTGCGTGGTG<br>GTGGATGTGTCCCACGAGGATCCCGAAGTGAAGTTCAATTGGT<br>ACGTGGACGGCGTGGAAGTGCACAACGCCAAGACCAAGCCCA<br>GAGAGGAACAGTACAACAGCACCTACCGGGTGGTGTCCGTGC<br>TGACCGTGCTGCACCAGGACTGGCTGAACGGCAAAGAGTACA<br>AGTGCAAGGTGTCCAACAAGGCCCTGCCTGCCCCTATCGAGAA<br>AACCATCAGCAAGGCCAAGGGCCAGCCTAGAGAGCCTCAGGT<br>CTGCACCCTGCCTCCCAGCCGGGAAGAGATGACCAAGAACCA<br>GGTGTCCCTGTCCTGCGCCGTGAAGGGCTTCTACCCCTCCGAT<br>ATCGCCGTGGAATGGGAGAGCAACGGCCAGCCCGAGAACAAC<br>TACAAGACCACCCCTCCCGTGCTGGACAGCGACGGCAGCTTCT<br>TCCTGGTGTCCAAACTGACCGTGGACAAGAGCCGGTGGCAGC<br>AGGGCAATGTGTTCAGCTGTAGCGTGATGCACGAGGCCCTGCA<br>CAACCACTACACCCAGAAGTCTCTGAGCCTGAGCCCCGGCAA<br>GTAATGA |
| SEQ ID NO: 91 | CH1 | GCCAGCACCAAGGGCCCTAGCGTGTTCCCTCTGGCCCCTAGCT<br>CTAAGAGCACATCTGGCGGAACAGCCGCCCTGGGCTGCCTGGT<br>CAAGGATTACTTTCCTGAGCCCGTGACCGTGTCCTGGAACTCT<br>GGTGCTCTGACCAGCGGCGTGCACACCTTTCCAGCTGTGCTGC<br>AGAGCAGCGGCCTGTACAGCCTGTCTAGCGTGGTCACAGTGCC<br>TAGCAGCAGCCTGGGCACACAGACCTACATCTGCAACGTGAA<br>CCACAAGCCCAGCAACACCAAGGTGGACAAGCGGGTGGAACC<br>CAAGAGCTGC |
| SEQ ID NO: 92 | CL (kappa) | AGAACAGTGGCCGCTCCCAGCGTGTTCATCTTCCCACCCAGCG<br>ACGAGCAGCTGAAGTCTGGCACAGCCAGCGTCGTGTGCCTGCT<br>GAACAACTTCTACCCCAGAGAAGCCAAGGTGCAGTGGAAGGT<br>GGACAACGCCCTGCAGTCCGGCAACAGCCAGGAAAGCGTCAC<br>CGAGCAGGACAGCAAGGACTCCACCTACAGCCTGTCCAGCAC<br>CCTGACCCTGAGCAAGGCCGACTACGAGAAGCACAAAGTGTA<br>CGCCTGCGAAGTGACCCACCAGGGCCTGAGCAGCCCCGTGAC<br>CAAGAGCTTCAATAGAGGCGAGTGCTAATGA |
| SEQ ID NO: 93 | CL (lambda) | GGCCAGCCCAAGGCCAACCCCACCGTGACCCTGTTCCCTCCAT<br>CCTCCGAGGAACTGCAGGCTAACAAGGCCACCCTCGTGTGCCT<br>GATCTCCGACTTCTACCCTGGCGCCGTGACCGTGGCTTGGAAG<br>GCTGATGGCTCTCCTGTGAAGGCCGGCGTGGAAACCACCAAG<br>CCCTCCAAGCAGTCCAACAACAAATACGCCGCCTCCAGCTACC<br>TGTCCCTGACCCCTGAGCAGTGGAAGTCCCACCGGTCCTACAG<br>CTGCCAGGTCACACATGAGGGCTCCACCGTGGAAAAGACCGT<br>GGCCCCTACCGAGTGCTCCTAATGA |
| SEQ ID NO: 94 | αPD1L1 Avelumab VH | GAGGTGCAGCTGCTGGAATCTGGCGGAGGACTGGTGCAGCCT<br>GGCGGCTCTCTGAGACTGTCTTGTGCCGCCTCCGGCTTCACCTT<br>CTCCAGCTATATCATGATGTGGGTCCGACAGGCCCCTGGCAAG<br>GGCCTGGAATGGGTGTCCTCTATCTACCCCTCCGGCGGCATCA<br>CCTTTTACGCCGACACCGTGAAGGGCCGGTTCACCATCTCCCG<br>GGACAACTCCAAGAACACCCTGTACCTGCAGATGAACTCCCTG<br>CGGGCCGAGGACACCGCCGTGTACTACTGCGCTAGAATCAAG<br>CTGGGCACCGTGACCACCGTGGACTATTGGGGCCAGGGCACC<br>CTGGTCACCGTGTCCTCT |
| SEQ ID NO: 95 | αPD1L1 Avelumab VL | CAGTCTGCTCTGACCCAGCCTGCCTCTGTGTCTGGCTCCCCTGG<br>CCAGTCCATCACCATCAGCTGTACCGGCACCTCCTCCGACGTG<br>GGCGGCTACAACTACGTGTCCTGGTATCAGCAGCATCCCGGCA<br>AGGCCCCTAAGCTGATGATCTACGACGTGTCCAACCGGCCCTC<br>CGGCGTGTCCAATCGGTTCTCTGGCTCCAAGTCCGGCAACACC<br>GCCTCCCTGACAATCAGCGGACTGCAGGCCGAGGACGAGGCC<br>GACTACTACTGCTCCTCCTACACCTCCAGCTCTACCCGGGTGTT<br>CGGCACCGGCACCAAAGTGACAGTGCTG |
| SEQ ID NO: 96 | 3x4GS linker | GGCGGCGGAGGATCTGGCGGAGGTGGAAGCGGAGGCGGTGG<br>ATCT |
| SEQ ID NO: 97 | αNKp46 VH | CAGGTTCAGTTGCAGCAGTCCGGACCTGAGCTGGTTAAGCCTG<br>GCGCTTCCGTGAAGATGTCCTGCAAGGCTTCCGGCTACACCTT<br>CACCGACTACGTGATCAACTGGGGCAAGCAGAGATCTGGCCA<br>GGGACTCGAGTGGATCGGCGAGATCTATCCTGGCTCCGGCACC<br>AATTACTACAACGAGAAGTTCAAGGCTAAGGCTACCCTGACC |

TABLE 1-continued

Nucleic acid sequences.

| Sequence ID | Description | Nucleic Acid Sequence |
|---|---|---|
| | | GCCGACAAGTCCTCCAATATCGCCTACATGCAGCTGTCCAGCC<br>TGACCTCTGAGGACTCCGCTGTGTACTTCTGCGCTCGGAGAGG<br>CAGATACGGCCTGTATGCCATGGATTACTGGGGACAGGGAAC<br>CAGTGTGACAGTGTCAAGT |
| SEQ ID NO: 98 | αNKp46 VL | GATATTCAGATGACCCAGACCACCTCCAGCCTGTCCGCTTCTC<br>TGGGCGACAGAGTGACAATCAGCTGCAGAGCCAGCCAGGACA<br>TCAGCAACTACCTGAACTGGTATCAACAGAAACCCGACGGCA<br>CCGTGAAGCTGCTGATCTACTACACCTCTCGGCTGCACTCTGG<br>CGTGCCCTCTAGATTTTCTGGCAGCGGAAGCGGCACCGACTAT<br>TCCCTGACCATCAACAACCTGGAACAAGAGGATATCGCTACCT<br>ACTTCTGCCAGCAAGGCAACACCCGGCCTTGGACATTTGGCGG<br>CGGAACAAAGCTGGAAATCAAGTGATGA |
| SEQ ID NO: 99 | 4x 4GS linker | GGTGGCGGAGGAAGCGGCGGAGGCGGCTCTGGTGGTGGTGGT<br>TCTGGTGGCGGTGGCTCC |
| SEQ ID NO: 100 | αMesothelin M912 VH | CAGGTCCAGCTGCAGGAATCTGGCCCTGGCCTGGTCAAGCCCT<br>CCGAGACACTGTCTCTGACCTGCACCGTGTCCGGCGGCTCTGT<br>GTCCTCCGGCTCCTACTACTGGTCCTGGATCCGGCAGCCTCCA<br>GGCAAGGGACTGGAATGGATCGGCTACATCTACTACTCCGGC<br>AGCACCAACTACAACCCCAGCCTGAAGTCCAGAGTGACCATCT<br>CCGTGGACACCTCCAAGAACCAGTTCTCCCTGAAGCTGTCCTC<br>CGTGACCGCCGCTGACACCGCCGTGTACTACTGTGCCAGAGAG<br>GGCAAGAACGGCGCCTTCGATATCTGGGGCCAGGGCACCATG<br>GTCACCGTGTCTAGC |
| SEQ ID NO: 101 | αMesothelin M912 VL | GACATCCAGATGACCCAGAGCCCTTCCAGCCTGTCCGCCTCTG<br>TGGGCGACAGAGTGACCATCACCTGTCGGGCCTCCCAGTCCAT<br>CTCCTCCTACCTGAACTGGTATCAGCAGAAGCCCGGCAAGGCC<br>CCTAAGCTGCTGATCTACGCCGCCTCCAGTCTGCAGTCTGGCG<br>TGCCATCTGGCTTCTCCGGCTCTGGCTCTGGCACCGACTTCACC<br>CTGACCATCTCCAGCCTGCAGCCCGAGGACTTCGCCACCTACT<br>ACTGCCAGCAGTCCTACTCCACCCCTCTGACCTTCGGCGGAGG<br>CACCAAGGTGGAAATCAAG |
| SEQ ID NO: 102 | 1x4GS | GGCGGCGGAGGCTCC |
| SEQ ID NO: 103 | αNKp30 | DNA sequence corresponding to BioLegend Catalog #325207 |
| SEQ ID NO: 104 | Human IL7 | GACTGTGACATCGAAGGCAAGGACGGCAAGCAGTACGAGAGC<br>GTGCTGATGGTGTCCATCGACCAGCTGCTGGACAGCATGAAGG<br>AAATCGGCTCCAACTGCCTGAACAACGAGTTCAACTTCTTCAA<br>GCGGCACATCTGCGACGCCAACAAAGAAGGCATGTTCCTGTTC<br>AGAGCCGCCAGAAAGCTGCGGCAGTTCCTGAAGATGAACTCC<br>ACCGGCGACTTCGACCTGCATCTGCTGAAAGTGTCTGAGGGCA<br>CCACCATCCTGCTGAACTGTACCGGCCAAGTGAAGGGCAGAA<br>AGCCTGCTGCTCTGGGCGAAGCCCAGCCTACCAAGTCTCTGGA<br>AGAGAACAAGAGCCTGAAAGAGCAGAAGAAGCTGAACGACC<br>TCTGCTTCCTGAAGCGGCTGCTGCAAGAGATCAAGACCTGCTG<br>GAACAAGATTCTGATGGGGACCAAAGAGCAC |
| SEQ ID NO: 105 | αIGF1R heavy | GAAGTGCAGCTGTTGCAGTCTGGCGGAGGATTGGTTCAGCCTG<br>GCGGATCCCTGAGACTGTCTTGTGCCGCCTCTGGCTTCATGTTC<br>AGCAGATACCCCATGCACTGGGTCCGACAGGCCCCTGGAAAA<br>GGACTGGAATGGGTCGGATCCATCTCCGGAAGTGGCGGCGCT<br>ACCCCTTACGCCGATTCTGTGAAGGGCAGATTCACCATCAGCC<br>GGGACAACTCCAAGAACACCCTGTACCTGCAGATGAACTCCCT<br>GAGAGCCGAGGACACCGCCGTGTACTACTGCGCCAAGGACTT<br>CTACCAGATCCTGACCGGCAACGCCTTCGACTATTGGGGCCAG<br>GGCACAACCGTGACCGTGTCCTCT |
| SEQ ID NO: 106 | αIGF1R light | GACATCCAGATGACCCAGTCTCCATCCTCTCTGTCTGCCAGCC<br>TGGGCGACAGAGTGACCATCACCTGTAGAGCCTCTCAGGGCAT<br>CTCCTCCTACCTGGCCTGGTATCAGCAGAAGCCTGGCAAGGCT<br>CCCAAGCTGCTGATCTACGCCAAGAGCACACTGCAGTCTGGCG<br>TGCCCTCTAGATTCTCCGGCTCTGGCTCTGGCACCGACTTTACC<br>CTGACAATCTCCAGCCTGCAGCCTGAGGACTCCGCCACCTACT<br>ACTGTCAGCAGTACTGGACCTTTCCACTGACCTTCGGCGGAGG<br>CACCAAGGTGGAAATCAAG |
| SEQ ID NO: 107 | αHER3 heavy | CAGGTGCAGCTGGTTCAGTCTGGCGGAGGATTGGTTCAGCCAG<br>GCGGATCCCTGAGACTGTCTTGTGCCGCTTCTGGCTTCACCTTC<br>GACGACTACGCTATGCACTGGGTCCGACAGGCCCCTGGAAA |

TABLE 1-continued

Nucleic acid sequences.

| Sequence ID | Description | Nucleic Acid Sequence |
|---|---|---|
| | | GGATTGGAATGGGTGGCCGGCATCTCTTGGGACTCTGGCTCTA<br>CCGGCTACGCCGACTCTGTGAAGGGCAGATTCACCATCTCTCG<br>GGACAACGCCAAGAACTCCCTGTACCTGCAGATGAACAGCCT<br>GAGAGCCGAGGACACCGCTCTGTACTACTGCGCTAGAGATCTG<br>GGCGCCTACCAGTGGGTGGAAGGCTTTGATTATTGGGGCCAGG<br>GCACCCTGGTCACCGTGTCTAGT |
| SEQ ID NO: 108 | αHER3 light | TCTTACGAGCTGACCCAGGATCCAGCCGTGTCTGTTGCTCTGG<br>GCCAGACAGTGCGGATTACCTGCCAGGGCGACTCCCTGAGATC<br>CTACTACGCCTCCTGGTATCAGCAGAAGCCAGGCCAGGCTCCT<br>GTGCTGGTCATCTACGGCAAGAACAACCGGCCTAGCGGCATCC<br>CTGACAGATTCTCCGGCTCTACCTCCGGCAACTCTGCCAGCCT<br>GACAATTACTGGCGCCCAGGCTGAGGACGAGGCCGACTACTA<br>CTGCAACTCCAGAGACAGCCCTGGCAATCAGTGGGTTTTCGGC<br>GGAGGCACCAAAGTGACAGTTCTTGGT |
| SEQ ID NO: 109 | αCD3 heavy | CAAGTTCAGTTGGTTCAAAGCGGTGGCGGCGTGGTGCAGCCTG<br>GAAGATCTCTCAGACTGTCCTGCAAGGCCTCCGGCTACACCTT<br>CACCAGATACACCATGCATTGGGTTCGACAAGCACCAGGCAA<br>GGGCCTCGAGTGGATCGGCTACATCAACCCTTCCAGAGGCTAC<br>ACCAACTACAACCAGAAAGTGAAGGACCGGTTCACCATCAGC<br>AGAGACAACAGCAAGAATACCGCCTTTCTGCAGATGGACTCC<br>CTGCGGCCTGAAGATACCGGCGTGTACTTTTGCGCCCGGTACT<br>ACGACGACCACTACTCCCTGGATTACTGGGGACAGGGAACAC<br>CCGTGACAGTGTCTAGC |
| SEQ ID NO: 110 | αCD3 light | GATATTCAGATGACCCAGTCTCCTTCCAGCCTGTCCGCTTCTGT<br>GGGCGACAGAGTGACTATTACCTGCTCCGCCTCTTCCTCCGTG<br>TCCTACATGAACTGGTATCAACAAACACCCGGCAAGGCCCCTA<br>AGAGATGGATCTACGACACCAGCAAGCTGGCCTCTGGCGTGC<br>CCTCTAGATTTTCTGGCTCTGGCTCCGGCACCGACTATACCTTT<br>ACAATCTCCAGCCTGCAGCCTGAGGATATCGCCACCTACTACT<br>GTCAGCAGTGGTCTAGCAACCCCCTTCACCTTTGGACAGGGCAC<br>CAAGCTGCAGATCACCTGATGA |
| SEQ ID NO: 111 | Human IL2 F42A Y45A | GCTCCTACCTCCTCCAGCACCAAGAAAACCCAGCTGCAGTTGG<br>AGCATCTGCTGCTGGACCTCCAGATGATCCTGAATGGCATCAA<br>CAATTACAAGAACCCCAAGCTCACCCGATGCTGACCGCCAA<br>GTTTGCCATGCCTAAGAAGGCCACCGAGCTGAAACATCTGCAG<br>TGCCTGGAAGAGGAACTGAAGCCCCTGGAAGAAGTGCTGAAT<br>CTGGCCCAGTCCAAGAACTTCCACCTGAGGCCTCGGGACCTGA<br>TCTCCAACATCAACGTGATCGTGCTCGAGCTGAAGGGCTCCGA<br>GACAACCTTCATGTGCGAGTACGCCGACGAGCAGCTACCATC<br>GTGGAATTTCTGAACCGGTGGATCACCTTCTGTCAGTCCATCA<br>TCAGCACCCTGACC |
| SEQ ID NO: 112 | αNKp46 2 heavy | GAAGTGCAGCTCCAAGAATCTGGACCCGGGCTCGTGAAGCCC<br>AGCCAGTCTCTGAGTCTGACCTGTACAGTGACCGGCTACTCCA<br>TCACCTCCGACTACGCTTGGAACTGGATCCGGCAGTTCCCCGG<br>CAACAAGTTGGAGTGGATGGGCTATATCACCTACAGCGGCAG<br>CACCTCTTACAACCCTTCTCTGGAATCCCGGATCAGCATCACC<br>CGGGACACCTCTACCAATCAGTTCTTTCTGCAGCTGAACAGCG<br>TGACCACCGAGGACACCGCCACCTACTATTGTGCTAGAGGCGG<br>CTACTACGGCTCCTCCTGGGGAGTGTTTGCTTACTGGGGACAG<br>GGAACCCTCGTGACTGTTTCTGCT |
| SEQ ID NO: 113 | αNKp46 2 light | GACATCCAGATGACCCAGTCTCCAGCCAGCCTGTCTGCTTCTG<br>TGGGCGAGACAGTGACCATTACCTGCCGGGTGTCCGAGAACA<br>TCTACTCCTACCTGGCCTGGTATCAACAGAAACAGGGCAAGTC<br>CCCTCAGCTGCTGGTGTACAATGCTAAGACCCTGGCTGAGGGC<br>GTGCCCTCTAGATTTTCTGGCTCTGGCAGCGGCACCCAGTTTA<br>GCCTGAAGATCAACTCCCTGCAGCCTGAGGACTTCGGCAGCTA<br>CTACTGCCAGCACCACTATGGCACCCCTTGGACATTTGGCGGA<br>GGCACCAAGCTGGAAATCAAG |
| SEQ ID NO: 114 | αNKp46 4 heavy | CAGGTTCAGTTGCAGCAGTCTGCCGTGAACTGGTAGACCTG<br>GCGCTTCCGTGAAGATGTCCTGCAAGGCCTCCGGCTACACCTT<br>CACCAGCTTCACCATGCACTGGGTCAAGCAGAGGCCTGGACA<br>AGGCTTGGAGTGGATTGGATATATCAACCCTAGCTCTGGCTAC<br>ACCGAGTACAACCAGAAGTTCAAGGACAAGACCACTCTGACC<br>GCCGACAAGTCCTCCAGCACCGCTTACATGCAGCTCGACTCCC |

TABLE 1-continued

Nucleic acid sequences.

| Sequence ID | Description | Nucleic Acid Sequence |
|---|---|---|
| | | TGACCTCTGACGACTCTGCTGTGTACTATTGCGTGCGGGGCTC CTCCAGAGGCTTCGATTATTGGGGACAAGGCACACTCGTGACA GTGTCAGCT |
| SEQ ID NO: 115 | αNKp46 4 light | GATATCCAGATGATCCAGTCTCCTGCCAGCCTGTCCGTGTCTG TGGGAGAGACTGTGACCATCACCTGTCGGGCCTCCGAGAACAT CTACTCCAACCTGGCCTGGTTCCAGCAGAAGCAGGGAAAGTCT CCTCAGCTGCTGGTGTACGCCGCCACCAATTTGGCTGATGGCG TGCCCTCTCGGTTCTCCGGATCTGGATCTGGCACACAGTATTCC CTGAAGATCAACTCCCTGCAGTCCGAGGACTTCGGCATCTACT ATTGCCAGCACTTCTGGGGCACCCCTAGAACCTTTGGCGGCGG AACAAAGCTGGAAATCAAG |

TABLE 2

Sequences used to construct ORFS.

| Construct SEQ ID NO: | N-term | Linker | Variable | Constant | Fc | Linker | C-term |
|---|---|---|---|---|---|---|---|
| SEQ ID NO: 116 | | | SEQ ID NO: 85 | SEQ ID NO: 91 | SEQ ID NO: 89 | | |
| SEQ ID NO: 117 | | | SEQ ID NO: 85 | SEQ ID NO: 91 | SEQ ID NO: 89 | SEQ ID NO: 96 | SEQ ID NO: 103 |
| SEQ ID NO: 118 | | | SEQ ID NO: 86 | SEQ ID NO: 92 | | | |
| SEQ ID NO: 119 | SEQ ID NO: 87 | SEQ ID NO: 88 | | | SEQ ID NO: 90 | | |
| SEQ ID NO: 120 | | | SEQ ID NO: 94 | SEQ ID NO: 91 | SEQ ID NO: 90 | SEQ ID NO: 96 | SEQ ID NO: 87 |
| SEQ ID NO: 121 | | | SEQ ID NO: 95 | SEQ ID NO: 93 | | | |
| SEQ ID NO: 122 | | | SEQ ID NO: 100 | SEQ ID NO: 91 | SEQ ID NO: 89 | | |
| SEQ ID NO: 123 | | | SEQ ID NO: 101 | SEQ ID NO: 92 | | | |
| SEQ ID NO: 124 | | | | | SEQ ID NO: 89 | | |
| SEQ ID NO: 125 | | | | | SEQ ID NO: 90 | | |
| SEQ ID NO: 126 | | | SEQ ID NO: 105 | SEQ ID NO: 91 | SEQ ID NO: 90 | | |
| SEQ ID NO: 127 | | | SEQ ID NO: 106 | SEQ ID NO: 92 | | | |
| SEQ ID NO: 128 | | | SEQ ID NO: 105 | SEQ ID NO: 91 | SEQ ID NO: 90 | SEQ ID NO: 96 | SEQ ID NO: 81 |
| SEQ ID NO: 129 | | | SEQ ID NO: 105 | SEQ ID NO: 91 | SEQ ID NO: 90 | SEQ ID NO: 96 | SEQ ID NO: 104 |
| SEQ ID NO: 130 | SEQ ID NO: 107 | SEQ ID NO: 99 | SEQ ID NO: 108 | SEQ ID NO: 88 | SEQ ID NO: 89 | | |
| SEQ ID NO: 131 | SEQ ID NO: 107 | SEQ ID NO: 99 | SEQ ID NO: 108 | SEQ ID NO: 88 | SEQ ID NO: 89 | SEQ ID NO: 96 | SEQ ID NO: 97, 98, 994 |
| SEQ ID NO: 132 | SEQ ID NO: 107 | SEQ ID NO: 99 | SEQ ID NO: 108 | SEQ ID NO: 88 | SEQ ID NO: 89 | SEQ ID NO: 96 | SEQ ID NO: 108, 99, 110 |
| SEQ ID NO: 133 | | | SEQ ID NO: 85 | SEQ ID NO: 91 | SEQ ID NO: 89 | SEQ ID NO: 96 | SEQ ID NO: 97, 98, 99 |
| SEQ ID NO: 134 | | | SEQ ID NO: 91 | SEQ ID NO: 93 | | SEQ ID NO: 96 | SEQ ID NO: 111 |
| SEQ ID NO: 135 | | | SEQ ID NO: 94 | SEQ ID NO: 91 | SEQ ID NO: 90 | | |
| SEQ ID NO: 136 | | | SEQ ID NO: 100 | SEQ ID NO: 91 | SEQ ID NO: 89 | SEQ ID NO: 96 | SEQ ID NO: 97, 98, 99 |
| SEQ ID NO: 137 | | | SEQ ID NO: 100 | SEQ ID NO: 91 | SEQ ID NO: 89 | SEQ ID NO: 96 | SEQ ID NO: 28, 15, 29 |

TABLE 2-continued

Sequences used to construct ORFS.

| Construct SEQ ID NO: | N-term | Linker | Variable | Constant | Fc | Linker | C-term |
|---|---|---|---|---|---|---|---|
| SEQ ID NO: 138 | | | SEQ ID NO: 100 | SEQ ID NO: 91 | SEQ ID NO: 89 | SEQ ID NO: 96 | SEQ ID NO: 114, 99, 115 |

TABLE 3

Nucleic acid sequences of ORFs.

| Sequence ID | Nucleic Acid Sequence |
|---|---|
| SEQ ID NO: 116 | ATGGAAACCGATACACTGCTGCTGTGGGTGCTGCTCCTCTGGGTGCC<br>AGGATCTACAGGCGCCCCTACCAGCAGCAGCACCAAGAAAACCCAG<br>CTCCAGCTCGAGCACCTCCTGCTGGACCTGCAGATGATCCTGAACGG<br>CATCAACAACTACAAGAACCCCAAGCTGACCCGGATGCTGACCTTC<br>AAGTTCTACATGCCCAAGAAGGCCACCGAGCTGAAGCACCTCCAGT<br>GCCTGGAAGAGGAACTGAAGCCCCTGGAAGAAGTGCTGAACCTGGC<br>CCAGAGCAAGAACTTCCACCTGAGGCCCAGGGACCTGATCAGCAAC<br>ATCAACGTGATCGTGCTGGAACTGAAAGGCAGCGAGACAACCTTCA<br>TGTGCGAGTACGCCGACGAGACAGCCACCATCGTGGAATTTCTGAA<br>CCGGTGGATCACCTTCTGCCAGAGCATCATCAGCACCCTGACAGGCG<br>GCGGAGGATCTGGCGGAGGCGGCAGCGATAAGACCCACACCTGTCC<br>TCCATGTCCCGCCCCTGAACTGCTGGGCGGACCTAGCGTGTTCCTGT<br>TCCCTCCAAAGCCCAAGGACACCCTGATGATCAGCCGGACCCCTGA<br>AGTGACCTGCGTGGTGGTGGATGTGTCCCACGAGGATCCCGAAGTG<br>AAGTTCAATTGGTACGTGGACGGCGTGGAAGTGCACAACGCCAAGA<br>CCAAGCCCAGAGAGGAACAGTACAACAGCACCTACCGGGTGGTGTC<br>CGTGCTGACCGTGCTGCACCAGGACTGGCTGAATGGCAAAGAGTAC<br>AAGTGCAAGGTGTCCAACAAGGCCCTGCCTGCCCCTATCGAGAAAA<br>CCATCAGCAAGGCCAAGGGCCAGCCTAGAGAGCCTCAGGTCTGCAC<br>CCTGCCTCCCAGCCGGGAAGAGATGACCAAGAACCAGGTGTCCCTG<br>AGCTGCGCCGTGAAGGGCTTCTACCCCTCCGATATCGCCGTGGAATG<br>GGAGAGCAACGGCCAGCCCGAGAACAATTACAAGACCACCCCTCCC<br>GTGCTGGACAGCGACGGCAGCTTCTTCCTGGTGTCCAAACTGACCGT<br>GGACAAGAGCCGGTGGCAGCAGGGCAATGTGTTCAGCTGTAGCGTG<br>ATGCACGAGGCCCTGCACAACCACTACACCCAGAAGTCTCTGAGCCT<br>GAGCCCCGGCAAGTAATGA |
| SEQ ID NO: 119 | ATGGAAACCGATACACTGCTGCTGTGGGTGCTGCTCCTCTGGGTGCC<br>AGGATCTACAGGCGCCCCTACCAGCAGCAGCACCAAGAAAACCCAG<br>CTCCAGCTCGAGCACCTCCTGCTGGACCTGCAGATGATCCTGAACGG<br>CATCAACAACTACAAGAACCCCAAGCTGACCCGGATGCTGACCTTC<br>AAGTTCTACATGCCCAAGAAGGCCACCGAGCTGAAGCACCTCCAGT<br>GCCTGGAAGAGGAACTGAAGCCCCTGGAAGAAGTGCTGAACCTGGC<br>CCAGAGCAAGAACTTCCACCTGAGGCCCAGGGACCTGATCAGCAAC<br>ATCAACGTGATCGTGCTGGAACTGAAAGGCAGCGAGACAACCTTCA<br>TGTGCGAGTACGCCGACGAGACAGCCACCATCGTGGAATTTCTGAA<br>CCGGTGGATCACCTTCTGCCAGAGCATCATCAGCACCCTGACAGGCG<br>GCGGAGGATCTGGCGGAGGCGGCAGCGATAAGACCCACACCTGTCC<br>TCCATGTCCCGCCCCTGAACTGCTGGGCGGACCTAGCGTGTTCCTGT<br>TCCCTCCAAAGCCCAAGGACACCCTGATGATCAGCCGGACCCCTGA<br>AGTGACCTGCGTGGTGGTGGATGTGTCCCACGAGGATCCCGAAGTG<br>AAGTTCAATTGGTACGTGGACGGCGTGGAAGTGCACAACGCCAAGA<br>CCAAGCCCAGAGAGGAACAGTACAACAGCACCTACCGGGTGGTGTC<br>CGTGCTGACCGTGCTGCACCAGGACTGGCTGAATGGCAAAGAGTAC<br>AAGTGCAAGGTGTCCAACAAGGCCCTGCCTGCCCCTATCGAGAAAA<br>CCATCAGCAAGGCCAAGGGCCAGCCTAGAGAGCCTCAGGTCTGCAC<br>CCTGCCTCCCAGCCGGGAAGAGATGACCAAGAACCAGGTGTCCCTG<br>AGCTGCGCCGTGAAGGGCTTCTACCCCTCCGATATCGCCGTGGAATG<br>GGAGAGCAACGGCCAGCCCGAGAACAATTACAAGACCACCCCTCCC<br>GTGCTGGACAGCGACGGCAGCTTCTTCCTGGTGTCCAAACTGACCGT<br>GGACAAGAGCCGGTGGCAGCAGGGCAATGTGTTCAGCTGTAGCGTG<br>ATGCACGAGGCCCTGCACAACCACTACACCCAGAAGTCTCTGAGCCT<br>GAGCCCCGGCAAGTAATGA |
| SEQ ID NO: 117 | ATGGAAACCGATACACTGCTGCTGTGGGTGCTGCTCCTCTGGGTGCC<br>AGGATCTACAGGCCAGGTCCAGCTGCAGGAAAGCGGCCCTGGACTG<br>GTCAAGCCTAGCCAGACCCTGAGCCTGACCTGTACCGTGTCCGGCGG<br>CAGCATCAACAACAACAATTACTACTGGACATGGATCCGGCAGCAC<br>CCCGGCAAGGGCCTGGAATGGATCGGCTACATCTACTACAGCGGCT<br>CCACCTTCTACAACCCCAGCCTGAAGTCCAGAGTGACCATCAGCGTG<br>GACACCAGCAAGACCCAGTTCTCCCTGAAGCTGAGCAGCGTGACAG |

TABLE 3-continued

Nucleic acid sequences of ORFs.

| Sequence ID | Nucleic Acid Sequence |
| --- | --- |
| | CCGCCGACACAGCCGTGTACTACTGCGCCAGAGAAGATACCATGAC<br>CGGCCTGGATGTGTGGGGCCAGGGCACCACAGTGACAGTGTCTAGC<br>GCCAGCACCAAGGGCCCTAGCGTGTTCCCTCTGGCCCCTAGCTCTAA<br>GAGCACATCTGGCGGAACAGCCGCCCTGGGCTGCCTGGTCAAGGAT<br>TACTTTCCTGAGCCCGTGACCGTGTCCTGGAACTCTGGTGCTCTGAC<br>CAGCGGCGTGCACACCTTTCCAGCTGTGCTGCAGAGCAGCGGCCTGT<br>ACAGCCTGTCTAGCGTGGTCACAGTGCCTAGCAGCAGCCTGGGCAC<br>ACAGACCTACATCTGCAACGTGAACCACAAGCCCAGCAACACCAAG<br>GTGGACAAGCGGGTGGAACCCAAGAGCTGCGACAAGACCCACACCT<br>GTCCTCCCTGTCCTGCCCCTGAACTGCTGGGCGGACCTTCCGTGTTCC<br>TGTTCCCTCCAAAGCCCAAGGACACCCTGATGATCAGCCGGACCCCT<br>GAAGTGACCTGCGTGGTGGTGGATGTGTCCCACGAGGATCCCGAAG<br>TGAAGTTCAATTGGTACGTGGACGGCGTGGAAGTGCACAACGCCAA<br>GACCAAGCCCAGAGAGGAACAGTACAACAGCACCTACCGGGTGGTG<br>TCCGTGCTGACCGTGCTGCACCAGGACTGGCTGAACGGCAAAGAGT<br>ACAAGTGCAAGGTGTCCAACAAGGCCCTGCCAGCCCCTATCGAGAA<br>AACCATCAGCAAGGCCAAGGGCCAGCCCCGCGAACCTCAGGTGTAC<br>ACACTGCCTCCCTGCCGGGAAGAGATGACCAAGAACCAGGTGTCCC<br>TGTGGTGTCTCGTGAAGGGCTTCTACCCCTCCGATATCGCCGTGGAA<br>TGGGAGAGCAACGGCCAGCCCGAGAACAACTACAAGACCACCCCTC<br>CCGTGCTGGACAGCGACGGCAGCTTCTTCCTGTACTCCAAACTGACC<br>GTGGACAAGAGCCGGTGGCAGCAGGGCAATGTGTTCAGCTGTAGCG<br>TGATGCACGAGGCCCTGCACAACCACTACACCCAGAAGTCCCTGTCC<br>CTGAGCCCTGGAAAAGGTGGCGGAGGAAGCGGAGGCGGAGGTTCTG<br>GCGGCGGAGGATCT + DNA sequence for BioLegend Catalog #325207. |
| SEQ ID NO: 125 | ATGGAAACCGATACACTGCTGCTGTGGGTGCTGCTCCTCTGGGTGCC<br>AGGCAGCACCGGCGATAAGACCCACACCTGTCCTCCATGTCCTGCCC<br>CTGAGCTGCTGGGCGGACCTAGCGTGTTCCTGTTCCCTCCAAAGCCC<br>AAGGACACCCTGATGATCAGCCGGACCCCTGAAGTGACCTGCGTGG<br>TGGTGGATGTGTCCCACGAGGATCCCGAAGTGAAGTTCAATTGGTAC<br>GTGGACGGCGTGGAAGTGCACAACGCCAAGACCAAGCCCAGAGAG<br>GAACAGTACAACAGCACCTACCGGGTGGTGTCCGTGCTGACCGTGCT<br>GCACCAGGACTGGCTGAACGGCAAAGAGTACAAGTGCAAGGTGTCC<br>AACAAGGCCCTGCCTGCCCCTATCGAGAAAACCATCAGCAAGGCCA<br>AGGGCCAGCCTAGAGAGCCTCAGGTCTGCACCCTGCCTCCCAGCCG<br>GGAAGAGATGACCAAGAACCAGGTGTCCCTGTCCTGCGCCGTGAAG<br>GGCTTCTACCCCTCCGATATCGCCGTGGAATGGGAGAGCAACGGCC<br>AGCCCGAGAACAACTACAAGACCACCCCTCCCGTGCTGGACAGCGA<br>CGGCAGCTTCTTCCTGGTGTCCAAACTGACCGTGGACAAGAGCCGGT<br>GGCAGCAGGGCAATGTGTTCAGCTGTAGCGTGATGCACGAGGCCCT<br>GCACAACCACTACACCCAGAAGTCTCTGAGCCTGAGCCCCGGCAAG<br>TAATGA |
| SEQ ID NO: 124 | ATGGAAACCGATACACTGCTGCTGTGGGTGCTGCTCCTCTGGGTGCC<br>AGGCAGCACCGGCGATAAGACCCACACCTGTCCTCCATGTCCTGCCC<br>CTGAGCTGCTGGGCGGACCTAGCGTGTTCCTGTTCCCTCCAAAGCCC<br>AAGGACACCCTGATGATCAGCCGGACCCCTGAAGTGACCTGCGTGG<br>TGGTGGATGTGTCCCACGAGGATCCCGAAGTGAAGTTCAATTGGTAC<br>GTGGACGGCGTGGAAGTGCACAACGCCAAGACCAAGCCCAGAGAG<br>GAACAGTACAACAGCACCTACCGGGTGGTGTCCGTGCTGACCGTGCT<br>GCACCAGGACTGGCTGAACGGCAAAGAGTACAAGTGCAAGGTGTCC<br>AACAAGGCCCTGCCTGCCCCTATCGAGAAAACCATCAGCAAGGCCA<br>AGGGCCAGCCCCGCGAACCTCAGGTGTACACACTGCCTCCCTGCCGG<br>GAAGAGATGACCAAGAACCAGGTGTCCCTGTGGTGCCTGGTCAAGG<br>GCTTCTACCCCTCCGATATCGCCGTGGAATGGGAGAGCAACGGCCA<br>GCCCGAGAACAACTACAAGACCACCCCTCCCGTGCTGGACAGCGAC<br>GGCAGCTTCTTCCTGTACTCCAAACTGACCGTGGACAAGAGCCGGTG<br>GCAGCAGGGCAATGTGTTCAGCTGTAGCGTGATGCACGAGGCCCTG<br>CACAACCACTACACCCAGAAGTCTCTGAGCCTGAGCCCCGGCAAGT<br>AATGA |
| SEQ ID NO: 126 | ATGGAAACCGACACACTGCTGCTGTGGGTGCTGCTCTTGTGGGTGCC<br>AGGATCTACAGGCGAAGTGCAGCTGTTGCAGTCTGGCGGAGGATTG<br>GTTCAGCCTGGCGGATCCCTGAGACTGTCTTGTGCCGCCTCTGGCTT<br>CATGTTCAGCAGATACCCCATGCACTGGGTCCGACAGGCCCCTGGAA<br>AAGGACTGGAATGGGTCGGATCCATCTCCGGAAGTGGCGGCGCTAC<br>CCCTTACGCCGATTCTGTGAAGGGCAGATTCACCATCAGCCGGGACA<br>ACTCCAAGAACACCCTGTACCTGCAGATGAACTCCCTGAGAGCCGA<br>GGACACCGCCGTGTACTACTGCGCCAAGGACTTCTACCAGATCCTGA<br>CCGGCAACGCCTTCGACTATTGGGGCCAGGGCACAACCGTGACCGT<br>GTCCTCTGCTTCTACCAAGGGACCCAGCGTGTTCCCTCTGGCTCCTTC<br>CAGCAAGTCTACCTCTGGCGGAACAGCTGCTCTGGGCTGCCTGGTCA<br>AGGACTACTTTCCTGAGCCTGTGACAGTGTCCTGGAACTCTGGCGCT<br>CTGACATCCGGCGTGCACACCTTTCCAGCTGTGCTGCAATCCAGCGG<br>CCTGTACTCTCTGTCCTCCGTCGTGACAGTGCCTTCCAGCTCTCTGGG |

TABLE 3-continued

Nucleic acid sequences of ORFs.

| Sequence ID | Nucleic Acid Sequence |
|---|---|
|  | AACCCAGACCTACATCTGCAATGTGAACCACAAGCCTTCCAACACCA<br>AGGTGGACAAGAGAGTGGAACCCAAGTCCTGCGACAAGACCCACAC<br>CTGTCCTCCATGTCCTGCTCCAGAACTGCTCGGCGGACCTTCCGTGTT<br>CCTGTTTCCTCCAAAGCCTAAGGACACCCTGATGATCTCTCGGACCC<br>CTGAAGTGACCTGCGTGGTGGTGGATGTGTCTCACGAGGATCCCGAA<br>GTGAAGTTCAATTGGTACGTGGACGGCGTGGAAGTGCACAACGCCA<br>AGACCAAGCCTAGAGAGGAACAGTACAACTCCACCTACAGAGTGGT<br>GTCCGTGCTGACCGTGCTGCACCAGGATTGGCTGAACGGCAAAGAG<br>TACAAGTGCAAGGTGTCCAACAAGGCCCTGCCTGCTCCTATCGAAAA<br>GACCATCTCCAAGGCCAAGGGCCAGCCTCGGGAACCTCAAGTCTGT<br>ACCCTGCCTCCTAGCCGGGAAGAGATGACCAAGAACCAGGTGTCCC<br>TGTCCTGTGCCGTGAAGGGCTTCTACCCTTCCGATATCGCCGTGGAA<br>TGGGAGAGCAATGGCCAGCCTGAGAACAACTACAAGACAACCCCTC<br>CTGTGCTGGACTCCGACGGCTCATTCTTCCTGGTGTCCAAGCTGACA<br>GTGGACAAGTCCAGATGGCAGCAGGGCAACGTGTTCTCCTGCTCCGT<br>GATGCACGAGGCCCTGCACAATCACTACACCCAGAAGTCCCTGTCTC<br>TGAGCCCCGGCAAGTGATGA |
| SEQ ID NO: 127 | ATGGAAACCGACACACTGCTGCTGTGGGTGCTGCTCTTGTGGGTGCC<br>AGGATCTACCGGCGACATCCAGATGACCCAGTCTCCATCCTCTCTGT<br>CTGCCAGCCTGGGCGACAGAGTGACCATCACCTGTAGAGCCTCTCAG<br>GGCATCTCCTCCTACCTGGCCTGGTATCAGCAGAAGCCTGGCAAGGC<br>TCCCAAGCTGCTGATCTACGCCAAGAGCACACTGCAGTCTGGCGTGC<br>CCTCTAGATTCTCCGGCTCTGGCTCTGGCACCGACTTTACCCTGACA<br>ATCTCCAGCCTGCAGCCTGAGGACTCCGCCACCTACTACTGTCAGCA<br>GTACTGGACCTTTCCACTGACCTTCGGCGGAGGCACCAAGGTGGAA<br>ATCAAGAGAACCGTGGCCGCTCCTTCCGTGTTCATCTTCCCACCTTCC<br>GACGAGCAGCTGAAGTCCGGCACAGCTTCGTCGTGTGCCTGCTGAA<br>CAACTTCTACCCTCGGGAAGCCAAAGTGCAGTGGAAGGTGGACAAC<br>GCTCTGCAGTCCGGCAACTCCCAAGAGTCTGTGACCGAGCAGGACTC<br>CAAGGACAGCACCTACAGCCTGTCCTCCACACTGACCCTGTCCAAGG<br>CCGACTACGAGAAGCACAAGGTGTACGCCTGCGAAGTGACCCATCA<br>GGGCCTGTCTAGCCCTGTGACCAAGTCTTTCAACCGGGGCGAGTGCT<br>GATGA |
| SEQ ID NO: 128 | ATGGAAACCGACACACTGCTGCTGTGGGTGCTGCTCTTGTGGGTGCC<br>AGGATCTACAGGCGAAGTGCAGCTGTTGCAGTCTGGCGGAGGATTG<br>GTTCAGCCTGGCGGATCCCTGAGACTGTCTTGTGCCGCCTCTGGCTT<br>CATGTTCAGCAGATACCCCATGCACTGGGTCCGACAGGCCCCTGGAA<br>AAGGACTGGAATGGGTCGGATCCATCTCCGGAAGTGGCGGCGCTAC<br>CCCTTACGCCGATTCTGTGAAGGGCAGATTCACCATCAGCCGGGACA<br>ACTCCAAGAACACCCTGTACCTGCAGATGAACTCCCTGAGAGCCGA<br>GGACACCGCCGTGTACTACTGCGCCAAGGACTTCTACCAGATCCTGA<br>CCGGCAACGCCTTCGACTATTGGGGCCAGGGCACAACCGTGACCGT<br>GTCCTCTGCTTCTACCAAGGGACCCAGCGTGTTCCCTCTGGCTCCTTC<br>CAGCAAGTCTACCTCTGGCGGAACAGCTGCTCTGGGCTGCCTGGTCA<br>AGGACTACTTTCCTGAGCCTGTGACAGTGTCCTGGAACTCTGGCGCT<br>CTGACATCCGGCGTGCACACCTTTCCAGCTGTGCTGCAATCCAGCGG<br>CCTGTACTCTCTGTCCTCCGTCGTGACAGTGCCTTCCAGCTCTCTGGG<br>AACCCAGACCTACATCTGCAATGTGAACCACAAGCCTTCCAACACCA<br>AGGTGGACAAGAGAGTGGAACCCAAGTCCTGCGACAAGACCCACAC<br>CTGTCCTCCATGTCCTGCTCCAGAACTGCTCGGCGGACCTTCCGTGTT<br>CCTGTTTCCTCCAAAGCCTAAGGACACCCTGATGATCTCTCGGACCC<br>CTGAAGTGACCTGCGTGGTGGTGGATGTGTCTCACGAGGATCCCGAA<br>GTGAAGTTCAATTGGTACGTGGACGGCGTGGAAGTGCACAACGCCA<br>AGACCAAGCCTAGAGAGGAACAGTACAACTCCACCTACAGAGTGGT<br>GTCCGTGCTGACCGTGCTGCACCAGGATTGGCTGAACGGCAAAGAG<br>TACAAGTGCAAGGTGTCCAACAAGGCCCTGCCTGCTCCTATCGAAAA<br>GACCATCTCCAAGGCCAAGGGCCAGCCTCGGGAACCTCAAGTCTGT<br>ACCCTGCCTCCTAGCCGGGAAGAGATGACCAAGAACCAGGTGTCCC<br>TGTCCTGTGCCGTGAAGGGCTTCTACCCTTCCGATATCGCCGTGGAA<br>TGGGAGAGCAATGGCCAGCCTGAGAACAACTACAAGACAACCCCTC<br>CTGTGCTGGACTCCGACGGCTCATTCTTCCTGGTGTCCAAGCTGACA<br>GTGGACAAGTCCAGATGGCAGCAGGGCAACGTGTTCTCCTGCTCCGT<br>GATGCACGAGGCCCTGCACAATCACTACACCCAGAAGTCCCTGTCTC<br>TGAGCCCTGGCAAAGGCGGAGGCGGATCTGGTGGTGGCGGTTCTGG<br>CGGCGGTGGATCTGCTCCTACATCCTCCAGCACCAAGAAAACCCAGC<br>TGCAGTTGGAGCATCTGCTGCTGGACCTCCAGATGATCCTGAATGGC<br>ATCAACAATTACAAGAACCCCAAGCTCACCCGGATGCTGACCTTCAA<br>GTTCTACATGCCCAAGAAGGCCACCGAGCTGAAACATCTGCAGTGC<br>CTGGAAGAGGAACTGAAGCCTCTGGAAGAAGTGCTGAATCTGGCCC<br>AGTCCAAGAACTTCCACCTGAGGCCTCGGGACCTGATCTCCAACATC<br>AACGTGATCGTGCTCGAGCTGAAGGGCTCCGAGACTACCTTCATGTG<br>CGAGTACGCCGACGAGACAGCTACCATCGTGGAATTTCTGAACCGG<br>TGGATCACCTTCTGCCAGTCCATCATCAGCACCCTGACCTGATGA |

TABLE 3-continued

Nucleic acid sequences of ORFs.

| Sequence ID | Nucleic Acid Sequence |
|---|---|
| SEQ ID NO: 129 | ATGGAAACCGACACACTGCTGCTGTGGGTGCTGCTCTTGTGGGTGCC<br>AGGATCTACAGGCGAAGTGCAGCTGTTGCAGTCTGGCGGAGGATTG<br>GTTCAGCCTGGCGGATCCCTGAGACTGTCTTGTGCCGCCTCTGGCTT<br>CATGTTCAGCAGATACCCCATGCACTGGGTCCGACAGGCCCCTGGAA<br>AAGGACTGGAATGGGTCGGATCCATCTCCGGAAGTGGCGGCGCTAC<br>CCCTTACGCCGATTCTGTGAAGGGCAGATTCACCATCAGCCGGGACA<br>ACTCCAAGAACACCCTGTACCTGCAGATGAACTCCCTGAGAGCCGA<br>GGACACCGCCGTGTACTACTGCGCCAAGGACTTCTACCAGATCCTGA<br>CCGGCAACGCCTTCGACTATTGGGGCCAGGGCACAACCGTGACCGT<br>GTCCTCTGCTTCTACCAAGGGACCCAGCGTGTTCCCTCTGGCTCCTTC<br>CAGCAAGTCTACCTCTGGCGGAACAGCTGCTCTGGGCTGCCTGGTCA<br>AGGACTACTTTCCTGAGCCTGTGACAGTGTCCTGGAACTCTGGCGCT<br>CTGACATCCGGCGTGCACACCTTTCCAGCTGTGCTGCAATCCAGCGG<br>CCTGTACTCTCTGTCCTCCGTCGTGACAGTGCCTTCCAGCTCTCTGGG<br>AACCCAGACCTACATCTGCAATGTGAACCACAAGCCTTCCAACACCA<br>AGGTGGACAAGAGAGTGGAACCCAAGTCCTGCGACAAGACCCACAC<br>CTGTCCTCCATGTCCTGCTCCAGAACTGCTCGGCGGACCTTCCGTGTT<br>CCTGTTTCCTCCAAAGCCTAAGGACACCCTGATGATCTCTCGGACCC<br>CTGAAGTGACCTGCGTGGTGGTGGATGTGTCTCACGAGGATCCCGAA<br>GTGAAGTTCAATTGGTACGTGGACGGCGTGGAAGTGCACAACGCCA<br>AGACCAAGCCTAGAGAGGAACAGTACAACTCCACCTACAGAGTGGT<br>GTCCGTGCTGACCGTGCTGCACCAGGATTGGCTGAACGGCAAAGAG<br>TACAAGTGCAAGGTGTCCAACAAGGCCCTGCCTGCTCCTATCGAAAA<br>GACCATCTCCAAGGCCAAGGGCCAGCCTCGGGAACCTCAAGTCTGT<br>ACCCTGCCTCCTAGCCGGGAAGAGATGACCAAGAACCAGGTGTCCC<br>TGTCCTGTGCCGTGAAGGGCTTCTACCCTTCCGATATCGCCGTGGAA<br>TGGGAGAGCAATGGCCAGCCTGAGAACAACTACAAGACAACCCCTC<br>CTGTGCTGGACTCCGACGGCTCATTCTTCCTGGTGTCCAAGCTGACA<br>GTGGACAAGTCCAGATGGCAGCAGGGCAACGTGTTCTCCTGCTCCGT<br>GATGCACGAGGCCCTGCACAATCACTACACCCAGAAGTCCCTGTCTC<br>TGAGCCCTGGCAAAGGCGGAGGCGGATCTGGTGGTGGCGGTTCTGG<br>CGGCGGTGGATCTGACTGTGATATCGAAGGCAAGGACGGCAAGCAG<br>TACGAGTCCGTCCTGATGGTGTCCATCGACCAGCTGCTGGACAGCAT<br>GAAGGAAATCGGCTCCAACTGCCTGAACAACGAGTTCAACTTCTTCA<br>AGCGGCACATCTGCGACGCCAACAAAGAAGGCATGTTTCTGTTCCG<br>GGCTGCCAGAAAGCTGCGGCAGTTCCTGAAGATGAACAGCACCGGC<br>GACTTCGACCTGCACCTGTTGAAAGTGTCTGAGGGCACCACCATCCT<br>GCTGAACTGTACCGGCCAAGTGAAGGGAAGAAAGCCTGCCGCTCTG<br>GGCGAAGCCCAGCCTACAAAGTCTCTGGAAGAGAACAAGTCCCTGA<br>AAGAGCAGAAGAAGCTGAACGACCTCTGTTTCCTGAAGCGGCTGCT<br>GCAAGAGATCAAGACCTGCTGGAACAAGATCCTGATGGGCACCAAA<br>GAGCACTGATAG |
| SEQ ID NO: 130 | ATGGAAACCGACACACTGCTGCTGTGGGTGCTGCTCTTGTGGGTGCC<br>AGGATCTACAGGACAGGTGCAGCTGGTTCAGTCTGGCGGAGGATTG<br>GTTCAGCCAGGCGGATCCCTGAGACTGTCTTGTGCCGCTTCTGGCTT<br>CACCCTTCGACGACTACGCTATGCACTGGGTCCGACAGGCCCCTGGCA<br>AAGGATTGGAATGGGTGGCCGGCATCTCTTGGGACTCTGGCTCTACC<br>GGCTACGCCGACTCTGTGAAGGGCAGATTCACCATCTCTCGGGACAA<br>CGCCAAGAACTCCCTGTACCTGCAGATGAACAGCCTGAGAGCCGAG<br>GACACCGCTCTGTACTACTGCGCTAGAGATCTGGGCGCCTACCAGTG<br>GGTGGAAGGCTTTGATTATTGGGGCCAGGGCACCCTGGTCACCGTGT<br>CTAGTGCTTCTACTGGTGGTGGCGGATCTGGCGGCGGAGGAAGCGG<br>AGGCGGAGGTAGTGGTGGCGGTGGATCTTCTTACGAGCTGACCCAG<br>GATCCAGCCGTGTCTGTTGCTCTGGGCCAGACAGTGCGGATTACCTG<br>CCAGGGCGACTCCCTGAGATCCTACTACGCCTCCTGGTATCAGCAGA<br>AGCCAGGCCAGGCTCCTGTGCTGGTCATCTACGGCAAGAACAACCG<br>GCCTAGCGGCATCCCTGACAGATTCTCCGGCTCTACCTCCGGCAACT<br>CTGCCAGCCTGACAATTACTGGCGCCCAGGCTGAGGACGAGGCCGA<br>CTACTACTGCAACTCCAGAGACAGCCCTGGCAATCAGTGGGTTTTCG<br>GCGGAGGCACCAAAGTGACAGTTCTTGGTGCGGAGGTGGAAGTGG<br>CGGAGGCGGTTCTGATAAGACCCACACCTGTCCACCTTGTCCTGCTC<br>CAGAACTGCTCGGCGGACCTTCCGTGTTCCTGTTTCCTCCAAAGCCT<br>AAGGACACCCTGATGATCTCTCGGACCCCTGAAGTGACCTGCGTGGT<br>GGTGGATGTGTCTCACGAGGATCCCGAAGTGAAGTTCAATTGGTACG<br>TGGACGGCGTGGAAGTGCACAATGCCAAGACCAAGCCTAGAGAGGA<br>ACAGTACAACTCCACCTATAGAGTGGTGTCCGTGCTGACCGTGCTGC<br>ACCAGGATTGGCTGAACGGCAAAGAGTACAAGTGCAAGGTGTCCAA<br>CAAGGCCCTGCCTGCTCCTATCGAAAAGACCATCTCCAAGGCCAAG<br>GGCCAGCCTAGGGAACCCCAGGTTTACACCCTGCCTCCATGCCGGGA<br>AGAGATGACCAAGAACCAGGTGTCCCTGTGGTGCCTGGTCAAGGGC<br>TTCTACCCTTCCGATATCGCCGTGGAATGGGAGAGCAATGGCCAGCC<br>AGAGAACAACTACAAGACCACACCTCCAGTGCTGGACTCCGACGGC<br>TCATTCTTCCTGTACTCCAAGCTGACAGTGGACAAGTCCAGATGGCA<br>GCAGGGCAACGTGTTCTCCTGCTCCGTGATGCACGAGGCCCTGCACA<br>ATCACTACACCCAGAAGTCCCTGTCTCTGAGCCCCGGCAAGTGATGA |

TABLE 3-continued

Nucleic acid sequences of ORFs.

| Sequence ID | Nucleic Acid Sequence |
|---|---|
| SEQ ID NO: 131 | ATGGAAACCGACACACTGCTGCTGTGGGTGCTGCTCTTGTGGGTGCC<br>AGGATCTACAGGACAGGTGCAGCTGGTTCAGTCTGGCGGAGGATTG<br>GTTCAGCCAGGCGGATCCCTGAGACTGTCTTGTGCCGCTTCTGGCTT<br>CACCTTCGACGACTACGCTATGCACTGGGTCCGACAGGCCCCTGGCA<br>AAGGATTGGAATGGGTGGCCGGCATCTCTTGGGACTCTGGCTCTACC<br>GGCTACGCCGACTCTGTGAAGGGCAGATTCACCATCTCTCGGGACAA<br>CGCCAAGAACTCCCTGTACCTGCAGATGAACAGCCTGAGAGCCGAG<br>GACACCGCTCTGTACTACTGCGCTAGAGATCTGGGCGCCTACCAGTG<br>GGTGGAAGGCTTTGATTATTGGGGCCAGGGCACCCTGGTCACCGTGT<br>CTAGTGCTTCTACTGGTGGTGGCGGATCTGGCGGCGGAGGAAGCGG<br>AGGCGGAGGTAGTGGTGGCGGTGGATCTTCTTACGAGCTGACCCAG<br>GATCCAGCCGTGTCTGTTGCTCTGGGCCAGACAGTGCGGATTACCTG<br>CCAGGGCGACTCCCTGAGATCCTACTACGCCTCCTGGTATCAGCAGA<br>AGCCAGGCCAGGCTCCTGTGCTGGTCATCTACGGCAAGAACAACCG<br>GCCTAGCGGCATCCCTGACAGATTCTCCGGCTCTACCTCCGGCAACT<br>CTGCCAGCCTGACAATTACTGGCGCCCAGGCTGAGGACGAGGCCGA<br>CTACTACTGCAACTCCAGAGACAGCCCTGGCAATCAGTGGGTTTTCG<br>GCGGAGGCACCAAAGTGACAGTTCTTGGTGGCGGAGGTGGAAGTGG<br>CGGAGGCGGTTCTGATAAGACCCACACCTGTCCACCTTGTCCTGCTC<br>CAGAACTGCTCGGCGGACCTTCCGTGTTCCTGTTTCCTCCAAAGCCT<br>AAGGACACCCTGATGATCTCTCGGACCCCTGAAGTGACCTGCGTGGT<br>GGTGGATGTGTCTCACGAGGATCCCGAAGTGAAGTTCAATTGGTACG<br>TGGACGGCGTGGAAGTGCACAATGCCAAGACCAAGCCTAGAGAGGA<br>ACAGTACAACTCCACCTATAGAGTGGTGTCCGTGCTGACCGTGCTGC<br>ACCAGGATTGGCTGAACGGCAAAGAGTACAAGTGCAAGGTGTCCAA<br>CAAGGCCCTGCCTGCTCCTATCGAAAAGACCATCTCCAAGGCCAAG<br>GGCCAGCCTAGGGAACCCCAGGTTTACACCCTGCCTCCATGCCGGGA<br>AGAGATGACCAAGAACCAGGTGTCCCTGTGGTGCCTGGTCAAGGGC<br>TTCTACCCTTCCGATATCGCCGTGGAATGGGAGAGCAATGGCCAGCC<br>AGAGAACAACTACAAGACCACACCTCCAGTGCTGGACTCCGACGGC<br>TCATTCTTCCTGTACTCCAAGCTGACAGTGGACAAGTCCAGATGGCA<br>GCAGGGCAACGTGTTCTCCTGCTCCGTGATGCACGAGGCCCTGCACA<br>ATCACTACACCCAGAAGTCCCTGTCTCTGTCTCCCGGAAAAGGCGGT<br>GGTGGATCAGGTGGCGGAGGCTCAGGCGGAGGCGGATCTCAAGTTC<br>AGTTGCAGCAGAGCGGACCCGAGCTGGTCAAACCTGGCGCTTCCGT<br>GAAGATGTCCTGCAAGGCCTCCGGCTACACCTTCACCGATTACGTGA<br>TCAACTGGGGCAAGCAGCGCTCTGGCCAAGGCCTGGAATGGATCGG<br>CGAGATCTATCCTGGCTCCGGCACCAACTACTACAACGAGAAGTTCA<br>AGGCTAAGGCTACCCTGACCGCCGACAAGTCCTCCAATATCGCCTAC<br>ATGCAGCTGTCTAGCCTGACCTCCGAGGACTCTGCCGTGTACTTCTG<br>CGCCAGAAGAGGCAGATACGGCCTGTACGCCATGGACTACTGGGGA<br>CAGGGAACCTCCGTGACAGTTAGTAGCGGTGGCGGCGGTAGCGGCG<br>GTGGTGGTTCTGGCGGTGGTGGTAGTGGCGGCGGAGGATCTGATATC<br>CAGATGACCCAGACCACCAGCAGCCTGTCTGCTTCCCTGGGCGATAG<br>AGTGACCATCTCTTGCAGAGCCAGCCAGGACATCAGCAACTACCTG<br>AACTGGTATCAACAAAAACCCGACGGCACCGTGAAGCTGCTGATCT<br>ACTACACCTCTCGGCTGCACTCTGGCGTGCCCTCTAGATTTTCTGGCA<br>GCGGCTCTGGAACCGACTACTCCCTGACCATCAACAACCTGGAACA<br>AGAGGATATCGCTACCTACTTCTGCCAGCAAGGCAACACCCGGCCTT<br>GGACATTTGGAGGCGGCACCAAGCTGGAAATCAAGTGATGA |
| SEQ ID NO: 132 | ATGGAAACCGACACACTGCTGCTGTGGGTGCTGCTCTTGTGGGTGCC<br>AGGATCTACAGGACAGGTGCAGCTGGTTCAGTCTGGCGGAGGATTG<br>GTTCAGCCAGGCGGATCCCTGAGACTGTCTTGTGCCGCTTCTGGCTT<br>CACCTTCGACGACTACGCTATGCACTGGGTCCGACAGGCCCCTGGCA<br>AAGGATTGGAATGGGTGGCCGGCATCTCTTGGGACTCTGGCTCTACC<br>GGCTACGCCGACTCTGTGAAGGGCAGATTCACCATCTCTCGGGACAA<br>CGCCAAGAACTCCCTGTACCTGCAGATGAACAGCCTGAGAGCCGAG<br>GACACCGCTCTGTACTACTGCGCTAGAGATCTGGGCGCCTACCAGTG<br>GGTGGAAGGCTTTGATTATTGGGGCCAGGGCACCCTGGTCACCGTGT<br>CTAGTGCTTCTACTGGTGGTGGCGGATCTGGCGGCGGAGGAAGCGG<br>AGGCGGAGGTAGTGGTGGCGGTGGATCTTCTTACGAGCTGACCCAG<br>GATCCAGCCGTGTCTGTTGCTCTGGGCCAGACAGTGCGGATTACCTG<br>CCAGGGCGACTCCCTGAGATCCTACTACGCCTCCTGGTATCAGCAGA<br>AGCCAGGCCAGGCTCCTGTGCTGGTCATCTACGGCAAGAACAACCG<br>GCCTAGCGGCATCCCTGACAGATTCTCCGGCTCTACCTCCGGCAACT<br>CTGCCAGCCTGACAATTACTGGCGCCCAGGCTGAGGACGAGGCCGA<br>CTACTACTGCAACTCCAGAGACAGCCCTGGCAATCAGTGGGTTTTCG<br>GCGGAGGCACCAAAGTGACAGTTCTTGGTGGCGGAGGTGGAAGTGG<br>CGGAGGCGGTTCTGATAAGACCCACACCTGTCCACCTTGTCCTGCTC<br>CAGAACTGCTCGGCGGACCTTCCGTGTTCCTGTTTCCTCCAAAGCCT<br>AAGGACACCCTGATGATCTCTCGGACCCCTGAAGTGACCTGCGTGGT<br>GGTGGATGTGTCTCACGAGGATCCCGAAGTGAAGTTCAATTGGTACG<br>TGGACGGCGTGGAAGTGCACAATGCCAAGACCAAGCCTAGAGAGGA<br>ACAGTACAACTCCACCTATAGAGTGGTGTCCGTGCTGACCGTGCTGC |

TABLE 3-continued

Nucleic acid sequences of ORFs.

| Sequence ID | Nucleic Acid Sequence |
|---|---|
|  | ACCAGGATTGGCTGAACGGCAAAGAGTACAAGTGCAAGGTGTCCAA<br>CAAGGCCCTGCCTGCTCCTATCGAAAAGACCATCTCCAAGGCCAAG<br>GGCCAGCCTAGGGAACCCCAGGTTTACACCCTGCCTCCATGCCGGGA<br>AGAGATGACCAAGAACCAGGTGTCCCTGTGGTGCCTGGTCAAGGGC<br>TTCTACCCTTCCGATATCGCCGTGGAATGGGAGAGCAATGGCCAGCC<br>AGAGAACAACTACAAGACCACACCTCCAGTGCTGGACTCCGACGGC<br>TCATTCTTCCTGTACTCCAAGCTGACAGTGGACAAGTCCAGATGGCA<br>GCAGGGCAACGTGTTCTCCTGCTCCGTGATGCACGAGGCCCTGCACA<br>ATCACTACACCCAGAAGTCCCTGTCTCTGTCTCCCGGAAAAGGCGGT<br>GGTGGATCAGGTGGCGGAGGCTCAGGCGGAGGCGGATCTCAAGTTC<br>AGTTGGTTCAAAGCGGTGGCGGCGTGGTGCAGCCTGGAAGATCTCTC<br>AGACTGTCCTGCAAGGCCTCCGGCTACACCTTCACCAGATACACCAT<br>GCATTGGGTTCGACAAGCACCAGGCAAGGGCCTCGAGTGGATCGGC<br>TACATCAACCCTTCCAGAGGCTACACCAACTACAACCAGAAAGTGA<br>AGGACCGGTTCACCATCAGCAGAGACAACAGCAAGAATACCGCCTT<br>TCTGCAGATGGACTCCCTGCGGCCTGAAGATACCGGCGTGTACTTTT<br>GCGCCCGGTACTACGACGACCACTACTCCCTGGATTACTGGGGACAG<br>GGAACACCCGTGACAGTGTCTAGCGGTGGCGGTGGTTCAGGCGGCG<br>GTGGTAGTGGCGGCGGAGGTAGCGGCGGTGGCGGATCTGATATTCA<br>GATGACCCAGTCTCCTTCCAGCCTGTCCGCTTCTGTGGGCGACAGAG<br>TGACTATTACCTGCTCCGCCTCTTCCTCCGTGTCCTACATGAACTGGT<br>ATCAACAAACACCCGGCAAGGCCCCTAAGAGATGGATCTACGACAC<br>CAGCAAGCTGGCCTCTGGCGTGCCCTCTAGATTTTCTGGCTCTGGCT<br>CCGGCACCGACTATACCTTTACAATCTCCAGCCTGCAGCCTGAGGAT<br>ATCGCCACCTACTACTGTCAGCAGTGGTCTAGCAACCCCTTCACCTT<br>TGGACAGGGCACCAAGCTGCAGATCACCTGATGA |
| SEQ ID NO: 133 | ATGGAAACCGACACACTGCTGCTGTGGGTGCTGCTCTTGTGGGTGCC<br>AGGATCTACAGGACAGGTCCAGCTGCAAGAGTCTGGCCCTGGACTG<br>GTCAAGCCCTCTCAGACCCTGTCTCTGACCTGTACCGTGTCCGGCGG<br>CTCCATCAACAACAACAATTACTACTGGACCTGGATCCGGCAGCACC<br>CTGGCAAAGGACTGGAATGGATCGGCTACATCTACTACTCCGGCTCC<br>ACCTTCTACAACCCCAGCCTGAAGTCCAGAGTGACCATCTCCGTGGA<br>CACCAGCAAGACCCAGTTCTCCCTGAAGCTGTCCTCTGTGACCGCCG<br>CTGATACCGCCGTGTACTACTGCGCCAGAGAAGATACCATGACCGG<br>CCTGGATGTGTGGGGCCAGGGAACAACAGTGACCGTGTCCTCCGCTT<br>CCACCAAGGGACCTTCCGTGTTTCCTCTGGCTCCCTCCAGCAAGTCT<br>ACCTCTGGTGGAACAGCTGCCCTGGGCTGCCTGGTCAAGGATTACTT<br>TCCTGAGCCTGTGACAGTGTCCTGGAACTCTGGCGCTCTGACATCCG<br>GCGTGCACACCTTTCCAGCTGTGCTGCAATCCTCCGGCCTGTACTCTC<br>TGTCCTCCGTCGTGACCGTGCCTTCTAGCTCTCTGGGCACCCAGACCT<br>ACATCTGCAATGTGAACCACAAGCCTTCCAACACCAAGGTGGACAA<br>GAGAGTGGAACCCAAGTCCTGCGACAAGACCCACACCTGTCCTCCA<br>TGTCCTGCTCCAGAACTGCTCGGCGGACCCTCTGTGTTCCTGTTTCCA<br>CCTAAGCCTAAGGACACCCTGATGATCTCTCGGACCCCTGAAGTGAC<br>CTGCGTGGTGGTGGATGTGTCTCACGAGGATCCCGAAGTGAAGTTCA<br>ATTGGTACGTGGACGGCGTGGAAGTGCACAACGCCAAGACCAAGCC<br>TAGAGAGGAACAGTACAACTCCACCTACAGAGTGGTGTCCGTGCTG<br>ACCGTGCTGCACCAGGATTGGCTGAACGGCAAAGAGTACAAGTGCA<br>AGGTGTCCAACAAGGCCCTGCCTGCTCCTATCGAAAAGACCATCAGC<br>AAGGCCAAGGGCCAGCCTAGGGAACCCCAGGTTTACACCCTGCCTC<br>CATGCCGGGAAGAGATGACCAAGAACCAGGTGTCCCTGTGGTGCCT<br>CGTGAAGGGCTTCTACCCTTCCGATATCGCCGTGGAATGGGAGAGCA<br>ATGGCCAGCCTGAGAACAACTACAAGACAACCCCTCCTGTGCTGGA<br>CTCCGACGGCTCATTCTTCCTGTACTCCAAGCTGACAGTGGACAAGT<br>CCAGATGGCAGCAGGGCAACGTGTTCTCCTGCTCCGTGATGCACGAG<br>GCCCTGCACAATCACTACACCCAGAAGAGTCTGTCTCTGTCTCCCGG<br>CAAAGGCGGCGGAGGATCTGGCGGAGGCGGTAGCGGTGGTGGCGG<br>ATCTCAGGTTCAGTTGCAGCAGTCCGGACCTGAGCTGGTTAAGCCTG<br>GCGCCTCCGTGAAGATGTCCTGCAAGGCTTCTGGCTACACCTTCACC<br>GACTACGTGATCAACTGGGGCAAGCAGAGATCTGGCCAGGGACTCG<br>AGTGGATCGGAGAGATCTATCCTGGCTCCGGCACCAACTACTACAAT<br>GAGAAGTTCAAGGCTAAGGCTACCCTGACCGCCGACAAGTCCTCCA<br>ATATCGCCTACATGCAGCTGTCCAGCCTGACCTCTGAGGACTCCGCT<br>GTGTACTTCTGTGCTCGGAGAGGCAGATACGGCCTGTATGCCATGGA<br>TTACTGGGGACAGGGCACCTCCGTGACTGTCTCTAGCGGTGGCGGAG<br>GTAGCGGAGGCGGTGGTTCAGGCGGAGGCGGCTCTGGTGGCGGTGG<br>ATCTGATATTCAGATGACCCAGACCACCTCCAGCCTGTCCGCTTCTC<br>TGGGCGACAGAGTGACAATCAGCTGCAGAGCCAGCCAGGACATCAG<br>CAACTACCTGAACTGGTATCAGCAGAAACCCGACGGCACCGTGAAG<br>CTGCTGATCTACTACACCTCTCGGCTGCACTCTGGCGTGCCCTCTAG<br>ATTTTCTGGCAGCGGAAGCGGCACCGATTACTCCCTGACAATCAACA<br>ACCTCGAGCAAGAGGATATCGCTACCTACTTCTGCCAGCAAGGCAA<br>CACCCGGCCTTGGACATTTGGCGGCGGAACAAAGCTGGAAATCAAG<br>TGATGA |

TABLE 3-continued

Nucleic acid sequences of ORFs.

| Sequence ID | Nucleic Acid Sequence |
| --- | --- |
| SEQ ID NO: 121 | ATGGAAACCGATACCCTGCTGCTGTGGGTGCTGCTCCTCTGGGTGCC<br>AGGCTCTACCGGCCAGTCTGCTCTGACCCAGCCTGCCTCTGTGTCTG<br>GCTCCCCTGGCCAGTCCATCACCATCAGCTGTACCGGCACCTCCTCC<br>GACGTGGGCGGCTACAACTACGTGTCCTGGTATCAGCAGCATCCCGG<br>CAAGGCCCCTAAGCTGATGATCTACGACGTGTCCAACCGGCCCTCCG<br>GCGTGTCCAATCGGTTCTCTGGCTCCAAGTCCGGCAACACCGCCTCC<br>CTGACAATCAGCGGACTGCAGGCCGAGGACGAGGCCGACTACTACT<br>GCTCCTCCTACACCTCCAGCTCTACCCGGGTGTTCGGCACCGGCACC<br>AAAGTGACAGTGCTGGGCCAGCCCAAGGCCAACCCCACCGTGACCC<br>TGTTCCCTCCATCCTCCGAGGAACTGCAGGCTAACAAGGCCACCCTC<br>GTGTGCCTGATCTCCGACTTCTACCCTGGCGCCGTGACCGTGGCTTG<br>GAAGGCTGATGGCTCTCCTGTGAAGGCCGGCGTGGAAACCACCAAG<br>CCCTCCAAGCAGTCCAACAACAAATACGCCGCCTCCAGCTACCTGTC<br>CCTGACCCCTGAGCAGTGGAAGTCCCACCGGTCCTACAGCTGCCAGG<br>TCACACATGAGGGCTCCACCGTGGAAAAGACCGTGGCCCCTACCGA<br>GTGCTCCTAATGA |
| SEQ ID NO: 122 | ATGGAAACCGATACCCTGCTGCTGTGGGTGCTGCTCCTCTGGGTGCC<br>AGGCTCTACAGGACAGGTCCAGCTGCAGGAATCTGGCCCTGGCCTG<br>GTCAAGCCCTCCGAGACACTGTCTCTGACCTGCACCGTGTCCGGCGG<br>CTCTGTGTCCTCCGGCTCCTACTACTGGTCCTGGATCCGGCAGCCTCC<br>AGGCAAGGGACTGGAATGGATCGGCTACATCTACTACTCCGGCAGC<br>ACCAACTACAACCCCAGCCTGAAGTCCAGAGTGACCATCTCCGTGG<br>ACACCTCCAAGAACCAGTTCTCCCTGAAGCTGTCCTCCGTGACCGCC<br>GCTGACACCGCCGTGTACTACTGTGCCAGAGAGGGCAAGAACGGCG<br>CCTTCGATATCTGGGGCCAGGGCACCATGGTCACCGTGTCTAGCGCT<br>TCCACCAAGGGCCCCTCCGTGTTCCCTCTGGCCCCTTCCAGCAAGTC<br>CACCTCTGGCGGAACCGCTGCTCTGGGCTGCCTCGTGAAGGACTACT<br>TCCCCGAGCCTGTGACCGTGTCCTGGAACTCTGGCGCCCTGACATCC<br>GGCGTGCACACCTTTCCAGCCGTGCTGCAGTCCAGCGGCCTGTACTC<br>TCTGTCCAGCGTCGTGACCGTGCCTTCCAGCTCTCTGGGCACACAGA<br>CCTACATCTGCAACGTGAACCACAAGCCTTCCAACACCAAGGTGGA<br>CAAGCGGGTGGAACCCAAGTCCTGCGACAAGACCCACACCTGTCCT<br>CCCTGTCCTGCCCCTGAACTGCTGGGCGGACCCAGCGTGTTCCTGTT<br>CCCTCCAAAGCCCAAGGACACCCTGATGATCTCCCGGACCCCTGAAG<br>TGACCTGCGTGGTGGTGGACGTGTCCCACGAGGATCCCGAAGTGAA<br>GTTCAATTGGTACGTGGACGGCGTGGAAGTGCACAACGCCAAGACC<br>AAGCCTAGAGAGGAACAGTACAACTCCACCTACCGGGTGGTGTCCG<br>TGCTGACAGTGCTGCACCAGGACTGGCTGAACGGCAAAGAGTACAA<br>GTGCAAGGTGTCCAACAAGGCCCTGCCAGCCCCTATCGAAAAGACC<br>ATCAGCAAGGCTAAGGGCCAGCCCCGCGAGCCCCAGGTTTACACAC<br>TGCCTCCCTGCCGGGAAGAGATGACCAAGAATCAGGTGTCCCTGTG<br>GTGTCTGGTCAAGGGCTTCTACCCCTCCGATATCGCCGTGGAATGGG<br>AGTCCAACGGCCAGCCCGAGAACAACTACAAGACCACCCCTCCCGT<br>GCTGGACTCCGACGGCTCATTCTTCCTGTACTCCAAGCTGACCGTGG<br>ACAAGTCCCGGTGGCAGCAGGGCAACGTGTTCTCCTGCTCTGTGATG<br>CACGAGGCCCTGCACAACCACTACACCCAGAAGTCCCTGTCCCTGAG<br>CCCCGGCAAGTAATGA |
| SEQ ID NO: 123 | ATGGAAACCGATACCCTGCTGCTGTGGGTGCTGCTCCTCTGGGTGCC<br>AGGCTCTACCGGCGACATCCAGATGACCCAGAGCCCTTCCAGCCTGT<br>CCGCCTCTGTGGGCGACAGAGTGACCATCACCTGTCGGGCCTCCCAG<br>TCCATCTCCTCCTACCTGAACTGGTATCAGCAGAAGCCCGGCAAGGC<br>CCCTAAGCTGCTGATCTACGCCGCCTCCAGTCTGCAGTCTGGCGTGC<br>CATCTGGCTTCTCCGGCTCTGGCTCTGGCACCGACTTCACCCTGACC<br>ATCTCCAGCCTGCAGCCCGAGGACTTCGCCACCTACTACTGCCAGCA<br>GTCCTACTCCACCCCTCTGACCTTCGGCGGAGGCACCAAGGTGGAAA<br>TCAAGCGGACCGTGGCCGCTCCCTCCGTGTTCATCTTCCCACCTTCCG<br>ACGAGCAGCTGAAGTCCGGCACCGCTTCTGTCGTGTGCCTGCTGAAC<br>AACTTCTACCCTCGGGAAGCCAAGGTGCAGTGGAAGGTGGACAATG<br>CCCTGCAGTCCGGCAACTCCCAGGAATCCGTCACCGAGCAGGACTCC<br>AAGGACAGCACCTACTCCCTGTCCTCTACCCTGACCCTGTCCAAGGC<br>CGACTACGAGAAGCACAAGGTGTACGCCTGCGAAGTGACCCACCAG<br>GGCCTGAGCAGCCCCGTGACCAAGTCCTTCAACAGAGGCGAGTGCT<br>AATGA |
| SEQ ID NO: 118 | ATGGAAACCGATACACTGCTGCTGTGGGTGCTGCTCCTCTGGGTGCC<br>AGGCAGCACCGGCGATATCCAGATGACACAGAGCCCTAGCAGCCTG<br>AGCGCCAGCGTGGGCGATAGAGTGACCATCACCTGTCGGGCCAGCC<br>AGAGCATCAACAACTACCTGAACTGGTATCAGCAGAAGCCCGGCAA<br>GGCCCCTACCCTGCTGATCTATGCCGCTTCTAGCCTGCAGAGCGGCG<br>TGCCCAGCAGATTTTCTGGCAGCAGATCCGGCACCGACTTCACCCTG<br>ACAATCAGCAGCCTGCAGCCCGAGGACTTCGCCGCCTACTTCTGCCA<br>GCAGACCTACAGCAATCCCACCTTCGGCCAGGGCACCAAGGTGGAA<br>GTGAAGAGAACAGTGGCCGCTCCCAGCGTGTTCATCTTCCCACCCAG<br>CGACGAGCAGCTGAAGTCTGGCACAGCCAGCGTCGTGTGCCTGCTG |

TABLE 3-continued

Nucleic acid sequences of ORFs.

| Sequence ID | Nucleic Acid Sequence |
|---|---|
| | AACAACTTCTACCCCAGAGAAGCCAAGGTGCAGTGGAAGGTGGACA<br>ACGCCCTGCAGTCCGGCAACAGCCAGGAAAGCGTCACCGAGCAGGA<br>CAGCAAGGACTCCACCTACAGCCTGTCCAGCACCCTGACCCTGAGCA<br>AGGCCGACTACGAGAAGCACAAAGTGTACGCCTGCGAAGTGACCCA<br>CCAGGGCCTGAGCAGCCCCGTGACCAAGAGCTTCAATAGAGGCGAG<br>TGCTAATGA |
| SEQ ID NO: 134 | ATGGAAACCGACACACTGCTGCTGTGGGTGCTGCTCTTGTGGGTGCC<br>AGGATCTACCGGACAGTCTGCTCTGACCCAGCCTGCTTCTGTGTCTG<br>GCTCTCCCGGCCAGTCCATCACCATCTCTTGTACCGGCACCTCCTCTG<br>ACGTCGGCGGCTACAACTACGTGTCCTGGTATCAGCAGCATCCCGGC<br>AAGGCCCCTAAGCTGATGATCTACGACGTGTCCAACCGGCCTTCCGG<br>CGTGTCCAATAGATTCTCCGGCTCCAAGTCCGGCAACACCGCTTCTC<br>TGACAATCAGCGGACTGCAGGCCGAGGACGAGGCCGACTACTACTG<br>TTCCTCCTACACCTCCTCCAGCACCAGAGTGTTTGGCACCGGCACCA<br>AAGTGACCGTGCTGGGACAGCCTAAGGCCAATCCTACCGTGACACT<br>GTTCCCTCCATCCTCCGAGGAACTGCAGGCTAACAAGGCTACCCTCG<br>TGTGCCTGATCTCCGACTTTTACCCTGGCGCTGTGACCGTGGCCTGG<br>AAGGCTGATGGATCTCCTGTGAAGGCTGGCGTGGAAACCACCAAGC<br>CTTCCAAGCAGTCCAACAACAAATACGCCGCCTCCTCCTACCTGTCT<br>CTGACCCCTGAACAGTGGAAGTCCCACCGGTCCTACAGCTGCCAAGT<br>GACCCATGAGGGCTCCACCGTGGAAAAGACCGTGGCTCCTACTGAG<br>TGTTCTGGCGGCGGAGGATCTGGCGGAGGTGGAAGCGGAGGCGGTG<br>GATCTGCTCCTACCTCCAGCTCCACCAAGAAAACCCAGCTGCAGTTG<br>GAGCATCTGCTGCTGGACCTGCAGATGATCCTGAACGGCATCAACA<br>ACTACAAGAACCCCAAGCTGACCCGGATGCTGACCGCCAAGTTTGC<br>CATGCCTAAGAAGGCCACCGAGCTGAAACATCTGCAGTGCCTGGAA<br>GAGGAACTGAAGCCCCTGGAAGAAGTGCTGAATCTGGCCCAGTCCA<br>AGAACTTCCACCTGAGGCCTCGGGACCTGATCAGCAACATCAACGT<br>GATCGTGCTCGAGCTGAAGGGCTCCGAGACAACCTTCATGTGCGAGT<br>ACGCCGACGAGACAGCTACCATCGTGGAATTTCTGAACCGGTGGAT<br>CACCTTCTGCCAGAGCATCATCAGCACCCTGACCTGATGA |
| SEQ ID NO: 135 | ATGGAAACCGATACCCTGCTGCTGTGGGTGCTGCTCCTCTGGGTGCC<br>AGGATCTACAGGCGAGGTGCAGCTGCTGGAATCTGGCGGAGGACTG<br>GTGCAGCCTGGCGGCTCTCTGAGACTGTCTTGTGCCGCCTCCGGCTT<br>CACCTTCTCCAGCTATATCATGATGTGGGTCCGACAGGCCCCTGGCA<br>AGGGCCTGGAATGGGTGTCCTCTATCTACCCCTCCGGCGGCATCACC<br>TTTTACGCCGACACCGTGAAGGGCCGGTTCACCATCTCCCGGGACAA<br>CTCCAAGAACACCCTGTACCTGCAGATGAACTCCCTGCGGGCCGAG<br>GACACCGCCGTGTACTACTGCGCTAGAATCAAGCTGGGCACCGTGA<br>CCACCGTGGACTATTGGGGCCAGGGCACCCTGGTCACCGTGTCCTCT<br>GCTTCTACCAAGGGCCCCTCCGTGTTCCCTCTGGCCCCTTCCAGCAA<br>GTCCACCTCTGGCGGAACCGCTGCTCTGGGCTGCCTGGTCAAGGACT<br>ACTTCCCCGAGCCCGTGACCGTGTCTTGGAACTCTGGCGCCCTGACC<br>AGCGGCGTGCACACATTTCCAGCCGTGCTGCAGTCCAGCGGCCTGTA<br>CTCTCTGTCCTCCGTCGTGACAGTGCCCTCCAGCTCTCTGGGCACAC<br>AGACCTACATCTGCAACGTGAACCACAAGCCCTCCAACACCAAGGT<br>GGACAAGCGGGTGGAACCCAAGTCCTGCGACAAGACCCACACCTGT<br>CCTCCCTGTCCTGCCCCTGAACTGCTGGGCGGACCCAGCGTGTTCCT<br>GTTCCCTCCAAAGCCTAAGGACACCCTGATGATCTCCCGGACCCCTG<br>AAGTGACCTGCGTGGTGGTGGACGTGTCCCACGAGGATCCCGAAGT<br>GAAGTTCAATTGGTACGTGGACGGCGTGGAAGTGCACAACGCCAAG<br>ACCAAGCCTAGAGAGGAACAGTACAACTCCACCTACCGGGTGGTGT<br>CCGTGCTGACAGTGCTGCATCAGGACTGGCTGAACGGCAAAGAGTA<br>CAAGTGCAAGGTGTCCAACAAGGCCCTGCCAGCCCCTATCGAAAAG<br>ACCATCTCCAAGGCCAAGGGCCAGCCAAGAGAGCCTCAAGTCTGCA<br>CACTGCCTCCCAGCCGGGAAGAGATGACCAAGAACCAGGTGTCCCT<br>GAGCTGCGCTGTGAAGGGCTTCTACCCTTCCGATATCGCCGTGGAAT<br>GGGAGAGCAACGGCCAGCCCGAGAACAATTACAAGACCACCCCTCC<br>CGTGCTGGACTCCGACGGCTCATTCTTCCTGGTGTCCAAGCTGACCG<br>TGGACAAGTCCCGGTGGCAGCAGGGCAACGTGTTCTCCTGCTCTGTG<br>ATGCACGAGGCCCTGCACAACCACTACACCCAGAAGTCCCTGTCCCT<br>GTCTCCCGGCAAGTAATGA |
| SEQ ID NO: 137 | ATGGAAACCGACACACTGCTGCTGTGGGTGCTGCTCTTGTGGGTGCC<br>AGGATCTACAGGACAGGTCCAGCTGCAAGAGTCTGGCCCTGGACTG<br>GTCAAGCCTTCCGAGACACTGTCTCTGACCTGCACCGTGTCTGGCGG<br>CTCTGTGTCCTCTGGCTCCTACTACTGGTCCTGGATCAGACAGCCTCC<br>TGGCAAAGGCCTGGAATGGATCGGCTACATCTACTACTCCGGCTCCA<br>CCAACTACAACCCCAGCCTGAAGTCCAGAGTGACCATCTCCGTGGAC<br>ACCTCCAAGAACCAGTTCTCCCTGAAGCTGTCCTCCGTGACCGCTGC<br>TGATACCGCCGTGTACTACTGTGCCAGAGAGGGCAAGAACGGCGCC<br>TTCGATATTTGGGGCCAGGGCACCATGGTCACCGTGTCCAGTGCTTC<br>TACCAAGGGACCCAGCGTGTTCCCACTGGCTCCAGCTCTAAGTCTA<br>CCTCTGGCGGAACAGCTGCCCTGGGCTGTCTGGTCAAGGATTACTTC |

TABLE 3-continued

Nucleic acid sequences of ORFs.

| Sequence ID | Nucleic Acid Sequence |
|---|---|
| | CCTGAGCCTGTGACCGTGTCCTGGAATTCTGGCGCTCTGACATCCGG<br>CGTGCACACCTTTCCAGCTGTGCTGCAATCCTCCGGCCTGTACTCTCT<br>GTCCAGCGTCGTGACCGTGCCTTCTAGCTCTCTGGGCACCCAGACCT<br>ACATCTGCAATGTGAACCACAAGCCTAGCAACACCAAGGTGGACAA<br>GAGAGTGGAACCCAAGTCCTGCGACAAGACCCACACCTGTCCTCCA<br>TGTCCTGCTCCAGAACTGCTCGGCGGACCTTCCGTGTTCCTGTTTCCT<br>CCAAAGCCTAAGGACACCCTGATGATCTCTCGGACCCCTGAAGTGAC<br>CTGCGTGGTGGTGGATGTGTCTCACGAGGATCCCGAAGTGAAGTTCA<br>ATTGGTACGTGGACGGCGTGGAAGTGCACAACGCCAAGACCAAGCC<br>TAGAGAGGAACAGTACAACTCCACCTACAGAGTGGTGTCCGTGCTG<br>ACCGTGCTGCACCAGGATTGGCTGAACGGCAAAGAGTACAAGTGCA<br>AGGTGTCCAACAAGGCCCTGCCTGCTCCTATCGAAAAGACCATCAGC<br>AAGGCCAAGGGCCAGCCTAGGGAACCCCAGGTTTACACCCTGCCTC<br>CATGCCGGGAAGAGATGACCAAGAATCAGGTGTCCCTGTGGTGCCT<br>CGTGAAGGGCTTCTACCCTTCCGATATCGCCGTGGAATGGGAGAGCA<br>ATGGCCAGCCTGAGAACAACTACAAGACAACCCCTCCTGTGCTGGA<br>CTCCGACGGCTCATTCTTCCTGTACTCCAAGCTGACAGTGGACAAGT<br>CCAGATGGCAGCAGGGCAACGTGTTCTCCTGCTCCGTGATGCACGAG<br>GCCCTGCACAATCACTACACCCAGAAGTCCCTGTCTCTGTCCCCTGG<br>AAAAGGCGGCGGAGGATCTGGCGGAGGTGGAAGCGGAGGCGGTGG<br>ATCTGAAGTGCAGCTCCAAGAATCTGGACCCGGGCTCGTGAAGCCC<br>AGCCAGTCTCTGAGTCTGACCTGTACAGTGACCGGCTACTCCATCAC<br>CTCCGACTACGCTTGGAACTGGATCCGGCAGTTCCCCGGCAACAAGT<br>TGGAGTGGATGGGCTATATCACCTACAGCGGCAGCACCTCTTACAAC<br>CCTTCTCTGGAATCCCGGATCAGCATCACCCGGGACACCTCTACCAA<br>TCAGTTCTTTCTGCAGCTGAACAGCGTGACCACCGAGGACACCGCCA<br>CCTACTATTGTGCTAGAGGCGGCTACTACGGCTCCTCCTGGGGAGTG<br>TTTGCTTACTGGGGACAGGGAACCCTCGTGACTGTTTCTGCTGGTGG<br>CGGAGGAAGCGGCGGAGGCGGCTCTGGTGGTGGTGGTTCTGGTGGC<br>GGCGGATCTGACATCCAGATGACCCAGTCTCCAGCCAGCCTGTCTGC<br>TTCTGTGGGCGAGACAGTGACCATTACCTGCCGGGTGTCCGAGAACA<br>TCTACTCCTACCTGGCCTGGTATCAACAGAAACAGGGCAAGTCCCCT<br>CAGCTGCTGGTGTACAATGCTAAGACCCTGGCTGAGGGCGTGCCCTC<br>TAGATTTTCTGGCTCTGGCAGCGGCACCCAGTTTAGCCTGAAGATCA<br>ACTCCCTGCAGCCTGAGGACTTCGGCAGCTACTACTGCCAGCACCAC<br>TATGGCACCCCTTGGACATTTGGCGGAGGCACCAAGCTGGAAATCA<br>AGTGATGA |
| SEQ ID NO: 138 | ATGGAAACCGACACACTGCTGCTGTGGGTGCTGCTCTTGTGGGTGCC<br>AGGATCTACAGGACAGGTCCAGCTGCAAGAGTCTGGCCCTGGACTG<br>GTCAAGCCTTCCGAGACACTGTCTCTGACCTGCACCGTGTCTGGCGG<br>CTCTGTGTCCTCTGGCTCCTACTACTGGTCCTGGATCAGACAGCCTCC<br>TGGCAAAGGCCTGGAATGGATCGGCTACATCTACTACTCCGGCTCCA<br>CCAACTACAACCCCAGCCTGAAGTCCAGAGTGACCATCTCCGTGGAC<br>ACCTCCAAGAACCAGTTCTCCCTGAAGCTGTCCTCCGTGACCGCTGC<br>TGATACCGCCGTGTACTACTGTGCCAGAGAGGGCAAGAACGGCGCC<br>TTCGATATTTGGGGCCAGGGCACCATGGTCACCGTGTCCAGTGCTTC<br>TACCAAGGGACCCAGCGTGTTCCCACTGGCTCCAGCTCTAAGTCTA<br>CCTCTGGCGGAACAGCTGCCCTGGGCTGTCTGGTCAAGGATTACTTC<br>CCTGAGCCTGTGACCGTGTCCTGGAATTCTGGCGCTCTGACATCCGG<br>CGTGCACACCTTTCCAGCTGTGCTGCAATCCTCCGGCCTGTACTCTCT<br>GTCCAGCGTCGTGACCGTGCCTTCTAGCTCTCTGGGCACCCAGACCT<br>ACATCTGCAATGTGAACCACAAGCCTAGCAACACCAAGGTGGACAA<br>GAGAGTGGAACCCAAGTCCTGCGACAAGACCCACACCTGTCCTCCA<br>TGTCCTGCTCCAGAACTGCTCGGCGGACCTTCCGTGTTCCTGTTTCCT<br>CCAAAGCCTAAGGACACCCTGATGATCTCTCGGACCCCTGAAGTGAC<br>CTGCGTGGTGGTGGATGTGTCTCACGAGGATCCCGAAGTGAAGTTCA<br>ATTGGTACGTGGACGGCGTGGAAGTGCACAACGCCAAGACCAAGCC<br>TAGAGAGGAACAGTACAACTCCACCTACAGAGTGGTGTCCGTGCTG<br>ACCGTGCTGCACCAGGATTGGCTGAACGGCAAAGAGTACAAGTGCA<br>AGGTGTCCAACAAGGCCCTGCCTGCTCCTATCGAAAAGACCATCAGC<br>AAGGCCAAGGGCCAGCCTAGGGAACCCCAGGTTTACACCCTGCCTC<br>CATGCCGGGAAGAGATGACCAAGAATCAGGTGTCCCTGTGGTGCCT<br>CGTGAAGGGCTTCTACCCTTCCGATATCGCCGTGGAATGGGAGAGCA<br>ATGGCCAGCCTGAGAACAACTACAAGACAACCCCTCCTGTGCTGGA<br>CTCCGACGGCTCATTCTTCCTGTACTCCAAGCTGACAGTGGACAAGT<br>CCAGATGGCAGCAGGGCAACGTGTTCTCCTGCTCCGTGATGCACGAG<br>GCCCTGCACAATCACTACACCCAGAAGTCCCTGTCTCTGTCCCCTGG<br>AAAAGGCGGCGGAGGATCTGGCGGAGGTGGAAGCGGAGGCGGTGG<br>ATCTCAGGTTCAGTTGCAGCAGTCTGCCGTGGAACTGGCTAGACCTG<br>GCGCTTCCGTGAAGATGTCCTGCAAGGCCTCCGGCTACACCTTCACC<br>AGCTTCACCATGCACTGGGTCAAGCAGAGGCCTGGACAAGGCTTGG<br>AGTGGATTGGATATATCAACCCTAGCTCTGGCTACACCGAGTACAAC<br>CAGAAGTTCAAGGACAAGACCACTCTGACCGCCGACAAGTCCTCCA<br>GCACCGCTTACATGCAGCTCGACTCCCTGACCTCTGACGACTCTGCT<br>GTGTACTATTGCGTGCGGGGCTCCTCCAGAGGCTTCGATTATTGGGG |

TABLE 3-continued

Nucleic acid sequences of ORFs.

| Sequence ID | Nucleic Acid Sequence |
|---|---|
| | ACAAGGCACACTCGTGACAGTGTCAGCTGGTGGTGGCGGTAGTGGC<br>GGTGGCGGTTCAGGTGGCGGAGGAAGCGGCGGAGGCGGATCTGATA<br>TCCAGATGATCCAGTCTCCTGCCAGCCTGTCCGTGTCTGTGGGAGAG<br>ACTGTGACCATCACCTGTCGGGCCTCCGAGAACATCTACTCCAACCT<br>GGCCTGGTTCCAGCAGAAGCAGGGAAAGTCTCCTCAGCTGCTGGTGT<br>ACGCCGCCACCAATTTGGCTGATGGCGTGCCCTCTCGGTTCTCCGGA<br>TCTGGATCTGGCACACAGTATTCCCTGAAGATCAACTCCCTGCAGTC<br>CGAGGACTTCGGCATCTACTATTGCCAGCACTTCTGGGGCACCCCTA<br>GAACCTTTGGCGGCGGAACAAAGCTGGAAATCAAGTGATGA |

TABLE 4

Nucleic acid sequences of antigens.

| Sequence ID | Description | Nucleic Acid Sequence |
|---|---|---|
| SEQ ID NO: 139 | hIL2Rα | ATGGAAACCGACACACTGCTGCTGTGGGTGCTGCTCTTGTGGG<br>TGCCAGGATCTACAGGCGAGCTGTGCGACGATGACCCTCCTGA<br>GATCCCTCACGCCACCTTCAAGGCCATGGCTTACAAAGAGGGC<br>ACCATGCTGAACTGCGAGTGCAAGCGGGGCTTCAGACGGATC<br>AAGTCCGGCAGCCTGTACATGCTGTGCACCGGCAACTCCTCTC<br>ACTCCTCCTGGGACAACCAGTGCCAGTGCACCTCCTGCCAC<br>CAGAAACACCACCAAGCAAGTGACCCCTCAGCCTGAGGAACA<br>GAAAGAGCGCAAGACCACCGAGATGCAGAGCCCCATGCAGCC<br>TGTGGATCAGGCTTCTCTGCCTGGCCACTGTAGAGAGCCTCCA<br>CCTTGGGAGAATGAGGCACCGAGCGGATCTACCACTTTGTCG<br>TGGGCCAGATGGTGTACTACCAGTGCGTGCAGGGATACAGAG<br>CCCTGCATAGAGGCCCTGCTGAGTCCGTGTGCAAGATGACCCA<br>TGGCAAGACCAGATGGACCCAGCCTCAGCTGATCTGTACAGG<br>CGGAGGCGGAGGATCTGGTGGTGGTGGATCTGGCCTGAACGA<br>CATCTTCGAGGCCCAGAAAATCGAGTGGCACGAAGGCGGTGG<br>CGGCTCCCACCATCATCATCACCACCATCACTGATGA |
| SEQ ID NO: 140 | hMesothelin | ATGGAAACCGACACCCTGCTGCTGTGGGTGCTGCTGCTCTGGG<br>TCCCAGGCTCCACCGGCGGACTGAACGACATCTTCGAGGCCCA<br>GAAAATCGAGTGGCACGAGGGCGGAGGCGGCTCCGAGCCTAG<br>AACCGACACCGACACCTGTCCCAACCCCCCCGACCCCTGCCCT<br>ACCTGTCCTACCCCTGATCTGCTGGGCGGACCCTCCGTGTTCAT<br>CTTCCCACCCAAGCCTAAGGACGTGCTGATGATCTCCCTGACC<br>CCCAAGATCACCTGTGTGGTGGTGGACGTGTCCGAAGAGGAA<br>CCCGACGTGCAGTTCAATTGGTACGTGAACAACGTGGAAGAT<br>AAGACCGCCCAGACCGAGACACGGCAGCGGCAGTACAACTCC<br>ACCTACCGGGTGGTGTCCGTGCTGCCCATCAAGCACCAGGACT<br>GGATGTCCGGCAAGGTGTTCAAGTGCAAAGTGAACAACAACG<br>CCCTGCCCAGCCCCATCGAAAAGACCATCTCCAAGCCTCGGGG<br>CCAAGTCCGAGTGCCCCAGATCTACACCTTCCCACCCCCTATC<br>GAGCAGACCGTGAAGAAAGACGTGTCCGTGACCTGCCTCGTG<br>ACCGGATTCCTGCCACAAGACATCCACGTGGAATGGGAGTCC<br>AACGGCCAGCCCCAGCCCGAGCAGAACTACAAGAACACCCAG<br>CCCGTGCTGGACTCCGACGGCTCCTACTTCCTGTACTCCAAGC<br>TGAACGTGCCCAAGTCCAGATGGGACCAGGGCGACTCCTTCAC<br>CTGTTCCGTGATCCACGAGGCCCTGCACAACCACCACATGACC<br>AAGACCATCAGCCGGTCCCTGGGCAATGGCGGCGGAGGCTCC<br>GAGGTGGAAAAGACCGCCTGCCCCTCCGGCAAGAAGGCCAGA<br>GAGATCGACGAGTCCCTGATCTTCTACAAGAAGTGGGAGCTG<br>GAAGCCTGCGTGGACGCCGCCCTGCTGGCCACCCAGATGGAC<br>AGAGTGAACGCCATCCCCTTCACCTACGAGCAGCTGGATGTGC<br>TGAAGCACAAGCTGGACGAGCTGTACCCCCAGGGCTACCCCG<br>AGAGCGTGATCCAGCACCTGGGCTACCTGTTTCTGAAGATGTC<br>CCCCGAGGACATCCGGAAGTGGAACGTGACCTCCTGGAAAC<br>CCTGAAGGCCCTGCTGGAAGTGAACAAGGGCCACGAGATGAG<br>CCCCCAGGCCCCAGACGACCTCTGCCTCAGGTGGCAACCCTG<br>ATCGATAGATTCGTGAAGGGCAGAGGCCAGCTGGACAAGGAC<br>ACCCTGGACACACTGACCGCCTTCTACCCCGGCTACCTGTGCT<br>CCCTGTCCCCTGAGGAACTGTCCTCCGTGCCCCCCTCCTCTATC<br>TGGGCCGTGCGGCCTCAGGATCTGGACACCTGTGACCCTCGGC<br>AGCTGGATGTCCTGTATCCCAAGGCCCGGCTGGCCTTCCAGAA<br>CATGAACGGCTCCGAGTACTTCGTGAAGATCCAGTCCTTCCTG<br>GGCGGAGCCCCCACCGAGGACCTGAAGGCTCTGTCCCAGCAG<br>AACGTGTCCATGGACCTGGCCACCTTCATGAAGCTGCGGACCG |

TABLE 4-continued

Nucleic acid sequences of antigens.

| Sequence ID | Description | Nucleic Acid Sequence |
|---|---|---|
| | | ACGCCGTGCTGCCTCTGACCGTGGCTGAGGTGCAGAAGCTGCT GGGCCCCCACGTGGAAGGCCTGAAGGCCGAGGAACGGCACAG ACCCGTGCGGGACTGGATCCTGCGGCAGAGACAGGACGACCT GGATACCCTGGGCCTGGGCCTGCAGTAATGA |
| SEQ ID NO: 141 | hPD1L1 | ATGAGAATCTTCGCCGTGTTCATCTTCATGACCTACTGGCATCT GCTGAACGCCTTCACCGTGACCGTGCCCAAGGACCTGTACGTG GTGGAATACGGCTCCAACATGACCATCGAGTGCAAGTTCCCCG TGGAAAAGCAGCTGGACCTGGCCGCCCTGATCGTGTACTGGG AGATGGAAGATAAGAACATCATCCAGTTCGTGCACGGGGAAG AGGACCTGAAGGTGCAGCACTCCTCCTACCGGCAGAGAGCCA GACTGCTGAAGGACCAGCTGTCCCTGGGCAATGCCGCCCTGCA GATCACCGACGTGAAGCTGCAGGATGCCGGCGTGTACCGGTG CATGATCTCTTACGGCGGAGCCGACTACAAGCGGATCACCGTG AAAGTGAACGCCCCCTACAACAAGATCAACCAGCGGATCCTG GTGGTGGACCCCGTGACCTCTGAGCACGAGCTGACCTGTCAGG CCGAGGGCTACCCTAAGGCCGAAGTGATCTGGACCTCCTCCGA CCACCAGGTGCTGTCCGGCAAGACCACCACCACAAACTCCAA GCGGGAAGAGAAGCTGTTCAACGTGACCTCCACCCTGCGGAT CAACACAACCACCAACGAGATCTTCTACTGTACCTTCCGGCGG CTGGACCCCGAGGAAAATCACACCGCTGAGCTCGTGATCCCCG AGCTGCCTCTGGCCCACCCTCCTAATGAGAGAACAGGCGGCG GAGGCTCCGGCCTGAACGACATCTTTGAGGCCCAGAAAATCG AGTGGCACGAGGGCGGAGGCGGCTCCCACCATCATCACCACC ACCATCACTGATGA |
| SEQ ID NO: 142 | hNKp30 | ATGGCTTGGATGCTGCTGCTGATCCTGATCATGGTGCACCCCG GCTCTTGCGCCCTGTGGGTGTCCCAGCCTCCTGAGATCAGAAC CCTGGAAGGCTCCTCCGCCTTCCTGCCCTGCTCCTTCAATGCCT CTCAGGGCAGACTGGCCATCGGCTCCGTGACCTGGTTCAGGGA TGAGGTGGTGCCCGGCAAAGAAGTGCGGAACGGCACACCTGA GTTCAGAGGCAGACTCGCCCCTCTGGCCTCCTCTAGATTCCTG CACGATCACCAGGCCGAGCTGCACATCAGAGATGTGCGGGGC CACGACGCCTCCATCTACGTGTGCAGAGTGGAAGTGCTGGGCC TGGGCGTGGGCACCGGCAATGGAACACGGCTGGTGGTGGAAA AGAGGGCGGAGGCGGATCTGGCGGCGGAGGCTCTGATAAGA CCCACACCTGTCCTCCCTGTCCTGCCCCTGAACTGCTGGGCGG ACCTTCCGTGTTCCTGTTCCCTCCAAAGCCCAAGGACACCCTG ATGATCTCCCGGACCCCTGAAGTGACCTGCGTGGTGGTGGACG TGTCCCACGAGGATCCCGAAGTGAAGTTCAATTGGTACGTGGA CGGCGTGGAAGTGCACAACGCCAAGACCAAGCCCAGAGAGGA ACAGTACAACTCCACCTACCGGGTGGTGTCCGTGCTGACCGTG CTGCACCAGGACTGGCTGAACGGCAAAGAGTACAAGTGCAAG GTGTCCAACAAGGCCCTGCCAGCCCCAATCGAAAAGACCATCT CCAAGGCCAAGGGCCAGCCCCGCGAGCCTCAGGTGTACACAC TGCCTCCCAGCCGGGAAGAGATGACCAAGAACCAGGTGTCCC TGACCTGTCTGGTCAAGGGCTTCTACCCCTCCGATATCGCCGT GGAATGGGAGTCCAACGGCCAGCCCGAGAACAACTACAAGAC CACCCCTCCCGTGCTGGACTCCGACGGCTCATTCTTCCTGTACT CCAAGCTGACCGTGGACAAGTCCCGGTGGCAGCAGGGCAACG TGTTCTCCTGCTCTGTGATGCACGAGGCCCTGCACAACCACTA CACCCAGAAGTCCCTGTCCCTGAGCCCTGGCAAAGGTGGTGGT GGTAGCGGTGGCGGAGGCAGCGGCCTGAACGATATCTTCGAG GCCCAGAAAATCGAGTGGCACGAGTAATGA |
| SEQ ID NO: 143 | hNKp46 | ATGGAAACCGACACACTGCTGCTGTGGGTGCTGCTCTTGTGGG TGCCAGGATCTACCGGCCAGCAGCAGACACTGCCCAAGCCTTT TATCTGGGCCGAGCCTCACTTCATGGTGCCCAAAGAAAAGCAA GTGACCATCTGCTGCCAGGGCAACTACGGCGCTGTGGAATACC AGCTGCACTTCGAGGGCTCCCTGTTCGCCGTGGATAGACCTAA GCCTCCTGAGCGGATCAACAAAGTGAAGTTCTACATCCCCGAC ATGAACTCCCGGATGGCTGGCCAGTACTCCTGCATCTATAGAG TGGGCGAGCTTTGGAGCGAGCCCTCCAATCTGCTGGATCTGGT GGTCACCGAGATGTACGACACCCCTACACTGAGCGTGCACCCC GGACCTGAAGTGATCTCTGGCGAGAAAGTGACCTTCTACTGCA GACTGGATACCGCCACCTCCATGTTTCTGCTGCTCAAAGAGGG CAGATCCTCTCACGTGCAGCGCGGCTATGGAAAGGTGCAGGCT GAGTTTCCTCTGGGCCCTGTGACCACCGCTCACAGAGGCACCT ACAGATGCTTCGGCTCCTACAACAACCACGCCTGGTCTTTCCC ATCCGAGCCTGTGAAGCTGCTGGTCACCGGCGACATCGAGAA CACATCTCTGGCCCCTGAGGACCCCACCTTTCCTGATACCTGG GGCACCTATCTGCTGACCACCGAGACAGGCCTGCAGAAAGAT CACGCCCTGTGGGATCACACCGCTCAGAATGGTGGCGGAGGA TCTGGCGGAGGCGGATCTGAACCTAGAACCGACACCGACACC TGTCCTAATCCTCCAGATCCTTGTCCTACCTGTCCAACACCTGA CCTGCTCGGCGGACCTTCCGTGTTCATCTTCCCACCTAAGCCA |

TABLE 4-continued

Nucleic acid sequences of antigens.

| Sequence ID | Description | Nucleic Acid Sequence |
|---|---|---|
| | | AAGGACGTGCTGATGATCTCTCTGACCCCTAAGATCACCTGTG<br>TGGTGGTGGACGTGTCCGAAGAGGAACCCGACGTGCAGTTCA<br>ATTGGTACGTGAACAACGTCGAGGACAAGACAGCCCAGACCG<br>AGACACGGCAGCGGCAGTACAACTCTACCTACAGAGTGGTGT<br>CCGTGCTGCCCATCAAGCACCAGGATTGGATGTCCGGCAAGGT<br>GTTCAAGTGCAAAGTGAACAACAACGCCCTGCCTTCTCCAATC<br>GAAAAGACCATCTCCAAGCCTCGGGGCCAAGTGCGAGTGCCC<br>CAGATCTATACCTTTCCACCTCCTATCGAGCAGACCGTGAAGA<br>AGATGTGTCCGTGACCTGCCTCGTGACCGGCTTCCTGCCTCA<br>AGACATCCATGTGGAATGGGAGTCCAACGGCCAGCCTCAGCC<br>TGAGCAGAACTACAAGAACACCCAGCCTGTGCTGGACTCCGA<br>CGGCAGCTACTTCCTGTACTCCAAGCTGAACGTGCCCAAGTCC<br>AGATGGGACCAGGGCGACTCCTTCACCTGTTCCGTGATCCACG<br>AGGCCCTGCACAACCACCACATGACCAAGACCATCAGCAGAT<br>CCCTCGGCAATGGCGGTGGTGGTTCTGGCGGCGGAGGTTCCGG<br>ACTGAACGATATCTTCGAGGCCCAGAAAATCGAGTGGCACGA<br>GTGATGA |
| SEQ ID NO: 144 | BirA | ATGGAAACTGACACCCTCCTCCTTTGGGTGCTGCTGCTTTGGG<br>TGCCTGGATCGACCGGGATGAAGGACAATACCGTGCCTCTGA<br>AGCTCATTGCCCTGCTGGCCAACGGAGAATTCCATTCCGGCGA<br>ACAGCTGGGGGAGACTCTCGGGATGTCCCGGGCCGCCATCAA<br>CAAGCACATCCAGACTTTGCGCGACTGGGGAGTCGACGTGTTC<br>ACGGTGCCGGGGAAGGGCTACTCGCTCCCGGAACCGATCCAG<br>CTGCTGAACGCCAAGCAGATTCTGGGACAGCTGGATGGCGGA<br>AGCGTGGCAGTGCTGCCCCGTGATCGACTCAACCAACCAGTATC<br>TGCTGGATAGAATCGGTGAACTGAAATCCGGCGACGCTTGCAT<br>TGCCGAGTACCAACAGGCCGGAAGGGGACGGCGCGGCAGGAA<br>GTGGTTCTCTCCATTCGGCGCGAACCTCTACCTGAGCATGTTCT<br>GGAGATTGGAGCAGGGTCCCGCCGCGGCCATCGGCCTCTCCCT<br>GGTCATCGGCATTGTGATGGCTGAAGTGCTGAGGAAGTTGGGT<br>GCCGACAAGGTCCGCGTGAAGTGGCCGAACGACCTGTACCTC<br>CAAGACCGGAAATTGGCGGGGATTCTCGTCGAGCTTACCGGA<br>AAGACTGGCGATGCCGCACAAATTGTGATCGGGGCGGGAATC<br>AACATGGCGATGCGACGGGTGGAAGAGAGCGTCGTGAACCAG<br>GGATGGATCACCCTGCAAGAGGCCGGAATCAACCTGGATCGC<br>AACACCCTGGCTGCCATGCTCATTCGCGAACTGAGAGCCGCAC<br>TGGAGCTGTTTGAGCAGGAGGGTCTGGCCCCCTACCTGTCACG<br>CTGGGAAAAGCTTGATAACTTCATCAATCGGCCTGTGAAGCTG<br>ATCATCGGAGACAAGGAGATTTTCGGCATCTCGAGAGGCATC<br>GACAAACAAGGAGCCCTCCTGCTGGAACAGGACGGAATCATT<br>AAGCCCTGGATGGGTGGAGAGATCTCCCTGCGGTCCGCCGAA<br>AAGTCCGGGAAGGATGAACTC |

TABLE 5

Amino Acid sequences.

| Sequence ID | Description | Amino Acid Sequence |
|---|---|---|
| SEQ ID NO: 145 | αMesothelin Ab237 VH | QVQLQESGPGLVKPSQTLSLTCTVSGGSINNNNYYWTWIRQHPGKGLE<br>WIGYIYYSGSTFYNPSLKSRVTISVDTSKTQFSLKLSSVTAADTAVYYC<br>AREDTMTGLDVWGQGTTVTSS |
| SEQ ID NO: 146 | αMesothelin Ab237 VL | DIQMTQSPSSLSASVGDRVTITCRASQSINNYLNWYQQKPGKAPTLLIY<br>AASSLQSGVPSRFSGSRSGTDFTLTISSLQPEDFAAYFCQQTYSNPTFGQ<br>GTKVEVK |
| SEQ ID NO: 20 | hIL2 | APTSSSTKKTQLQLEHLLLDLQMILNGINNYKNPKLTRMLTFKFYMPK<br>KATELKHLQCLEEELKPLEEVLNLAQSKNFHLRPRDLISNINVIVLELKG<br>SETTFMCEYADETATIVEFLNRWITFCQSIISTLT |
| SEQ ID: 43 | 2x4GS linker | GGGGSGGGGS |
| SEQ ID: 83 | Human CH2, CH3 knob | DKTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLN<br>GKEYKCKVSNKALPAPIEKTISKAKGQPREPQVYTLPPCREEMTKNQV<br>SLWCLVKGFYPSDIAVEWESNGQPENNYKTTPPVLDSDGSFFLYSKLT<br>VDKSRWQQGNVFSCSVMHEALHNHYTQKSLSLSPGK |
| SEQ ID: 82 | Human CH2, CH3 hole | DKTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLN<br>GKEYKCKVSNKALPAPIEKTISKAKGQPREPQVCTLPPSREEMTKNQVS |

TABLE 5-continued

Amino Acid sequences.

| Sequence ID | Description | Amino Acid Sequence |
|---|---|---|
| | | LSCAVKGFYPSDIAVEWESNGQPENNYKTTPPVLDSDGSFFLVSKLTVD KSRWQQGNVFSCSVMHEALHNHYTQKSLSLSPGK |
| SEQ ID: 14 | CH1 | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKRV EPKSC |
| SEQ ID: 11 | CL (kappa) | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSP VTKSFNRGEC |
| SEQ ID: 147 | CL (lambda) | GQPKANPTVTLFPPSSEELQANKATLVCLISDFYPGAVTVAWKADGSP VKAGVETTKPSKQSNNKYAASSYLSLTPEQWKSHRSYSCQVTHEGSTV EKTVAPTECS |
| SEQ ID: 148 | αPD1L1 Avelumab VH | EVQLLESGGGLVQPGGSLRLSCAASGFTFSSYIMMWVRQAPGKGLEW VSSIYPSGGITFYADTVKGRFTISRDNSKNTLYLQMNSLRAEDTAVYYC ARIKLGTVTTVDYWGQGTLVTVSS |
| SEQ ID: 149 | αPD1L1 Avelumab VL | QSALTQPASVSGSPGQSITISCTGTSSDVGGYNYVSWYQQHPGKAPKL MIYDVSNRPSGVSNRFSGSKSGNTASLTISGLQAEDEADYYCSSYTSSS TRVFGTGTKVTVL |
| SEQ ID: 96 | 3x4GS linker | GGCGGCGGAGGATCTGGCGGAGGTGGAAGCGGAGGCGGTGGATCT |
| SEQ ID: 150 | αNKp46 VH | QVQLQQSGPELVKPGASVKMSCKASGYTFTDYVINWGKQRSGQGLE WIGEIYPGSGTNYYNEKFKAKATLTADKSSNIAYMQLSSLTSEDSAVYF CARRGRYGLYAMDYWGQGTSVTVSS |
| SEQ ID: 151 | αNKp46 VL | DIQMTQTTSSLSASLGDRVTISCRASQDISNYLNWYQQKPDGTVKLLIY YTSRLHSGVPSRFSGSGSGTDYSLTINNLEQEDIATYFCQQGNTRPWTF GGGTKLEIK |
| SEQ ID: 152 | 4x 4GS linker | GGGGSGGGGSGGGGSGGGGS |
| SEQ ID: 153 | αMesothelin M912 VH | QVQLQESGPGLVKPSETLSLTCTVSGGSVSSGSYYWSWIRQPPGKGLE WIGYIYYSGSTNYNPSLKSRVTISVDTSKNQFSLKLSSVTAADTAVYYC AREGKNGAFDIWGQGTMVTVSS |
| SEQ ID: 154 | αMesothelin M912 VL | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSP VTKSFNRGEC |
| SEQ ID: 42 | 1x4GS | GGGGS |
| SEQ ID: 155 | αNKp30 scFv | BioLegend Catalog #325207 |
| SEQ ID NO: 156 | hIL7 | DCDIEGKDGKQYESVLMVSIDQLLDSMKEIGSNCLNNEFNFFKRHICDA NKEGMFLFRAARKLRQFLKMNSTGDFDLHLLKVSEGTTILLNCTGQVK GRKPAALGEAQPTKSLEENKSLKEQKKLNDLCFLKRLLQEIKTCWNKI LMGTKEH |
| SEQ ID NO: 157 | αIGF1R, Istiratumab heavy | EVQLLQSGGGLVQPGGSLRLSCAASGFMFSRYPMHWVRQAPGKGLE WVGSISGSGGATPYADSVKGRFTISRDNSKNTLYLQMNSLRAEDTAVY YCAKDFYQILTGNAFDYWGQGTTVTVSS |
| SEQ ID NO: 158 | αIGF1R, Istiratumab light | DIQMTQSPSSLSASLGDRVTITCRASQGISSYLAWYQQKPGKAPKLLIY AKSTLQSGVPSRFSGSGSGTDFTLTISSLQPEDSATYYCQQYWTFPLTFG GGTKVEIK |
| SEQ ID NO: 159 | αHER3 Istiratumab heavy | QVQLVQSGGGLVQPGGSLRLSCAASGFTFDDYAMHWVRQAPGKGLE WVAGISWDSGSTGYADSVKGRFTISRDNAKNSLYLQMNSLRAEDTAL YYCARDLGAYQWVEGFDYWGQGTLVTVSS |
| SEQ ID NO: 160 | αHER3 Istiratumab light | SYELTQDPAVSVALGQTVRITCQGDSLRSYYASWYQQKPGQAPVLVIY GKNNRPSGIPDRFSGSTSGNSASLTITGAQAEDEADYYCNSRDSPGNQ WVFGGGTKVTVLG |
| SEQ ID NO: 161 | αCD3 Teplizumab heavy | QVQLVQSGGGVVQPGRSLRLSCKASGYTFTRYTMHWVRQAPGKGLE WIGYINPSRGYTNYNQKVKDRFTISRDNSKNTAFLQMDSLRPEDTGVY FCARYYDDHYSLDYWGQGTPVTVSS |
| SEQ ID NO: 162 | αCD3 Teplizumab light | DIQMTQSPSSLSASVGDRVTITCSASSSVSYMNWYQQTPGKAPKRWIY DTSKLASGVPSRFSGSGSGTDYTFTISSLQPEDIATYYCQQWSSNPFTFG QGTKLQIT |

TABLE 5-continued

Amino Acid sequences.

| Sequence ID | Description | Amino Acid Sequence |
|---|---|---|
| SEQ ID NO: 163 | hIL2 F42A Y45A | APTSSSTKKTQLQLEHLLLDLQMILNGINNYKNPKLTRMLTAKFAMPK KATELKHLQCLEEELKPLEEVLNLAQSKNFHLRPRDLISNINVIVLELKG SETTFMCEYADETATIVEFLNRWITFCQSIISTLT |
| SEQ ID NO: 164 | αNKp46 2 heavy | QLQESGPGLVKPSQSLSLTCTVTGYSITSDYAWNWIRQFPGNKLEWMG YITYSGSTSYNPSLESRISITRDTSTNQFFLQLNSVTTEDTATYYCARGG YYGSSWGVFAYWGQGTLVTVSAGGGGSGGGGSGGGGSGGGGS |
| SEQ ID NO: 165 | αNKp46 2 light | DIQMTQSPASLSASVGETVTITCRVSENIYSYLAWYQQKQGKSPQLLVY NAKTLAEGVPSRFSGSGSGTQFSLKINSLQPEDFGSYYCQHHYGTPWTF GGGTKLEIK |
| SEQ ID NO: 166 | αNKp46 heavy 4 | QVQLQQSAVELARPGASVKMSCKASGYTFTSFTMHWVKQRPGQGLE WIGYINPSSGYTEYNQKFKDKTTLTADKSSSTAYMQLDSLTSDDSAVY YCVRGSSRGFDYWGQGTLVTVSA |
| SEQ ID NO: 167 | αNKp46 light 4 | DIQMIQSPASLSVSVGETVTITCRASENIYSNLAWFQQKQGKSPQLLVY AATNLADGVPSRFSGSGSGTQYSLKINSLQSEDFGIYYCQHFWGTPRTF GGGTKLEIK |

TABLE 6

Amino Acid sequences for full heavy and light chains.

| Construct SEQ ID NO: | N-term | Linker | Variable | Constant | Fc | Linker | C-term |
|---|---|---|---|---|---|---|---|
| SEQ ID NO: 168 | | | SEQ ID NO: 145 | SEQ ID NO: 14 | SEQ ID NO: 83 | | |
| SEQ ID NO: 169 | | | SEQ ID NO: 146 | SEQ ID NO: 11 | | | |
| SEQ ID NO: 170 | SEQ ID NO: 20 | SEQ ID NO: 43 | | | SEQ ID NO: 82 | | |
| SEQ ID NO: 120 | | | SEQ ID NO: 148 | SEQ ID NO: 14 | SEQ ID NO: 82 | SEQ ID NO: 96 | SEQ ID NO: 20 |
| SEQ ID NO: 171 | | | SEQ ID NO: 149 | SEQ ID NO: 147 | | | |
| SEQ ID NO: 172 | | | SEQ ID NO: 153 | SEQ ID NO: 14 | SEQ ID NO: 83 | | |
| SEQ ID NO: 173 | | | SEQ ID NO: 154 | SEQ ID NO: 11 | | | |
| SEQ ID NO: 174 | | | SEQ ID NO: 145 | SEQ ID NO: 14 | SEQ ID NO: 83 | SEQ ID NO: 96 | SEQ ID NO: 155 |
| SEQ ID NO: 175 | | | | | SEQ ID NO: 82 | | |
| SEQ ID NO: 176 | | | | | SEQ ID NO: 83 | | |
| SEQ ID NO: 177 | | | SEQ ID NO: 148 | SEQ ID NO: 14 | SEQ ID NO: 82 | SEQ ID NO: 96 | SEQ ID NO: 20 |
| SEQ ID NO: 178 | | SEQ ID NO: 42 | | | | SEQ ID NO: 42 | |
| SEQ ID NO: 179 | | SEQ ID NO: 43 | | | | SEQ ID NO: 43 | |
| SEQ ID NO: 180 | | SEQ ID NO: 43 | | | | SEQ ID NO: 43 | |
| SEQ ID NO: 181 | | SEQ ID NO: 42 | | | | SEQ ID NO: 42 | |
| SEQ ID NO: 182 | SEQ ID NO: | SEQ ID NO: 43 | | | | SEQ ID NO: 42 | |
| SEQ ID NO: 183 | | | SEQ ID NO: 157 | SEQ ID NO: 14 | SEQ ID NO: 82 | | |
| SEQ ID NO: 184 | | | SEQ ID NO: 158 | SEQ ID NO: 11 | | | |
| SEQ ID NO: 185 | | | SEQ ID NO: 157 | SEQ ID NO: 14 | SEQ ID NO: 82 | SEQ ID NO: 96 | SEQ ID NO: 20 |
| SEQ ID | | | SEQ ID | SEQ ID | SEQ ID | SEQ ID | SEQ ID |

TABLE 6-continued

Amino Acid sequences for full heavy and light chains.

| Construct SEQ ID NO: | N-term | Linker | Variable | Constant | Fc | Linker | C-term |
|---|---|---|---|---|---|---|---|
| NO: 186 | | | NO: 157 | NO: 14 | NO: 82 | NO: 96 | NO: 156 |
| SEQ ID NO: 187 | SEQ ID NO: 159 | SEQ ID NO: 152 | SEQ ID NO: 160 | SEQ ID NO: 43 | SEQ ID NO: 83 | | |
| SEQ ID NO: 188 | SEQ ID NO: 159 | SEQ ID NO: 152 | SEQ ID NO: 160 | SEQ ID NO: 43 | SEQ ID NO: 83 | SEQ ID NO: 96 | SEQ ID NO: 150, 152, 151 |
| SEQ ID NO: 189 | SEQ ID NO: 159 | SEQ ID NO: 152 | SEQ ID NO: 160 | SEQ ID NO: 43 | SEQ ID NO: 83 | SEQ ID NO: 96 | SEQ ID NO: 161, 152, 162 |
| SEQ ID NO: 190 | | | SEQ ID NO: 145 | SEQ ID NO: 14 | SEQ ID NO: 83 | SEQ ID NO: 96 | SEQ ID NO: 150, 152, 151 |
| SEQ ID NO: 191 | | | SEQ ID NO: 149 | SEQ ID NO: 147 | | SEQ ID NO: 96 | SEQ ID NO: 163 |
| SEQ ID NO: 192 | | | SEQ ID NO: 148 | SEQ ID NO: 14 | SEQ ID NO: 82 | | |
| SEQ ID NO: 193 | | | SEQ ID NO: 153 | SEQ ID NO: 11 | SEQ ID NO: 83 | SEQ ID NO: 96 | SEQ ID NO: 150, 152 151 |
| SEQ ID NO: 194 | | | SEQ ID NO: 153 | SEQ ID NO: 11 | SEQ ID NO: 83 | SEQ ID NO: 96 | SEQ ID NO: 164, 152, 165 |
| SEQ ID NO: 195 | | | SEQ ID NO: 153 | SEQ ID NO: 11 | SEQ ID NO: 83 | SEQ ID NO: 96 | SEQ ID NO: 166, 152, 167 |

TABLE 7

Amino acid sequences of the chains used to construct multispecific molecules.

| Sequence ID | Amino Acid Sequence |
|---|---|
| SEQ ID NO: 168 | QVQLQESGPGLVKPSQTLSLTCTVSGGSINNNNYYWTWIRQHPGKGLE WIGYIYYSGSTFYNPSLKSRVTISVDTSKTQFSLKLSSVTAADTAVYYCA REDTMTGLDVWGQGTTVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPELLGGPSVFL FPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISK AKGQPREPQVYTLPPCREEMTKNQVSLWCLVKGFYPSDIAVEWESNGQ PENNYKTTPPVLDSDGSFFLYSKLTVDKSRWQQGNVFSCSVMHEALHN HYTQKSLSLSPGK |
| SEQ ID NO: 169 | DIQMTQSPSSLSASVGDRVTITCRASQSINNYLNWYQQKPGKAPTLLIY AASSLQSGVPSRFSGSRSGTDFTLTISSLQPEDFAAYFCQQTYSNPTFGQ GTKVEVKRTVAAPSVFIFPPSDEQLKSGTASVVCLLNNFYPREAKVQW KVDNALQSGNSQESVTEQDSKDSTYSLSSTLTLSKADYEKHKVYACEV THQGLSSPVTKSFNRGEC |
| SEQ ID NO: 170 | APTSSSTKKTQLQLEHLLLDLQMILNGINNYKNPKLTRMLTFKFYMPKK ATELKHLQCLEEELKPLEEVLNLAQSKNFHLRPRDLISNINVIVLELKGS ETTFMCEYADETATIVEFLNRWITFCQSIISTLTGGGGSGGGGSDKTHTC PPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCK VSNKALPAPIEKTISKAKGQPREPQVCTLPPSREEMTKNQVSLSCAVKGF YPSDIAVEWESNGQPENNYKTTPPVLDSDGSFFLVSKLTVDKSRWQG NVFSCSVMHEALHNHYTQKSLSLSPGK |
| SEQ ID NO: 174 | QVQLQESGPGLVKPSQTLSLTCTVSGGSINNNNYYWTWIRQHPGKGLE WIGYIYYSGSTFYNPSLKSRVTISVDTSKTQFSLKLSSVTAADTAVYYCA REDTMTGLDVWGQGTTVTVSSASTKGPSVFPLAPSSKSTSGGTAALGC LVKDYFPEPVTVSWNSGALTSGVHTFPAVLQSSGLYSLSSVVTVPSSSL GTQTYICNVNHKPSNTKVDKRVEPKSCDKTHTCPPCPAPELLGGPSVFL FPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISK AKGQPREPQVYTLPPCREEMTKNQVSLWCLVKGFYPSDIAVEWESNGQ PENNYKTTPPVLDSDGSFFLYSKLTVDKSRWQQGNVFSCSVMHEALHN HYTQKSLSLSPGKGGGGSGGGGSGGGGS (+protein sequence of BioLegend Catalog #325207) |

TABLE 7-continued

Amino acid sequences of the chains used to construct multispecific molecules.

| Sequence ID | Amino Acid Sequence |
| --- | --- |
| SEQ ID NO: 197 | GQPKANPTVTLFPPSSEELQANKATLVCLISDFYPGAVTVAWKADGSPV KAGVETTKPSKQSNNKYAASSYLSLTPEQWKSHRSYSCQVTHEGSTVE KTVAPTECS |
| SEQ ID NO: 176 knob | EVQLLESGGGLVQPGGSLRLSCAASGFTFSSYIMMWVRQAPGKGLEWV SSIYPSGGITFYADTVKGRFTISRDNSKNTLYLQMNSLRAEDTAVYYCA RIKLGTVTTVDYWGQGTLVTVSS |
| SEQ ID NO: 177 | EVQLLESGGGLVQPGGSLRLSCAASGFTFSSYIMMWVRQAPGKGLEWV SSIYPSGGITFYADTVKGRFTISRDNSKNTLYLQMNSLRAEDTAVYYCA RIKLGTVTTVDYWGQGTLVTVSSASTKGPSVFPLAPSSKSTSGGTAALG CLVKDYFPEPVTVSWNSGALTSGVHTFPAVLQSSGLYSLSSVVTVPSSS LGTQTYICNVNHKPSNTKVDKRVEPKSCDKTHTCPPCPAPELLGGPSVF LFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTIS KAKGQPREPQVCTLPPSREEMTKNQVSLSCAVKGFYPSDIAVEWESNG QPENNYKTTPPVLDSDGSFFLVSKLTVDKSRWQQGNVFSCSVMHEALH NHYTQKSLSLSPGKGGGGSGGGGSGGGGSAPTSSSTKKTQLQLEHLLL DLQMILNGINNYKNPKLTRMLTFKFYMPKKATELKHLQCLEEELKPLEE VLNLAQSKNFHLRPRDLISNINVIVLELKGSETTFMCEYADETATIVEFL NRWITFCQSIISTLT |
| SEQ ID NO: 183 | EVQLLQSGGGLVQPGGSLRLSCAASGFMFSRYPMHWVRQAPGKGLEW VGSISGSGGATPYADSVKGRFTISRDNSKNTLYLQMNSLRAEDTAVYYC AKDFYQILTGNAFDYWGQGTTVTVSSASTKGPSVFPLAPSSKSTSGGTA ALGCLVKDYFPEPVTVSWNSGALTSGVHTFPAVLQSSGLYSLSSVVTVP SSSLGTQTYICNVNHKPSNTKVDKRVEPKSCDKTHTCPPCPAPELLGGPS VFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKT ISKAKGQPREPQVCTLPPSREEMTKNQVSLSCAVKGFYPSDIAVEWESN GQPENNYKTTPPVLDSDGSFFLVSKLTVDKSRWQQGNVFSCSVMHEAL HNHYTQKSLSLSPGK |
| SEQ ID NO: 184 | DIQMTQSPSSLSASLGDRVTITCRASQGISSYLAWYQQKPGKAPKLLIYA KSTLQSGVPSRFSGSGSGTDFTLTISSLQPEDSATYYCQQYWTFPLTFGG GTKVEIKRTVAAPSVFIFPPSDEQLKSGTASVVCLLNNFYPREAKVQWK VDNALQSGNSQESVTEQDSKDSTYSLSSTLTLSKADYEKHKVYACEVT HQGLSSPVTKSFNRGEC |
| SEQ ID NO: 185 | EVQLLQSGGGLVQPGGSLRLSCAASGFMFSRYPMHWVRQAPGKGLEW VGSISGSGGATPYADSVKGRFTISRDNSKNTLYLQMNSLRAEDTAVYYC AKDFYQILTGNAFDYWGQGTTVTVSSASTKGPSVFPLAPSSKSTSGGTA ALGCLVKDYFPEPVTVSWNSGALTSGVHTFPAVLQSSGLYSLSSVVTVP SSSLGTQTYICNVNHKPSNTKVDKRVEPKSCDKTHTCPPCPAPELLGGPS VFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKT ISKAKGQPREPQVCTLPPSREEMTKNQVSLSCAVKGFYPSDIAVEWESN GQPENNYKTTPPVLDSDGSFFLVSKLTVDKSRWQQGNVFSCSVMHEAL HNHYTQKSLSLSPGKGGGGSGGGGSGGGGSAPTSSSTKKTQLQLEHLL LDLQMILNGINNYKNPKLTRMLTFKFYMPKKATELKHLQCLEEELKPLE EVLNLAQSKNFHLRPRDLISNINVIVLELKGSETTFMCEYADETATIVEF LNRWITFCQSIISTLT |
| SEQ ID NO: 186 | EVQLLQSGGGLVQPGGSLRLSCAASGFMFSRYPMHWVRQAPGKGLEW VGSISGSGGATPYADSVKGRFTISRDNSKNTLYLQMNSLRAEDTAVYYC AKDFYQILTGNAFDYWGQGTTVTVSSASTKGPSVFPLAPSSKSTSGGTA ALGCLVKDYFPEPVTVSWNSGALTSGVHTFPAVLQSSGLYSLSSVVTVP SSSLGTQTYICNVNHKPSNTKVDKRVEPKSCDKTHTCPPCPAPELLGGPS VFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKT ISKAKGQPREPQVCTLPPSREEMTKNQVSLSCAVKGFYPSDIAVEWESN GQPENNYKTTPPVLDSDGSFFLVSKLTVDKSRWQQGNVFSCSVMHEAL HNHYTQKSLSLSPGKGGGGSGGGGSGGGGSDCDIEGKDGKQYESVLM VSIDQLLDSMKEIGSNCLNNEFNFFKRHICDANKEGMFLFRAARKLRQF LKMNSTGDFDLHLLKVSEGTTILLNCTGQVKGRKPAALGEAQPTKSLEE NKSLKEQKKLNDLCFLKRLLQEIKTCWNKILMGTKEH |
| SEQ ID NO: 187 | QVQLVQSGGGLVQPGGSLRLSCAASGFTFDDYAMHWVRQAPGKGLE WVAGISWDSGSTGYADSVKGRFTISRDNAKNSLYLQMNSLRAEDTALY YCARDLGAYQWVEGFDYWGQGTLVTVSSASTGGGGSGGGGSGGGGS GGGGSSYELTQDPAVSVALGQTVRITCQGDSLRSYYASWYQQKPGQAP VLVIYGKNNRPSGIPDRFSGSTSGNSASLTITGAQAEDEADYYCNSRDSP GNQWVFGGGTKVTVLGGGGSGGGGSDKTHTCPPCPAPELLGGPSVFL FPPKPKDTLMISRTPEVTCVVVDVSHEDPEVKFNWYVDGVEVHNAKTK |

TABLE 7-continued

Amino acid sequences of the chains used to construct multispecific molecules.

| Sequence ID | Amino Acid Sequence |
|---|---|
| | PREEQYNSTYRVVSVLTVLHQDWLNGKEYKCKVSNKALPAPIEKTISK<br>AKGQPREPQVYTLPPCREEMTKNQVSLWCLVKGFYPSDIAVEWESNGQ<br>PENNYKTTPPVLDSDGSFFLYSKLTVDKSRWQQGNVFSCSVMHEALHN<br>HYTQKSLSLSPGK |
| SEQ ID NO: 188 | QVQLVQSGGGLVQPGGSLRLSCAASGFTFDDYAMHWVRQAPGKGLE<br>WVAGISWDSGSTGYADSVKGRFTISRDNAKNSLYLQMNSLRAEDTALY<br>YCARDLGAYQWVEGFDYWGQGTLVTVSSASTGGGGSGGGGSGGGGS<br>GGGGSSYELTQDPAVSVALGQTVRITCQGDSLRSYYASWYQQKPGQAP<br>VLVIYGKNNRPSGIPDRFSGSTSGNSASLTITGAQAEDEADYYCNSRDSP<br>GNQWVFGGGTKVTVLGGGGSGGGGSDKTHTCPPCPAPELLGGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISK<br>AKGQPREPQVYTLPPCREEMTKNQVSLWCLVKGFYPSDIAVEWESNGQ<br>PENNYKTTPPVLDSDGSFFLYSKLTVDKSRWQQGNVFSCSVMHEALHN<br>HYTQKSLSLSPGKGGGGSGGGGSGGGGSQVQLQQSGPELVKPGASVK<br>MSCKASGYTFTDYVINWGKQRSGQGLEWIGEIYPGSGTNYYNEKFKAK<br>ATLTADKSSNIAYMQLSSLTSEDSAVYFCARRGRYGLYAMDYWGQGT<br>SVTVSSGGGGSGGGGSGGGGSGGGGSDIQMTQTTSSLSASLGDRVTISC<br>RASQDISNYLNWYQQKPDGTVKLLIYYTSRLHSGVPSRFSGSGSGTDYS<br>LTINNLEQEDIATYFCQQGNTRPWTFGGGTKLEIK |
| SEQ ID NO: 189 | QVQLVQSGGGLVQPGGSLRLSCAASGFTFDDYAMHWVRQAPGKGLE<br>WVAGISWDSGSTGYADSVKGRFTISRDNAKNSLYLQMNSLRAEDTALY<br>YCARDLGAYQWVEGFDYWGQGTLVTVSSASTGGGGSGGGGSGGGGS<br>GGGGSSYELTQDPAVSVALGQTVRITCQGDSLRSYYASWYQQKPGQAP<br>VLVIYGKNNRPSGIPDRFSGSTSGNSASLTITGAQAEDEADYYCNSRDSP<br>GNQWVFGGGTKVTVLGGGGSGGGGSDKTHTCPPCPAPELLGGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISK<br>AKGQPREPQVYTLPPCREEMTKNQVSLWCLVKGFYPSDIAVEWESNGQ<br>PENNYKTTPPVLDSDGSFFLYSKLTVDKSRWQQGNVFSCSVMHEALHN<br>HYTQKSLSLSPGKGGGGSGGGGSGGGGSQVQLVQSGGGVVQPGRSLR<br>LSCKASGYTFTRYTMHWVRQAPGKGLEWIGYINPSRGYTNYNQKVKD<br>RFTISRDNSKNTAFLQMDSLRPEDTGVYFCARYYDDHYSLDYWGQGTP<br>VTVSSGGGGSGGGGSGGGGSGGGGSDIQMTQSPSSLSASVGDRVTITCS<br>ASSSVSYMNWYQQTPGKAPKRWIYDTSKLASGVPSRFSGSGSGTDYTF<br>TISSLQPEDIATYYCQQWSSNPFTFGQGTKLQIT |
| SEQ ID NO: 190 | QVQLQESGPGLVKPSQTLSLTCTVSGGSINNNNYYWTWIRQHPGKGLE<br>WIGYIYYSGSTFYNPSLKSRVTISVDTSKTQFSLKLSSVTAADTAVYYCA<br>REDTMTGLDVWGQGTTVTVSSASTKGPSVFPLAPSSKSTSGGTAALGC<br>LVKDYFPEPVTVSWNSGALTSGVHTFPAVLQSSGLYSLSSVVTVPSSSL<br>GTQTYICNVNHKPSNTKVDKRVEPKSCDKTHTCPPCPAPELLGGPSVFL<br>FPPKPKDTLMISRTPEVTCVVVDVSHEDPEVKFNWYVDGVEVHNAKTK<br>PREEQYNSTYRVVSVLTVLHQDWLNGKEYKCKVSNKALPAPIEKTISK<br>AKGQPREPQVYTLPPCREEMTKNQVSLWCLVKGFYPSDIAVEWESNGQ<br>PENNYKTTPPVLDSDGSFFLYSKLTVDKSRWQQGNVFSCSVMHEALHN<br>HYTQKSLSLSPGKGGGGSGGGGSGGGGSQVQLQQSGPELVKPGASVK<br>MSCKASGYTFTDYVINWGKQRSGQGLEWIGEIYPGSGTNYYNEKFKAK<br>ATLTADKSSNIAYMQLSSLTSEDSAVYFCARRGRYGLYAMDYWGQGT<br>SVTVSSGGGGSGGGGSGGGGSGGGGSDIQMTQTTSSLSASLGDRVTISC<br>RASQDISNYLNWYQQKPDGTVKLLIYYTSRLHSGVPSRFSGSGSGTDYS<br>LTINNLEQEDIATYFCQQGNTRPWTFGGGTKLEIK |
| SEQ ID NO: 193 | QVQLQESGPGLVKPSETLSLTCTVSGGSVSSGSYYWSWIRQPPGKGLEW<br>IGYIYYSGSTNYNPSLKSRVTISVDTSKNQFSLKLSSVTAADTAVYYCAR<br>EGKNGAFDIWGQGTMVTVSSASTKGPSVFPLAPSSKSTSGGTAALGCLV<br>KDYFPEPVTVSWNSGALTSGVHTFPAVLQSSGLYSLSSVVTVPSSSLGT<br>QTYICNVNHKPSNTKVDKRVEPKSCDKTHTCPPCPAPELLGGPSVFLFPP<br>KPKDTLMISRTPEVTCVVVDVSHEDPEVKFNWYVDGVEVHNAKTKPR<br>EEQYNSTYRVVSVLTVLHQDWLNGKEYKCKVSNKALPAPIEKTISKAK<br>GQPREPQVYTLPPCREEMTKNQVSLWCLVKGFYPSDIAVEWESNGQPE<br>NNYKTTPPVLDSDGSFFLYSKLTVDKSRWQQGNVFSCSVMHEALHNH<br>YTQKSLSLSPGKGGGGSGGGGSGGGGSQVQLQQSGPELVKPGASVKMS<br>CKASGYTFTDYVINWGKQRSGQGLEWIGEIYPGSGTNYYNEKFKAKAT<br>LTADKSSNIAYMQLSSLTSEDSAVYFCARRGRYGLYAMDYWGQGTSV<br>TVSSGGGGSGGGGSGGGGSGGGGSDIQMTQTTSSLSASLGDRVTISCRA<br>SQDISNYLNWYQQKPDGTVKLLIYYTSRLHSGVPSRFSGSGSGTDYSLTI<br>NNLEQEDIATYFCQQGNTRPWTFGGGTKLEIK |
| SEQ ID NO: 173 | DIQMTQSPSSLSASVGDRVTITCRASQSISSYLNWYQQKPGKAPKLLIYA<br>ASSLQSGVPSGFSGSGSGTDFTLTISSLQPEDFATYYCQQSYSTPLTFGGG<br>TKVEIKRTVAAPSVFIFPPSDEQLKSGTASVVCLLNNFYPREAKVQWKV |

TABLE 7-continued

Amino acid sequences of the chains used to construct multispecific molecules.

| Sequence ID | Amino Acid Sequence |
|---|---|
| | DNALQSGNSQESVTEQDSKDSTYSLSSTLTLSKADYEKHKVYACEVTH QGLSSPVTKSFNRGEC |
| SEQ ID NO: 171 | QSALTQPASVSGSPGQSITISCTGTSSDVGGYNYVSWYQQHPGKAPKLM IYDVSNRPSGVSNRFSGSKSGNTASLTISGLQAEDEADYYCSSYTSSSTR VFGTGTKVTVLGQPKANPTVTLFPPSSEELQANKATLVCLISDFYPGAV TVAWKADGSPVKAGVETTKPSKQSNNKYAASSYLSLTPEQWKSHRSYS CQVTHEGSTVEKTVAPTECS |
| SEQ ID NO: 172 | QVQLQESGPGLVKPSETLSLTCTVSGGSVSSGSYYWSWIRQPPGKGLEW IGYIYYSGSTNYNPSLKSRVTISVDTSKNQFSLKLSSVTAADTAVYYCAR EGKNGAFDIWGQGTMVTVSSASTKGPSVFPLAPSSKSTSGGTAALGCLV KDYFPEPVTVSWNSGALTSGVHTFPAVLQSSGLYSLSSVVTVPSSSLGT QTYICNVNHKPSNTKVDKRVEPKSCDKTHTCPPCPAPELLGGPSVFLFPP KPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAK GQPREPQVYTLPPCREEMTKNQVSLWCLVKGFYPSDIAVEWESNGQPE NNYKTTPPVLDSDGSFFLYSKLTVDKSRWQQGNVFSCSVMHEALHNH YTQKSLSLSPGK |
| SEQ ID NO: 191 | QSALTQPASVSGSPGQSITISCTGTSSDVGGYNYVSWYQQHPGKAPKLM IYDVSNRPSGVSNRFSGSKSGNTASLTISGLQAEDEADYYCSSYTSSSTR VFGTGTKVTVLGQPKANPTVTLFPPSSEELQANKATLVCLISDFYPGAV TVAWKADGSPVKAGVETTKPSKQSNNKYAASSYLSLTPEQWKSHRSYS CQVTHEGSTVEKTVAPTECSGGGGSGGGGSGGGGSAPTSSSTKKTQLQ LEHLLLDLQMILNGINNYKNPKLTRMLTAKFAMPKKATELKHLQCLEE ELKPLEEVLNLAQSKNFHLRPRDLISNINVIVLELKGSETTFMCEYADET ATIVEFLNRWITFCQSIISTLT |
| SEQ ID NO: 192 | EVQLLESGGGLVQPGGSLRLSCAASGFTFSSYIMMWVRQAPGKGLEWV SSIYPSGGITFYADTVKGRFTISRDNSKNTLYLQMNSLRAEDTAVYYCA RIKLGTVTTVDYWGQGTLVTVSSASTKGPSVFPLAPSSKSTSGGTAALG CLVKDYFPEPVTVSWNSGALTSGVHTFPAVLQSSGLYSLSSVVTVPSSS LGTQTYICNVNHKPSNTKVDKRVEPKSCDKTHTCPPCPAPELLGGPSVF LFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTIS KAKGQPREPQVCTLPPSREEMTKNQVSLSCAVKGFYPSDIAVEWESNG QPENNYKTTPPVLDSDGSFFLVSKLTVDKSRWQQGNVFSCSVMHEALH NHYTQKSLSLSPGK |
| SEQ ID NO: 194 | QVQLQESGPGLVKPSETLSLTCTVSGGSVSSGSYYWSWIRQPPGKGLEW IGYIYYSGSTNYNPSLKSRVTISVDTSKNQFSLKLSSVTAADTAVYYCAR EGKNGAFDIWGQGTMVTVSSASTKGPSVFPLAPSSKSTSGGTAALGCLV KDYFPEPVTVSWNSGALTSGVHTFPAVLQSSGLYSLSSVVTVPSSSLGT QTYICNVNHKPSNTKVDKRVEPKSCDKTHTCPPCPAPELLGGPSVFLFPP KPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAK GQPREPQVYTLPPCREEMTKNQVSLWCLVKGFYPSDIAVEWESNGQPE NNYKTTPPVLDSDGSFFLYSKLTVDKSRWQQGNVFSCSVMHEALHNH YTQKSLSLSPGKGGGGSGGGGSGGGGSEVQLQESGPGLVKPSQSLSLTC TVTGYSITSDYAWNWIRQFPGNKLEWMGYITYSGSTSYNPSLESRISITR DTSTNQFFLQLNSVTTEDTATYYCARGGYYGSSWGVFAYWGQGTLVT VSAGGGGSGGGGSGGGGSGGGGSDIQMTQSPASLSASVGETVTITCRVS ENIYSYLAWYQQKQGKSPQLLVYNAKTLAEGVPSRFSGSGSGTQFSLKI NSLQPEDFGSYYCQHHYGTPWTFGGGTKLEIK |
| SEQ ID NO: 195 | QVQLQESGPGLVKPSETLSLTCTVSGGSVSSGSYYWSWIRQPPGKGLEW IGYIYYSGSTNYNPSLKSRVTISVDTSKNQFSLKLSSVTAADTAVYYCAR EGKNGAFDIWGQGTMVTVSSASTKGPSVFPLAPSSKSTSGGTAALGCLV KDYFPEPVTVSWNSGALTSGVHTFPAVLQSSGLYSLSSVVTVPSSSLGT QTYICNVNHKPSNTKVDKRVEPKSCDKTHTCPPCPAPELLGGPSVFLFPP KPKDTLMISRTPEVTCVVVDVSHEDPEVKFNWYVDGVEVHNAKTKPR EEQYNSTYRVVSVLTVLHQDWLNGKEYKCKVSNKALPAPIEKTISKAK GQPREPQVYTLPPCREEMTKNQVSLWCLVKGFYPSDIAVEWESNGQPE NNYKTTPPVLDSDGSFFLYSKLTVDKSRWQQGNVFSCSVMHEALHNH YTQKSLSLSPGKGGGGSGGGGSGGGGSQVQLQQSAVELARPGASVKM SCKASGYTFTSFTMHWVKQRPGQGLEWIGYINPSSGYTEYNQKFKDKT TLTADKSSSTAYMQLDSLTSDDSAVYYCVRGSSRGFDYWGQGTLVTVS AGGGGSGGGGSGGGGSGGGGSDIQMIQSPASLSVSVGETVTITCRASEN IYSNLAWFQQKQGKSPQLLVYAATNLADGVPSRFSGSGSGTQYSLKINS LQSEDFGIYYCQHFWGTPRTFGGGTKLEIK |

TABLE 8

Amino Acid sequences of antigens.

| Sequence ID | Description | Amino Acid Sequence |
|---|---|---|
| SEQ ID NO: 181 | hMeso 1-7 | GLNDIFEAQKIEWHEGGGGSEPRTDTDTCPNPPDPCPTCPTPDLLG GPSVFIFPPKPKDVLMISLTPKITCVVVDVSEEEPDVQFNWYVNN VEDKTAQTETRQRQYNSTYRVVSVLPIKHQDWMSGKVFKCKVN NNALPSPIEKTISKPRGQVRVPQIYTFPPPIEQTVKKDVSVTCLVTG FLPQDIHVEWESNGQPQPEQNYKNTQPVLDSDGSYFLYSKLNVP KSRWDQGDSFTCSVIHEALHNHHMTKTISRSLGNGGGGSEVEKT ACPSGKKAREIDESLIFYKKWELEACVDAALLATQMDRVNAIPFT YEQLDVLKHKLDELYPQGYPESVIQHLGYLFLKMSPEDIRKWNV TSLETLKALLEVNKGHEMSPQAPRRPLPQVATLIDRFVKGRGQLD KDTLDTLTAFYPGYLCSLSPEELSSVPPSSIWAVRPQDLDTCDPRQ LDVLYPKARLAFQNMNGSEYFVKIQSFLGGAPTEDLKALSQQNV SMDLATFMKLRTDAVLPLTVAEVQKLLGPHVEGLKAEERHRPV RDWILRQRQDDLDTLGLGLQ |
| SEQ ID NO: 178 | hPD1L1 | FTVTVPKDLYVVEYGSNMTIECKFPVEKQLDLAALIVYWEMEDK NIIQFVHGEEDLKVQHSSYRQRARLLKDQLSLGNAALQITDVKLQ DAGVYRCMISYGGADYKRITVKVNAPYNKINQRILVVDPVTSEH ELTCQAEGYPKAEVIWTSSDHQVLSGKTTTTNSKREEKLFNVTST LRINTTTNEIFYCTFRRLDPEENHTAELVIPELPLAHPPNERTGGGG SGLNDIFEAQKIEWHEGGGGSHHHHHHHH |
| SEQ ID NO: 182 | hIL2Rα | ELCDDDPPEIPHATFKAMAYKEGTMLNCECKRGFRRIKSGSLYM LCTGNSSHSSWDNQCQCTSSATRNTTKQVTPQPEEQKERKTTEM QSPMQPVDQASLPGHCREPPPWENEATERIYHFVVGQMVYYQC VQGYRALHRGPAESVCKMTHGKTRWTQPQLICTGGGGGSGGGG SGLNDIFEAQKIEWHEGGGGSHHHHHHHH |
| SEQ ID NO: 180 | hNKp30 | LWVSQPPEIRTLEGSSAFLPCSFNASQGRLAIGSVTWFRDEVVPG KEVRNGTPEFRGRLAPLASSRFLHDHQAELHIRDVRGHDASIYVC RVEVLGLGVGTGNGTRLVVEKEGGGGSGGGGSDKTHTCPPCPAP ELLGGPSVFLFPPKPKDTLMISRTPEVTCVVVDVSHEDPEVKFNW YVDGVEVHNAKTKPREEQYNSTYRVVSVLTVLHQDWLNGKEY KCKVSNKALPAPIEKTISKAKGQPREPQVYTLPPSREEMTKNQVS LTCLVKGFYPSDIAVEWESNGQPENNYKTTPPVLDSDGSFFLYSK LTVDKSRWQQGNVFSCSVMHEALHNHYTQKSLSLSPGKGGGGS GGGGSGLNDIFEAQKIEWHE |
| SEQ ID NO: 179 | hNKp46 | TEMYDTPTLSVHPGPEVISGEKVTFYCRLDTATSMFLLLKEGRSS HVQRGYGKVQAEFPLGPVTTAHRGTYRCFGSYNNHAWSFPSEPV KLLVTGDIENTSLAPEDPTFPDTWGTYLLTTETGLQKDHALWDH TAQNGGGGSGGGGSEPRTDTDTCPNPPDPCPTCPTPDLLGGPSVFI FPPKPKDVLMISLTPKITCVVVDVSEEEPDVQFNWYVNNVEDKT AQTETRQRQYNSTYRVVSVLPIKHQDWMSGKVFKCKVNNNALP SPIEKTISKPRGQVRVPQIYTFPPPIEQTVKKDVSVTCLVTGFLPQD IHVEWESNGQPQPEQNYKNTQPVLDSDGSYFLYSKLNVPKSRWD QGDSFTCSVIHEALHNHHMTKTISRSLGNGGGGSGGGGSGLNDIF EAQKIEWHE |

TABLE 9

Sequences used to generate multispecific molecules.

| Multispecific Molecule | Heavy Chain 1 | Light Chain 1 | Heavy Chain 2 | Light Chain 2 |
|---|---|---|---|---|
| 1 | SEQ ID NO: 168 | SEQ ID NO: 169 | SEQ ID NO: 196 | |
| 2 | SEQ ID NO: 174 | SEQ ID NO: 169 | SEQ ID NO: 196 | |
| 3 | SEQ ID NO: 174 | SEQ ID NO: 169 | SEQ ID NO: 197 | |
| 4 | SEQ ID NO: 176 | | SEQ ID NO: 196 | |
| 5 | SEQ ID NO: 172 | SEQ ID NO: 173 | SEQ ID NO: 192 | SEQ ID NO: 171 |
| 6 | SEQ ID NO: 172 | SEQ ID NO: 173 | SEQ ID NO: 177 | SEQ ID NO: 171 |
| 7 | SEQ ID NO: 193 | SEQ ID NO: 173 | SEQ ID NO: 192 | SEQ ID NO: 171 |
| 8 | SEQ ID NO: 193 | SEQ ID NO: 173 | SEQ ID NO: 177 | SEQ ID NO: 171 |
| 9 | SEQ ID NO: 194 | SEQ ID NO: 173 | SEQ ID NO: 192 | SEQ ID NO: 171 |
| 10 | SEQ ID NO: 194 | SEQ ID NO: 173 | SEQ ID NO: 177 | SEQ ID NO: 171 |
| 11 | SEQ ID NO: 195 | SEQ ID NO: 173 | SEQ ID NO: 192 | SEQ ID NO: 171 |
| 12 | SEQ ID NO: 195 | SEQ ID NO: 173 | SEQ ID NO: 177 | SEQ ID NO: 171 |
| 13 | SEQ ID NO: 187 | | SEQ ID NO: 185 | SEQ ID NO: 184 |
| 14 | SEQ ID NO: 188 | | SEQ ID NO: 183 | SEQ ID NO: 184 |
| 15 | SEQ ID NO: 189 | | SEQ ID NO: 183 | SEQ ID NO: 184 |
| 16 | SEQ ID NO: 188 | | SEQ ID NO: 185 | SEQ ID NO: 184 |
| 17 | SEQ ID NO: 189 | | SEQ ID NO: 185 | SEQ ID NO: 184 |

TABLE 9-continued

Sequences used to generate multispecific molecules.

| Multispecific Molecule | Heavy Chain 1 | Light Chain 1 | Heavy Chain 2 | Light Chain 2 |
|---|---|---|---|---|
| 18 | SEQ ID NO: 187 | | SEQ ID NO: 183 | SEQ ID NO: 184 |
| 19 | SEQ ID NO: 187 | | SEQ ID NO: 186 | SEQ ID NO: 184 |
| 20 | SEQ ID NO: 189 | | SEQ ID NO: 186 | SEQ ID NO: 184 |
| 21 | SEQ ID NO: 190 | SEQ ID NO: 169 | SEQ ID NO: 186 | SEQ ID NO: 184 |
| 22 | SEQ ID NO: 190 | SEQ ID NO: 169 | SEQ ID NO: 192 | SEQ ID NO: 191 |
| 23 | SEQ ID NO: 168 | SEQ ID NO: 169 | SEQ ID NO: 192 | SEQ ID NO: 171 |

TABLE 10

Nucleic acid sequences.

| Sequence ID | Description | Nucleic Acid Sequence |
|---|---|---|
| SEQ ID NO: 88 | 2x4GS linker | GGCGGCGGAGGATCTGGCGGAGGCGGCAGC |
| SEQ ID NO: 89 | Human CH2, CH3 knob | GATAAGACCCACACCTGTCCTCCATGTCCTGCCCCTGAGCTGCTGGG CGGACCTAGCGTGTTCCTGTTCCCTCCAAAGCCCAAGGACACCCTG ATGATCAGCCGGACCCCTGAAGTGACCTGCGTGGTGGTGGATGTGT CCCACGAGGATCCCGAAGTGAAGTTCAATTGGTACGTGGACGGCGT GGAAGTGCACAACGCCAAGACCAAGCCCAGAGAGGAACAGTACAA CAGCACCTACCGGGTGGTGTCCGTGCTGACCGTGCTGCACCAGGAC TGGCTGAACGGCAAAGAGTACAAGTGCAAGGTGTCCAACAAGGCC CTGCCTGCCCCTATCGAGAAAACCATCAGCAAGGCCAAGGGCCAGC CCCGCGAACCTCAGGTGTACACACTGCCTCCCTGCCGGGAAGAGAT GACCAAGAACCAGGTGTCCCTGTGGTGCCTGGTCAAGGGCTTCTAC CCCTCCGATATCGCCGTGGAATGGGAGAGCAACGGCCAGCCCGAGA ACAACTACAAGACCACCCCTCCCGTGCTGGACAGCGACGGCAGCTT CTTCCTGTACTCCAAACTGACCGTGGACAAGAGCCGGTGGCAGCAG GGCAATGTGTTCAGCTGTAGCGTGATGCACGAGGCCCTGCACAACC ACTACACCCAGAAGTCTCTGAGCCTGAGCCCCGGCAAGTAATGA |
| SEQ ID NO: 90 | Human CH2, CH3 hole | GATAAGACCCACACCTGTCCTCCATGTCCTGCCCCTGAGCTGCTGGG CGGACCTAGCGTGTTCCTGTTCCCTCCAAAGCCCAAGGACACCCTG ATGATCAGCCGGACCCCTGAAGTGACCTGCGTGGTGGTGGATGTGT CCCACGAGGATCCCGAAGTGAAGTTCAATTGGTACGTGGACGGCGT GGAAGTGCACAACGCCAAGACCAAGCCCAGAGAGGAACAGTACAA CAGCACCTACCGGGTGGTGTCCGTGCTGACCGTGCTGCACCAGGAC TGGCTGAACGGCAAAGAGTACAAGTGCAAGGTGTCCAACAAGGCC CTGCCTGCCCCTATCGAGAAAACCATCAGCAAGGCCAAGGGCCAGC CTAGAGAGCCTCAGGTCTGCACCCTGCCTCCCAGCCGGGAAGAGAT GACCAAGAACCAGGTGTCCCTGTCCTGCGCCGTGAAGGGCTTCTAC CCCTCCGATATCGCCGTGGAATGGGAGAGCAACGGCCAGCCCGAGA ACAACTACAAGACCACCCCTCCCGTGCTGGACAGCGACGGCAGCTT CTTCCTGGTGTCCAAACTGACCGTGGACAAGAGCCGGTGGCAGCAG GGCAATGTGTTCAGCTGTAGCGTGATGCACGAGGCCCTGCACAACC ACTACACCCAGAAGTCTCTGAGCCTGAGCCCCGGCAAGTAATGA |
| SEQ ID NO: 91 | CH1 | GCCAGCACCAAGGGCCCTAGCGTGTTCCCTCTGGCCCCTAGCTCTAA GAGCACATCTGGCGGAACAGCCGCCCTGGGCTGCCTGGTCAAGGAT TACTTTCCTGAGCCCGTGACCGTGTCCTGGAACTCTGGTGCTCTGAC CAGCGGCGTGCACACCTTTCCAGCTGTGCTGCAGAGCAGCGGCCTG TACAGCCTGTCTAGCGTGGTCACAGTGCCTAGCAGCAGCCTGGGCA CACAGACCTACATCTGCAACGTGAACCACAAGCCCAGCAACACCAA GGTGGACAAGCGGGTGGAACCCAAGAGCTGC |
| SEQ ID NO: 92 | CL (kappa) | AGAACAGTGGCCGCTCCCAGCGTGTTCATCTTCCCACCCAGCGACG AGCAGCTGAAGTCTGGCACAGCCAGCGTCGTGTGCCTGCTGAACAA CTTCTACCCCAGAGAAGCCAAGGTGCAGTGGAAGGTGGACAACGCC CTGCAGTCCGGCAACAGCCAGGAAAGCGTCACCGAGCAGGACAGC AAGGACTCCACCTACAGCCTGTCCAGCACCCTGACCCTGAGCAAGG CCGACTACGAGAAGCACAAAGTGTACGCCTGCGAAGTGACCCACCA GGGCCTGAGCAGCCCCGTGACCAAGAGCTTCAATAGAGGCGAGTGC TAATGA |
| SEQ ID NO: 93 | CL (lambda) | GGCCAGCCCAAGGCCAACCCCACCGTGACCCTGTTCCCTCCATCCTC CGAGGAACTGCAGGCTAACAAGGCCACCCTCGTGTGCCTGATCTCC GACTTCTACCCTGGCGCCGTGACCGTGGCTTGGAAGGCTGATGGCT CTCCTGTGAAGGCCGGCGTGGAAACCACCAAGCCCTCCAAGCAGTC CAACAACAAATACGCCGCCTCCAGCTACCTGTCCCTGACCCCTGAG CAGTGGAAGTCCCACCGGTCCTACAGCTGCCAGGTCACACATGAGG GCTCCACCGTGGAAAAGACCGTGGCCCCTACCGAGTGCTCCTAATGA |

TABLE 10-continued

Nucleic acid sequences.

| Sequence ID | Description | Nucleic Acid Sequence |
|---|---|---|
| SEQ ID NO: 94 | αPD1L1 Avelumab VH | GAGGTGCAGCTGCTGGAATCTGGCGGAGGACTGGTGCAGCCTGGCG GCTCTCTGAGACTGTCTTGTGCCGCCTCCGGCTTCACCTTCTCCAGC TATATCATGATGTGGGTCCGACAGGCCCCTGGCAAGGGCCTGGAAT GGGTGTCCTCTATCTACCCCTCCGGCGGCATCACCTTTTACGCCGAC ACCGTGAAGGGCCGGTTCACCATCTCCCGGGACAACTCCAAGAACA CCCTGTACCTGCAGATGAACTCCCTGCGGGCCGAGGACACCGCCGT GTACTACTGCGCTAGAATCAAGCTGGGCACCGTGACCACCGTGGAC TATTGGGGCCAGGGCACCCTGGTCACCGTGTCCTCT |
| SEQ ID NO: 95 | αPD1L1 Avelumab VL | CAGTCTGCTCTGACCCAGCCTGCCTCTGTGTCTGGCTCCCCTGGCCA GTCCATCACCATCAGCTGTACCGGCACCTCCTCCGACGTGGGCGGCT ACAACTACGTGTCCTGGTATCAGCAGCATCCCGGCAAGGCCCCTAA GCTGATGATCTACGACGTGTCCAACCGGCCCTCCGGCGTGTCCAATC GGTTCTCTGGCTCCAAGTCCGGCAACACCGCCTCCCTGACAATCAGC GGACTGCAGGCCGAGGACGAGGCCGACTACTACTGCTCCTCCTACA CCTCCAGCTCTACCCGGGTGTTCGGCACCGGCACCAAAGTGACAGT GCTG |
| SEQ ID NO: 96 | 3x4GS linker | GGCGGCGGAGGATCTGGCGGAGGTGGAAGCGGAGGCGGTGGATCT |
| SEQ ID NO: 97 | αNKp46 VH | CAGGTTCAGTTGCAGCAGTCCGGACCTGAGCTGGTTAAGCCTGGCG CTTCCGTGAAGATGTCCTGCAAGGCTTCCGGCTACACCTTCACCGAC TACGTGATCAACTGGGGCAAGCAGAGATCTGGCCAGGGACTCGAGT GGATCGGCGAGATCTATCCTGGCTCCGGCACCAATTACTACAACGA GAAGTTCAAGGCTAAGGCTACCCTGACCGCCGACAAGTCCTCCAAT ATCGCCTACATGCAGCTGTCCAGCCTGACCTCTGAGGACTCCGCTGT GTACTTCTGCGCTCGGAGAGGCAGATACGGCCTGTATGCCATGGAT TACTGGGGACAGGGAACCAGTGTGACAGTGTCAAGT |
| SEQ ID NO: 98 | αNKp46 VL | GATATTCAGATGACCCAGACCACCTCCAGCCTGTCCGCTTCTCTGGG CGACAGAGTGACAATCAGCTGCAGAGCCAGCCAGGACATCAGCAA CTACCTGAACTGGTATCAACAGAAACCCGACGGCACCGTGAAGCTG CTGATCTACTACACCTCTCGGCTGCACTCTGGCGTGCCCTCTAGATT TTCTGGCAGCGGAAGCGGCACCGACTATTCCCTGACCATCAACAAC CTGGAACAAGAGGATATCGCTACCTACTTCTGCCAGCAAGGCAACA CCCCGGCCTTGGACATTTGGCGGCGGAACAAAGCTGGAAATCAAGTG ATGA |
| SEQ ID NO: 99 | 4x 4GS linker | GGTGGCGGAGGAAGCGGCGGAGGCGGCTCTGGTGGTGGTGGTTCTG GTGGCGGTGGCTCC |
| SEQ ID NO: 102 | 1x4GS | GGCGGCGGAGGCTCC |
| SEQ ID NO: 198 | MMP2 | TACAACTTCTTCCCACGGAAACCCAAGTGGGACAAGAACCAGATCA CCTACCGGATCATCGGCTACACCCCTGACCTGGATCCTGAGACAGT GGACGATGCCTTCGCCAGAGCCTTCCAAGTTTGGAGCGACGTGACC CCTCTGCGGTTCTCCAGAATCCATGATGGCGAGGCCGACATCATGA TCAACTTCGGCAGATGGGAGCACGGCGACGGCTACCCTTTTGATGG CAAGGATGGCCTGCTGGCCCACGCTTTTGCCCCTGGAACAGGTGTT GGCGGCGACTCTCACTTCGACGACGATGAGTTGTGGACCCTCGGCC AAGGACAGGTCGTCAGAGTGAAGTACGGCAACGCCGATGGCGAGT ACTGCAAGTTCCCCTTCCTGTTCAACGGCAAAGAGTACAACTCCTGC ACCGACACCGGCAGATCTGACGGCTTCCTGTGGTGCTCCACCACCT ACAACTTTGAGAAGGACGGCAAATACGGCTTCTGCCCTCACGAGGC CCTGTTTACCATGGGCGGAAATGCTGAGGGCCAGCCATGCAAGTTT CCATTCCGGTTCCAAGGGACCTCCTACGACAGCTGTACCACCGAGG GAAGAACCGATGGCTATCGTTGGTGCGGCACCACAGAGGACTACGA CAGAGACAAGAAGTATGGCTTCTGTCCCGAGACAGCCATGTCTACC GTCGGCGGCAATTCTGAAGGCGCCCCTTGTGTGTTCCCTTTTCACCTT CCTGGGCAACAAATACGAGTCCTGCACCTCCGCTGGCCGCTCTGAT GGAAAAATGTGGTGCGCTACCACCGCCAACTACGACGACGACAGA AGTGGGGCTTTTGTCCTGACCAGGGCTACTCCCTGTTTCTGGTGGC CGCTCACGAGTTTGGCCATGCTATGGGCCTCGAGCACTCTCAAGATC CCGGTGCACTGATGGCCCCTATCTACACCTACACCAAGAACTTCCG GCTGTCCCAGGACGACATCAAGGGCATCAAGAGCTGTACGGCGCC TCTCCTGATATCGATCTCGGCACCGGACCTACTCCTACACTGGGACC TGTGACACCCGAGATCTGCAAGCAGGACATCGTGTTCGACGGAATC GCCCAGATCCGGGGCGAGATCTTCTTTTTTAAGGACCGGTTCATCTG GCGGACAGTGACCCCTAGAGACAAGCCTATGGGACCTCTGCTGGTG GCTACCTTCTGGCCTGAGCTGCCTGAGAAGATCGACGCCGTGTACG AGGCCCCTCAAGAGGAAAAGGCCGTCTTTTTCGCCGGCAACGAGTA CTGGATCTACTCCGCTTCTACCCTGGAACGGGGCTACCCCAAGCCTC TGACATCTCTGGGACTGCCTCCAGACGTGCAGAGAGTGGACGCCGC CTTCAACTGGTCCAAGAACAAGAAAACCTACATCTTCGCCGGGGAC AAGTTCTGGCGGTACAACGAAGTGAAGAAAAAGATGGACCCTGGCT TCCCCAAGCTGATCGCCGATGCCTGGAACGCTATCCCCGATAACCT |

TABLE 10-continued

Nucleic acid sequences.

| Sequence ID | Description | Nucleic Acid Sequence |
|---|---|---|
| | | GGACGCTGTGGTGGATCTCCAAGGCGGCGGACACTCCTACTTTTTCA AGGGCGCCTACTACCTGAAGCTGGAAAACCAGAGCCTGAAGTCCGT GAAGTTCGGCTCCATCAAGTCCGACTGGCTCGGATGT |
| SEQ ID NO: 199 | HYAL1 | TTCAGAGGCCCTCTGCTGCCCAACAGACCCTTCACCACCGTGTGGA ACGCCAACACCCAGTGGTGCCTGGAAAGACACGGCGTGGACGTGG ACGTGTCCGTGTTCGATGTGGTGGCCAACCCCGGCCAGACCTTCAG GGGCCCTGACATGACCATCTTCTACTCCAGCCAGCTGGGCACCTACC CCTACTACACCCCTACAGGCGAGCCTGTGTTTGGCGGCCTGCCTCAG AACGCCTCTCTGATCGCTCACCTGGCCCGGACCTTCCAGGACATCCT GGCTGCTATCCCTGCCCCCGACTTTTCTGGCCTGGCCGTGATCGATT GGGAGGCCTGGCGACCTAGATGGGCCTTCAACTGGGACACCAAGGA CATCTACCGGCAGCGGTCCAGAGCCCTGGTGCAGGCTCAGCATCCT GATTGGCCTGCCCCTCAGGTGGAAGCCGTGGCCCAGGATCAGTTTC AGGGCGCTGCCAGAGCTTGGATGGCTGGCACACTGCAGCTGGGAAG GGCCCTGAGGCCTAGAGGACTGTGGGGCTTCTACGGCTTCCCCGAC TGCTACAACTACGACTTCCTGTCCCCCAACTACACCGGCCAGTGCCC CTCTGGAATCCGGGCCCAGAATGATCAGCTGGGCTGGCTGTGGGGC CAGTCTAGAGCCCTGTACCCCTCCATCTACATGCCCGCCGTGCTGGA AGGCACCGGCAAGTCCCAGATGTACGTGCAGCACAGAGTGGCCGA GGCCTTCAGGGTGGCAGTGGCTGCTGGCGATCTCTAACCTGCCCGTG CTGCCCTACGTGCAGATCTTCTACGATACCACCAACCACTTTCTGCC CCTGGACGAGCTGGAACACTCCCTGGGAGAGTCTGCTGCTCAGGGT GCTGCAGGCGTGGTGCTGTGGGTGTCCTGGGAGAACACCCGGACCA AAGAGTCCTGCCAGGCCATCAAAGAGTACATGGACACCACCCTGGG CCCCTTCATCCTGAACGTGACCTCTGGCGCCCTGCTGTGTAGCCAGG CTCTGTGTTCTGGCCACGGCAGATGCGTGCGGAGAACCTCTCACCCT AAGGCTCTGCTGCTGCTGAACCCCGCCTCCTTCAGCATCCAGCTGAC ACCTGGCGGCGGACCCCTGTCTCTGAGAGGTGCTCTGTCCCTGGAA GATCAGGCCCAGATGGCCGTGGAATTCAAGTGCCGGTGCTACCCTG GCTGGCAGGCCCCTTGGTGCGAGCGGAAATCTATGTGG |
| SEQ ID NO: 200 | αFAP Heavy | CAGGTGCAGCTGGTTCAGTCTGGCGCCGAAGTGAAGAAACCTGGCG CCTCTGTGAAGGTGTCCTGCAAGACCTCTCGGTACACCTTTACCGAG TACACCATCCACTGGGTCCGACAGGCTCCAGGCCAGAGACTGGAAT GGATCGGCGGCATCAACCCCAACAACGGCATCCCCAACTACAACCA GAAATTCAAGGGCCGCGTGACCATCACCGTGGACACCTCTGCTTCT ACCGCCTACATGGAACTGTCCAGCCTGAGATCTGAGGACACCGCCG TGTACTACTGCGCCAGAAGAAGAATCGCCTACGGCTACGATGAGGG CCACGCCATGGATTATTGGGGCCAGGGAACACTGGTCACCGTGTCC TCT |
| SEQ ID NO: 201 | αFAP light | GACATCGTGATGACCCAGTCTCCAGACTCTCTGGCCGTGTCTCTGGG CGAGAGAGCCACCATCAACTGCAAGTCCTCTCAGTCCCTGCTGTACT CCCGGAACCAGAAGAACTACCTGGCCTGGTATCAGCAGAAGCCCGG CCAGCCTCCTAAGCTGCTGATCTTCTGGGCCTCCACCAGAGAATCTG GCGTGCCCGATAGATTCTCCGGCTCTGGCTTTGGCACCGACTTTACC CTGACCATCAGCTCCCTGCAGGCCGAGGATGTGGCCGTGTACTACT GCCAGCAGTACTTCAGCTACCCTCTGACCTTTGGCCAGGGCACCAA GGTGGAAATCAAG |
| SEQ ID NO: 111 | hIL2 F42A Y45A | GCTCCTACCTCCTCCAGCACCAAGAAAACCCAGCTGCAGTTGGAGC ATCTGCTGCTGGACCTCCAGATGATCCTGAATGGCATCAACAATTAC AAGAACCCCAAGCTCACCCGGATGCTGACCGCCAAGTTTGCCATGC CTAAGAAGGCCACCGAGCTGAAACATCTGCAGTGCCTGGAAGAGG AACTGAAGCCCCTGGAAGAAGTGCTGAATCTGGCCCAGTCCAAGAA CTTCCACCTGAGGCCTCGGGACCTGATCTCCAACATCAACGTGATCG TGCTCGAGCTGAAGGGCTCCGAGACAACCTTCATGTGCGAGTACGC CGACGAGACAGCTACCATCGTGGAATTTCTGAACCGGTGGATCACC TTCTGTCAGTCCATCATCAGCACCCTGACC |

TABLE 11

Sequences used to construct ORFs.

| Construct SEQ ID NO | N-term | Linker | Variable | Constant | Fc | Linker | C-term |
|---|---|---|---|---|---|---|---|
| SEQ ID NO: 202 | | | SEQ ID NO: 200 | SEQ ID NO: 91 | SEQ ID NO: 89 | | |
| SEQ ID NO: 203 | | | SEQ ID NO: 201 | SEQ ID NO: 92 | | | |
| SEQ ID | | | SEQ ID | SEQ ID | SEQ ID | SEQ ID | SEQ ID |

TABLE 11-continued

Sequences used to construct ORFs.

| Construct SEQ ID NO | N-term | Linker | Variable | Constant | Fc | Linker | C-term |
|---|---|---|---|---|---|---|---|
| SEQ ID NO: 204 | | | SEQ ID NO: 200 | SEQ ID NO: 91 | SEQ ID NO: 90 | SEQ ID NO: 96 | SEQ ID NO: 198 |
| SEQ ID NO: 205 | SEQ ID NO: 198 | SEQ ID NO: 96 | | | SEQ ID NO: 90 | | |
| SEQ ID NO: 206 | | | SEQ ID NO: 200 | SEQ ID NO: 91 | SEQ ID NO: 89 | SEQ ID NO: 96 | SEQ ID NO: 111 |
| SEQ ID NO: 207 | | | SEQ ID NO: 200 | SEQ ID NO: 91 | SEQ ID NO: 90 | SEQ ID NO: 96 | SEQ ID NO: 199 |
| SEQ ID NO: 208 | | | SEQ ID NO: 94 | SEQ ID NO: 91 | SEQ ID NO: 89 | | |
| SEQ ID NO: 209 | | | SEQ ID NO: 94 | SEQ ID NO: 91 | SEQ ID NO: 89 | SEQ ID NO: 96 | SEQ ID NO: 111 |
| SEQ ID NO: 210 | | | SEQ ID NO: 97 | SEQ ID NO: 91 | SEQ ID NO: 90 | SEQ ID NO: 96 | SEQ ID NO: 199 |
| SEQ ID NO: 211 | | | SEQ ID NO: 98 | SEQ ID NO: 92 | | | |
| SEQ ID NO: 121 | | | SEQ ID NO: 95 | SEQ ID NO: 93 | | | |
| SEQ ID NO: 212 | SEQ ID NO: 199 | SEQ ID NO: 16 | | | SEQ ID NO: 90 | | |

TABLE 12

Nucleic acid sequences for ORFs.

| Sequence ID | Nucleic Acid Sequence |
|---|---|
| SEQ ID NO: 202 | ATGGAAACCGACACACTGCTGCTGTGGGTGCTGCTCTTGTGGGTGCC AGGATCTACAGGACAGGTGCAGCTGGTTCAGTCTGGCGCCGAAGTG AAGAAACCTGGCGCCTCTGTGAAGGTGTCCTGCAAGACCTCTCGGTA CACCTTTACCGAGTACACCATCCACTGGGTCCGACAGGCTCCAGGCC AGAGACTGGAATGGATCGGCGGCATCAACCCCAACAACGGCATCCC CAACTACAACCAGAAATTCAAGGGCCGCGTGACCATCACCGTGGAC ACCTCTGCTTCTACCGCCTACATGGAACTGTCCAGCCTGAGATCTGA GGACACCGCCGTGTACTACTGCGCCAGAAGAAGAATCGCCTACGGC TACGATGAGGGCCACGCCATGGATTATTGGGGCCAGGGAACACTGG TCACCGTGTCCTCTGCCTCTACAAAGGGCCCCTCTGTGTTCCCTCTGG CTCCTTCCAGCAAGTCTACCTCTGGCGGAACAGCTGCTCTGGGCTGC CTGGTCAAGGACTACTTTCCTGAGCCTGTGACCGTGTCTTGGAACTC TGGCGCTCTGACATCCGGCGTGCACACCTTTCCAGCTGTGCTGCAAT CTTCCGGCCTGTACTCCCTGTCCTCCGTCGTGACAGTGCCTTCTAGCT CTCTGGGCACCCAGACCTACATCTGCAATGTGAACCACAAGCCTTCC AACACCAAGGTGGACAAGAGAGTGGAACCCAAGTCCTGCGACAAGA CCCACACCTGTCCACCATGTCCTGCTCCAGAACTGCTCGGCGGACCT TCCGTGTTCCTGTTTCCTCCAAAGCCTAAGGACACCCTGATGATCTCT CGGACCCCTGAAGTGACCTGCGTGGTGGTGGATGTGTCTCACGAGG ACCCAGAAGTGAAGTTCAATTGGTACGTGGACGGCGTGGAAGTGCA CAACGCCAAGACCAAGCCTAGAGAGGAACAGTACAACTCCACCTAC AGAGTGGTGTCCGTGCTGACCGTGCTGCACCAGGATTGGCTGAACG GCAAAGAGTACAAGTGCAAGGTGTCCAACAAGGCCCTGCCTGCTCC TATCGAAAAGACCATCTCCAAGGCCAAGGGCCAGCCTAGGGAACCC CAGGTTTACACCCTGCCTCCATGCCGGGAAGAGATGACCAAGAACC AGGTGTCCCTGTGGTGCCTCGTGAAGGGCTTCTACCCTTCCGATATC GCCGTGGAATGGGAGAGCAATGGCCAGCCAGAGAACAACTACAAG ACAACCCCTCCTGTGCTGGACTCCGACGGCTCATTCTTCCTGTACAG CAAGCTGACAGTGGACAAGTCCAGATGGCAGCAGGGCAACGTGTTC TCCTGCTCCGTGATGCACGAGGCCCTGCACAATCACTACACACAGAA GTCCCTGTCTCTGTCCCCTGGCAAGTGATGA |
| SEQ ID NO: 203 | ATGGAAACCGACACACTGCTGCTGTGGGTGCTGCTCTTGTGGGTGCC AGGATCTACCGGCGACATCGTGATGACCCAGTCTCCAGACTCTCTGG CCGTGTCTCTGGGCGAGAGAGCCACCATCAACTGCAAGTCCTCTCAG TCCCTGCTGTACTCCCGGAACCAGAAGAACTACCTGGCCTGGTATCA GCAGAAGCCCGGCCAGCCTCCTAAGCTGCTGATCTTCTGGGCCTCCA CCAGAGAATCTGGCGTGCCCGATAGATTCTCCGGCTCTGGCTTTGGC ACCGACTTTACCCTGACCATCAGCTCCCTGCAGGCCGAGGATGTGGC CGTGTACTACTGCCAGCAGTACTTCAGCTACCCTCTGACCTTTGGCC AGGGCACCAAGGTGGAAATCAAGCGGACAGTGGCCGCTCCTTCCGT GTTCATCTTCCCACCTTCCGACGAGCAGCTGAAGTCTGGCACAGCCT CTGTCGTGTGCCTGCTGAACAACTTCTACCCTCGGGAAGCCAAGGTG CAGTGGAAGGTGGACAATGCCCTGCAGTCCGGCAACTCCCAAGAGT CTGTGACCGAGCAGGACTCCAAGGACAGCACCTACAGCCTGTCCTCC ACACTGACCCTGTCCAAGGCCGACTACGAGAAGCACAAGGTGTACG |

TABLE 12-continued

Nucleic acid sequences for ORFs.

| Sequence ID | Nucleic Acid Sequence |
| --- | --- |
| | CCTGCGAAGTGACCCATCAGGGCCTGTCTAGCCCTGTGACCAAGTCT<br>TTCAACCGGGGCGAGTGCTGATGA |
| SEQ ID NO: 204 | ATGGAAACCGACACACTGCTGCTGTGGGTGCTGCTCTTGTGGGTGCC<br>AGGATCTACAGGACAGGTGCAGCTGGTTCAGTCTGGCGCCGAAGTG<br>AAGAAACCTGGCGCCTCTGTGAAGGTGTCCTGCAAGACCTCTCGGTA<br>CACCTTTACCGAGTACACCATCCACTGGGTCCGACAGGCTCCAGGCC<br>AGAGACTGGAATGGATCGGCGGCATCAACCCCAACAACGGCATCCC<br>CAACTACAACCAGAAATTCAAGGGCCGCGTGACCATCACCGTGGAC<br>ACCTCTGCTTCTACCGCCTACATGGAACTGTCCAGCCTGAGATCTGA<br>GGACACCGCCGTGTACTACTGCGCCAGAAGAAGAATCGCCTACGGC<br>TACGATGAGGGCCACGCCATGGATTATTGGGGCCAGGGAACACTGG<br>TCACCGTGTCCTCTGCCTCTACAAAGGGCCCCTCTGTGTTCCCTCTGG<br>CTCCTTCCAGCAAGTCTACCTCTGGCGGAACAGCTGCTCTGGGCTGC<br>CTGGTCAAGGACTACTTTCCTGAGCCTGTGACCGTGTCTTGGAACTC<br>TGGCGCTCTGACATCCGGCGTGCACACCTTTCCAGCTGTGCTGCAAT<br>CTTCCGGCCTGTACTCCCTGTCCTCCGTCGTGACAGTGCCTTCTAGCT<br>CTCTGGGCACCCAGACCTACATCTGCAATGTGAACCACAAGCCTTCC<br>AACACCAAGGTGGACAAGAGAGTGGAACCCAAGTCCTGCGACAAGA<br>CCCACACCTGTCCACCATGTCCTGCTCCAGAACTGCTCGGCGGACCT<br>TCCGTGTTCCTGTTTCCTCCAAAGCCTAAGGACACCCTGATGATCTCT<br>CGGACCCCTGAAGTGACCTGCGTGGTGGTGGATGTGTCTCACGAGG<br>ACCCAGAAGTGAAGTTCAATTGGTACGTGGACGGCGTGGAAGTGCA<br>CAACGCCAAGACCAAGCCTAGAGAGGAACAGTACAACTCCACCTAC<br>AGAGTGGTGTCCGTGCTGACCGTGCTGCACCAGGATTGGCTGAACG<br>GCAAAGAGTACAAGTGCAAGGTGTCCAACAAGGCCCTGCCTGCTCC<br>TATCGAAAAGACCATCTCCAAGGCCAAGGGCCAGCCTCGGGAACCT<br>CAAGTCTGTACCCTGCCTCCTAGCCGGGAAGAGATGACCAAGAACC<br>AGGTGTCCCTGAGCTGCGCCGTGAAGGGCTTCTACCCTTCTGATATC<br>GCCGTGGAATGGGAGAGCAACGGCCAGCCAGAGAACAACTACAAG<br>ACAACCCCTCCTGTGCTGGACTCCGACGGCTCATTCTTCCTGGTGTCC<br>AAGCTGACAGTGGACAAGTCCAGATGGCAGCAGGGCAACGTGTTCT<br>CCTGCTCCGTGATGCACGAGGCCCTGCACAATCACTACACACAGAA<br>GTCCCTGTCTCTGTCCCCTGGCAAAGGTGGCGGAGGATCTGGCGGAG<br>GTGGAAGCGGCGGAGGCGGCTCTTACAACTTCTTCCCACGGAAACC<br>CAAGTGGGATAAGAACCAGATCACCTACCGGATCATCGGCTACACC<br>CCTGACCTGGATCCTGAGACTGTGGACGATGCCTTCGCCAGGGCCTT<br>CCAAGTTTGGAGCGACGTGACCCCTCTGCGGTTCTCCAGAATCCATG<br>ATGGCGAGGCCGACATCATGATCAACTTCGGCAGATGGGAGCACGG<br>CGACGGCTACCCTTTTGATGGCAAGGATGGCCTGCTGGCCCACGCTT<br>TTGCCCCTGGAACAGGTGTTGGCGGCGACTCTCACTTCGACGACGAT<br>GAGTTGTGGACCCTCGGCGAAGGACAGGTCGTCAGAGTGAAGTACG<br>GCAACGCCGATGGCGAGTACTGCAAGTTCCCCCTTCCTGTTCAATGGG<br>AAAGAGTATAACTCCTGCACCGACACCGGCAGATCTGACGGCTTCCT<br>GTGGTGCTCCACCACCTACAACTTCGAGAAGGACGGCAAATACGGC<br>TTCTGCCCTCACGAGGCTCTGTTCACCCATGGGCGGAAATGCTGAGG<br>ACAGCCCTGCAAGTTTCCATTCAGATTCCAAGGGACCTCCTACGACT<br>CTTGCACCACCGAGGGAAGAACCGATGGCTATCGTTGGTGCGGCAC<br>CACAGAGGACTACGACCGGGACAAGAAGTATGGCTTCTGTCCCGAG<br>ACAGCCATGTCTACCGTCGGCGGCAATTCTGAGGGTGCCCCTTGCGT<br>GTTCCCTTTCACCTTCCTGGGCAACAAATACGAGTCCTGCACCTCCG<br>CTGGCAGATCCGATGGAAAGATGTGGTGCGCTACCACCGCCAACTA<br>CGACGACGACAGAAAGTGGGGCTTTTGTCCTGACCAGGGCTACAGC<br>CTGTTTCTGGTGGCCGCTCACGAGTTCGGCCATGCTATGGGACTCGA<br>GCACTCTCAAGATCCCGGCGCACTGATGGCCCCTATCTACACCTACA<br>CCAAGAACTTCCGGCTGTCCCAGGACGACATCAAGGGCATCCAAGA<br>GCTGTACGGCGCCTCTCCTGATATCGATCTCGGCACCGGACCTACTC<br>CTACACTGGGACCTGTGACACCCGAGATCTGCAAGCAGGATATCGT<br>GTTCGACGGAATCGCCCAGATCCGGGGCGAGATCTTCTTTTTTAAGG<br>ACCGCTTCATTTGGCGGACCGTGACTCCTCGGGACAAGCCTATGGGA<br>CCTCTGCTGGTGGCTACCTTCTGGCCTGAACTGCCCGAGAAGATCGA<br>TGCCGTGTACGAGGCCCCTCAAGAGGAAAAGGCCGTCTTTTTCGCCG<br>GCAACGAGTACTGGATCTACTCCGCTAGCACCCTGGAACGGGGCTA<br>CCCTAAGCCTCTGACTTCTCTGGGACTGCCACCTGACGTGCAGCGAG<br>TGGATGCCGCCTTCAACTGGTCCAAGAACAAGAAAACCTATATCTTC<br>GCCGGGGACAAGTTCTGGCGGTACAACGAAGTCAAGAAAAAGATGG<br>ACCCTGGCTTCCCCAAGCTGATCGCCGATGCCTGGAACGCTATCCCC<br>GATAACCTGGACGCTGTGGTGGACTTGCAAGGCGGCGGACACTCCT<br>ACTTTTTCAAGGGCGCCTACTACCTGAAGCTGGAAAACCAGAGCCTG<br>AAGTCCGTGAAGTTCGGCTCCATCAAGTCCGACTGGCTGGGCTGCTG<br>ATGA |
| SEQ ID NO: 205 | ATGGAAACCGACACACTGCTGCTGTGGGTGCTGCTCTTGTGGGTGCC<br>AGGCTCTACCGGCTACAACTTCTTCCCACGGAAACCCAAGTGGGACA<br>AGAACCAGATCACCTACCGGATCATCGGCTACACCCCTGACCTGGAT<br>CCTGAGACAGTGGACGATGCCTTCGCCAGAGCCTTCCAAGTTTGGAG |

TABLE 12-continued

Nucleic acid sequences for ORFs.

| Sequence ID | Nucleic Acid Sequence |
|---|---|
| | CGACGTGACCCCTCTGCGGTTCTCCAGAATCCATGATGGCGAGGCCG
ACATCATGATCAACTTCGGCAGATGGGAGCACGGCGACGGCTACCC
TTTTGATGGCAAGGATGGCCTGCTGGCCCACGCTTTTGCCCCTGGAA
CAGGTGTTGGCGGCGACTCTCACTTCGACGACGATGAGTTGTGGACC
CTCGGCGAAGGACAGGTCGTCAGAGTGAAGTACGGCAACGCCGATG
GCGAGTACTGCAAGTTCCCCTTCCTGTTCAACGGCAAAGAGTACAAC
TCCTGCACCGACACCGGCAGATCTGACGGCTTCCTGTGGTGCTCCAC
CACCTACAACTTTGAGAAGGACGGCAAATACGGCTTCTGCCCCTCACG
AGGCCCTGTTTACCATGGGCGGAAATGCTGAGGGCCAGCCATGCAA
GTTTCCATTCCGGTTCCAAGGGACCTCCTACGACAGCTGTACCACCG
AGGGAAGAACCGATGGCTATCGTTGGTGCGGCACCACAGAGGACTA
CGACAGAGACAAGAAGTATGGCTTCTGTCCCGAGACAGCCATGTCT
ACCCGTCGGCGGCAATTCTGAAGGCGCCCCTTGTGTGTTCCCTTTCAC
CTTCCTGGGCAACAAATACGAGTCCTGCACCTCCGCTGGCCGCTCTG
ATGGAAAAATGTGGTGCGCTACCACCGCCAACTACGACGACGACAG
AAAGTGGGGCTTTTGTCCTGACCAGGGCTACTCCCTGTTTCTGGTGG
CCGCTCACGAGTTTGGCCATGCTATGGGCCTCGAGCACTCTCAAGAT
CCCGGTGCACTGATGGCCCCTATCTACACCTACACCAAGAACTTCCG
GCTGTCCCAGGACGACATCAAGGGCATCCAAGAGCTGTACGGCGCC
TCTCCTGATATCGATCTCGGCACCGGACCTACTCCTACACTGGGACC
TGTGACACCCGAGATCTGCAAGCAGGACATCGTGTTCGACGGAATC
GCCCAGATCCGGGGCGAGATCTTCTTTTTTAAGGACCGGTTCATCTG
GCGGACAGTGACCCCTAGAGACAAGCCTATGGGACCTCTGCTGGTG
GCTACCTTCTGGCCTGAGCTGCCTGAGAAGATCGACGCCGTGTACGA
GGCCCCTCAAGAGGAAAAGGCCGTCTTTTTCGCCGGCAACGAGTACT
GGATCTACTCCGCTTCTACCCTGGAACGGGGCTACCCCAAGCCTCTG
ACATCTCTGGGACTGCCTCCAGACGTGCAGAGAGTGGACGCCGCCTT
CAACTGGTCCAAGAACAAGAAAACCTACATCTTCGCCGGGGACAAG
TTCTGGCGGTACAACGAAGTGAAGAAAAAGATGGACCCTGGCTTCC
CCAAGCTGATCGCCGATGCCTGGAACGCTATCCCCGATAACCTGGAC
GCTGTGGTGGATCTCCAAGGCGGCGGACACTCCTACTTTTTCAAGGG
CGCCTACTACCTGAAGCTGGAAAACCAGAGCCTGAAGTCCGTGAAG
TTCGGCTCCATCAAGTCCGACTGGCTCGGATGTGGTGGCGGAGGAA
GCGGAGGCGGAGGATCTGGCGGTGGCGGATCTGATAAGACCCACAC
CTGTCCACCTTGTCCTGCTCCAGAACTGCTCGGCGGACCTTCCGTGTT
CCTGTTTCCTCCAAAGCCTAAGGACACCCTGATGATCTCTCGGACCC
CTGAAGTGACCTGCGTGGTGGTGGATGTGTCCCACGAGGACCCAGA
AGTGAAGTTCAATTGGTACGTGGACGGCGTGGAAGTGCACAACGCC
AAGACCAAGCCTAGAGAGGAACAGTACAACAGCACCTACAGAGTGG
TGTCCGTGCTGACCGTGCTGCACCAGGATTGGCTGAATGGGAAAGA
GTATAAGTGCAAGGTGTCCAACAAGGCCCTGCCTGCTCCTATCGAAA
AGACCATCAGCAAGGCCAAGGGACAGCCCCGGGAACCTCAAGTCTG
TACCCTGCCTCCTAGCCGGGAAGAGATGACCAAGAATCAGGTGTCC
CTGTCTTGCGCCGTGAAGGGCTTTTACCCCTCCGATATCGCCGTGGA
ATGGGAGTCTAATGGCCAGCCTGAGAACAACTACAAGACCACACCT
CCTGTGCTGGACTCCGACGGCTCATTCTTCCTGGTGTCCAAGCTGAC
TGTGGACAAGTCCAGATGGCAGCAGGGCAACGTGTTCTCCTGCTCCG
TGATGCACGAGGCTCTGCACAACCACTACACACAGAAGTCTCTGAG
CCTGTCTCCTGGCAAGTGATGA |
| SEQ ID NO: 206 | ATGGAAACCGACACACTGCTGCTGTGGGTGCTGCTCTTGTGGGTGCC
AGGATCTACAGGACAGGTGCAGCTGGTTCAGTCTGGCGCCGAAGTG
AAGAAACCTGGCGCCTCTGTGAAGGTGTCCTGCAAGACCTCTCGGTA
CACCTTTACCGAGTACACCATCCACTGGGTCCGACAGGCTCCAGGCC
AGAGACTGGAATGGATCGGCGGCATCAACCCCAACAACGGCATCCC
CAACTACAACCAGAAATTCAAGGGCCGCGTGACCATCACCGTGGAC
ACCTCTGCTTCTACCGCCTACATGGAACTGTCCAGCCTGAGATCTGA
GGACACCGCCGTGTACTACTGCGCCAGAAGAAGAATCGCCTACGGC
TACGATGAGGGCCACGCCATGGATTATTGGGGCCAGGGAACACTGG
TCACCGTGTCCTCTGCCTCTACAAAGGGCCCCTCTGTGTTCCCTCTGG
CTCCCTTCCAGCAAGTCTACCTCTGGCGGAACAGCTGCTCTGGGCTGC
CTGGTCAAGGACTACTTTCCTGAGCCTGTGACCGTGTCTTGGAACTC
TGGCGCTCTGACATCCGGCGTGCACACCTTTCCAGCTGTGCTGCAAT
CTTCCGGCCTGTACTCCCTGTCCTCCGTCGTGACAGTGCCTTCTAGCT
CTCTGGGCACCCAGACCTACATCTGCAATGTGAACCACAAGCCTTCC
AACACCAAGGTGGACAAGAGAGTGGAACCCAAGTCCTGCGACAAGA
CCCACACCTGTCCACCATGTCCTGCTCCAGAACTGCTCGGCGGACCT
TCCGTGTTCCTGTTTCCTCCAAAGCCTAAGGACACCCTGATGATCTCT
CGGACCCCTGAAGTGACCTGCGTGGTGGTGGATGTGTCTCACGAGG
ACCCAGAAGTGAAGTTCAATTGGTACGTGGACGGCGTGGAAGTGCA
CAACGCCAAGACCAAGCCTAGAGAGGAACAGTACAACTCCACCTAC
AGAGTGGTGTCCGTGCTGACCGTGCTGCACCAGGATTGGCTGAACG
GCAAAGAGTACAAGTGCAAGGTGTCCAACAAGGCCCTGCCTGCTCC
TATCGAAAAGACCATCTCCAAGGCCAAGGGCCAGCCTAGGGAACCC
CAGGTTTACACCCTGCCTCCATGCCGGGAAGAGATGACCAAGAACC
AGGTGTCCCTGTGGTGCCTCGTGAAGGGCTTCTACCCTTCCGATATC |

TABLE 12-continued

Nucleic acid sequences for ORFs.

| Sequence ID | Nucleic Acid Sequence |
| --- | --- |
| | GCCGTGGAATGGGAGAGCAATGGCCAGCCAGAGAACAACTACAAG<br>ACAACCCCTCCTGTGCTGGACTCCGACGGCTCATTCTTCCTGTACAG<br>CAAGCTGACAGTGGACAAGTCCAGATGGCAGCAGGGCAACGTGTTC<br>TCCTGCTCCGTGATGCACGAGGCCCTGCACAATCACTACACACAGAA<br>GTCCCTGTCTCTGTCCCCTGGCAAAGGTGGCGGAGGATCTGGCGGAG<br>GTGGAAGCGGCGGAGGCGGATCTGCTCCTACATCCTCCAGCACCAA<br>GAAAACCCAGCTGCAGTTGGAGCATCTGCTGCTGGACCTGCAGATG<br>ATCCTGAATGGCATCAACAATTACAAGAACCCCAAGCTGACCCGGA<br>TGCTGACCGCCAAGTTTGCCATGCCTAAGAAGGCCACCGAGCTGAA<br>ACATCTGCAGTGCCTGGAAGAGGAACTGAAGCCCCTGGAAGAAGTG<br>CTGAATCTGGCCCAGTCCAAGAACTTCCACCTGAGGCCTCGGGACCT<br>GATCTCCAACATCAACGTGATCGTGCTCGAGCTGAAGGGCTCCGAG<br>ACAACCTTCATGTGCGAGTACGCCGACGAGACAGCTACCATCGTGG<br>AATTTCTGAACCGGTGGATCACCTTCTGCCAGTCCATCATCAGCACC<br>CTGACCTGATGA |
| SEQ ID NO:<br>207 | ATGGAAACCGACACACTGCTGCTGTGGGTGCTGCTCTTGTGGGTGCC<br>AGGATCTACAGGACAGGTGCAGCTGGTTCAGTCTGGCGCCGAAGTG<br>AAGAAACCTGGCGCCTCTGTGAAGGTGTCCTGCAAGACCTCTCGGTA<br>CACCTTTACCGAGTACACCATCCACTGGGTCCGACAGGCTCCAGGCC<br>AGAGACTGGAATGGATCGGCGGCATCAACCCCAACAACGGCATCCC<br>CAACTACAACCAGAAATTCAAGGGCCGCGTGACCATCACCGTGGAC<br>ACCTCTGCTTCTACCGCCTACATGGAACTGTCCAGCCTGAGATCTGA<br>GGACACCGCCGTGTACTACTGCGCCAGAAGAAGAATCGCCTACGGC<br>TACGATGAGGGCCACGCCATGGATTATTGGGGCCAGGGAACACTGG<br>TCACCGTGTCCTCTGCCTCTACAAAGGGCCCCTCTGTGTTCCCTCTGG<br>CTCCTTCCAGCAAGTCTACCTCTGGCGGAACAGCTGCTCTGGGCTGC<br>CTGGTCAAGGACTACTTTCCTGAGCCTGTGACCGTGTCTTGGAACTC<br>TGGCGCTCTGACATCCGGCGTGCACACCTTTCCAGCTGTGCTGCAAT<br>CTTCCGGCCTGTACTCCCTGTCCTCCGTCGTGACAGTGCCTTCTAGCT<br>CTCTGGGCACCCAGACCTACATCTGCAATGTGAACCACAAGCCTTCC<br>AACACCAAGGTGGACAAGAGAGTGGAACCCAAGTCCTGCGACAAGA<br>CCCACACCTGTCCACCATGTCCTGCTCCAGAACTGCTCGGCGGACCT<br>TCCGTGTTCCTGTTTCCTCCAAAGCCTAAGGACACCCTGATGATCTCT<br>CGGACCCCTGAAGTGACCTGCGTGGTGGTGGATGTGTCTCACGAGG<br>ACCCAGAAGTGAAGTTCAATTGGTACGTGGACGGCGTGGAAGTGCA<br>CAACGCCAAGACCAAGCCTAGAGAGGAACAGTACAACTCCACCTAC<br>AGAGTGGTGTCCGTGCTGACCGTGCTGCACCAGGATTGGCTGAACG<br>GCAAAGAGTACAAGTGCAAGGTGTCCAACAAGGCCCTGCCTGCTCC<br>TATCGAAAAGACCATCTCCAAGGCCAAGGGCCAGCCTCGGGAACCT<br>CAAGTCTGTACCCTGCCTCCTAGCCGGGAAGAGATGACCAAGAACC<br>AGGTGTCCCTGAGCTGCGCCGTGAAGGGCTTCTACCCCTTCTGATATC<br>GCCGTGGAATGGGAGAGCAACGGCCAGCCAGAGAACAACTACAAG<br>ACAACCCCTCCTGTGCTGGACTCCGACGGCTCATTCTTCCTGGTGTCC<br>AAGCTGACAGTGGACAAGTCCAGATGGCAGCAGGGCAACGTGTTCT<br>CCTGCTCCGTGATGCACGAGGCCCTGCACAATCACTACACACAGAA<br>GTCCCTGTCTCTGTCCCCTGGCAAAGGTGGCGGAGGATCTGGCGGAG<br>GTGGAAGCGGCGGAGGCGGATCTTTTAGAGGACCTCTGCTGCCCAA<br>CCGGCCTTTCACCACAGTGTGGAACGCTAACACCCAGTGGTGCCTGG<br>AAAGACACGGCGTTGACGTGGACGTGTCCGTGTTCGATGTGGTGGCT<br>AATCCCGGCCAGACCTTCAGAGGCCCTGACATGACCATCTTCTACTC<br>CAGCCAGCTGGGCACCTATCCTTACTACACCCCTACAGGCGAGCCCG<br>TGTTTGGAGGCTTGCCTCAGAATGCCAGCCTGATCGCTCACCTGGCC<br>AGAACCTTTCAGGACATCCTGGCTGCTATCCCCGCTCCTGACTTTTCC<br>GGACTGGCCGTGATCGATTGGGAAGCCTGGCGACCTAGATGGGCCT<br>TCAACTGGGACACCAAGGACATCTACCGGCAGCGGTCTAGAGCACT<br>GGTGCAGGCTCAACATCCTGACTGGCCTGCTCCACAGGTTGAGGCTG<br>TTGCCCAGGATCAGTTTCAGGGCGCTGCCAGAGCTTGGATGGCTGGA<br>ACATTGCAGCTGGGGAGAGCCCTGAGGCCTAGAGGACTGTGGGGCT<br>TTTACGCTTCCCCGACTGCTACAACTACGACTTCCTGTCTCCTAACT<br>ACACCGGCCAGTGTCCTTCCGGCATCAGAGCCCAGAATGATCAGCTC<br>GGATGGCTCTGGGGACAGTCCAGGGCTCTGTACCCCTCCATCTACAT<br>GCCTGCTGTCCTGGAAGGCACCGGCAAGTCCCAGATGTACGTGCAG<br>CATAGAGTGGCCGAGGCCTTCAGAGTGGCTGTTGCTGCTGGCGATCC<br>TAACCTGCCTGTGCTGCCTTACGTGCAGATCTTCTACGATACCACCA<br>ACCACTTTCTGCCCCTGGACGAGCTGGAACACTCCCTGGGAGAATCT<br>GCTGCTCAAGGTGCTGCAGGCGTGGTGTTGTGGGTGTCCTGGGAAAA<br>CACCCGGACCAAAGAGTCCTGCCAGGCCATCAAAGAGTATATGGAC<br>ACCACACTGGGCCCTTCATCCTGAACGTGACATCTGGCGCACTGCT<br>GTGCAGCCAGGCACTGTGTTCTGGACACGGAAGATGCGTGCGGAGA<br>ACCTCTCATCCCAAGGCTCTGCTGCTGCTGAACCCTGCCAGCTTCTCC<br>ATCCAGTTGACACCAGGCGGAGGCCCTCTGTCTTTGAGAGGTGCACT<br>GTCCCTGGAAGATCAGGCCCAGATGGCTGTGGAATTCAAGTGCAGA<br>TGCTACCCCGGCTGGCAAGCTCCTTGGTGCGAGAGAAAGTCCATGTG<br>GTAGTGA |

TABLE 12-continued

Nucleic acid sequences for ORFs.

| Sequence ID | Nucleic Acid Sequence |
| --- | --- |
| SEQ ID NO: 208 | ATGGAAACCGACACACTGCTGCTGTGGGTGCTGCTCTTGTGGGTGCC<br>AGGATCTACAGGCGAGGTGCAGCTGTTGGAATCTGGCGGAGGATTG<br>GTTCAGCCTGGCGGCTCTCTGAGACTGTCTTGTGCCGCTTCCGGCTTC<br>ACCTTCTCCAGCTATATCATGATGTGGGTCCGACAGGCCCCTGGCAA<br>AGGACTGGAATGGGTGTCCTCTATCTACCCCTCTGGCGGCATCACCT<br>TTTACGCCGACACCGTGAAGGGCAGATTCACCATCTCTCGGGACAAC<br>TCCAAGAACACCCTGTACCTGCAGATGAACTCCCTGAGAGCCGAGG<br>ACACCGCCGTGTACTACTGCGCCAGAATCAAGCTGGGCACCGTGAC<br>CACCGTGGATTATTGGGGACAGGGCACCCTGGTCACCGTGTCCTCTG<br>CTTCTACCAAGGGACCCAGCGTGTTCCCTCTGGCTCCTTCCAGCAAG<br>TCTACCTCCGGTGGAACAGCTGCTCTGGGCTGCCTGGTCAAGGACTA<br>CTTTCCTGAGCCTGTGACCGTGTCTTGGAACTCCGGCGCTCTGACAT<br>CTGGCGTGCACACATTTCCAGCCGTGCTGCAGTCCTCCGGCCTGTAC<br>TCTCTCAGCTCTGTCGTGACCGTGCCTTCCAGCTCTCTGGGAACCCA<br>GACCTACATCTGCAATGTGAACCACAAGCCTTCCAACACCAAGGTG<br>GACAAGAGAGTGGAACCCAAGTCCTGCGACAAGACCCACACCTGTC<br>CTCCATGTCCTGCTCCAGAACTGCTCGGCGGACCTTCCGTGTTCCTGT<br>TTCCTCCAAAGCCTAAGGACACCCTGATGATCTCTCGGACCCCTGAA<br>GTGACCTGCGTGGTGGTGGATGTGTCTCACGAGGATCCCGAAGTGA<br>AGTTCAATTGGTACGTGGACGGCGTGGAAGTGCACAACGCCAAGAC<br>CAAGCCTAGAGAGGAACAGTACAACTCCACCTACAGAGTGGTGTCC<br>GTGCTGACAGTGCTGCACCAGGATTGGCTGAACGGCAAAGAGTACA<br>AGTGCAAGGTGTCCAACAAGGCCCTGCCTGCTCCTATCGAAAAGAC<br>CATCTCCAAGGCCAAGGGCCAGCCTAGGGAACCCCAGGTTTACACC<br>CTGCCTCCATGCCGGGAAGAGATGACCAAGAACCAGGTGTCCCTGT<br>GGTGCCTGGTTAAGGGCTTCTACCCTTCCGATATCGCCGTGGAATGG<br>GAGAGCAATGGCCAGCCTGAGAACAACTACAAGACAACCCCTCCTG<br>TGCTGGACTCCGACGGCTCATTCTTCCTGTACTCCAAGCTGACCGTG<br>GACAAGTCCAGATGGCAGCAGGGCAACGTGTTCTCCTGCTCCGTGAT<br>GCACGAGGCCCTGCACAATCACTACACCCAGAAGTCCCTGTCTCTGA<br>GCCCCGGCAAGTGATGA |
| SEQ ID NO: 209 | ATGGAAACCGACACACTGCTGCTGTGGGTGCTGCTCTTGTGGGTGCC<br>AGGATCTACAGGCGAGGTGCAGCTGTTGGAATCTGGCGGAGGATTG<br>GTTCAGCCTGGCGGCTCTCTGAGACTGTCTTGTGCCGCTTCCGGCTTC<br>ACCTTCTCCAGCTATATCATGATGTGGGTCCGACAGGCCCCTGGCAA<br>AGGACTGGAATGGGTGTCCTCTATCTACCCCTCTGGCGGCATCACCT<br>TTTACGCCGACACCGTGAAGGGCAGATTCACCATCTCTCGGGACAAC<br>TCCAAGAACACCCTGTACCTGCAGATGAACTCCCTGAGAGCCGAGG<br>ACACCGCCGTGTACTACTGCGCCAGAATCAAGCTGGGCACCGTGAC<br>CACCGTGGATTATTGGGGACAGGGCACCCTGGTCACCGTGTCCTCTG<br>CTTCTACCAAGGGACCCAGCGTGTTCCCTCTGGCTCCTTCCAGCAAG<br>TCTACCTCCGGTGGAACAGCTGCTCTGGGCTGCCTGGTCAAGGACTA<br>CTTTCCTGAGCCTGTGACCGTGTCTTGGAACTCCGGCGCTCTGACAT<br>CTGGCGTGCACACATTTCCAGCCGTGCTGCAGTCCTCCGGCCTGTAC<br>TCTCTCAGCTCTGTCGTGACCGTGCCTTCCAGCTCTCTGGGAACCCA<br>GACCTACATCTGCAATGTGAACCACAAGCCTTCCAACACCAAGGTG<br>GACAAGAGAGTGGAACCCAAGTCCTGCGACAAGACCCACACCTGTC<br>CTCCATGTCCTGCTCCAGAACTGCTCGGCGGACCTTCCGTGTTCCTGT<br>TTCCTCCAAAGCCTAAGGACACCCTGATGATCTCTCGGACCCCTGAA<br>GTGACCTGCGTGGTGGTGGATGTGTCTCACGAGGATCCCGAAGTGA<br>AGTTCAATTGGTACGTGGACGGCGTGGAAGTGCACAACGCCAAGAC<br>CAAGCCTAGAGAGGAACAGTACAACTCCACCTACAGAGTGGTGTCC<br>GTGCTGACAGTGCTGCACCAGGATTGGCTGAACGGCAAAGAGTACA<br>AGTGCAAGGTGTCCAACAAGGCCCTGCCTGCTCCTATCGAAAAGAC<br>CATCTCCAAGGCCAAGGGCCAGCCTAGGGAACCCCAGGTTTACACC<br>CTGCCTCCATGCCGGGAAGAGATGACCAAGAACCAGGTGTCCCTGT<br>GGTGCCTGGTTAAGGGCTTCTACCCTTCCGATATCGCCGTGGAATGG<br>GAGAGCAATGGCCAGCCTGAGAACAACTACAAGACAACCCCTCCTG<br>TGCTGGACTCCGACGGCTCATTCTTCCTGTACTCCAAGCTGACCGTG<br>GACAAGTCCAGATGGCAGCAGGGCAACGTGTTCTCCTGCTCCGTGAT<br>GCACGAGGCCCTGCACAATCACTACACCCAGAAGTCCCTGTCTCTGT<br>CTCCCGGAAAAGGCGGAGGTGGAAGCGGCGGAGGCGGATCTGGTGG<br>CGGTGGATCTGCTCCTACCTCCTCCAGCACCAAGAAAACCCAGCTGC<br>AGTTGGAGCATCTGCTGCTGGACCTCCAGATGATCCTGAATGGCATC<br>AACAATTACAAGAACCCCAAGCTCACCCGGATGCTGACCGCCAAGT<br>TTGCCATGCCTAAGAAGGCCACCGAGCTGAAACATCTGCAGTGCCTG<br>GAAGAGGAACTGAAGCCCCTGGAAGAAGTGCTGAATCTGGCCCAGT<br>CCAAGAACTTCCACCTGAGGCCTCGGGACCTGATCTCCAACATCAAC<br>GTGATCGTGCTCGAGCTGAAGGGCTCCGAGACAACCTTCATGTGCGA<br>GTACGCCGACGAGACAGCTACCATCGTGGAATTTCTGAACCGGTGG<br>ATCACCTTCTGTCAGTCCATCATCAGCACCCTGACCTGATGA |
| SEQ ID NO: 210 | ATGGAAACCGACACACTGCTGCTGTGGGTGCTGCTCTTTGGGTGCC<br>AGGATCTACAGGACAGGTCCAGCTGCAGCAGTCTGGCCCTGAACTT<br>GTGAAGCCTGGCGCCTCCGTGAAGATGTCCTGCAAGGCTTCTGGCTA |

TABLE 12-continued

Nucleic acid sequences for ORFs.

| Sequence ID | Nucleic Acid Sequence |
|---|---|
| | CACCTTCACCGACTACGTGATCAACTGGGGCAAGCAGAGATCTGGC<br>CAGGGCCTCGAGTGGATCGGCGAGATCTATCCTGGCTCCGGCACCA<br>ACTACTACAACGAGAAGTTCAAGGCCAAGGCTACCCTGACCGCCGA<br>CAAGTCCTCCAATATCGCCTACATGCAGCTGTCCAGCCTGACCTCTG<br>AGGACTCCGCCGTGTACTTCTGCGCCAGAAGAGGCAGATACGGCCT<br>GTACGCCATGGACTATTGGGGCCAGGGCACCTCTGTGACCGTGTCCT<br>CTGCTTCTACCAAGGGACCCAGCGTGTTCCCTCTGGCTCCTTCCAGC<br>AAGTCTACCTCTGGCGGAACAGCTGCTCTGGGCTGCCTGGTCAAGGA<br>CTACTTTCCTGAGCCTGTGACAGTGTCTTGGAACTCTGGCGCCCTGA<br>CATCCGGCGTGCACACATTTCCAGCTGTGCTGCAGTCCTCTGGCCTG<br>TACTCTCTGTCCTCCGTCGTGACCGTGCCTTCTAGCTCTCTGGGCACC<br>CAGACCTACATCTGCAATGTGAACCACAAGCCTTCCAACACCAAGGT<br>GGACAAGAGAGTGGAACCCAAGTCCTGCGACAAGACCCACACCTGT<br>CCTCCATGTCCTGCTCCAGAACTGCTCGGCGGACCTTCCGTGTTCCTG<br>TTTCCTCCAAAGCCTAAGGACACCCTGATGATCTCTCGGACCCCTGA<br>AGTGACCTGCGTGGTGGTGGATGTGTCTCACGAGGATCCCGAAGTG<br>AAGTTCAATTGGTACGTGGACGGCGTGGAAGTGCACAACGCCAAGA<br>CCAAGCCTAGAGAGGAACAGTACAACTCCACCTACAGAGTGGTGTC<br>CGTGCTGACCGTGCTGCACCAGGATTGGCTGAACGGCAAAGAGTAC<br>AAGTGCAAGGTGTCCAACAAGGCCCTGCCTGCTCCTATCGAAAAGA<br>CCATCTCCAAGGCTAAGGGCCAGCCTCGCGAACCCCAAGTCTGTACA<br>CTGCCTCCTAGCCGGGAAGAGATGACCAAGAACCAGGTGTCCCTGT<br>CCTGCGCCGTGAAGGGCTTCTACCCTTCTGATATCGCCGTGGAATGG<br>GAGTCCAACGGCCAGCCTGAGAACAACTACAAGACAACCCCTCCTG<br>TGCTGGACTCCGACGGCTCATTCTTCCTGGTGTCCAAGCTGACAGTG<br>GACAAGTCCCGATGGCAGCAGGGCAACGTGTTCTCCTGCTCTGTGAT<br>GCACGAGGCTCTGCACAACCACTACACCCAGAAGTCCCTGTCTCTGT<br>CCCCTGGAAAAGGCGGCGGAGGATCTGGCGGAGGTGGAAGCGGAG<br>GCGGTGGATCTTTTAGAGGACCTCTGCTGCCCAACCGGCCTTTCACC<br>ACAGTGTGGAACGCTAACACCCAGTGGTGCCTGGAAAGACATGGCG<br>TCGACGTGGACGTGTCCGTGTTCGATGTGGTGGCTAATCCCGGCCAG<br>ACCTTCAGAGGCCCCGACATGACCATCTTCTACTCCAGCCAGCTGGG<br>CACCTATCCTTACTACACCCCTACAGGCGAGCCCGTGTTTGGTGGCT<br>TGCCTCAGAATGCCTCTCTGATCGCCCACCTGGCTAGAACCTTCCAG<br>GATATTCTGGCTGCTATCCCCGCTCCTGACTTTTCTGGCCTGGCCGTG<br>ATCGATTGGGAAGCTTGGAGGCCTAGATGGGCCTTCAACTGGGACA<br>CCAAGGACATCTACCGGCAGCGGTCTAGAGCACTGGTGCAGGCTCA<br>ACATCCTGACTGGCCTGCTCCACAGGTTGAGGCTGTTGCCCAGGATC<br>AGTTTCAGGGCGCTGCCAGAGCTTGGATGGCTGGAACATTGCAGCTG<br>GGGAGAGCCCTGAGGCCAAGAGGATTGTGGGGCTTTTACGGCTTCC<br>CCGACTGCTACAACTACGACTTCCTGTCTCCTAACTACACCGGCCAG<br>TGTCCTTCCGGCATCAGAGCCCAGAATGATCAGCTCGGATGGCTCTG<br>GGGACAGTCCAGGGCTCTGTACCCCTCCATCTACATGCCTGCTGTGC<br>TCGAAGGCACCGGCAAGTCCCAGATGTACGTGCAGCATAGAGTGGC<br>CGAGGCCTTCAGAGTGGCTGTTGCTGCTGGCGATCCTAACCTGCCTG<br>TGCTGCCTTACGTGCAGATCTTCTACGATACCACCAACCACTTTCTGC<br>CCCTGGACGAGCTGGAACACTCCCTGGGAGAATCTGCTGCTCAAGGT<br>GCTGCAGGCGTGGTGTTGTGGGTGTCCTGGGAAAACACCCGGACCA<br>AAGAGTCCTGCCAGGCCATCAAAGAGTATATGGACACCACACTGGG<br>CCCCTTCATCCTGAACGTGACATCTGGCGCTCTGCTGTGCAGCCAGG<br>CTCTGTGTTCTGGCCATGGTAGATGCGTGCGGAGAACCTCTCATCCC<br>AAGGCTCTGCTGCTGCTGAACCCTGCCAGCTTCTCCATCCAGTTGAC<br>ACCAGGCGGAGGCCCTCTGTCTTTGAGAGGTGCACTGTCCCTGGAAG<br>ATCAGGCCCAGATGGCTGTGGAATTCAAGTGCAGATGCTACCCCGG<br>CTGGCAAGCTCCTTGGTGCGAGAGAAAGTCCATGTGGTAGTGA |
| SEQ ID NO:<br>211 | ATGGAAACCGACACACTGCTGCTGTGGGTGCTGCTCTTGTGGGTGCC<br>AGGATCTACCGGCGACATCCAGATGACCCAGACCACCTCTAGCCTGT<br>CTGCCTCTCTGGGCGACAGAGTGACCATCTCCTGTAGAGCCAGCCAG<br>GACATCTCCAACTACCTGAACTGGTATCAGCAGAAACCCGACGGCA<br>CCGTGAAGCTGCTGATCTACTACACCCTCTCGGCTGCACTCTGGCGTG<br>CCCTCTAGATTTTCTGGCTCCGGCTCTGGCACCGACTACTCCCTGACC<br>ATCAACAACCTGGAACAAGAGGATATCGCTACCTACTTCTGCCAGCA<br>AGGCAACACCCGGCCTTGGACATTTGGCGGCGGAACAAAGCTGGAA<br>ATCAAGCGGACAGTGGCCGCTCCTTCCGTGTTCATCTTCCCACCTTCC<br>GACGAGCAGCTGAAGTCCGGCACAGCTTCTGTCGTGTGCCTGCTGAA<br>CAACTTCTACCCTCGGGAAGCCAAGGTGCAGTGGAAGGTGGACAAT<br>GCCCTGCAGTCCGGCAACTCCCAAGAGTCTGTGACCGAGCAGGACT<br>CCAAGGACAGCACCTACAGCCTGTCCTCCACACTGACCCTGAGCAA<br>GGCCGACTACGAGAAGCACAAGGTGTACGCCTGCGAAGTGACCCAT<br>CAGGGGCCTGTCTAGCCCTGTGACCAAGTCTTTCAACCGGGGCGAGTG<br>CTGATGA |
| SEQ ID NO:<br>121 | ATGGAAACCGATACCCTGCTGCTGTGGGTGCTGCTCCTCTGGGTGCC<br>AGGCTCTACCGGCCAGTCTGCTCTGACCCAGCCTGCCTCTGTGTCTG<br>GCTCCCCTGGCCAGTCCATCACCATCAGCTGTACCGGCACCTCCTCC |

TABLE 12-continued

Nucleic acid sequences for ORFs.

| Sequence ID | Nucleic Acid Sequence |
|---|---|
| | GACGTGGGCGGCTACAACTACGTGTCCTGGTATCAGCAGCATCCCGG<br>CAAGGCCCCTAAGCTGATGATCTACGACGTGTCCAACCGGCCCTCCG<br>GCGTGTCCAATCGGTTCTCTGGCTCCAAGTCCGGCAACACCGCCTCC<br>CTGACAATCAGCGGACTGCAGGCCGAGGACGAGGCCGACTACTACT<br>GCTCCTCCTACACCTCCAGCTCTACCCGGGTGTTCGGCACCGGCACC<br>AAAGTGACAGTGCTGGGCCAGCCCAAGGCCAACCCCACCGTGACCC<br>TGTTCCCTCCATCCTCCGAGGAACTGCAGGCTAACAAGGCCACCCTC<br>GTGTGCCTGATCTCCGACTTCTACCCTGGCGCCGTGACCGTGGCTTG<br>GAAGGCTGATGGCTCTCTCCTGTGAAGGCCGGCGTGGAAACCACCAAG<br>CCCTCCAAGCAGTCCAACAACAAATACGCCGCCTCCAGCTACCTGTC<br>CCTGACCCCTGAGCAGTGGAAGTCCCACCGGTCCTACAGCTGCCAGG<br>TCACACATGAGGGCTCCACCGTGGAAAAGACCGTGGCCCCTACCGA<br>GTGCTCCTAATGA |
| SEQ ID NO: 212 | ATGGCTGCTCATCTGCTGCCTATCTGCGCCCTGTTCCTGACCCTGCTG<br>GATATGGCCCAGGGCTTCAGAGGCCCTCTGCTGCCCAACAGACCCTT<br>CACCACCGTGTGGAACGCCAACACCCAGTGGTGCCTGGAAAGACAC<br>GGCGTGGACGTGGACGTGTCCGTGTTCGATGTGGTGGCCAACCCCGG<br>CCAGACCTTCAGGGGCCCTGACATGACCATCTTCTACTCCAGCCAGC<br>TGGGCACCTACCCCTACTACACCCCTACAGGCGAGCCTGTGTTTGGC<br>GGCCTGCCTCAGAACGCCTCTCTGATCGCTCACCTGGCCCGGACCTT<br>CCAGGACATCCTGGCTGCTATCCCTGCCCCCGACTTTTCTGGCCTGG<br>CCGTGATCGATTGGGAGGCCTGGCGACCTAGATGGGCCTTCAACTGG<br>GACACCAAGGACATCTACCGGCAGCGGTCCAGAGCCCTGGTGCAGG<br>CTCAGCATCCTGATTGGCCTGCCCCTCAGGTGGAAGCCGTGGCCCAG<br>GATCAGTTTCAGGGCGCTGCCAGAGCTTGGATGGCTGGCACACTGCA<br>GCTGGGAAGGGCCCTGAGGCCTAGAGGACTGTGGGGCTTCTACGGC<br>TTCCCCGACTGCTACAACTACGACTTCCTGTCCCCCAACTACACCGG<br>CCAGTGCCCCTCTGGAATCCGGGCCCAGAATGATCAGCTGGGCTGGC<br>TGTGGGGCCAGTCTAGAGCCCTGTACCCCTCCATCTACATGCCCGCC<br>GTGCTGGAAGGCACCGGCAAGTCCCAGATGTACGTGCAGCACAGAG<br>TGGCCGAGGCCTTCAGGGTGGCAGTGGCTGCTGGCGATCCTAACCTG<br>CCCGTGCTGCCCTACGTGCAGATCTTCTACGATACCACCAACCACTT<br>TCTGCCCCTGGACGAGCTGGAACACTCCCTGGGAGAGTCTGCTGCTC<br>AGGGTGCTGCAGGCGTGGTGCTGTGGGTGTCCTGGGAGAACACCCG<br>GACCAAAGAGTCCTGCCAGGCCATCAAAGAGTACATGGACACCACC<br>CTGGGCCCCTTCATCCTGAACGTGACCTCTGGCGCCCTGCTGTGTAG<br>CCAGGCTCTGTGTTCTGGCCACGGCAGATGCGTGCGGAGAACCTCTC<br>ACCCTAAGGCTCTGCTGCTGCTGAACCCCGCCTCCTTCAGCATCCAG<br>CTGACACCTGGCGGCGGACCCCTGTCTCTGAGAGGTGCTCTGTCCCT<br>GGAAGATCAGGCCCAGATGGCCGTGGAATTCAAGTGCCGGTGCTAC<br>CCTGGCTGGCAGGCCCCTTGGTGCGAGCGGAAATCTATGTGGGGCG<br>GAGGCGGATCAGGCGGCGGAGGATCTGGGGGTGGTGGCTCTGATAA<br>GACCCACACCTGTCCTCCCTGCCCTGCCCCTGAACTGCTGGGAGGCC<br>CTTCCGTGTTCCTGTTCCCCCCAAAGCCCAAGGACACCCTGATGATC<br>TCCCGGACCCCCGAAGTGACCTGCGTGGTGGTGGATGTGTCCCACGA<br>GGACCCTGAAGTGAAGTTCAATTGGTACGTGGACGGGGTGGAAGTG<br>CACAACGCCAAGACCAAGCCCAGAGAGGAACAGTACAACTCCACCT<br>ACAGAGTGGTGTCCGTGCTGACCGTGCTGCATCAGGACTGGCTGAAC<br>GGCAAAGAGTATAAGTGCAAGGTGTCCAACAAGGCCCTGCCCGCTC<br>CCATCGAAAAGACCATCTCCAAGGCCAAGGGCCAGCCCCGGGAACC<br>TCAAGTGTGCACCCTGCCTCCATCCCGGGAAGAGATGACCAAGAAC<br>CAGGTGTCCCTGTCCTGCGCCGTGAAGGGCTTTTACCCCTCCGATAT<br>CGCTGTGGAATGGGAGTCCAACGGCCAGCCTGAGAACAACTACAAG<br>ACCACCCCCCCTGTGCTGGACTCCGACGGCTCATTCTTCCTGGTGTCC<br>AAGCTGACAGTGGACAAGTCCCGGTGGCAGCAGGGCAACGTGTTCT<br>CCTGCTCCGTGATGCACGAGGCCCTGCACAACCACTACACCCAGAA<br>GTCCCTGAGCCTGTCCCCTGGCAAGTGATGA |

TABLE 13

DNA sequences for antigens used.

| Sequence ID | Description | Nucleic Acid Sequence |
|---|---|---|
| SEQ ID NO: 141 | Human PD1L1 | ATGAGAATCTTCGCCGTGTTCATCTTCATGACCTACTGGCATCTGCT<br>GAACGCCTTCACCGTGACCGTGCCCAAGGACCTGTACGTGGTGGAA<br>TACGGCTCCAACATGACCATCGAGTGCAAGTTCCCCGTGGAAAAGC<br>AGCTGGACCTGGCCGCCCTGATCGTGTACTGGGAGATGGAAGATAA<br>GAACATCATCCAGTTCGTGCACGGGGAAGAGGACCTGAAGGTGCA<br>GCACTCCTCCTACCGGCAGAGAGCCAGCTGCTGAAGGACCAGCTG<br>TCCCTGGGCAATGCCGCCCTGCAGATCACCGACGTGAAGCTGCAGG<br>ATGCCGGCGTGTACCGGTGCATGATCTCTTACGGCGGAGCCGACTA |

TABLE 13-continued

DNA sequences for antigens used.

| Sequence ID Description | Nucleic Acid Sequence |
|---|---|
| | CAAGCGGATCACCGTGAAAGTGAACGCCCCCTACAACAAGATCAA<br>CCAGCGGATCCTGGTGGTGGACCCCGTGACCTCTGAGCACGAGCTG<br>ACCTGTCAGGCCGAGGGCTACCCTAAGGCCGAAGTGATCTGGACCT<br>CCTCCGACCACCAGGTGCTGTCCGGCAAGACCACCACCACAAACTC<br>CAAGCGGGAAGAGAAGCTGTTCAACGTGACCTCCACCCTGCGGATC<br>AACACAACCACCAACGAGATCTTCTACTGTACCTTCCGGCGGCTGG<br>ACCCCGAGGAAATCACACCGCTGAGCTCGTGATCCCCGAGCTGCC<br>TCTGGCCCACCCTCCTAATGAGAGAACAGGCGGCGGAGGCTCCGGC<br>CTGAACGACATCTTTGAGGCCCAGAAAATCGAGTGGCACGAGGGC<br>GGAGGCGGCTCCCACCATCATCACCACCACCATCACTGATGA |
| SEQ ID NO: hFAP<br>213 | ATGAAGACCTGGGTCAAGATCGTGTTTGGCGTGGCCACCTCTGCTG<br>TGCTGGCTCTGCTGGTCATGTGCATCGTGCTGCGGCCTTCCAGAGTG<br>CACAACTCCGAAGAGAACACCATGCGGGCTCTGACCCTGAAGGAC<br>ATCCTGAACGGCACCTTCAGCTACAAGACCTTCTTTCCCAACTGGAT<br>CTCCGGCCAAGAGTACCTGCACCAGTCCGCCGACAACAATATCGTG<br>CTGTACAACATCGAGACAGGCCAGTCCTACACCATCCTGTCCAACC<br>GGACCATGAAGTCCGTGAACGCCTCCAACTACGGACTGTCTCCTGA<br>CCGGCAGTTCGTGTACCTGGAATCCGACTACTCCAAGCTGTGGCGG<br>TACTCCTACACCGCCACCTACTACATCTACGACCTGAGCAACGGCG<br>AGTTCGTGCGGGGAAATGAGCTGCCCAGACCTATCCAGTACCTGTG<br>CTGGTCCCCTGTGGGCTCTAAGCTGGCTTACGTGTACCAGAACAAC<br>ATCTACCTGAAGCAGCGGCCTGGCGACCCTCCATTCCAGATCACCT<br>TCAACGGCAGAGAGAACAAGATCTTTAACGGCATCCCCGACTGGGT<br>GTACGAGGAAGAGATGCTGCCCACTAAGTACGCCCTCTGGTGGTCC<br>CCTAACGGCAAGTTTCTGGCCTACGCCGAGTTCAACGACAAGGATA<br>TCCCCGTGATCGCCTACTCCTACTACGGCGACGAGCAGTACCCTCG<br>GACCATCAACATCCCTTATCCTAAGGCTGGCGCCAAGAATCCCGTC<br>GTGCGGATCTTCATCATCGACACCACCTATCCTGCCTACGTGGGCCC<br>TCAAGAGGTGCCAGTGCCTGCTATGATCGCCTCCAGCGACTACTAC<br>TTCTCCTGGCTGACATGGGTCACCGACGAGCGAGTTTGTCTGCAGT<br>GGCTGAAGCGGGTGCAGAACGTGTCCGTGCTGTCCATCTGCGACTT<br>CAGAGAGGACTGGCAGACCTGGGACTGCCCCAAGACACAAGAGCA<br>CATCGAGGAATCTCGGACCGGATGGGCTGGCGGCTTCTTCGTGTCT<br>AGACCCGTGTTCTCCTACGACGCCATCAGCTACTATAAGATCTTCTC<br>CGACAAGGACGGCTACAAGCACATCCACTACATCAAGGACACCGTC<br>GAGAACGCCATCCAGATTACCTCCGGCAAGTGGGAAGCCATCAATA<br>TCTTCAGAGTGACCCAGGACTCCCTGTTCTACTCCTCCAACGAGTTC<br>GAGGAATACCCCGGCAGAGGAACATCTACAGAATCTCCATCGGCA<br>GCTACCCTCCATCCAAGAAATGCGTGACCTGCCACCTGAGAAAAGA<br>GCGGTGCCAGTACTATACCGCCAGCTTCTCTGACTACGCCAAGTAC<br>TACGCCCTCGTGTGTTACGGCCCTGGCATCCCTATCTCTACCCTGCA<br>CGATGGCAGAACCGACCAAGAGATCAAGATCCTGGAAGAAAACAA<br>AGAGCTGGAAAACGCCCTGAAGAACATTCAGCTGCCCAAAGAGGA<br>AATCAAGAAGCTGGAAGTCGACGAGATCACCCTGTGGTACAAGAT<br>GATCCTGCCTCCTCAGTTCGACCGGTCCAAGAAGTACCCTCTGCTGA<br>TCCAGGTGTACGGCGGACCTTGCTCTCAGTCCGTCAGATCTGTGTTC<br>GCCGTGAATTGGATCTCCTACCTGGCCTCCAAAGAAGGCATGGTTA<br>TCGCCCTGGTGGACGGCAGAGGCACAGCTTTTCAAGGCGACAAGCT<br>GCTGTACGCCGTGTACAGAAAGCTGGGCGTGTACGAAGTGGAAGAT<br>CAGATCACCGCCGTGCGGAAGTTCATCGAGATGGGCTTCATCGACG<br>AGAAGCGGATCGCTATCTGGGGCTGGTCTTACGGCGGCTACGTTTC<br>CTCTCTGGCCCTGGCTTCTGGCACCGGCCTGTTCAAGTGTGGAATCG<br>CTGTTGCCCCTGTGTCCTCCTGGGAGTACTATGCCTCTGTGTACACC<br>GAGCGGTTCATGGGCCTGCCTACCAAGGACGACAACCTGGAACACT<br>ACAAGAACAGCACCGTGATGGCCAGAGCCGAGTACTTCCGGAACG<br>TGGACTACCTGCTGATTCACGGCACCGCCGACGACAACGTGCACTT<br>CCAAAACAGCGCCCAGATCGCCAAGGCTCTGGTCAATGCCCAGGTG<br>GACTTTCAGGCCATGTGGTACTCCGACCAGAACCACGGCCTGTCTG<br>GCCTGAGCACCAATCACCTGTACACCCACATGACCCACTTTCTGAA<br>GCAGTGCTTCTCCCTGTCTGATGGCGGCGGAGGCTCTGGACTGAAC<br>GATATCTTCGAGGCCCAGAAAATCGAGTGGCACGAAGGCGGAGGC<br>GGCTCCCACCATCATCATCACCACCATCACTGATGA |
| SEQ ID NO: hNKp46<br>143 | ATGGAAACCGACACACTGCTGCTGTGGGTGCTGCTCTTGTGGGTGC<br>CAGGATCTACCGGCCAGCAGCAGACACTGCCCAAGCCTTTTATCTG<br>GGCCGAGCCTCACTTCATGGTGCCCAAAGAAAGCAAGTGACCATC<br>TGCTGCCAGGGCAACTACGGCGCTGTGGAATACCAGCTGCACTTCG<br>AGGGCTCCCTGTTCGCCGTGGATAGACCTAAGCCTCCTGAGCGGAT<br>CAACAAAGTGAAGTTCTACATCCCCGACATGAACTCCCGGATGGCT<br>GGCCAGTACTCCTGCATCTATAGAGTGGGCGAGCTTTGGAGCGAGC<br>CCTCCAATCTGCTGGATCTGGTGGTCACCGAGATGTACGACACCCC |

TABLE 13-continued

DNA sequences for antigens used.

| Sequence ID | Description | Nucleic Acid Sequence |
|---|---|---|
| | | TACACTGAGCGTGCACCCCGGACCTGAAGTGATCTCTGGCGAGAAA<br>GTGACCTTCTACTGCAGACTGGATACCGCCACCTCCATGTTTCTGCT<br>GCTCAAAGAGGGCAGATCCTCTCACGTGCAGCGCGGCTATGGAAAG<br>GTGCAGGCTGAGTTTCCTCTGGGCCCTGTGACCACCGCTCACAGAG<br>GCACCTACAGATGCTTCGGCTCCTACAACAACCACGCCTGGTCTTTC<br>CCATCCGAGCCTGTGAAGCTGCTGGTCACCGGCGACATCGAGAACA<br>CATCTCTGGCCCCTGAGGACCCCACCTTTCCTGATACCTGGGGCACC<br>TATCTGCTGACCACCGAGACAGGCCTGCAGAAAGATCACGCCCTGT<br>GGGATCACACCGCTCAGAATGGTGGCGGAGGATCTGGCGGAGGCG<br>GATCTGAACCTAGAACCGACACCGACACCTGTCCTAATCCTCCAGA<br>TCCTTGTCCTACCTGTCCAACACCTGACCTGCTCGGCGGACCTTCCG<br>TGTTCATCTTCCCACCTAAGCCAAAGGACGTGCTGATGATCTCTCTG<br>ACCCCTAAGATCACCTGTGTGGTGGTGGACGTGTCCGAAGAGGAAC<br>CCGACGTGCAGTTCAATTGGTACGTGAACAACGTCGAGGACAAGAC<br>AGCCCAGACCGAGACACGGCAGCGGCAGTACAACTCTACCTACAG<br>AGTGGTGTCCGTGCTGCCCATCAAGCACCAGGATTGGATGTCCGGC<br>AAGGTGTTCAAGTGCAAAGTGAACAACAACGCCCTGCCTTCTCCAA<br>TCGAAAAGACCATCTCCAAGCCTCGGGGCCAAGTGCGAGTGCCCCA<br>GATCTATACCTTTCCACCTCCTATCGAGCAGACCGTGAAGAAAGAT<br>GTGTCCGTGACCTGCCTCGTGACCGGCTTCCTGCCTCAAGACATCCA<br>TGTGGAATGGGAGTCCAACGGCCAGCCTCAGCCTGAGCAGAACTAC<br>AAGAACACCCAGCCTGTGCTGGACTCCGACGGCAGCTACTTCCTGT<br>ACTCCAAGCTGAACGTGCCCAAGTCCAGATGGGACCAGGGCGACTC<br>CTTCACCTGTTCCGTGATCCACGAGGCCCTGCACAACCACCACATG<br>ACCAAGACCATCAGCAGATCCCTCGGCAATGGCGGTGGTGGTTCTG<br>GCGGCGGAGGTTCCGGACTGAACGATATCTTCGAGGCCCAGAAAAT<br>CGAGTGGCACGAGTGATGA |
| SEQ ID NO: 139 | hIL2Rα | ATGGAAACCGACACACTGCTGCTGTGGGTGCTGCTCTTGTGGGTGC<br>CAGGATCTACAGGCGAGCTGTGCGACGATGACCCTCCTGAGATCCC<br>TCACGCCACCTTCAAGGCCATGGCTTACAAAGAGGGCACCATGCTG<br>AACTGCGAGTGCAAGCGGGGCTTCAGACGGATCAAGTCCGGCAGC<br>CTGTACATGCTGTGCACCGGCAACTCCTCTCACTCCTCCTGGGACAA<br>CCAGTGCCAGTGCACCTCCTCTGCCACCAGAAACACCACCAAGCAA<br>GTGACCCCTCAGCCTGAGGAACAGAAAGAGCGCAAGACCACCGAG<br>ATGCAGAGCCCCATGCAGCCTGTGGATCAGGCTTCTCTGCCTGGCC<br>ACTGTAGAGAGCCTCCACCTTGGGAGAATGAGGCCACCGAGCGGAT<br>CTACCACTTTGTCGTGGGCCAGATGGTGTACTACCAGTGCGTGCAG<br>GGATACAGAGCCCTGCATAGAGGCCCTGCTGAGTCCGTGTGCAAGA<br>TGACCCATGGCAAGACCAGATGGACCCAGCCTCAGCTGATCTGTAC<br>AGGCGGAGGCGGAGGATCTGGTGGTGGTGGATCTGGCCTGAACGA<br>CATCTTCGAGGCCCAGAAAATCGAGTGGCACGAAGGCGGTGGCGG<br>CTCCCACCATCATCATCACCACCATCACTGATGA |
| SEQ ID NO: 144 | BirA | ATGGAAACTGACACCCTCCTCCTTTGGGTGCTGCTGCTTTGGGTGCC<br>TGGATCGACCGGGATGAAGGACAATACCGTGCCTCTGAAGCTCATT<br>GCCCTGCTGGCCAACGGAGAATTCCATTCCGGCGAACAGCTGGGGG<br>AGACTCTCGGGATGTCCCGGGCCGCCATCAACAAGCACATCCAGAC<br>TTTGCGCGACTGGGGAGTCGACGTGTTCACGGTGCCGGGGAAGGGC<br>TACTCGCTCCCGGAACCGATCCAGCTGCTGAACGCCAAGCAGATTC<br>TGGGACAGCTGGATGGCGGAAGCGTGGCAGTGCTGCCCGTGATCGA<br>CTCAACCAACCAGTATCTGCTGGATAGAATCGGTGAACTGAAATCC<br>GGCGACGCTTGCATTGCCGAGTACCAACAGGCCGGAAGGGGACGG<br>CGCGGCAGGAAGTGGTTCTCTCCATTCGGCGCGAACCTCTACCTGA<br>GCATGTTCTGGAGATTGGAGCAGGGTCCCGCCGCGGCCATCGGCCT<br>CTCCCTGGTCATCGGCATTGTGATGGCTGAAGTGCTGAGGAAGTTG<br>GGTGCCGACAAGGTCCGCGTGAAGTGGCCGAACGACCTGTACCTCC<br>AAGACCGGAAATTGGCGGGATTCTCGTCGAGCTTACCGGAAAGAC<br>TGGCGATGCCGCACAAATTGTGATCGGGGCGGGAATCAACATGGCG<br>ATGCGACGGGTGGAAGAGAGCGTCGTGAACCAGGGATGGATCACC<br>CTGCAAGAGGCCGGAATCAACCTGGATCGCAACACCCTGGCTGCCA<br>TGCTCATTCGCGAACTGAGAGCCGCACTGGAGCTGTTTGAGCAGGA<br>GGGTCTGGCCCCCTACCTGTCACGCTGGGAAAAGCTTGATAACTTC<br>ATCAATCGGCCTGTGAAGCTGATCATCGGAGACAAGGAGATTTTCG<br>GCATCTCGAGAGGCATCGACAAACAAGGAGCCCTCCTGCTGGAACA<br>GGACGGAATCATTAAGCCCTGGATGGGTGGAGAGATCTCCCTGCGG<br>TCCGCCGAAAAGTCCGGGAAGGATGAACTC |

TABLE 14

Amino Acid sequences.

| Sequence ID | Description | Amino Acid Sequence |
|---|---|---|
| SEQ ID NO: 43 | 2x4GS linker | GGGGSGGGGS |
| SEQ ID NO: 83 | Human CH2, CH3 knob | DKTHTCPPCPAPELLGGPSVFLFPPKPKDTLMISRTPEVTCVVVDVS<br>HEDPEVKFNWYVDGVEVHNAKTKPREEQYNSTYRVVSVLTVLHQ<br>DWLNGKEYKCKVSNKALPAPIEKTISKAKGQPREPQVYTLPPCREE<br>MTKNQVSLWCLVKGFYPSDIAVEWESNGQPENNYKTTPPVLDSDG<br>SFFLYSKLTVDKSRWQQGNVFSCSVMHEALHNHYTQKSLSLSPGK |
| SEQ ID NO: 82 | Human CH2, CH3 hole | DKTHTCPPCPAPELLGGPSVFLFPPKPKDTLMISRTPEVTCVVVDVS<br>HEDPEVKFNWYVDGVEVHNAKTKPREEQYNSTYRVVSVLTVLHQ<br>DWLNGKEYKCKVSNKALPAPIEKTISKAKGQPREPQVCTLPPSREE<br>MTKNQVSLSCAVKGFYPSDIAVEWESNGQPENNYKTTPPVLDSDG<br>SFFLVSKLTVDKSRWQQGNVFSCSVMHEALHNHYTQKSLSLSPGK |
| SEQ ID NO: 14 | CH1 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTK<br>VDKRVEPKSC |
| SEQ ID NO: 11 | CL (kappa) | RTVAAPSVFIFPPSDEQLKSGTASVVCLLNNFYPREAKVQWKVDN<br>ALQSGNSQESVTEQDSKDSTYSLSSTLTLSKADYEKHKVYACEVTH<br>QGLSSPVTKSFNRGEC |
| SEQ ID NO: 147 | CL (lambda) | GQPKANPTVTLFPPSSEELQANKATLVCLISDFYPGAVTVAWKADG<br>SPVKAGVETTKPSKQSNNKYAASSYLSLTPEQWKSHRSYSCQVTH<br>EGSTVEKTVAPTECS |
| SEQ ID NO: 148 | αPD1L1 Avelumab VH | EVQLLESGGGLVQPGGSLRLSCAASGFTFSSYIMMWVRQAPGKGL<br>EWVSSIYPSGGITFYADTVKGRFTISRDNSKNTLYLQMNSLRAEDT<br>AVYYCARIKLGTVTTVDYWGQGTLVTVSS |
| SEQ ID NO: 149 | αPD1L1 Avelumab VL | QSALTQPASVSGSPGQSITISCTGTSSDVGGYNYVSWYQQHPGKAP<br>KLMIYDVSNRPSGVSNRFSGSKSGNTASLTISGLQAEDEADYYCSS<br>YTSSSTRVFGTGTKVTVL |
| SEQ ID NO: 96 | 3x4GS linker | GGGGSGGGGSGGGGS |
| SEQ ID NO: 150 | αNKp46 VH | QVQLQQSGPELVKPGASVKMSCKASGYTFTDYVINWGKQRSGQG<br>LEWIGEIYPGSGTNYYNEKFKAKATLTADKSSNIAYMQLSSLTSED<br>SAVYFCARRGRYGLYAMDYWGQGTSVTVSS |
| SEQ ID NO: 151 | αNKp46 VL | DIQMTQTTSSLSASLGDRVTISCRASQDISNYLNWYQQKPDGTVKL<br>LIYYTSRLHSGVPSRFSGSGSGTDYSLTINNLEQEDIATYFCQQGNT<br>RPWTFGGGTKLEIK |
| SEQ ID NO: 152 | 4x 4GS linker | GGGGSGGGGSGGGGSGGGGS |
| SEQ ID NO: 42 | 1x4GS | GGGGS |
| SEQ ID NO: 63 | MMP2 | YNFFPRKPKWDKNQITYRIIGYTPDLDPETVDDAFARAFQVWSDVT<br>PLRFSRIHDGEADIMINFGRWEHGDGYPFDGKDGLLAHAFAPGTGV<br>GGDSHFDDDELWTLGEGQVVRVKYGNADGEYCKFPFLFNGKEYN<br>SCTDTGRSDGFLWCSTTYNFEKDGKYGFCPHEALFTMGGNAEGQP<br>CKFPFRFQGTSYDSCTTEGRTDGYRWCGTTEDYDRDKKYGFCPET<br>AMSTVGGNSEGAPCVFPFTFLGNKYESCTSAGRSDGKMWCATTA<br>NYDDDRKWGFCPDQGYSLFLVAAHEFGHAMGLEHSQDPGALMAP<br>IYTYTKNFRLSQDDIKGIQELYGASPDIDLGTGPTPTLGPVTPEICKQ<br>DIVFDGIAQIRGEIFFFKDRFIWRTVTPRDKPMGPLLVATFWPELPEK<br>IDAVYEAPQEEKAVFFAGNEYWIYSASTLERGYPKPLTSLGLPPDV<br>QRVDAAFNWSKNKKTYIFAGDKFWRYNEVKKKMDPGFPKLIADA<br>WNAIPDNLDAVVDLQGGGHSYFFKGAYYLKLENQSLKSVKFGSIK<br>SDWLGC |
| SEQ ID NO: 62 | HYAL1 | FRGPLLPNRPFTTVWNANTQWCLERHGVDVDVSVFDVVANPGQT<br>FRGPDMTIFYSSQLGTYPYYTPTGEPVFGGLPQNASLIAHLARTFQD<br>ILAAIPAPDFSGLAVIDWEAWRPRWAFNWDTKDIYRQRSRALVQA<br>QHPDWPAPQVEAVAQDQFQGAARAWMAGTLQLGRALRPRGLWG<br>FYGFPDCYNYDFLSPNYTGQCPSGIRAQNDQLGWLWGQSRALYPS<br>IYMPAVLEGTGKSQMYVQHRVAEAFRVAVAAGDPNLPVLPYVQIF<br>YDTTNHFLPLDELEHSLGESAAQGAAGVVLWVSWENTRTKESCQA<br>IKEYMDTTLGPFILNVTSGALLCSQALCSGHGRCVRRTSHPKALLLL<br>NPASFSIQLTPGGGPLSLRGALSLEDQAQMAVEFKCRCYPGWQAP<br>WCERKSMW |
| SEQ ID NO: 65 | αFAP Heavy | QVQLVQSGAEVKKPGASVKVSCKTSRYTFTEYTIHWVRQAPGQRL<br>EWIGGINPNNGIPNYNQKFKGRVTITVDTSASTAYMELSSLRSEDTA<br>VYYCARRRIAYGYDEGHAMDYWGQGTLVTVSS |

TABLE 14-continued

Amino Acid sequences.

| Sequence ID | Description | Amino Acid Sequence |
|---|---|---|
| SEQ ID NO: 69 | αFAP light | DIVMTQSPDSLAVSLGERATINCKSSQSLLYSRNQKNYLAWYQQKP GQPPKLLIFWASTRESGVPDRFSGSGFGTDFTLTISSLQAEDVAVYY CQQYFSYPLTFGQGTKVEIK |
| SEQ ID NO: 163 | hIL2 F42A Y45A | APTSSSTKKTQLQLEHLLLDLQMILNGINNYKNPKLTRMLTAKFAM PKKATELKHLQCLEEELKPLEEVLNLAQSKNFHLRPRDLISNINVIV LELKGSETTFMCEYADETATIVEFLNRWITFCQSIISTLT |

TABLE 15

Amino Acid sequences for full heavy and light chains.

| Construct SEQ ID NO: | N-term | Linker | Variable | Constant | Fc | Linker | C-term |
|---|---|---|---|---|---|---|---|
| SEQ ID NO: 214 | | | SEQ ID NO: 65 | SEQ ID NO: 14 | SEQ ID NO: 83 | | |
| SEQ ID NO: 215 | | | SEQ ID NO: 69 | SEQ ID NO: 11 | | | |
| SEQ ID NO: 216 | | | SEQ ID NO: 65 | SEQ ID NO: 14 | SEQ ID NO: 82 | SEQ ID NO: 96 | SEQ ID NO: 63 |
| SEQ ID NO: 217 | SEQ ID NO: 63 | SEQ ID NO: 96 | | | SEQ ID NO: 82 | | |
| SEQ ID NO: 218 | | | SEQ ID NO: 65 | SEQ ID NO: 14 | SEQ ID NO: 83 | SEQ ID NO: 96 | SEQ ID NO: 163 |
| SEQ ID NO: 219 | | | SEQ ID NO: 65 | SEQ ID NO: 14 | SEQ ID NO: 82 | SEQ ID NO: 96 | SEQ ID NO: 62 |
| SEQ ID NO: 220 | | | SEQ ID NO: 148 | SEQ ID NO: 14 | SEQ ID NO: 83 | | |
| SEQ ID NO: 221 | | | SEQ ID NO: 148 | SEQ ID NO: 14 | SEQ ID NO: 83 | SEQ ID NO: 96 | SEQ ID NO: 163 |
| SEQ ID NO: 222 | | | SEQ ID NO: 150 | SEQ ID NO: 14 | SEQ ID NO: 82 | SEQ ID NO: 96 | SEQ ID NO: 62 |
| SEQ ID NO: 223 | | | SEQ ID NO: 151 | SEQ ID NO: 11 | | | |
| SEQ ID NO: 171 | | | SEQ ID NO: 149 | SEQ ID NO: 147 | | | |
| SEQ ID NO: 224 | SEQ ID NO: 62 | SEQ ID NO: 96 | | | SEQ ID NO: 82 | | |

TABLE 16

Amino acid sequences of the chains used to construct multispecific molecules.

| Sequence ID | Amino Acid Sequence |
|---|---|
| SEQ ID NO: 214 | QVQLVQSGAEVKKPGASVKVSCKTSRYTFTEYTIHWVRQAPGQRLEWI GGINPNNGIPNYNQKFKGRVTITVDTSASTAYMELSSLRSEDTAVYYCA RRRIAYGYDEGHAMDYWGQGTLVTVSSASTKGPSVFPLAPSSKSTSGG TAALGCLVKDYFPEPVTVSWNSGALTSGVHTFPAVLQSSGLYSLSSVVT VPSSSLGTQTYICNVNHKPSNTKVDKRVEPKSCDKTHTCPPCPAPELLG GPSVFLFPPKPKDTLMISRTPEVTCVVVDVSHEDPEVKFNWYVDGVEV HNAKTKPREEQYNSTYRVVSVLTVLHQDWLNGKEYKCKVSNKALPAP IEKTISKAKGQPREPQVYTLPPCREEMTKNQVSLWCLVKGFYPSDIAVE WESNGQPENNYKTTPPVLDSDGSFFLYSKLTVDKSRWQQGNVFSCSVM HEALHNHYTQKSLSLSPGK |
| SEQ ID NO: 215 | DIVMTQSPDSLAVSLGERATINCKSSQSLLYSRNQKNYLAWYQQKPGQ PPKLLIFWASTRESGVPDRFSGSGFGTDFTLTISSLQAEDVAVYYCQQYF SYPLTFGQGTKVEIKRTVAAPSVFIFPPSDEQLKSGTASVVCLLNNFYPR EAKVQWKVDNALQSGNSQESVTEQDSKDSTYSLSSTLTLSKADYEKHK VYACEVTHQGLSSPVTKSFNRGEC |

TABLE 16-continued

Amino acid sequences of the chains
used to construct multispecific molecules.

| Sequence ID | Amino Acid Sequence |
|---|---|
| SEQ ID NO: 216 | QVQLVQSGAEVKKPGASVKVSCKTSRYTFTEYTIHWVRQAPGQRLEWI<br>GGINPNNGIPNYNQKFKGRVTITVDTSASTAYMELSSLRSEDTAVYYCA<br>RRRIAYGYDEGHAMDYWGQGTLVTVSSASTKGPSVFPLAPSSKSTSGG<br>TAALGCLVKDYFPEPVTVSWNSGALTSGVHTFPAVLQSSGLYSLSSVVT<br>VPSSSLGTQTYICNVNHKPSNTKVDKRVEPKSCDKTHTCPPCPAPELLG<br>GPSVFLFPPKPKDTLMISRTPEVTCVVVDVSHEDPEVKFNWYVDGVEV<br>HNAKTKPREEQYNSTYRVVSVLTVLHQDWLNGKEYKCKVSNKALPAP<br>IEKTISKAKGQPREPQVCTLPPSREEMTKNQVSLSCAVKGFYPSDIAVEW<br>ESNGQPENNYKTTPPVLDSDGSFFLVSKLTVDKSRWQQGNVFSCSVMH<br>EALHNHYTQKSLSLSPGKGGGGSGGGGSGGGGSYNFFPRKPKWDKNQI<br>TYRIIGYTPDLDPETVDDAFARAFQVWSDVTPLRFSRIHDGEADIMINFG<br>RWEHGDGYPFDGKDGLLAHAFAPGTGVGGDSHFDDDELWTLGEGQV<br>VRVKYGNADGEYCKFPFLFNGKEYNSCTDTGRSDGFLWCSTTYNFEKD<br>GKYGFCPHEALFTMGGNAEGQPCKFPFRFQGTSYDSCTTEGRTDGYRW<br>CGTTEDYDRDKKYGFCPETAMSTVGGNSEGAPCVFPFTFLGNKYESCT<br>SAGRSDGKMWCATTANYDDDRKWGFCPDQGYSLFLVAAHEFGHAMG<br>LEHSQDPGALMAPIYTYTKNFRLSQDDIKGIQELYGASPDIDLGTGPTPT<br>LGPVTPEICKQDIVFDGIAQIRGEIFFFKDRFIWRTVTPRDKPMGPLLVAT<br>FWPELPEKIDAVYEAPQEEKAVFFAGNEYWIYSASTLERGYPKPLTSLG<br>LPPDVQRVDAAFNWSKNKKTYIFAGDKFWRYNEVKKKMDPGFPKLIA<br>DAWNAIPDNLDAVVDLQGGGHSYFFKGAYYLKLENQSLKSVKFGSIKS<br>DWLGC |
| SEQ ID NO: 217 | YNFFPRKPKWDKNQITYRIIGYTPDLDPETVDDAFARAFQVWSDVTPLR<br>FSRIHDGEADIMINFGRWEHGDGYPFDGKDGLLAHAFAPGTGVGGDSH<br>FDDDELWTLGEGQVVRVKYGNADGEYCKFPFLFNGKEYNSCTDTGRS<br>DGFLWCSTTYNFEKDGKYGFCPHEALFTMGGNAEGQPCKFPFRFQGTS<br>YDSCTTEGRTDGYRWCGTTEDYDRDKKYGFCPETAMSTVGGNSEGAP<br>CVFPFTFLGNKYESCTSAGRSDGKMWCATTANYDDDRKWGFCPDQGY<br>SLFLVAAHEFGHAMGLEHSQDPGALMAPIYTYTKNFRLSQDDIKGIQEL<br>YGASPDIDLGTGPTPTLGPVTPEICKQDIVFDGIAQIRGEIFFFKDRFIWRT<br>VTPRDKPMGPLLVATFWPELPEKIDAVYEAPQEEKAVFFAGNEYWIYS<br>ASTLERGYPKPLTSLGLPPDVQRVDAAFNWSKNKKTYIFAGDKFWRYN<br>EVKKKMDPGFPKLIADAWNAIPDNLDAVVDLQGGGHSYFFKGAYYLK<br>LENQSLKSVKFGSIKSDWLGCGGGGSGGGGSGGGGSDKTHTCPPCPAP<br>ELLGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKAL<br>PAPIEKTISKAKGQPREPQVCTLPPSREEMTKNQVSLSCAVKGFYPSDIA<br>VEWESNGQPENNYKTTPPVLDSDGSFFLVSKLTVDKSRWQQGNVFSCS<br>VMHEALHNHYTQKSLSLSPGK |
| SEQ ID NO: 218 | QVQLVQSGAEVKKPGASVKVSCKTSRYTFTEYTIHWVRQAPGQRLEWI<br>GGINPNNGIPNYNQKFKGRVTITVDTSASTAYMELSSLRSEDTAVYYCA<br>RRRIAYGYDEGHAMDYWGQGTLVTVSSASTKGPSVFPLAPSSKSTSGG<br>TAALGCLVKDYFPEPVTVSWNSGALTSGVHTFPAVLQSSGLYSLSSVVT<br>VPSSSLGTQTYICNVNHKPSNTKVDKRVEPKSCDKTHTCPPCPAPELLG<br>GPSVFLFPPKPKDTLMISRTPEVTCVVVDVSHEDPEVKFNWYVDGVEV<br>HNAKTKPREEQYNSTYRVVSVLTVLHQDWLNGKEYKCKVSNKALPAP<br>IEKTISKAKGQPREPQVYTLPPCREEMTKNQVSLWCLVKGFYPSDIAVE<br>WESNGQPENNYKTTPPVLDSDGSFFLYSKLTVDKSRWQQGNVFSCSVM<br>HEALHNHYTQKSLSLSPGKGGGGSGGGGSGGGGSAPTSSSTKKTQLQL<br>EHLLLDLQMILNGINNYKNPKLTRMLTAKFAMPKKATELKHLQCLEEE<br>LKPLEEVLNLAQSKNFHLRPRDLISNINIVVLELKGSETTFMCEYADETA<br>TIVEFLNRWITFCQSIISTLT |
| SEQ ID NO: 219 | QVQLVQSGAEVKKPGASVKVSCKTSRYTFTEYTIHWVRQAPGQRLEWI<br>GGINPNNGIPNYNQKFKGRVTITVDTSASTAYMELSSLRSEDTAVYYCA<br>RRRIAYGYDEGHAMDYWGQGTLVTVSSASTKGPSVFPLAPSSKSTSGG<br>TAALGCLVKDYFPEPVTVSWNSGALTSGVHTFPAVLQSSGLYSLSSVVT<br>VPSSSLGTQTYICNVNHKPSNTKVDKRVEPKSCDKTHTCPPCPAPELLG<br>GPSVFLFPPKPKDTLMISRTPEVTCVVVDVSHEDPEVKFNWYVDGVEV<br>HNAKTKPREEQYNSTYRVVSVLTVLHQDWLNGKEYKCKVSNKALPAP<br>IEKTISKAKGQPREPQVCTLPPSREEMTKNQVSLSCAVKGFYPSDIAVEW<br>ESNGQPENNYKTTPPVLDSDGSFFLVSKLTVDKSRWQQGNVFSCSVMH<br>EALHNHYTQKSLSLSPGKGGGGSGGGGSGGGGSFRGPLLPNRPFTTVW<br>NANTQWCLERHGVDVDSVFDVVANPGQTFRGPDMTIFYSSQLGTYP<br>YYTPTGEPVFGGLPQNASLIAHLARTFQDILAAIPAPDFSGLAVIDWEAW<br>RPRWAFNWDTKDIYRQRSRALVQAHPDWPAPQVEAVAQDQFQGAA<br>RAWMAGTLQLGRALRPRGLWGFYGFPDCYNYDFLSPNYTGQCPSGIR<br>AQNDQLGWLWGQSRALYPSIYMPAVLEGTGKSQMYVQHRVAEAFRV<br>AVAAGDPNLPVLPVYQIFYDTTNHFLPLDELEHSLGESAAQGAAGVVL<br>WVSWENTRTKESCQAIKEYMDTTLGPPILNVTSGALLCSQALCSGHGR<br>CVRRTSHPKALLLLNPASFSIQLTPGGGPLSLRGALSLEDQAMAVEFK<br>CRCYPGWQAPWCERKSMW |

TABLE 16-continued

Amino acid sequences of the chains
used to construct multispecific molecules.

| Sequence ID | Amino Acid Sequence |
| --- | --- |
| SEQ ID NO: 220 | EVQLLESGGGLVQPGGSLRLSCAASGFTFSSYIMMWVRQAPGKGLEWV<br>SSIYPSGGITFYADTVKGRFTISRDNSKNTLYLQMNSLRAEDTAVYYCA<br>RIKLGTVTTVDYWGQGTLVTVSSASTKGPSVFPLAPSSKSTSGGTAALG<br>CLVKDYFPEPVTVSWNSGALTSGVHTFPAVLQSSGLYSLSSVVTVPSSS<br>LGTQTYICNVNHKPSNTKVDKRVEPKSCDKTHTCPPCPAPELLGGPSVF<br>LFPPKPKDTLMISRTPEVTCVVVDVSHEDPEVKFNWYVDGVEVHNAKT<br>KPREEQYNSTYRVVSVLTVLHQDWLNGKEYKCKVSNKALPAPIEKTIS<br>KAKGQPREPQVYTLPPCREEMTKNQVSLWCLVKGFYPSDIAVEWESNG<br>QPENNYKTTPPVLDSDGSFFLYSKLTVDKSRWQQGNVFSCSVMHEALH<br>NHYTQKSLSLSPGK |
| SEQ ID NO: 221 | EVQLLESGGGLVQPGGSLRLSCAASGFTFSSYIMMWVRQAPGKGLEWV<br>SSIYPSGGITFYADTVKGRFTISRDNSKNTLYLQMNSLRAEDTAVYYCA<br>RIKLGTVTTVDYWGQGTLVTVSSASTKGPSVFPLAPSSKSTSGGTAALG<br>CLVKDYFPEPVTVSWNSGALTSGVHTFPAVLQSSGLYSLSSVVTVPSSS<br>LGTQTYICNVNHKPSNTKVDKRVEPKSCDKTHTCPPCPAPELLGGPSVF<br>LFPPKPKDTLMISRTPEVTCVVVDVSHEDPEVKFNWYVDGVEVHNAKT<br>KPREEQYNSTYRVVSVLTVLHQDWLNGKEYKCKVSNKALPAPIEKTIS<br>KAKGQPREPQVYTLPPCREEMTKNQVSLWCLVKGFYPSDIAVEWESNG<br>QPENNYKTTPPVLDSDGSFFLYSKLTVDKSRWQQGNVFSCSVMHEALH<br>NHYTQKSLSLSPGKGGGGSGGGGSGGGGSAPTSSSTKKTQLQLEHLLL<br>DLQMILNGINNYKNPKLTRMLTAKFAMPKKATELKHLQCLEEELKPLE<br>EVLNLAQSKNFHLRPRDLISNINVIVLELKGSETTFMCEYADETATIVEF<br>LNRWITFCQSIISTLT |
| SEQ ID NO: 222 | QVQLQQSGPELVKPGASVKMSCKASGYTFTDYVINWGKQRSGQGLEW<br>IGEIYPGSGTNYYNEKFKAKATLTADKSSNIAYMQLSSLTSEDSAVYFC<br>ARRGRYGLYAMDYWGQGTSVTVSSASTKGPSVFPLAPSSKSTSGGTAA<br>LGCLVKDYFPEPVTVSWNSGALTSGVHTFPAVLQSSGLYSLSSVVTVPS<br>SSLGTQTYICNVNHKPSNTKVDKRVEPKSCDKTHTCPPCPAPELLGGPS<br>VFLFPPKPKDTLMISRTPEVTCVVVDVSHEDPEVKFNWYVDGVEVHNA<br>KTKPREEQYNSTYRVVSVLTVLHQDWLNGKEYKCKVSNKALPAPIEKT<br>ISKAKGQPREPQVCTLPPSREEMTKNQVSLSCAVKGFYPSDIAVEWESN<br>GQPENNYKTTPPVLDSDGSFFLVSKLTVDKSRWQQGNVFSCSVMHEAL<br>HNHYTQKSLSLSPGKGGGGSGGGGSGGGGSFRGPLLPNRPFTTVWNAN<br>TQWCLERHGVDVDSVFDVVANPGQTFRGPDMTIFYSSQLGTYPYYTP<br>TGEPVFGGLPQNASLIAHLARTFQDILAAIPAPDFSGLAVIDWEAWRPR<br>WAFNWDTKDIYRQRSRALVQAQHPDWPAPQVEAVAQDQFQGAARAW<br>MAGTLQLGRALRPRGLWGFYGFPDCYNYDFLSPNYTGQCPSGIRAQND<br>QLGWLWGQSRALYPSIYMPAVLEGTGKSQMYVQHRVAEAFRVAVAA<br>GDPNLPVLPYVQIFYDTTNHFLPLDELEHSLGESAAQGAAGVVLWVSW<br>ENTRTKESCQAIKEYMDTTLGPFILNVTSGALLCSQALCSGHGRCVRRT<br>SHPKALLLLNPASFSIQLTPGGGPLSLRGALSLEDQAMAVEFKCRCYP<br>GWQAPWCERKSMW |
| SEQ ID NO: 223 | DIQMTQTTSSLSASLGDRVTISCRASQDISNYLNWYQQKPDGTVKLLIY<br>YTSRLHSGVPSRFSGSGSGTDYSLTINNLEQEDIATYFCQQGNTRPWTFG<br>GGTKLEIKRTVAAPSVFIFPPSDEQLKSGTASVVCLLNNFYPREAKVQW<br>KVDNALQSGNSQESVTEQDSKDSTYSLSSTLTLSKADYEKHKVYACEV<br>THQGLSSPVTKSFNRGEC |
| SEQ ID NO: 171 | QSALTQPASVSGSPGQSITISCTGTSSDVGGYNYVSWYQQHPGKAPKLM<br>IYDVSNRPSGVSNRFSGSKSGNTASLTISGLQAEDEADYYCSSYTSSSTR<br>VFGTGTKVTVLGQPKANPTVTLFPPSSEELQANKATLVCLISDFYPGAV<br>TVAWKADGSPVKAGVETTKPSKQSNNKYAASSYLSLTPEQWKSHRSYS<br>CQVTHEGSTVEKTVAPTECS |
| SEQ ID NO: 224 | FRGPLLPNRPFTTVWNANTQWCLERHGVDVDSVFDVVANPGQTFRG<br>PDMTIFYSSQLGTYPYYTPTGEPVFGGLPQNASLIAHLARTFQDILAAIPA<br>PDFSGLAVIDWEAWRPRWAFNWDTKDIYRQRSRALVQAQHPDWPAPQ<br>VEAVAQDQFQGAARAWMAGTLQLGRALRPRGLWGFYGFPDCYNYDF<br>LSPNYTGQCPSGIRAQNDQLGWLWGQSRALYPSIYMPAVLEGTGKSQM<br>YVQHRVAEAFRVAVAAGDPNLPVLPYVQIFYDTTNHFLPLDELEHSLG<br>ESAAQGAAGVVLWVSWENTRTKESCQAIKEYMDTTLGPFILNVTSGAL<br>LCSQALCSGHGRCVRRTSHPKALLLLNPASFSIQLTPGGGPLSLRGALSL<br>EDQAMAVEFKCRCYPGWQAPWCERKSMWGGGGSGGGGSGGGGSD<br>KTHTCPPCPAPELLGGPSVFLFPPKPKDTLMISRTPEVTCVVVDVSHEDP<br>EVKFNWYVDGVEVHNAKTKPREEQYNSTYRVVSVLTVLHQDWLNGK<br>EYKCKVSNKALPAPIEKTISKAKGQPREPQVCTLPPSREEMTKNQVSLSC<br>AVKGFYPSDIAVEWESNGQPENNYKTTPPVLDSDGSFFLVSKLTVDKSR<br>WQQGNVFSCSVMHEALHNHYTQKSLSLSPGK |

TABLE 17

Sequences of antigens.

| Sequence ID | Description | Amino Acid Sequence |
|---|---|---|
| SEQ ID NO: 178 | hPD1L1 | FTVTVPKDLYVVEYGSNMTIECKFPVEKQLDLAALIVYWEMED KNIIQFVHGEEDLKVQHSSYRQRARLLKDQLSLGNAALQITDVK LQDAGVYRCMISYGGADYKRITVKVNAPYNKINQRILVVDPVTS EHELTCQAEGYPKAEVIWTSSDHQVLSGKTTTTNSKREEKLFNV TSTLRINTTTNEIFYCTFRRLDPEENHTAELVIPELPLAHPPNERTG GGGSGLNDIFEAQKIEWHEGGGGSHHHHHHHH |
| SEQ ID NO: 225 | hFAP | LLVMCIVLRPSRVHNSEENTMRALTLKDILNGTFSYKTFFPNWIS GQEYLHQSADNNIVLYNIETGQSYTILSNRTMKSVNASNYGLSP DRQFVYLESDYSKLWRYSYTATYYIYDLSNGEFVRGNELPRPIQ YLCWSPVGSKLAYVYQNNIYLKQRPGDPPFQITFNGRENKIFNGI PDWVYEEEMLPTKYALWWSPNGKFLAYAEFNDKDIPVIAYSYY GDEQYPRTINIPYPKAGAKNPVVRIFIIDTTYPAYVGPQEVPVPA MIASSDYYFSWLTWVTDERVCLQWLKRVQNVSVLSICDFREDW QTWDCPKTQEHIEESRTGWAGGFFVSRPVFSYDAISYYKIFSDK DGYKHIHYIKDTVENAIQITSGKWEAINIFRVTQDSLFYSSNEFEE YPGRRNIYRISIGSYPPSKKCVTCHLRKERCQYYTASFSDYAKYY ALVCYGPGIPISTLHDGRTDQEIKILEENKELENALKNIQLPKEEI KKLEVDEITLWYKMILPPQFDRSKKYPLLIQVYGGPCSQSVRSVF AVNWISYLASKEGMVIALVDGRGTAFQGDKLLYAVYRKLGVY EVEDQITAVRKFIEMGFIDEKRIAIWGWSYGGYVSSLALASGTGL FKCGIAVAPVSSWEYYASVYTERFMGLPTKDDNLEHYKNSTVM ARAEYFRNVDYLLIHGTADDNVHFQNSAQIAKALVNAQVDFQA MWYSDQNHGLSGLSTNHLYTHMTHFLKQCFSLDGGGGSGLN DIFEAQKIEWHEGGGGSHHHHHHHH |
| SEQ ID NO: 179 | hNKp46 | QQQTLPKPFIWAEPHFMVPKEKQVTICCQGNYGAVEYQLHFEGS LFAVDRPKPPERINKVKFYIPDMNSRMAGQYSCIYRVGELWSEP SNLLDLVVTEMYDTPTLSVHPGPEVISGEKVTFYCRLDTATSMF LLLKEGRSSHVQRGYGKVQAEFPLGPVTTAHRGTYRCFGSYNN HAWSFPSEPVKLLVTGDIENTSLAPEDPTFPDTWGTYLLTTETGL QKDHALWDHTAQNGGGGSGGGGSEPRTDTDTCPNPPDPCPTCP TPDLLGGPSVFIFPPKPKDVLMISLTPKITCVVVDVSEEEPDVQFN WYVNNVEDKTAQTETRQRQYNSTYRVVSVLPIKHQDWMSGKV FKCKVNNALPSPIEKTISKPRGQVRVPQIYTFPPPIEQTVKKDVS VTCLVTGFLPQDIHVEWESNGQPQPEQNYKNTQPVLDSDGSYFL YSKLNVPKSRWDQGSFTCSVIHEALHNHHMTKTISRSLGNGG GGSGGGGSGLNDIFEAQKIEWHE |
| SEQ ID NO: 182 | hIL2Rα | ELCDDDPPEIPHATFKAMAYKEGTMLNCECKRGFRRIKSGSLYM LCTGNSSHSSWDNQCQCTSSATRNTTKQVTPQPEEQKERKTTE MQSPMQPVDQASLPGHCREPPPWENEATERIYHFVVGQMVYYQ CVQGYRALHRGPAESVCKMTHGKTRWTQPQLICTGGGGSGG GGSGLNDIFEAQKIEWHEGGGGSHHHHHHHH |
| SEQ ID: 226 | BirA | MKDNTVPLKLIALLANGEFHSGEQLGETLGMSRAAINKHIQTLR DWGVDVFTVPGKGYSLPEPIQLLNAKQILGQLDGGSVAVLPVID STNQYLLDRIGELKSGDACIAEYQQAGRGRRGRKWFSPFGANL YLSMFWRLEQGPAAAIGLSLVIGIVMAEVLRKLGADKVRVKWP NDLYLQDRKLAGILVELTGKTGDAAQIVIGAGINMAMRRVEES VVNQGWITLQEAGINLDRNTLAAMLIRELRAALELFEQEGLAPY LSRWEKLDNFINRPVKLIIGDKEIFGISRGIDKQGALLLEQDGIIKP WMGGEISLRSAEKSGKDEL |

TABLE 18

Sequences used to generate multispecific molecules.

| Multispecific Molecule | Heavy Chain 1 | Light Chain 1 | Heavy Chain 2 | Light Chain 2 |
|---|---|---|---|---|
| 24 | SEQ ID NO: 214 | SEQ ID NO: 215 | SEQ ID NO: 219 | SEQ ID NO: 215 |
| 25 | SEQ ID NO: 218 | SEQ ID NO: 215 | SEQ ID NO: 219 | SEQ ID NO: 215 |
| 26 | SEQ ID NO: 214 | SEQ ID NO: 215 | SEQ ID NO: 224 | |
| 27 | SEQ ID NO: 220 | SEQ ID NO: 171 | SEQ ID NO: 219 | SEQ ID NO: 215 |
| 28 | SEQ ID NO: 221 | SEQ ID NO: 171 | SEQ ID NO: 219 | SEQ ID NO: 215 |
| 29 | SEQ ID NO: 221 | SEQ ID NO: 171 | SEQ ID NO: 222 | SEQ ID NO: 223 |
| 30 | SEQ ID NO: 214 | SEQ ID NO: 215 | SEQ ID NO: 216 | SEQ ID NO: 215 |

TABLE 18-continued

Sequences used to generate multispecific molecules.

| Multispecific Molecule | Heavy Chain 1 | Light Chain 1 | Heavy Chain 2 | Light Chain 2 |
|---|---|---|---|---|
| 31 | SEQ ID NO: 214 | SEQ ID NO: 215 | SEQ ID NO: 217 | |
| 32 | SEQ ID NO: 221 | SEQ ID NO: 171 | SEQ ID NO: 216 | SEQ ID NO: 215 |

Nucleic Acids

The invention also features nucleic acids comprising nucleotide sequences that encode heavy and light chain variable regions and CDRs or hypervariable loops of the antibody molecules, as described herein. For example, the invention features a first and second nucleic acid encoding heavy and light chain variable regions, respectively, of an antibody molecule chosen from one or more of the antibody molecules disclosed herein. The nucleic acid can comprise a nucleotide sequence as set forth in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein.

In certain embodiments, the nucleic acid can comprise a nucleotide sequence encoding at least one, two, or three CDRs or hypervariable loops from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In other embodiments, the nucleic acid can comprise a nucleotide sequence encoding at least one, two, or three CDRs or hypervariable loops from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In yet another embodiment, the nucleic acid can comprise a nucleotide sequence encoding at least one, two, three, four, five, or six CDRs or hypervariable loops from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs or hypervariable loops from a heavy chain variable region having the nucleotide sequence as set forth in the tables herein, a sequence substantially homologous thereto (e.g., a sequence at least about 85%, 90%, 95%, 99% or more identical thereto, and/or capable of hybridizing under the stringency conditions described herein). In another embodiment, the nucleic acid can comprise a nucleotide sequence encoding at least one, two, or three CDRs or hypervariable loops from a light chain variable region having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein). In yet another embodiment, the nucleic acid can comprise a nucleotide sequence encoding at least one, two, three, four, five, or six CDRs or hypervariable loops from heavy and light chain variable regions having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein).

In another aspect, the application features host cells and vectors containing the nucleic acids described herein. The nucleic acids may be present in a single vector or separate vectors present in the same host cell or separate host cell, as described in more detail hereinbelow.

Vectors

Further provided herein are vectors comprising the nucleotide sequences encoding an antibody molecule described herein. In one embodiment, the vectors comprise nucleotides encoding an antibody molecule described herein. In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

In another aspect, the application features host cells and vectors containing the nucleic acids described herein. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell.

The invention also provides host cells comprising a nucleic acid encoding an antibody molecule as described herein.

In one embodiment, the host cells are genetically engineered to comprise nucleic acids encoding the antibody molecule.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

Uses and Combination Therapies

Methods described herein include treating a cancer in a subject by using a multispecific molecule described herein, e.g., using a pharmaceutical composition described herein. Also provided are methods for reducing or ameliorating a symptom of a cancer in a subject, as well as methods for inhibiting the growth of a cancer and/or killing one or more cancer cells. In embodiments, the methods described herein decrease the size of a tumor and/or decrease the number of cancer cells in a subject administered with a described herein or a pharmaceutical composition described herein.

In embodiments, the cancer is a hematological cancer. In embodiments, the hematological cancer is a leukemia or a lymphoma. As used herein, a "hematologic cancer" refers to a tumor of the hematopoietic or lymphoid tissues, e.g., a tumor that affects blood, bone marrow, or lymph nodes. Exemplary hematologic malignancies include, but are not limited to, leukemia (e.g., acute lymphoblastic leukemia (ALL), acute myeloid leukemia (AML), chronic lymphocytic leukemia (CLL), chronic myelogenous leukemia (CML), hairy cell leukemia, acute monocytic leukemia (AMoL), chronic myelomonocytic leukemia (CMML), juvenile myelomonocytic leukemia (JMML), or large granular lymphocytic leukemia), lymphoma (e.g., AIDS-related lymphoma, cutaneous T-cell lymphoma, Hodgkin lymphoma (e.g., classical Hodgkin lymphoma or nodular lymphocyte-predominant Hodgkin lymphoma), mycosis fungoides, non-Hodgkin lymphoma (e.g., B-cell non-Hodgkin lymphoma (e.g., Burkitt lymphoma, small lymphocytic lymphoma (CLL/SLL), diffuse large B-cell lymphoma, follicular lymphoma, immunoblastic large cell lymphoma, precursor B-lymphoblastic lymphoma, or mantle cell lymphoma) or T-cell non-Hodgkin lymphoma (mycosis fungoides, anaplastic large cell lymphoma, or precursor T-lymphoblastic lymphoma)), primary central nervous system lymphoma, Sézary syndrome, Waldenström macroglobulinemia), chronic myeloproliferative neoplasm, Langerhans cell histiocytosis, multiple myeloma/plasma cell neoplasm, myelodysplastic syndrome, or myelodysplastic/myeloproliferative neoplasm.

In embodiments, the cancer is a solid cancer. Exemplary solid cancers include, but are not limited to, ovarian cancer, rectal cancer, stomach cancer, testicular cancer, cancer of the anal region, uterine cancer, colon cancer, rectal cancer, renal-cell carcinoma, liver cancer, non-small cell carcinoma of the lung, cancer of the small intestine, cancer of the esophagus, melanoma, Kaposi's sarcoma, cancer of the endocrine system, cancer of the thyroid gland, cancer of the parathyroid gland, cancer of the adrenal gland, bone cancer, pancreatic cancer, skin cancer, cancer of the head or neck, cutaneous or intraocular malignant melanoma, uterine cancer, brain stem glioma, pituitary adenoma, epidermoid cancer, carcinoma of the cervix squamous cell cancer, carcinoma of the fallopian tubes, carcinoma of the endometrium, carcinoma of the vagina, sarcoma of soft tissue, cancer of the urethra, carcinoma of the vulva, cancer of the penis, cancer of the bladder, cancer of the kidney or ureter, carcinoma of the renal pelvis, spinal axis tumor, neoplasm of the central nervous system (CNS), primary CNS lymphoma, tumor angiogenesis, metastatic lesions of said cancers, or combinations thereof.

In embodiments, the multispecific molecules (or pharmaceutical composition) are administered in a manner appropriate to the disease to be treated or prevented. The quantity and frequency of administration will be determined by such factors as the condition of the patient, and the type and severity of the patient's disease. Appropriate dosages may be determined by clinical trials. For example, when "an effective amount" or "a therapeutic amount" is indicated, the precise amount of the pharmaceutical composition (or multispecific molecules) to be administered can be determined by a physician with consideration of individual differences in tumor size, extent of infection or metastasis, age, weight, and condition of the subject. In embodiments, the pharmaceutical composition described herein can be administered at a dosage of $10^4$ to $10^9$ cells/kg body weight, e.g., $10^5$ to $10^6$ cells/kg body weight, including all integer values within those ranges. In embodiments, the pharmaceutical composition described herein can be administered multiple times at these dosages. In embodiments, the pharmaceutical composition described herein can be administered using infusion techniques described in immunotherapy (see, e.g., Rosenberg et al., New Eng. J. of Med. 319:1676, 1988).

In embodiments, the multispecific molecules or pharmaceutical composition is administered to the subject parenterally. In embodiments, the cells are administered to the subject intravenously, subcutaneously, intratumorally, intranodally, intramuscularly, intradermally, or intraperitoneally. In embodiments, the cells are administered, e.g., injected, directly into a tumor or lymph node. In embodiments, the cells are administered as an infusion (e.g., as described in Rosenberg et al., New Eng. J. of Med. 319: 1676, 1988) or an intravenous push. In embodiments, the cells are administered as an injectable depot formulation. In embodiments, the subject is a mammal. In embodiments, the subject is a human, monkey, pig, dog, cat, cow, sheep, goat, rabbit, rat, or mouse. In embodiments, the subject is a human. In embodiments, the subject is a pediatric subject, e.g., less than 18 years of age, e.g., less than 17, 16, 15, 14, 13, 12, 11, 10, 9, 8, 7, 6, 5, 4, 3, 2, 1 or less years of age. In embodiments, the subject is an adult, e.g., at least 18 years of age, e.g., at least 19, 20, 21, 22, 23, 24, 25, 25-30, 30-35, 35-40, 40-50, 50-60, 60-70, 70-80, or 80-90 years of age.

Combination Therapies

The multispecific molecules disclosed herein can be used in combination with a second therapeutic agent or procedure.

In embodiments, the multispecific molecule and the second therapeutic agent or procedure are administered/performed after a subject has been diagnosed with a cancer, e.g., before the cancer has been eliminated from the subject. In embodiments, the multispecific molecule and the second therapeutic agent or procedure are administered/performed simultaneously or concurrently. For example, the delivery of one treatment is still occurring when the delivery of the second commences, e.g., there is an overlap in administration of the treatments. In other embodiments, the multispecific molecule and the second therapeutic agent or procedure are administered/performed sequentially. For example, the delivery of one treatment ceases before the delivery of the other treatment begins.

In embodiments, combination therapy can lead to more effective treatment than monotherapy with either agent alone. In embodiments, the combination of the first and second treatment is more effective (e.g., leads to a greater reduction in symptoms and/or cancer cells) than the first or second treatment alone. In embodiments, the combination therapy permits use of a lower dose of the first or the second treatment compared to the dose of the first or second treatment normally required to achieve similar effects when administered as a monotherapy. In embodiments, the combination therapy has a partially additive effect, wholly additive effect, or greater than additive effect.

In one embodiment, the multispecific molecule is administered in combination with a therapy, e.g., a cancer therapy (e.g., one or more of anti-cancer agents, immunotherapy, photodynamic therapy (PDT), surgery and/or radiation). The terms "chemotherapeutic," "chemotherapeutic agent," and "anti-cancer agent" are used interchangeably herein. The administration of the multispecific molecule and the therapy, e.g., the cancer therapy, can be sequential (with or without overlap) or simultaneous. Administration of the multispecific molecule can be continuous or intermittent during the course of therapy (e.g., cancer therapy). Certain therapies described herein can be used to treat cancers and non-cancerous diseases. For example, PDT efficacy can be enhanced in cancerous and non-cancerous conditions (e.g., tuberculosis) using the methods and compositions described herein (reviewed in, e.g., Agostinis, P. et al. (2011) *CA Cancer J. Clin.* 61:250-281).

Anti-Cancer Therapies

In other embodiments, the multispecific molecule is administered in combination with a low or small molecular weight chemotherapeutic agent. Exemplary low or small molecular weight chemotherapeutic agents include, but not limited to, 13-cis-retinoic acid (isotretinoin, ACCU-TANE®), 2-CdA (2-chlorodeoxyadenosine, cladribine, LEUSTATIN™), 5-azacitidine (azacitidine, VIDAZA®), 5-fluorouracil (5-FU, fluorouracil, ADRUCIL®), 6-mercaptopurine (6-MP, mercaptopurine, PURINETHOL®), 6-TG (6-thioguanine, thioguanine, THIOGUANINE TAB-LOID®), abraxane (paclitaxel protein-bound), actinomycin-D (dactinomycin, COSMEGEN®), alitretinoin (PAN-RETIN®), all-transretinoic acid (ATRA, tretinoin, VESANOID®), altretamine (hexamethylmelamine, HMM, HEXALEN®), amethopterin (methotrexate, methotrexate sodium, MTX, TREXALL™, RHEUMATREX®), amifostine (ETHYOL®), arabinosylcytosine (Ara-C, cytarabine, CYTOSAR-U®), arsenic trioxide (TRISENOX®), asparaginase (Erwinia L-asparaginase, L-asparaginase, ELSPAR®, KIDROLASE®), BCNU (carmustine, BiCNU®), bendamustine (TREANDA®), bexarotene (TARGRETIN®), bleomycin (BLENOXANE®), busulfan (BUSULFEX®, MYLERAN®), calcium leucovorin (Citrovorum Factor, folinic acid, leucovorin), camptothecin-11 (CPT-11, irinotecan, CAMPTOSAR®), capecitabine (XE-LODA®), carboplatin (PARAPLATIN®), carmustine wafer (prolifeprospan 20 with carmustine implant, GLIADEL® wafer), CCI-779 (temsirolimus, TORISEL®), CCNU (lomustine, CeeNU), CDDP (cisplatin, PLATINOL®, PLATI-NOL-AQ®), chlorambucil (leukeran), cyclophosphamide (CYTOXAN®, NEOSAR®), dacarbazine (DIC, DTIC, imidazole carboxamide, DTIC-DOME®), daunomycin (daunorubicin, daunorubicin hydrochloride, rubidomycin hydrochloride, CERUBIDINE®), decitabine (DACOGEN®), dexrazoxane (ZINECARD®), DHAD (mitoxantrone, NOVANTRONE®), docetaxel (TAXOTERE®), doxorubicin (ADRIAMYCIN®, RUBEX®), epirubicin (EL-LENCE™), estramustine (EMCYT®), etoposide (VP-16, etoposide phosphate, TOPOSAR®, VEPESID®, ETO-POPHOS®), floxuridine (FUDR®), fludarabine (FLU-DARA®), fluorouracil (cream) (CARAC™, EFUDEX®, FLUOROPLEX®), gemcitabine (GEMZAR®), hydroxyurea (HYDREA®, DROXIA™, MYLOCEL™), idarubicin (IDAMYCIN®), ifosfamide (IFEX®), ixabepilone (IXEMPRA™), LCR (leurocristine, vincristine, VCR, ONCOVIN®, VINCASAR PFS®), L-PAM (L-sarcolysin, melphalan, phenylalanine mustard, ALKERAN®), mechlorethamine (mechlorethamine hydrochloride, mustine, nitrogen mustard, MUSTARGEN®), mesna (MESNEX™), mitomycin (mitomycin-C, MTC, MUTAMYCIN®), nelarabine (ARRANON®), oxaliplatin (ELOXATIN™), paclitaxel (TAXOL®, ONXAL™), pegaspargase (PEG-L-asparaginase, ONCOSPAR®), PEMETREXED (ALIMTA®), pentostatin (NIPENT®), procarbazine (MATULANE®), streptozocin (ZANOSAR®), temozolomide (TEMO-DAR®), teniposide (VM-26, VUMON®), TESPA (thiophosphoamide, thiotepa, TSPA, THIOPLEX®), topotecan (HYCAMTIN®), vinblastine (vinblastine sulfate, vincaleukoblastine, VLB, ALKABAN-AQ®, VELBAN®), vinorelbine (vinorelbine tartrate, NAVELBINE®), and vorinostat (ZOLINZA®).

In another embodiment, the multispecific molecule is administered in conjunction with a biologic. Biologics useful in the treatment of cancers are known in the art and a binding molecule of the invention may be administered, for example, in conjunction with such known biologics. For example, the FDA has approved the following biologics for the treatment of breast cancer: HERCEPTIN® (trastuzumab, Genentech Inc., South San Francisco, Calif.; a humanized monoclonal antibody that has anti-tumor activity in HER2-positive breast cancer); FASLODEX® (fulvestrant, AstraZeneca Pharmaceuticals, LP, Wilmington, Del.; an estrogen-receptor antagonist used to treat breast cancer); ARIMIDEX® (anastrozole, AstraZeneca Pharmaceuticals, LP; a nonsteroidal aromatase inhibitor which blocks aromatase, an enzyme needed to make estrogen); Aromasin® (exemestane, Pfizer Inc., New York, N.Y.; an irreversible, steroidal aromatase inactivator used in the treatment of breast cancer); FEMARA® (letrozole, Novartis Pharmaceuticals, East Hanover, N.J.; a nonsteroidal aromatase inhibitor approved by the FDA to treat breast cancer); and NOLVADEX® (tamoxifen, AstraZeneca Pharmaceuticals, LP; a nonsteroidal antiestrogen approved by the FDA to treat breast cancer). Other biologics with which the binding molecules of the invention may be combined include: AVASTIN® (bevacizumab, Genentech Inc.; the first FDA-approved therapy designed to inhibit angiogenesis); and ZEVALIN® (ibritumomab tiuxetan, Biogen Idec, Cambridge, Mass.; a radiolabeled monoclonal antibody currently approved for the treatment of B-cell lymphomas).

In addition, the FDA has approved the following biologics for the treatment of colorectal cancer: AVASTIN®; ERBITUX® (cetuximab, ImClone Systems Inc., New York, N.Y., and Bristol-Myers Squibb, New York, N.Y.; is a monoclonal antibody directed against the epidermal growth factor receptor (EGFR)); GLEEVEC® (imatinib mesylate; a protein kinase inhibitor); and ERGAMISOL® (levamisole hydrochloride, Janssen Pharmaceutica Products, LP, Titusville, N.J.; an immunomodulator approved by the FDA in 1990 as an adjuvant treatment in combination with 5-fluorouracil after surgical resection in patients with Dukes' Stage C colon cancer).

For the treatment of lung cancer, exemplary biologics include TARCEVA® (erlotinib HCL, OSI Pharmaceuticals Inc., Melville, N.Y.; a small molecule designed to target the human epidermal growth factor receptor 1 (HER1) pathway).

For the treatment of multiple myeloma, exemplary biologics include VELCADE® Velcade (bortezomib, Millennium Pharmaceuticals, Cambridge Mass.; a proteasome inhibitor). Additional biologics include THALIDOMID® (thalidomide, Clegene Corporation, Warren, N.J.; an immunomodulatory agent and appears to have multiple actions, including the ability to inhibit the growth and survival of myeloma cells and anti-angiogenesis).

Additional exemplary cancer therapeutic antibodies include, but are not limited to, 3F8, abagovomab, adecatumumab, afutuzumab, alacizumab pegol, alemtuzumab (CAMPATH®, MABCAMPATH®), altumomab pentetate (HYBRI-CEAKER®), anatumomab mafenatox, anrukinzumab (IMA-638), apolizumab, arcitumomab (CEA-SCAN®), bavituximab, bectumomab (LYMPHOSCAN®), belimumab (BENLYSTA®, LYMPHOSTAT-B®), besilesomab (SCINTIMUN®), bevacizumab (AVASTIN®), bivatuzumab mertansine, blinatumomab, brentuximab vedotin, cantuzumab mertansine, capromab pendetide (PROSTASCINT®), catumaxomab (REMOVAB®), CC49, cetuximab (C225, ERBITUX®), citatuzumab bogatox, cixutumumab, clivatuzumab tetraxetan, conatumumab, dacetuzumab, denosumab (PROLIA®), detumomab, ecromeximab, edrecolomab (PANOREX®), elotuzumab, epitumomab cituxetan, epratuzumab, ertumaxomab (REXOMUN®), etaracizumab, farletuzumab, figitumumab, fresolimumab, galiximab, gemtuzumab ozogamicin (MYLOTARG®), girentuximab, glembatumumab vedotin, ibritumomab (ibritumomab tiuxetan, ZEVALIN®), igovomab (INDIMACIS-125®), intetumumab, inotuzumab ozogamicin, ipilimumab, iratumumab, labetuzumab (CEA-CIDE®), lexatumumab, lintuzumab, lucatumumab, lumiliximab, mapatumumab, matuzumab, milatuzumab, minretumomab, mitumomab, nacolomab tafenatox, naptumomab estafenatox, necitumumab, nimotuzumab (THERACIM®, THERALOC®), nofetumomab merpentan (VERLUMA®), ofatumumab (ARZERRA®), olaratumab, oportuzumab monatox, oregovomab (OVAREX®), panitumumab (VECTIBIX®), pemtumomab (THERAGYN®), pertuzumab (OMNITARG®), pintumomab, pritumumab, ramucirumab, ranibizumab (LUCENTIS®), rilotumumab, rituximab (MABTHERA®, RITUXAN®), robatumumab, satumomab pendetide, sibrotuzumab, siltuximab, sontuzumab, tacatuzumab tetraxetan (AFP-CIDE®), taplitumomab paptox, tenatumomab, TGN1412, ticilimumab (tremelimumab), tigatuzumab, TNX-650, tositumomab (BEXXAR®), trastuzumab (HERCEPTIN®), tremelimumab, tucotuzumab celmoleukin, veltuzumab, volociximab, votumumab (HUMASPECT®), zalutumumab (HUMAX-EGFR®), and zanolimumab (HUMAX-CD4®).

In other embodiments, the multispecific molecule is administered in combination with a viral cancer therapeutic agent. Exemplary viral cancer therapeutic agents include, but not limited to, vaccinia virus (vvDD-CDSR), carcinoembryonic antigen-expressing measles virus, recombinant vaccinia virus (TK-deletion plus GM-CSF), Seneca Valley virus-001, Newcastle virus, coxsackie virus A21, GL-ONC1, EBNA1 C-terminal/LMP2 chimeric protein-expressing recombinant modified vaccinia Ankara vaccine, carcinoembryonic antigen-expressing measles virus, G207 oncolytic virus, modified vaccinia virus Ankara vaccine expressing p53, OncoVEX GM-CSF modified herpes-simplex 1 virus, fowlpox virus vaccine vector, recombinant vaccinia prostate-specific antigen vaccine, human papillomavirus 16/18 L1 virus-like particle/AS04 vaccine, MVA-EBNA1/LMP2 Inj. vaccine, quadrivalent HPV vaccine, quadrivalent human papillomavirus (types 6, 11, 16, 18) recombinant vaccine (GARDASIL®), recombinant fowlpox-CEA(6D)/TRICOM vaccine; recombinant vaccinia-CEA(6D)-TRICOM vaccine, recombinant modified vaccinia Ankara-5T4 vaccine, recombinant fowlpox-TRICOM vaccine, oncolytic herpes virus NV1020, HPV L1 VLP vaccine V504, human papillomavirus bivalent (types 16 and 18) vaccine (CERVARIX®), herpes simplex virus HF10, Ad5CMV-p53 gene, recombinant vaccinia DF3/MUC1 vaccine, recombinant vaccinia-MUC-1 vaccine, recombinant vaccinia-TRICOM vaccine, ALVAC MART-1 vaccine, replication-defective herpes simplex virus type I (HSV-1) vector expressing human Preproenkephalin (NP2), wild-type reovirus, reovirus type 3 Dearing (REOLYSIN®), oncolytic virus HSV1716, recombinant modified vaccinia Ankara (MVA)-based vaccine encoding Epstein-Barr virus target antigens, recombinant fowlpox-prostate specific antigen vaccine, recombinant vaccinia prostate-specific antigen vaccine, recombinant vaccinia-B7.1 vaccine, rAd-p53 gene, Ad5-delta24RGD, HPV vaccine 580299, JX-594 (thymidine kinase-deleted vaccinia virus plus GM-CSF), HPV-16/18 L1/AS04, fowlpox virus vaccine vector, vaccinia-tyrosinase vaccine, MEDI-517 HPV-16/18 VLP AS04 vaccine, adenoviral vector containing the thymidine kinase of herpes simplex virus TK99UN, HspE7, FP253/Fludarabine, ALVAC(2) melanoma multi-antigen therapeutic vaccine, ALVAC-hB7.1, canarypox-hIL-12 melanoma vaccine, Ad-REIC/Dkk-3, rAd-IFN SCH 721015, TIL-Ad-INFg, Ad-ISF35, and coxsackievirus A21 (CVA21, CAVATAK®).

In other embodiments, the multispecific molecule is administered in combination with a nanopharmaceutical. Exemplary cancer nanopharmaceuticals include, but not limited to, ABRAXANE® (paclitaxel bound albumin nanoparticles), CRLX101 (CPT conjugated to a linear cyclodextrin-based polymer), CRLX288 (conjugating docetaxel to the biodegradable polymer poly (lactic-co-glycolic acid)), cytarabine liposomal (liposomal Ara-C, DEPOCYT™), daunorubicin liposomal (DAUNOXOME®), doxorubicin liposomal (DOXIL®, CAELYX®), encapsulated-daunorubicin citrate liposome (DAUNOXOME®), and PEG anti-VEGF aptamer (MACUGEN®).

In some embodiments, the multispecific molecule is administered in combination with paclitaxel or a paclitaxel formulation, e.g., TAXOL®, protein-bound paclitaxel (e.g., ABRAXANE®). Exemplary paclitaxel formulations include, but are not limited to, nanoparticle albumin-bound paclitaxel (ABRAXANE®, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., Biopolymers (2007) 87:225-230), and glucose-conjugated paclitaxel (e.g., 2'-paclitaxel methyl 2-glucopyranosyl succinate, see Liu et al., *Bioorganic & Medicinal Chemistry Letters* (2007) 17:617-620).

Exemplary RNAi and antisense RNA agents for treating cancer include, but not limited to, CALAA-01, siG12D LODER (Local Drug EluteR), and ALN-VSP02.

Other cancer therapeutic agents include, but not limited to, cytokines (e.g., aldesleukin (IL-2, Interleukin-2, PROLEUKIN®), alpha Interferon (IFN-alpha, Interferon alfa, INTRON® A (Interferon alfa-2b), ROFERON-A® (Interferon alfa-2a)), Epoetin alfa (PROCRIT®), filgrastim (G-CSF, Granulocyte—Colony Stimulating Factor, NEUPOGEN®), GM-CSF (Granulocyte Macrophage Colony Stimulating Factor, sargramostim, LEUKINE™), IL-11 (Interleukin-11, oprelvekin, NEUMEGA®), Interferon alfa-2b (PEG conjugate) (PEG interferon, PEG-INTRON™), and pegfilgrastim (NEULASTA™)), hormone therapy agents (e.g., aminoglutethimide (CYTADREN®), anastrozole (ARIMIDEX®), bicalutamide (CASODEX®), exemestane (AROMASIN®), fluoxymesterone (HALOTESTIN®), flutamide (EULEXIN®), fulvestrant (FASLODEX®), goserelin (ZOLADEX®), letrozole (FEMARA®), leuprolide (ELIGARD™, LUPRON®, LUPRON DEPOT®, VIADUR™), megestrol (megestrol acetate, MEGACE®), nilutamide (ANANDRON®, NILANDRON®), octreotide (octreotide acetate, SANDOSTATIN®, SANDOSTATIN LAR®), raloxifene (EVISTA®), romiplostim (NPLATE®), tamoxifen (NOVALDEX®), and toremifene (FARESTON®)), phospholipase A2 inhibitors (e.g., anagrelide (AGRYLIN®)), biologic response modifiers (e.g., BCG (THERACYS®, TICE®), and Darbepoetin alfa (ARANESP®)), target therapy agents (e.g., bortezomib (VELCADE®), dasatinib (SPRYCEL™), denileukin diftitox (ONTAK®), erlotinib (TARCEVA®), everolimus (AFINITOR®), gefitinib (IRESSA®), imatinib mesylate (STI-571, GLEEVEC™), lapatinib (TYKERB®), sorafenib (NEXAVAR®), and SU11248 (sunitinib, SUTENT®)), immunomodulatory and antiangiogenic agents (e.g., CC-5013 (lenalidomide, REVLIMID®), and thalidomide (THALOMID®)), glucocorticosteroids (e.g., cortisone (hydrocortisone, hydrocortisone sodium phosphate, hydrocortisone sodium succinate, ALA-CORT®, HYDROCORT ACETATE®, hydrocortone phosphate LANACORT®, SOLU-CORTEF®), decadron (dexamethasone, dexamethasone acetate, dexamethasone sodium phosphate, DEXASONE®, DIODEX®, HEXADROL®, MAXIDEX®), methylprednisolone (6-methylprednisolone, methylprednisolone acetate, methylprednisolone sodium succinate, DURALONE®, MEDRALONE®, MEDROL®, M-PREDNISOL®, SOLU-MEDROL®), prednisolone (DELTA-CORTEF®, ORAPRED®, PEDIAPRED®, PRELONE®), and prednisone (DELTASONE®, LIQUID PRED®, METICORTEN®, ORASONE®)), and bisphosphonates (e.g., pamidronate (AREDIA®), and zoledronic acid (ZOMETA®))

In some embodiments, the multispecific molecule is used in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., an antibody against VEGF, a VEGF trap, a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a RAF-1 inhibitor, a KIT inhibitor and a RET inhibitor. In some embodiments, the anti-cancer agent used in combination with the AHCM agent is selected from the group consisting of: axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951(tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074, nSorafenib Tosylate (Bay 43-9006), SU 5402, TSU-68(SU6668), vatalanib, XL880 (GSK1363089, EXEL-2880). Selected tyrosine kinase inhibitors are chosen from sunitinib, erlotinib, gefitinib, or sorafenib. In one embodiment, the tyrosine kinase inhibitor is sunitinib.

In one embodiment, the multispecific molecule is administered in combination with one of more of: an anti-angiogenic agent, or a vascular targeting agent or a vascular disrupting agent. Exemplary anti-angiogenic agents include, but are not limited to, VEGF inhibitors (e.g., anti-VEGF antibodies (e.g., bevacizumab); VEGF receptor inhibitors (e.g., itraconazole); inhibitors of cell proliferation and/or migration of endothelial cells (e.g., carboxyamidotriazole, TNP-470); inhibitors of angiogenesis stimulators (e.g., suramin), among others. A vascular-targeting agent (VTA) or vascular disrupting agent (VDA) is designed to damage the vasculature (blood vessels) of cancer tumors causing central necrosis (reviewed in, e.g., Thorpe, P. E. (2004) *Clin. Cancer Res. Vol.* 10:415-427). VTAs can be small-molecule. Exemplary small-molecule VTAs include, but are not limited to, microtubule destabilizing drugs (e.g., combretastatin A-4 disodium phosphate (CA4P), ZD6126, AVE8062, Oxi 4503); and vadimezan (ASA404).

Immune Checkpoint Inhibitors

In other embodiments, methods described herein comprise use of an immune checkpoint inhibitor in combination with the multispecific molecule. The methods can be used in a therapeutic protocol in vivo.

In embodiments, an immune checkpoint inhibitor inhibits a checkpoint molecule. Exemplary checkpoint molecules include but are not limited to CTLA4, PD1, PD-L1, PD-L2, TIM3, LAG3, CD160, 2B4, CD80, CD86, B7-H3 (CD276), B7-H4 (VTCN1), HVEM (TNFRSF14 or CD270), BTLA, KIR, MHC class I, MHC class II, GAL9, VISTA, BTLA, TIGIT, LAIR1, and A2aR. See, e.g., Pardoll. Nat. Rev. Cancer 12.4(2012):252-64, incorporated herein by reference.

In embodiments, the immune checkpoint inhibitor is a PD-1 inhibitor, e.g., an anti-PD-1 antibody such as Nivolumab, Pembrolizumab or Pidilizumab. Nivolumab (also called MDX-1106, MDX-1106-04, ONO-4538, or BMS-936558) is a fully human IgG4 monoclonal antibody that specifically inhibits PD1. See, e.g., U.S. Pat. No. 8,008,449 and WO2006/121168. Pembrolizumab (also called Lambrolizumab, MK-3475, MK03475, SCH-900475 or KEYTRUDA®; Merck) is a humanized IgG4 monoclonal antibody that binds to PD-1. See, e.g., Hamid, O. et al. (2013) *New England Journal of Medicine* 369 (2): 134-44, U.S. Pat. No. 8,354,509 and WO2009/114335. Pidilizumab (also called CT-011 or Cure Tech) is a humanized IgG1k monoclonal antibody that binds to PD1. See, e.g., WO2009/101611. In one embodiment, the inhibitor of PD-1 is an antibody molecule having a sequence substantially identical or similar thereto, e.g., a sequence at least 85%, 90%, 95% identical or higher to the sequence of Nivolumab, Pembrolizumab or Pidilizumab. Additional anti-PD1 antibodies, e.g., AMP 514 (Amplimmune), are described, e.g., in U.S. Pat. No. 8,609,089, US 2010028330, and/or US 20120114649.

In some embodiments, the PD-1 inhibitor is an immunoadhesin, e.g., an immunoadhesin comprising an extracellular/PD-1 binding portion of a PD-1 ligand (e.g., PD-L1 or PD-L2) that is fused to a constant region (e.g., an Fc region of an immunoglobulin). In embodiments, the PD-1 inhibitor is AMP-224 (B7-DCIg, e.g., described in WO2011/066342 and WO2010/027827), a PD-L2 Fc fusion soluble receptor that blocks the interaction between B7-H1 and PD-1.

In embodiments, the immune checkpoint inhibitor is a PD-L1 inhibitor, e.g., an antibody molecule. In some embodiments, the PD-L1 inhibitor is YW243.55.S70, MPDL3280A, MEDI-4736, MSB-0010718C, or MDX-1105. In some embodiments, the anti-PD-L1 antibody is MSB0010718C (also called A09-246-2; Merck Serono), which is a monoclonal antibody that binds to PD-L1. Exemplary humanized anti-PD-L1 antibodies are described, e.g., in WO2013/079174. In one embodiment, the PD-L1 inhibitor is an anti-PD-L1 antibody, e.g., YW243.55.S70. The YW243.55.S70 antibody is described, e.g., in WO 2010/077634. In one embodiment, the PD-L1 inhibitor is MDX-1105 (also called BMS-936559), which is described, e.g., in WO2007/005874. In one embodiment, the PD-L1 inhibitor is MDPL3280A (Genentech/Roche), which is a human Fc-optimized IgG1 monoclonal antibody against PD-L1. See, e.g., U.S. Pat. No. 7,943,743 and U.S Publication No.: 20120039906. In one embodiment, the inhibitor of PD-L1 is an antibody molecule having a sequence substantially identical or similar thereto, e.g., a sequence at least 85%, 90%, 95% identical or higher to the sequence of YW243.55.570, MPDL3280A, MEDI-4736, MSB-0010718C, or MDX-1105.

In embodiments, the immune checkpoint inhibitor is a PD-L2 inhibitor, e.g., AMP-224 (which is a PD-L2 Fc fusion soluble receptor that blocks the interaction between PD1 and B7-H1. See, e.g., WO2010/027827 and WO2011/066342.

In one embodiment, the immune checkpoint inhibitor is a LAG-3 inhibitor, e.g., an anti LAG-3 antibody molecule. In embodiments, the anti-LAG-3 antibody is BMS-986016 (also called BMS986016; Bristol-Myers Squibb). BMS-986016 and other humanized anti-LAG-3 antibodies are described, e.g., in US 2011/0150892, WO2010/019570, and WO2014/008218.

In embodiments, the immune checkpoint inhibitor is a TIM-3 inhibitor, e.g., anti-TIM3 antibody molecule, e.g., described in U.S. Pat. No. 8,552,156, WO 2011/155607, EP 2581113 and U.S Publication No.: 2014/044728.

In embodiments, the immune checkpoint inhibitor is a CTLA-4 inhibitor, e.g., anti-CTLA-4 antibody molecule. Exemplary anti-CTLA4 antibodies include Tremelimumab (IgG2 monoclonal antibody from Pfizer, formerly known as ticilimumab, CP-675,206); and Ipilimumab (also called MDX-010, CAS No. 477202-00-9). Other exemplary anti-CTLA-4 antibodies are described, e.g., in U.S. Pat. No. 5,811,097.

EXAMPLES

The following examples are intended to be illustrative, and are not meant in any way to be limiting.

Examples Directed to Multispecific Molecules and Uses Thereof

General Methods:
1. Construction of the Plasmids.
The DNA encoding the protein sequences was optimized for expression in *Cricetulus griseus*, synthesized, and cloned into the pcDNA3.4-TOPO (Life Technologies A14697) using Gateway cloning. All constructs contained an Ig Kappa leader sequence (SEQ ID NO: 84 ATGGAAA-CCGACACACTGCTGCTGTGGGTGCTGCTCTTGTGG-GTGCCAGGATCTACA GGA, SEQ ID NO 16: METD-TLLLWVLLLWVPGSTG). The nucleic acid sequences used are shown in Table 1.
2. Expression and Purification.
The plasmids were co-transfected into either Expi293 cells (Life Technologies A14527) or ExpiCHO cells (Life Technologies A29127). Transfections were performed using 1 mg of total DNA for a multispecific construct with a 1:1 knob to hole heavy chain ratio and 3:2 light chain to heavy chain ratio. When biotinylation was required, 250 μg of SEQ ID NO: 226 BirA was added per liter in addition to the multispecific construct DNA. Transfection in Expi293 cells was done using linear 25,000 Da polyethylenimine (PEI, Polysciences Inc 23966) in a 3:1 ratio with the total DNA. The DNA and PEI were each added to 50 mL of OptiMem (Life Technologies 31985088) medium and sterile filtered. The DNA and PEI were combined for 10 minutes and added to the Expi293 cells with a cell density of $1.8\text{-}2.8\times10^6$ cells/mL and a viability of at least 95%. The ExpiCHO transfection was performed according to the manufacturer's instructions. Expi293 cells were grown in a humidified incubator at 37° C. with 8% $CO_2$ for 5-7 days after transfection and ExpiCHO cells were grown for 14 days at 32° C. with 5% $CO_2$. The cells were pelleted by centrifugation at 4500×g and the supernatant was filtered through a 0.2 μm membrane. Protein A resin (GE 17-1279-03) was added to the filtered supernatant and incubated for 1-3 hours at room temperature. The resin was packed into a column, washed with 3×10 column volumes of Dulbecco's phosphate-buffered saline (DPBS, Life Technologies 14190-144). The bound protein was eluted from the column with 20 mM citrate, 100 mM NaCl, pH 2.9. When necessary, the proteins were further purified using ligand affinity and/or size exclusion chromatography on a Superdex 200 column with a running buffer of DPBS.

3. ELISA Assay.

ELISA assays were performed using either Pierce 96-well streptavidin coated high capacity plates (15500) or Nunc-Immuno 96-well maxisorp plates (Invitrogen 44-2404-21). The plates were washed with 1× phosphate buffered saline tween 20 (Pierce 28352) and then coated with 10 μg/mL of the capture protein. After incubating for 2 hours at room temperature with shaking, the plate was washed with 1×PBST and the molecule was added in rows A-G using a serial dilution of 1 μM-1 pM. The plate was incubated for 30 minutes, washed, and 100 μL of either peroxidase-conjugated affinipure goat anti-human IgG (109-035-008) or streptavidin-HRP (R&D Systems DY998) was added to each well. The plate was incubated for 30 minutes with shaking, washed, and 100 μL of 1-step Turbo TMB-ELISA substrate solution (Thermo Scientific 34022) was added to each well. The plate was incubated for 5 minutes, the reaction was stopped with 100 μL of 1 M HCl, and the plate was read using the absorbance at 450 nm on a SpectraMax i3x plate reader.

4. Cell-Killing Assay.

To assess the activity of the constructs produced, a BxPC3-luciferase cell-killing assay was performed. BxPC3 cells containing luciferase (Genecopia SCL-0012-HLG) were grown in RPMI 1640 (Gibco 11875119) and 10% fetal bovine serum (Gibco 10082147) with 1 μg/mL puromycin (Gibco A1113802). The cells were used to seed a 96-well plate with 15,000 cells per well. After incubating for a day, the media was removed and replaced with the serum-free media RPMI 1640 with 0.5% Pen/Strep (Gibco 15140122). PBMCs (C.T.L. Lot #LP_123) in the serum-free media were added to rows A-G of the 96-well plate at 450,000 cells/well. The compounds were added to columns, in triplicate, with concentrations ranging from 1 μM to 1 pM in rows A-F. The plates were incubated for 6 or 24 hours before measuring. Before proceeding with the cell-killing measurement, 120 μL was removed from each well and added to a 96-well low-binding protein plate. This left 80 μL in the plate, and 80 μL of Bright-Glo (Promega E2610) was added to each well. The plate was then read on a SpectraMax i3x plate reader.

5. Cytokine Release Assay.

For the cytokine release assay, the supernatant removed from the cell-killing plate was diluted 5-fold with the quansys wash buffer. The manufacturer's instructions were followed for the Quansys human IFNγ (Quansys 464649HU) singleplex assay kit. The plates were imaged on a BioRad ChemiDoc XRS+ and analyzed using the Quansys Q-view software.

Example 1

Multispecific molecule 1 containing a Fab arm targeting mesothelin and an IL2 effector arm, comprising of three distinct protein chains: SEQ ID:168, SEQ ID: 169, and SEQ ID: 170, was expressed by co-transfecting cells with SEQ ID NO: 116, SEQ ID NO: 118, and SEQ ID NO: 119. Multispecific molecule 1 was purified and a SDS-PAGE gel of the final product is shown in FIG. 21. FIG. 43 shows the size exclusion chromatogram of multispecific molecule 1. An ELISA performed with human mesothelin of SEQ ID NO: 181 gave an $EC_{50}$ of 112 pM (FIG. 48). FIG. 53 shows binding with human IL2 receptor α of SEQ ID NO: 182 was assessed and gave an $EC_{50}$ of 111 pM. The $EC_{50}$ in the cell-killing assay was 79 pM (FIG. 58). FIG. 59 shows the cytokine release data of IFNγ for multispecific molecule 1 in the assay.

Example 2

Multispecific molecule 2 containing a Fab arm targeting mesothelin, an IL2 effector arm, and an anti-NKp30 NK-cell engager, comprising of: SEQ ID: 174, SEQ ID: 169, SEQ ID: 170, was expressed by co-transfecting cells with SEQ ID NO: 117, SEQ ID NO: 118, and SEQ ID NO: 119. Multispecific molecule 2 was purified and a SDS-PAGE gel of the final product is shown in FIG. 22. An ELISA performed with human mesothelin of SEQ ID NO: 181 gave an $EC_{50}$ of 1.38 nM (FIG. 48). FIG. 53 shows binding with human IL2 receptor α of SEQ ID NO: 182 with an $EC_{50}$ of 154 pM. Binding with human NKp30 generated from SEQ ID NO: 180 gave an $EC_{50}$ of 230 nM (FIG. 55). The $EC_{50}$ in the cell-killing assay was 4.7 pM (FIG. 58). FIG. 59 shows the cytokine release data of IFNγ for multispecific molecule 2 in the assay.

Example 3

Multispecific molecule 3 containing a mesothelin targeting arm and an anti-NKp30 NK-cell engager, comprising of: SEQ ID NO: 174, SEQ ID NO: 169, and SEQ ID NO: 197, was expressed by co-transfecting cells with SEQ ID NO: 117, SEQ ID NO:118, and SEQ ID NO:125. Multispecific molecule 3 was purified and a SDS-PAGE gel of the final product is shown in FIG. 23. An ELISA performed with human mesothelin of SEQ ID NO: 181 gave an $EC_{50}$ of 152 pM (FIG. 48). Binding with human NKp30 generated from SEQ ID NO: 180 gave an $EC_{50}$ of 93.4 nM (FIG. 55). The $EC_{50}$ in the cell-killing assay was 5.9 pM (FIG. 58). FIG. 59 shows the cytokine release data of IFNγ for multispecific molecule 3 in the assay.

Example 4

Multispecific molecule 4 containing an IL2 effector arm, comprising of: SEQ ID: 176 and SEQ ID: 170, was expressed by co-transfecting cells with SEQ ID NO: 124 and SEQ ID NO:119. Multispecific molecule 4 was purified and a SDS-PAGE gel of the final product is shown in FIG. 24. FIG. 53 shows binding with human IL2 receptor α of SEQ ID NO: 182 was assessed and gave an $EC_{50}$ of 110 pM. The $EC_{50}$ in the cell-killing assay was 41 pM (FIG. 58). FIG. 59 shows the cytokine release data of IFNγ for multispecific molecule 4 in the assay.

Example 5

Multispecific molecule 5 containing a mesothelin targeting arm and a PDL1 targeting arm, comprising of: SEQ ID: 172, SEQ ID NO: 173, SEQ ID NO: 192, and SEQ ID: 171, was expressed by co-transfecting cells with SEQ ID NO:

122, SEQ ID NO: 123, SEQ ID NO: 135, and SEQ ID NO: 121. Multispecific molecule 5 was purified and a SDS-PAGE gel of the final product is shown in FIG. 25. FIG. 44 shows the size exclusion chromatogram of multispecific molecule 5. An ELISA performed with human mesothelin of SEQ ID NO: 181 gave an $EC_{50}$ of 163 nM (FIG. 49). An ELISA performed with human PDL1 of SEQ ID NO: 178 gave an $EC_{50}$ of 250 pM (FIG. 51). Multispecific molecule 5 had no significant effect in the cell-killing assay (FIG. 60).

Example 6

Multispecific molecule 6 containing a mesothelin targeting arm, a PDL1 targeting arm, and an IL2 effector arm, containing comprising of: SEQ ID: 172, SEQ ID NO: 173, SEQ ID NO: 177, and SEQ ID: 171, was expressed by co-transfecting cells with SEQ ID NO: 122, SEQ ID NO: 123, SEQ ID NO: 120, and SEQ ID NO: 121. Multispecific molecule 6 was purified and a SDS-PAGE gel of the final product is shown in FIG. 26. An ELISA performed with human mesothelin of SEQ ID NO: 181 gave an $EC_{50}$ of 13.1 nM (FIG. 49). An ELISA performed with human PDL1 of SEQ ID NO: 178 gave an $EC_{50}$ of 363 pM (FIG. 51). FIG. 54 shows binding with human IL2 receptor α of SEQ ID NO: 182 was assessed and gave an $EC_{50}$ of 156 pM. Multispecific molecule 6 displayed an $EC_{50}$ of 159 pM in the cell-killing assay shown in FIG. 60.

Example 7

Multispecific molecule 7 containing a mesothelin targeting arm, a PDL1 targeting arm, and an anti-NKp46 NK-cell engager, comprising of: SEQ ID: 193, SEQ ID: 173, SEQ ID NO: 192, and SEQ ID NO: 171, was expressed by co-transfecting cells with SEQ ID NO: 136, SEQ ID NO: 123, SEQ ID NO: 135, and SEQ ID NO: 121. Multispecific molecule 7 was purified and a SDS-PAGE gel of the final product is shown in FIG. 27. An ELISA performed with human mesothelin of SEQ ID NO: 181 gave an $EC_{50}$ of 2.37 nM (FIG. 49). An ELISA performed with human PDL1 of SEQ ID NO: 178 gave an $EC_{50}$ of 158 pM (FIG. 51). FIG. 56 shows binding with human NKp46 from SEQ ID NO: 179, with an $EC_{50}$ of 450 pM. Multispecific molecule 7 showed proliferation of cells in the cell-killing assay with an $EC_{50}$ of 15 pM (FIG. 60).

Example 8

Multispecific molecule 8 containing a mesothelin targeting arm, a PDL1 targeting arm, an IL2 effector arm, and an anti-NKp46 NK-cell engager, comprising of: SEQ ID: 193, SEQ ID NO: 173, SEQ ID NO: 192, and SEQ ID: 171, was expressed by co-transfecting cells with SEQ ID NO: 136, SEQ ID NO: 123, SEQ ID NO: 135, and SEQ ID NO: 121. Multispecific molecule 8 was purified and a SDS-PAGE gel of the final product is shown in FIG. 28. An ELISA performed with human mesothelin of SEQ ID NO: 181 gave an $EC_{50}$ of 1.77 nM (FIG. 49). An ELISA performed with human PDL1 of SEQ ID NO: 178 gave an $EC_{50}$ of 255 pM (FIG. 52). FIG. 54 shows binding with human IL2 receptor α of SEQ ID NO: 182 with an $EC_{50}$ of 84 pM. FIG. 57 shows binding with human NKp46 from SEQ ID NO: 179, with an $EC_{50}$ of 670 pM. Multispecific molecule 8 showed proliferation of cells in the cell-killing assay with an $EC_{50}$ of 44 pM (FIG. 60).

Example 9

Multispecific molecule 9 containing a mesothelin targeting arm, a PDL1 targeting arm, and an anti-NKp46 NK-cell engager, comprising of: SEQ ID: 193, SEQ ID: 173, SEQ ID NO: 192, and SEQ ID NO: 171, was expressed by co-transfecting cells with SEQ ID NO: 136, SEQ ID NO: 123, SEQ ID NO: 135, and SEQ ID NO: 121. Multispecific molecule 9 was purified and a SDS-PAGE gel of the final product is shown in FIG. 29. An ELISA performed with protein 1 of SEQ ID NO: 181 gave an $EC_{50}$ of 275 nM (FIG. 50). An ELISA performed with human PDL1 of SEQ ID NO: 178 gave an $EC_{50}$ of 124 pM (FIG. 51). FIG. 56 shows binding with human NKp46 from SEQ ID NO: 179, with an $EC_{50}$ of 6.2 nM. Multispecific molecule 9 showed proliferation of cells in the cell-killing assay with an $EC_{50}$ of 84 pM (FIG).

Example 10

Multispecific molecule 10 containing a mesothelin targeting arm, a PDL1 targeting arm, an IL2 effector arm, and an anti-NKp46 NK-cell engager, comprising of: SEQ ID: 193, SEQ ID NO: 173, SEQ ID NO: 192, and SEQ ID: 171, was expressed by co-transfecting cells with SEQ ID NO: 136, SEQ ID NO: 123, SEQ ID NO: 135, and SEQ ID NO: 121. Multispecific molecule 10 was purified and a SDS-PAGE gel of the final product is shown in FIG. 30. An ELISA performed with human mesothelin of SEQ ID NO: 181 gave an $EC_{50}$ of 263 nM (FIG. 50). An ELISA performed with human PDL1 of SEQ ID NO: 178 gave an $EC_{50}$ of 1.91 nM (FIG. 52). FIG. 54 shows binding with human IL2 receptor α of SEQ ID NO: 182 with an $EC_{50}$ of 88 pM. FIG. 57 shows binding with human NKp46 from SEQ ID NO: 179, with an $EC_{50}$ of 1.8 nM. Multispecific molecule 10 showed proliferation of cells in the cell-killing assay with an $EC_{50}$ of 35 pM (FIG. 61).

Example 11

Multispecific molecule 11 containing a mesothelin targeting arm, a PDL1 targeting arm, and an anti-NKp46 NK-cell engager, comprising of: SEQ ID: 193, SEQ ID: 173, SEQ ID NO: 192, and SEQ ID NO: 171, was expressed by co-transfecting cells with SEQ ID NO: 136, SEQ ID NO: 123, SEQ ID NO: 135, and SEQ ID NO: 121. Multispecific molecule 11 was purified and a SDS-PAGE gel of the final product is shown in FIG. 31. FIG. 45 shows the size exclusion chromatogram of multispecific molecule 11. An ELISA performed with human PDL1 of SEQ ID NO: 178 gave an $EC_{50}$ of 206 pM (FIG. 52). FIG. 56 shows binding with human NKp46 from SEQ ID NO: 179, with an $EC_{50}$ of 8.7 nM. Multispecific molecule 11 showed proliferation of cells in the cell-killing assay with an $EC_{50}$ of 119 pM (FIG. 62).

Example 12

Multispecific molecule 12 containing a mesothelin targeting arm, a PDL1 targeting arm, an IL2 effector arm, and an anti-NKp46 NK-cell engager, comprising of: SEQ ID: 193, SEQ ID NO: 173, SEQ ID NO: 192, and SEQ ID: 171, was expressed by co-transfecting cells with SEQ ID NO: 136, SEQ ID NO: 123, SEQ ID NO: 135, and SEQ ID NO: 121. Multispecific molecule 12 was purified and a SDS-PAGE gel of the final product is shown in FIG. 32. FIG. 26 shows the size exclusion chromatogram of multispecific molecule 12. An ELISA performed with human mesothelin of SEQ ID NO: 181 gave an $EC_{50}$ of 216 nM (FIG. 50). An ELISA performed with human PDL1 of SEQ ID NO: 178 gave an $EC_{50}$ of 1.82 nM (FIG. 52). FIG. 54 shows binding with human IL2 receptor α of SEQ ID NO: 182 with an $EC_{50}$ of 107 pM. FIG. 57 shows binding with human NKp46 from SEQ ID NO: 179, with an $EC_{50}$ of 19.3 nM. Multispecific molecule 12 showed proliferation of cells in the cell-killing assay with an $EC_{50}$ of 16 pM (FIG. 62).

Example 13

Multispecific molecule 13 containing a HER3 targeting arm, an IGF1R targeting arm, and an IL2 effector arm, comprising of: SEQ ID: 187, SEQ ID NO: 185, and SEQ ID: 184, was expressed by co-transfecting cells with SEQ ID NO: DNA BH022, SEQ ID NO: 128, and SEQ ID NO: 127. Multispecific molecule 13 was purified and a SDS-PAGE gel of the final product is shown in FIG. 33. FIG. 47 shows the size exclusion chromatogram of multispecific molecule 13. An ELISA of multispecific molecule 13 with human IL2Rα from SEQ ID NO: 182 gave an $EC_{50}$ of 85 pM (FIG. 65). The $EC_{50}$ in the cell-killing assay was 14 pM (FIG. 67). FIG. 68 shows the cytokine release data of IFNγ for multispecific molecule 13 in the assay.

Example 14

Multispecific molecule 14 containing a HER3 targeting arm, an IGF1R targeting arm, and an anti-NKp46 NK-cell engager, comprising of: SEQ ID: 188, SEQ ID NO: 183, and SEQ ID: 184, was expressed by co-transfecting cells with SEQ ID NO: 131, SEQ ID NO: 126, and SEQ ID NO: 127. Multispecific molecule 14 was purified and a SDS-PAGE gel of the final product is shown in FIG. 34. FIG. 66 shows binding with human NKp46 from SEQ ID NO: 179 with an $EC_{50}$ of 2.3 nM. The $EC_{50}$ in the cell-killing assay was 100 pM (FIG. 67). FIG. 68 shows the cytokine release data of IFNγ for multispecific molecule 14 in the assay.

Example 15

Multispecific molecule 15 containing a HER3 targeting arm, an IGF1R targeting arm, and a CD3 targeting arm, comprising of: SEQ ID: 189, SEQ ID NO: 183, and SEQ ID: 184, was expressed by co-transfecting cells with SEQ ID NO: 132, SEQ ID NO: 126, and SEQ ID NO: 127. Multispecific molecule 15 was purified and a SDS-PAGE gel of the final product is shown in FIG. 35. The $EC_{50}$ in the cell-killing assay was 277 pM (FIG. 69). FIG. 70 shows the cytokine release data of IFNγ for multispecific molecule 15 in the assay.

Example 16

Multispecific molecule 16 containing a HER3 targeting arm, an IGF1R targeting arm, an anti-NKp46 NK-cell engager, and an IL2 effector arm, comprising of: SEQ ID: 188, SEQ ID NO: 185, and SEQ ID: 184, was expressed by co-transfecting cells with SEQ ID NO: 131, SEQ ID NO: 128, and SEQ ID NO: 127. Multispecific molecule 16 was purified and a SDS-PAGE gel of the final product is shown in FIG. 36. An ELISA of multispecific molecule 16 with human IL2Rα from SEQ ID NO: 182 gave an $EC_{50}$ of 167 pM (FIG. 65). The $EC_{50}$ in the cell-killing assay was 330 pM (FIG. 67). FIG. 68 shows the cytokine release data of IFNγ for multispecific molecule 16 in the assay.

Example 17

Multispecific molecule 17 containing a HER3 targeting arm, an IGF1R targeting arm, a CD3 targeting arm, and an IL2 effector arm, comprising of: SEQ ID: 189, SEQ ID NO: 185, and SEQ ID: 184, was expressed by co-transfecting cells with SEQ ID NO: 132, SEQ ID NO: 128, and SEQ ID NO: 127. Multispecific molecule 17 was purified and a SDS-PAGE gel of the final product is shown in FIG. 37. An ELISA of multispecific molecule 17 with human IL2Rα from SEQ ID NO: 182 gave an $EC_{50}$ of 116 pM (FIG. 65). The $EC_{50}$ in the cell-killing assay was 18 pM (FIG. 69). FIG. 70 shows the cytokine release data of IFNγ for multispecific molecule 17 in the assay.

Example 18

Multispecific molecule 18 containing a HER3 targeting arm and an IGF1R targeting arm, comprising of: SEQ ID: 187, SEQ ID NO: 183, and SEQ ID: 184, was expressed by co-transfecting cells with SEQ ID NO: DNA BH022, SEQ ID NO: 126, and SEQ ID NO: 127. Multispecific molecule 18 was purified and a SDS-PAGE gel of the final product is shown in FIG. 38. The $EC_{50}$ in the cell-killing assay was 28 pM (FIG. 67). FIG. 68 shows the cytokine release data of IFNγ for multispecific molecule 18 in the assay.

Example 19

Multispecific molecule 19 containing a HER3 targeting arm, an IGF1R targeting arm, and an IL7 effector arm, comprising of: SEQ ID: 187, SEQ ID NO: 186, and SEQ ID: 184, was expressed by co-transfecting cells with SEQ ID NO: 130, SEQ ID NO: 129, and SEQ ID NO: 127. Multispecific molecule 19 was purified and a SDS-PAGE gel of the final product is shown in FIG. 39.

Example 20

Multispecific molecule 20 containing a HER3 targeting arm, an IGF1R targeting arm, a CD3 targeting arm, and an IL7 effector arm, comprising of: SEQ ID: 189, SEQ ID NO: 186, and SEQ ID: 184, was expressed by co-transfecting cells with SEQ ID NO: 132, SEQ ID NO: 129, and SEQ ID NO: 127. Multispecific molecule 20 was purified and a SDS-PAGE gel of the final product is shown in FIG. 40. The $EC_{50}$ in the cell-killing assay was 445 pM (FIG. 71). FIG. 72 shows the cytokine release data of IFNγ for multispecific molecule 20 in the assay.

Example 21

Multispecific molecule 21 containing a HER3 targeting arm, an IGF1R targeting arm, an anti-NKp46 NK-cell engager, and an IL7 effector arm, comprising of: SEQ ID: 190, SEQ ID NO: 169, SEQ ID NO: 186, and SEQ ID: 184, was expressed by co-transfecting cells with SEQ ID NO: 133, SEQ ID NO: 118, SEQ ID NO: 128, and SEQ ID NO: 127. Multispecific molecule 21 was purified and a SDS-PAGE gel of the final product is shown in FIG. 41. FIG. 46 shows binding with human NKp46 from SEQ ID NO: 179 with an $EC_{50}$ of 1.3 nM. The $EC_{50}$ in the cell-killing assay was 770 pM (FIG. 73). FIG. 74 shows the cytokine release data of IFNγ for multispecific molecule 21 in the assay.

Example 22

Multispecific molecule 22 containing a mesothelin targeting arm, a PDL1 targeting arm with an IL2 effector, and an anti-NKp46 NK-cell engager, comprising of: SEQ ID: 190, SEQ ID NO: 169, SEQ ID NO: 192, and SEQ ID: 191, was expressed by co-transfecting cells with SEQ ID NO: 133, SEQ ID NO: 118, SEQ ID NO: 135, and SEQ ID NO: 134. Multispecific molecule 22 was purified and a SDS-PAGE gel of the final product is shown in FIG. 42. An ELISA of multispecific molecule 22 with human mesothelin from SEQ ID NO: 181 gave an $EC_{50}$ of 310 pM (FIG. 63). FIG. 44 displays the data for multispecific molecule 22 binding to human PDL1 from SEQ ID NO: 178 with an $EC_{50}$ of 8 pM. An ELISA of multispecific molecule 22 with human IL2Rα from SEQ ID NO: 182 gave an $EC_{50}$ of 8.2 nM (FIG. 65). FIG. 46 shows binding with human NKp46 from SEQ ID NO: 179 with an $EC_{50}$ of 2.4 nM. The $EC_{50}$ in the cell-killing assay was 995 pM (FIG. 75). FIG. 76 shows the cytokine release data of IFNγ for multispecific molecule 22 in the assay.

Example 23

Multispecific molecule 23 containing a mesothelin targeting arm and a PDL1 targeting arm comprising of SEQ ID NO:168, SEQ ID NO: 169, SEQ ID NO: 192, and SEQ ID NO: 171, was expressed by co-transfecting cells with SEQ ID NO: 116, SEQ ID NO: 118, SEQ ID NO: 135, and SEQ ID NO: 121. Multispecific molecule 23 was purified and used in the cell-killing assay shown in FIG. 75, giving an $EC_{50}$ of 250 pM. FIG. 76 shows the cytokine release data of IFNγ for multispecific molecule 23 in the assay.

Examples Directed to Multispecific Molecules Comprising a Stromal Modifying Moiety and Uses Thereof General Methods:
1. Construction of the Plasmids.

The DNA encoding the protein sequences was optimized for expression in *Cricetulus griseus*, synthesized, and cloned into the pcDNA3.4-TOPO (Life Technologies A14697) using Gateway cloning. All constructs contained an Ig Kappa leader sequence (SEQ ID NO: 84 ATGGAAACCG-ACACACTGCTGCTGTGGGTGCTGCTCTTGTGGGT-GCCAGGATCTACA GGA, SEQ ID NO:64 METDTLLL-WVLLLWVPGSTG). The nucleic acid sequences used are shown in Table 10.

2. Expression and Purification.

The plasmids were co-transfected into either Expi293 cells (Life Technologies A14527) or ExpiCHO cells (Life Technologies A29127). Transfection were performed using 1 mg of total DNA for a multispecific construct with a 1:1 knob to hole heavy chain ratio and 3:2 light chain to heavy chain ratio. When biotinylation was required, 250 μg of SEQ ID:144 226 BirA was added per liter in addition to the multispecific construct DNA. Transfection in Expi293 cells was done using linear 25,000 Da polyethylenimine (PEI, Polysciences Inc 23966) in a 3:1 ratio with the total DNA. The DNA and PEI were each added to 50 mL of OptiMem (Life Technologies 31985088) medium and sterile filtered. The DNA and PEI were combined for 10 minutes and added to the Expi293 cells with a cell density of $1.8\text{-}2.8\times10^{6}$ cells/mL and a viability of at least 95%. The ExpiCHO transfection was performed according to the manufacturer's instructions. Expi293 cells were grown in a humidified incubator at 37° C. with 8% $CO_2$ for 5-7 days after transfection and ExpiCHO cells were grown for 14 days at 32° C. with 5% $CO_2$. The cells were pelleted by centrifugation at 4500×g and the supernatant was filtered through a 0.2 μm membrane. Protein A resin (GE 17-1279-03) was added to the filtered supernatant and incubated for 1-3 hours at room temperature. The resin was packed into a column, washed with 3×10 column volumes of Dulbecco's phosphate-buffered saline (DPBS, Life Technologies 14190-144). The bound protein was eluted from the column with 20 mM citrate, 100 mM NaCl, pH 2.9. When necessary, the proteins were further purified using ligand affinity and/or size exclusion chromatography on a Superdex 200 column with a running buffer of DPBS.

3. ELISA Assay.

ELISA assays were performed using either Pierce 96-well streptavidin coated high capacity plates (15500) or Nunc-Immuno 96-well maxisorp plates (Invitrogen 44-2404-21). The plates were washed with 1× phosphate buffered saline tween 20 (Pierce 28352) and then coated with 10 μg/mL of the capture protein. After incubating for 2 hours at room temperature with shaking, the plate was washed with 1×PBST and the molecule was added in rows A-G using a serial dilution of 1 μM-1 pM. The plate was incubated for 30 minutes, washed, and 100 μL of either peroxidase-conjugated affinipure goat anti-human IgG (109-035-008) or streptavidin-HRP (R&D Systems DY998) was added to each well. The plate was incubated for 30 minutes with shaking, washed, and 100 μL of 1-step Turbo TMB-ELISA substrate solution (Thermo Scientific 34022) was added to each well. The plate was incubated for 5 minutes, the reaction was stopped with 100 μL of 1 M HCl, and the plate was read using the absorbance at 450 nm on a SpectraMax i3x plate reader.

4. Cell-Killing Assay.

To assess the activity of the constructs produced, a BxPC3-luciferase cell-killing assay was performed. BxPC3 cells containing luciferase (Genecopia SCL-0012-HLG) were grown in RPMI 1640 (Gibco 11875119) and 10% fetal bovine serum (Gibco 10082147) with 1 μg/mL puromycin (Gibco A1113802). The cells were used to seed a 96-well plate with 15,000 cells per well. After incubating for a day, the media was removed and replaced with the serum-free media RPMI 1640 with 0.5% Pen/Strep (Gibco 15140122). PBMCs (C.T.L. Lot #LP_123) in the serum-free media were added to rows A-G of the 96-well plate at 450,000 cells/well. The compounds were added to columns, in triplicate, with concentrations ranging from 1 μM to 10 pM in rows A-F. The plates were incubated for 6 or 24 hours before measuring. Before proceeding with the cell-killing measurement, 120 μL was removed from each well and added to a 96-well low-binding protein plate. This left 80 μL in the plate, and 80 μL of Bright-Glo (Promega E2610) was added to each well. The plate was then read on a SpectraMax i3x plate reader.

5. Cytokine Release Assay.

For the cytokine release assay, the supernatant removed from the cell-killing plate was diluted 5-fold with the quansys wash buffer. The manufacturer's instructions were followed for the Quansys human IFNγ (Quansys 464649HU) singleplex assay kit. The plates were imaged on a BioRad ChemiDoc XRS+ and analyzed using the Quansys Q-view software.

6. Turbidimetric Hyaluronidase Enzyme Assay.

To test hyaluronidase activity, enzyme assays were performed as described previously (Dorfman, A., Ott, M. L. A Turbidimetric Method for the Assay of Hyaluronidase, *Journal of Biological Chemistry*, 1948). A stock solution of hyaluronic acid (Sigma 53747) was prepared at 1 mg/mL in 300 mM sodium phosphate, pH 5.35. The hyaluronidase-containing constructs were diluted to 1 mg/mL in 20 mM sodium phosphate, pH 7.0, 77 mM sodium chloride, 0.01% bovine serum albumin (Sigma A6003). Enzyme constructs from 0.01 mg/mL to 1 mg/mL were combined with 1 mg/mL hyaluronic acid and incubated at 37° C. for 45 minutes. An acidified BSA solution (24 mM sodium acetate, 79 mM acetic acid, 0.1% bovine serum albumin, pH 3.75) was then added to the enzyme and substrate. After incubating for 10 minutes at room temperature, the activity was measured with the absorbance at 540 nm. Hyaluronidase activity is seen as a decrease in absorbance, as the enzyme breaks down the hyaluronic acid.

7. Hyaluronidase Zymogram.

To further demonstrate hyaluronidase activity, a 12% SDS-PAGE gel was made containing 0.1 mg/mL hyaluronic acid (Sigma 53747). The constructs were run on the gel and then the gel was incubated in 3% Triton X-100 (Sigma 93443) for one hour. The gel was then incubated in assay buffer (20 mM citrate, 150 mM sodium chloride, pH 3.5) for 16 hours at 37° C. The gel was stained for hyaluronidase activity using 0.5% Alcian Blue (Sigma B8438), which stains hyaluronic acid blue and leaves clear spots where the enzyme degraded hyaluronic acid.

8. Gelatinase a Enzyme Assay.

Enzymatic activity of constructs containing MMP-2 was determined using the EnzChek gelatinase/collagenase assay kit (Molecular Probes E-12055), according to the manufacturer's instructions.

Example 24

Multispecific molecule 24 containing Fab arms targeting FAP and a hyaluronidase arm, comprising of three distinct protein chains: SEQ ID: 214, SEQ ID: 215, and SEQ ID: 219, was expressed by co-transfecting cells with SEQ ID NO: 202, SEQ ID NO:203, and SEQ ID NO: 207. Multispecific molecule 23 was purified and a SDS-PAGE gel of the final product is shown in FIG. 77. The size exclusion chromatogram of multispecific molecule 23 is shown in FIG. 86. An ELISA was performed with human FAP generated from SEQ ID NO: 225 and gave an $EC_{50}$ of 144 nM (FIG. 94). FIG. 98 demonstrates that multispecific molecule 24 has hyaluronidase activity. The presence of white bands on the blue background in the hyaluronidase zymogram (FIG. 100) further demonstrates hyaluronidase activity of multispecific molecule 24.

Example 25

Multispecific molecule 25 containing Fab arms targeting FAP, an IL2 effector arm, and a hyaluronidase arm, comprising of: SEQ ID: 218, SEQ ID: 215, SEQ ID: 219, was expressed by co-transfecting cells with SEQ ID NO: 206, SEQ ID NO: 203, and SEQ ID NO: 207. Multispecific molecule 24 was purified and a SDS-PAGE gel of the final product is shown in FIG. 78. The size exclusion chromatogram of multispecific molecule 24 is shown in FIG. 87. An ELISA was performed with human FAP generated from SEQ ID NO: 225 and gave an $EC_{50}$ of 128 nM (FIG. 94). FIG. 781 shows binding of multispecific molecule 25 to human IL2Ra (generated from SEQ ID NO: 182) with an $EC_{50}$ of 101 nM. FIG. 98 demonstrates that multispecific molecule 25 has hyaluronidase activity. The presence of white bands on the blue background in the hyaluronidase zymogram (FIG. 100) further demonstrates hyaluronidase activity of multispecific molecule 25.

Example 26

Multispecific molecule 26 containing a FAP targeting arm and a hyaluronidase arm, comprising of: SEQ ID NO: 214, SEQ ID NO: 215, and SEQ ID NO: 224, was expressed by co-transfecting cells with SEQ ID NO: 202, SEQ ID NO:203, and SEQ ID NO:212. Multispecific molecule 25 was purified and a SDS-PAGE gel of the final product is shown in FIG. 79. The size exclusion chromatogram of multispecific molecule 25 is shown in FIG. 88. An ELISA was performed with human FAP generated from SEQ ID NO: 225 and gave an $EC_{50}$ of 18.5 nM (FIG. 94). FIG. 98 demonstrates that multispecific molecule 26 has hyaluronidase activity. The presence of white bands on the blue background in the hyaluronidase zymogram (FIG. 100) further demonstrates hyaluronidase activity of multispecific molecule 26.

Example 27

Multispecific molecule 27 containing a PDL1 targeting arm, a FAP targeting arm, and a hyaluronidase arm, comprising of: SEQ ID: 220, SEQ ID: 171, SEQ ID NO: 219, and SEQ ID NO: 215, was expressed by co-transfecting cells with SEQ ID NO: 121, SEQ ID NO: 207, and SEQ ID NO: 208. Multispecific molecule 26 was purified and a SDS-PAGE gel of the final product is shown in FIG. 80. An ELISA performed with human PDL1 of SEQ ID NO: 178 gave an $EC_{50}$ of 52 pM (FIG. 93). An ELISA was performed with human FAP generated from SEQ ID NO: 225 and gave an $EC_{50}$ of 44 nM (FIG. 94). FIG. 99 demonstrates that multispecific molecule 27 has hyaluronidase activity. The presence of white bands on the blue background in the hyaluronidase zymogram (FIG. 100) further demonstrates hyaluronidase activity of multispecific molecule 27.

Example 28

Multispecific molecule 28 containing a PDL1 targeting arm, a FAP targeting arm, an IL2 effector arm, and a hyaluronidase arm, comprising of: SEQ ID: 221, SEQ ID: 171, SEQ ID NO: 219, and SEQ ID NO: 215, was expressed by co-transfecting cells with SEQ ID NO: 209, SEQ ID NO: 121, SEQ ID NO: 207, and SEQ ID NO: 208. Multispecific molecule 27 was purified and a SDS-PAGE gel of the final product is shown in FIG. 81. The size exclusion chromatogram of multispecific molecule 27 is shown in FIG. 90. An ELISA performed with human PDL1 of SEQ ID NO: 178 gave an $EC_{50}$ of 0.207 nM (FIG. 93). An ELISA was performed with human FAP generated from SEQ ID NO: 225 and gave an $EC_{50}$ of 69 nM (FIG. 95). FIG. 97 shows binding of multispecific molecule 27 to human IL2Rα (generated from SEQ ID NO: 182) with an $EC_{50}$ of 97 nM. FIG. 99 demonstrates that multispecific molecule 28 has hyaluronidase activity. The presence of white bands on the blue background in the hyaluronidase zymo gram (FIG. 100) further demonstrates hyaluronidase activity of multispecific molecule 28.

Example 29

Multispecific molecule 29 containing a PDL1 targeting arm, an anti-NKp46 NK-cell engager, an IL2 effector arm, and a hyaluronidase arm, comprising of: SEQ ID: 221, SEQ ID: 171, SEQ ID NO: 222, and SEQ ID NO: 223, was expressed by co-transfecting cells with SEQ ID NO: 209, SEQ ID NO: 121, SEQ ID NO: 210, and SEQ ID NO: 211. Multispecific molecule 28 was purified and a SDS-PAGE gel of the final product is shown in FIG. 82. The size exclusion chromatogram of multispecific molecule 28 is shown in FIG. 91. An ELISA performed with human PDL1 of SEQ ID NO: 178 gave an EC$_{50}$ of 866 pM (FIG. 93). An ELISA with human NKp46 from SEQ ID NO: 179 gave an EC$_{50}$ of 126 pM (FIG. 96). FIG. 97 shows binding of multispecific molecule 6 to human IL2Rα (generated from SEQ ID NO: 182) with an EC$_{50}$ of 48 nM. FIG. 99 demonstrates that multispecific molecule 29 has hyaluronidase activity. The presence of white bands on the blue background in the hyaluronidase zymogram (FIG. 100) further demonstrates hyaluronidase activity of multispecific molecule 29.

Example 30

Multispecific molecule 30 containing FAP targeting arms and a gelatinase arm, comprising of: SEQ ID: 214, SEQ ID: 215, and SEQ ID NO: 216, was expressed by co-transfecting cells with SEQ ID NO: 202, SEQ ID NO: 203, and SEQ ID NO: 207. Multispecific molecule 29 was purified and a SDS-PAGE gel of the final product is shown in FIG. 83. The size exclusion chromatogram of multispecific molecule 30 is shown in FIG. 92. An ELISA was performed with human FAP generated from SEQ ID NO: 225 and gave an EC$_{50}$ of 385 nM (FIG. 95). FIG. 101 demonstrates that multispecific molecule 30 has collagenase activity.

Example 31

Multispecific molecule 31 containing a FAP targeting arm and a gelatinase arm, comprising of: SEQ ID: 214, SEQ ID: 215, and SEQ ID NO: 217, was expressed by co-transfecting cells with SEQ ID NO: 202, SEQ ID NO: 203, and SEQ ID NO: D205. Multispecific molecule 30 was purified and a SDS-PAGE gel of the final product is shown in FIG. 84. The size exclusion chromatogram of multispecific molecule 31 is shown in FIG. 93. An ELISA was performed with human FAP generated from SEQ ID NO: 225 and gave an EC$_{50}$ of 466 nM (FIG. 95). FIG. 101 demonstrates that multispecific molecule 31 has collagenase activity.

Example 32

Multispecific molecule 32 containing a PDL1 targeting arm, a FAP targeting arm, an IL2 effector arm, and a gelatinase arm, comprising of: SEQ ID: 221, SEQ ID: 171, SEQ ID NO: 216, and SEQ ID NO: 215, was expressed by co-transfecting cells with SEQ ID NO: 209, SEQ ID NO: 121, SEQ ID NO: 204, and SEQ ID NO: 203. Multispecific molecule 31 was purified and a SDS-PAGE gel of the final product is shown in FIG. 85. An ELISA performed with human PDL1 of SEQ ID NO: 178 gave an EC$_{50}$ of 155 pM (FIG. 93). An ELISA was performed with human FAP generated from SEQ ID NO: 225 and gave an EC$_{50}$ of 85 nM (FIG. 95). FIG. 97 shows binding of multispecific molecule 32 to human IL2Rα (generated from SEQ ID NO: 182) with an EC$_{50}$ of 36 nM. FIG. 101 demonstrates that multispecific molecule 32 has collagenase activity.

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

---

We claim:

1. A multispecific or multifunctional molecule polypeptide, comprising:
   (i) a first tumor-targeting moiety comprising a first antibody molecule that binds to a first cancer antigen;
   (ii) a second tumor-targeting moiety comprising a second antibody molecule that binds to a second cancer antigen;
   (iii) a third antibody molecule that binds to NKp30 or NKp46; and
   (iv) a cytokine molecule selected from the group consisting of interleukin-2 (IL-2) or a functional variant thereof, interleukin-7 (IL-7) or a functional variant thereof, interleukin-12 (IL-12) or a functional variant thereof, interleukin-15 (IL-15) or a functional variant thereof, interleukin-18 (IL-18) or a functional variant thereof, interleukin-21 (IL-21) or a functional variant thereof, and interferon gamma or a functional variant thereof,
   wherein the multispecific or multifunctional molecule polypeptide comprises:
   (1) (1-a) a first non-contiguous polypeptide comprising, in the N-to-C orientation, the first tumor-targeting moiety comprising a VH-CH1 of a Fab molecule, connected to the cytokine molecule or the third antibody molecule that binds to NKp30 or NKp46; and
   (1-b) a second non-contiguous polypeptide comprising, in the N-to-C orientation, a VL-CL of the Fab molecule of prong (1-a);
   (2) (2-a) a first non-contiguous polypeptide comprising, in the N-to-C orientation, the first tumor-targeting moiety comprising a VH-CH1 of a Fab molecule, connected to a first domain that promotes association between the first non-contiguous polypeptide and a second non-contiguous polypeptide;
   (2-b) the second non-contiguous polypeptide comprising, in the N-to-C orientation, the cytokine molecule or the third antibody molecule that binds to NKp30 or NKp46, connected to a second domain that promotes association between the first non-contiguous polypeptide and the second non-contiguous polypeptide; and
   (2-c) a third non-contiguous polypeptide comprising, in the N-to-C orientation, the VL-CL of the Fab molecule of prong (2-a);
   (3) (3-a) a first non-contiguous polypeptide comprising, in the N-to-C orientation, the first tumor-targeting moiety comprising a VH-CH1 of a Fab molecule, connected to a first domain that promotes association between the first non-contiguous polypeptide and a second non-contiguous polypeptide;

(3-b) the second non-contiguous polypeptide comprising, in the N-to-C orientation, the cytokine molecule or the third antibody molecule that binds to NKp30 or NKp46, connected to a second domain that promotes association between the first non-contiguous polypeptide and the second non-contiguous polypeptide; and (3-c) a third non-contiguous polypeptide comprising, in the N-to-C orientation, the VL-CL of the Fab molecule of prong (3-a), wherein either the first non-contiguous polypeptide or the second non-contiguous polypeptide further comprises the cytokine molecule or the third antibody molecule that binds to NKp30 or NKp46; or (4) (4-a) a first non-contiguous polypeptide comprising, in the N-to-C orientation, the first tumor-targeting moiety comprising a VH-CH1 of a Fab molecule connected to a first domain that promotes association between the first non-contiguous polypeptide and a second non-contiguous polypeptide;

(4-b) the second non-contiguous polypeptide comprising, in the N-to-C orientation, the cytokine molecule or the third antibody molecule that binds to NKp30 or NKp46, connected to a second domain that promotes association between the first non-contiguous polypeptide and the second non-contiguous polypeptide; and (4-c) [[the]] a third non-contiguous polypeptide comprising, in the N-to-C orientation, the VL-CL of the Fab molecule of prong (4-a), wherein the first non-contiguous polypeptide and the second non-contiguous polypeptide further comprise the cytokine molecule, the third antibody molecule that binds to NKp30 or NKp46, or a combination thereof.

2. The multispecific or multifunctional molecule polypeptide of claim 1, wherein:

the combined affinity for the cancer antigens of the first tumor-targeting moiety and the second tumor-targeting moiety is equal to or greater than the affinity of the third antibody molecule for NKp30 or NKp46 or the affinity of the cytokine molecule for its corresponding binding membe either alone or as part of the multispecific molecule;

the combined affinity for the cancer antigens of the first tumor-targeting moiety and the second tumor-targeting moiety is at least 2 times greater than the affinity of the third antibody molecule for NKp30 or NKp46 or the affinity of the cytokine molecule for its corresponding binding member, either alone or as part of the multispecific molecule;

the combined affinity of the first tumor-targeting moiety and the second tumor-targeting moiety for the tumor is equal to or greater than the affinity of an otherwise identical multispecific multifunctional molecule polypeptide having only one of the first tumor-targeting moiety or the second tumor-targeting moiety; or the combined affinity of the first tumor-targeting moiety and the second tumor-targeting moiety for the tumor is at least 2 times greater than the affinity of an otherwise identical multispecific or multifunctional molecule polypeptide having only one of the first tumor-targeting moiety or the second tumor-targeting moiety.

3. The multispecific or multifunctional molecule polypeptide of claim 1, comprising:

A, B-[dimerization module]-C, -D wherein:

(1) the dimerization module comprises an immunoglobulin constant domain; and (2) A, B, C, and D are independently (i) the first tumor-targeting moiety; (ii) the second tumor-targeting moiety; (iii) the third antibody molecule that binds to NKp30 or NKp46; and (iv) the cytokine molecule.

4. The multispecific or multifunctional molecule polypeptide of claim 1, wherein:

the first cancer antigen or the second cancer antigen is present on a hematological cancer, a solid tumor, a metastatic cancer, soft tissue tumor, metastatic lesion, or a combination thereof;

the first cancer antigen or the second cancer antigen is a tumor antigen, a stromal antigen, or a hematological antigen; or the first cancer antigen or the second cancer antigen is a tumor antigen or stromal antigen present on a fibrotic or desmoplastic solid tumor.

5. The multispecific or multifunctional molecule polypeptide of claim 4, wherein:

the first cancer antigen or the second cancer antigen is present on a solid tumor selected from the group consisting of one or more of pancreatic, breast, colorectal, lung, skin, ovarian, and liver cancer; or the first cancer antigen or the second cancer antigen is present on a hematological cancer chosen selected from the group consisting of Hodgkin's lymphoma, Non-Hodgkin's lymphoma, acute myeloid leukemia, chronic myeloid leukemia, myelodysplastic syndrome, multiple myeloma, and acute lymphocytic leukemia.

6. The multispecific or multifunctional molecule polypeptide of claim 1, wherein:

the first cancer antigen or the second cancer antigen is selected from the group consisting of PDL1, mesothelin, CD47, prostate stem cell antigen (PSCA), prostate specific membrane antigen (PSMA), prostate-specific antigen (PSA), carcinoembryonic antigen (CEA), Ron Ep-Kinase, c-Met, Immature laminin receptor, TAG-72, Calcium-activated chloride channel 2, CAM, EphA3, Her2/neu, SAP-1, MC1R, Fibronectin, TGF-B receptor, AFP, ETA, CA-125, NY-ESO-1, a actinin-4, gangliosides, WT1, Epidermal growth factor receptor (EGFR), CD20, MUC2, MUM1, MUM2, MUM3, OA1, Folate receptor alpha, L1-CAM, CAIX, EGFRvIII, gpA33, VEGFR, Integrin, IGF1R, TRAILR1, TRAILR2, and RANKL;

the first cancer antigen or the second cancer antigen is a stromal antigen selected from the group consisting of fibroblast activating protease (FAP), TGF-beta, hyaluronic acid, collagen, tenascin C, and tenascin W; or the first cancer antigen or the second cancer antigen is a hematological antigen selected from the group consisting of CD19, CD33, CD123, CD99, CD30, BCMA, CD38, CD22, and SLAMF7.

7. The multispecific or multifunctional molecule polypeptide of claim 1, wherein:

the first antibody molecule binds to mesothelin, PDL1, HER3, IGF1R, FAP, CD47 or CD123;

the first antibody molecule binds to PDL1 and inhibits an interaction of PDL1 with PD1;

the first antibody molecule binds to PDL1 and does not inhibit an interaction of PD L1 with PD1; or the first antibody molecule binds to PDL1, the second antibody molecule binds to mesothelin, and the cytokine molecule is IL-2.

8. The multispecific or multifunctional molecule polypeptide of claim 1, wherein:
the cytokine molecule is a dimer;
the cytokine molecule comprises a receptor dimerizing domain;
the cytokine molecule comprises an IL15Ralpha dimerizing domain; or
the cytokine molecule comprises a receptor dimerizing domain, wherein the cytokine molecule and the receptor dimerizing domain are not covalently linked.

9. The multispecific or multifunctional molecule polypeptide of claim 1, comprising a first Fc region and a second Fc region, wherein dimerization of the first Fc region and the second Fc region is enhanced by providing an Fc interface of the first Fc region and the second Fc region with one or more of: a paired cavity-protuberance, an electrostatic interaction, or a strand-exchange, such that a greater ratio of heteromultimer:homomultimer forms relative to a non-engineered interface.

10. The multispecific or multifunctional molecule polypeptide of claim 9, wherein the first Fc region and the second Fc region comprise an amino acid substitution at a position selected from the group consisting of one or more of 347, 349, 350, 351, 366, 368, 370, 392, 394, 395, 397, 398, 399, 405, 407, and 409.

11. The multispecific or multifunctional molecule polypeptide of claim 9, wherein the first Fc region and the second Fc region comprise an amino acid substitution selected from the group consisting of T366S, L368A, Y407V, T366W, and a combination thereof.

12. The multispecific or multifunctional molecule polypeptide of claim 1, wherein the first tumor-targeting moiety or the second tumor-targeting moiety comprises:
an antibody molecule against a solid tumor antigen selected from the group consisting of: PDL1, Mesothelin, HER3, IGF-1R, GD2, PSMA, CEA, Ron Kinase, and c-Met;
an antibody molecule against a stromal antigen selected from the group consisting of: FAP, hyaluronic acid, collagen IV, tenascin C, and tenascin W; or
a combination of the antibody molecule against the solid tumor antigen and the antibody molecule against the stromal antigen.

13. A cell comprising the multispecific or multifunctional molecule polypeptide of claim 1.

14. A pharmaceutical composition comprising the multispecific or multifunctional molecule polypeptide of claim 1 and a pharmaceutically acceptable carrier, excipient, or stabilizer.

15. A multispecific or multifunctional molecule polypeptide, comprising:
(i) a first tumor-targeting moiety comprising a first antibody molecule that binds to a first cancer antigen;
(ii) a second tumor-targeting moiety comprising a second antibody molecule that binds to a second cancer antigen;
(iii) a third antibody molecule that binds to NKp30 or NKp46;
(iv) a cytokine molecule selected from the group consisting of interleukin-2 (IL-2) or a functional variant thereof, interleukin-7 (IL-7) or a functional variant thereof, interleukin-12 (IL-12) or a functional variant thereof, interleukin-15 (IL-15) or a functional variant thereof, interleukin-18 (IL-18) or a functional variant thereof, interleukin-21 (IL-21) or a functional variant thereof, and interferon gamma or a functional variant thereof; and (v) an immune cell engager selected from the group consisting of a T cell engager, a B cell engager, a dendritic cell engager, a macrophage cell engager, and a combination thereof;
wherein the B cell engager is a CD40 ligand, [[a]]an OX40 ligand, a CD70 ligand, an antibody molecule that binds to OX40, an antibody molecule that binds to CD40, or an antibody molecule that binds to CD70;
wherein the macrophage cell engager is a CD2 agonist, a CD40 ligand, an OX40 ligand, an antibody molecule that binds to OX40, an antibody molecule that binds to CD40, an antibody molecule that binds to CD70, an agonist of a Toll-like receptor, CD47, or a STING agonist;
wherein the dendritic cell engager is a CD2 agonist, an antibody molecule that binds to OX40, an OX40 ligand, a 41BB agonist, an agonist of a Toll-like receptor, a CD47 agonist, or a STING agonist; or
wherein the T cell engager binds to CD3, TCRα, TCRβ, TCRγ, TCRζ, ICOS, CD28, CD27, HVEM, 4-1BB, OX40, DR3, GITR, CD30, TIMI, SLAM, CD2, or CD226.

16. The multispecific or multifunctional molecule polypeptide of claim 15, wherein the immune cell engager is the STING agonist,
wherein the STING agonist comprises a cyclic dinucleotide, and
wherein the STING agonist is covalently coupled to the multispecific or multifunctional molecule polypeptide.

17. A multispecific or multifunctional molecule polypeptide, comprising:
(i) a first tumor-targeting moiety,
(ii) a second tumor-targeting moiety,
(iii) an antibody molecule that binds to NKp30 or NKp46, and
(iv) a cytokine molecule selected from the group consisting of interleukin-2 (IL-2) or a functional variant thereof, interleukin-7 (IL-7) or a functional variant thereof, interleukin-12 (IL-12) or a functional variant thereof, interleukin-15 (IL-15) or a functional variant thereof, interleukin-18 (IL-18) or a functional variant thereof, interleukin-21 (IL-21) or a functional variant thereof, and interferon gamma or a functional variant thereof,
wherein the first tumor-targeting moiety and the second tumor-targeting moiety bind to two cancer antigens selected from the group consisting of mesothelin, PDL1, HER3, Fibroblast Activation Protein (FAP), insulin growth factor 1R (IGF1R), CD47, and CD123, provided that the two cancer antigens are not FAP and IGF1R.

18. The multispecific or multifunctional molecule polypeptide of claim 17, wherein:
the first tumor-targeting moiety or the second tumor-targeting moiety is an anti-mesothelin antibody molecule or an anti-PDL1 antibody molecule;
the first tumor-targeting moiety or the second tumor-targeting moiety is an anti-FAP antibody molecule or an anti-PDL1 antibody molecule;
the first tumor-targeting moiety or the second tumor-targeting moiety is an anti-HER3 antibody molecule or an anti-IGF1R antibody molecule; or
the first tumor-targeting moiety or the second tumor-targeting moiety is an anti-CD123 antibody molecule or an anti-CD47 antibody molecule.

19. A method of treating a cancer in a subject in need thereof, comprising administering to the subject the multispecific or multifunctional molecule polypeptide of claim 1 wherein the multispecific or multifunctional molecule polypeptide is administered in an amount effective to treat the cancer.

20. The method of claim 19, further comprising administering a second therapeutic treatment to the subject, wherein the second therapeutic treatment comprises a therapeutic agent, radiation, or surgery.

21. The method of claim 19, wherein:

the cancer is a solid tumor cancer, or a metastatic lesion; or the cancer is a hematological cancer.

22. The method of claim 19, wherein the cancer is one or more of pancreatic, breast, colorectal, lung, skin, ovarian, or liver cancer.

* * * * *

UNITED STATES PATENT AND TRADEMARK OFFICE
CERTIFICATE OF CORRECTION

PATENT NO. : 11,291,721 B2
APPLICATION NO. : 15/465564
DATED : April 5, 2022
INVENTOR(S) : Andreas Loew and Brian Edward Vash It is certified that error appears in the above-identified patent and that said Letters Patent is hereby corrected as shown below:

In the Claims

At Column 607, Line 28 Claim 1 "[[the]] a third non-contiguous" should read "a third non-contiguous"

At Column 607, Line 43 Claim 2 "membe" should read "member"

At Column 607, Line 55 Claim 2 "multispecific multifunctional" should read "multispecific or multifunctional"

At Column 608, Line 30 Claim 5 "cancer chosen selected from" should read "cancer selected from"

At Column 608, Lines 41-42 Claim 6 "Ron Ep-Kinase" should read "Ron Kinase"

At Column 608, Line 43 Claim 6 "CAM" should read "Ep-CAM"

At Column 608, Line 45 Claim 6 "a actinin-4" should read "α actinin-4"

At Column 610, Lines 5-6 Claim 15 "[[a]]an OX40 ligand" should read "an OX40 ligand"

At Column 610, Line 19 Claim 15 "TCRPβ" should read "TCRβ"

At Column 610, Line 21 Claim 15 "TIMI" should read "TIM1"

At Column 611, Line 1 Claim 19 "claim 1" should read "claim 1,"

Signed and Sealed this
Fifteenth Day of April, 2025

Coke Morgan Stewart
*Acting Director of the United States Patent and Trademark Office*